(12) United States Patent
Szigethy et al.

(10) Patent No.: US 9,911,931 B2
(45) Date of Patent: Mar. 6, 2018

(54) ORGANIC ELECTROLUMINESCENT MATERIALS AND DEVICES

(71) Applicant: Universal Display Corporation, Ewing, NJ (US)

(72) Inventors: Geza Szigethy, Ewing, NJ (US); Jason Brooks, Philadelphia, PA (US); Scott Beers, Flemington, NJ (US); Nicholas J. Thompson, Trenton, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 290 days.

(21) Appl. No.: 14/728,553

(22) Filed: Jun. 2, 2015

(65) Prior Publication Data
US 2015/0380666 A1 Dec. 31, 2015

Related U.S. Application Data

(60) Provisional application No. 62/017,341, filed on Jun. 26, 2014.

(51) Int. Cl.
| H01L 51/00 | (2006.01) |
| C09K 11/06 | (2006.01) |
| C07F 15/00 | (2006.01) |

(52) U.S. Cl.
CPC ...... *H01L 51/0087* (2013.01); *C07F 15/0033* (2013.01); *C07F 15/0086* (2013.01);
(Continued)

(58) Field of Classification Search
CPC ........ H01L 51/0085–51/0089; H01L 51/0091; H01L 51/0054; H01L 51/0071;
(Continued)

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Ruiyun Zhang
(74) *Attorney, Agent, or Firm* — Duane Morris LLP

(57) ABSTRACT

Compounds having the structure of Formula $M(L_A)_x(L_B)_y$ and Formula III, (Continued)

are disclosed. In Formula $M(L_A)_x(L_B)_y$, Ligand $L_A$ is

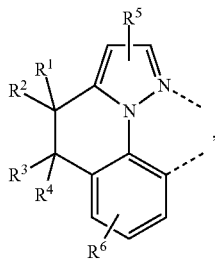

and ligand $L_B$ is a mono anionic bidentate ligand. In these compounds, metal M has an atomic number greater than 40; x is 1, 2, or 3; y is 0, 1, or 2; x+y is the oxidation state of metal M; $L^{11}$ represents a linking group selected from alkyl, cycloalkyl, aryl, and heteroaryl; $L^{12}$ represents a linking group selected from $NR^{15}$ and $PR^{15}$; each $R^1$, $R^2$, $R^3$, $R^4$, $R^5$, $R^6$, $R^{11}$, $R^{12}$, $R^{13}$, $R^{14}$, and $R^{15}$ is independently selected from a group of substituents, wherein any adjacent substituents are optionally joined to form a fused or unfused ring; and $L_A$ and $L_B$ are optionally joined to form a ligand that is at least tetradentate. Formulations and devices, such as OLEDs, that include the compound of Formula $M(L_A)_x(L_B)_y$ are also described.

25 Claims, 6 Drawing Sheets

(52) U.S. Cl.
CPC .......... *C09K 11/06* (2013.01); H01L 51/0085
(2013.01); *C09K 2211/1007* (2013.01); *C09K 2211/1011* (2013.01); *C09K 2211/1014* (2013.01); *C09K 2211/1044* (2013.01); *C09K 2211/185* (2013.01); *H01L 51/0054* (2013.01); *H01L 51/0071* (2013.01); *H01L 51/0072* (2013.01); *H01L 51/0074* (2013.01)

(58) Field of Classification Search
CPC ............. H01L 51/0072; H01L 51/0074; C07F 15/0033; C07F 15/0086; C09K 11/06; C09K 2211/1007; C09K 2211/1011; C09K 2211/1014; C09K 2211/1044; C09K 2211/185
USPC ............... 428/690, 917; 313/504; 546/4, 10; 548/103, 108; 257/E51.044
See application file for complete search history.

(56) References Cited

U.S. PATENT DOCUMENTS

| | | | |
|---|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0227112 A1 | 10/2005 | Ise et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260445 A1 | 11/2005 | Walters et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0204787 A1 | 9/2006 | Sano et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1* | 8/2007 | Knowles ............ C07F 15/0033 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0036373 A1 | 2/2008 | Itoh et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0079340 A1 | 3/2009 | Kinoshita et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0267500 A1 | 10/2009 | Kinoshita et al. |
| 2010/0051928 A1 | 3/2010 | Fukuzaki |
| 2011/0049496 A1 | 3/2011 | Fukuzaki |
| 2012/0153816 A1 | 6/2012 | Takizawa et al. |
| 2013/0033174 A1 | 2/2013 | Takaku |
| 2015/0008419 A1 | 1/2015 | Li |

FOREIGN PATENT DOCUMENTS

| | | | |
|---|---|---|---|
| EP | 2034538 | 3/2009 | |
| EP | 2551274 A1 * | 1/2013 | .......... C07F 15/0086 |
| GB | 2423518 | 8/2006 | |
| JP | 200511610 | 1/2005 | |

(56) References Cited

FOREIGN PATENT DOCUMENTS

| JP | 2007123392 | 5/2007 |
|---|---|---|
| JP | 2007254297 | 10/2007 |
| JP | 2008074939 | 4/2008 |
| JP | 2009266943 | 11/2009 |
| JP | 2009272339 | 11/2009 |
| JP | 2011213674 | 10/2011 |
| JP | 2011213915 | 10/2011 |
| JP | 2011213918 | 10/2011 |
| JP | 2011216628 | 10/2011 |
| JP | 2011228238 | 11/2011 |
| JP | 2012079899 | 4/2012 |
| KR | 20130043459 | 4/2013 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005113704 | 12/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012141109 | 10/2012 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhicliang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).

(56) References Cited

OTHER PUBLICATIONS

Noda, Tetsuya and Shirota, Yasuhiko, "5,5'-Bis(dimesitylboryl)-2,2'-bithiophene and 5,5'-Bis(dimesitylboryl)-2,2'5',2"-terthiophene as a Novel Family of Electron-Transporting Amorphous Molecular Materials," J. Am. Chem. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C,, "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew, Chem. Int. Ed., 45:7800-7803 (2006).

* cited by examiner

Formula III

Ligand L_A

ORGANIC ELECTROLUMINESCENT MATERIALS AND DEVICES

CROSS-REFERENCE TO RELATED APPLICATIONS

This application is a non-provisional of U.S. Patent Application Ser. No. 62/017,341, filed Jun. 26, 2014, the entire content of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

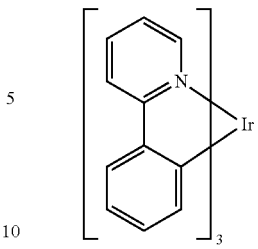

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound having a structure according to formula $M(L_A)_x(L_B)_y$ is provided. In formula $M(L_A)_x(L_B)_y$:

ligand $L_A$ is

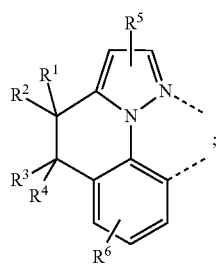

ligand $L_B$ is a mono anionic bidentate ligand;

each $L_A$ and $L_B$ can be the same or different;

M is a metal having an atomic number greater than 40;

x is 1, 2, or 3;

y is 0, 1, or 2;

x+y is the oxidation state of the metal M;

$R^5$ represents mono, or di substitution, or no substitution;

$R^6$ represents mono, di, or tri substitution, or no substitution;

each $R^1$, $R^2$, $R^3$, $R^4$, $R^5$, and $R^6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

any adjacent $R^1$, $R^2$, $R^3$, $R^4$, $R^5$, and $R^6$ groups are optionally joined to form a fused or unfused ring; and $L_A$ and $L_B$ are optionally joined to form a ligand that is at least tetradentate.

According to another aspect of the present disclosure, a compound having the structure of Formula III,

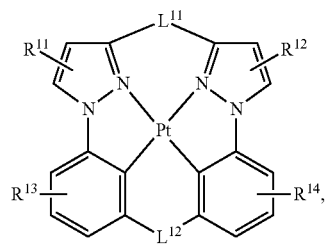

is provided. In the structure of Formula III:

$R^{11}$, and $R^{12}$ each independently represent mono, or di substitution, or no substitution;

$R^{13}$ and $R^{14}$ each independently represent mono, di, tri, or tetra substitution, or no substitution;

$L^{11}$ represents a linking group selected from the group consisting of alkyl, cycloalkyl, aryl, and heteroaryl;

$L^{12}$ represents a linking group selected from the group consisting of $NR^{15}$, and $PR^{15}$;

$R^{11}$, $R^{12}$, $R^{13}$, $R^{14}$, and $R^{15}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent $L^{11}$, $L^{12}$, $R^{11}$, $R^{12}$, $R^{13}$, $R^{14}$, and $R^{15}$ are optionally joined to form a fused or unfused ring.

According to another embodiment, a device comprising one or more organic light emitting devices is also provided. At least one of the one or more organic light emitting devices can include an anode, a cathode, and an organic layer, disposed between the anode and the cathode, wherein the organic layer can include a compound selected from the group consisting of Formula $M(L_A)_x(L_B)_y$, Formula III, and combinations thereof. The device can be a consumer product, an electronic component module, an organic light-emitting device, and/or a lighting panel.

According to yet another embodiment, a formulation containing a compound selected from the group consisting of Formula $M(L_A)_x(L_B)_y$, Formula III, and combinations thereof is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
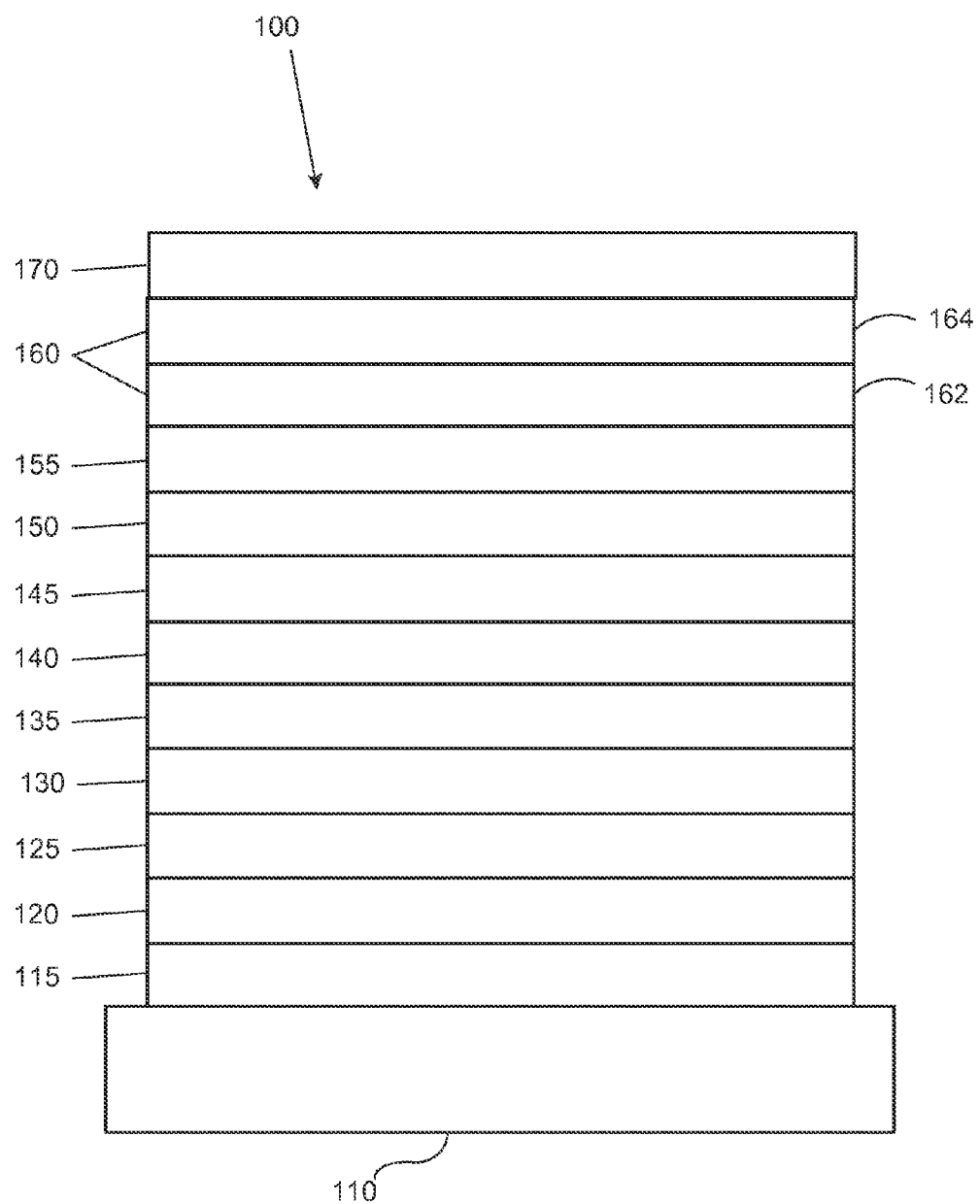
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
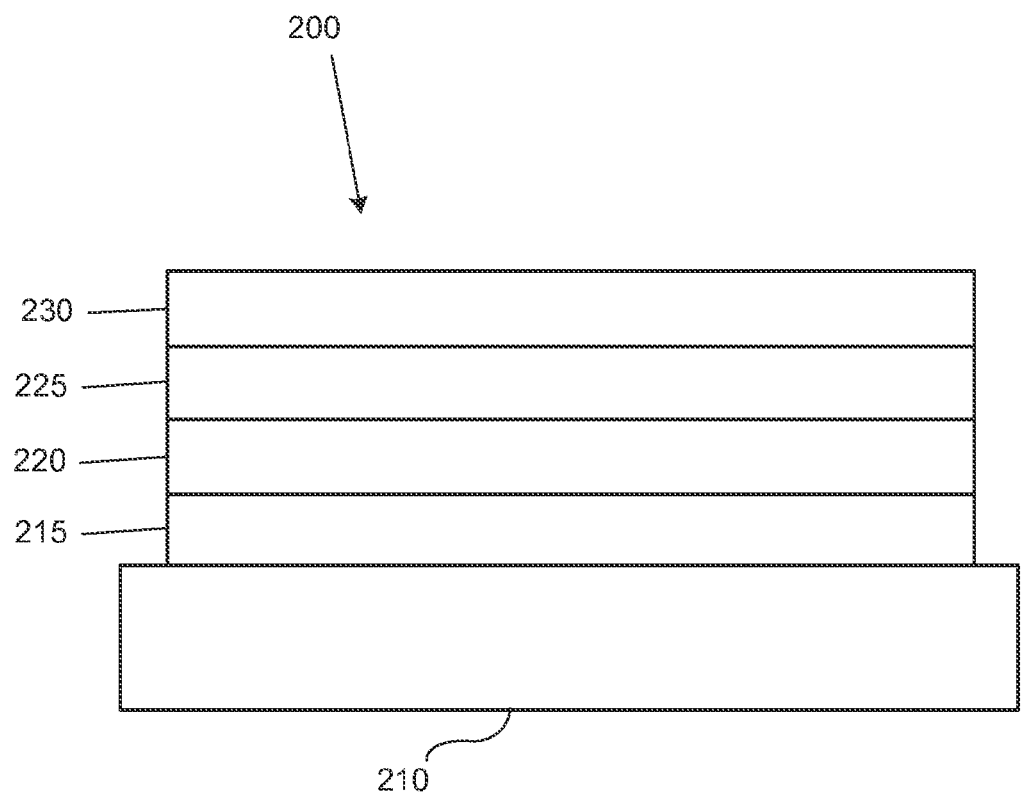
FIG. 2 shows an inverted organic light emitting device that does not have a separate electron transport layer.
Figure 3:
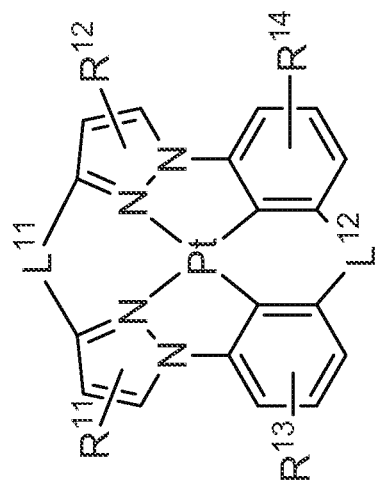
FIG. 3 shows Ligand LA and Formula III as disclosed herein.
Figure 3:
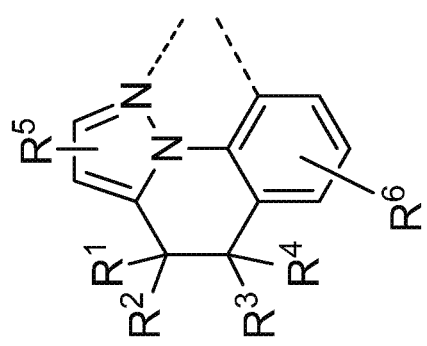

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to one embodiment, a compound having a structure according to formula $M(L_A)_x(L_B)_y$ is described. In Formula $M(L_A)_x(L_B)_y$:

ligand $L_A$ is

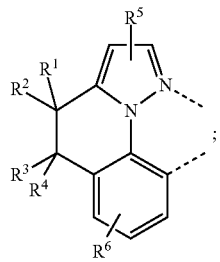

ligand $L_B$ is a mono anionic bidentate ligand;
each $L_A$ and $L_B$ can be the same or different;
M is a metal having an atomic number greater than 40;

x is 1, 2, or 3;
y is 0, 1, or 2;
x+y is the oxidation state of the metal M;
$R^5$ represents mono, or di substitution, or no substitution;
$R^6$ represents mono, di, or tri substitution, or no substitution;
each $R^1$, $R^2$, $R^3$, $R^4$, $R^5$, and $R^6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

any adjacent $R^1$, $R^2$, $R^3$, $R^4$, $R^5$, and $R^6$ groups are optionally joined to form a fused or unfused ring; and $L_A$ and $L_B$ are optionally joined to form a ligand that is at least tetradentate.

In some embodiments, M is selected from the group consisting of Ir, Rh, Re, Ru, Os, Pt, Au, and Cu. In some embodiments, M is Pt.

In some embodiments, at least one of $R^1$, $R^2$, $R^3$, and $R^4$ is not hydrogen or deuterium. In some embodiments, $R^1$, $R^2$, $R^3$, and $R^4$ are each independently selected from the group consisting of hydrogen, deuterium, alkyl, cycloalkyl, and combinations thereof.

In some more specific embodiments, the compound has the structure of Formula I:

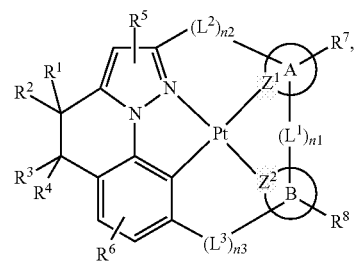

where ring A and ring B are each independently a 5- or 6-membered carbocyclic or heterocyclic ring. In some such embodiments, $L^1$, $L^2$ and $L^3$ are independently selected from the group consisting of a direct bond, alkyl, cycloalkyl, BR, NR, PR, O, S, Se, C=O, S=O, $SO_2$, SiRR', and GeRR'; In some such embodiments, $Z^1$ and $Z^2$ are each independently a nitrogen atom or a carbon atom; In some embodiments, $R^7$ and $R^8$ each represent mono, di, tri, or tetra substitution, or no substitution, and R, R', $R^7$ and $R^8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. In some embodiments, two adjacent substituents R, R', $R^7$ and $R^8$ are optionally joined to form a fused or unfused ring. In some embodiments, n1 is 0 or 1; n2 is 0 or 1; and n3 is 0 or 1. In some embodiments, n1+n2+n3 is at least 2. In some embodiments, direct bonds disclosed herein can be selected from a single bond and a double bond.

In some embodiments, n2 is 1 and n3 is 0. In some embodiments, n2 is 0 and n3 is 1. In some embodiments, n2 is 1 and n3 is 1.

In some embodiments, rings A and B are selected from the group consisting of benzene, pyridine, pyrazole, benzopyrazole, naphthalene, isoquinoline, aza-isoquinoline, carbazole, and dibenzofuran, each of which may be, optionally, further substituted.

In some more specific embodiments, the compound has the structure of Formula II:

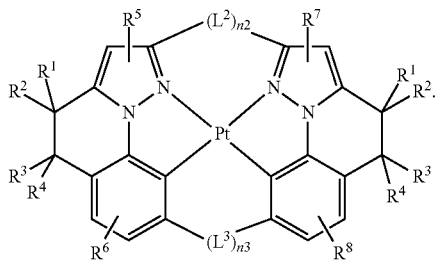

In some embodiments, the compound is selected from the group consisting of:
Compound Pt1 through Pt12, each represented by the formula

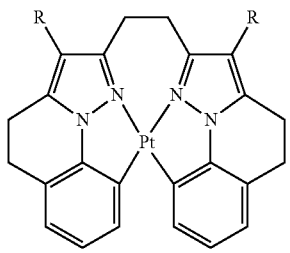

wherein in Compound Pt1: R=H,
in Compound Pt2: R=Me,
in Compound Pt3: R=Et,
in Compound Pt4: R=$^i$Pr,
in Compound Pt5: R=neopentyl,
in Compound Pt6: R=$^i$Bu,
in Compound Pt7: R=$^t$Bu,
in Compound Pt8: R=Ph,
in Compound Pt9: R=4-biphenyl,
in Compound Pt10: R=2,6-($^i$Pr)$_2$Ph,
in Compound Pt11: R=2,6-($^i$Pr)$_2$-4-biphenyl,
in Compound Pt12: R=2,4-($^i$Pr)$_2$-3-dibenzofuran,
Compound Pt13 through Pt21, each represented by the formula

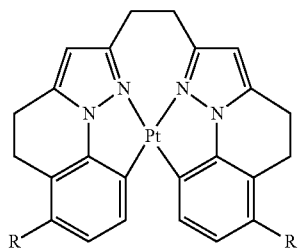

wherein in Compound Pt13: R=Me,
in Compound Pt14: R=Et,
in Compound Pt15: R=$^i$Pr,
in Compound Pt16: R=neopentyl,
in Compound Pt17: R=$^i$Bu,
in Compound Pt18: R=$^t$Bu,
in Compound Pt19: R=Ph,
in Compound Pt20: R=2,6-(Me)$_2$Ph,
in Compound Pt21: R=2,6-($^i$Pr)$_2$Ph,
Compound Pt22 through Pt30, each represented by the formula

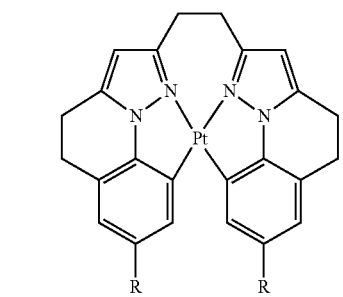

wherein in Compound Pt22: R=Me,
in Compound Pt23: R=Et,
in Compound Pt24: R=$^i$Pr,
in Compound Pt25: R=neopentyl,
in Compound Pt26: R=$^i$Bu,
in Compound Pt27: R=$^t$Bu,
in Compound Pt28: R=Ph,
in Compound Pt29: R=2,6-(Me)$_2$Ph,
in Compound Pt30: R=2,6-($^i$Pr)$_2$Ph,
Compound Pt31 through Pt42, each represented by the formula

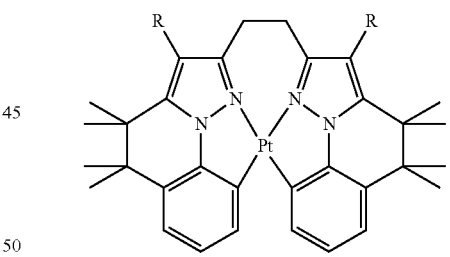

wherein in Compound Pt31: R=H,
in Compound Pt32: R=Me,
in Compound Pt33: R=Et,
in Compound Pt34: R=$^i$Pr,
in Compound Pt35: R=neopentyl,
in Compound Pt36: R=$^i$Bu,
in Compound Pt37: R=$^t$Bu,
in Compound Pt38: R=Ph,
in Compound Pt39: R=4-biphenyl,
in Compound Pt40: R=2,6-($^i$Pr)$_2$Ph,
in Compound Pt41: R=2,6-($^i$Pr)$_2$-4-biphenyl,
in Compound Pt42: R=2,4-($^i$Pr)$_2$-3-dibenzofuran, Compound Pt43 through Pt54, each represented by the formula

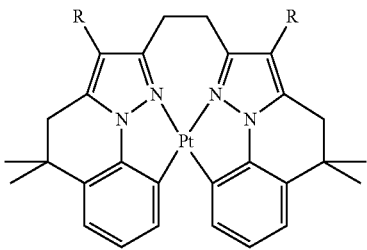

wherein in Compound Pt43: R=H,
in Compound Pt44: R=Me,
in Compound Pt45: R=Et,
in Compound Pt46: R=$^i$Pr,
in Compound Pt47: R=neopentyl,
in Compound Pt48: R=$^i$Bu,
in Compound Pt49: R=$^t$Bu,
in Compound Pt50: R=Ph,
in Compound Pt51: R=4-biphenyl,
in Compound Pt52: R=2,6-($^i$Pr)$_2$Ph,
in Compound Pt53: R=2,6-($^i$Pr)$_2$-4-biphenyl,
in Compound Pt54: R=2,4-($^i$Pr)$_2$-3-dibenzofuran,
Compound Pt55 through Pt66, each represented by the formula

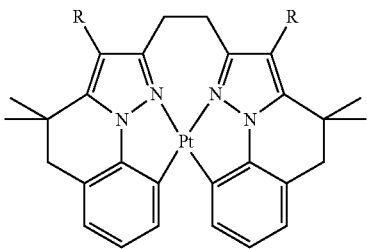

wherein in Compound Pt55: R=H,
in Compound Pt56: R=Me,
in Compound Pt57: R=Et,
in Compound Pt58: R=$^i$Pr,
in Compound Pt59: R=neopentyl,
in Compound Pt60: R=$^i$Bu,
in Compound Pt61: R=$^t$Bu,
in Compound Pt62: R=Ph,
in Compound Pt63: R=4-biphenyl,
in Compound Pt64: R=2,6-($^i$Pr)$_2$Ph,
in Compound Pt65: R=2,6-($^i$Pr)$_2$-4-biphenyl,
in Compound Pt66: R=2,4-($^i$Pr)$_2$-3-dibenzofuran,
Compound Pt67 through Pt75, each represented by the formula

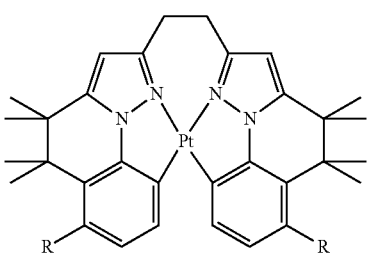

wherein in Compound Pt67: R=Me,
in Compound Pt68: R=Et,
in Compound Pt69: R=$^i$Pr,
in Compound Pt70: R=neopentyl,
in Compound Pt71: R=$^i$Bu,
in Compound Pt72: R=$^t$Bu,
in Compound Pt73: R=Ph,
in Compound Pt74: R=2,6-(Me)$_2$Ph,
in Compound Pt75: R=2,6-($^i$Pr)$_2$Ph,
Compound Pt76 through Pt84, each represented by the formula

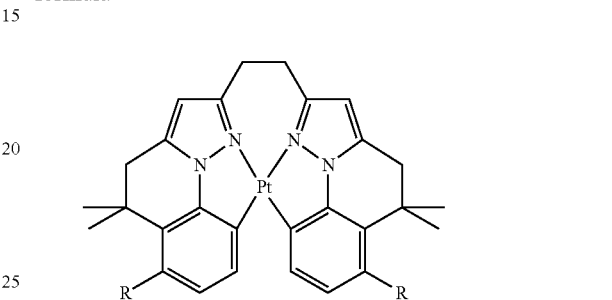

wherein in Compound Pt76: R=Me,
in Compound Pt77: R=Et,
in Compound Pt78: R=$^i$Pr,
in Compound Pt79: R=neopentyl,
in Compound Pt80: R=$^i$Bu,
in Compound Pt81: R=$^t$Bu,
in Compound Pt82: R=Ph,
in Compound Pt83: R=2,6-(Me)$_2$Ph,
in Compound Pt84: R=2,6-($^i$Pr)$_2$Ph,
Compound Pt85 through Pt93, each represented by the formula

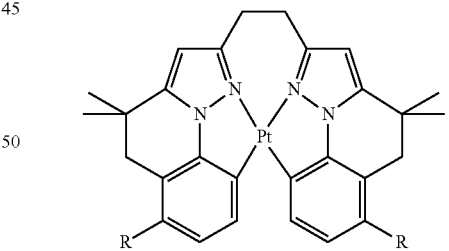

wherein in Compound Pt85: R=Me,
in Compound Pt86: R=Et,
in Compound Pt87: R=$^i$Pr,
in Compound Pt88: R=neopentyl,
in Compound Pt89: R=$^i$Bu,
in Compound Pt90: R=$^t$Bu,
in Compound Pt91: R=Ph,
in Compound Pt92: R=2,6-(Me)$_2$Ph,
in Compound Pt93: R=2,6-($^i$Pr)$_2$Ph, Compound Pt94 through Pt102, each represented by the formula

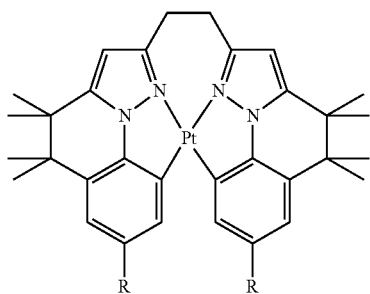

wherein in Compound Pt94: R=Me,
in Compound Pt95: R=Et,
in Compound Pt96: R=$^i$Pr,
in Compound Pt97: R=neopentyl,
in Compound Pt98: R=$^i$Bu,
in Compound Pt99: R=$^t$Bu,
in Compound Pt100: R=Ph,
in Compound Pt101: R=2,6-(Me)$_2$Ph,
in Compound Pt102: R=2,6-($^i$Pr)$_2$Ph,
Compound Pt103 through Pt111, each represented by the formula

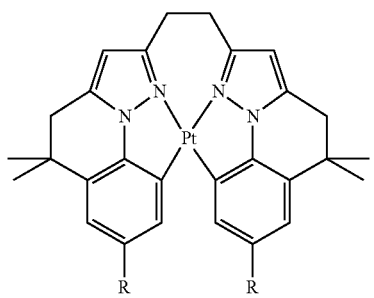

wherein in Compound Pt103: R=Me,
in Compound Pt104: R=Et,
in Compound Pt105: R=$^i$Pr,
in Compound Pt106: R=neopentyl,
in Compound Pt107: R=$^i$Bu,
in Compound Pt108: R=$^t$Bu,
in Compound Pt109: R=Ph,
in Compound Pt110: R=2,6-(Me)$_2$Ph,
in Compound Pt111: R=2,6-($^i$Pr)$_2$Ph,
Compound Pt112 through Pt120, each represented by the formula

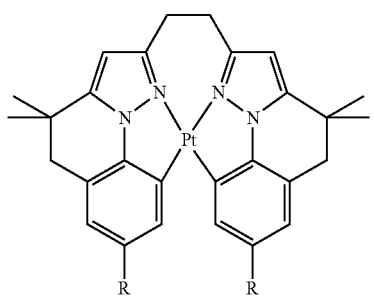

wherein in Compound Pt112: R=Me,
in Compound Pt113: R=Et,
in Compound Pt114: R=$^i$Pr,
in Compound Pt115: R=neopentyl,
in Compound Pt116: R=$^i$Bu,
in Compound Pt117: R=$^t$Bu,
in Compound Pt118: R=Ph,
in Compound Pt119: R=2,6-(Me)$_2$Ph,
in Compound Pt120: R=2,6-($^i$Pr)$_2$Ph,
Compound Pt121 through Pt132, each represented by the formula

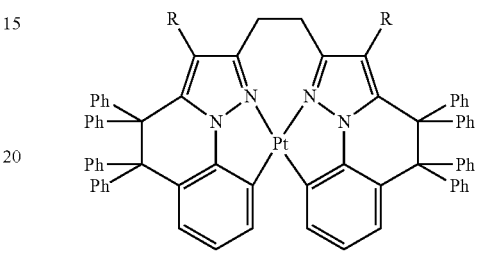

wherein in Compound Pt121: R=H,
in Compound Pt122: R=Me,
in Compound Pt123: R=Et,
in Compound Pt124: R=$^i$Pr,
in Compound Pt125: R=neopentyl,
in Compound Pt126: R=$^i$Bu,
in Compound Pt127: R=$^t$Bu,
in Compound Pt128: R=Ph,
in Compound Pt129: R=4-biphenyl,
in Compound Pt130: R=2,6-($^i$Pr)$_2$Ph,
in Compound Pt131: R=2,6-($^i$Pr)$_2$-4-biphenyl,
in Compound Pt132: R=2,4-($^i$Pr)$_2$-3-dibenzofuran,
Compound Pt133 through Pt144, each represented by the formula

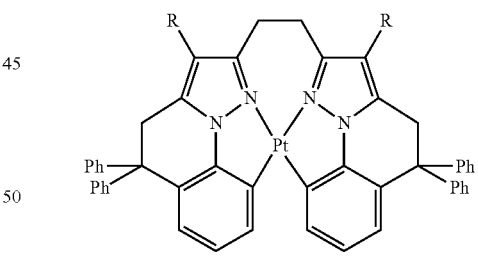

wherein in Compound Pt133: R=H,
in Compound Pt134: R=Me,
in Compound Pt135: R=Et,
in Compound Pt136: R=$^i$Pr,
in Compound Pt137: R=neopentyl,
in Compound Pt138: R=$^i$Bu,
in Compound Pt139: R=$^t$Bu,
in Compound Pt140: R=Ph,
in Compound Pt141: R=4-biphenyl,
in Compound Pt142: R=2,6-($^i$Pr)$_2$Ph,
in Compound Pt143: R=2,6-($^i$Pr)$_2$-4-biphenyl,
in Compound Pt144: R=2,4-($^i$Pr)$_2$-3-dibenzofuran, Compound Pt145 through Pt156, each represented by the formula

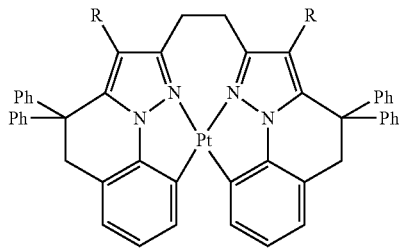

wherein in Compound Pt145: R=H,
in Compound Pt146: R=Me,
in Compound Pt147: R=Et,
in Compound Pt148: R=$^i$Pr,
in Compound Pt149: R=neopentyl,
in Compound Pt150: R=$^i$Bu,
in Compound Pt151: R=$^t$Bu,
in Compound Pt152: R=Ph,
in Compound Pt153: R=4-biphenyl,
in Compound Pt154: R=2,6-($^i$Pr)$_2$Ph,
in Compound Pt155: R=2,6-($^i$Pr)$_2$-4-biphenyl,
in Compound Pt156: R=2,4-($^i$Pr)$_2$-3-dibenzofuran,
Compound Pt157 through Pt165, each represented by the formula

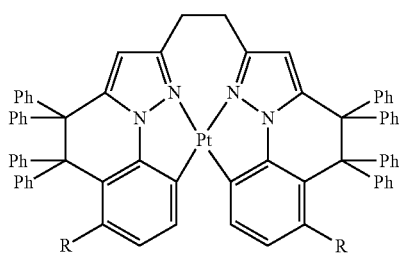

wherein in Compound Pt157: R=Me,
in Compound Pt158: R=Et,
in Compound Pt159: R=$^i$Pr,
in Compound Pt160: R=neopentyl,
in Compound Pt161: R=$^i$Bu,
in Compound Pt162: R=$^t$Bu,
in Compound Pt163: R=Ph,
in Compound Pt164: R=2,6-(Me)$_2$Ph,
in Compound Pt165: R=2,6-($^i$Pr)$_2$Ph,
Compound Pt166 through Pt174, each represented by the formula

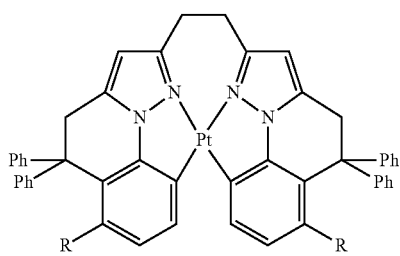

wherein in Compound Pt166: R=Me,
in Compound Pt167: R=Et,
in Compound Pt168: R=$^i$Pr,
in Compound Pt169: R=neopentyl,
in Compound Pt170: R=$^i$Bu,
in Compound Pt171: R=$^t$Bu,
in Compound Pt172: R=Ph,
in Compound Pt173: R=2,6-(Me)$_2$Ph,
in Compound Pt174: R=2,6-($^i$Pr)$_2$Ph,
Compound Pt175 through Pt183, each represented by the formula

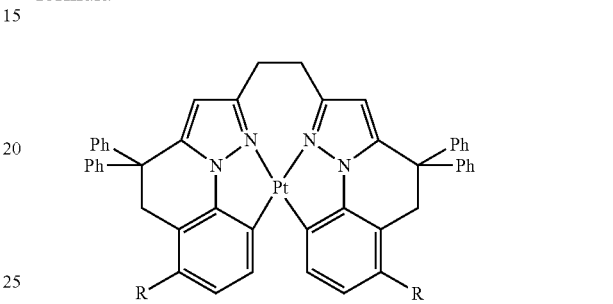

wherein in Compound Pt175: R=Me
in Compound Pt176: R=Et
in Compound Pt177: R=$^i$Pr
in Compound Pt178: R=neopentyl
in Compound Pt179: R=$^i$Bu
in Compound Pt180: R=$^t$Bu
in Compound Pt181: R=Ph
in Compound Pt182: R=2,6-(Me)$_2$Ph
in Compound Pt183: R=2,6-($^i$Pr)$_2$Ph,
Compound Pt184 through Pt192, each represented by the formula

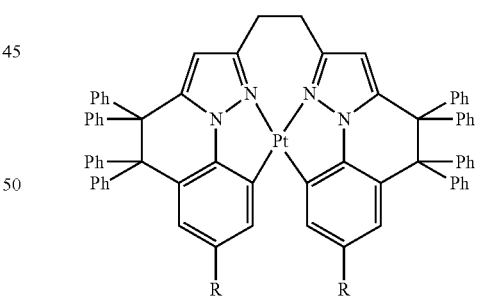

wherein in Compound Pt184: R=Me,
in Compound Pt185: R=Et,
in Compound Pt186: R=$^i$Pr,
in Compound Pt187: R=neopentyl,
in Compound Pt188: R=$^i$Bu,
in Compound Pt189: R=$^t$Bu,
in Compound Pt190: R=Ph,
in Compound Pt191: R=2,6-(Me)$_2$Ph,
in Compound Pt192: R=2,6-($^i$Pr)$_2$Ph, Compound Pt193 through Pt201, each represented by the formula

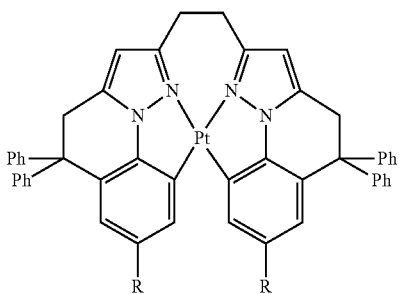

wherein in Compound Pt193: R=Me,
in Compound Pt194: R=Et,
in Compound Pt195: R=$^i$Pr,
in Compound Pt196: R=neopentyl,
in Compound Pt197: R=$^i$Bu,
in Compound Pt198: R=$^t$Bu,
in Compound Pt199: R=Ph,
in Compound Pt200: R=2,6-(Me)$_2$Ph,
in Compound Pt201: R=2,6-($^i$Pr)$_2$Ph,
Compound Pt202 through Pt210, each represented by the formula

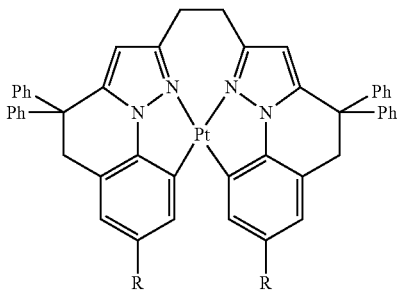

wherein in Compound Pt202: R=Me,
in Compound Pt203: R=Et,
in Compound Pt204: R=$^i$Pr,
in Compound Pt205: R=neopentyl,
in Compound Pt206: R=$^i$Bu,
in Compound Pt207: R=$^t$Bu,
in Compound Pt208: R=Ph,
in Compound Pt209: R=2,6-(Me)$_2$Ph,
in Compound Pt210: R=2,6-($^i$Pr)$_2$Ph,
Compound Pt211 through Pt222, each represented by the formula

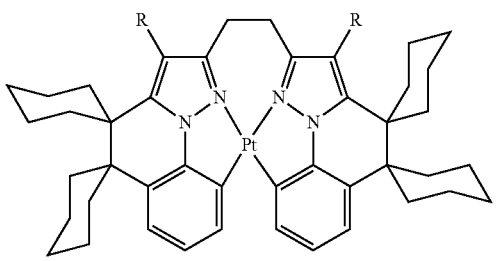

wherein in Compound Pt211: R=H,
in Compound Pt212: R=Me,
in Compound Pt213: R=Et,
in Compound Pt214: R=$^i$Pr,
in Compound Pt215: R=neopentyl,
in Compound Pt216: R=$^i$Bu,
in Compound Pt217: R=$^t$Bu,
in Compound Pt218: R=Ph,
in Compound Pt219: R=4-biphenyl,
in Compound Pt220: R=2,6-($^i$Pr)$_2$Ph,
in Compound Pt221: R=2,6-($^i$Pr)$_2$-4-biphenyl,
in Compound Pt222: R=2,4-($^i$Pr)$_2$-3-dibenzofuran,
Compound Pt223 through Pt234, each represented by the formula

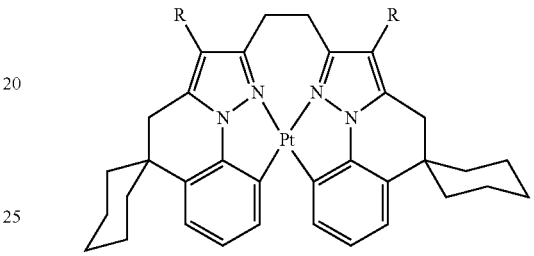

wherein in Compound Pt223: R=H
in Compound Pt224: R=Me
in Compound Pt225: R=Et
in Compound Pt226: R=$^i$Pr
in Compound Pt227: R=neopentyl
in Compound Pt228: R=$^i$Bu
in Compound Pt229: R=$^t$Bu
in Compound Pt230: R=Ph
in Compound Pt231: R=4-biphenyl
in Compound Pt232: R=2,6-($^i$Pr)$_2$Ph
in Compound Pt233: R=2,6-($^i$Pr)$_2$-4-biphenyl
in Compound Pt234: R=2,4-($^i$Pr)$_2$-3-dibenzofuran,
Compound Pt235 through Pt246, each represented by the formula

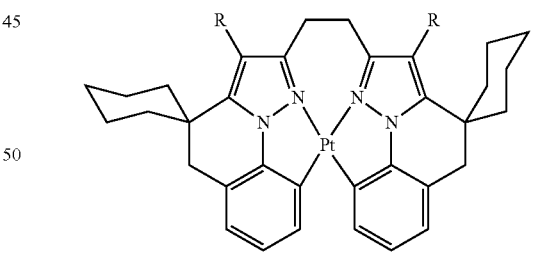

wherein in Compound Pt235: R=H
in Compound Pt236: R=Me
in Compound Pt237: R=Et
in Compound Pt238: R=$^i$Pr
in Compound Pt239: R=neopentyl
in Compound Pt240: R=$^i$Bu
in Compound Pt241: R=$^t$Bu
in Compound Pt242: R=Ph
in Compound Pt243: R=4-biphenyl
in Compound Pt244: R=2,6-($^i$Pr)$_2$Ph
in Compound Pt245: R=2,6-($^i$Pr)$_2$-4-biphenyl
in Compound Pt246: R=2,4-($^i$Pr)$_2$-3-dibenzofuran, Compound Pt247 through Pt255, each represented by the formula

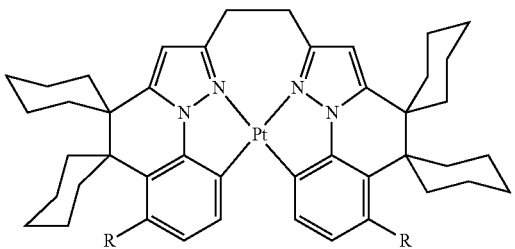

wherein in Compound Pt247: R=Me,
in Compound Pt248: R=Et,
in Compound Pt249: R=$^i$Pr,
in Compound Pt250: R=neopentyl,
in Compound Pt251: R=$^i$Bu,
in Compound Pt252: R=$^t$Bu,
in Compound Pt253: R=Ph,
in Compound Pt254: R=2,6-(Me)$_2$Ph,
in Compound Pt255: R=2,6-($^i$Pr)$_2$Ph,
Compound Pt256 through Pt264, each represented by the formula

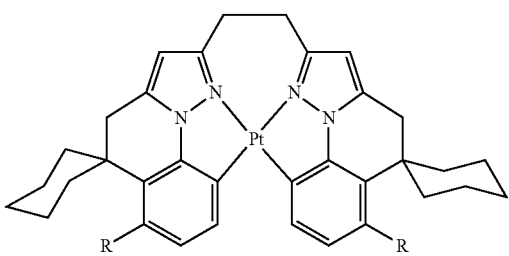

wherein in Compound Pt256: R=Me,
in Compound Pt257: R=Et,
in Compound Pt258: R=$^i$Pr,
in Compound Pt259: R=neopentyl,
in Compound Pt260: R=$^i$Bu,
in Compound Pt261: R=$^t$Bu,
in Compound Pt262: R=Ph,
in Compound Pt263: R=2,6-(Me)$_2$Ph,
in Compound Pt264: R=2,6-($^i$Pr)$_2$Ph,
Compound Pt265 through Pt273, each represented by the formula

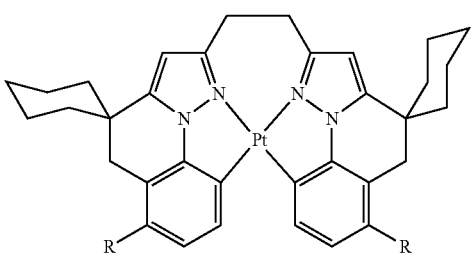

wherein in Compound Pt265: R=Me,
in Compound Pt266: R=Et,
in Compound Pt267: R=$^i$Pr,
in Compound Pt268: R=neopentyl,
in Compound Pt269: R=$^i$Bu,
in Compound Pt270: R=$^t$Bu,
in Compound Pt271: R=Ph,
in Compound Pt272: R=2,6-(Me)$_2$Ph,
in Compound Pt273: R=2,6-($^i$Pr)$_2$Ph,
Compound Pt274 through Pt282, each represented by the formula

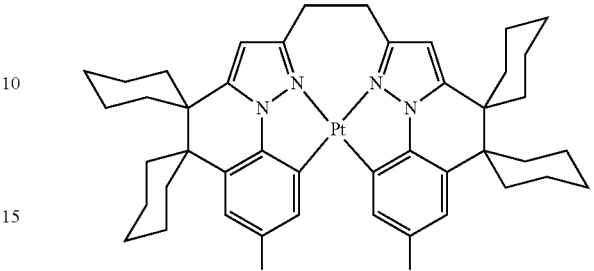

wherein in Compound Pt274: R=Me,
in Compound Pt275: R=Et,
in Compound Pt276: R=$^i$Pr,
in Compound Pt277: R=neopentyl,
in Compound Pt278: R=$^i$Bu,
in Compound Pt279: R=$^t$Bu,
in Compound Pt280: R=Ph,
in Compound Pt281: R=2,6-(Me)$_2$Ph,
in Compound Pt282: R=2,6-($^i$Pr)$_2$Ph,
Compound Pt283 through Pt291, each represented by the formula

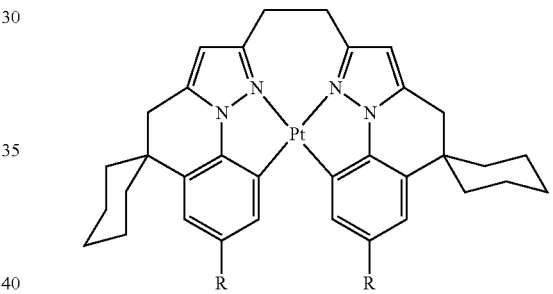

wherein in Compound Pt283: R=Me,
in Compound Pt284: R=Et,
in Compound Pt285: R=$^i$Pr,
in Compound Pt286: R=neopentyl,
in Compound Pt287: R=$^i$Bu,
in Compound Pt288: R=$^t$Bu,
in Compound Pt289: R=Ph,
in Compound Pt290: R=2,6-(Me)$_2$Ph,
in Compound Pt291: R=2,6-($^i$Pr)$_2$Ph,
Compound Pt292 through Pt300, each represented by the formula

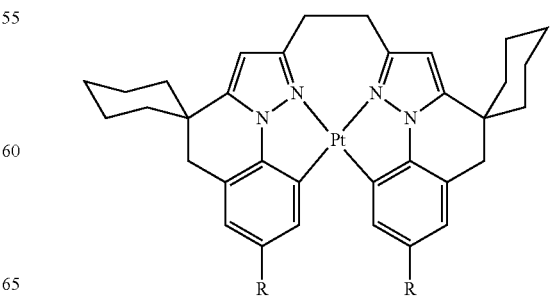

wherein in Compound Pt292: R=Me,
in Compound Pt293: R=Et,
in Compound Pt294: R=$^i$Pr,
in Compound Pt295: R=neopentyl,
in Compound Pt296: R=$^i$Bu,
in Compound Pt297: R=$^t$Bu,
in Compound Pt298: R=Ph,
in Compound Pt299: R=2,6-(Me)$_2$Ph,
in Compound Pt300: R=2,6-($^i$Pr)$_2$Ph,
Compound Pt301 through Pt312, each represented by the formula

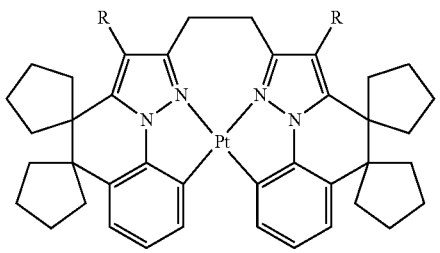

wherein in Compound Pt301: R=H,
in Compound Pt302: R=Me,
in Compound Pt303: R=Et,
in Compound Pt304: R=$^i$Pr,
in Compound Pt305: R=neopentyl,
in Compound Pt306: R=$^i$Bu,
in Compound Pt307: R=$^t$Bu,
in Compound Pt308: R=Ph,
in Compound Pt309: R=4-biphenyl,
in Compound Pt310: R=2,6-($^i$Pr)$_2$Ph,
in Compound Pt311: R=2,6-($^i$Pr)$_2$-4-biphenyl,
in Compound Pt312: R=2,4-($^i$Pr)$_2$-3-dibenzofuran,
Compound Pt313 through Pt324, each represented by the formula

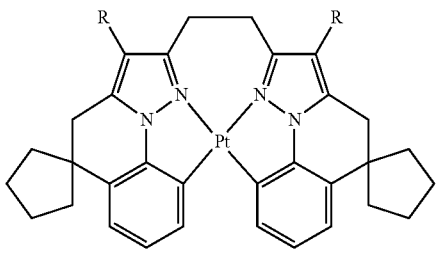

wherein in Compound Pt313: R=H,
in Compound Pt314: R=Me,
in Compound Pt315: R=Et,
in Compound Pt316: R=$^i$Pr,
in Compound Pt317: R=neopentyl,
in Compound Pt318: R=$^i$Bu,
in Compound Pt319: R=$^t$Bu,
in Compound Pt320: R=Ph,
in Compound Pt321: R=4-biphenyl,
in Compound Pt322: R=2,6-($^i$Pr)$_2$Ph,
in Compound Pt323: R=2,6-($^i$Pr)$_2$-4-biphenyl,
in Compound Pt324: R=2,4-($^i$Pr)$_2$-3-dibenzofuran, Compound Pt325 through Pt336, each represented by the formula

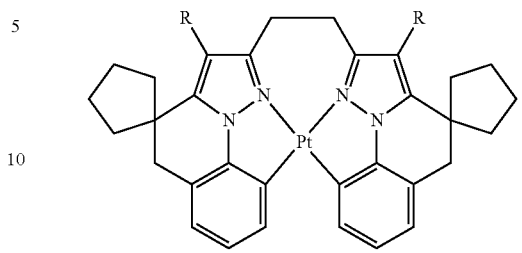

wherein in Compound Pt325: R=H,
in Compound Pt326: R=Me,
in Compound Pt327: R=Et,
in Compound Pt328: R=$^i$Pr,
in Compound Pt329: R=neopentyl,
in Compound Pt330: R=$^i$Bu,
in Compound Pt331: R=$^t$Bu,
in Compound Pt332: R=Ph,
in Compound Pt333: R=4-biphenyl,
in Compound Pt334: R=2,6-($^i$Pr)$_2$Ph,
in Compound Pt335: R=2,6-($^i$Pr)$_2$-4-biphenyl,
in Compound Pt336: R=2,4-($^i$Pr)$_2$-3-dibenzofuran,
Compound Pt337 through Pt345, each represented by the formula

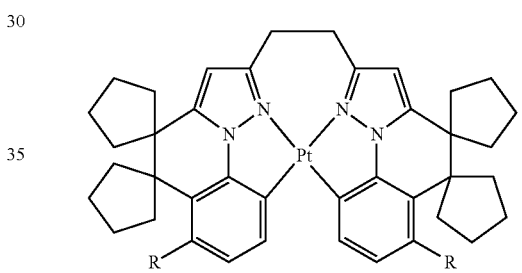

wherein in Compound Pt337: R=Me,
in Compound Pt338: R=Et,
in Compound Pt339: R=$^i$Pr,
in Compound Pt340: R=neopentyl,
in Compound Pt341: R=$^i$Bu,
in Compound Pt342: R=$^t$Bu,
in Compound Pt343: R=Ph,
in Compound Pt344: R=2,6-(Me)$_2$Ph,
in Compound Pt345: R=2,6-($^i$Pr)$_2$Ph,
Compound Pt346 through Pt354, each represented by the formula

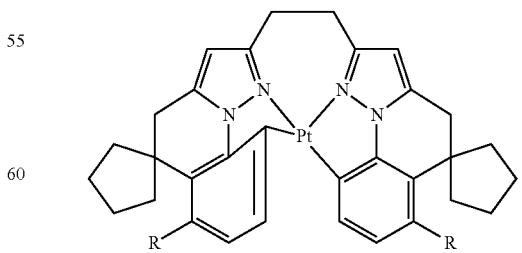

wherein in Compound Pt346: R=Me,
in Compound Pt347: R=Et,
in Compound Pt348: R=$^i$Pr, in Compound Pt349: R=neopentyl,
in Compound Pt350: R=$^i$Bu,
in Compound Pt351: R=$^t$Bu,
in Compound Pt352: R=Ph,
in Compound Pt353: R=2,6-(Me)$_2$Ph,
in Compound Pt354: R=2,6-($^i$Pr)$_2$Ph,
Compound Pt355 through Pt363, each represented by the formula

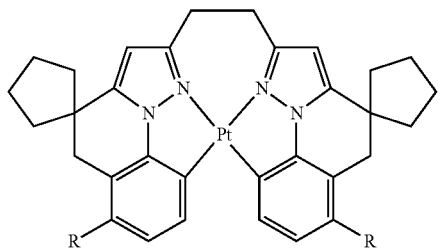

wherein in Compound Pt355: R=Me,
in Compound Pt356: R=Et,
in Compound Pt357: R=$^i$Pr,
in Compound Pt358: R=neopentyl,
in Compound Pt359: R=$^i$Bu,
in Compound Pt360: R=$^t$Bu,
in Compound Pt361: R=Ph,
in Compound Pt362: R=2,6-(Me)$_2$Ph,
in Compound Pt363: R=2,6-($^i$Pr)$_2$Ph,
Compound Pt364 through Pt372, each represented by the formula

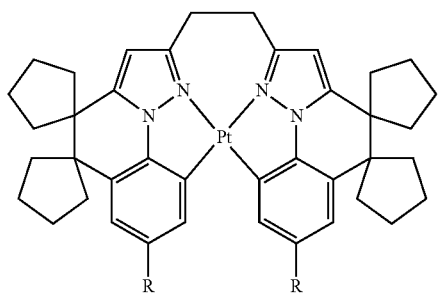

wherein in Compound Pt364: R=Me,
in Compound Pt365: R=Et,
in Compound Pt366: R=$^i$Pr,
in Compound Pt367: R=neopentyl,
in Compound Pt368: R=$^i$Bu,
in Compound Pt369: R=$^t$Bu,
in Compound Pt370: R=Ph,
in Compound Pt371: R=2,6-(Me)$_2$Ph,
in Compound Pt372: R=2,6-($^i$Pr)$_2$Ph,
Compound Pt373 through Pt381, each represented by the formula

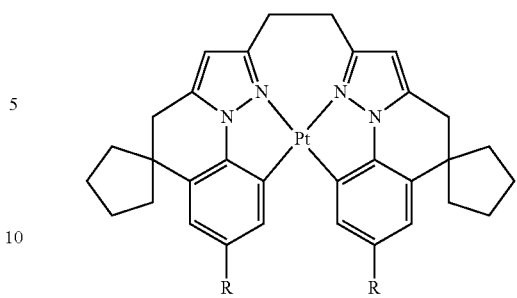

wherein in Compound Pt373: R=Me,
in Compound Pt374: R=Et,
in Compound Pt375: R=$^i$Pr,
in Compound Pt376: R=neopentyl,
in Compound Pt377: R=$^i$Bu,
in Compound Pt378: R=$^t$Bu,
in Compound Pt379: R=Ph,
in Compound Pt380: R=2,6-(Me)$_2$Ph,
in Compound Pt381: R=2,6-($^i$Pr)$_2$Ph,
Compound Pt382 through Pt390 represented by the formula

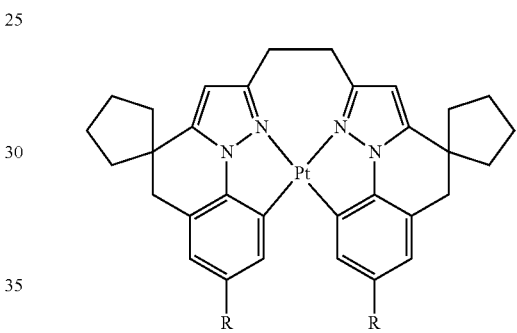

wherein in Compound Pt382: R=Me,
in Compound Pt383: R=Et,
in Compound Pt384: R=$^i$Pr,
in Compound Pt385: R=neopentyl,
in Compound Pt386: R=$^i$Bu,
in Compound Pt387: R=$^t$Bu,
in Compound Pt388: R=Ph,
in Compound Pt389: R=2,6-(Me)$_2$Ph,
in Compound Pt390: R=2,6-($^i$Pr)$_2$Ph,
Compound Pt391 through Pt402 each represented by the formula

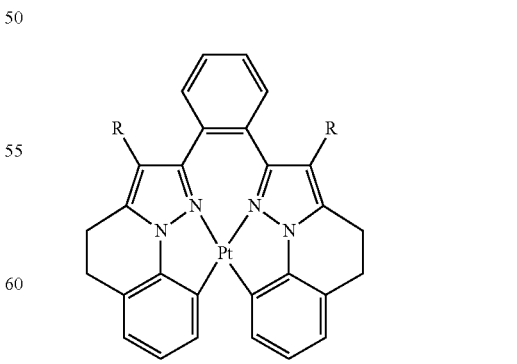

wherein in Compound Pt391: R=H,
in Compound Pt392: R=Me,
in Compound Pt393: R=Et, in Compound Pt394: R=$^i$Pr,
in Compound Pt395: R=neopentyl,
in Compound Pt396: R=$^i$Bu,
in Compound Pt397: R=$^t$Bu,
in Compound Pt398: R=Ph,
in Compound Pt399: R=4-biphenyl,
in Compound Pt400: R=2,6-($^i$Pr)$_2$Ph,
in Compound Pt401: R=2,6-($^i$Pr)$_2$-4-biphenyl,
in Compound Pt402: R=2,4-($^i$Pr)$_2$-3-dibenzofuran,
Compound Pt403 through Pt411, each represented by the formula

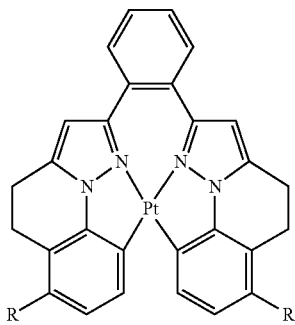

wherein in Compound Pt403: R=Me,
in Compound Pt404: R=Et,
in Compound Pt405: R=$^i$Pr,
in Compound Pt406: R=neopentyl,
in Compound Pt407: R=$^i$Bu,
in Compound Pt408: R=$^t$Bu,
in Compound Pt409: R=Ph
in Compound Pt410: R=2,6-(Me)$_2$Ph,
in Compound Pt411: R=2,6-($^i$Pr)$_2$Ph,
Compound Pt412 through Pt420, each represented by the formula

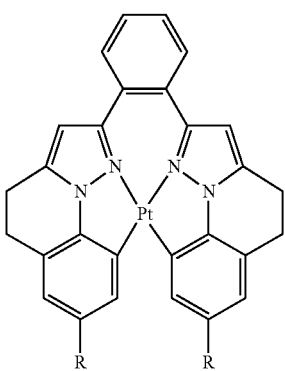

wherein in Compound Pt412: R=Me,
in Compound Pt413: R=Et,
in Compound Pt414: R=$^i$Pr,
in Compound Pt415: R=neopentyl,
in Compound Pt416: R=$^i$Bu,
in Compound Pt417: R=$^t$Bu,
in Compound Pt418: R=Ph,
in Compound Pt419: R=2,6-(Me)$_2$Ph,
in Compound Pt420: R=2,6-($^i$Pr)$_2$Ph,
Compound Pt421 through Pt432, each represented by the formula

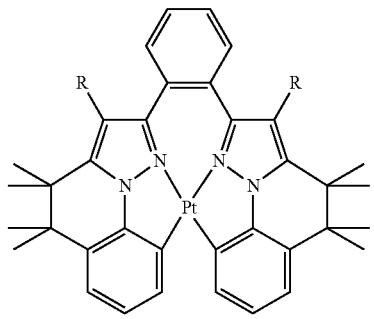

wherein in Compound Pt421: R=H,
in Compound Pt422: R=Me,
in Compound Pt423: R=Et,
in Compound Pt424: R=$^i$Pr,
in Compound Pt425: R=neopentyl,
in Compound Pt426: R=$^i$Bu,
in Compound Pt427: R=$^t$Bu,
in Compound Pt428: R=Ph,
in Compound Pt429: R=4-biphenyl,
in Compound Pt430: R=2,6-($^i$Pr)$_2$Ph,
in Compound Pt431: R=2,6-($^i$Pr)$_2$-4-biphenyl,
in Compound Pt432: R=2,4-($^i$Pr)$_2$-3-dibenzofuran,
Compound Pt433 through Pt444, each represented by the formula

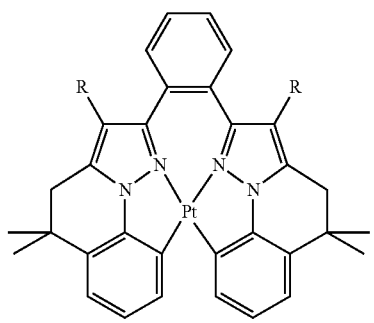

wherein in Compound Pt433: R=H,
in Compound Pt434: R=Me,
in Compound Pt435: R=Et,
in Compound Pt436: R=$^i$Pr,
in Compound Pt437: R=neopentyl,
in Compound Pt438: R=$^i$Bu,
in Compound Pt439: R=$^t$Bu,
in Compound Pt440: R=Ph,
in Compound Pt441: R=4-biphenyl,
in Compound Pt442: R=2,6-($^i$Pr)$_2$Ph,
in Compound Pt443: R=2,6-($^i$Pr)$_2$-4-biphenyl,
in Compound Pt444: R=2,4-($^i$Pr)$_2$-3-dibenzofuran,
Compound Pt445 through Pt456, each represented by the formula

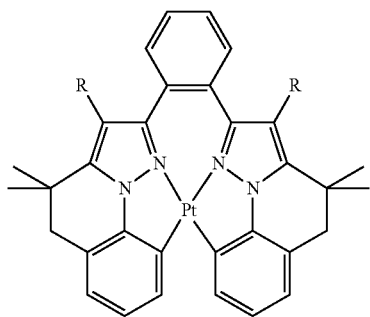

wherein in Compound Pt445: R=H,
in Compound Pt446: R=Me,
in Compound Pt447: R=Et,
in Compound Pt448: R=$^i$Pr,
in Compound Pt449: R=neopentyl,
in Compound Pt450: R=$^i$Bu,
in Compound Pt451: R=$^t$Bu,
in Compound Pt452: R=Ph,
in Compound Pt453: R=4-biphenyl,
in Compound Pt454: R=2,6-($^i$Pr)$_2$Ph,
in Compound Pt455: R=2,6-($^i$Pr)$_2$-4-biphenyl,
in Compound Pt456: R=2,4-($^i$Pr)$_2$-3-dibenzofuran,
Compound Pt457 through Pt465, each represented by the formula

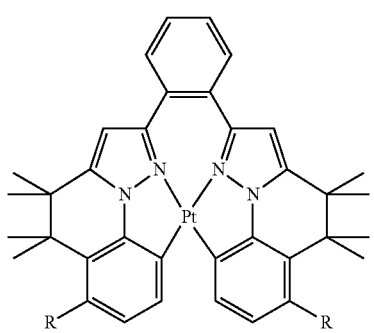

wherein in Compound Pt457: R=Me,
in Compound Pt458: R=Et,
in Compound Pt459: R=$^i$Pr,
in Compound Pt460: R=neopentyl,
in Compound Pt461: R=$^i$Bu,
in Compound Pt462: R=$^t$Bu,
in Compound Pt463: R=Ph,
in Compound Pt464: R=2,6-(Me)$_2$Ph,
in Compound Pt465: R=2,6-($^i$Pr)$_2$Ph,
Compound Pt466 through Pt474, each represented by the formula

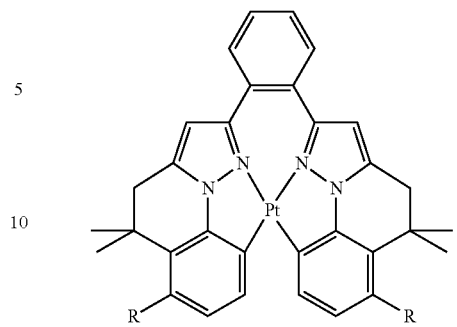

wherein in Compound Pt466: R=Me,
in Compound Pt467: R=Et,
in Compound Pt468: R=$^i$Pr,
in Compound Pt469: R=neopentyl,
in Compound Pt470: R=$^i$Bu,
in Compound Pt471: R=$^t$Bu,
in Compound Pt472: R=Ph,
in Compound Pt473: R=2,6-(Me)$_2$Ph,
in Compound Pt474: R=2,6-($^i$Pr)$_2$Ph,
Compound Pt475 through Pt483, each represented by the formula

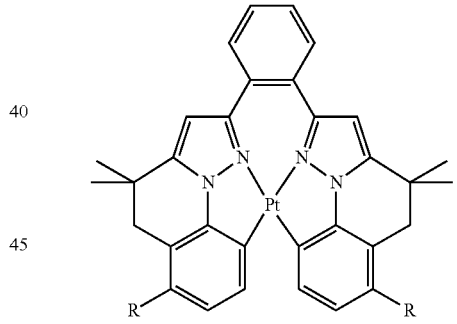

wherein in Compound Pt475: R=Me,
in Compound Pt476: R=Et,
in Compound Pt477: R=$^i$Pr,
in Compound Pt478: R=neopentyl,
in Compound Pt479: R=$^i$Bu,
in Compound Pt480: R=$^t$Bu,
in Compound Pt481: R=Ph,
in Compound Pt482: R=2,6-(Me)$_2$Ph,
in Compound Pt483: R=2,6-($^i$Pr)$_2$Ph,
Compound Pt484 through Pt492, each represented by the formula

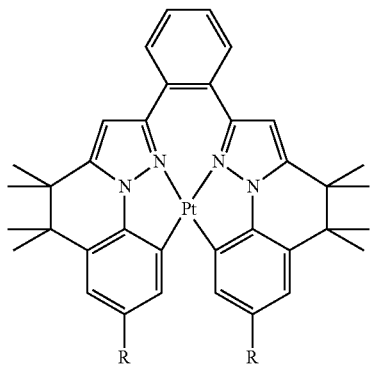

wherein in Compound Pt484: R=Me,
in Compound Pt485: R=Et,
in Compound Pt486: R=$^i$Pr,
in Compound Pt487: R=neopentyl,
in Compound Pt488: R=$^i$Bu,
in Compound Pt489: R=$^t$Bu,
in Compound Pt490: R=Ph,
in Compound Pt491: R=2,6-(Me)$_2$Ph,
in Compound Pt492: R=2,6-($^i$Pr)$_2$Ph,
Compound Pt493 through Pt501, each represented by the formula

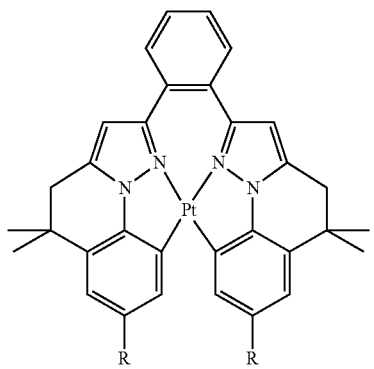

wherein in Compound Pt493: R=Me,
in Compound Pt494: R=Et,
in Compound Pt495: R=$^i$Pr,
in Compound Pt496: R=neopentyl,
in Compound Pt497: R=$^i$Bu,
in Compound Pt498: R=$^t$Bu,
in Compound Pt499: R=Ph,
in Compound Pt500: R=2,6-(Me)$_2$Ph,
in Compound Pt501: R=2,6-($^i$Pr)$_2$Ph,
Compound Pt502 through Pt510, each represented by the formula

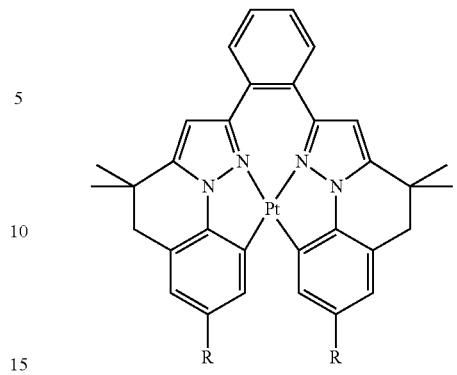

wherein in Compound Pt502: R=Me,
in Compound Pt503: R=Et,
in Compound Pt504: R=$^i$Pr,
in Compound Pt505: R=neopentyl,
in Compound Pt506: R=$^i$Bu,
in Compound Pt507: R=$^t$Bu,
in Compound Pt508: R=Ph,
in Compound Pt509: R=2,6-(Me)$_2$Ph,
in Compound Pt510: R=2,6-($^i$Pr)$_2$Ph,
Compound Pt511 through Pt522, each represented by the formula

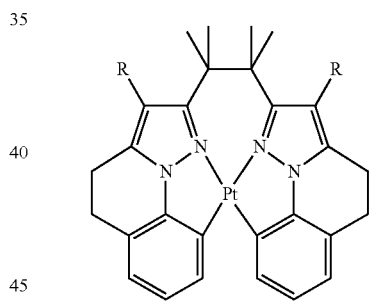

wherein in Compound Pt511: R=H,
in Compound Pt512: R=Me,
in Compound Pt513: R=Et,
in Compound Pt514: R=$^i$Pr,
in Compound Pt515: R=neopentyl,
in Compound Pt516: R=$^i$Bu,
in Compound Pt517: R=$^t$Bu,
in Compound Pt518: R=Ph,
in Compound Pt519: R=4-biphenyl,
in Compound Pt520: R=2,6-($^i$Pr)$_2$Ph,
in Compound Pt521: R=2,6-($^i$Pr)$_2$-4-biphenyl,
in Compound Pt522: R=2,4-($^i$Pr)$_2$-3-dibenzofuran,
Compound Pt523 through Pt531, each represented by the formula

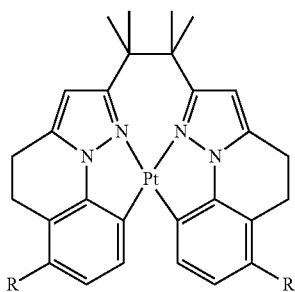

wherein in Compound Pt523: R=Me,
in Compound Pt524: R=Et,
in Compound Pt525: R=$^i$Pr,
in Compound Pt526: R=neopentyl,
in Compound Pt527: R=$^i$Bu,
in Compound Pt528: R=$^t$Bu,
in Compound Pt529: R=Ph,
in Compound Pt530: R=2,6-(Me)$_2$Ph,
in Compound Pt531: R=2,6-($^i$Pr)$_2$Ph,
Compound Pt532 through Pt540, each represented by the formula

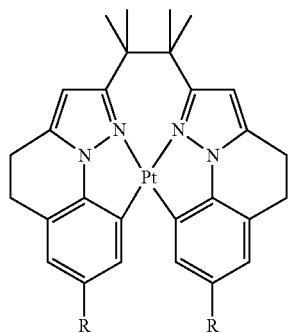

wherein in Compound Pt532: R=Me,
in Compound Pt533: R=Et,
in Compound Pt534: R=$^i$Pr,
in Compound Pt535: R=neopentyl,
in Compound Pt536: R=$^i$Bu,
in Compound Pt537: R=$^t$Bu,
in Compound Pt538: R=Ph,
in Compound Pt539: R=2,6-(Me)$_2$Ph,
in Compound Pt540: R=2,6-($^i$Pr)$_2$Ph,
Compound Pt541 through Pt552, each represented by the formula

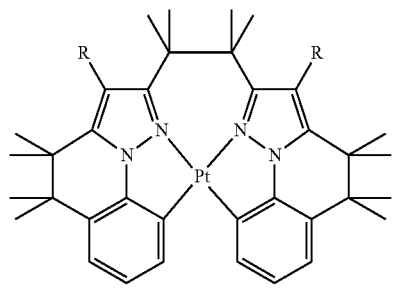

wherein in Compound Pt541: R=H,
in Compound Pt542: R=Me,
in Compound Pt543: R=Et,
in Compound Pt544: R=$^i$Pr,
in Compound Pt545: R=neopentyl,
in Compound Pt546: R=$^i$Bu,
in Compound Pt547: R=$^t$Bu,
in Compound Pt548: R=Ph,
in Compound Pt549: R=4-biphenyl,
in Compound Pt550: R=2,6-($^i$Pr)$_2$Ph,
in Compound Pt551: R=2,6-($^i$Pr)$_2$-4-biphenyl,
in Compound Pt552: R=2,4-($^i$Pr)$_2$-3-dibenzofuran,
Compound Pt553 through Pt564, each represented by the formula

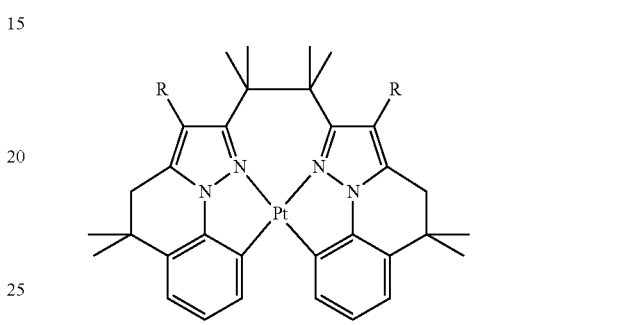

wherein in Compound Pt553: R=H,
in Compound Pt554: R=Me,
in Compound Pt555: R=Et,
in Compound Pt556: R=$^i$Pr,
in Compound Pt557: R=neopentyl,
in Compound Pt558: R=$^i$Bu,
in Compound Pt559: R=$^t$Bu,
in Compound Pt560: R=Ph,
in Compound Pt561: R=4-biphenyl,
in Compound Pt562: R=2,6-($^i$Pr)$_2$Ph,
in Compound Pt563: R=2,6-($^i$Pr)$_2$-4-biphenyl,
in Compound Pt564: R=2,4-($^i$Pr)$_2$-3-dibenzofuran,
Compound Pt565 through Pt576, each represented by the formula

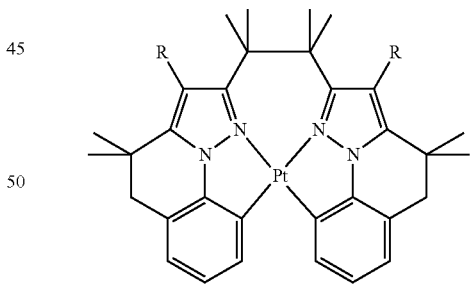

wherein in Compound Pt565: R=H,
in Compound Pt566: R=Me,
in Compound Pt567: R=Et,
in Compound Pt568: R=$^i$Pr,
in Compound Pt569: R=neopentyl,
in Compound Pt570: R=$^i$Bu,
in Compound Pt571: R=$^t$Bu,
in Compound Pt572: R=Ph,
in Compound Pt573: R=4-biphenyl,
in Compound Pt574: R=2,6-($^i$Pr)$_2$Ph,
in Compound Pt575: R=2,6-($^i$Pr)$_2$-4-biphenyl,
in Compound Pt576: R=2,4-($^i$Pr)$_2$-3-dibenzofuran, Compound Pt577 through Pt585, each represented by the formula

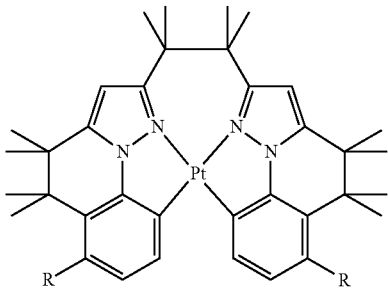

wherein in Compound Pt577: R=Me,
in Compound Pt578: R=Et,
in Compound Pt579: R=$^i$Pr,
in Compound Pt580: R=neopentyl,
in Compound Pt581: R=$^i$Bu,
in Compound Pt582: R=$^t$Bu,
in Compound Pt583: R=Ph,
in Compound Pt584: R=2,6-(Me)$_2$Ph,
in Compound Pt585: R=2,6-($^i$Pr)$_2$Ph,
Compound Pt586 through Pt594, each represented by the formula

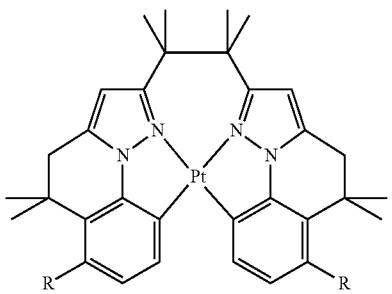

wherein in Compound Pt586: R=Me,
in Compound Pt587: R=Et,
in Compound Pt588: R=$^i$Pr,
in Compound Pt589: R=neopentyl,
in Compound Pt590: R=$^i$Bu,
in Compound Pt591: R=$^t$Bu,
in Compound Pt592: R=Ph,
in Compound Pt593: R=2,6-(Me)$_2$Ph,
in Compound Pt594: R=2,6-($^i$Pr)$_2$Ph,
Compound Pt595 through Pt603, each represented by the formula

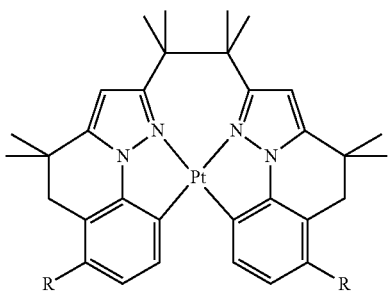

wherein in Compound Pt595: R=Me,
in Compound Pt596: R=Et,
in Compound Pt597: R=$^i$Pr,
in Compound Pt598: R=neopentyl,
in Compound Pt599: R=$^i$Bu,
in Compound Pt600: R=$^t$Bu,
in Compound Pt601: R=Ph,
in Compound Pt602: R=2,6-(Me)$_2$Ph,
in Compound Pt603: R=2,6-($^i$Pr)$_2$Ph,
Compound Pt604 through Pt612, each represented by the formula


wherein in Compound Pt604: R=Me,
in Compound Pt605: R=Et,
in Compound Pt606: R=$^i$Pr,
in Compound Pt607: R=neopentyl,
in Compound Pt608: R=$^i$Bu,
in Compound Pt609: R=$^t$Bu,
in Compound Pt610: R=Ph,
in Compound Pt611: R=2,6-(Me)$_2$Ph,
in Compound Pt612: R=2,6-($^i$Pr)$_2$Ph,
Compound Pt613 through Pt621, each represented by the formula

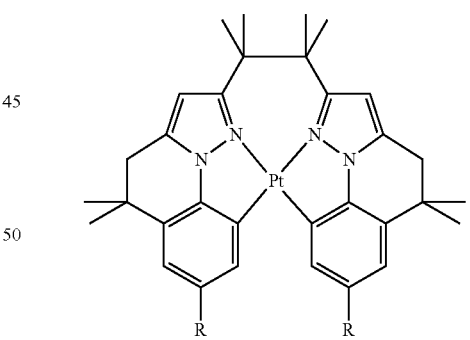

wherein in Compound Pt613: R=Me,
in Compound Pt614: R=Et,
in Compound Pt615: R=$^i$Pr,
in Compound Pt616: R=neopentyl,
in Compound Pt617: R=$^i$Bu,
in Compound Pt618: R=$^t$Bu,
in Compound Pt619: R=Ph,
in Compound Pt620: R=2,6-(Me)$_2$Ph,
in Compound Pt621: R=2,6-($^i$Pr)$_2$Ph,
Compound Pt622 through Pt630, each represented by the formula

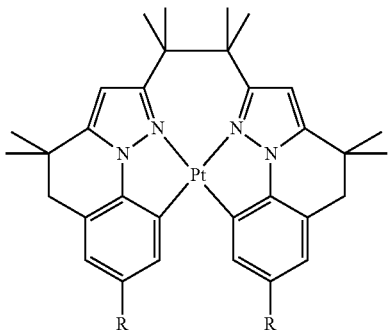

wherein in Compound Pt622: R=Me,
in Compound Pt623: R=Et,
in Compound Pt624: R=$^i$Pr,
in Compound Pt625: R=neopentyl,
in Compound Pt626: R=$^i$Bu,
in Compound Pt627: R=$^t$Bu,
in Compound Pt628: R=Ph,
in Compound Pt629: R=2,6-(Me)$_2$Ph,
in Compound Pt630: R=2,6-($^i$Pr)$_2$Ph,
Compound Pt631 through Pt645, each represented by the formula

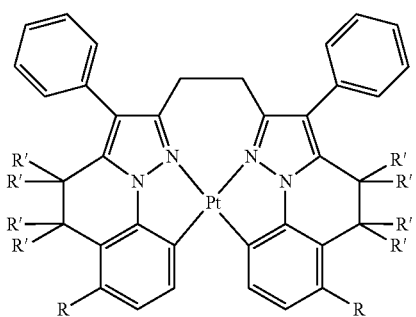

wherein in Compound Pt631: R'=H, R=Me,
in Compound Pt632: R'=H, R=Et,
in Compound Pt633: R'=H, R=$^i$Pr,
in Compound Pt634: R'=H, R=Ph,
in Compound Pt635: R'=H, R=2,6-($^i$Pr)$_2$Ph,
in Compound Pt636: R'=Me, R=Me,
in Compound Pt637: R'=Me, R=Et,
in Compound Pt638: R'=Me, R=$^i$Pr,
in Compound Pt639: R'=Me, R=Ph,
in Compound Pt640: R'=Me, R=2,6-($^i$Pr)$_2$Ph,
in Compound Pt641: R'=Ph, R=Me,
in Compound Pt642: R'=Ph, R=Et,
in Compound Pt643: R'=Ph, R=$^i$Pr,
in Compound Pt644: R'=Ph, R=Ph,
in Compound Pt645: R'=Ph, R=2,6-($^i$Pr)$_2$Ph,
Compound Pt646 through Pt660, each represented by the formula

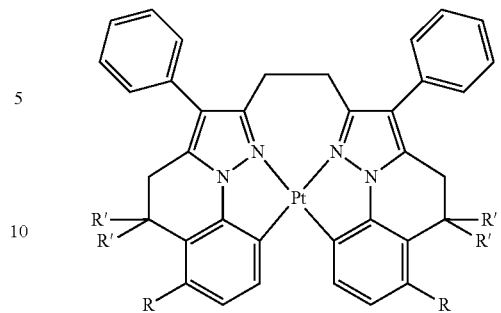

wherein in Compound Pt646: R'=H, R=Me,
in Compound Pt647: R'=H, R=Et,
in Compound Pt648: R'=H, R=$^i$Pr,
in Compound Pt649: R'=H, R=Ph,
in Compound Pt650: R'=H, R=2,6-($^i$Pr)$_2$Ph,
in Compound Pt651: R'=Me, R=Me,
in Compound Pt652: R'=Me, R=Et,
in Compound Pt653: R'=Me, R=$^i$Pr,
in Compound Pt654: R'=Me, R=Ph,
in Compound Pt655: R'=Me, R=2,6-($^i$Pr)$_2$Ph,
in Compound Pt656: R'=Ph, R=Me,
in Compound Pt657: R'=Ph, R=Et,
in Compound Pt658: R'=Ph, R=$^i$Pr,
in Compound Pt659: R'=Ph, R=Ph,
in Compound Pt660: R'=Ph, R=2,6-($^i$Pr)$_2$Ph,
Compound Pt661 through Pt675, each represented by the formula

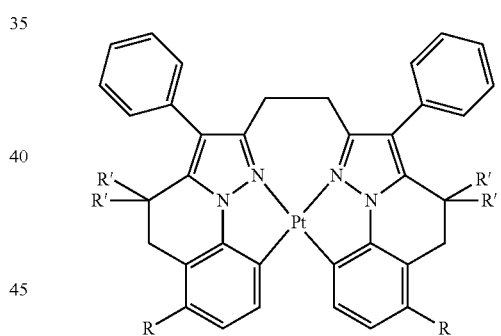

wherein in Compound Pt661: R'=H, R=Me,
in Compound Pt662: R'=H, R=Et,
in Compound Pt663: R'=H, R=$^i$Pr,
in Compound Pt664: R'=H, R=Ph,
in Compound Pt665: R'=H, R=2,6-($^i$Pr)$_2$Ph,
in Compound Pt666: R'=Me, R=Me,
in Compound Pt667: R'=Me, R=Et,
in Compound Pt668: R'=Me, R=$^i$Pr,
in Compound Pt669: R'=Me, R=Ph,
in Compound Pt670: R'=Me, R=2,6-($^i$Pr)$_2$Ph,
in Compound Pt671: R'=Ph, R=Me,
in Compound Pt672: R'=Ph, R=Et,
in Compound Pt673: R'=Ph, R=$^i$Pr,
in Compound Pt674: R'=Ph, R=Ph,
in Compound Pt675: R'=Ph, R=2,6-($^i$Pr)$_2$Ph,
Compound Pt676 through Pt690, each represented by the formula

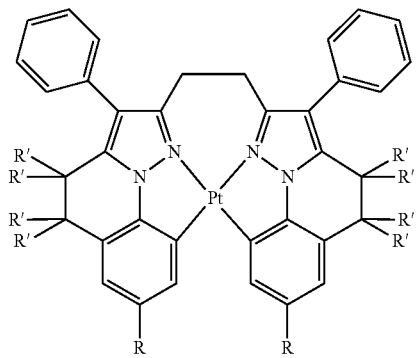

wherein in Compound Pt676: R'=H, R=Me,
in Compound Pt677: R'=H, R=Et,
in Compound Pt678: R'=H, R=$^i$Pr,
in Compound Pt679: R'=H, R=Ph,
in Compound Pt680: R'=H, R=2,6-($^i$Pr)$_2$Ph,
in Compound Pt681: R'=Me, R=Me,
in Compound Pt682: R'=Me, R=Et,
in Compound Pt683: R'=Me, R=$^i$Pr,
in Compound Pt684: R'=Me, R=Ph,
in Compound Pt685: R'=Me, R=2,6-($^i$Pr)$_2$Ph,
in Compound Pt686: R'=Ph, R=Me,
in Compound Pt687: R'=Ph, R=Et,
in Compound Pt688: R'=Ph, R=$^i$Pr,
in Compound Pt689: R'=Ph, R=Ph,
in Compound Pt690: R'=Ph, R=2,6-($^i$Pr)$_2$Ph,
Compound Pt691 through Pt705, each represented by the formula

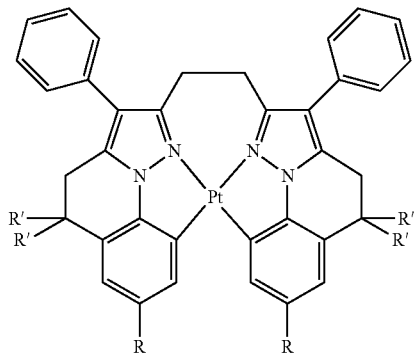

wherein in Compound Pt691: R'=H, R=Me,
in Compound Pt692: R'=H, R=Et,
in Compound Pt693: R'=H, R=$^i$Pr,
in Compound Pt694: R'=H, R=Ph,
in Compound Pt695: R'=H, R=2,6-($^i$Pr)$_2$Ph,
in Compound Pt696: R'=Me, R=Me,
in Compound Pt697: R'=Me, R=Et,
in Compound Pt698: R'=Me, R=$^i$Pr,
in Compound Pt699: R'=Me, R=Ph,
in Compound Pt700: R'=Me, R=2,6-($^i$Pr)$_2$Ph,
in Compound Pt701: R'=Ph, R=Me,
in Compound Pt702: R'=Ph, R=Et,
in Compound Pt703: R'=Ph, R=$^i$Pr,
in Compound Pt704: R'=Ph, R=Ph,
in Compound Pt705: R'=Ph, R=2,6-($^i$Pr)$_2$Ph,
Compound Pt706 through Pt720, each represented by the formula

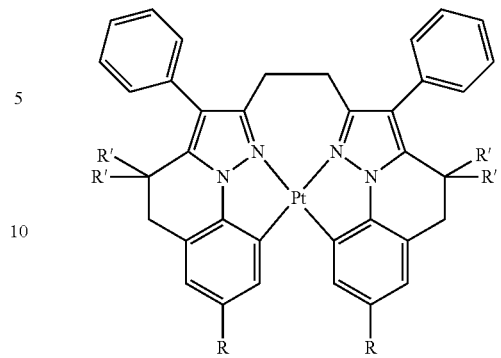

wherein in Compound Pt706: R'=H, R=Me,
in Compound Pt707: R'=H, R=Et,
in Compound Pt708: R'=H, R=$^i$Pr,
in Compound Pt709: R'=H, R=Ph,
in Compound Pt710: R'=H, R=2,6-($^i$Pr)$_2$Ph,
in Compound Pt711: R'=Me, R=Me,
in Compound Pt712: R'=Me, R=Et,
in Compound Pt713: R'=Me, R=$^i$Pr,
in Compound Pt714: R'=Me, R=Ph,
in Compound Pt715: R'=Me, R=2,6-($^i$Pr)$_2$Ph,
in Compound Pt716: R'=Ph, R=Me,
in Compound Pt717: R'=Ph, R=Et,
in Compound Pt718: R'=Ph, R=$^i$Pr,
in Compound Pt719: R'=Ph, R=Ph,
in Compound Pt720: R'=Ph, R=2,6-($^i$Pr)$_2$Ph,
Compound Pt721 through Pt735, each represented by the formula

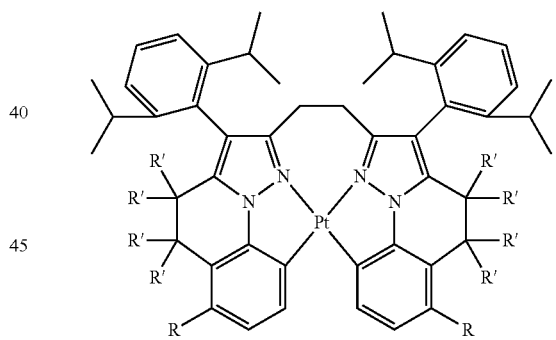

wherein in Compound Pt721: R'=H, R=Me,
in Compound Pt722: R'=H, R=Et,
in Compound Pt723: R'=H, R=$^i$Pr,
in Compound Pt724: R'=H, R=Ph,
in Compound Pt725: R'=H, R=2,6-($^i$Pr)$_2$Ph,
in Compound Pt726: R'=Me, R=Me,
in Compound Pt727: R'=Me, R=Et,
in Compound Pt728: R'=Me, R=$^i$Pr,
in Compound Pt729: R'=Me, R=Ph,
in Compound Pt730: R'=Me, R=2,6-($^i$Pr)$_2$Ph,
in Compound Pt731: R'=Ph, R=Me,
in Compound Pt732: R'=Ph, R=Et,
in Compound Pt733: R'=Ph, R=$^i$Pr,
in Compound Pt734: R'=Ph, R=Ph,
in Compound Pt735: R'=Ph, R=2,6-($^i$Pr)$_2$Ph,
Compound Pt736 through Pt750, each represented by the formula

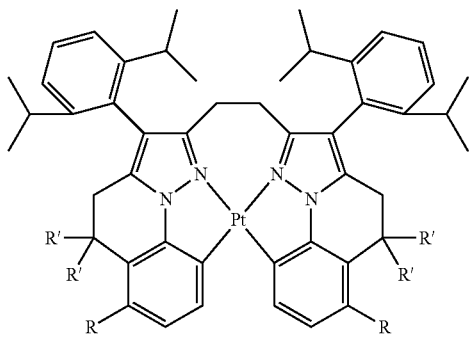

wherein in Compound Pt736: R'=H, R=Me,
in Compound Pt737: R'=H, R=Et,
in Compound Pt738: R'=H, R=$^i$Pr,
in Compound Pt739: R'=H, R=Ph,
in Compound Pt740: R'=H, R=2,6-($^i$Pr)$_2$Ph,
in Compound Pt741: R'=Me, R=Me,
in Compound Pt742: R'=Me, R=Et,
in Compound Pt743: R'=Me, R=$^i$Pr,
in Compound Pt744: R'=Me, R=Ph,
in Compound Pt745: R'=Me, R=2,6-($^i$Pr)$_2$Ph,
in Compound Pt746: R'=Ph, R=Me,
in Compound Pt747: R'=Ph, R=Et,
in Compound Pt748: R'=Ph, R=$^i$Pr,
in Compound Pt749: R'=Ph, R=Ph,
in Compound Pt750: R'=Ph, R=2,6-($^i$Pr)$_2$Ph,
Compound Pt751 through Pt765, each represented by the formula

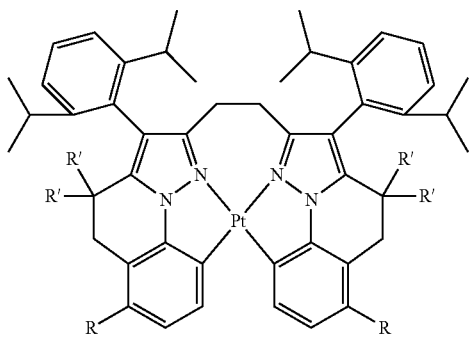

wherein in Compound Pt751: R'=H, R=Me,
in Compound Pt752: R'=H, R=Et,
in Compound Pt753: R'=H, R=$^i$Pr,
in Compound Pt754: R'=H, R=Ph,
in Compound Pt755: R'=H, R=2,6-($^i$Pr)$_2$Ph,
in Compound Pt756: R'=Me, R=Me,
in Compound Pt757: R'=Me, R=Et,
in Compound Pt758: R'=Me, R=$^i$Pr,
in Compound Pt759: R'=Me, R=Ph,
in Compound Pt760: R'=Me, R=2,6-($^i$Pr)$_2$Ph,
in Compound Pt761: R'=Ph, R=Me,
in Compound Pt762: R'=Ph, R=Et,
in Compound Pt763: R'=Ph, R=$^i$Pr,
in Compound Pt764: R'=Ph, R=Ph,
in Compound Pt765: R'=Ph, R=2,6-($^i$Pr)$_2$Ph,
Compound Pt766 through Pt780, each represented by the formula

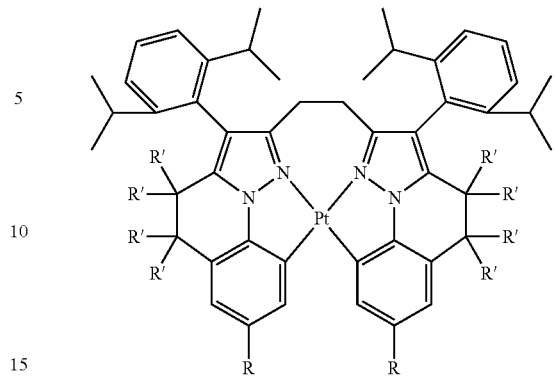

wherein in Compound Pt766: R'=H, R=Me,
in Compound Pt767: R'=H, R=Et,
in Compound Pt768: R'=H, R=$^i$Pr,
in Compound Pt769: R'=H, R=Ph,
in Compound Pt770: R'=H, R=2,6-($^i$Pr)$_2$Ph,
in Compound Pt771: R'=Me, R=Me,
in Compound Pt772: R'=Me, R=Et,
in Compound Pt773: R'=Me, R=$^i$Pr,
in Compound Pt774: R'=Me, R=Ph,
in Compound Pt775: R'=Me, R=2,6-($^i$Pr)$_2$Ph,
in Compound Pt776: R'=Ph, R=Me,
in Compound Pt777: R'=Ph, R=Et,
in Compound Pt778: R'=Ph, R=$^i$Pr,
in Compound Pt779: R'=Ph, R=Ph,
in Compound Pt780: R'=Ph, R=2,6-($^i$Pr)$_2$Ph,
Compound Pt781 through Pt795, each represented by the formula

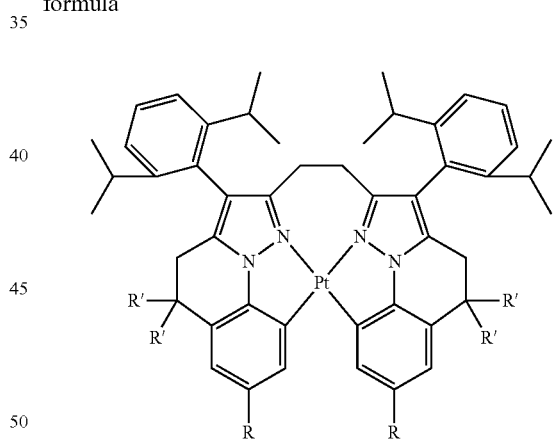

wherein in Compound Pt781: R'=H, R=Me,
in Compound Pt782: R'=H, R=Et,
in Compound Pt783: R'=H, R=$^i$Pr,
in Compound Pt784: R'=H, R=Ph,
in Compound Pt785: R'=H, R=2,6-($^i$Pr)$_2$Ph,
in Compound Pt786: R'=Me, R=Me,
in Compound Pt787: R'=Me, R=Et,
in Compound Pt788: R'=Me, R=$^i$Pr,
in Compound Pt789: R'=Me, R=Ph,
in Compound Pt790: R'=Me, R=2,6-($^i$Pr)$_2$Ph,
in Compound Pt791: R'=Ph, R=Me,
in Compound Pt792: R'=Ph, R=Et,
in Compound Pt793: R'=Ph, R=$^i$Pr,
in Compound Pt794: R'=Ph, R=Ph,
in Compound Pt795: R'=Ph, R=2,6-($^i$Pr)$_2$Ph, Compound Pt796 through Pt810, each represented by the formula

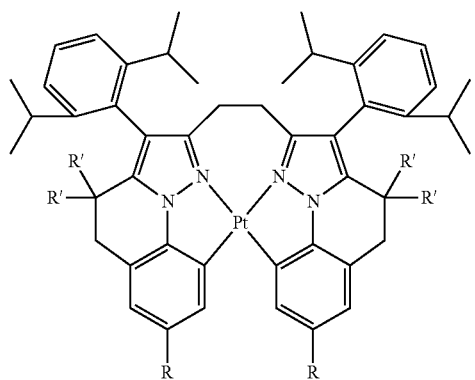

wherein in Compound Pt796: R'=H, R=Me,
in Compound Pt797: R'=H, R'=Et,
in Compound Pt798: R'=H, R=$^i$Pr,
in Compound Pt799: R'=H, R=Ph,
in Compound Pt800: R'=H, R=2,6-($^i$Pr)$_2$Ph,
in Compound Pt801: R'=Me, R=Me,
in Compound Pt802: R'=Me, R=Et,
in Compound Pt803: R'=Me, R=$^i$Pr,
in Compound Pt804: R'=Me, R=Ph,
in Compound Pt805: R'=Me, R=2,6-($^i$Pr)$_2$Ph,
in Compound Pt806: R'=Ph, R=Me,
in Compound Pt807: R'=Ph, R=Et,
in Compound Pt808: R'=Ph, R=$^i$Pr,
in Compound Pt809: R'=Ph, R=Ph,
in Compound Pt810: R'=Ph, R=2,6-($^i$Pr)$_2$Ph, Compound Pt811 through Pt825, each represented by the formula

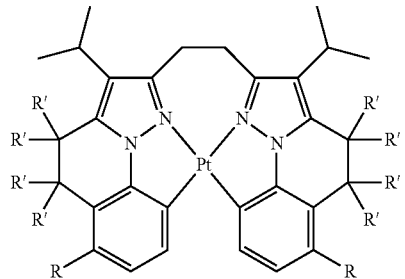

wherein in Compound Pt811: R'=H, R=Me,
in Compound Pt812: R'=H, R=Et,
in Compound Pt813: R'=H, R=$^i$Pr,
in Compound Pt814: R'=H, R=Ph,
in Compound Pt815: R'=H, R=2,6-($^i$Pr)$_2$Ph,
in Compound Pt816: R'=Me, R=Me,
in Compound Pt817: R'=Me, R=Et,
in Compound Pt818: R'=Me, R=$^i$Pr,
in Compound Pt819: R'=Me, R=Ph,
in Compound Pt820: R'=Me, R=2,6-($^i$Pr)$_2$Ph,
in Compound Pt821: R'=Ph, R=Me,
in Compound Pt822: R'=Ph, R=Et,
in Compound Pt823: R'=Ph, R=$^i$Pr,
in Compound Pt824: R'=Ph, R=Ph,
in Compound Pt825: R'=Ph, R=2,6-($^i$Pr)$_2$Ph, Compound Pt826 through Pt840, each represented by the formula

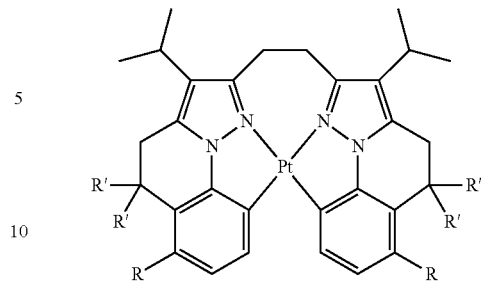

wherein in Compound Pt826: R'=H, R=Me,
in Compound Pt827: R'=H, R=Et,
in Compound Pt828: R'=H, R=$^i$Pr,
in Compound Pt829: R'=H, R=Ph,
in Compound Pt830: R'=H, R=2,6-($^i$Pr)$_2$Ph,
in Compound Pt831: R'=Me, R=Me,
in Compound Pt832: R'=Me, R=Et,
in Compound Pt833: R'=Me, R=$^i$Pr,
in Compound Pt834: R'=Me, R=Ph,
in Compound Pt835: R'=Me, R=2,6-($^i$Pr)$_2$Ph,
in Compound Pt836: R'=Ph, R=Me,
in Compound Pt837: R'=Ph, R=Et,
in Compound Pt838: R'=Ph, R=$^i$Pr,
in Compound Pt839: R'=Ph, R=Ph,
in Compound Pt840: R'=Ph, R=2,6-($^i$Pr)$_2$Ph, Compound Pt841 through Pt855, each represented by the formula

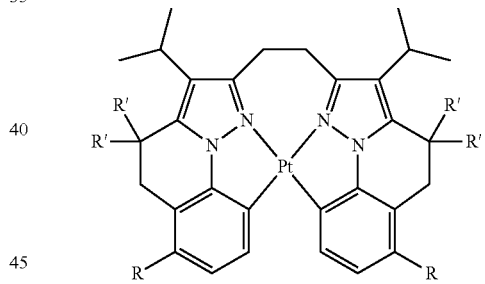

wherein in Compound Pt841: R'=H, R=Me,
in Compound Pt842: R'=H, R=Et,
in Compound Pt843: R'=H, R=$^i$Pr,
in Compound Pt844: R'=H, R=Ph,
in Compound Pt845: R'=H, R=2,6-($^i$Pr)$_2$Ph,
in Compound Pt846: R'=Me, R=Me,
in Compound Pt847: R'=Me, R=Et,
in Compound Pt848: R'=Me, R=$^i$Pr,
in Compound Pt849: R'=Me, R=Ph,
in Compound Pt850: R'=Me, R=2,6-($^i$Pr)$_2$Ph,
in Compound Pt851: R'=Ph, R=Me,
in Compound Pt852: R'=Ph, R=Et,
in Compound Pt853: R'=Ph, R=$^i$Pr,
in Compound Pt854: R'=Ph, R=Ph,
in Compound Pt855: R'=Ph, R=2,6-($^i$Pr)$_2$Ph, Compound Pt856 through Pt870, each represented by the formula

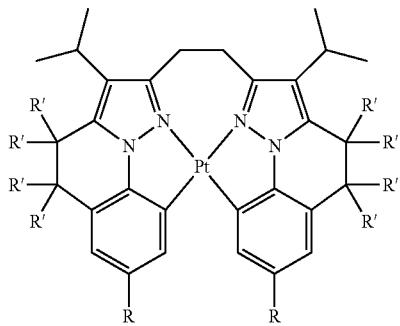

wherein in Compound Pt856: R'=H, R=Me,
in Compound Pt857: R'=H, R=Et,
in Compound Pt858: R'=H, R=$^i$Pr,
in Compound Pt859: R'=H, R=Ph,
in Compound Pt860: R'=H, R=2,6-($^i$Pr)$_2$Ph,
in Compound Pt861: R'=Me, R=Me,
in Compound Pt862: R'=Me, R=Et,
in Compound Pt863: R'=Me, R=$^i$Pr,
in Compound Pt864: R'=Me, R=Ph,
in Compound Pt865: R'=Me, R=2,6-($^i$Pr)$_2$Ph,
in Compound Pt866: R'=Ph, R=Me,
in Compound Pt867: R'=Ph, R=Et,
in Compound Pt868: R'=Ph, R=$^i$Pr,
in Compound Pt869: R'=Ph, R=Ph,
in Compound Pt870: R'=Ph, R=2,6-($^i$Pr)$_2$Ph,
Compound Pt871 through Pt885, each represented by the formula

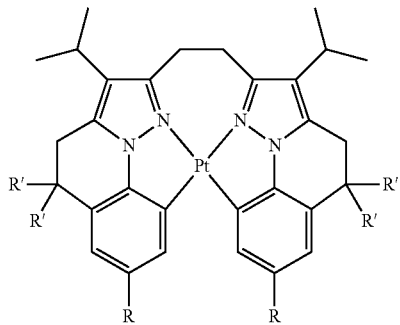

wherein in Compound Pt871: R'=H, R=Me,
in Compound Pt872: R'=H, R=Et,
in Compound Pt873: R'=H, R=$^i$Pr,
in Compound Pt874: R'=H, R=Ph,
in Compound Pt875: R'=H, R=2,6-($^i$Pr)$_2$Ph,
in Compound Pt876: R'=Me, R=Me,
in Compound Pt877: R'=Me, R=Et,
in Compound Pt878: R'=Me, R=$^i$Pr,
in Compound Pt879: R'=Me, R=Ph,
in Compound Pt880: R'=Me, R=2,6-($^i$Pr)$_2$Ph,
in Compound Pt881: R'=Ph, R=Me,
in Compound Pt882: R'=Ph, R=Et,
in Compound Pt883: R'=Ph, R=$^i$Pr,
in Compound Pt884: R'=Ph, R=Ph,
in Compound Pt885: R'=Ph, R=2,6-($^i$Pr)$_2$Ph,
Compound Pt886 through Pt900, each represented by the formula

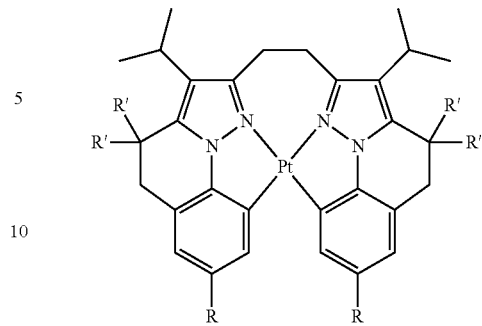

wherein in Compound Pt886: R'=H, R=Me,
in Compound Pt887: R'=H, R=Et,
in Compound Pt888: R'=H, R=$^i$Pr,
in Compound Pt889: R'=H, R=Ph,
in Compound Pt890: R'=H, R=2,6-($^i$Pr)$_2$Ph,
in Compound Pt891: R'=Me, R=Me,
in Compound Pt892: R'=Me, R=Et,
in Compound Pt893: R'=Me, R=$^i$Pr,
in Compound Pt894: R'=Me, R=Ph,
in Compound Pt895: R'=Me, R=2,6-($^i$Pr)$_2$Ph,
in Compound Pt896: R'=Ph, R=Me,
in Compound Pt897: R'=Ph, R=Et,
in Compound Pt898: R'=Ph, R=$^i$Pr,
in Compound Pt899: R'=Ph, R=Ph,
in Compound Pt900: R'=Ph, R=2,6-($^i$Pr)$_2$Ph,
Compound Pt901 through Pt912, each represented by the formula

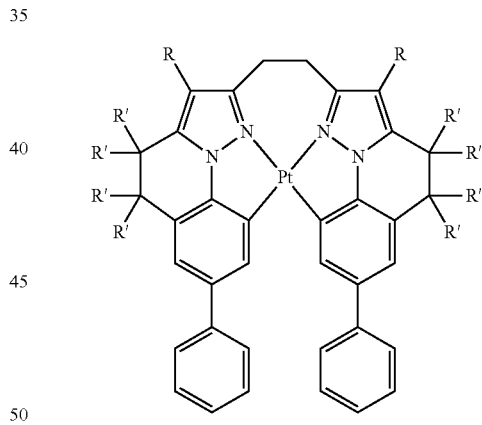

wherein in Compound Pt901: R'=H, R=Me,
in Compound Pt902: R'=H, R=Et,
in Compound Pt903: R'=H, R=2,6-($^i$Pr)$_2$-4-biphenyl,
in Compound Pt904: R'=H, R=2,4-($^i$Pr)$_2$-3-dibenzofuran,
in Compound Pt905: R'=Me, R=Me,
in Compound Pt906: R'=Me, R=Et,
in Compound Pt907: R'=Me, R=2,6-($^i$Pr)$_2$-4-biphenyl,
in Compound Pt908: R'=Me, R=2,4-($^i$Pr)$_2$-3-dibenzofuran,
in Compound Pt909: R'=Ph, R=Me,
in Compound Pt910: R'=Ph, R=Et,
in Compound Pt911: R'=Ph, R=2,6-($^i$Pr)$_2$-4-biphenyl,
in Compound Pt912: R'=Ph, R=2,4-($^i$Pr)$_2$-3-dibenzofuran,
Compound Pt913 through Pt924, each represented by the formula


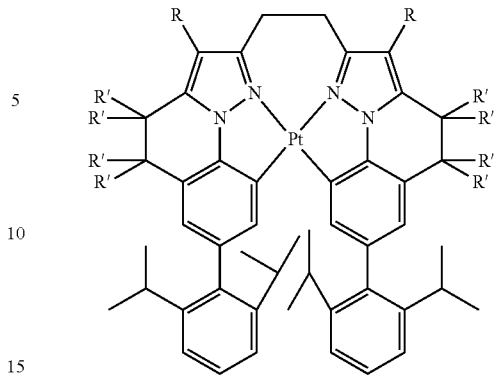

wherein in Compound Pt913: R'=H, R=Me,
in Compound Pt914: R'=H, R=Et,
in Compound Pt915: R'=H, R=2,6-($^i$Pr)$_2$-4-biphenyl,
in Compound Pt916: R'=H, R=2,4-($^i$Pr)$_2$-3-dibenzofuran,
in Compound Pt917: R'=Me, R=Me,
in Compound Pt918: R'=Me, R=Et,
in Compound Pt919: R'=Me, R=2,6-($^i$Pr)$_2$-4-biphenyl,
in Compound Pt920: R'=Me, R=2,4-($^i$Pr)$_2$-3-dibenzofuran,
in Compound Pt921: R'=Ph, R=Me,
in Compound Pt922: R'=Ph, R=Et,
in Compound Pt923: R'=Ph, R=2,6-($^i$Pr)$_2$-4-biphenyl,
in Compound Pt924: R'=Ph, R=2,4-($^i$Pr)$_2$-3-dibenzofuran,
Compound Pt925 through Pt936, each represented by the formula wherein in Compound Pt937: R'=H, R=Me,
in Compound Pt938: R'=H, R=Et,
in Compound Pt939: R'=H, R=2,6-($^i$Pr)$_2$-4-biphenyl,
in Compound Pt940: R'=H, R=2,4-($^i$Pr)$_2$-3-dibenzofuran,
in Compound Pt941: R'=Me, R=Me,
in Compound Pt942: R'=Me, R=Et,
in Compound Pt943: R'=Me, R=2,6-($^i$Pr)$_2$-4-biphenyl,
in Compound Pt944: R'=Me, R=2,4-($^i$Pr)$_2$-3-dibenzofuran,
in Compound Pt945: R'=Ph, R=Me,
in Compound Pt946: R'=Ph, R=Et,
in Compound Pt947: R'=Ph, R=2,6-($^i$Pr)$_2$-4-biphenyl,
in Compound Pt948: R'=Ph, R=2,4-($^i$Pr)$_2$-3-dibenzofuran,
Compound Pt949 through Pt960, each represented by the formula

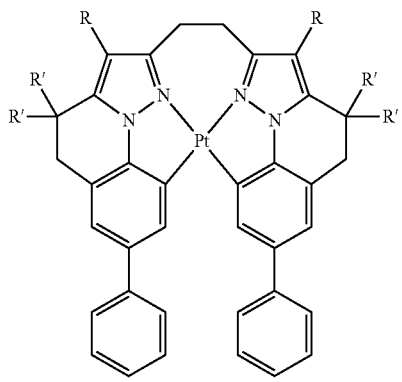

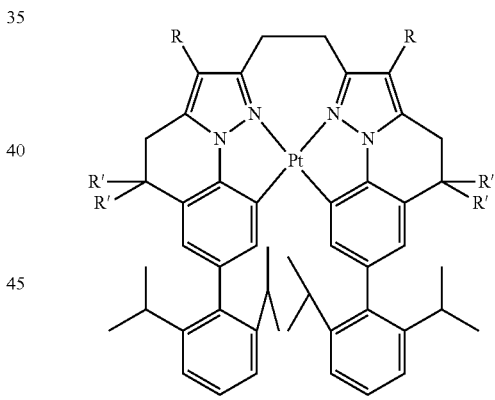

wherein in Compound Pt925: R'=H, R=Me,
in Compound Pt926: R'=H, R=Et,
in Compound Pt927: R'=H, R=2,6-($^i$Pr)$_2$-4-biphenyl,
in Compound Pt928: R'=H, R=2,4-($^i$Pr)$_2$-3-dibenzofuran,
in Compound Pt929: R'=Me, R=Me,
in Compound Pt930: R'=Me, R=Et,
in Compound Pt931: R'=Me, R=2,6-($^i$Pr)$_2$-4-biphenyl,
in Compound Pt932: R'=Me, R=2,4-($^i$Pr)$_2$-3-dibenzofuran,
in Compound Pt933: R'=Ph, R=Me,
in Compound Pt934: R'=Ph, R=Et,
in Compound Pt935: R'=Ph, R=2,6-($^i$Pr)$_2$-4-biphenyl,
in Compound Pt936: R'=Ph, R=2,4-($^i$Pr)$_2$-3-dibenzofuran,
Compound Pt937 through Pt948, each represented by the formula wherein in Compound Pt949: R'=H, R=Me,
in Compound Pt950: R'=H, R=Et,
in Compound Pt951: R'=H, R=2,6-($^i$Pr)$_2$-4-biphenyl,
in Compound Pt952: R'=H, R=2,4-($^i$Pr)$_2$-3-dibenzofuran,
in Compound Pt953: R'=Me, R=Me,
in Compound Pt954: R'=Me, R=Et,
in Compound Pt955: R'=Me, R=2,6-($^i$Pr)$_2$-4-biphenyl,
in Compound Pt956: R'=Me, R=2,4-($^i$Pr)$_2$-3-dibenzofuran,
in Compound Pt957: R'=Ph, R=Me,
in Compound Pt958: R'=Ph, R=Et,
in Compound Pt959: R'=Ph, R=2,6-($^i$Pr)$_2$-4-biphenyl,
in Compound Pt960: R'=Ph, R=2,4-($^i$Pr)$_2$-3-dibenzofuran,
Compound Pt961 through Pt972, each represented by the formula

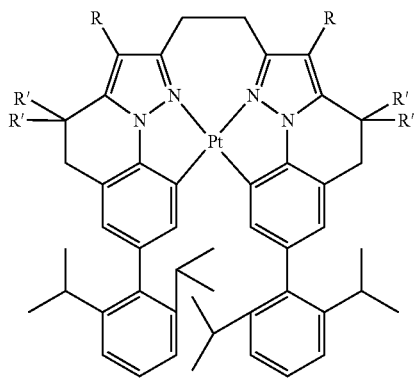

wherein in Compound Pt961: R'=H, R=Me,
in Compound Pt962: R'=H, R=Et,
in Compound Pt963: R'=H, R=2,6-($^i$Pr)$_2$-4-biphenyl,
in Compound Pt964: R'=H, R=2,4-($^i$Pr)$_2$-3-dibenzofuran,
in Compound Pt965: R'=Me, R=Me,
in Compound Pt966: R'=Me, R=Et,
in Compound Pt967: R'=Me, R=2,6-($^i$Pr)$_2$-4-biphenyl,
in Compound Pt968: R'=Me, R=2,4-($^i$Pr)$_2$-3-dibenzofuran,
in Compound Pt969: R'=Ph, R=Me,
in Compound Pt970: R'=Ph, R=Et,
in Compound Pt971: R'=Ph, R=2,6-($^i$Pr)$_2$-4-biphenyl,
in Compound Pt972: R'=Ph, R=2,4-($^i$Pr)$_2$-3-dibenzofuran,
Compound Pt973 through Pt984, each represented by the formula

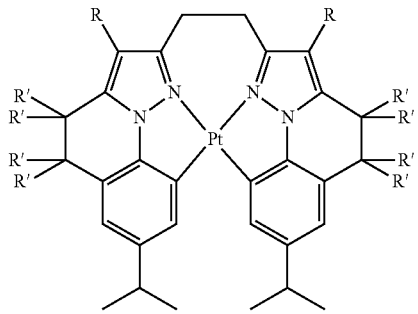

wherein in Compound Pt973: R'=H, R=Me,
in Compound Pt974: R'=H, R=Et,
in Compound Pt975: R'=H, R=2,6-($^i$Pr)$_2$-4-biphenyl,
in Compound Pt976: R'=H, R=2,4-($^i$Pr)$_2$-3-dibenzofuran,
in Compound Pt977: R'=Me, R=Me,
in Compound Pt978: R'=Me, R=Et,
in Compound Pt979: R'=Me, R=2,6-($^i$Pr)$_2$-4-biphenyl,
in Compound Pt980: R'=Me, R=2,4-($^i$Pr)$_2$-3-dibenzofuran,
in Compound Pt981: R'=Ph, R=Me,
in Compound Pt982: R'=Ph, R=Et,
in Compound Pt983: R'=Ph, R=2,6-($^i$Pr)$_2$-4-biphenyl,
in Compound Pt984: R'=Ph, R=2,4-($^i$Pr)$_2$-3-dibenzofuran,
Compound Pt985 through Pt996, each represented by the formula

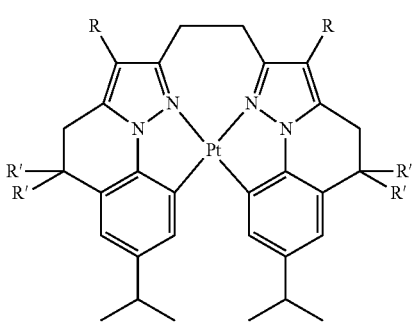

wherein in Compound Pt985: R'=H, R=Me,
in Compound Pt986: R'=H, R=Et,
in Compound Pt987: R'=H, R=2,6-($^i$Pr)$_2$-4-biphenyl,
in Compound Pt988: R'=H, R=2,4-($^i$Pr)$_2$-3-dibenzofuran,
in Compound Pt989: R'=Me, R=Me,
in Compound Pt990: R'=Me, R=Et,
in Compound Pt991: R'=Me, R=2,6-($^i$Pr)$_2$-4-biphenyl,
in Compound Pt992: R'=Me, R=2,4-($^i$Pr)$_2$-3-dibenzofuran,
in Compound Pt993: R'=Ph, R=Me,
in Compound Pt994: R'=Ph, R=Et,
in Compound Pt995: R'=Ph, R=2,6-($^i$Pr)$_2$-4-biphenyl,
in Compound Pt996: R'=Ph, R=2,4-($^i$Pr)$_2$-3-dibenzofuran,
Compound Pt997 through Pt1008, each represented by the formula

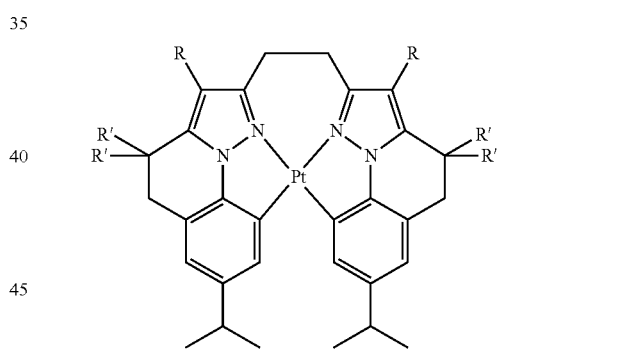

wherein in Compound Pt997: R'=H, R=Me,
in Compound Pt998: R'=H, R=Et,
in Compound Pt999: R'=H, R=2,6-($^i$Pr)$_2$-4-biphenyl,
in Compound Pt1000: R'=H, R=2,4-($^i$Pr)$_2$-3-dibenzofuran,
in Compound Pt1001: R'=Me, R=Me,
in Compound Pt1002: R'=Me, R=Et,
in Compound Pt1003: R'=Me, R=2,6-($^i$Pr)$_2$-4-biphenyl,
in Compound Pt1004: R'=Me, R=2,4-($^i$Pr)$_2$-3-dibenzofuran,
in Compound Pt1005: R'=Ph, R=Me,
in Compound Pt1006: R'=Ph, R=Et,
in Compound Pt1007: R'=Ph, R=2,6-($^i$Pr)$_2$-4-biphenyl,
in Compound Pt1008: R'=Ph, R=2,4-($^i$Pr)$_2$-3-dibenzofuran,
Compound Pt1009 through Pt1023, each represented by the formula

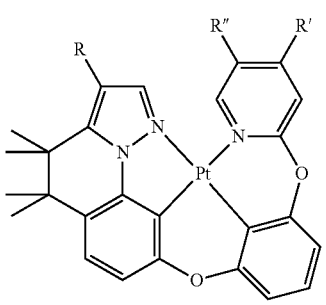

wherein in Compound Pt1009: R'=H, R"=H, R=H,
in Compound Pt1010: R'=H, R"=H, R=Me,
in Compound Pt1011: R'=H, R"=H, R=Ph,
in Compound Pt1012: R'=H, R"=H, R=2,6-($^{i}$Pr)$_2$Ph,
in Compound Pt1013: R'=H, R"=H, R=2,6-($^{i}$Pr)$_2$-4-biphenyl,
in Compound Pt1014: R'=H, R"=Me, R=H,
in Compound Pt1015: R'=H, R"=Me, R=Me,
in Compound Pt1016: R'=H, R"=Me, R=Ph,
in Compound Pt1017: R'=H, R"=Me, R=2,6-($^{i}$Pr)$_2$Ph,
in Compound Pt1018: R'=H, R"=Me, R=2,6-($^{i}$Pr)$_2$-4-biphenyl,
in Compound Pt1019: R'=Me, R"=H, R=H,
in Compound Pt1020: R'=Me, R"=H, R=Me,
in Compound Pt1021: R'=Me, R"=H, R=Ph,
in Compound Pt1022: R'=Me, R"=H, R=2,6-($^{i}$Pr)$_2$Ph,
in Compound Pt1023: R'=Me, R"=H, R=2,6-($^{i}$Pr)$_2$-4-biphenyl,
Compound Pt1024 through Pt1038, each represented by the formula

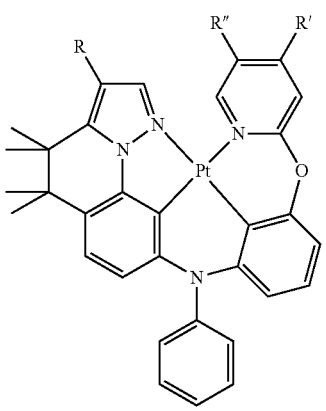

wherein in Compound Pt1024: R'=H, R"=H, R=H,
in Compound Pt1025: R'=H, R"=H, R=Me,
in Compound Pt1026: R'=H, R"=H, R=Ph,
in Compound Pt1027: R'=H, R"=H, R=2,6-($^{i}$Pr)$_2$Ph,
in Compound Pt1028: R'=H, R"=H, R=2,6-($^{i}$Pr)$_2$-4-biphenyl,
in Compound Pt1029: R'=H, R"=Me, R=H,
in Compound Pt1030: R'=H, R"=Me, R=Me,
in Compound Pt1031: R'=H, R"=Me, R=Ph,
in Compound Pt1032: R'=H, R"=Me, R=2,6-($^{i}$Pr)$_2$Ph,
in Compound Pt1033: R'=H, R"=Me, R=2,6-($^{i}$Pr)$_2$-4-biphenyl,
in Compound Pt1034: R'=Me, R"=H, R=H,
in Compound Pt1035: R'=Me, R"=H, R=Me,
in Compound Pt1036: R'=Me, R"=H, R=Ph,
in Compound Pt1037: R'=Me, R"=H, R=2,6-($^{i}$Pr)$_2$Ph,
in Compound Pt1038: R'=Me, R"=H, R=2,6-($^{i}$Pr)$_2$-4-biphenyl,
Compound Pt1039 through Pt1053, each represented by the formula

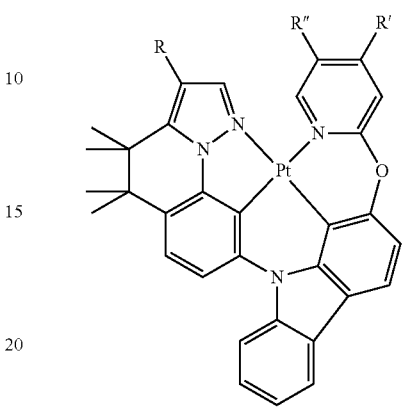

wherein in Compound Pt1039: R'=H, R"=H, R=H,
in Compound Pt1040: R'=H, R"=H, R=Me,
in Compound Pt1041: R'=H, R"=H, R=Ph,
in Compound Pt1042: R'=H, R"=H, R=2,6-($^{i}$Pr)$_2$Ph,
in Compound Pt1043: R'=H, R"=H, R=2,6-($^{i}$Pr)$_2$-4-biphenyl,
in Compound Pt1044: R'=H, R"=Me, R=H,
in Compound Pt1045: R'=H, R"=Me, R=Me,
in Compound Pt1046: R'=H, R"=Me, R=Ph,
in Compound Pt1047: R'=H, R"=Me, R=2,6-($^{i}$Pr)$_2$Ph,
in Compound Pt1048: R'=H, R"=Me, R=2,6-($^{i}$Pr)$_2$-4-biphenyl,
in Compound Pt1049: R'=Me, R"=H, R=H,
in Compound Pt1050: R'=Me, R"=H, R=Me,
in Compound Pt1051: R'=Me, R"=H, R=Ph,
in Compound Pt1052: R'=Me, R"=H, R=2,6-($^{i}$Pr)$_2$Ph,
in Compound Pt1053: R'=Me, R"=H, R=2,6-($^{i}$Pr)$_2$-4-biphenyl,
Compound Pt1054 through Pt1068, each represented by the formula

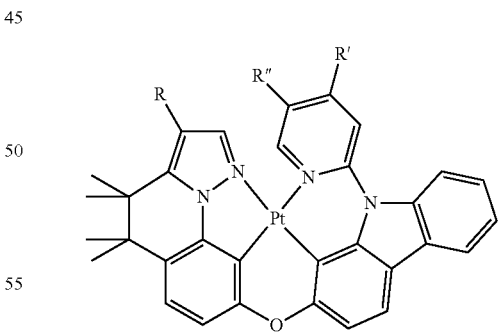

wherein in Compound Pt1054: R'=H, R"=H, R=H,
in Compound Pt1055: R'=H, R"=H, R=Me,
in Compound Pt1056: R'=H, R"=H, R=Ph,
in Compound Pt1057: R'=H, R"=H, R=2,6-($^{i}$Pr)$_2$Ph,
in Compound Pt1058: R'=H, R"=H, R=2,6-($^{i}$Pr)$_2$-4-biphenyl,
in Compound Pt1059: R'=H, R"=Me, R=H,
in Compound Pt1060: R'=H, R"=Me, R=Me,
in Compound Pt1061: R'=H, R"=Me, R=Ph, in Compound Pt1062: R'=H, R"=Me, R=2,6-($^i$Pr)$_2$Ph,
in Compound Pt1063: R'=H, R"=Me, R=2,6-($^i$Pr)$_2$-4-biphenyl,
in Compound Pt1064: R'=Me, R"=H, R=H,
in Compound Pt1065: R'=Me, R"=H, R=Me,
in Compound Pt1066: R'=Me, R"=H, R=Ph,
in Compound Pt1067: R'=Me, R"=H, R=2,6-($^i$Pr)$_2$Ph,
in Compound Pt1068: R'=Me, R"=H, R=2,6-($^i$Pr)$_2$-4-biphenyl,
Compound Pt1069 through Pt1083, each represented by the formula

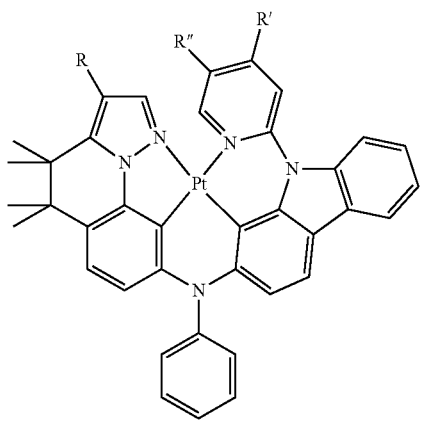

wherein in Compound Pt1069: R'=H, R"=H, R=H,
in Compound Pt1070: R'=H, R"=H, R=Me,
in Compound Pt1071: R'=H, R"=H, R=Ph,
in Compound Pt1072: R'=H, R"=H, R=2,6-($^i$Pr)$_2$Ph,
in Compound Pt1073: R'=H, R"=H, R=2,6-($^i$Pr)$_2$-4-biphenyl,
in Compound Pt1074: R'=H, R"=Me, R=H,
in Compound Pt1075: R'=H, R"=Me, R=Me,
in Compound Pt1076: R'=H, R"=Me, R=Ph,
in Compound Pt1077: R'=H, R"=Me, R=2,6-($^i$Pr)$_2$Ph,
in Compound Pt1078: R'=H, R"=Me, R=2,6-($^i$Pr)$_2$-4-biphenyl,
in Compound Pt1079: R'=Me, R"=H, R=H,
in Compound Pt1080: R'=Me, R"=H, R=Me,
in Compound Pt1081: R'=Me, R"=H, R=Ph,
in Compound Pt1082: R'=Me, R"=H, R=2,6-($^i$Pr)$_2$Ph,
in Compound Pt1083: R'=Me, R"=H, R=2,6-($^i$Pr)$_2$-4-biphenyl,
Compound Pt1084 through Pt1097, each represented by the formula

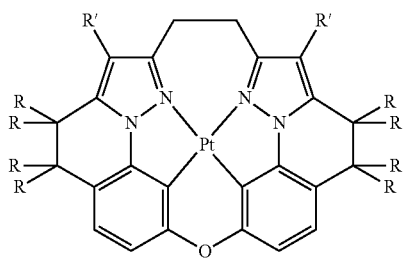

wherein in Compound Pt1084: R=Me, R'=H,
in Compound Pt1085: R=Me, R'=Me,
in Compound Pt1086: R=Me, R'=$^i$Pr,
in Compound Pt1087: R=Me, R'=Ph,
in Compound Pt1088: R=Me, R'=2,6-($^i$Pr)$_2$Ph,
in Compound Pt1089: R=Me, R'=2,6-($^i$Pr)$_2$-4-biphenyl,
in Compound Pt1090: R=Me, R'=2,4-($^i$Pr)$_2$-3-dibenzofuran,
in Compound Pt1091: R=Ph, R'=H,
in Compound Pt1092: R=Ph, R'=Me,
in Compound Pt1093: R=Ph, R'=$^i$Pr,
in Compound Pt1094: R=Ph, R'=Ph,
in Compound Pt1095: R=Ph, R'=2,6-($^i$Pr)$_2$Ph,
in Compound Pt1096: R=Ph, R'=2,6-($^i$Pr)$_2$-4-biphenyl,
in Compound Pt1097: R=Ph, R'=2,4-($^i$Pr)$_2$-3-dibenzofuran,
Compound Pt1098 through Pt1111, each represented by the formula

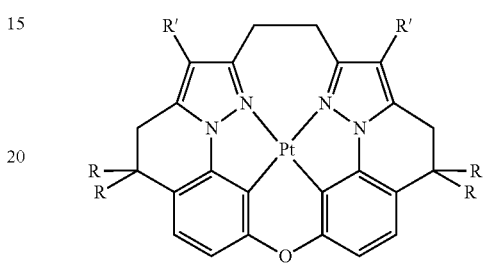

wherein in Compound Pt1098: R=Me, R'=H,
in Compound Pt1099: R=Me, R'=Me,
in Compound Pt1100: R=Me, R'=$^i$Pr,
in Compound Pt1101: R=Me, R'=Ph,
in Compound Pt1102: R=Me, R'=2,6-($^i$Pr)$_2$Ph,
in Compound Pt1103: R=Me, R'=2,6-($^i$Pr)$_2$-4-biphenyl,
in Compound Pt1104: R=Me, R'=2,4-($^i$Pr)$_2$-3-dibenzofuran,
in Compound Pt1105: R=Ph, R'=H,
in Compound Pt1106: R=Ph, R'=Me,
in Compound Pt1107: R=Ph, R'=$^i$Pr,
in Compound Pt1108: R=Ph, R'=Ph,
in Compound Pt1109: R=Ph, R'=2,6-($^i$Pr)$_2$Ph,
in Compound Pt1110: R=Ph, R'=2,6-($^i$Pr)$_2$-4-biphenyl,
in Compound Pt1111: R=Ph, R'=2,4-($^i$Pr)$_2$-3-dibenzofuran,
Compound Pt1112 through Pt1125, each represented by the formula

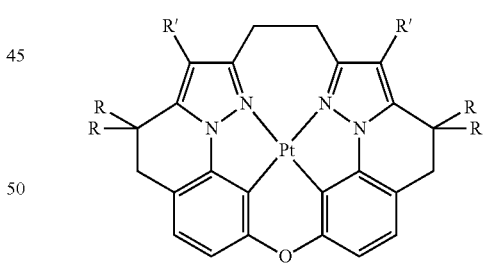

wherein in Compound Pt1112: R=Me, R'=H,
in Compound Pt1113: R=Me, R'=Me,
in Compound Pt1114: R=Me, R'=$^i$Pr,
in Compound Pt1115: R=Me, R'=Ph,
in Compound Pt1116: R=Me, R'=2,6-($^i$Pr)$_2$Ph,
in Compound Pt1117: R=Me, R'=2,6-($^i$Pr)$_2$-4-biphenyl,
in Compound Pt1118: R=Me, R'=2,4-($^i$Pr)$_2$-3-dibenzofuran,
in Compound Pt1119: R=Ph, R'=H,
in Compound Pt1120: R=Ph, R'=Me,
in Compound Pt1121: R=Ph, R'=$^i$Pr,
in Compound Pt1122: R=Ph, R'=Ph,
in Compound Pt1123: R=Ph, R'=2,6-($^i$Pr)$_2$Ph,
in Compound Pt1124: R=Ph, R'=2,6-($^i$Pr)$_2$-4-biphenyl, in Compound Pt1125: R=Ph, R'=2,4-($^{i}$Pr)$_2$-3-dibenzofuran, Compound Pt1126 through Pt1139, each represented by the formula

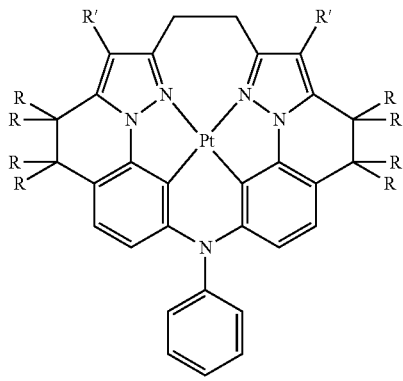

wherein in Compound Pt1126: R=Me, R'=H,
in Compound Pt1127: R=Me, R'=Me,
in Compound Pt1128: R=Me, R'=$^{i}$Pr,
in Compound Pt1129: R=Me, R'=Ph,
in Compound Pt1130: R=Me, R'=2,6-($^{i}$Pr)$_2$Ph,
in Compound Pt1131: R=Me, R'=2,6-($^{i}$Pr)$_2$-4-biphenyl,
in Compound Pt1132: R=Me, R'=2,4-($^{i}$Pr)$_2$-3-dibenzofuran,
in Compound Pt1133: R=Ph, R'=H,
in Compound Pt1134: R=Ph, R'=Me,
in Compound Pt1135: R=Ph, R'=$^{i}$Pr,
in Compound Pt1136: R=Ph, R'=Ph,
in Compound Pt1137: R=Ph, R'=2,6-($^{i}$Pr)$_2$Ph,
in Compound Pt1138: R=Ph, R'=2,6-($^{i}$Pr)$_2$-4-biphenyl,
in Compound Pt1139: R=Ph, R'=2,4-($^{i}$Pr)$_2$-3-dibenzofuran,
Compound Pt1140 through Pt1153, each represented by the formula

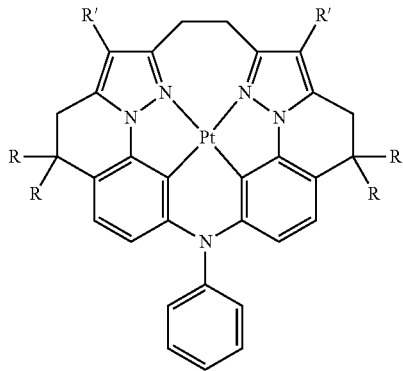

wherein in Compound Pt1140: R=Me, R'=H,
in Compound Pt1141: R=Me, R'=Me,
in Compound Pt1142: R=Me, R'=$^{i}$Pr,
in Compound Pt1143: R=Me, R'=Ph,
in Compound Pt1144: R=Me, R'=2,6-($^{i}$Pr)$_2$Ph,
in Compound Pt1145: R=Me, R'=2,6-($^{i}$Pr)$_2$-4-biphenyl,
in Compound Pt1146: R=Me, R'=2,4-($^{i}$Pr)$_2$-3-dibenzofuran,
in Compound Pt1147: R=Ph, R'=H,
in Compound Pt1148: R=Ph, R'=Me,
in Compound Pt1149: R=Ph, R'=$^{i}$Pr,
in Compound Pt1150: R=Ph, R'=Ph,
in Compound Pt1151: R=Ph, R'=2,6-($^{i}$Pr)$_2$Ph,
in Compound Pt1152: R=Ph, R'=2,6-($^{i}$Pr)$_2$-4-biphenyl, in Compound Pt1153: R=Ph, R'=2,4-($^{i}$Pr)$_2$-3-dibenzofuran, Compound Pt1154 through Pt1167, each represented by the formula

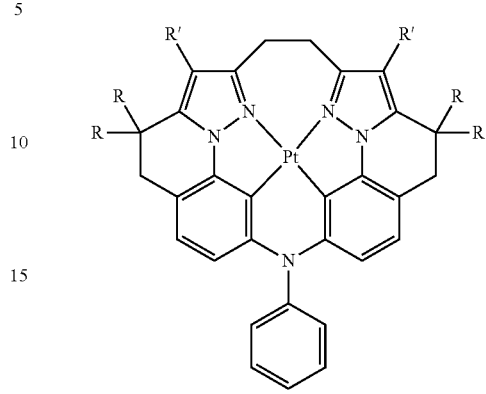

wherein in Compound Pt1154: R=Me, R'=H,
in Compound Pt1155: R=Me, R'=Me,
in Compound Pt1156: R=Me, R'=$^{i}$Pr,
in Compound Pt1157: R=Me, R'=Ph,
in Compound Pt1158: R=Me, R'=2,6-($^{i}$Pr)$_2$Ph,
in Compound Pt1159: R=Me, R'=2,6-($^{i}$Pr)$_2$-4-biphenyl,
in Compound Pt1160: R=Me, R'=2,4-($^{i}$Pr)$_2$-3-dibenzofuran,
in Compound Pt1161: R=Ph, R'=H,
in Compound Pt1162: R=Ph, R'=Me,
in Compound Pt1163: R=Ph, R'=$^{i}$Pr,
in Compound Pt1164: R=Ph, R'=Ph,
in Compound Pt1165: R=Ph, R'=2,6-($^{i}$Pr)$_2$Ph,
in Compound Pt1166: R=Ph, R'=2,6-($^{i}$Pr)$_2$-4-biphenyl,
in Compound Pt1167: R=Ph, R'=2,4-($^{i}$Pr)$_2$-3-dibenzofuran,
Compound Pt1168 through Pt1181, each represented by the formula

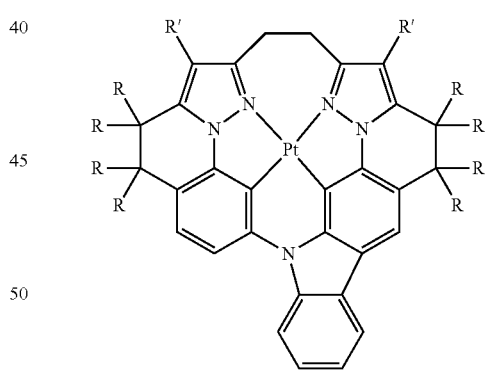

wherein in Compound Pt1168: R=Me, R'=H,
in Compound Pt1169: R=Me, R'=Me,
in Compound Pt1170: R=Me, R'=$^{i}$Pr,
in Compound Pt1171: R=Me, R'=Ph,
in Compound Pt1172: R=Me, R'=2,6-($^{i}$Pr)$_2$Ph,
in Compound Pt1173: R=Me, R'=2,6-($^{i}$Pr)$_2$-4-biphenyl,
in Compound Pt1174: R=Me, R'=2,4-($^{i}$Pr)$_2$-3-dibenzofuran,
in Compound Pt1175: R=Ph, R'=H,
in Compound Pt1176: R=Ph, R'=Me,
in Compound Pt1177: R=Ph, R'=$^{i}$Pr,
in Compound Pt1178: R=Ph, R'=Ph,
in Compound Pt1179: R=Ph, R'=2,6-($^{i}$Pr)$_2$Ph,
in Compound Pt1180: R=Ph, R'=2,6-($^{i}$Pr)$_2$-4-biphenyl, in Compound Pt1181: R=Ph, R'=2,4-($^{i}$Pr)$_2$-3-dibenzofuran, Compound Pt1182 through Pt1195, each represented by the formula

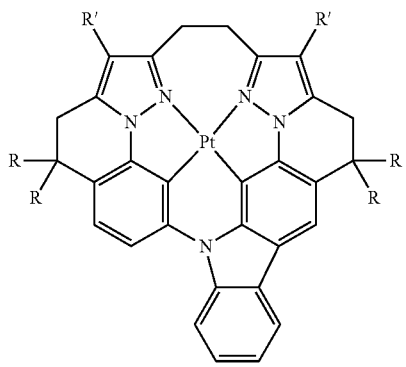

wherein in Compound Pt1182: R=Me, R'=H,
in Compound Pt1183: R=Me, R'=Me,
in Compound Pt1184: R=Me, R'=$^{i}$Pr,
in Compound Pt1185: R=Me, R'=Ph,
in Compound Pt1186: R=Me, R'=2,6-($^{i}$Pr)$_2$Ph,
in Compound Pt1187: R=Me, R'=2,6-($^{i}$Pr)$_2$-4-biphenyl,
in Compound Pt1188: R=Me, R'=2,4-($^{i}$Pr)$_2$-3-dibenzofuran,
in Compound Pt1189: R=Ph, R'=H,
in Compound Pt1190: R=Ph, R'=Me,
in Compound Pt1191: R=Ph, R'=$^{i}$Pr,
in Compound Pt1192: R=Ph, R'=Ph,
in Compound Pt1193: R=Ph, R'=2,6-($^{i}$Pr)$_2$Ph,
in Compound Pt1194: R=Ph, R'=2,6-($^{i}$Pr)$_2$-4-biphenyl,
in Compound Pt1195: R=Ph, R'=2,4-($^{i}$Pr)$_2$-3-dibenzofuran,
Compound Pt1196 through Pt1209, each represented by the formula

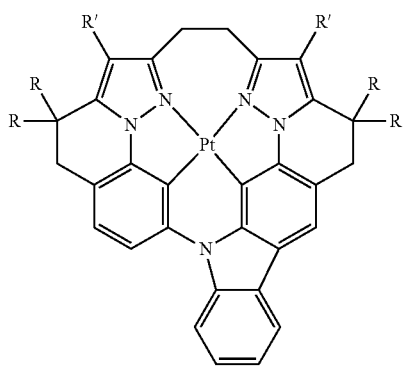

wherein in Compound Pt1196: R=Me, R'=H,
in Compound Pt1197: R=Me, R'=Me,
in Compound Pt1198: R=Me, R'=$^{i}$Pr,
in Compound Pt1199: R=Me, R'=Ph,
in Compound Pt1200: R=Me, R'=2,6-($^{i}$Pr)$_2$Ph,
in Compound Pt1201: R=Me, R'=2,6-($^{i}$Pr)$_2$-4-biphenyl,
in Compound Pt1202: R=Me, R'=2,4-($^{i}$Pr)$_2$-3-dibenzofuran,
in Compound Pt1203: R=Ph, R'=H,
in Compound Pt1204: R=Ph, R'=Me,
in Compound Pt1205: R=Ph, R'=$^{i}$Pr,
in Compound Pt1206: R=Ph, R'=Ph,
in Compound Pt1207: R=Ph, R'=2,6-($^{i}$Pr)$_2$Ph,
in Compound Pt1208: R=Ph, R'=2,6-($^{i}$Pr)$_2$-4-biphenyl,
in Compound Pt1209: R=Ph, R'=2,4-($^{i}$Pr)$_2$-3-dibenzofuran, Compound Pt1210 through Pt1223, each represented by the formula

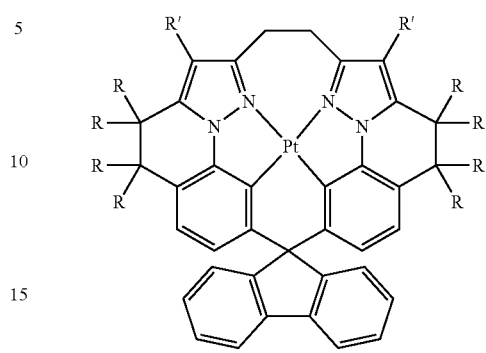

wherein in Compound Pt1210: R=Me, R'=H,
in Compound Pt1211: R=Me, R'=Me,
in Compound Pt1212: R=Me, R'=$^{i}$Pr,
in Compound Pt1213: R=Me, R'=Ph,
in Compound Pt1214: R=Me, R'=2,6-($^{i}$Pr)$_2$Ph,
in Compound Pt1215: R=Me, R'=2,6-($^{i}$Pr)$_2$-4-biphenyl,
in Compound Pt1216: R=Me, R'=2,4-($^{i}$Pr)$_2$-3-dibenzofuran,
in Compound Pt1217: R=Ph, R'=H,
in Compound Pt1218: R=Ph, R'=Me,
in Compound Pt1219: R=Ph, R'=$^{i}$Pr,
in Compound Pt1220: R=Ph, R'=Ph,
in Compound Pt1221: R=Ph, R'=2,6-($^{i}$Pr)$_2$Ph,
in Compound Pt1222: R=Ph, R'=2,6-($^{i}$Pr)$_2$-4-biphenyl,
in Compound Pt1223: R=Ph, R'=2,4-($^{i}$Pr)$_2$-3-dibenzofuran,
Compound Pt1224 through Pt1237, each represented by the formula

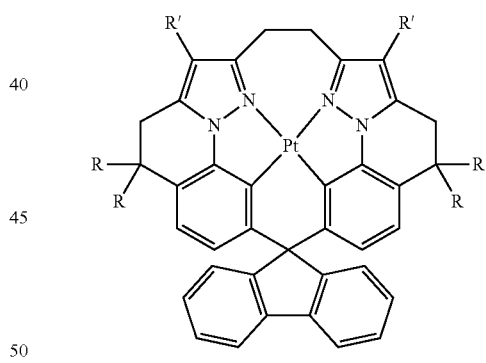

wherein in Compound Pt1224: R=Me, R'=H,
in Compound Pt1225: R=Me, R'=Me,
in Compound Pt1226: R=Me, R'=$^{i}$Pr,
in Compound Pt1227: R=Me, R'=Ph,
in Compound Pt1228: R=Me, R'=2,6-($^{i}$Pr)$_2$Ph,
in Compound Pt1229: R=Me, R'=2,6-($^{i}$Pr)$_2$-4-biphenyl,
in Compound Pt1230: R=Me, R'=2,4-($^{i}$Pr)$_2$-3-dibenzofuran,
in Compound Pt1231: R=Ph, R'=H,
in Compound Pt1232: R=Ph, R'=Me,
in Compound Pt1233: R=Ph, R'=$^{i}$Pr,
in Compound Pt1234: R=Ph, R'=Ph,
in Compound Pt1235: R=Ph, R'=2,6-($^{i}$Pr)$_2$Ph,
in Compound Pt1236: R=Ph, R'=2,6-($^{i}$Pr)$_2$-4-biphenyl,
in Compound Pt1237: R=Ph, R'=2,4-($^{i}$Pr)$_2$-3-dibenzofuran,
Compound Pt1238 through Pt1251, each represented by the formula

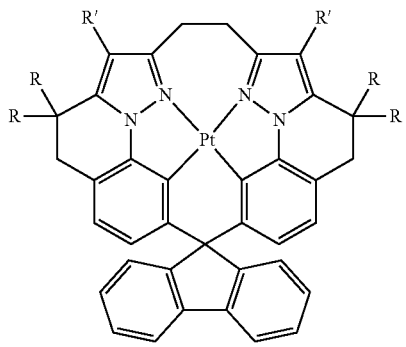

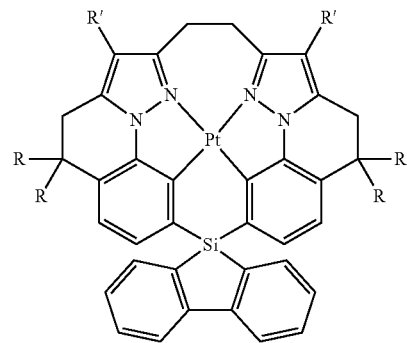

wherein in Compound Pt1238: R=Me, R'=H,
in Compound Pt1239: R=Me, R'=Me,
in Compound Pt1240: R=Me, R'=$^i$Pr,
in Compound Pt1241: R=Me, R'=Ph,
in Compound Pt1242: R=Me, R'=2,6-($^i$Pr)$_2$Ph,
in Compound Pt1243: R=Me, R'=2,6-($^i$Pr)$_2$-4-biphenyl,
in Compound Pt1244: R=Me, R'=2,4-($^i$Pr)$_2$-3-dibenzofuran,
in Compound Pt1245: R=Ph, R'=H,
in Compound Pt1246: R=Ph, R'=Me,
in Compound Pt1247: R=Ph, R'=$^i$Pr,
in Compound Pt1248: R=Ph, R'=Ph,
in Compound Pt1249: R=Ph, R'=2,6-($^i$Pr)$_2$Ph,
in Compound Pt1250: R=Ph, R'=2,6-($^i$Pr)$_2$-4-biphenyl,
in Compound Pt1251: R=Ph, R'=2,4-($^i$Pr)$_2$-3-dibenzofuran,
Compound Pt1252 through Pt1265, each represented by the formula wherein in Compound Pt1266: R=Me, R'=H,
in Compound Pt1267: R=Me, R'=Me,
in Compound Pt1268: R=Me, R'=$^i$Pr,
in Compound Pt1269: R=Me, R'=Ph,
in Compound Pt1270: R=Me, R'=2,6-($^i$Pr)$_2$Ph,
in Compound Pt1271: R=Me, R'=2,6-($^i$Pr)$_2$-4-biphenyl,
in Compound Pt1272: R=Me, R'=2,4-($^i$Pr)$_2$-3-dibenzofuran,
in Compound Pt1273: R=Ph, R'=H,
in Compound Pt1274: R=Ph, R'=Me,
in Compound Pt1275: R=Ph, R'=$^i$Pr,
in Compound Pt1276: R=Ph, R'=Ph,
in Compound Pt1277: R=Ph, R'=2,6-($^i$Pr)$_2$Ph,
in Compound Pt1278: R=Ph, R'=2,6-($^i$Pr)$_2$-4-biphenyl,
in Compound Pt1279: R=Ph, R'=2,4-($^i$Pr)$_2$-3-dibenzofuran,
Compound Pt1280 through Pt1293, each represented by the formula

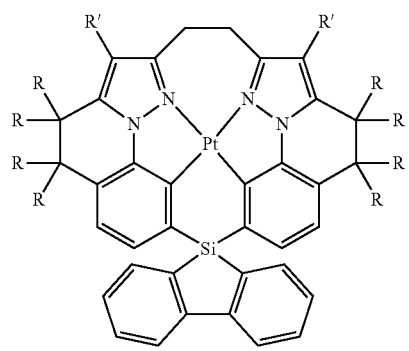

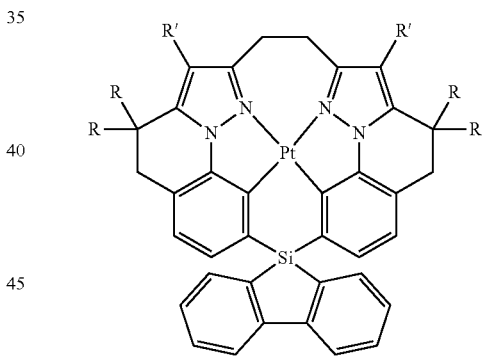

wherein in Compound Pt1252: R=Me, R'=H,
in Compound Pt1253: R=Me, R'=Me,
in Compound Pt1254: R=Me, R'=$^i$Pr,
in Compound Pt1255: R=Me, R'=Ph,
in Compound Pt1256: R=Me, R'=2,6-($^i$Pr)$_2$Ph,
in Compound Pt1257: R=Me, R'=2,6-($^i$Pr)$_2$-4-biphenyl,
in Compound Pt1258: R=Me, R'=2,4-($^i$Pr)$_2$-3-dibenzofuran,
in Compound Pt1259: R=Ph, R'=H,
in Compound Pt1260: R=Ph, R'=Me,
in Compound Pt1261: R=Ph, R'=$^i$Pr,
in Compound Pt1262: R=Ph, R'=Ph,
in Compound Pt1263: R=Ph, R'=2,6-($^i$Pr)$_2$Ph,
in Compound Pt1264: R=Ph, R'=2,6-($^i$Pr)$_2$-4-biphenyl,
in Compound Pt1265: R=Ph, R'=2,4-($^i$Pr)$_2$-3-dibenzofuran,
Compound Pt1266 through Pt1279, each represented by the formula wherein in Compound Pt1280: R=Me, R'=H,
in Compound Pt1281: R=Me, R'=Me,
in Compound Pt1282: R=Me, R'=$^i$Pr,
in Compound Pt1283: R=Me, R'=Ph,
in Compound Pt1284: R=Me, R'=2,6-($^i$Pr)$_2$Ph,
in Compound Pt1285: R=Me, R'=2,6-($^i$Pr)$_2$-4-biphenyl,
in Compound Pt1286: R=Me, R'=2,4-($^i$Pr)$_2$-3-dibenzofuran,
in Compound Pt1287: R=Ph, R'=H,
in Compound Pt1288: R=Ph, R'=Me,
in Compound Pt1289: R=Ph, R'=$^i$Pr,
in Compound Pt1290: R=Ph, R'=Ph,
in Compound Pt1291: R=Ph, R'=2,6-($^i$Pr)$_2$Ph,
in Compound Pt1292: R=Ph, R'=2,6-($^i$Pr)$_2$-4-biphenyl,
in Compound Pt1293: R=Ph, R'=2,4-($^i$Pr)$_2$-3-dibenzofuran,
Compound Pt1294 through Pt1307, each represented by the formula

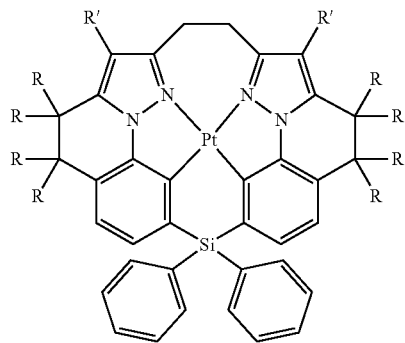

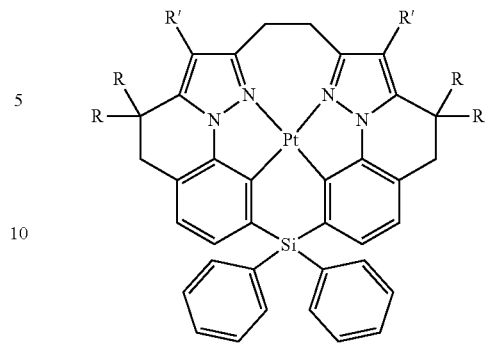

wherein in Compound Pt1294: R=Me, R'=H,
in Compound Pt1295: R=Me, R'=Me,
in Compound Pt1296: R=Me, R'=$^i$Pr,
in Compound Pt1297: R=Me, R'=Ph,
in Compound Pt1298: R=Me, R'=2,6-($^i$Pr)$_2$Ph,
in Compound Pt1299: R=Me, R'=2,6-($^i$Pr)$_2$-4-biphenyl,
in Compound Pt1300: R=Me, R'=2,4-($^i$Pr)$_2$-3-dibenzofuran,
in Compound Pt1301: R=Ph, R'=H,
in Compound Pt1302: R=Ph, R'=Me,
in Compound Pt1303: R=Ph, R'=$^i$Pr,
in Compound Pt1304: R=Ph, R'=Ph,
in Compound Pt1305: R=Ph, R'=2,6-($^i$Pr)$_2$Ph,
in Compound Pt1306: R=Ph, R'=2,6-($^i$Pr)$_2$-4-biphenyl,
in Compound Pt1307: R=Ph, R'=2,4-($^i$Pr)$_2$-3-dibenzofuran,
Compound Pt1308 through Pt1321, each represented by the formula wherein in Compound Pt1322: R=Me, R'=H,
in Compound Pt1323: R=Me, R'=Me,
in Compound Pt1324: R=Me, R'=$^i$Pr,
in Compound Pt1325: R=Me, R'=Ph,
in Compound Pt1326: R=Me, R'=2,6-($^i$Pr)$_2$Ph,
in Compound Pt1327: R=Me, R'=2,6-($^i$Pr)$_2$-4-biphenyl,
in Compound Pt1328: R=Me, R'=2,4-($^i$Pr)$_2$-3-dibenzofuran,
in Compound Pt1329: R=Ph, R'=H,
in Compound Pt1330: R=Ph, R'=Me,
in Compound Pt1331: R=Ph, R'=$^i$Pr,
in Compound Pt3332: R=Ph, R'=Ph,
in Compound Pt1333: R=Ph, R'=2,6-($^i$Pr)$_2$Ph,
in Compound Pt1334: R=Ph, R'=2,6-($^i$Pr)$_2$-4-biphenyl,
in Compound Pt1335: R=Ph, R'=2,4-($^i$Pr)$_2$-3-dibenzofuran,
Compound Pt1336 through Pt1349, each represented by the formula

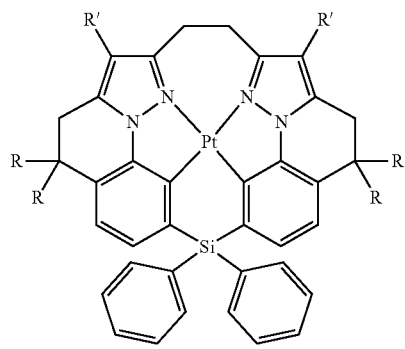

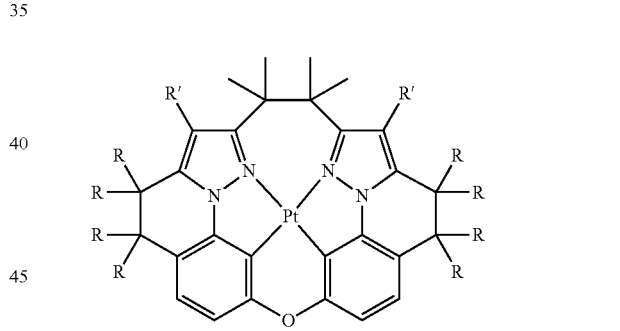

wherein in Compound Pt1308: R=Me, R'=H,
in Compound Pt1309: R=Me, R'=Me,
in Compound Pt1310: R=Me, R'=$^i$Pr,
in Compound Pt1311: R=Me, R'=Ph,
in Compound Pt1312: R=Me, R'=2,6-($^i$Pr)$_2$Ph,
in Compound Pt1313: R=Me, R'=2,6-($^i$Pr)$_2$-4-biphenyl,
in Compound Pt1314: R=Me, R'=2,4-($^i$Pr)$_2$-3-dibenzofuran,
in Compound Pt1315: R=Ph, R'=H,
in Compound Pt1316: R=Ph, R'=Me,
in Compound Pt1317: R=Ph, R'=$^i$Pr,
in Compound Pt1318: R=Ph, R'=Ph,
in Compound Pt1319: R=Ph, R'=2,6-($^i$Pr)$_2$Ph,
in Compound Pt1320: R=Ph, R'=2,6-($^i$Pr)$_2$-4-biphenyl,
in Compound Pt1321: R=Ph, R'=2,4-($^i$Pr)$_2$-3-dibenzofuran,
Compound Pt1322 through Pt1335, each represented by the formula wherein in Compound Pt1336: R=Me, R'=H,
in Compound Pt1337: R=Me, R'=Me,
in Compound Pt1338: R=Me, R'=$^i$Pr,
in Compound Pt1339: R=Me, R'=Ph,
in Compound Pt1340: R=Me, R'=2,6-($^i$Pr)$_2$Ph,
in Compound Pt1341: R=Me, R'=2,6-($^i$Pr)$_2$-4-biphenyl,
in Compound Pt1342: R=Me, R'=2,4-($^i$Pr)$_2$-3-dibenzofuran,
in Compound Pt1343: R=Ph, R'=H,
in Compound Pt1344: R=Ph, R'=Me,
in Compound Pt1345: R=Ph, R'=$^i$Pr,
in Compound Pt1346: R=Ph, R'=Ph,
in Compound Pt1347: R=Ph, R'=2,6-($^i$Pr)$_2$Ph,
in Compound Pt1348: R=Ph, R'=2,6-($^i$Pr)$_2$-4-biphenyl,
in Compound Pt1349: R=Ph, R'=2,4-($^i$Pr)$_2$-3-dibenzofuran,
Compound Pt1350 through Pt1363, each represented by the formula

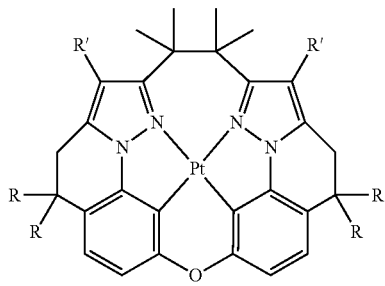

wherein in Compound Pt1350: R=Me, R'=H,
in Compound Pt1351: R=Me, R'=Me,
in Compound Pt1352: R=Me, R'=$^i$Pr,
in Compound Pt1353: R=Me, R'=Ph,
in Compound Pt1354: R=Me, R'=2,6-($^i$Pr)$_2$Ph,
in Compound Pt1355: R=Me, R'=2,6-($^i$Pr)$_2$-4-biphenyl,
in Compound Pt1356: R=Me, R'=2,4-($^i$Pr)$_2$-3-dibenzofuran,
in Compound Pt1357: R=Ph, R'=H,
in Compound Pt1358: R=Ph, R'=Me,
in Compound Pt1359: R=Ph, R'=$^i$Pr,
in Compound Pt1360: R=Ph, R'=Ph,
in Compound Pt1361: R=Ph, R'=2,6-($^i$Pr)$_2$Ph,
in Compound Pt1362: R=Ph, R'=2,6-($^i$Pr)$_2$-4-biphenyl,
in Compound Pt1363: R=Ph, R'=2,4-($^i$Pr)$_2$-3-dibenzofuran,
Compound Pt1364 through Pt1377, each represented by the formula

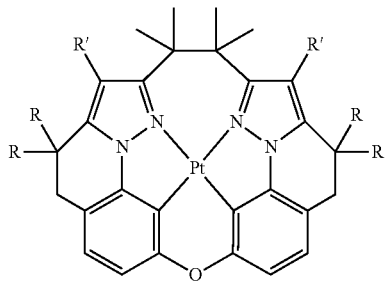

wherein in Compound Pt1364: R=Me, R'=H,
in Compound Pt1365: R=Me, R'=Me,
in Compound Pt1366: R=Me, R'=$^i$Pr,
in Compound Pt1367: R=Me, R'=Ph,
in Compound Pt1368: R=Me, R'=2,6-($^i$Pr)$_2$Ph,
in Compound Pt1369: R=Me, R'=2,6-($^i$Pr)$_2$-4-biphenyl,
in Compound Pt1370: R=Me, R'=2,4-($^i$Pr)$_2$-3-dibenzofuran,
in Compound Pt1371: R=Ph, R'=H,
in Compound Pt1372: R=Ph, R'=Me,
in Compound Pt1373: R=Ph, R'=$^i$Pr,
in Compound Pt1374: R=Ph, R'=Ph,
in Compound Pt1375: R=Ph, R'=2,6-($^i$Pr)$_2$Ph,
in Compound Pt1376: R=Ph, R'=2,6-($^i$Pr)$_2$-4-biphenyl,
in Compound Pt1377: R=Ph, R'=2,4-($^i$Pr)$_2$-3-dibenzofuran,
Compound Pt1378 through Pt1391, each represented by the formula

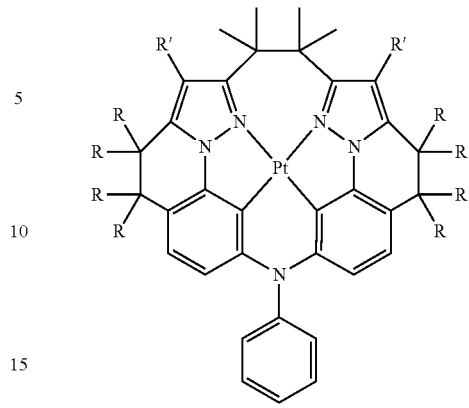

wherein in Compound Pt1378: R=Me, R'=H,
in Compound Pt1379: R=Me, R'=Me,
in Compound Pt1380: R=Me, R'=$^i$Pr,
in Compound Pt1381: R=Me, R'=Ph,
in Compound Pt1382: R=Me, R'=2,6-($^i$Pr)$_2$Ph,
in Compound Pt1383: R=Me, R'=2,6-($^i$Pr)$_2$-4-biphenyl,
in Compound Pt1384: R=Me, R'=2,4-($^i$Pr)$_2$-3-dibenzofuran,
in Compound Pt1385: R=Ph, R'=H,
in Compound Pt1386: R=Ph, R'=Me,
in Compound Pt1387: R=Ph, R'=$^i$Pr,
in Compound Pt1388: R=Ph, R'=Ph,
in Compound Pt1389: R=Ph, R'=2,6-($^i$Pr)$_2$Ph,
in Compound Pt1390: R=Ph, R'=2,6-($^i$Pr)$_2$-4-biphenyl,
in Compound Pt1391: R=Ph, R'=2,4-($^i$Pr)$_2$-3-dibenzofuran,
Compound Pt1392 through Pt1405, each represented by the formula

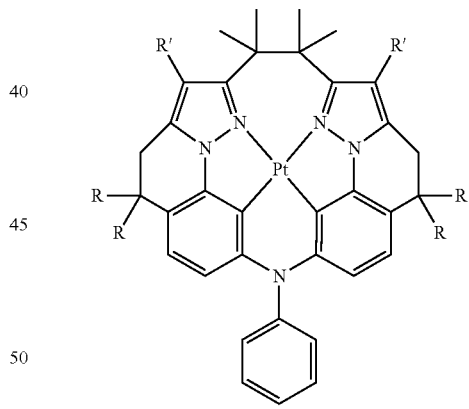

wherein in Compound Pt1392: R=Me, R'=H
in Compound Pt1393: R=Me, R'=Me
in Compound Pt1394: R=Me, R'=$^i$Pr
in Compound Pt1395: R=Me, R'=Ph
in Compound Pt1396: R=Me, R'=2,6-($^i$Pr)$_2$Ph
in Compound Pt1397: R=Me, R'=2,6-($^i$Pr)$_2$-4-biphenyl
in Compound Pt1398: R=Me, R'=2,4-($^i$Pr)$_2$-3-dibenzofuran
in Compound Pt1399: R=Ph, R'=H
in Compound Pt1400: R=Ph, R'=Me
in Compound Pt1401: R=Ph, R'=$^i$Pr
in Compound Pt1402: R=Ph, R'=Ph
in Compound Pt1403: R=Ph, R'=2,6-($^i$Pr)$_2$Ph
in Compound Pt1404: R=Ph, R'=2,6-($^i$Pr)$_2$-4-biphenyl
in Compound Pt1405: R=Ph, R'=2,4-($^i$Pr)$_2$-3-dibenzofuran Compound Pt1406 through Pt1419, each represented by the formula

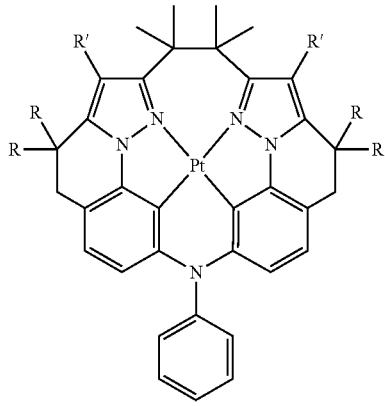

wherein in Compound Pt1406: R=Me, R'=H,
in Compound Pt1407: R=Me, R'=Me,
in Compound Pt1408: R=Me, R'=$^i$Pr,
in Compound Pt1409: R=Me, R'=Ph,
in Compound Pt1410: R=Me, R'=2,6-($^i$Pr)$_2$Ph,
in Compound Pt1411: R=Me, R'=2,6-($^i$Pr)$_2$-4-biphenyl,
in Compound Pt1412: R=Me, R'=2,4-($^i$Pr)$_2$-3-dibenzofuran,
in Compound Pt1413: R=Ph, R'=H,
in Compound Pt1414: R=Ph, R'=Me,
in Compound Pt1415: R=Ph, R'=$^i$Pr,
in Compound Pt1416: R=Ph, R'=Ph,
in Compound Pt1417: R=Ph, R'=2,6-($^i$Pr)$_2$Ph,
in Compound Pt1418: R=Ph, R'=2,6-($^i$Pr)$_2$-4-biphenyl,
in Compound Pt1419: R=Ph, R'=2,4-($^i$Pr)$_2$-3-dibenzofuran,
Compound Pt1420 through Pt1433, each represented by the formula

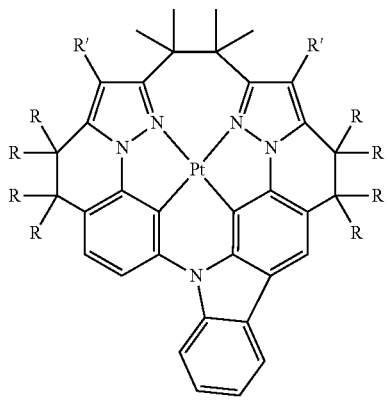

wherein in Compound Pt1420: R=Me, R'=H,
in Compound Pt1421: R=Me, R'=Me,
in Compound Pt1422: R=Me, R'=$^i$Pr,
in Compound Pt1423: R=Me, R'=Ph,
in Compound Pt1424: R=Me, R'=2,6-($^i$Pr)$_2$Ph,
in Compound Pt1425: R=Me, R'=2,6-($^i$Pr)$_2$-4-biphenyl,
in Compound Pt1426: R=Me, R'=2,4-($^i$Pr)$_2$-3-dibenzofuran,
in Compound Pt1427: R=Ph, R'=H,
in Compound Pt1428: R=Ph, R'=Me,
in Compound Pt1429: R=Ph, R'=$^i$Pr,
in Compound Pt1430: R=Ph, R'=Ph,
in Compound Pt1431: R=Ph, R'=2,6-($^i$Pr)$_2$Ph,
in Compound Pt1432: R=Ph, R'=2,6-($^i$Pr)$_2$-4-biphenyl,
in Compound Pt1433: R=Ph, R'=2,4-($^i$Pr)$_2$-3-dibenzofuran,
Compound Pt1434 through Pt1447, each represented by the formula

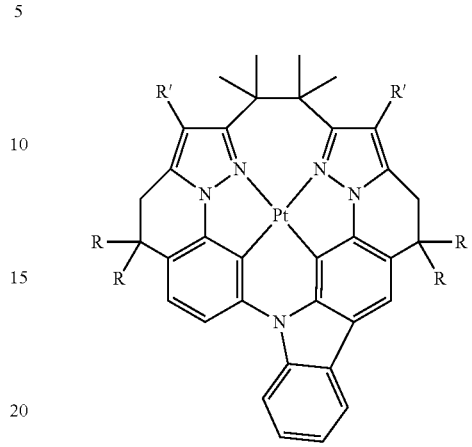

wherein in Compound Pt1434: R=Me, R'=H,
in Compound Pt1435: R=Me, R'=Me,
in Compound Pt1436: R=Me, R'=$^i$Pr,
in Compound Pt1437: R=Me, R'=Ph,
in Compound Pt1438: R=Me, R'=2,6-($^i$Pr)$_2$Ph,
in Compound Pt1439: R=Me, R'=2,6-($^i$Pr)$_2$-4-biphenyl,
in Compound Pt1440: R=Me, R'=2,4-($^i$Pr)$_2$-3-dibenzofuran,
in Compound Pt1441: R=Ph, R'=H,
in Compound Pt1442: R=Ph, R'=Me,
in Compound Pt1443: R=Ph, R'=$^i$Pr,
in Compound Pt1444: R=Ph, R'=Ph,
in Compound Pt1445: R=Ph, R'=2,6-($^i$Pr)$_2$Ph,
in Compound Pt1446: R=Ph, R'=2,6-($^i$Pr)$_2$-4-biphenyl,
in Compound Pt1447: R=Ph, R'=2,4-($^i$Pr)$_2$-3-dibenzofuran,
Compound Pt1448 through Pt1461, each represented by the formula

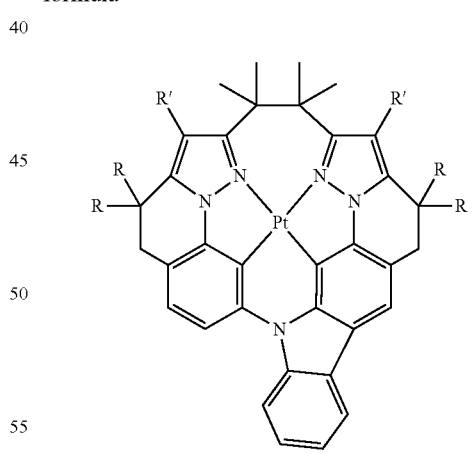

wherein in Compound Pt1448: R=Me, R'=H,
in Compound Pt1449: R=Me, R'=Me,
in Compound Pt1450: R=Me, R'=$^i$Pr,
in Compound Pt1451: R=Me, R'=Ph,
in Compound Pt1452: R=Me, R'=2,6-($^i$Pr)$_2$Ph,
in Compound Pt1453: R=Me, R'=2,6-($^i$Pr)$_2$-4-biphenyl,
in Compound Pt1454: R=Me, R'=2,4-($^i$Pr)$_2$-3-dibenzofuran,
in Compound Pt1455: R=Ph, R'=H,
in Compound Pt1456: R=Ph, R'=Me,
in Compound Pt1457: R=Ph, R'=$^i$Pr, in Compound Pt1458: R=Ph, R'=Ph,
in Compound Pt1459: R=Ph, R'=2,6-($^i$Pr)$_2$Ph,
in Compound Pt1460: R=Ph, R'=2,6-($^i$Pr)$_2$-4-biphenyl,
in Compound Pt1461: R=Ph, R'=2,4-($^i$Pr)$_2$-3-dibenzofuran,
Compound Pt1462 through Pt1475, each represented by the formula

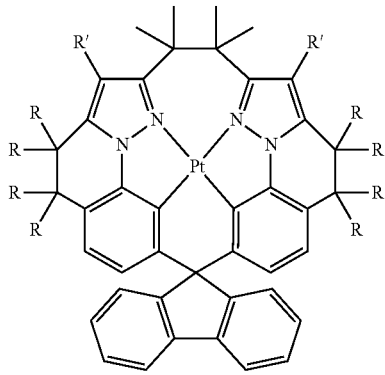

wherein in Compound Pt1462: R=Me, R'=H,
in Compound Pt1463: R=Me, R'=Me,
in Compound Pt1464: R=Me, R'=$^i$Pr,
in Compound Pt1465: R=Me, R'=Ph,
in Compound Pt1466: R=Me, R'=2,6-($^i$Pr)$_2$Ph,
in Compound Pt1467: R=Me, R'=2,6-($^i$Pr)$_2$-4-biphenyl,
in Compound Pt1468: R=Me, R'=2,4-($^i$Pr)$_2$-3-dibenzofuran,
in Compound Pt1469: R=Ph, R'=H,
in Compound Pt1470: R=Ph, R'=Me,
in Compound Pt1471: R=Ph, R'=$^i$Pr,
in Compound Pt1472: R=Ph, R'=Ph,
in Compound Pt1473: R=Ph, R'=2,6-($^i$Pr)$_2$Ph,
in Compound Pt1474: R=Ph, R'=2,6-($^i$Pr)$_2$-4-biphenyl,
in Compound Pt1475: R=Ph, R'=2,4-($^i$Pr)$_2$-3-dibenzofuran,
Compound Pt1476 through Pt1489, each represented by the formula

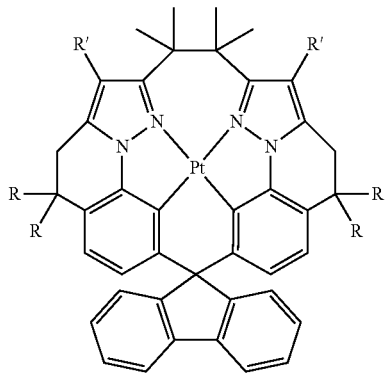

wherein in Compound Pt1476: R=Me, R'=H,
in Compound Pt1477: R=Me, R'=Me,
in Compound Pt1478: R=Me, R'=$^i$Pr,
in Compound Pt1479: R=Me, R'=Ph,
in Compound Pt1480: R=Me, R'=2,6-($^i$Pr)$_2$Ph,
in Compound Pt1481: R=Me, R'=2,6-($^i$Pr)$_2$-4-biphenyl,
in Compound Pt1482: R=Me, R'=2,4-($^i$Pr)$_2$-3-dibenzofuran,
in Compound Pt1483: R=Ph, R'=H,
in Compound Pt1484: R=Ph, R'=Me,
in Compound Pt1485: R=Ph, R'=$^i$Pr, in Compound Pt1486: R=Ph, R'=Ph,
in Compound Pt1487: R=Ph, R'=2,6-($^i$Pr)$_2$Ph,
in Compound Pt1488: R=Ph, R'=2,6-($^i$Pr)$_2$-4-biphenyl,
in Compound Pt1489: R=Ph, R'=2,4-($^i$Pr)$_2$-3-dibenzofuran,
Compound Pt1490 through Pt1503, each represented by the formula

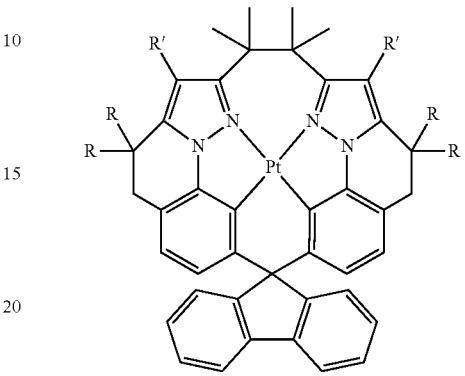

wherein in Compound Pt1490: R=Me, R'=H,
in Compound Pt1491: R=Me, R'=Me,
in Compound Pt1492: R=Me, R'=$^i$Pr,
in Compound Pt1493: R=Me, R'=Ph,
in Compound Pt1494: R=Me, R'=2,6-($^i$Pr)$_2$Ph,
in Compound Pt1495: R=Me, R'=2,6-($^i$Pr)$_2$-4-biphenyl,
in Compound Pt1496: R=Me, R'=2,4-($^i$Pr)$_2$-3-dibenzofuran,
in Compound Pt1497: R=Ph, R'=H,
in Compound Pt1498: R=Ph, R'=Me,
in Compound Pt1499: R=Ph, R'=$^i$Pr,
in Compound Pt1500: R=Ph, R'=Ph,
in Compound Pt1501: R=Ph, R'=2,6-($^i$Pr)$_2$Ph,
in Compound Pt1502: R=Ph, R'=2,6-($^i$Pr)$_2$-4-biphenyl,
in Compound Pt1503: R=Ph, R'=2,4-($^i$Pr)$_2$-3-dibenzofuran,
Compound Pt1504 through Pt1517, each represented by the formula


wherein in Compound Pt1504: R=Me, R'=H,
in Compound Pt1505: R=Me, R'=Me,
in Compound Pt1506: R=Me, R'=$^i$Pr,
in Compound Pt1507: R=Me, R'=Ph,
in Compound Pt1508: R=Me, R'=2,6-($^i$Pr)$_2$Ph,
in Compound Pt1509: R=Me, R'=2,6-($^i$Pr)$_2$-4-biphenyl,
in Compound Pt1510: R=Me, R'=2,4-($^i$Pr)$_2$-3-dibenzofuran,
in Compound Pt1511: R=Ph, R'=H,
in Compound Pt1512: R=Ph, R'=Me,
in Compound Pt1513: R=Ph, R'=$^i$Pr, in Compound Pt1514: R=Ph, R'=Ph,
in Compound Pt1515: R=Ph, R'=2,6-($^i$Pr)$_2$Ph,
in Compound Pt1516: R=Ph, R'=2,6-($^i$Pr)$_2$-4-biphenyl,
in Compound Pt1517: R=Ph, R'=2,4-($^i$Pr)$_2$-3-dibenzofuran,
Compound Pt1518 through Pt1531, each represented by the formula

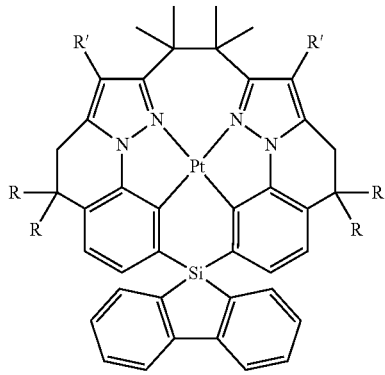

wherein in Compound Pt1518: R=Me, R'=H,
in Compound Pt1519: R=Me, R'=Me,
in Compound Pt1520: R=Me, R'=$^i$Pr,
in Compound Pt1521: R=Me, R'=Ph,
in Compound Pt1522: R=Me, R'=2,6-($^i$Pr)$_2$Ph,
in Compound Pt1523: R=Me, R'=2,6-($^i$Pr)$_2$-4-biphenyl,
in Compound Pt1524: R=Me, R'=2,4-($^i$Pr)$_2$-3-dibenzofuran,
in Compound Pt1525: R=Ph, R'=H,
in Compound Pt1526: R=Ph, R'=Me,
in Compound Pt1527: R=Ph, R'=$^i$Pr,
in Compound Pt1528: R=Ph, R'=Ph,
in Compound Pt1529: R=Ph, R'=2,6-($^i$Pr)$_2$Ph,
in Compound Pt1530: R=Ph, R'=2,6-($^i$Pr)$_2$-4-biphenyl,
in Compound Pt1531: R=Ph, R'=2,4-($^i$Pr)$_2$-3-dibenzofuran,
Compound Pt1532 through Pt1545, each represented by the formula

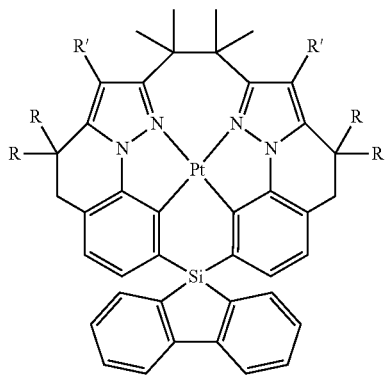

wherein in Compound Pt1532: R=Me, R'=H,
in Compound Pt1533: R=Me, R'=Me,
in Compound Pt1534: R=Me, R'=$^i$Pr,
in Compound Pt1535: R=Me, R'=Ph,
in Compound Pt1536: R=Me, R'=2,6-($^i$Pr)$_2$Ph,
in Compound Pt1537: R=Me, R'=2,6-($^i$Pr)$_2$-4-biphenyl,
in Compound Pt1538: R=Me, R'=2,4-($^i$Pr)$_2$-3-dibenzofuran,
in Compound Pt1539: R=Ph, R'=H,
in Compound Pt1540: R=Ph, R'=Me,
in Compound Pt1541: R=Ph, R'=$^i$Pr, in Compound Pt1542: R=Ph, R'=Ph,
in Compound Pt1543: R=Ph, R'=2,6-($^i$Pr)$_2$Ph,
in Compound Pt1544: R=Ph, R'=2,6-($^i$Pr)$_2$-4-biphenyl,
in Compound Pt1545: R=Ph, R'=2,4-($^i$Pr)$_2$-3-dibenzofuran,
Compound Pt1546 through Pt1559, each represented by the formula

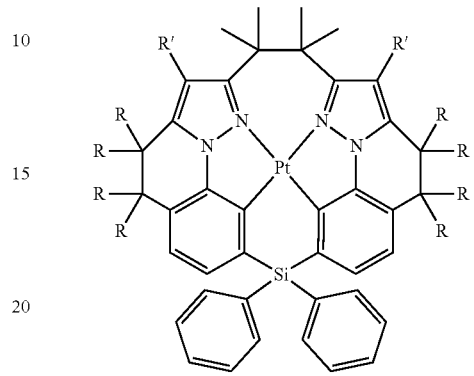

wherein in Compound Pt1546: R=Me, R'=H,
in Compound Pt1547: R=Me, R'=Me,
in Compound Pt1548: R=Me, R'=$^i$Pr,
in Compound Pt1549: R=Me, R'=Ph,
in Compound Pt1550: R=Me, R'=2,6-($^i$Pr)$_2$Ph,
in Compound Pt1551: R=Me, R'=2,6-($^i$Pr)$_2$-4-biphenyl,
in Compound Pt1552: R=Me, R'=2,4-($^i$Pr)$_2$-3-dibenzofuran,
in Compound Pt1553: R=Ph, R'=H,
in Compound Pt1554: R=Ph, R'=Me,
in Compound Pt1555: R=Ph, R'=$^i$Pr,
in Compound Pt1556: R=Ph, R'=Ph,
in Compound Pt1557: R=Ph, R'=2,6-($^i$Pr)$_2$Ph,
in Compound Pt1558: R=Ph, R'=2,6-($^i$Pr)$_2$-4-biphenyl,
in Compound Pt1559: R=Ph, R'=2,4-($^i$Pr)$_2$-3-dibenzofuran,
Compound Pt1560 through Pt1573, each represented by the formula

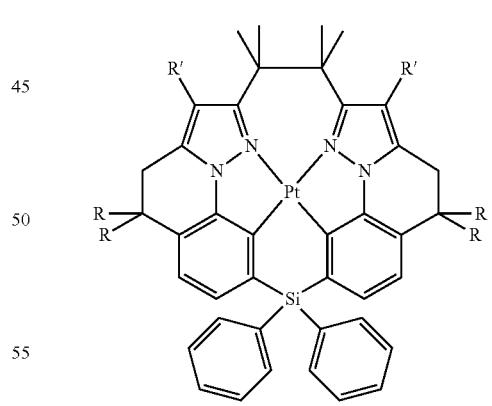

wherein in Compound Pt1560: R=Me, R'=H,
in Compound Pt1561: R=Me, R'=Me,
in Compound Pt1562: R=Me, R'=$^i$Pr,
in Compound Pt1563: R=Me, R'=Ph,
in Compound Pt1564: R=Me, R'=2,6-($^i$Pr)$_2$Ph,
in Compound Pt1565: R=Me, R'=2,6-($^i$Pr)$_2$-4-biphenyl,
in Compound Pt1566: R=Me, R'=2,4-($^i$Pr)$_2$-3-dibenzofuran,
in Compound Pt1567: R=Ph, R'=H,
in Compound Pt1568: R=Ph, R'=Me, in Compound Pt1569: R=Ph, R'=$^i$Pr,
in Compound Pt1570: R=Ph, R'=Ph,
in Compound Pt1571: R=Ph, R'=2,6-($^i$Pr)$_2$Ph,
in Compound Pt1572: R=Ph, R'=2,6-($^i$Pr)$_2$-4-biphenyl,
in Compound Pt1573: R=Ph, R'=2,4-($^i$Pr)$_2$-3-dibenzofuran,
Compound Pt1574 through Pt1587, each represented by the formula

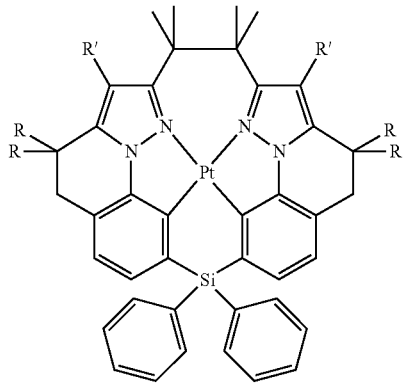

wherein in Compound Pt1574: R=Me, R'=H,
in Compound Pt1575: R=Me, R'=Me,
in Compound Pt1576: R=Me, R'=$^i$Pr,
in Compound Pt1577: R=Me, R'=Ph,
in Compound Pt1578: R=Me, R'=2,6-($^i$Pr)$_2$Ph,
in Compound Pt1579: R=Me, R'=2,6-($^i$Pr)$_2$-4-biphenyl,
in Compound Pt1580: R=Me, R'=2,4-($^i$Pr)$_2$-3-dibenzofuran,
in Compound Pt1581: R=Ph, R'=H,
in Compound Pt1582: R=Ph, R'=Me,
in Compound Pt1583: R=Ph, R'=$^i$Pr,
in Compound Pt1584: R=Ph, R'=Ph,
in Compound Pt1585: R=Ph, R'=2,6-($^i$Pr)$_2$Ph,
in Compound Pt1586: R=Ph, R'=2,6-($^i$Pr)$_2$-4-biphenyl,
in Compound Pt1587: R=Ph, R'=2,4-($^i$Pr)$_2$-3-dibenzofuran,
Compound Pt1588 through Pt1601, each represented by the formula

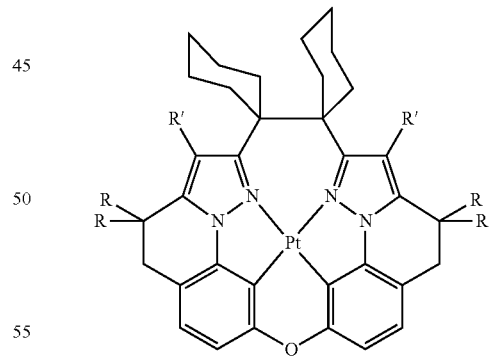

wherein in Compound Pt1588: R=Me, R'=H,
in Compound Pt1589: R=Me, R'=Me,
in Compound Pt1590: R=Me, R'=$^i$Pr,
in Compound Pt1591: R=Me, R'=Ph,
in Compound Pt1592: R=Me, R'=2,6-($^i$Pr)$_2$Ph,
in Compound Pt1593: R=Me, R'=2,6-($^i$Pr)$_2$-4-biphenyl,
in Compound Pt1594: R=Me, R'=2,4-($^i$Pr)$_2$-3-dibenzofuran,
in Compound Pt1595: R=Ph, R'=H,
in Compound Pt1596: R=Ph, R'=Me, in Compound Pt1597: R=Ph, R'=$^i$Pr,
in Compound Pt1598: R=Ph, R'=Ph,
in Compound Pt1599: R=Ph, R'=2,6-($^i$Pr)$_2$Ph,
in Compound Pt1600: R=Ph, R'=2,6-($^i$Pr)$_2$-4-biphenyl,
in Compound Pt1601: R=Ph, R'=2,4-($^i$Pr)$_2$-3-dibenzofuran,
Compound Pt1602 through Pt1615, each represented by the formula

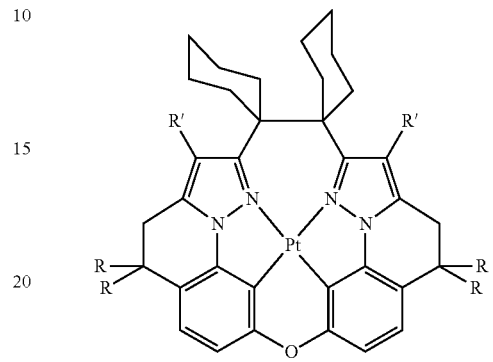

wherein in Compound Pt1602: R=Me, R'=H,
in Compound Pt1603: R=Me, R'=Me,
in Compound Pt1604: R=Me, R'=$^i$Pr,
in Compound Pt1605: R=Me, R'=Ph,
in Compound Pt1606: R=Me, R'=2,6-($^i$Pr)$_2$Ph,
in Compound Pt1607: R=Me, R'=2,6-($^i$Pr)$_2$-4-biphenyl,
in Compound Pt1608: R=Me, R'=2,4-($^i$Pr)$_2$-3-dibenzofuran,
in Compound Pt1609: R=Ph, R'=H,
in Compound Pt1610: R=Ph, R'=Me,
in Compound Pt1611: R=Ph, R'=$^i$Pr,
in Compound Pt1612: R=Ph, R'=Ph,
in Compound Pt1613: R=Ph, R'=2,6-($^i$Pr)$_2$Ph,
in Compound Pt1614: R=Ph, R'=2,6-($^i$Pr)$_2$-4-biphenyl,
in Compound Pt1615: R=Ph, R'=2,4-($^i$Pr)$_2$-3-dibenzofuran,
Compound Pt1616 through Pt1629, each represented by the formula wherein in Compound Pt1616: R=Me, R'=H,
in Compound Pt1617: R=Me, R'=Me,
in Compound Pt1618: R=Me, R'=$^i$Pr,
in Compound Pt1619: R=Me, R'=Ph,
in Compound Pt1620: R=Me, R'=2,6-($^i$Pr)$_2$Ph,
in Compound Pt1621: R=Me, R'=2,6-($^i$Pr)$_2$-4-biphenyl,
in Compound Pt1622: R=Me, R'=2,4-($^i$Pr)$_2$-3-dibenzofuran,
in Compound Pt1623: R=Ph, R'=H,
in Compound Pt1624: R=Ph, R'=Me,
in Compound Pt1625: R=Ph, R'=$^i$Pr, in Compound Pt1626: R=Ph, R'=Ph,
in Compound Pt1627: R=Ph, R'=2,6-($^i$Pr)$_2$Ph,
in Compound Pt1628: R=Ph, R'=2,6-($^i$Pr)$_2$-4-biphenyl,
in Compound Pt1629: R=Ph, R'=2,4-($^i$Pr)$_2$-3-dibenzofuran,
Compound Pt1630 through Pt1643, each represented by the formula

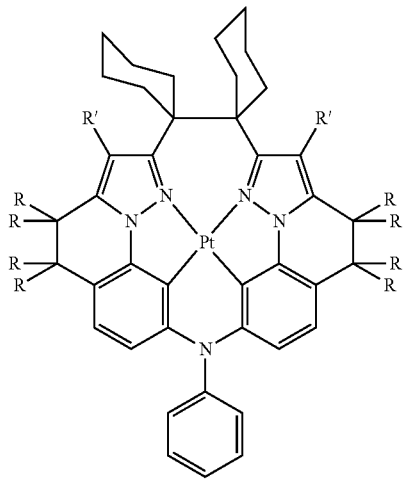

wherein in Compound Pt1630: R=Me, R'=H,
in Compound Pt1631: R=Me, R'=Me,
in Compound Pt1632: R=Me, R'=$^i$Pr,
in Compound Pt1633: R=Me, R'=Ph,
in Compound Pt1634: R=Me, R'=2,6-($^i$Pr)$_2$Ph,
in Compound Pt1635: R=Me, R'=2,6-($^i$Pr)$_2$-4-biphenyl,
in Compound Pt1636: R=Me, R'=2,4-($^i$Pr)$_2$-3-dibenzofuran,
in Compound Pt1637: R=Ph, R'=H,
in Compound Pt1638: R=Ph, R'=Me,
in Compound Pt1639: R=Ph, R'=$^i$Pr,
in Compound Pt1640: R=Ph, R'=Ph,
in Compound Pt1641: R=Ph, R'=2,6-($^i$Pr)$_2$Ph,
in Compound Pt1642: R=Ph, R'=2,6-($^i$Pr)$_2$-4-biphenyl,
in Compound Pt1643: R=Ph, R'=2,4-($^i$Pr)$_2$-3-dibenzofuran,
Compound Pt1644 through Pt1657, each represented by the formula

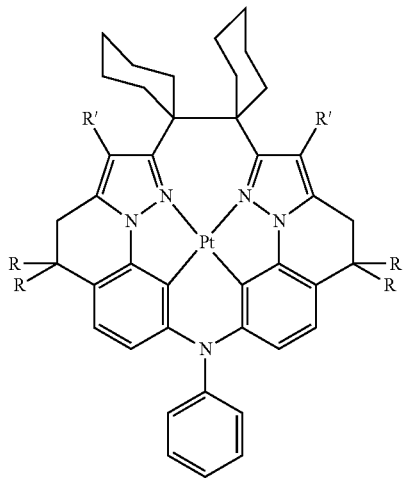

wherein in Compound Pt1644: R=Me, R'=H,
in Compound Pt1645: R=Me, R'=Me,
in Compound Pt1646: R=Me, R'=$^i$Pr,
in Compound Pt1647: R=Me, R'=Ph,
in Compound Pt1648: R=Me, R'=2,6-($^i$Pr)$_2$Ph,
in Compound Pt1649: R=Me, R'=2,6-($^i$Pr)$_2$-4-biphenyl,
in Compound Pt1650: R=Me, R'=2,4-($^i$Pr)$_2$-3-dibenzofuran,
in Compound Pt1651: R=Ph, R'=H,
in Compound Pt1652: R=Ph, R'=Me,
in Compound Pt1653: R=Ph, R'=$^i$Pr,
in Compound Pt1654: R=Ph, R'=Ph,
in Compound Pt1655: R=Ph, R'=2,6-($^i$Pr)$_2$Ph,
in Compound Pt1656: R=Ph, R'=2,6-($^i$Pr)$_2$-4-biphenyl,
in Compound Pt1657: R=Ph, R'=2,4-($^i$Pr)$_2$-3-dibenzofuran,
Compound Pt1658 through Pt1671, each represented by the formula

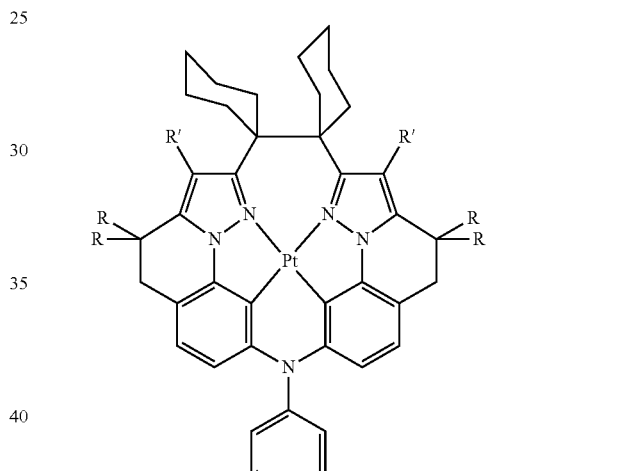

wherein in Compound Pt1658: R=Me, R'=H,
in Compound Pt1659: R=Me, R'=Me,
in Compound Pt1660: R=Me, R'=$^i$Pr,
in Compound Pt1661: R=Me, R'=Ph,
in Compound Pt1662: R=Me, R'=2,6-($^i$Pr)$_2$Ph,
in Compound Pt1663: R=Me, R'=2,6-($^i$Pr)$_2$-4-biphenyl,
in Compound Pt1664: R=Me, R'=2,4-($^i$Pr)$_2$-3-dibenzofuran,
in Compound Pt1665: R=Ph, R'=H,
in Compound Pt1666: R=Ph, R'=Me,
in Compound Pt1667: R=Ph, R'=$^i$Pr,
in Compound Pt1668: R=Ph, R'=Ph,
in Compound Pt1669: R=Ph, R'=2,6-($^i$Pr)$_2$Ph,
in Compound Pt1670: R=Ph, R'=2,6-($^i$Pr)$_2$-4-biphenyl,
in Compound Pt1671: R=Ph, R'=2,4-($^i$Pr)$_2$-3-dibenzofuran,
Compound Pt1672 through Pt1685, each represented by the formula

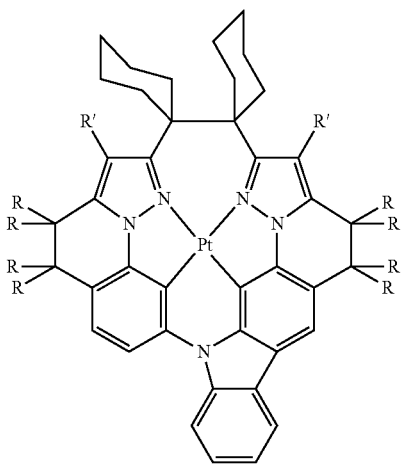

wherein in Compound Pt1672: R=Me, R'=H,
in Compound Pt1673: R=Me, R'=Me,
in Compound Pt1674: R=Me, R'=$^i$Pr,
in Compound Pt1675: R=Me, R'=Ph,
in Compound Pt1676: R=Me, R'=2,6-($^i$Pr)$_2$Ph,
in Compound Pt1677: R=Me, R'=2,6-($^i$Pr)$_2$-4-biphenyl,
in Compound Pt1678: R=Me, R'=2,4-($^i$Pr)$_2$-3-dibenzofuran,
in Compound Pt1679: R=Ph, R'=H,
in Compound Pt1680: R=Ph, R'=Me,
in Compound Pt1681: R=Ph, R'=$^i$Pr,
in Compound Pt1682: R=Ph, R'=Ph,
in Compound Pt1683: R=Ph, R'=2,6-($^i$Pr)$_2$Ph,
in Compound Pt1684: R=Ph, R'=2,6-($^i$Pr)$_2$-4-biphenyl,
in Compound Pt1685: R=Ph, R'=2,4-($^i$Pr)$_2$-3-dibenzofuran,
Compound Pt1686 through Pt1699, each represented by the formula

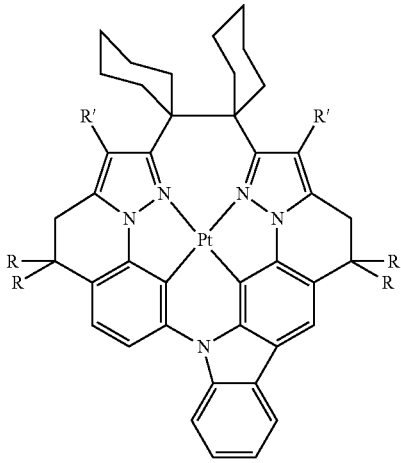

wherein in Compound Pt1686: R=Me, R'=H,
in Compound Pt1687: R=Me, R'=Me,
in Compound Pt1688: R=Me, R'=$^i$Pr,
in Compound Pt1689: R=Me, R'=Ph,
in Compound Pt1690: R=Me, R'=2,6-($^i$Pr)$_2$Ph,
in Compound Pt1691: R=Me, R'=2,6-($^i$Pr)$_2$-4-biphenyl,
in Compound Pt1692: R=Me, R'=2,4-($^i$Pr)$_2$-3-dibenzofuran,
in Compound Pt1693: R=Ph, R'=H,
in Compound Pt1694: R=Ph, R'=Me,
in Compound Pt1695: R=Ph, R'=$^i$Pr,
in Compound Pt1696: R=Ph, R'=Ph,
in Compound Pt1697: R=Ph, R'=2,6-($^i$Pr)$_2$Ph,
in Compound Pt1698: R=Ph, R'=2,6-($^i$Pr)$_2$-4-biphenyl,
in Compound Pt1699: R=Ph, R'=2,4-($^i$Pr)$_2$-3-dibenzofuran,
Compound Pt1700 through Pt1713, each represented by the formula

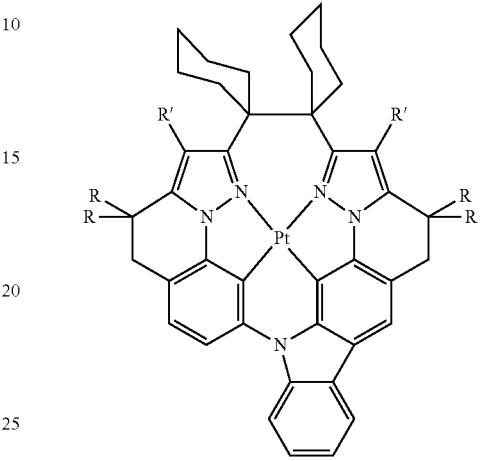

wherein in Compound Pt1700: R=Me, R'=H,
in Compound Pt1701: R=Me, R'=Me,
in Compound Pt1702: R=Me, R'=$^i$Pr,
in Compound Pt1703: R=Me, R'=Ph,
in Compound Pt1704: R=Me, R'=2,6-($^i$Pr)$_2$Ph,
in Compound Pt1705: R=Me, R'=2,6-($^i$Pr)$_2$-4-biphenyl,
in Compound Pt1706: R=Me, R'=2,4-($^i$Pr)$_2$-3-dibenzofuran,
in Compound Pt1707: R=Ph, R'=H,
in Compound Pt1708: R=Ph, R'=Me,
in Compound Pt1709: R=Ph, R'=$^i$Pr,
in Compound Pt1710: R=Ph, R'=Ph,
in Compound Pt1711: R=Ph, R'=2,6-($^i$Pr)$_2$Ph,
in Compound Pt1712: R=Ph, R'=2,6-($^i$Pr)$_2$-4-biphenyl,
in Compound Pt1713: R=Ph, R'=2,4-($^i$Pr)$_2$-3-dibenzofuran,
Compound Pt1714 through Pt1727, each represented by the formula

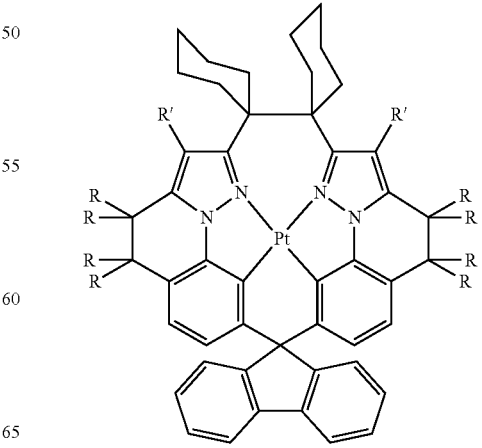

wherein in Compound Pt1714: R=Me, R'=H,
in Compound Pt1715: R=Me, R'=Me,
in Compound Pt1716: R=Me, R'=$^i$Pr,
in Compound Pt1717: R=Me, R'=Ph,
in Compound Pt1718: R=Me, R'=2,6-($^i$Pr)$_2$Ph,
in Compound Pt1719: R=Me, R'=2,6-($^i$Pr)$_2$-4-biphenyl,
in Compound Pt1720: R=Me, R'=2,4-($^i$Pr)$_2$-3-dibenzofuran,
in Compound Pt1721: R=Ph, R'=H,
in Compound Pt1722: R=Ph, R'=Me,
in Compound Pt1723: R=Ph, R'=$^i$Pr,
in Compound Pt1724: R=Ph, R'=Ph,
in Compound Pt1725: R=Ph, R'=2,6-($^i$Pr)$_2$Ph,
in Compound Pt1726: R=Ph, R'=2,6-($^i$Pr)$_2$-4-biphenyl,
in Compound Pt1727: R=Ph, R'=2,4-($^i$Pr)$_2$-3-dibenzofuran,
Compound Pt1728 through Pt1741, each represented by the formula

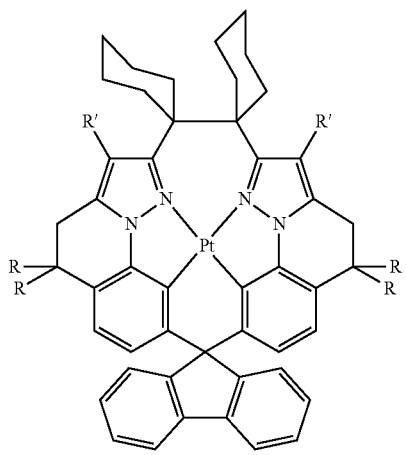

wherein in Compound Pt1728: R=Me, R'=H,
in Compound Pt1729: R=Me, R'=Me,
in Compound Pt1730: R=Me, R'=$^i$Pr,
in Compound Pt1731: R=Me, R'=Ph,
in Compound Pt1732: R=Me, R'=2,6-($^i$Pr)$_2$Ph,
in Compound Pt1733: R=Me, R'=2,6-($^i$Pr)$_2$-4-biphenyl,
in Compound Pt1734: R=Me, R'=2,4-($^i$Pr)$_2$-3-dibenzofuran,
in Compound Pt1735: R=Ph, R'=H,
in Compound Pt1736: R=Ph, R'=Me,
in Compound Pt1737: R=Ph, R'=$^i$Pr,
in Compound Pt1738: R=Ph, R'=Ph,
in Compound Pt1739: R=Ph, R'=2,6-($^i$Pr)$_2$Ph,
in Compound Pt1740: R=Ph, R'=2,6-($^i$Pr)$_2$-4-biphenyl,
in Compound Pt1741: R=Ph, R'=2,4-($^i$Pr)$_2$-3-dibenzofuran,
Compound Pt1742 through Pt1755, each represented by the formula

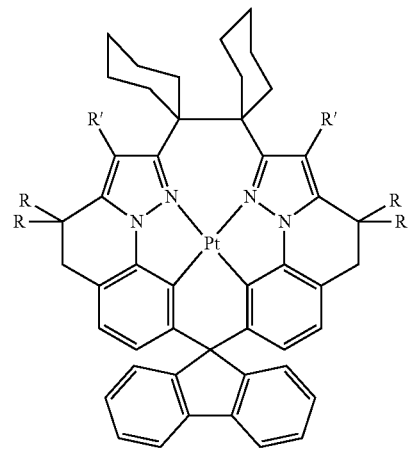

wherein in Compound Pt1742: R=Me, R'=H,
in Compound Pt1743: R=Me, R'=Me,
in Compound Pt1744: R=Me, R'=$^i$Pr,
in Compound Pt1745: R=Me, R'=Ph,
in Compound Pt1746: R=Me, R'=2,6-($^i$Pr)$_2$Ph,
in Compound Pt1747: R=Me, R'=2,6-($^i$Pr)$_2$-4-biphenyl,
in Compound Pt1748: R=Me, R'=2,4-($^i$Pr)$_2$-3-dibenzofuran,
in Compound Pt1749: R=Ph, R'=H,
in Compound Pt1750: R=Ph, R'=Me,
in Compound Pt1751: R=Ph, R'=$^i$Pr,
in Compound Pt1752: R=Ph, R'=Ph,
in Compound Pt1753: R=Ph, R'=2,6-($^i$Pr)$_2$Ph,
in Compound Pt1754: R=Ph, R'=2,6-($^i$Pr)$_2$-4-biphenyl,
in Compound Pt1755: R=Ph, R'=2,4-($^i$Pr)$_2$-3-dibenzofuran,
Compound Pt1756 through Pt1769, each represented by the formula

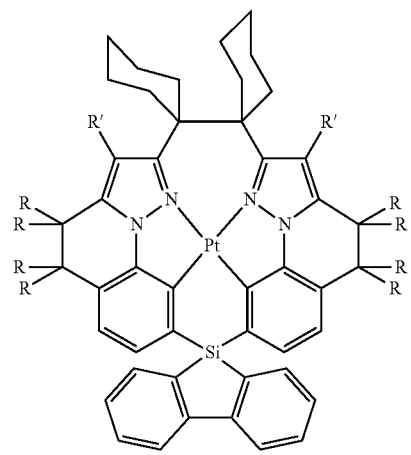

wherein in Compound Pt1756: R=Me, R'=H,
in Compound Pt1757: R=Me, R'=Me,
in Compound Pt1758: R=Me, R'=$^i$Pr,
in Compound Pt1759: R=Me, R'=Ph,
in Compound Pt1760: R=Me, R'=2,6-($^i$Pr)$_2$Ph,
in Compound Pt1761: R=Me, R'=2,6-($^i$Pr)$_2$-4-biphenyl,
in Compound Pt1762: R=Me, R'=2,4-($^i$Pr)$_2$-3-dibenzofuran,
in Compound Pt1763: R=Ph, R'=H,
in Compound Pt1764: R=Ph, R'=Me,
in Compound Pt1765: R=Ph, R'=$^i$Pr,
in Compound Pt1766: R=Ph, R'=Ph, in Compound Pt1767: R=Ph, R'=2,6-($^i$Pr)$_2$Ph,
in Compound Pt1768: R=Ph, R'=2,6-($^i$Pr)$_2$-4-biphenyl,
in Compound Pt1769: R=Ph, R'=2,4-($^i$Pr)$_2$-3-dibenzofuran,
Compound Pt1770 through Pt1783, each represented by the formula

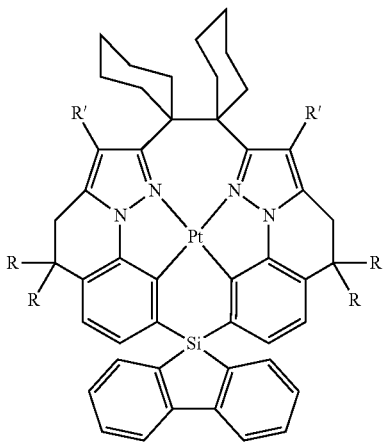

wherein in Compound Pt1770: R=Me, R'=H,
in Compound Pt1771: R=Me, R'=Me,
in Compound Pt1772: R=Me, R'=$^i$Pr,
in Compound Pt1773: R=Me, R'=Ph,
in Compound Pt1774: R=Me, R'=2,6-($^i$Pr)$_2$Ph,
in Compound Pt1775: R=Me, R'=2,6-($^i$Pr)$_2$-4-biphenyl,
in Compound Pt1776: R=Me, R'=2,4-($^i$Pr)$_2$-3-dibenzofuran,
in Compound Pt1777: R=Ph, R'=H,
in Compound Pt1778: R=Ph, R'=Me,
in Compound Pt1779: R=Ph, R'=$^i$Pr,
in Compound Pt1780: R=Ph, R'=Ph,
in Compound Pt1781: R=Ph, R'=2,6-($^i$Pr)$_2$Ph,
in Compound Pt1782: R=Ph, R'=2,6-($^i$Pr)$_2$-4-biphenyl,
in Compound Pt1783: R=Ph, R'=2,4-($^i$Pr)$_2$-3-dibenzofuran,
Compound Pt1784 through Pt1797, each represented by the formula

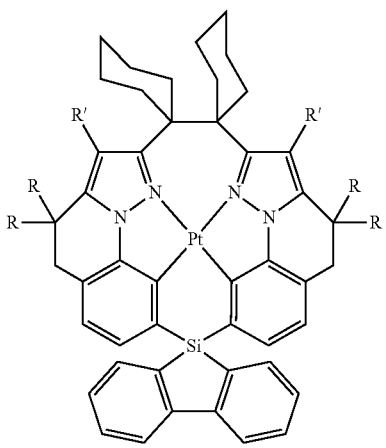

wherein in Compound Pt1784: R=Me, R'=H,
in Compound Pt1785: R=Me, R'=Me,
in Compound Pt1786: R=Me, R'=$^i$Pr,
in Compound Pt1787: R=Me, R'=Ph,
in Compound Pt1788: R=Me, R'=2,6-($^i$Pr)$_2$Ph,
in Compound Pt1789: R=Me, R'=2,6-($^i$Pr)$_2$-4-biphenyl, in Compound Pt1790: R=Me, R'=2,4-($^i$Pr)$_2$-3-dibenzofuran,
in Compound Pt1791: R=Ph, R'=H,
in Compound Pt1792: R=Ph, R'=Me,
in Compound Pt1793: R=Ph, R'=$^i$Pr,
in Compound Pt1794: R=Ph, R'=Ph,
in Compound Pt1795: R=Ph, R'=2,6-($^i$Pr)$_2$Ph,
in Compound Pt1796: R=Ph, R'=2,6-($^i$Pr)$_2$-4-biphenyl,
in Compound Pt1797: R=Ph, R'=2,4-($^i$Pr)$_2$-3-dibenzofuran,
Compound Pt1798 through Pt1811, each represented by the formula

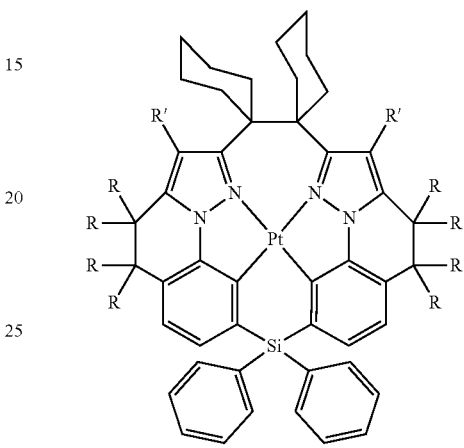

wherein in Compound Pt1798: R=Me, R'=H,
in Compound Pt1799: R=Me, R'=Me,
in Compound Pt1800: R=Me, R'=$^i$Pr,
in Compound Pt1801: R=Me, R'=Ph,
in Compound Pt1802: R=Me, R'=2,6-($^i$Pr)$_2$Ph,
in Compound Pt1803: R=Me, R'=2,6-($^i$Pr)$_2$-4-biphenyl,
in Compound Pt1804: R=Me, R'=2,4-($^i$Pr)$_2$-3-dibenzofuran,
in Compound Pt1805: R=Ph, R'=H,
in Compound Pt1806: R=Ph, R'=Me,
in Compound Pt1807: R=Ph, R'=$^i$Pr,
in Compound Pt1808: R=Ph, R'=Ph,
in Compound Pt1809: R=Ph, R'=2,6-($^i$Pr)$_2$Ph,
in Compound Pt1810: R=Ph, R'=2,6-($^i$Pr)$_2$-4-biphenyl,
in Compound Pt1811: R=Ph, R'=2,4-($^i$Pr)$_2$-3-dibenzofuran,
Compound Pt1812 through Pt1825, each represented by the formula

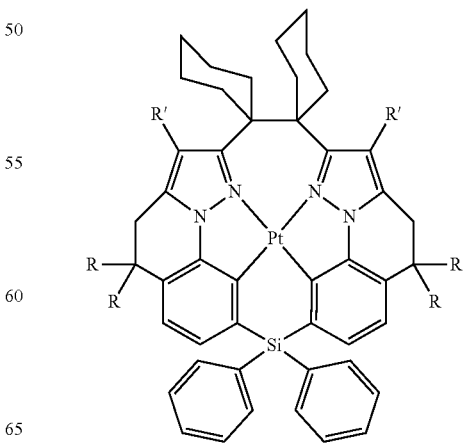

wherein in Compound Pt1812: R=Me, R'=H,
in Compound Pt1813: R=Me, R'=Me,
in Compound Pt1814: R=Me, R'=$^i$Pr,
in Compound Pt1815: R=Me, R'=Ph,
in Compound Pt1816: R=Me, R'=2,6-($^i$Pr)$_2$Ph,
in Compound Pt1817: R=Me, R'=2,6-($^i$Pr)$_2$-4-biphenyl,
in Compound Pt1818: R=Me, R'=2,4-($^i$Pr)$_2$-3-dibenzofuran,
in Compound Pt1819: R=Ph, R'=H,
in Compound Pt1820: R=Ph, R'=Me,
in Compound Pt1821: R=Ph, R'=$^i$Pr,
in Compound Pt1822: R=Ph, R'=Ph,
in Compound Pt1823: R=Ph, R'=2,6-($^i$Pr)$_2$Ph,
in Compound Pt1824: R=Ph, R'=2,6-($^i$Pr)$_2$-4-biphenyl,
in Compound Pt1825: R=Ph, R'=2,4-($^i$Pr)$_2$-3-dibenzofuran,
Compound Pt1826 through Pt1839, each represented by the formula

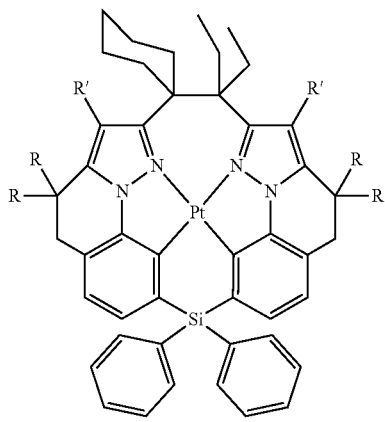

wherein in Compound Pt1826: R=Me, R'=H,
in Compound Pt1827: R=Me, R'=Me,
in Compound Pt1828: R=Me, R'=$^i$Pr,
in Compound Pt1829: R=Me, R'=Ph,
in Compound Pt1830: R=Me, R'=2,6-($^i$Pr)$_2$Ph,
in Compound Pt1831: R=Me, R'=2,6-($^i$Pr)$_2$-4-biphenyl,
in Compound Pt1832: R=Me, R'=2,4-($^i$Pr)$_2$-3-dibenzofuran,
in Compound Pt1833: R=Ph, R'=H,
in Compound Pt1834: R=Ph, R'=Me,
in Compound Pt1835: R=Ph, R'=$^i$Pr,
in Compound Pt1836: R=Ph, R'=Ph,
in Compound Pt1837: R=Ph, R'=2,6-($^i$Pr)$_2$Ph,
in Compound Pt1838: R=Ph, R'=2,6-($^i$Pr)$_2$-4-biphenyl,
in Compound Pt1839: R=Ph, R'=2,4-($^i$Pr)$_2$-3-dibenzofuran,
Compound Pt1840 through Pt1853, each represented by the formula

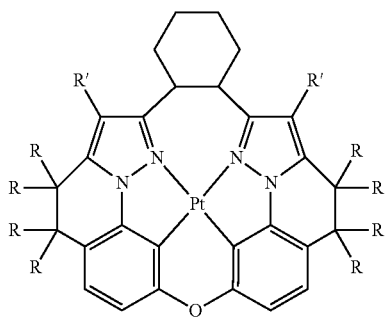

wherein in Compound Pt1840: R=Me, R'=H,
in Compound Pt1841: R=Me, R'=Me,
in Compound Pt1842: R=Me, R'=$^i$Pr,
in Compound Pt1843: R=Me, R'=Ph,
in Compound Pt1844: R=Me, R'=2,6-($^i$Pr)$_2$Ph,
in Compound Pt1845: R=Me, R'=2,6-($^i$Pr)$_2$-4-biphenyl,
in Compound Pt1846: R=Me, R'=2,4-($^i$Pr)$_2$-3-dibenzofuran,
in Compound Pt1847: R=Ph, R'=H,
in Compound Pt1848: R=Ph, R'=Me,
in Compound Pt1849: R=Ph, R'=$^i$Pr,
in Compound Pt1850: R=Ph, R'=Ph,
in Compound Pt1851: R=Ph, R'=2,6-($^i$Pr)$_2$Ph,
in Compound Pt1852: R=Ph, R'=2,6-($^i$Pr)$_2$-4-biphenyl,
in Compound Pt1853: R=Ph, R'=2,4-($^i$Pr)$_2$-3-dibenzofuran,
Compound Pt1854 through Pt1867, each represented by the formula

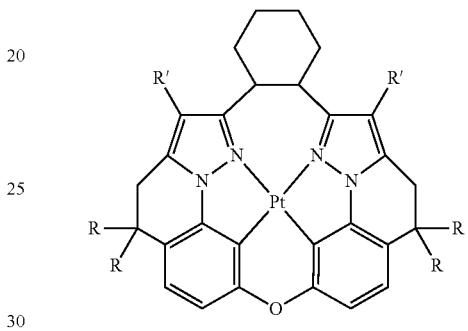

wherein in Compound Pt1854: R=Me, R'=H,
in Compound Pt1855: R=Me, R'=Me,
in Compound Pt1856: R=Me, R'=$^i$Pr,
in Compound Pt1857: R=Me, R'=Ph,
in Compound Pt1858: R=Me, R'=2,6-($^i$Pr)$_2$Ph,
in Compound Pt1859: R=Me, R'=2,6-($^i$Pr)$_2$-4-biphenyl,
in Compound Pt1860: R=Me, R'=2,4-($^i$Pr)$_2$-3-dibenzofuran,
in Compound Pt1861: R=Ph, R'=H,
in Compound Pt1862: R=Ph, R'=Me,
in Compound Pt1863: R=Ph, R'=$^i$Pr,
in Compound Pt1864: R=Ph, R'=Ph,
in Compound Pt1865: R=Ph, R'=2,6-($^i$Pr)$_2$Ph,
in Compound Pt1866: R=Ph, R'=2,6-($^i$Pr)$_2$-4-biphenyl,
in Compound Pt1867: R=Ph, R'=2,4-($^i$Pr)$_2$-3-dibenzofuran,
Compound Pt1868 through Pt1881, each represented by the formula

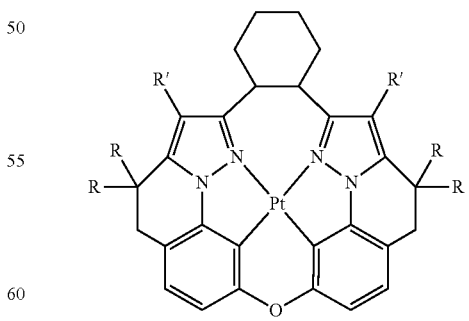

wherein in Compound Pt1868: R=Me, R'=H,
in Compound Pt1869: R=Me, R'=Me,
in Compound Pt1870: R=Me, R'=$^i$Pr,
in Compound Pt1871: R=Me, R'=Ph,
in Compound Pt1872: R=Me, R'=2,6-($^i$Pr)$_2$Ph, in Compound Pt1873: R=Me, R'=2,6-($^i$Pr)$_2$-4-biphenyl,
in Compound Pt1874: R=Me, R'=2,4-($^i$Pr)$_2$-3-dibenzofuran,
in Compound Pt1875: R=Ph, R'=H,
in Compound Pt1876: R=Ph, R'=Me,
in Compound Pt1877: R=Ph, R'=$^i$Pr,
in Compound Pt1878: R=Ph, R'=Ph,
in Compound Pt1879: R=Ph, R'=2,6-($^i$Pr)$_2$Ph,
in Compound Pt1880: R=Ph, R'=2,6-($^i$Pr)$_2$-4-biphenyl,
in Compound Pt1881: R=Ph, R'=2,4-($^i$Pr)$_2$-3-dibenzofuran,
Compound Pt1882 through Pt1895, each represented by the formula

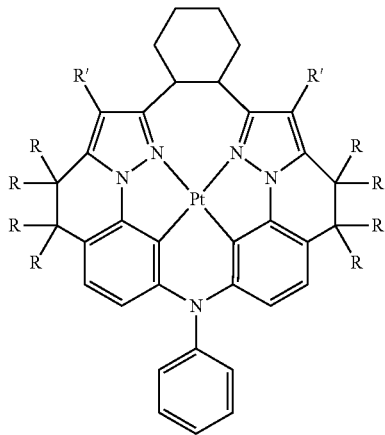

wherein in Compound Pt1882: R=Me, R'=H,
in Compound Pt1883: R=Me, R'=Me,
in Compound Pt1884: R=Me, R'=$^i$Pr,
in Compound Pt1885: R=Me, R'=Ph,
in Compound Pt1886: R=Me, R'=2,6-($^i$Pr)$_2$Ph,
in Compound Pt1887: R=Me, R'=2,6-($^i$Pr)$_2$-4-biphenyl,
in Compound Pt1888: R=Me, R'=2,4-($^i$Pr)$_2$-3-dibenzofuran,
in Compound Pt1889: R=Ph, R'=H,
in Compound Pt1890: R=Ph, R'=Me,
in Compound Pt1891: R=Ph, R'=$^i$Pr,
in Compound Pt1892: R=Ph, R'=Ph,
in Compound Pt1893: R=Ph, R'=2,6-($^i$Pr)$_2$Ph,
in Compound Pt1894: R=Ph, R'=2,6-($^i$Pr)$_2$-4-biphenyl,
in Compound Pt1895: R=Ph, R'=2,4-($^i$Pr)$_2$-3-dibenzofuran,
Compound Pt1896 through Pt1909, each represented by the formula

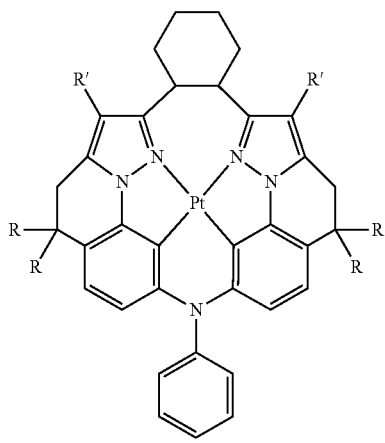

wherein in Compound Pt1896: R=Me, R'=H,
in Compound Pt1897: R=Me, R'=Me,
in Compound Pt1898: R=Me, R'=$^i$Pr,
in Compound Pt1899: R=Me, R'=Ph,
in Compound Pt1900: R=Me, R'=2,6-($^i$Pr)$_2$Ph,
in Compound Pt1901: R=Me, R'=2,6-($^i$Pr)$_2$-4-biphenyl,
in Compound Pt1902: R=Me, R'=2,4-($^i$Pr)$_2$-3-dibenzofuran,
in Compound Pt1903: R=Ph, R'=H,
in Compound Pt1904: R=Ph, R'=Me,
in Compound Pt1905: R=Ph, R'=$^i$Pr,
in Compound Pt1906: R=Ph, R'=Ph,
in Compound Pt1907: R=Ph, R'=2,6-($^i$Pr)$_2$Ph,
in Compound Pt1908: R=Ph, R'=2,6-($^i$Pr)$_2$-4-biphenyl,
in Compound Pt1909: R=Ph, R'=2,4-($^i$Pr)$_2$-3-dibenzofuran,
Compound Pt1910 through Pt1923, each represented by the formula

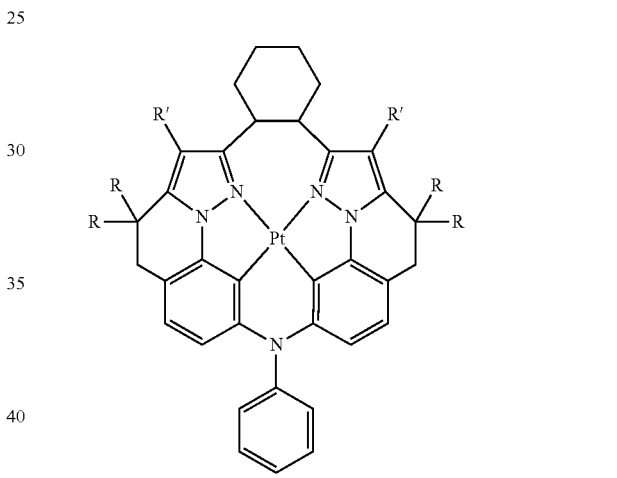

wherein in Compound Pt1910: R=Me, R'=H,
in Compound Pt1911: R=Me, R'=Me,
in Compound Pt1912: R=Me, R'=$^i$Pr,
in Compound Pt1913: R=Me, R'=Ph,
in Compound Pt1914: R=Me, R'=2,6-($^i$Pr)$_2$Ph,
in Compound Pt1915: R=Me, R'=2,6-($^i$Pr)$_2$-4-biphenyl,
in Compound Pt1916: R=Me, R'=2,4-($^i$Pr)$_2$-3-dibenzofuran,
in Compound Pt1917: R=Ph, R'=H,
in Compound Pt1918: R=Ph, R'=Me,
in Compound Pt1919: R=Ph, R'=$^i$Pr,
in Compound Pt1920: R=Ph, R'=Ph,
in Compound Pt1921: R=Ph, R'=2,6-($^i$Pr)$_2$Ph,
in Compound Pt1922: R=Ph, R'=2,6-($^i$Pr)$_2$-4-biphenyl,
in Compound Pt1923: R=Ph, R'=2,4-($^i$Pr)$_2$-3-dibenzofuran,
Compound Pt1924 through Pt1937, each represented by the formula

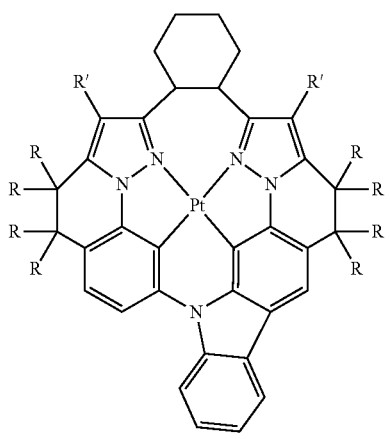

wherein in Compound Pt1924: R=Me, R'=H,
in Compound Pt1925: R=Me, R'=Me,
in Compound Pt1926: R=Me, R'=$^i$Pr,
in Compound Pt1927: R=Me, R'=Ph,
in Compound Pt1928: R=Me, R'=2,6-($^i$Pr)$_2$Ph,
in Compound Pt1929: R=Me, R'=2,6-($^i$Pr)$_2$-4-biphenyl,
in Compound Pt1930: R=Me, R'=2,4-($^i$Pr)$_2$-3-dibenzofuran,
in Compound Pt1931: R=Ph, R'=H,
in Compound Pt1932: R=Ph, R'=Me,
in Compound Pt1933: R=Ph, R'=$^i$Pr,
in Compound Pt1934: R=Ph, R'=Ph,
in Compound Pt1935: R=Ph, R'=2,6-($^i$Pr)$_2$Ph,
in Compound Pt1936: R=Ph, R'=2,6-($^i$Pr)$_2$-4-biphenyl,
in Compound Pt1937: R=Ph, R'=2,4-($^i$Pr)$_2$-3-dibenzofuran,
Compound Pt1938 through Pt1951, each represented by the formula

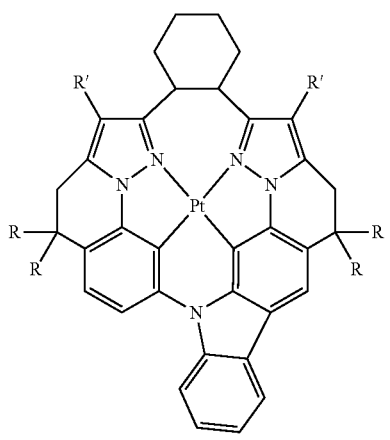

wherein in Compound Pt1938: R=Me, R'=H,
in Compound Pt1939: R=Me, R'=Me,
in Compound Pt1940: R=Me, R'=$^i$Pr,
in Compound Pt1941: R=Me, R'=Ph,
in Compound Pt1942: R=Me, R'=2,6-($^i$Pr)$_2$Ph,
in Compound Pt1943: R=Me, R'=2,6-($^i$Pr)$_2$-4-biphenyl,
in Compound Pt1944: R=Me, R'=2,4-($^i$Pr)$_2$-3-dibenzofuran,
in Compound Pt1945: R=Ph, R'=H,
in Compound Pt1946: R=Ph, R'=Me,
in Compound Pt1947: R=Ph, R'=$^i$Pr,
in Compound Pt1948: R=Ph, R'=Ph,
in Compound Pt1949: R=Ph, R'=2,6-($^i$Pr)$_2$Ph,
in Compound Pt1950: R=Ph, R'=2,6-($^i$Pr)$_2$-4-biphenyl,
in Compound Pt1951: R=Ph, R'=2,4-($^i$Pr)$_2$-3-dibenzofuran,
Compound Pt1952 through Pt1965, each represented by the formula

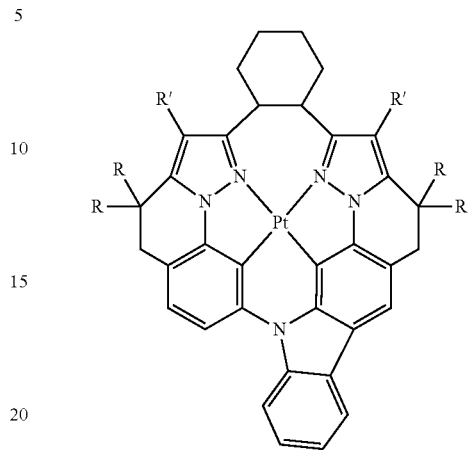

wherein in Compound Pt1952: R=Me, R'=H,
in Compound Pt1953: R=Me, R'=Me,
in Compound Pt1954: R=Me, R'=$^i$Pr,
in Compound Pt1955: R=Me, R'=Ph,
in Compound Pt1956: R=Me, R'=2,6-($^i$Pr)$_2$Ph,
in Compound Pt1957: R=Me, R'=2,6-($^i$Pr)$_2$-4-biphenyl,
in Compound Pt1958: R=Me, R'=2,4-($^i$Pr)$_2$-3-dibenzofuran,
in Compound Pt1959: R=Ph, R'=H,
in Compound Pt1960: R=Ph, R'=Me,
in Compound Pt1961: R=Ph, R'=$^i$Pr,
in Compound Pt1962: R=Ph, R'=Ph,
in Compound Pt1963: R=Ph, R'=2,6-($^i$Pr)$_2$Ph,
in Compound Pt1964: R=Ph, R'=2,6-($^i$Pr)$_2$-4-biphenyl,
in Compound Pt1965: R=Ph, R'=2,4-($^i$Pr)$_2$-3-dibenzofuran,
Compound Pt1966 through Pt1979, each represented by the formula

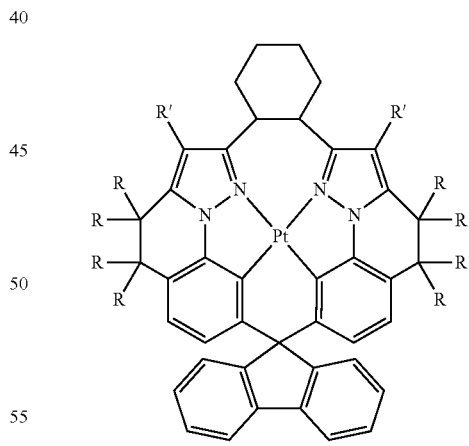

wherein in Compound Pt1966: R=Me, R'=H,
in Compound Pt1967: R=Me, R'=Me,
in Compound Pt1968: R=Me, R'=$^i$Pr,
in Compound Pt1969: R=Me, R'=Ph,
in Compound Pt1970: R=Me, R'=2,6-($^i$Pr)$_2$Ph,
in Compound Pt1971: R=Me, R'=2,6-($^i$Pr)$_2$-4-biphenyl,
in Compound Pt1972: R=Me, R'=2,4-($^i$Pr)$_2$-3-dibenzofuran,
in Compound Pt1973: R=Ph, R'=H,
in Compound Pt1974: R=Ph, R'=Me,
in Compound Pt1975: R=Ph, R'=$^i$Pr, in Compound Pt1976: R=Ph, R'=Ph,
in Compound Pt1977: R=Ph, R'=2,6-($^i$Pr)$_2$Ph,
in Compound Pt1978: R=Ph, R'=2,6-($^i$Pr)$_2$-4-biphenyl,
in Compound Pt1979: R=Ph, R'=2,4-($^i$Pr)$_2$-3-dibenzofuran,
Compound Pt1980 through Pt1993, each represented by the formula

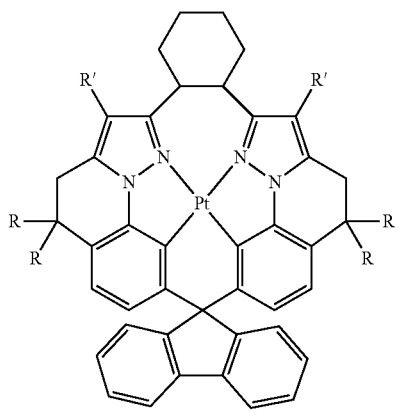

wherein in Compound Pt1980: R=Me, R'=H,
in Compound Pt1981: R=Me, R'=Me,
in Compound Pt1982: R=Me, R'=$^i$Pr,
in Compound Pt1983: R=Me, R'=Ph,
in Compound Pt1984: R=Me, R'=2,6-($^i$Pr)$_2$Ph,
in Compound Pt1985: R=Me, R'=2,6-($^i$Pr)$_2$-4-biphenyl,
in Compound Pt1986: R=Me, R'=2,4-($^i$Pr)$_2$-3-dibenzofuran,
in Compound Pt1987: R=Ph, R'=H,
in Compound Pt1988: R=Ph, R'=Me,
in Compound Pt1989: R=Ph, R'=$^i$Pr,
in Compound Pt1990: R=Ph, R'=Ph,
in Compound Pt1991: R=Ph, R'=2,6-($^i$Pr)$_2$Ph,
in Compound Pt1992: R=Ph, R'=2,6-($^i$Pr)$_2$-4-biphenyl,
in Compound Pt1993: R=Ph, R'=2,4-($^i$Pr)$_2$-3-dibenzofuran,
Compound Pt1994 through Pt2007, each represented by the formula

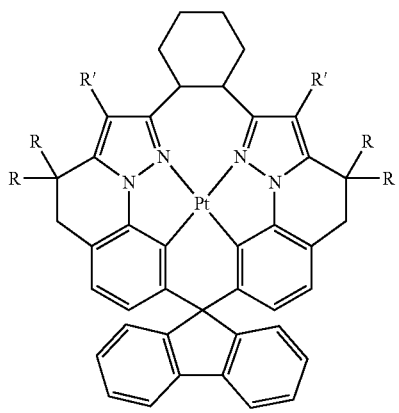

wherein in Compound Pt1994: R=Me, R'=H,
in Compound Pt1995: R=Me, R'=Me,
in Compound Pt1996: R=Me, R'=$^i$Pr,
in Compound Pt1997: R=Me, R'=Ph,
in Compound Pt1998: R=Me, R'=2,6-($^i$Pr)$_2$Ph,
in Compound Pt1999: R=Me, R'=2,6-($^i$Pr)$_2$-4-biphenyl,
in Compound Pt2000: R=Me, R'=2,4-($^i$Pr)$_2$-3-dibenzofuran, in Compound Pt2001: R=Ph, R'=H,
in Compound Pt2002: R=Ph, R'=Me,
in Compound Pt2003: R=Ph, R'=$^i$Pr,
in Compound Pt2004: R=Ph, R'=Ph,
in Compound Pt2005: R=Ph, R'=2,6-($^i$Pr)$_2$Ph,
in Compound Pt2006: R=Ph, R'=2,6-($^i$Pr)$_2$-4-biphenyl,
in Compound Pt2007: R=Ph, R'=2,4-($^i$Pr)$_2$-3-dibenzofuran,
Compound Pt2008 through Pt2021, each represented by the formula

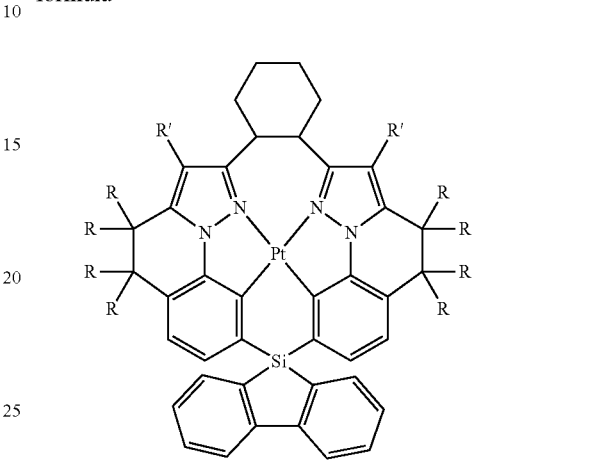

wherein in Compound Pt2008: R=Me, R'=H,
in Compound Pt2009: R=Me, R'=Me,
in Compound Pt2010: R=Me, R'=$^i$Pr,
in Compound Pt2011: R=Me, R'=Ph,
in Compound Pt2012: R=Me, R'=2,6-($^i$Pr)$_2$Ph,
in Compound Pt2013: R=Me, R'=2,6-($^i$Pr)$_2$-4-biphenyl,
in Compound Pt2014: R=Me, R'=2,4-($^i$Pr)$_2$-3-dibenzofuran,
in Compound Pt2015: R=Ph, R'=H,
in Compound Pt2016: R=Ph, R'=Me,
in Compound Pt2017: R=Ph, R'=$^i$Pr,
in Compound Pt2018: R=Ph, R'=Ph,
in Compound Pt2019: R=Ph, R'=2,6-($^i$Pr)$_2$Ph,
in Compound Pt2020: R=Ph, R'=2,6-($^i$Pr)$_2$-4-biphenyl,
in Compound Pt2021: R=Ph, R'=2,4-($^i$Pr)$_2$-3-dibenzofuran,
Compound Pt2022 through Pt2035, each represented by the formula

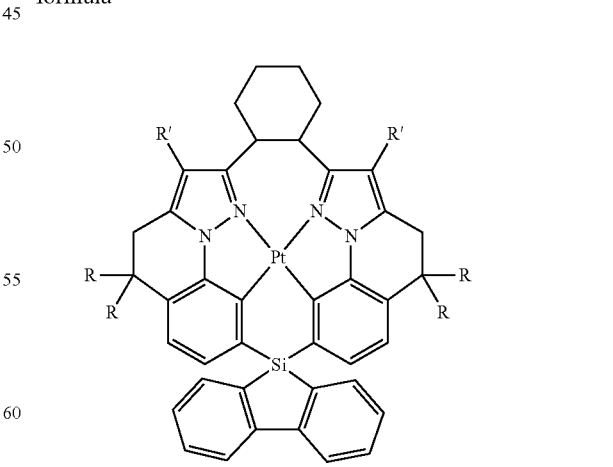

wherein in Compound Pt2022: R=Me, R'=H,
in Compound Pt2023: R=Me, R'=Me,
in Compound Pt2024: R=Me, R'=$^i$Pr,
in Compound Pt2025: R=Me, R'=Ph, in Compound Pt2026: R=Me, R'=2,6-($^i$Pr)$_2$Ph,
in Compound Pt2027: R=Me, R'=2,6-($^i$Pr)$_2$-4-biphenyl,
in Compound Pt2028: R=Me, R'=2,4-($^i$Pr)$_2$-3-dibenzofuran,
in Compound Pt2029: R=Ph, R'=H,
in Compound Pt2030: R=Ph, R'=Me,
in Compound Pt2031: R=Ph, R'=$^i$Pr,
in Compound Pt2032: R=Ph, R'=Ph,
in Compound Pt2033: R=Ph, R'=2,6-($^i$Pr)$_2$Ph,
in Compound Pt2034: R=Ph, R'=2,6-($^i$Pr)$_2$-4-biphenyl,
in Compound Pt2035: R=Ph, R'=2,4-($^i$Pr)$_2$-3-dibenzofuran,
Compound Pt2036 through Pt2049, each represented by the formula

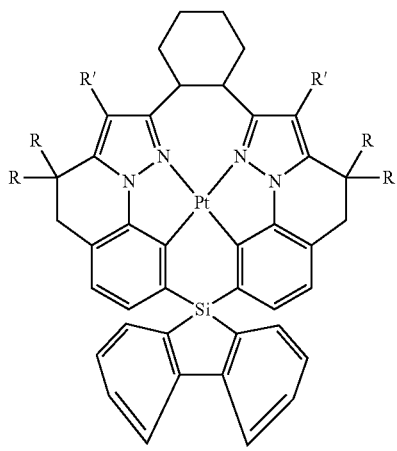

wherein in Compound Pt2036: R=Me, R'=H,
in Compound Pt2037: R=Me, R'=Me,
in Compound Pt2038: R=Me, R'=$^i$Pr,
in Compound Pt2039: R=Me, R'=Ph,
in Compound Pt2040: R=Me, R'=2,6-($^i$Pr)$_2$Ph,
in Compound Pt2041: R=Me, R'=2,6-($^i$Pr)$_2$-4-biphenyl,
in Compound Pt2042: R=Me, R'=2,4-($^i$Pr)$_2$-3-dibenzofuran,
in Compound Pt2043: R=Ph, R'=H,
in Compound Pt2044: R=Ph, R'=Me,
in Compound Pt2045: R=Ph, R'=$^i$Pr,
in Compound Pt2046: R=Ph, R'=Ph,
in Compound Pt2047: R=Ph, R'=2,6-($^i$Pr)$_2$Ph,
in Compound Pt2048: R=Ph, R'=2,6-($^i$Pr)$_2$-4-biphenyl,
in Compound Pt2049: R=Ph, R'=2,4-($^i$Pr)$_2$-3-dibenzofuran,
Compound Pt2050 through Pt2063, each represented by the formula

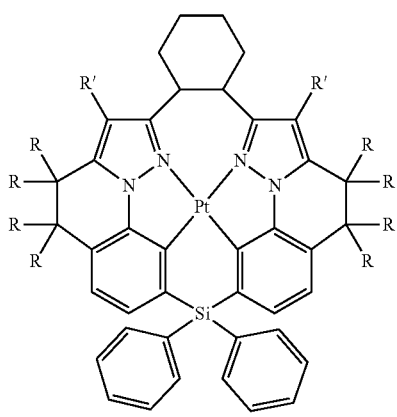

wherein in Compound Pt2050: R=Me, R'=H,
in Compound Pt2051: R=Me, R'=Me,
in Compound Pt2052: R=Me, R'=$^i$Pr,
in Compound Pt2053: R=Me, R'=Ph,
in Compound Pt2054: R=Me, R'=2,6-($^i$Pr)$_2$Ph,
in Compound Pt2055: R=Me, R'=2,6-($^i$Pr)$_2$-4-biphenyl,
in Compound Pt2056: R=Me, R'=2,4-($^i$Pr)$_2$-3-dibenzofuran,
in Compound Pt2057: R=Ph, R'=H,
in Compound Pt2058: R=Ph, R'=Me,
in Compound Pt2059: R=Ph, R'=$^i$Pr,
in Compound Pt2060: R=Ph, R'=Ph,
in Compound Pt2061: R=Ph, R'=2,6-($^i$Pr)$_2$Ph,
in Compound Pt2062: R=Ph, R'=2,6-($^i$Pr)$_2$-4-biphenyl,
in Compound Pt2063: R=Ph, R'=2,4-($^i$Pr)$_2$-3-dibenzofuran,
Compound Pt2064 through Pt2077, each represented by the formula

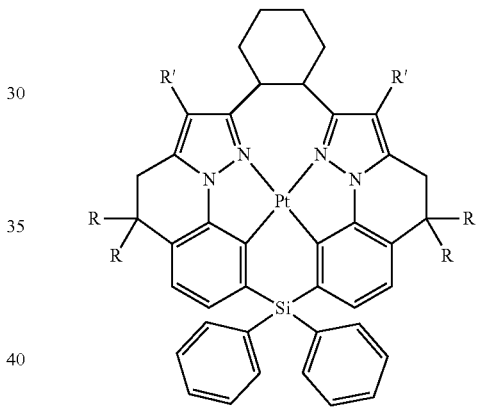

wherein in Compound Pt2064: R=Me, R'=H,
in Compound Pt2065: R=Me, R'=Me,
in Compound Pt2066: R=Me, R'=$^i$Pr,
in Compound Pt2067: R=Me, R'=Ph,
in Compound Pt2068: R=Me, R'=2,6-($^i$Pr)$_2$Ph,
in Compound Pt2069: R=Me, R'=2,6-($^i$Pr)$_2$-4-biphenyl,
in Compound Pt2070: R=Me, R'=2,4-($^i$Pr)$_2$-3-dibenzofuran,
in Compound Pt2071: R=Ph, R'=H,
in Compound Pt2072: R=Ph, R'=Me,
in Compound Pt2073: R=Ph, R'=$^i$Pr,
in Compound Pt2074: R=Ph, R'=Ph,
in Compound Pt2075: R=Ph, R'=2,6-($^i$Pr)$_2$Ph,
in Compound Pt2076: R=Ph, R'=2,6-($^i$Pr)$_2$-4-biphenyl,
in Compound Pt2077: R=Ph, R'=2,4-($^i$Pr)$_2$-3-dibenzofuran,
Compound Pt2078 through Pt2091, each represented by the formula

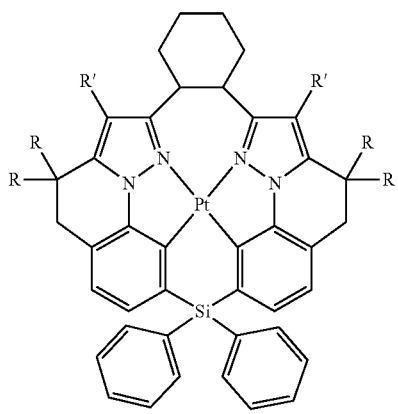

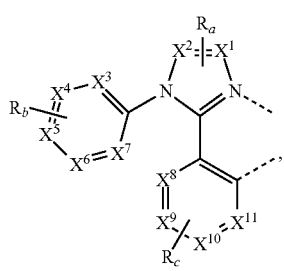


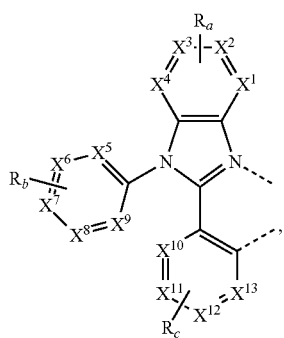

wherein in Compound Pt2078: R=Me, R'=H,
in Compound Pt2079: R=Me, R'=Me,
in Compound Pt2080: R=Me, R'=$^{i}$Pr,
in Compound Pt2081: R=Me, R'=Ph,
in Compound Pt2082: R=Me, R'=2,6-($^{i}$Pr)$_2$Ph,
in Compound Pt2083: R=Me, R'=2,6-($^{i}$Pr)$_2$-4-biphenyl,
in Compound Pt2084: R=Me, R'=2,4-($^{i}$Pr)$_2$-3-dibenzofuran,
in Compound Pt2085: R=Ph, R'=H,
in Compound Pt2086: R=Ph, R'=Me,
in Compound Pt2087: R=Ph, R'=$^{i}$Pr,
in Compound Pt2088: R=Ph, R'=Ph,
in Compound Pt2089: R=Ph, R'=2,6-($^{i}$Pr)$_2$Ph,
in Compound Pt2090: R=Ph, R'=2,6-($^{i}$Pr)$_2$-4-biphenyl,
in Compound Pt2091: R=Ph, R'=2,4-($^{i}$Pr)$_2$-3-dibenzofuran,
and Compound Pt2092

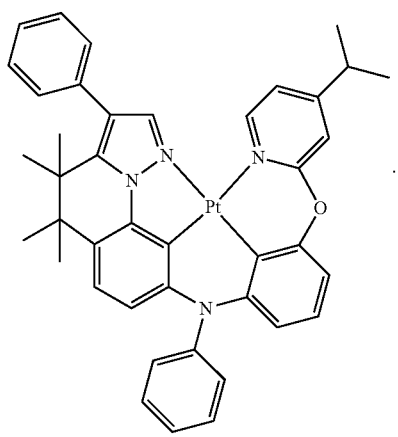

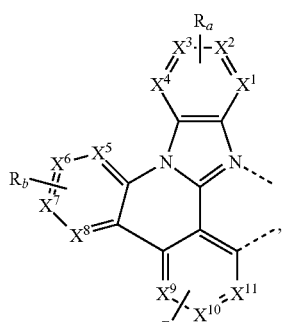

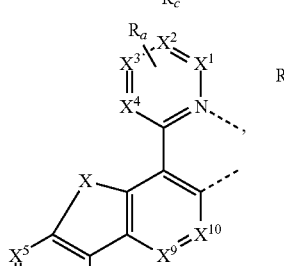


In some embodiments, M is Ir. In some embodiments, the compound is heteroleptic. In some embodiments, the compound is homoleptic.

In some embodiments, L$_B$ is different from L$_A$, and L$_B$ is selected from the group consisting of:

-continued

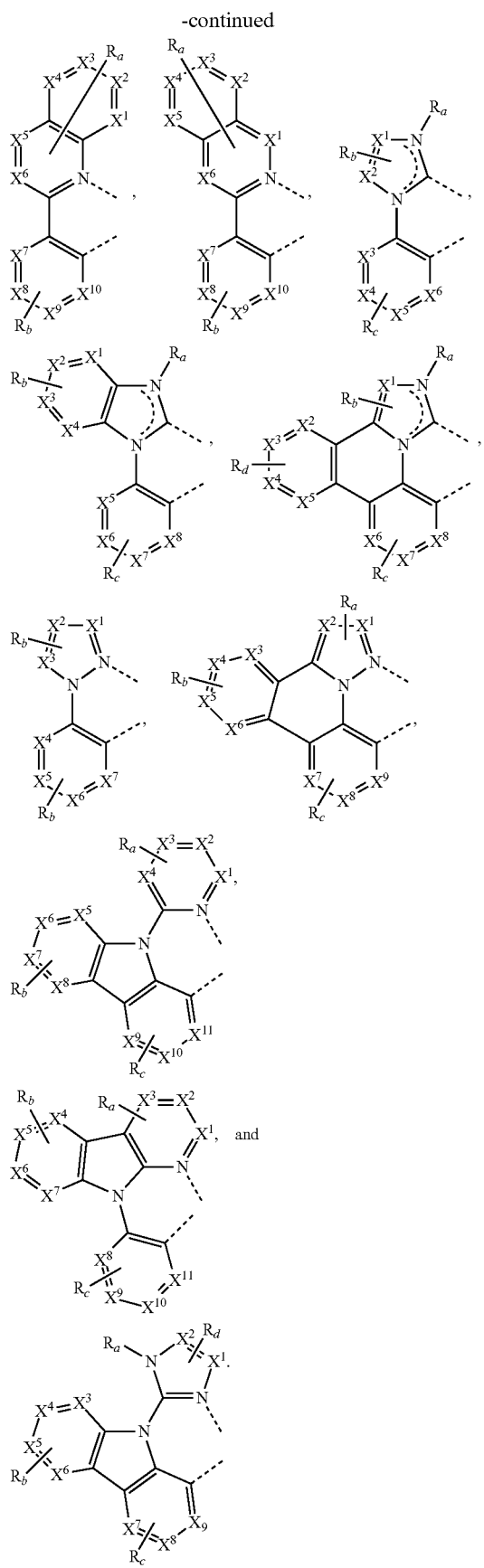

In some embodiments, in the structure of $L_B$:

each of $X^1$ to $X^{13}$ is independently selected from the group consisting of carbon and nitrogen;

X is selected from the group consisting of BR', NR', PR', O, S, Se, C=O, S=O, SO$_2$, CR'R", SiR'R", and GeR'R";

R' and R" are optionally joined to form a fused or unfused ring;

each $R_a$, $R_b$, $R_c$, and $R_d$ may represent from mono substitution to the possible maximum number of substitution, or no substitution;

R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any two adjacent substituents of $R_a$, $R_b$, $R_c$, and $R_d$ are optionally joined to form a fused or unfused ring or form a multidentate ligand.

In some embodiments, the compound is selected from the group consisting of:

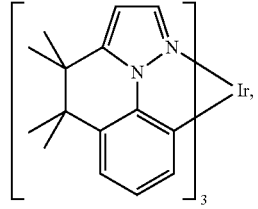

Ir1

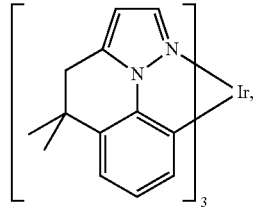

Ir2

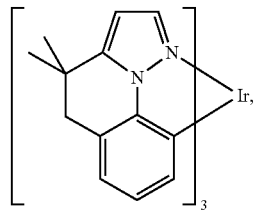

Ir3

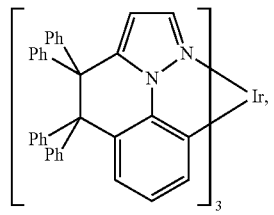

Ir4

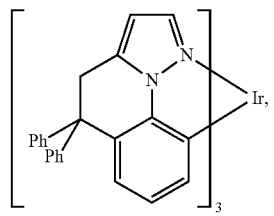

Ir5

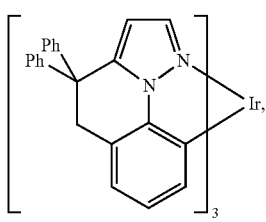
Ir6

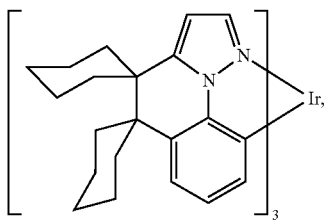
Ir7

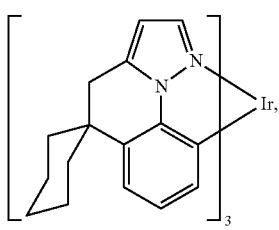
Ir8

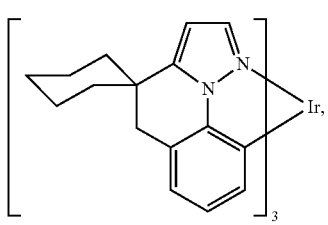
Ir9

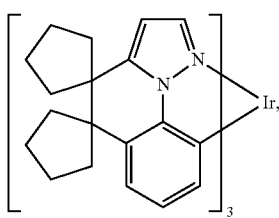
Ir10

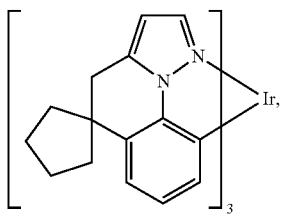
Ir11

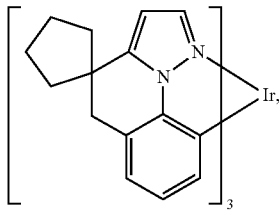
Ir12

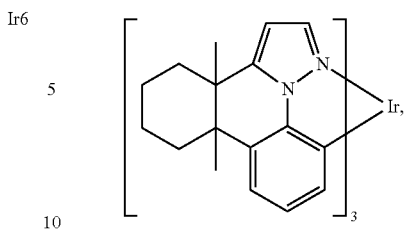
Ir13

Compound Ir14 through Ir26, each represented by the formula

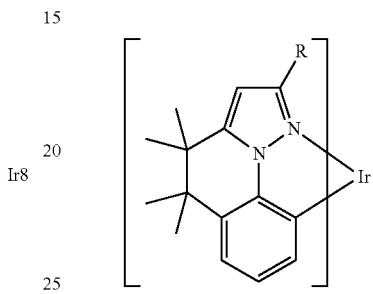

wherein in Compound Ir14: R=Me,
in Compound Ir15: R=Et,
in Compound Ir16: R=$^i$Pr,
in Compound Ir17: R=Cy,
in Compound Ir18: R=$^i$Bu,
in Compound Ir19: R=$^t$Bu,
in Compound Ir20: R=CN,
in Compound Ir21: R=neopentyl,
in Compound Ir22: R=Ph,
in Compound Ir23: R=4-biphenyl,
in Compound Ir24: R=2,6-($^i$Pr)$_2$Ph,
in Compound Ir25: R=2,6-($^i$Pr)$_2$-4-biphenyl,
in Compound Ir26: R=2,4-($^i$Pr)$_2$-3-dibenzofuran,
Compound Ir27 through Ir39, each represented by the formula

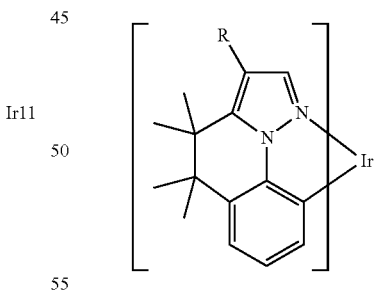

wherein in Compound Ir27: R=Me,
in Compound Ir28: R=Et,
in Compound Ir29: R=$^i$Pr,
in Compound Ir30: R=Cy,
in Compound Ir31: R=$^i$Bu,
in Compound Ir32: R=$^t$Bu,
in Compound Ir33: R=CN,
in Compound Ir34: R=neopentyl,
in Compound Ir35: R=Ph,
in Compound Ir36: R=4-biphenyl, in Compound Ir37: R=2,6-($^i$Pr)$_2$Ph,
in Compound Ir38: R=2,6-($^i$Pr)$_2$-4-biphenyl,
in Compound Ir39: R=2,4-($^i$Pr)$_2$-3-dibenzofuran,
Compound Ir40 through Ir52, each represented by the formula

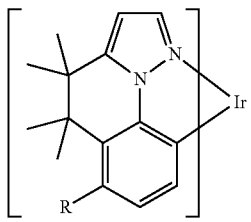

wherein in Compound Ir40: R=Me,
in Compound Ir41: R=Et,
in Compound Ir42: R=$^i$Pr,
in Compound Ir43: R=Cy,
in Compound Ir44: R=$^i$Bu,
in Compound Ir45: R=$^t$Bu,
in Compound Ir46: R=CN,
in Compound Ir47: R=neopentyl,
in Compound Ir48: R=Ph,
in Compound Ir49: R=4-biphenyl,
in Compound Ir50: R=2,6-($^i$Pr)$_2$Ph,
in Compound Ir51: R=2,6-($^i$Pr)$_2$-4-biphenyl,
in Compound Ir52: R=2,4-($^i$Pr)$_2$-3-dibenzofuran,
Compound Ir53 through Ir65, each represented by the formula

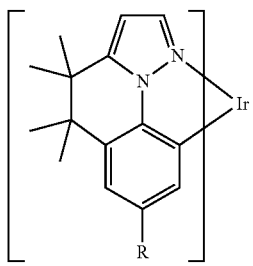

wherein in Compound Ir53: R=Me,
in Compound Ir54: R=Et,
in Compound Ir55: R=$^i$Pr,
in Compound Ir56: R=Cy,
in Compound Ir57: R=$^i$Bu,
in Compound Ir58: R=$^t$Bu,
in Compound Ir59: R=CN,
in Compound Ir60: R=neopentyl,
in Compound Ir61: R=Ph,
in Compound Ir62: R=4-biphenyl,
in Compound Ir63: R=2,6-($^i$Pr)$_2$Ph,
in Compound Ir64: R=2,6-($^i$Pr)$_2$-4-biphenyl,
in Compound Ir65: R=2,4-($^i$Pr)$_2$-3-dibenzofuran,
Compound Ir66 through Ir78, each represented by the formula

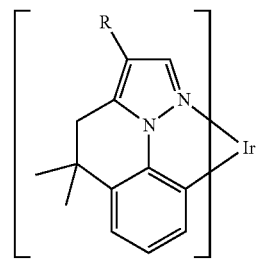

wherein in Compound Ir66: R=Me,
in Compound Ir67: R=Et,
in Compound Ir68: R=$^i$Pr,
in Compound Ir69: R=Cy,
in Compound Ir70: R=$^i$Bu,
in Compound Ir71: R=$^t$Bu,
in Compound Ir72: R=CN,
in Compound Ir73: R=neopentyl,
in Compound Ir74: R=Ph,
in Compound Ir75: R=4-biphenyl,
in Compound Ir76: R=2,6-($^i$Pr)$_2$Ph,
in Compound Ir77: R=2,6-($^i$Pr)$_2$-4-biphenyl,
in Compound Ir78: R=2,4-($^i$Pr)$_2$-3-dibenzofuran,
Compound Ir79 through Ir91, each represented by the formula

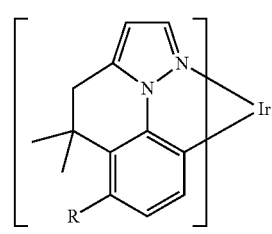

wherein in Compound Ir79: R=Me,
in Compound Ir80: R=Et,
in Compound Ir81: R=$^i$Pr,
in Compound Ir82: R=Cy,
in Compound Ir83: R=$^i$Bu,
in Compound Ir84: R=$^t$Bu,
in Compound Ir85: R=CN,
in Compound Ir86: R=neopentyl,
in Compound Ir87: R=Ph,
in Compound Ir88: R=4-biphenyl,
in Compound Ir89: R=2,6-($^i$Pr)$_2$Ph,
in Compound Ir90: R=2,6-($^i$Pr)$_2$-4-biphenyl,
in Compound Ir91: R=2,4-($^i$Pr)$_2$-3-dibenzofuran,
Compound Ir92 through Ir104, each represented by the formula wherein in Compound Ir92: R=Me,
in Compound Ir93: R=Et,
in Compound Ir94: R=$^i$Pr,
in Compound Ir95: R=Cy,
in Compound Ir96: R=$^i$Bu,
in Compound Ir97: R=$^t$Bu,
in Compound Ir98: R=CN,
in Compound Ir99: R=neopentyl,
in Compound Ir100: R=Ph,
in Compound Ir101: R=4-biphenyl,
in Compound Ir102: R=2,6-($^i$Pr)$_2$Ph,
in Compound Ir103: R=2,6-($^i$Pr)$_2$-4-biphenyl,
in Compound Ir104: R=2,4-($^i$Pr)$_2$-3-dibenzofuran,
Compound Ir105 through Ir117, each represented by the formula

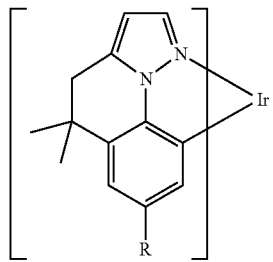

wherein in Compound Ir105: R=Me,
in Compound Ir106: R=Et,
in Compound Ir107: R=$^i$Pr,
in Compound Ir108: R=Cy,
in Compound Ir109: R=$^i$Bu,
in Compound Ir110: R=$^t$Bu,
in Compound Ir111: R=CN,
in Compound Ir112: R=neopentyl,
in Compound Ir113: R=Ph,
in Compound Ir114: R=4-biphenyl,
in Compound Ir115: R=2,6-($^i$Pr)$_2$Ph,
in Compound Ir116: R=2,6-($^i$Pr)$_2$-4-biphenyl,
in Compound Ir117: R=2,4-($^i$Pr)$_2$-3-dibenzofuran,
Compound Ir118 through Ir130, each represented by the formula

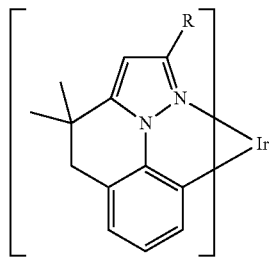

wherein in Compound Ir118: R=Me,
in Compound Ir119: R=Et,
in Compound Ir120: R=$^i$Pr,
in Compound Ir121: R=Cy,
in Compound Ir122: R=$^i$Bu,
in Compound Ir123: R=$^t$Bu,
in Compound Ir124: R=CN,
in Compound Ir125: R=neopentyl,
in Compound Ir126: R=Ph,
in Compound Ir127: R=4-biphenyl,
in Compound Ir128: R=2,6-($^i$Pr)$_2$Ph,
in Compound Ir129: R=2,6-($^i$Pr)$_2$-4-biphenyl,
in Compound Ir130: R=2,4-($^i$Pr)$_2$-3-dibenzofuran,
Compound Ir131 through Ir143, each represented by the formula

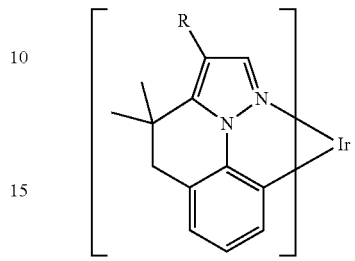

wherein in Compound Ir131: R=Me,
in Compound Ir132: R=Et,
in Compound Ir133: R=$^i$Pr,
in Compound Ir134: R=Cy,
in Compound Ir135: R=$^i$Bu,
in Compound Ir136: R=$^t$Bu,
in Compound Ir137: R=CN,
in Compound Ir138: R=neopentyl,
in Compound Ir139: R=Ph,
in Compound Ir140: R=4-biphenyl,
in Compound Ir141: R=2,6-($^i$Pr)$_2$Ph,
in Compound Ir142: R=2,6-($^i$Pr)$_2$-4-biphenyl,
in Compound Ir143: R=2,4-($^i$Pr)$_2$-3-dibenzofuran,
Compound Ir144 through Ir156, each represented by the formula

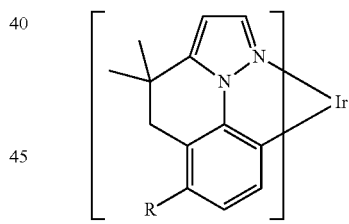

wherein in Compound Ir144: R=Me,
in Compound Ir145: R=Et,
in Compound Ir146: R=$^i$Pr,
in Compound Ir147: R=Cy,
in Compound Ir148: R=$^i$Bu,
in Compound Ir149: R=$^t$Bu,
in Compound Ir150: R=CN,
in Compound Ir151: R=neopentyl,
in Compound Ir152: R=Ph,
in Compound Ir153: R=4-biphenyl,
in Compound Ir154: R=2,6-($^i$Pr)$_2$Ph,
in Compound Ir155: R=2,6-($^i$Pr)$_2$-4-biphenyl,
in Compound Ir156: R=2,4-($^i$Pr)$_2$-3-dibenzofuran,
Compound Ir157 through Ir169, each represented by the formula

101

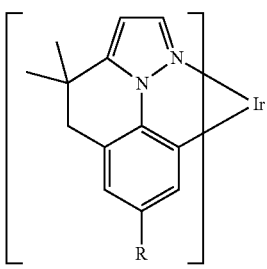

wherein in Compound Ir157: R=Me,
in Compound Ir158: R=Et,
in Compound Ir159: R=$^i$Pr,
in Compound Ir160: R=Cy,
in Compound Ir161: R=$^i$Bu,
in Compound Ir162: R=$^t$Bu,
in Compound Ir163: R=CN,
in Compound Ir164: R=neopentyl,
in Compound Ir165: R=Ph,
in Compound Ir166: R=4-biphenyl,
in Compound Ir167: R=2,6-($^i$Pr)$_2$Ph,
in Compound Ir168: R=2,6-($^i$Pr)$_2$-4-biphenyl,
in Compound Ir169: R=2,4-($^i$Pr)$_2$-3-dibenzofuran,
Compound Ir170 through Ir182, each represented by the formula

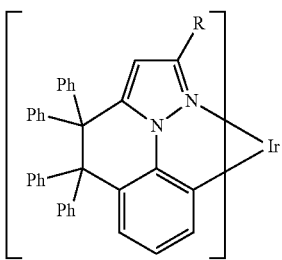

wherein in Compound Ir170: R=Me,
in Compound Ir171: R=Et,
in Compound Ir172: R=$^i$Pr,
in Compound Ir173: R=Cy,
in Compound Ir174: R=$^i$Bu,
in Compound Ir175: R=$^t$Bu,
in Compound Ir176: R=CN,
in Compound Ir177: R=neopentyl,
in Compound Ir178: R=Ph,
in Compound Ir179: R=4-biphenyl,
in Compound Ir180: R=2,6-($^i$Pr)$_2$Ph,
in Compound Ir181: R=2,6-($^i$Pr)$_2$-4-biphenyl,
in Compound Ir182: R=2,4-($^i$Pr)$_2$-3-dibenzofuran,
Compound Ir183 through Ir195, each represented by the formula

102

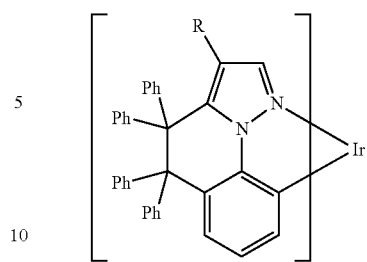

wherein in Compound Ir183: R=Me,
in Compound Ir184: R=Et,
in Compound Ir185: R=$^i$Pr,
in Compound Ir186: R=Cy,
in Compound Ir187: R=$^i$Bu,
in Compound Ir188: R=$^t$Bu,
in Compound Ir189: R=CN,
in Compound Ir190: R=neopentyl,
in Compound Ir191: R=Ph,
in Compound Ir192: R=4-biphenyl,
in Compound Ir193: R=2,6-($^i$Pr)$_2$Ph,
in Compound Ir194: R=2,6-($^i$Pr)$_2$-4-biphenyl,
in Compound Ir195: R=2,4-($^i$Pr)$_2$-3-dibenzofuran,
Compound Ir196 through Ir208, each represented by the formula

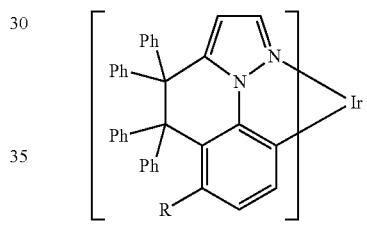

wherein in Compound Ir196: R=Me,
in Compound Ir197: R=Et,
in Compound Ir198: R=$^i$Pr,
in Compound Ir199: R=Cy,
in Compound Ir200: R=$^i$Bu,
in Compound Ir201: R=$^t$Bu,
in Compound Ir202: R=CN,
in Compound Ir203: R=neopentyl,
in Compound Ir204: R=Ph,
in Compound Ir205: R=4-biphenyl,
in Compound Ir206: R=2,6-($^i$Pr)$_2$Ph,
in Compound Ir207: R=2,6-($^i$Pr)$_2$-4-biphenyl,
in Compound Ir208: R=2,4-($^i$Pr)$_2$-3-dibenzofuran,
Compound Ir209 through Ir221, each represented by the formula

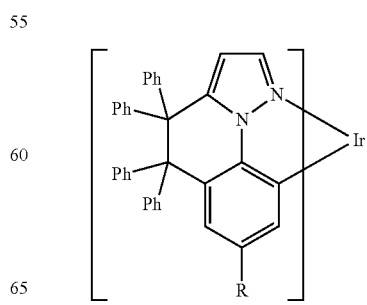

wherein in Compound Ir209: R=Me,
in Compound Ir210: R=Et,
in Compound Ir211: R=$^i$Pr,
in Compound Ir212: R=Cy,
in Compound Ir213: R=$^i$Bu,
in Compound Ir214: R=$^t$Bu,
in Compound Ir215: R=CN,
in Compound Ir216: R=neopentyl,
in Compound Ir217: R=Ph,
in Compound Ir218: R=4-biphenyl,
in Compound Ir219: R=2,6-($^i$Pr)$_2$Ph,
in Compound Ir220: R=2,6-($^i$Pr)$_2$-4-biphenyl,
in Compound Ir221: R=2,4-($^i$Pr)$_2$-3-dibenzofuran,
Compound Ir222 through Ir234, each represented by the formula

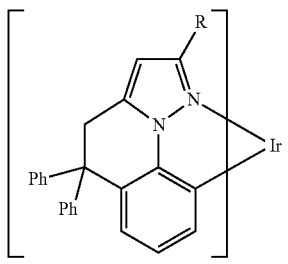

wherein in Compound Ir222: R=Me,
in Compound Ir223: R=Et,
in Compound Ir224: R=$^i$Pr,
in Compound Ir225: R=Cy,
in Compound Ir226: R=$^i$Bu,
in Compound Ir227: R=$^t$Bu,
in Compound Ir228: R=CN,
in Compound Ir229: R=neopentyl,
in Compound Ir230: R=Ph,
in Compound Ir231: R=4-biphenyl,
in Compound Ir232: R=2,6-($^i$Pr)$_2$Ph,
in Compound Ir233: R=2,6-($^i$Pr)$_2$-4-biphenyl,
in Compound Ir234: R=2,4-($^i$Pr)$_2$-3-dibenzofuran,
Compound Ir235 through Ir247, each represented by the formula

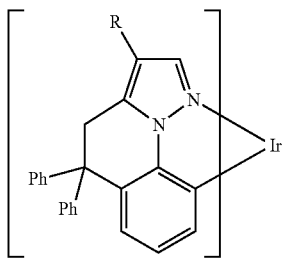

wherein in Compound Ir235: R=Me,
in Compound Ir236: R=Et,
in Compound Ir237: R=$^i$Pr,
in Compound Ir238: R=Cy,
in Compound Ir239: R=$^i$Bu,
in Compound Ir240: R=$^t$Bu,
in Compound Ir241: R=CN,
in Compound Ir242: R=neopentyl,
in Compound Ir243: R=Ph.
in Compound Ir244: R=4-biphenyl,
in Compound Ir245: R=2,6-($^i$Pr)$_2$Ph,
in Compound Ir246: R=2,6-($^i$Pr)$_2$-4-biphenyl,
in Compound Ir247: R=2,4-($^i$Pr)$_2$-3-dibenzofuran,
Compound Ir248 through Ir260, each represented by the formula

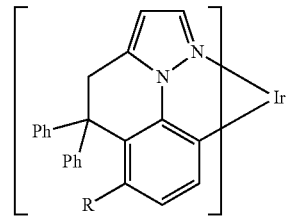

wherein in Compound Ir248: R=Me,
in Compound Ir249: R=Et,
in Compound Ir250: R=$^i$Pr,
in Compound Ir251: R=Cy,
in Compound Ir252: R=$^i$Bu,
in Compound Ir253: R=$^t$Bu,
in Compound Ir254: R=CN,
in Compound Ir255: R=neopentyl,
in Compound Ir256: R=Ph,
in Compound Ir257: R=4-biphenyl,
in Compound Ir258: R=2,6-($^i$Pr)$_2$Ph,
in Compound Ir259: R=2,6-($^i$Pr)$_2$-4-biphenyl,
in Compound Ir260: R=2,4-($^i$Pr)$_2$-3-dibenzofuran,
Compound Ir261 through Ir273, each represented by the formula

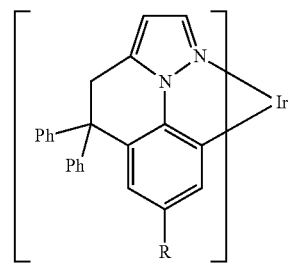

wherein in Compound Ir261: R=Me,
in Compound Ir262: R=Et,
in Compound Ir263: R=$^i$Pr,
in Compound Ir264: R=Cy,
in Compound Ir265: R=$^i$Bu,
in Compound Ir266: R=$^t$Bu,
in Compound Ir267: R=CN,
in Compound Ir268: R=neopentyl,
in Compound Ir269: R=Ph,
in Compound Ir270: R=4-biphenyl,
in Compound Ir271: R=2,6-($^i$Pr)$_2$Ph,
in Compound Ir272: R=2,6-($^i$Pr)$_2$-4-biphenyl,
in Compound Ir273: R=2,4-($^i$Pr)$_2$-3-dibenzofuran,
Compound Ir274 through Ir286, each represented by the formula

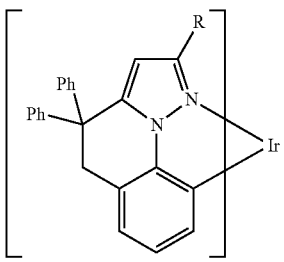

wherein in Compound Ir274: R=Me,
in Compound Ir275: R=Et,
in Compound Ir276: R=$^i$Pr,
in Compound Ir277: R=Cy,
in Compound Ir278: R=$^i$Bu,
in Compound Ir279: R=$^t$Bu,
in Compound Ir280: R=CN,
in Compound Ir281: R=neopentyl,
in Compound Ir282: R=Ph,
in Compound Ir283: R=4-biphenyl,
in Compound Ir284: R=2,6-($^i$Pr)$_2$Ph,
in Compound Ir285: R=2,6-($^i$Pr)$_2$-4-biphenyl,
in Compound Ir286: R=2,4-($^i$Pr)$_2$-3-dibenzofuran,
Compound Ir287 through Ir299, each represented by the formula

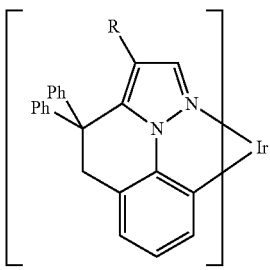

wherein in Compound Ir287: R=Me,
in Compound Ir288: R=Et,
in Compound Ir289: R=$^i$Pr,
in Compound Ir290: R=Cy,
in Compound Ir291: R=$^i$Bu,
in Compound Ir292: R=$^t$Bu,
in Compound Ir293: R=CN,
in Compound Ir294: R=neopentyl,
in Compound Ir295: R=Ph,
in Compound Ir296: R=4-biphenyl,
in Compound Ir297: R=2,6-($^i$Pr)$_2$Ph,
in Compound Ir298: R=2,6-($^i$Pr)$_2$-4-biphenyl,
in Compound Ir299: R=2,4-($^i$Pr)$_2$-3-dibenzofuran,
Compound Ir300 through Ir312, each represented by the formula

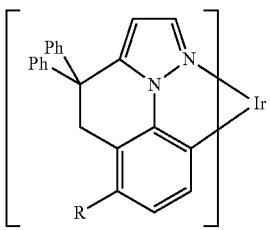

wherein in Compound Ir300: R=Me,
in Compound Ir301: R=Et,
in Compound Ir302: R=$^i$Pr,
in Compound Ir303: R=Cy,
in Compound Ir304: R=$^i$Bu,
in Compound Ir305: R=$^t$Bu,
in Compound Ir306: R=CN,
in Compound Ir307: R=neopentyl,
in Compound Ir308: R=Ph,
in Compound Ir309: R=4-biphenyl,
in Compound Ir310: R=2,6-($^i$Pr)$_2$Ph,
in Compound Ir311: R=2,6-($^i$Pr)$_2$-4-biphenyl,
in Compound Ir312: R=2,4-($^i$Pr)$_2$-3-dibenzofuran,
Compound Ir313 through Ir325, each represented by the formula

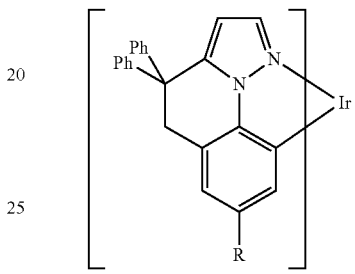

wherein in Compound Ir313: R=Me,
in Compound Ir314: R=Et,
in Compound Ir315: R=$^i$Pr,
in Compound Ir316: R=Cy,
in Compound Ir317: R=$^i$Bu,
in Compound Ir318: R=$^t$Bu,
in Compound Ir319: R=CN,
in Compound Ir320: R=neopentyl,
in Compound Ir321: R=Ph,
in Compound Ir322: R=4-biphenyl,
in Compound Ir323: R=2,6-($^i$Pr)$_2$Ph,
in Compound Ir324: R=2,6-($^i$Pr)$_2$-4-biphenyl,
in Compound Ir325: R=2,4-($^i$Pr)$_2$-3-dibenzofuran,
Compound Ir326 through Ir338, each represented by the formula

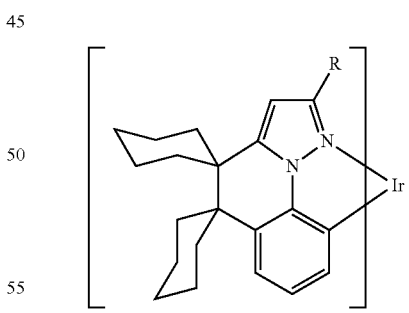

wherein in Compound Ir326: R=Me,
in Compound Ir327: R=Et,
in Compound Ir328: R=$^i$Pr,
in Compound Ir329: R=Cy,
in Compound Ir330: R=$^i$Bu,
in Compound Ir331: R=$^t$Bu,
in Compound Ir332: R=CN,
in Compound Ir333: R=neopentyl,
in Compound Ir334: R=Ph,
in Compound Ir335: R=4-biphenyl, in Compound Ir336: R=2,6-($^i$Pr)$_2$Ph,
in Compound Ir337: R=2,6-($^i$Pr)$_2$-4-biphenyl,
in Compound Ir338: R=2,4-($^i$Pr)$_2$-3-dibenzofuran,
Compound Ir339 through Ir351, each represented by the formula

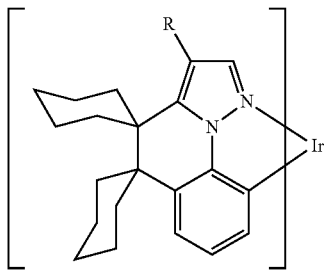

wherein in Compound Ir339: R=Me,
in Compound Ir340: R=Et,
in Compound Ir341: R=$^i$Pr,
in Compound Ir342: R=Cy,
in Compound Ir343: R=$^i$Bu,
in Compound Ir344: R=$^t$Bu,
in Compound Ir345: R=CN,
in Compound Ir346: R=neopentyl,
in Compound Ir347: R=Ph,
in Compound Ir348: R=4-biphenyl,
in Compound Ir349: R=2,6-($^i$Pr)$_2$Ph,
in Compound Ir350: R=2,6-($^i$Pr)$_2$-4-biphenyl,
in Compound Ir351: R=2,4-($^i$Pr)$_2$-3-dibenzofuran,
Compound Ir352 through Ir364, each represented by the formula

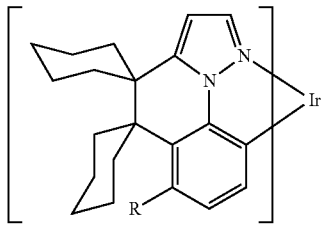

wherein in Compound Ir352: R=Me,
in Compound Ir353: R=Et,
in Compound Ir354: R=$^i$Pr,
in Compound Ir355: R=Cy,
in Compound Ir356: R=$^i$Bu,
in Compound Ir357: R=$^t$Bu,
in Compound Ir358: R=CN,
in Compound Ir359: R=neopentyl,
in Compound Ir360: R=Ph,
in Compound Ir361: R=4-biphenyl,
in Compound Ir362: R=2,6-($^i$Pr)$_2$Ph,
in Compound Ir363: R=2,6-($^i$Pr)$_2$-4-biphenyl,
in Compound Ir364: R=2,4-($^i$Pr)$_2$-3-dibenzofuran,
Compound Ir365 through Ir377, each represented by the formula

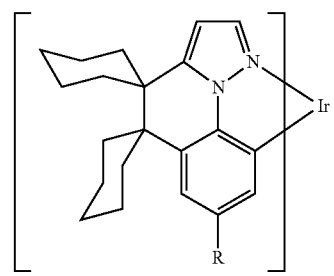

wherein in Compound Ir365: R=Me,
in Compound Ir366: R=Et,
in Compound Ir367: R=$^i$Pr,
in Compound Ir368: R=Cy,
in Compound Ir369: R=$^i$Bu,
in Compound Ir370: R=$^t$Bu,
in Compound Ir371: R=CN,
in Compound Ir372: R=neopentyl,
in Compound Ir373: R=Ph,
in Compound Ir374: R=4-biphenyl,
in Compound Ir375: R=2,6-($^i$Pr)$_2$Ph,
in Compound Ir376: R=2,6-($^i$Pr)$_2$-4-biphenyl,
in Compound Ir377: R=2,4-($^i$Pr)$_2$-3-dibenzofuran,
Compound Ir378 through Ir390, each represented by the formula

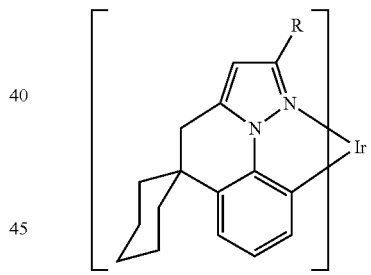

wherein in Compound Ir378: R=Me,
in Compound Ir379: R=Et,
in Compound Ir380: R=$^i$Pr,
in Compound Ir381: R=Cy,
in Compound Ir382: R=$^i$Bu,
in Compound Ir383: R=$^t$Bu,
in Compound Ir384: R=CN,
in Compound Ir385: R=neopentyl,
in Compound Ir386: R=Ph,
in Compound Ir387: R=4-biphenyl,
in Compound Ir388: R=2,6-($^i$Pr)$_2$Ph,
in Compound Ir389: R=2,6-($^i$Pr)$_2$-4-biphenyl,
in Compound Ir390: R=2,4-($^i$Pr)$_2$-3-dibenzofuran,
Compound Ir391 through Ir403, each represented by the formula

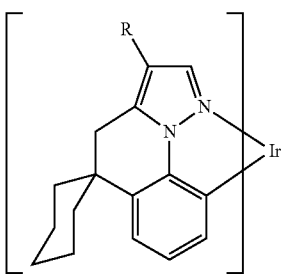

wherein in Compound Ir391: R=Me,
in Compound Ir392: R=Et,
in Compound Ir393: R=$^i$Pr,
in Compound Ir394: R=Cy,
in Compound Ir395: R=$^i$Bu,
in Compound Ir396: R=$^t$Bu,
in Compound Ir397: R=CN,
in Compound Ir398: R=neopentyl,
in Compound Ir399: R=Ph,
in Compound Ir400: R=4-biphenyl,
in Compound Ir401: R=2,6-($^i$Pr)$_2$Ph,
in Compound Ir402: R=2,6-($^i$Pr)$_2$-4-biphenyl,
in Compound Ir403: R=2,4-($^i$Pr)$_2$-3-dibenzofuran,
Compound Ir404 through Ir416, each represented by the formula

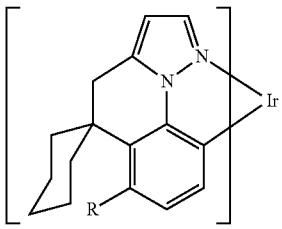

wherein in Compound Ir404: R=Me,
in Compound Ir405: R=Et,
in Compound Ir406: R=$^i$Pr,
in Compound Ir407: R=Cy,
in Compound Ir408: R=$^i$Bu,
in Compound Ir409: R=$^t$Bu,
in Compound Ir410: R=CN,
in Compound Ir411: R=neopentyl,
in Compound Ir412: R=Ph,
in Compound Ir413: R=4-biphenyl,
in Compound Ir414: R=2,6-($^i$Pr)$_2$Ph,
in Compound Ir415: R=2,6-($^i$Pr)$_2$-4-biphenyl,
in Compound Ir416: R=2,4-($^i$Pr)$_2$-3-dibenzofuran,
Compound Ir417 through Ir429, each represented by the formula

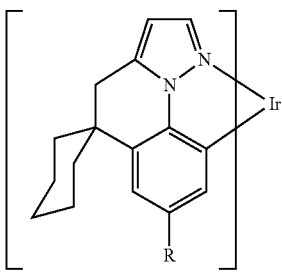

wherein in Compound Ir417: R=Me,
in Compound Ir418: R=Et,
in Compound Ir419: R=$^i$Pr,
in Compound Ir420: R=Cy,
in Compound Ir421: R=$^i$Bu,
in Compound Ir422: R=$^t$Bu,
in Compound Ir423: R=CN,
in Compound Ir424: R=neopentyl,
in Compound Ir425: R=Ph,
in Compound Ir426: R=4-biphenyl,
in Compound Ir427: R=2,6-($^i$Pr)$_2$Ph,
in Compound Ir428: R=2,6-($^i$Pr)$_2$-4-biphenyl,
in Compound Ir429: R=2,4-($^i$Pr)$_2$-3-dibenzofuran,
Compound Ir430 through Ir442, each represented by the formula

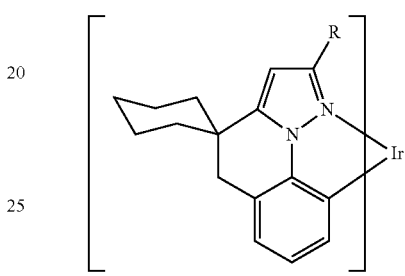

wherein in Compound Ir430: R=Me,
in Compound Ir431: R=Et,
in Compound Ir432: R=$^i$Pr,
in Compound Ir433: R=Cy,
in Compound Ir434: R=$^i$Bu,
in Compound Ir435: R=$^t$Bu,
in Compound Ir436: R=CN,
in Compound Ir437: R=neopentyl,
in Compound Ir438: R=Ph,
in Compound Ir439: R=4-biphenyl,
in Compound Ir440: R=2,6-($^i$Pr)$_2$Ph,
in Compound Ir441: R=2,6-($^i$Pr)$_2$-4-biphenyl,
in Compound Ir442: R=2,4-($^i$Pr)$_2$-3-dibenzofuran,
Compound Ir443 through Ir455, each represented by the formula

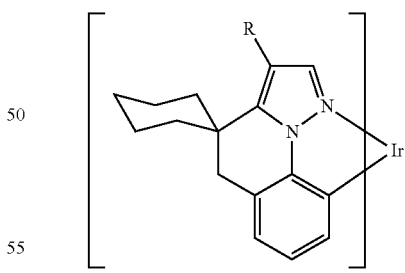

wherein in Compound Ir443: R=Me,
in Compound Ir444: R=Et,
in Compound Ir445: R=$^i$Pr,
in Compound Ir446: R=Cy,
in Compound Ir447: R=$^i$Bu,
in Compound Ir448: R=$^t$Bu,
in Compound Ir449: R=CN,
in Compound Ir450: R=neopentyl,
in Compound Ir451: R=Ph,
in Compound Ir452: R=4-biphenyl, in Compound Ir453: R=2,6-($^i$Pr)$_2$Ph,
in Compound Ir454: R=2,6-($^i$Pr)$_2$-4-biphenyl,
in Compound Ir455: R=2,4-($^i$Pr)$_2$-3-dibenzofuran,
Compound Ir456 through Ir468, each represented by the formula

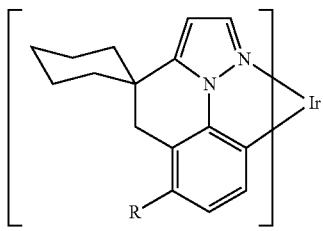

wherein in Compound Ir456: R=Me,
in Compound Ir457: R=Et,
in Compound Ir458: R=$^i$Pr,
in Compound Ir459: R=Cy,
in Compound Ir460: R=$^i$Bu,
in Compound Ir461: R=$^t$Bu,
in Compound Ir462: R=CN,
in Compound Ir463: R=neopentyl,
in Compound Ir464: R=Ph,
in Compound Ir465: R=4-biphenyl,
in Compound Ir466: R=2,6-($^i$Pr)$_2$Ph,
in Compound Ir467: R=2,6-($^i$Pr)$_2$-4-biphenyl,
in Compound Ir468: R=2,4-($^i$Pr)$_2$-3-dibenzofuran,
Compound Ir469 through Ir481, each represented by the formula

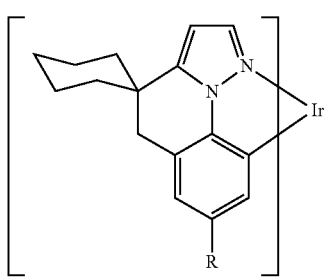

wherein in Compound Ir469: R=Me,
in Compound Ir470: R=Et,
in Compound Ir471: R=$^i$Pr,
in Compound Ir472: R=Cy,
in Compound Ir473: R=$^i$Bu,
in Compound Ir474: R=$^t$Bu,
in Compound Ir475: R=CN,
in Compound Ir476: R=neopentyl,
in Compound Ir477: R=Ph,
in Compound Ir478: R=4-biphenyl,
in Compound Ir479: R=2,6-($^i$Pr)$_2$Ph,
in Compound Ir480: R=2,6-($^i$Pr)$_2$-4-biphenyl,
in Compound Ir481: R=2,4-($^i$Pr)$_2$-3-dibenzofuran,
Compound Ir482 through Ir494, each represented by the formula

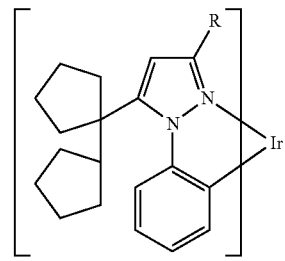

wherein in Compound Ir482: R=Me,
in Compound Ir483: R=Et,
in Compound Ir484: R=$^i$Pr,
in Compound Ir485: R=Cy,
in Compound Ir486: R=$^i$Bu,
in Compound Ir487: R=$^t$Bu,
in Compound Ir488: R=CN,
in Compound Ir489: R=neopentyl,
in Compound Ir490: R=Ph,
in Compound Ir491: R=4-biphenyl,
in Compound Ir492: R=2,6-($^i$Pr)$_2$Ph,
in Compound Ir493: R=2,6-($^i$Pr)$_2$-4-biphenyl,
in Compound Ir494: R=2,4-($^i$Pr)$_2$-3-dibenzofuran,
Compound Ir495 through Ir507, each represented by the formula

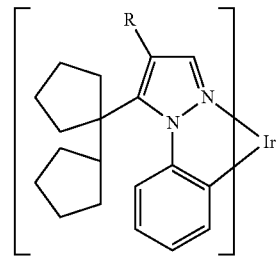

wherein in Compound Ir495: R=Me,
in Compound Ir496: R=Et,
in Compound Ir497: R=$^i$Pr,
in Compound Ir498: R=Cy,
in Compound Ir499: R=$^i$Bu,
in Compound Ir500: R=$^t$Bu,
in Compound Ir501: R=CN,
in Compound Ir502: R=neopentyl,
in Compound Ir503: R=Ph,
in Compound Ir504: R=4-biphenyl,
in Compound Ir505: R=2,6-($^i$Pr)$_2$Ph,
in Compound Ir506: R=2,6-($^i$Pr)$_2$-4-biphenyl,
in Compound Ir507: R=2,4-($^i$Pr)$_2$-3-dibenzofuran,
Compound Ir508 through Ir520, each represented by the formula

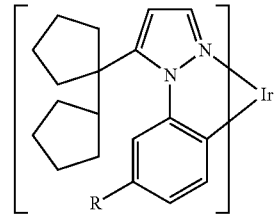

wherein in Compound Ir508: R=Me,
in Compound Ir509: R=Et,
in Compound Ir510: R=$^i$Pr,
in Compound Ir511: R=Cy,
in Compound Ir512: R=$^i$Bu,
in Compound Ir513: R=$^t$Bu,
in Compound Ir514: R=CN,
in Compound Ir515: R=neopentyl,
in Compound Ir516: R=Ph,
in Compound Ir517: R=4-biphenyl,
in Compound Ir518: R=2,6-($^i$Pr)$_2$Ph,
in Compound Ir519: R=2,6-($^i$Pr)$_2$-4-biphenyl,
in Compound Ir520: R=2,4-($^i$Pr)$_2$-3-dibenzofuran,
Compound Ir521 through Ir533, each represented by the formula

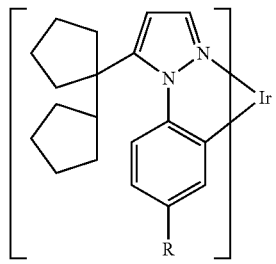

wherein in Compound Ir521: R=Me,
in Compound Ir522: R=Et,
in Compound Ir523: R=$^i$Pr,
in Compound Ir524: R=Cy,
in Compound Ir525: R=$^i$Bu,
in Compound Ir526: R=$^t$Bu,
in Compound Ir527: R=CN,
in Compound Ir528: R=neopentyl,
in Compound Ir529: R=Ph,
in Compound Ir530: R=4-biphenyl,
in Compound Ir531: R=2,6-($^i$Pr)$_2$Ph,
in Compound Ir532: R=2,6-($^i$Pr)$_2$-4-biphenyl,
in Compound Ir533: R=2,4-($^i$Pr)$_2$-3-dibenzofuran,
Compound Ir534 through Ir546, each represented by the formula

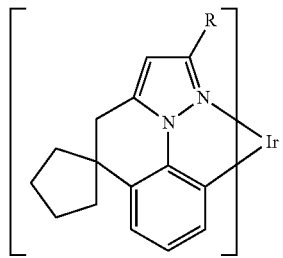

wherein in Compound Ir534: R=Me,
in Compound Ir535: R=Et,
in Compound Ir536: R=$^i$Pr,
in Compound Ir537: R=Cy,
in Compound Ir538: R=$^i$Bu,
in Compound Ir539: R=$^t$Bu,
in Compound Ir540: R=CN,
in Compound Ir541: R=neopentyl,
in Compound Ir542: R=Ph,
in Compound Ir543: R=4-biphenyl, in Compound Ir544: R=2,6-($^i$Pr)$_2$Ph,
in Compound Ir545: R=2,6-($^i$Pr)$_2$-4-biphenyl,
in Compound Ir546: R=2,4-($^i$Pr)$_2$-3-dibenzofuran,
Compound Ir547 through Ir559, each represented by the formula

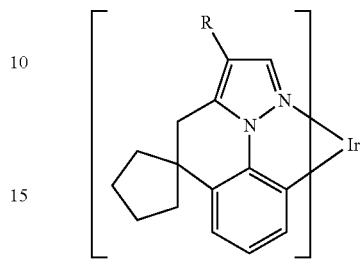

wherein in Compound Ir547: R=Me,
in Compound Ir548: R=Et,
in Compound Ir549: R=$^i$Pr,
in Compound Ir550: R=Cy,
in Compound Ir551: R=$^i$Bu,
in Compound Ir552: R=$^t$Bu,
in Compound Ir553: R=CN,
in Compound Ir554: R=neopentyl,
in Compound Ir555: R=Ph,
in Compound Ir556: R=4-biphenyl,
in Compound Ir557: R=2,6-($^i$Pr)$_2$Ph,
in Compound Ir558: R=2,6-($^i$Pr)$_2$-4-biphenyl,
in Compound Ir559: R=2,4-($^i$Pr)$_2$-3-dibenzofuran,
Compound Ir560 through Ir572, each represented by the formula

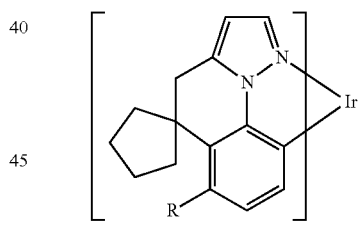

wherein in Compound Ir560: R=Me,
in Compound Ir561: R=Et,
in Compound Ir562: R=$^i$Pr,
in Compound Ir563: R=Cy,
in Compound Ir564: R=$^i$Bu,
in Compound Ir565: R=$^t$Bu,
in Compound Ir566: R=CN,
in Compound Ir567: R=neopentyl,
in Compound Ir568: R=Ph,
in Compound Ir569: R=4-biphenyl,
in Compound Ir570: R=2,6-($^i$Pr)$_2$Ph,
in Compound Ir571: R=2,6-($^i$Pr)$_2$-4-biphenyl,
in Compound Ir572: R=2,4-($^i$Pr)$_2$-3-dibenzofuran,
Compound Ir573 through Ir585, each represented by the formula

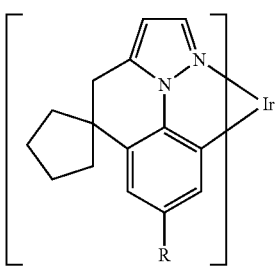

wherein in Compound Ir573: R=Me,
in Compound Ir574: R=Et,
in Compound Ir575: R=$^i$Pr,
in Compound Ir576: R=Cy,
in Compound Ir577: R=$^i$Bu,
in Compound Ir578: R=$^t$Bu,
in Compound Ir579: R=CN,
in Compound Ir580: R=neopentyl,
in Compound Ir581: R=Ph,
in Compound Ir582: R=4-biphenyl,
in Compound Ir583: R=2,6-($^i$Pr)$_2$Ph,
in Compound Ir584: R=2,6-($^i$Pr)$_2$-4-biphenyl,
in Compound Ir585: R=2,4-($^i$Pr)$_2$-3-dibenzofuran,
Compound Ir586 through Ir598, each represented by the formula

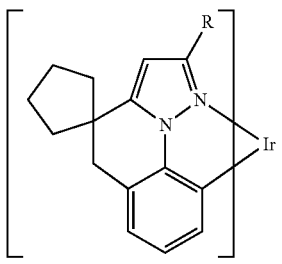

wherein in Compound Ir586: R=Me,
in Compound Ir587: R=Et,
in Compound Ir588: R=$^i$Pr,
in Compound Ir589: R=Cy,
in Compound Ir590: R=$^i$Bu,
in Compound Ir591: R=$^t$Bu,
in Compound Ir592: R=CN,
in Compound Ir593: R=neopentyl,
in Compound Ir594: R=Ph,
in Compound Ir595: R=4-biphenyl,
in Compound Ir596: R=2,6-($^i$Pr)$_2$Ph,
in Compound Ir597: R=2,6-($^i$Pr)$_2$-4-biphenyl,
in Compound Ir598: R=2,4-($^i$Pr)$_2$-3-dibenzofuran,
Compound Ir599 through Ir611, each represented by the formula

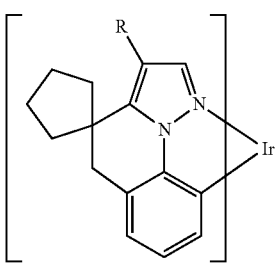

wherein in Compound Ir599: R=Me,
in Compound Ir600: R=Et,
in Compound Ir601: R=$^i$Pr,
in Compound Ir602: R=Cy,
in Compound Ir603: R=$^i$Bu,
in Compound Ir604: R=$^t$Bu,
in Compound Ir605: R=CN,
in Compound Ir606: R=neopentyl,
in Compound Ir607: R=Ph,
in Compound Ir608: R=4-biphenyl,
in Compound Ir609: R=2,6-($^i$Pr)$_2$Ph,
in Compound Ir610: R=2,6-($^i$Pr)$_2$-4-biphenyl,
in Compound Ir611: R=2,4-($^i$Pr)$_2$-3-dibenzofuran,
Compound Ir612 through Ir624, each represented by the formula

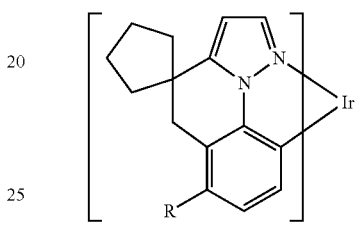

wherein in Compound Ir612: R=Me,
in Compound Ir613: R=Et,
in Compound Ir614: R=$^i$Pr,
in Compound Ir615: R=Cy,
in Compound Ir616: R=Bu,
in Compound Ir617: R=$^t$Bu,
in Compound Ir618: R=CN,
in Compound Ir619: R=neopentyl,
in Compound Ir620: R=Ph,
in Compound Ir621: R=4-biphenyl,
in Compound Ir622: R=2,6-($^i$Pr)$_2$Ph,
in Compound Ir623: R=2,6-($^i$Pr)$_2$-4-biphenyl,
in Compound Ir624: R=2,4-($^i$Pr)$_2$-3-dibenzofuran,
Compound Ir625 through Ir637, each represented by the formula

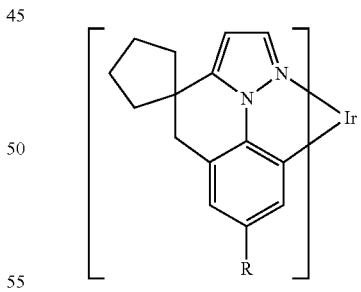

wherein in Compound Ir625: R=Me,
in Compound Ir626: R=Et,
in Compound Ir627: R=$^i$Pr,
in Compound Ir628: R=Cy,
in Compound Ir629: R=$^i$Bu,
in Compound Ir630: R=$^t$Bu,
in Compound Ir631: R=CN,
in Compound Ir632: R=neopentyl,
in Compound Ir633: R=Ph,
in Compound Ir634: R=4-biphenyl, in Compound Ir635: R=2,6-($^i$Pr)$_2$Ph,
in Compound Ir636: R=2,6-($^i$Pr)$_2$-4-biphenyl,
in Compound Ir637: R=2,4-($^i$Pr)$_2$-3-dibenzofuran,
Compound Ir638 through Ir650, each represented by the formula

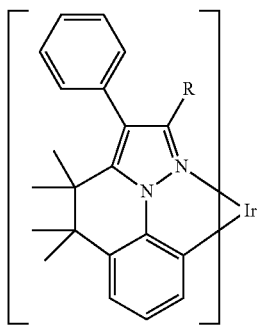

wherein in Compound Ir638: R=Me,
in Compound Ir639: R=Et,
in Compound Ir640: R=$^i$Pr,
in Compound Ir641: R=Cy,
in Compound Ir642: R=$^i$Bu,
in Compound Ir643: R=$^t$Bu,
in Compound Ir644: R=CN,
in Compound Ir645: R=neopentyl,
in Compound Ir646: R=Ph,
in Compound Ir647: R=4-biphenyl,
in Compound Ir648: R=2,6-($^i$Pr)$_2$Ph,
in Compound Ir649: R=2,6-($^i$Pr)$_2$-4-biphenyl,
in Compound Ir650: R=2,4-($^i$Pr)$_2$-3-dibenzofuran,
Compound Ir651 through Ir663, each represented by the formula

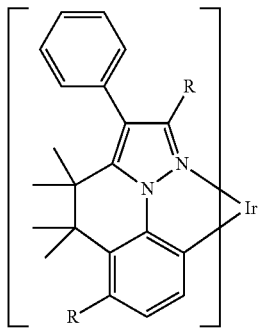

wherein in Compound Ir651: R=Me,
in Compound Ir652: R=Et,
in Compound Ir653: R=$^i$Pr,
in Compound Ir654: R=Cy,
in Compound Ir655: R=$^i$Bu,
in Compound Ir656: R=$^t$Bu,
in Compound Ir657: R=CN,
in Compound Ir658: R=neopentyl,
in Compound Ir659: R=Ph,
in Compound Ir660: R=4-biphenyl,
in Compound Ir661: R=2,6-($^i$Pr)$_2$Ph,
in Compound Ir662: R=2,6-($^i$Pr)$_2$-4-biphenyl,
in Compound Ir663: R=2,4-($^i$Pr)$_2$-3-dibenzofuran,
Compound Ir664 through Ir676, each represented by the formula

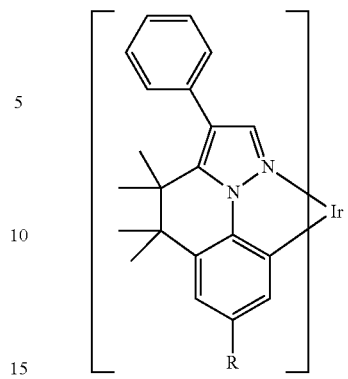

wherein in Compound Ir664: R=Me,
in Compound Ir665: R=Et,
in Compound Ir666: R=$^i$Pr,
in Compound Ir667: R=Cy,
in Compound Ir668: R=$^i$Bu,
in Compound Ir669: R=$^t$Bu,
in Compound Ir670: R=CN,
in Compound Ir671: R=neopentyl,
in Compound Ir672: R=Ph,
in Compound Ir673: R=4-biphenyl,
in Compound Ir674: R=2,6-($^i$Pr)$_2$Ph,
in Compound Ir675: R=2,6-($^i$Pr)$_2$-4-biphenyl,
in Compound Ir676: R=2,4-($^i$Pr)$_2$-3-dibenzofuran,
Compound Ir677 through Ir689, each represented by the formula

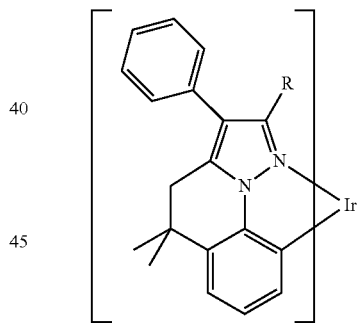

wherein in Compound Ir677: R=Me,
in Compound Ir678: R=Et,
in Compound Ir679: R=$^i$Pr,
in Compound Ir680: R=Cy,
in Compound Ir681: R=$^i$Bu,
in Compound Ir682: R=$^t$Bu,
in Compound Ir683: R=CN,
in Compound Ir684: R=neopentyl,
in Compound Ir685: R=Ph,
in Compound Ir686: R=4-biphenyl,
in Compound Ir687: R=2,6-($^i$Pr)$_2$Ph,
in Compound Ir688: R=2,6-($^i$Pr)$_2$-4-biphenyl,
in Compound Ir689: R=2,4-($^i$Pr)$_2$-3-dibenzofuran,
Compound Ir690 through Ir702, each represented by the formula

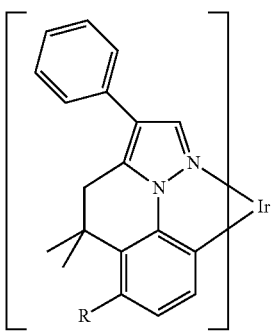

wherein in Compound Ir690: R=Me,
in Compound Ir691: R=Et,
in Compound Ir692: R=$^i$Pr,
in Compound Ir693: R=Cy,
in Compound Ir694: R=$^i$Bu,
in Compound Ir695: R=$^t$Bu,
in Compound Ir696: R=CN,
in Compound Ir697: R=neopentyl,
in Compound Ir698: R=Ph,
in Compound Ir699: R=4-biphenyl,
in Compound Ir700: R=2,6-($^i$Pr)$_2$Ph,
in Compound Ir701: R=2,6-($^i$Pr)$_2$-4-biphenyl,
in Compound Ir702: R=2,4-($^i$Pr)$_2$-3-dibenzofuran,
Compound Ir703 through Ir715, each represented by the formula

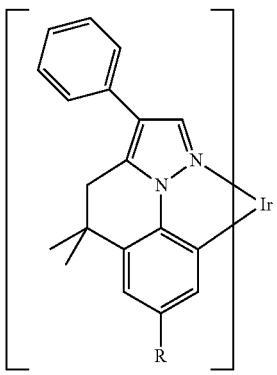

wherein in Compound Ir703: R=Me,
in Compound Ir704: R=Et,
in Compound Ir705: R=$^i$Pr,
in Compound Ir706: R=Cy,
in Compound Ir707: R=$^i$Bu,
in Compound Ir708: R=$^t$Bu,
in Compound Ir709: R=CN,
in Compound Ir710: R=neopentyl,
in Compound Ir711: R=Ph,
in Compound Ir712: R=4-biphenyl,
in Compound Ir713: R=2,6-($^i$Pr)$_2$Ph,
in Compound Ir714: R=2,6-($^i$Pr)$_2$-4-biphenyl,
in Compound Ir715: R=2,4-($^i$Pr)$_2$-3-dibenzofuran,
Compound Ir716 through Ir728, each represented by the formula

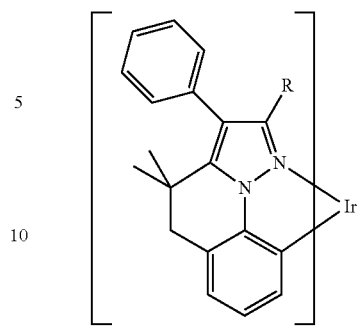

wherein in Compound Ir716: R=Me,
in Compound Ir717: R=Et,
in Compound Ir718: R=$^i$Pr,
in Compound Ir719: R=Cy,
in Compound Ir720: R=$^i$Bu,
in Compound Ir721: R=$^t$Bu,
in Compound Ir722: R=CN,
in Compound Ir723: R=neopentyl,
in Compound Ir724: R=Ph,
in Compound Ir725: R=4-biphenyl,
in Compound Ir726: R=2,6-($^i$Pr)$_2$Ph,
in Compound Ir727: R=2,6-($^i$Pr)$_2$-4-biphenyl,
in Compound Ir728: R=2,4-($^i$Pr)$_2$-3-dibenzofuran,
Compound Ir729 through Ir741, each represented by the formula

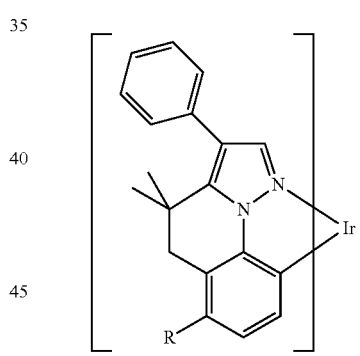

wherein in Compound Ir729: R=Me,
in Compound Ir730: R=Et,
in Compound Ir731: R=$^i$Pr,
in Compound Ir732: R=Cy,
in Compound Ir733: R=$^i$Bu,
in Compound Ir734: R=$^t$Bu,
in Compound Ir735: R=CN,
in Compound Ir736: R=neopentyl,
in Compound Ir737: R=Ph,
in Compound Ir738: R=4-biphenyl,
in Compound Ir739: R=2,6-($^i$Pr)$_2$Ph,
in Compound Ir740: R=2,6-($^i$Pr)$_2$-4-biphenyl,
in Compound Ir741: R=2,4-($^i$Pr)$_2$-3-dibenzofuran,
Compound Ir742 through Ir754, each represented by the formula

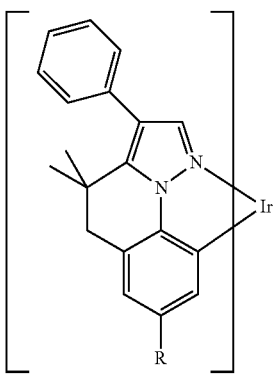

wherein in Compound Ir742: R=Me,
in Compound Ir743: R=Et,
in Compound Ir744: R=$^i$Pr,
in Compound Ir745: R=Cy,
in Compound Ir746: R=$^i$Bu,
in Compound Ir747: R=$^t$Bu,
in Compound Ir748: R=CN,
in Compound Ir749: R=neopentyl,
in Compound Ir750: R=Ph,
in Compound Ir751: R=4-biphenyl,
in Compound Ir752: R=2,6-($^i$Pr)$_2$Ph,
in Compound Ir753: R=2,6-($^i$Pr)$_2$-4-biphenyl,
in Compound Ir754: R=2,4-($^i$Pr)$_2$-3-dibenzofuran,
Compound Ir755 through Ir767, each represented by the formula

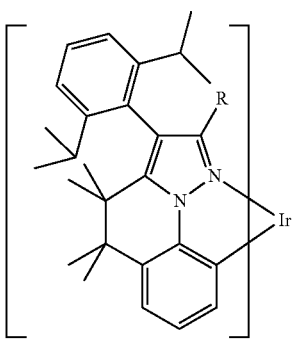

wherein in Compound Ir755: R=Me,
in Compound Ir756: R=Et,
in Compound Ir757: R=$^i$Pr,
in Compound Ir758: R=Cy,
in Compound Ir759: R=$^i$Bu,
in Compound Ir760: R=$^t$Bu,
in Compound Ir761: R=CN,
in Compound Ir762: R=neopentyl,
in Compound Ir763: R=Ph,
in Compound Ir764: R=4-biphenyl,
in Compound Ir765: R=2,6-($^i$Pr)$_2$Ph,
in Compound Ir766: R=2,6-($^i$Pr)$_2$-4-biphenyl,
in Compound Ir767: R=2,4-($^i$Pr)$_2$-3-dibenzofuran,
Compound Ir768 through Ir780, each represented by the formula

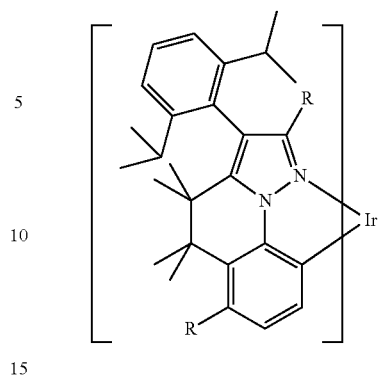

wherein in Compound Ir768: R=Me,
in Compound Ir769: R=Et,
in Compound Ir770: R=$^i$Pr,
in Compound Ir771: R=Cy,
in Compound Ir772: R=$^i$Bu,
in Compound Ir773: R=$^t$Bu,
in Compound Ir774: R=CN,
in Compound Ir775: R=neopentyl,
in Compound Ir776: R=Ph,
in Compound Ir777: R=4-biphenyl,
in Compound Ir778: R=2,6-($^i$Pr)$_2$Ph,
in Compound Ir779: R=2,6-($^i$Pr)$_2$-4-biphenyl,
in Compound Ir780: R=2,4-($^i$Pr)$_2$-3-dibenzofuran,
Compound Ir781 through Ir793, each represented by the formula

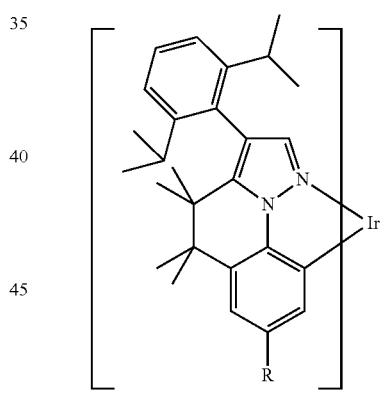

wherein in Compound Ir781: R=Me,
in Compound Ir782: R=Et,
in Compound Ir783: R=$^i$Pr,
in Compound Ir784: R=Cy,
in Compound Ir785: R=$^i$Bu,
in Compound Ir786: R=$^t$Bu,
in Compound Ir787: R=CN,
in Compound Ir788: R=neopentyl,
in Compound Ir789: R=Ph,
in Compound Ir790: R=4-biphenyl,
in Compound Ir791: R=2,6-($^i$Pr)$_2$Ph,
in Compound Ir792: R=2,6-($^i$Pr)$_2$-4-biphenyl,
in Compound Ir793: R=2,4-($^i$Pr)$_2$-3-dibenzofuran,
Compound Ir794 through Ir806, each represented by the formula

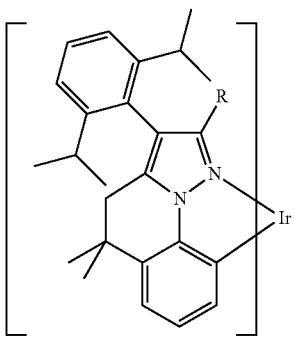

wherein in Compound Ir794: R=Me,
in Compound Ir795: R=Et,
in Compound Ir796: R=$^i$Pr,
in Compound Ir797: R=Cy,
in Compound Ir798: R=$^i$Bu,
in Compound Ir799: R=$^t$Bu,
in Compound Ir800: R=CN,
in Compound Ir801: R=neopentyl,
in Compound Ir802: R=Ph,
in Compound Ir803: R=4-biphenyl,
in Compound Ir804: R=2,6-($^i$Pr)$_2$Ph,
in Compound Ir805: R=2,6-($^i$Pr)$_2$-4-biphenyl,
in Compound Ir806: R=2,4-($^i$Pr)$_2$-3-dibenzofuran,
Compound Ir807 through Ir819, each represented by the formula

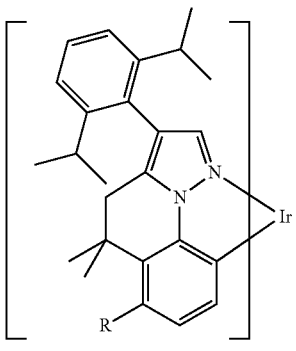

wherein in Compound Ir807: R=Me,
in Compound Ir808: R=Et,
in Compound Ir809: R=$^i$Pr,
in Compound Ir810: R=Cy,
in Compound Ir811: R=$^i$Bu,
in Compound Ir812: R=$^t$Bu,
in Compound Ir813: R=CN,
in Compound Ir814: R=neopentyl,
in Compound Ir815: R=Ph,
in Compound Ir816: R=4-biphenyl,
in Compound Ir817: R=2,6-($^i$Pr)$_2$Ph,
in Compound Ir818: R=2,6-($^i$Pr)$_2$-4-biphenyl,
in Compound Ir819: R=2,4-($^i$Pr)$_2$-3-dibenzofuran,
Compound Ir820 through Ir832, each represented by the formula

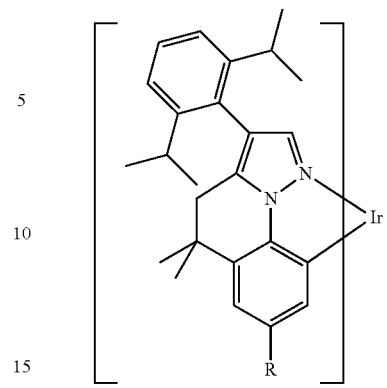

wherein in Compound Ir820: R=Me,
in Compound Ir821: R=Et,
in Compound Ir822: R=$^i$Pr,
in Compound Ir823: R=Cy,
in Compound Ir824: R=$^i$Bu,
in Compound Ir825: R=$^t$Bu,
in Compound Ir826: R=CN,
in Compound Ir827: R=neopentyl,
in Compound Ir828: R=Ph,
in Compound Ir829: R=4-biphenyl,
in Compound Ir830: R=2,6-($^i$Pr)$_2$Ph,
in Compound Ir831: R=2,6-($^i$Pr)$_2$-4-biphenyl,
in Compound Ir832: R=2,4-($^i$Pr)$_2$-3-dibenzofuran,
Compound Ir833 through Ir845, each represented by the formula

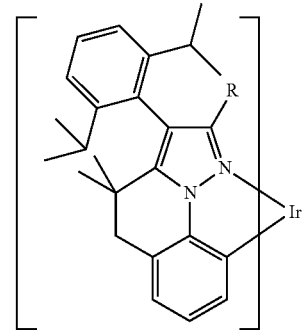

wherein in Compound Ir833: R=Me,
in Compound Ir834: R=Et,
in Compound Ir835: R=$^i$Pr,
in Compound Ir836: R=Cy,
in Compound Ir837: R=$^i$Bu,
in Compound Ir838: R=$^t$Bu,
in Compound Ir839: R=CN,
in Compound Ir840: R=neopentyl,
in Compound Ir841: R=Ph,
in Compound Ir842: R=4-biphenyl,
in Compound Ir843: R=2,6-($^i$Pr)$_2$Ph,
in Compound Ir844: R=2,6-($^i$Pr)$_2$-4-biphenyl,
in Compound Ir845: R=2,4-($^i$Pr)$_2$-3-dibenzofuran,
Compound Ir846 through Ir858, each represented by the formula

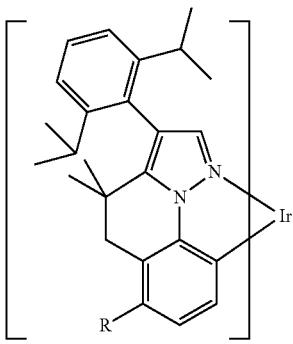

wherein in Compound Ir846: R=Me,
in Compound Ir847: R=Et,
in Compound Ir848: R=$^i$Pr,
in Compound Ir849: R=Cy,
in Compound Ir850: R=$^i$Bu,
in Compound Ir851: R=$^t$Bu,
in Compound Ir852: R=CN,
in Compound Ir853: R=neopentyl,
in Compound Ir854: R=Ph,
in Compound Ir855: R=4-biphenyl,
in Compound Ir856: R=2,6-($^i$Pr)$_2$Ph,
in Compound Ir857: R=2,6-($^i$Pr)$_2$-4-biphenyl,
in Compound Ir858: R=2,4-($^i$Pr)$_2$-3-dibenzofuran,
Compound Ir859 through Ir871, each represented by the formula

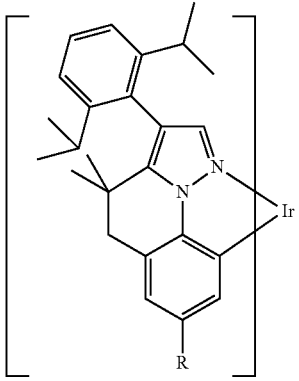

wherein in Compound Ir859: R=Me,
in Compound Ir860: R=Et,
in Compound Ir861: R=$^i$Pr,
in Compound Ir862: R=Cy,
in Compound Ir863: R=$^i$Bu,
in Compound Ir864: R=$^t$Bu,
in Compound Ir865: R=CN,
in Compound Ir866: R=neopentyl,
in Compound Ir867: R=Ph,
in Compound Ir868: R=4-biphenyl,
in Compound Ir869: R=2,6-($^i$Pr)$_2$Ph,
in Compound Ir870: R=2,6-($^i$Pr)$_2$-4-biphenyl,
in Compound Ir871: R=2,4-($^i$Pr)$_2$-3-dibenzofuran,
Compound Ir872 through Ir873, each represented by the formula

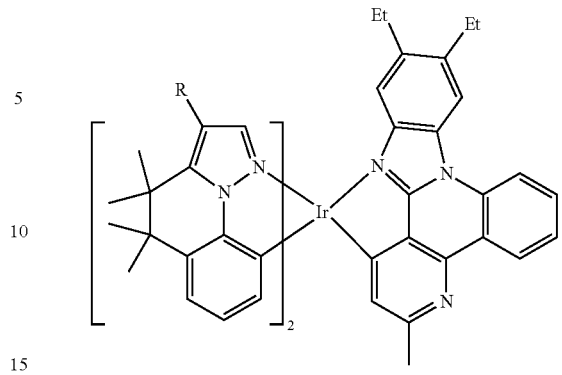

wherein in Compound Ir872: R=H,
in Compound Ir873: R=Ph,
Compound Ir874 through Ir875, each represented by the formula


wherein in Compound Ir874: R=H,
in Compound Ir875: R=Ph,
Compound Ir876 through Ir887, each represented by the formula

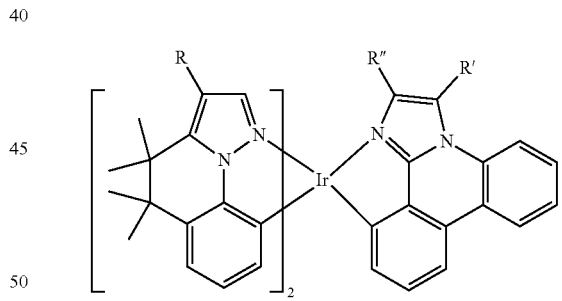

wherein in Compound Ir876: R=H, R'=2,6-($^i$Pr)Ph, R"=H,
in Compound Ir877: R=H, R'=2,6-($^t$Bu)Ph, R"=H,
in Compound Ir878: R=H, R'=Cy, R"=H,
in Compound Ir879: R=Ph, R'=2,6-($^i$Pr)Ph, R"=H,
in Compound Ir880: R=Ph, R'=2,6-($^t$Bu)Ph, R"=H,
in Compound Ir881: R=Ph, R'=Cy, R"=H,
in Compound Ir882: R=H, R'=2,6-($^i$Pr)Ph, R"=Me,
in Compound Ir883: R=H, R'=2,6-($^t$Bu)Ph, R"=Me,
in Compound Ir884: R=H, R'=Cy, R"=Me,
in Compound Ir885: R=Ph, R'=2,6-($^i$Pr)Ph, R"=Me,
in Compound Ir886: R=Ph, R'=2,6-($^t$Bu)Ph, R"=Me,
in Compound Ir887: R=Ph, R'=Cy, R"=Me,
Compound Ir888 through Ir889, each represented by the formula

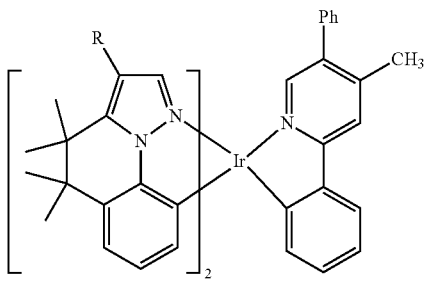

wherein in Compound Ir888: R=H,
in Compound Ir889: R=Ph,
Compound Ir890 through Ir891, each represented by the formula

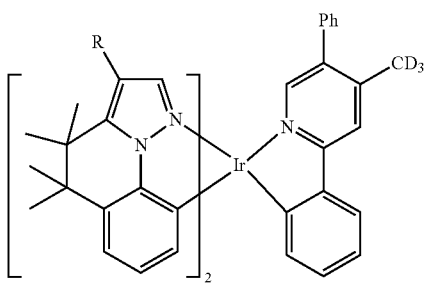

wherein in Compound Ir890: R=H,
in Compound Ir891: R=Ph,
Compound Ir892 through Ir895, each represented by the formula

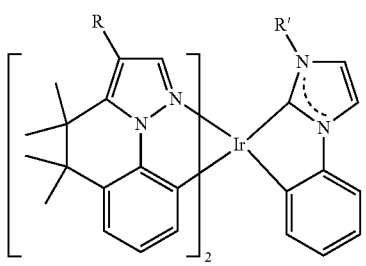

wherein in Compound Ir892: R=H, R'=Me,
in Compound Ir893: R=H, R'=Ph,
in Compound Ir894: R=Ph, R'=Me,
in Compound Ir895: R=Ph, R'=Ph,
Compound Ir896 through Ir899, each represented by the formula

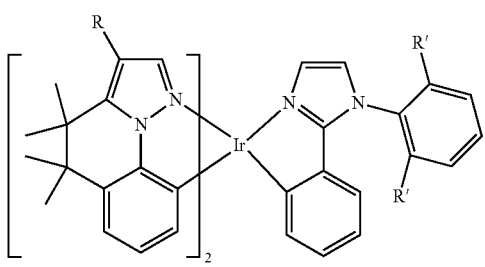

wherein in Compound Ir896: R=H, R'=Me,
in Compound Ir897: R=H, R'=$^i$Pr,
in Compound Ir898: R=Ph, R'=Me,
in Compound Ir899: R=Ph, R'=$^i$Pr,
Compound Ir900 through Ir903, each represented by the formula

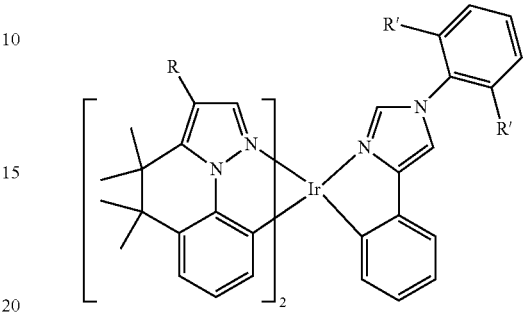

wherein in Compound Ir900: R=H, R'=Me,
in Compound Ir901: R=H, R'=$^i$Pr,
in Compound Ir902: R=Ph, R'=Me,
in Compound Ir903: R=Ph, R'=$^i$Pr, and
Compound Ir904 through Ir907, each represented by the formula

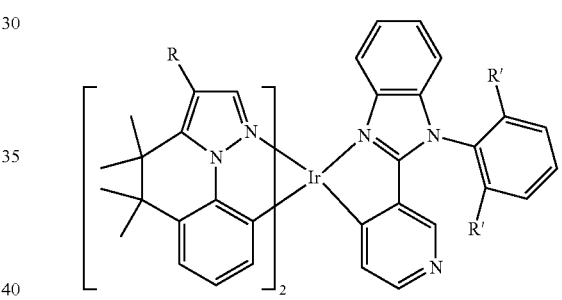

wherein in Compound Ir904: R=H, R'=Me,
in Compound Ir905: R=H, R'=$^i$Pr,
in Compound Ir906: R=Ph, R'=Me,
in Compound Ir907: R=Ph, R'=$^i$Pr, According to another aspect of the present disclosure, a compound having the structure of Formula III,

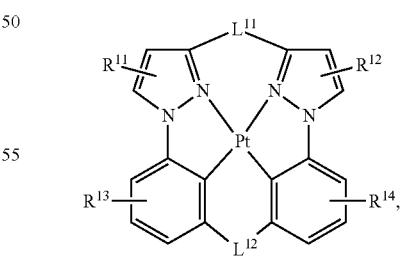

is disclosed. In the structure of Formula III:
$R^{11}$, and $R^{12}$ each independently represent mono, or di substitution, or no substitution;
$R^{13}$ and $R^{14}$ each independently represent mono, di, tri, or tetra substitution, or no substitution;
$L^{11}$ represents a linking group selected from the group consisting of alkyl, cycloalkyl, aryl, and heteroaryl;

$L^{12}$ represents a linking group selected from the group consisting of $NR^{15}$, and $PR^{15}$;

$R^{11}$, $R^{12}$, $R^{13}$, $R^{14}$, and $R^{15}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent $L^{11}$, $L^{12}$, $R^{11}$, $R^{12}$, $R^{13}$, $R^{14}$, and $R^{15}$ are optionally joined to form a fused or unfused ring.

In some embodiments, $L^{11}$ comprises two different atoms, each one bonded to a different pyrazole, and $L^{12}$ comprises one atom bonded to both phenyl rings.

In some embodiments, L" has the structure selected from the group consisting of:

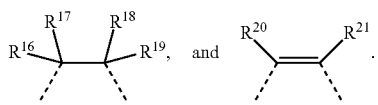

In such embodiments, $R^{16}$, $R^{17}$, $R^{18}$, $R^{19}$, $R^{20}$, and $R^{21}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent $R^{16}$, $R^{17}$, $R^{18}$, $R^{19}$, $R^{20}$, and $R^{21}$ are optionally joined to form a fused or unfused ring.

In some embodiments, $L^{11}$ is selected from the group consisting of:

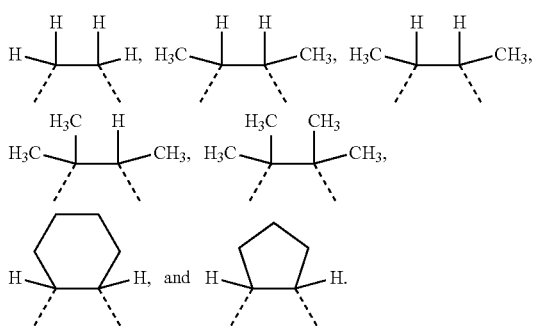

In some embodiments, $L^{11}$ is selected from the group consisting of:

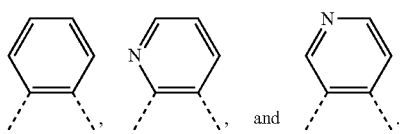

In some embodiments, $L^{12}$ is $NR^{15}$. In some embodiments, $L^{12}$ is selected from the group consisting of:

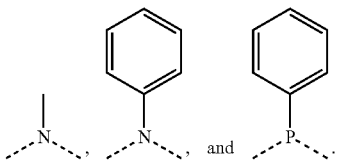

In some embodiments, at least one pair of adjacent $L^{11}$, $L^{12}$, $R^{11}$, $R^{12}$, $R^{13}$, $R^{14}$, and $R^{15}$ are joined or fused into a ring.

In some embodiments, the compound has the structure of Formula VI,

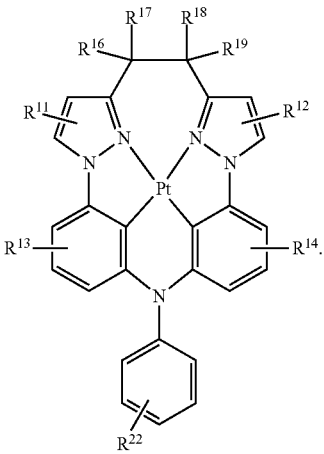

In some embodiments, $R^{22}$ represents mono, di, tri, tetra, or penta substitution, or no substitution; $R^{16}$, $R^{17}$, $R^{18}$, $R^{19}$, and $R^{22}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent $R^{16}$, $R^{17}$, $R^{18}$, $R^{19}$, and $R^{22}$ are optionally joined to form a fused or unfused ring.

In some embodiments, the compound has the structure of Formula V,

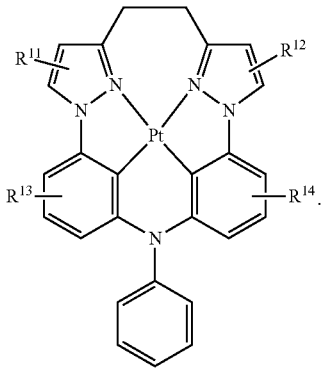

In some more specific embodiments, the compound is selected from the group consisting of:
Compound PtM1 through PtM12, each represented by the formula

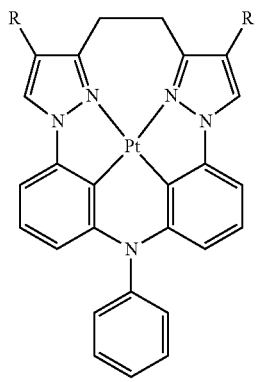

wherein in Compound PtM1: R=H,
in Compound PtM2: R=Me,
in Compound PtM3: R=Et,
in Compound PtM4: R=$^i$Pr,
in Compound PtM5: R=neopentyl,
in Compound PtM6: R=$^i$Bu,
in Compound PtM7: R=$^t$Bu,
in Compound PtM8: R=Ph,
in Compound PtM9: R=4-biphenyl,
in Compound PtM10: R=2,6-($^i$Pr)$_2$Ph,
in Compound PtM11: R=2,6-($^i$Pr)$_2$-4-biphenyl,
in Compound PtM12: R=2,4-($^i$Pr)$_2$-3-dibenzofuran, Compound PtM13 through PtM21, each represented by the formula

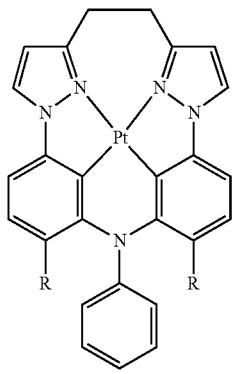

wherein in Compound PtM13: R=Me,
in Compound PtM14: R=Et,
in Compound PtM15: R=$^i$Pr,
in Compound PtM16: R=neopentyl,
in Compound PtM17: R=$^i$Bu,
in Compound PtM18: R=$^t$Bu,
in Compound PtM19: R=Ph,
in Compound PtM20: R=2,6-(Me)$_2$Ph,
in Compound PtM21: R=2,6-($^i$Pr)$_2$Ph, Compound PtM22 through PtM30, each represented by the formula

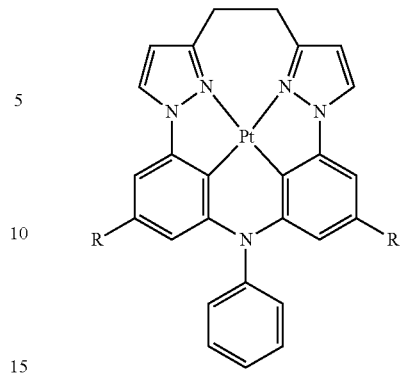

wherein in Compound PtM22: R=Me,
in Compound PtM23: R=Et,
in Compound PtM24: R=$^i$Pr,
in Compound PtM25: R=neopentyl,
in Compound PtM26: R=$^i$Bu,
in Compound PtM27: R=$^t$Bu,
in Compound PtM28: R=Ph,
in Compound PtM29: R=2,6-(Me)$_2$Ph,
in Compound PtM30: R=2,6-($^i$Pr)$_2$Ph, Compound PtM31 through PtM42, each represented by the formula

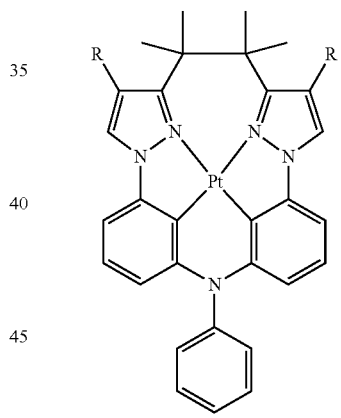

wherein in Compound PtM31: R=H,
in Compound PtM32: R=Me,
in Compound PtM33: R=Et,
in Compound PtM34: R=$^i$Pr,
in Compound PtM35: R=neopentyl,
in Compound PtM36: R=$^i$Bu,
in Compound PtM37: R=$^t$Bu,
in Compound PtM38: R=Ph,
in Compound PtM39: R=4-biphenyl,
in Compound PtM40: R=2,6-($^i$Pr)$_2$Ph,
in Compound PtM41: R=2,6-($^i$Pr)$_2$-4-biphenyl,
in Compound PtM42: R=2,4-($^i$Pr)$_2$-3-dibenzofuran, Compound PtM43 through PtM51, each represented by the formula

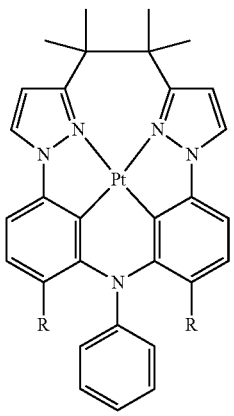

wherein in Compound PtM43: R=Me,
in Compound PtM44: R=Et,
in Compound PtM45: R=$^i$Pr,
in Compound PtM46: R=neopentyl,
in Compound PtM47: R=$^i$Bu,
in Compound PtM48: R=$^t$Bu,
in Compound PtM49: R=Ph,
in Compound PtM50: R=2,6-(Me)$_2$Ph,
in Compound PtM51: R=2,6-($^i$Pr)$_2$Ph,
Compound PtM52 through PtM60, each represented by the formula

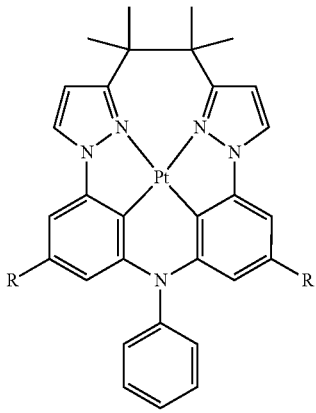

wherein in Compound PtM52: R=Me,
in Compound PtM53: R=Et,
in Compound PtM54: R=$^i$Pr,
in Compound PtM55: R=neopentyl,
in Compound PtM56: R=$^i$Bu,
in Compound PtM57: R=$^t$Bu,
in Compound PtM58: R=Ph,
in Compound PtM59: R=2,6-(Me)$_2$Ph,
in Compound PtM60: R=2,6-($^i$Pr)$_2$Ph,
Compound PtM61 through PtM72, each represented by the formula

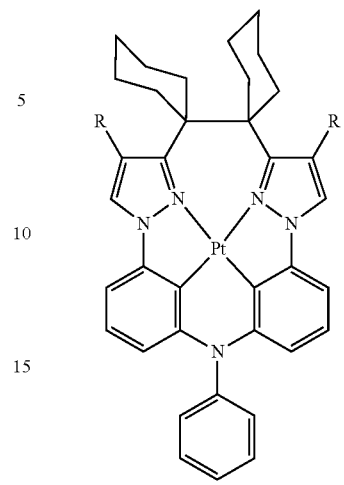

wherein in Compound PtM61: R=H,
in Compound PtM62: R=Me,
in Compound PtM63: R=Et,
in Compound PtM64: R=$^i$Pr,
in Compound PtM65: R=neopentyl,
in Compound PtM66: R=$^i$Bu,
in Compound PtM67: R=$^t$Bu,
in Compound PtM68: R=Ph,
in Compound PtM69: R=4-biphenyl,
in Compound PtM70: R=2,6-($^i$Pr)$_2$Ph,
in Compound PtM71: R=2,6-($^i$Pr)$_2$-4-biphenyl,
in Compound PtM72: R=2,4-($^i$Pr)$_2$-3-dibenzofuran,
Compound PtM73 through PtM81, each represented by the formula

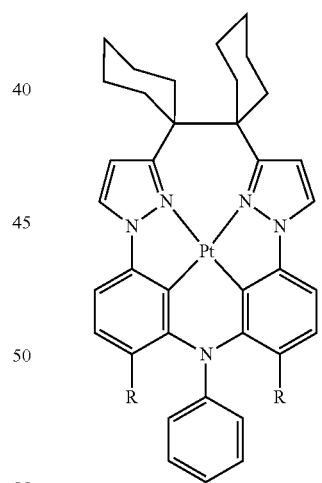

wherein in Compound PtM73: R=Me,
in Compound PtM74: R=Et,
in Compound PtM75: R=$^i$Pr,
in Compound PtM76: R=neopentyl,
in Compound PtM77: R=$^i$Bu,
in Compound PtM78: R=$^t$Bu,
in Compound PtM79: R=Ph,
in Compound PtM80: R=2,6-(Me)$_2$Ph,
in Compound PtM81: R=2,6-($^i$Pr)$_2$Ph,
Compound PtM82 through PtM90, each represented by the formula

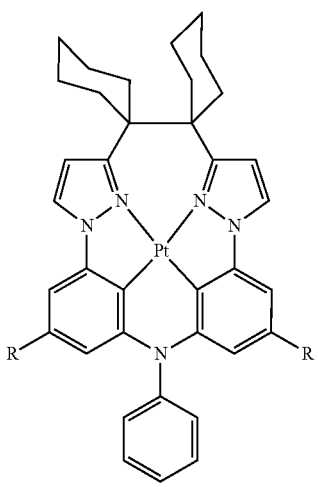

wherein in Compound PtM82: R=Me,
in Compound PtM83: R=Et,
in Compound PtM84: R=$^i$Pr,
in Compound PtM85: R=neopentyl,
in Compound PtM86: R=$^i$Bu,
in Compound PtM87: R=$^t$Bu,
in Compound PtM88: R=Ph,
in Compound PtM89: R=2,6-(Me)$_2$Ph,
in Compound PtM90: R=2,6-($^i$Pr)$_2$Ph,
Compound PtM91 through PtM102, each represented by the formula

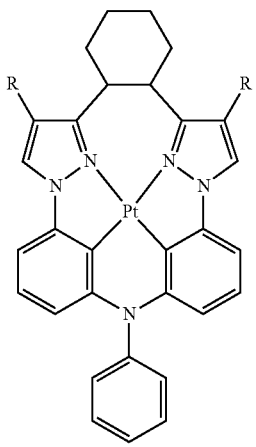

wherein in Compound PtM91: R=H,
in Compound PtM92: R=Me,
in Compound PtM93: R=Et,
in Compound PtM94: R=$^i$Pr,
in Compound PtM95: R=neopentyl,
in Compound PtM96: R=$^i$Bu,
in Compound PtM97: R=$^t$Bu,
in Compound PtM98: R=Ph,
in Compound PtM99: R=4-biphenyl,
in Compound PtM100: R=2,6-($^i$Pr)$_2$Ph,
in Compound PtM101: R=2,6-($^i$Pr)$_2$-4-biphenyl,
in Compound PtM102: R=2,4-($^i$Pr)$_2$-3-dibenzofuran,
Compound PtM103 through PtM111, each represented by the formula

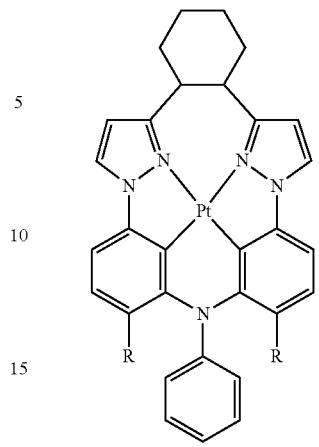

wherein in Compound PtM103: R=Me,
in Compound PtM104: R=Et,
in Compound PtM105: R=$^i$Pr,
in Compound PtM106: R=neopentyl,
in Compound PtM107: R=$^i$Bu,
in Compound PtM108: R=$^t$Bu,
in Compound PtM109: R=Ph,
in Compound PtM110: R=2,6-(Me)$_2$Ph,
in Compound PtM111: R=2,6-($^i$Pr)$_2$Ph,
Compound PtM112 through PtM120, each represented by the formula

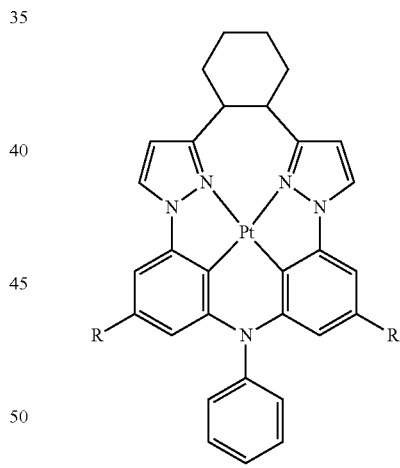

wherein in Compound PtM112: R=Me,
in Compound PtM113: R=Et,
in Compound PtM114: R=$^i$Pr,
in Compound PtM115: R=neopentyl,
in Compound PtM116: R=$^i$Bu,
in Compound PtM117: R=$^t$Bu,
in Compound PtM118: R=Ph,
in Compound PtM119: R=2,6-(Me)$_2$Ph,
in Compound PtM120: R=2,6-($^i$Pr)$_2$Ph,
Compound PtM121 through PtM132, each represented by the formula

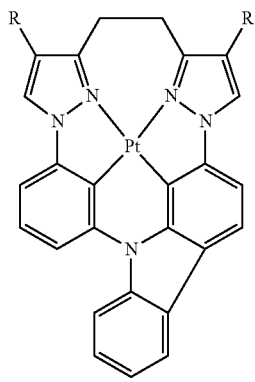

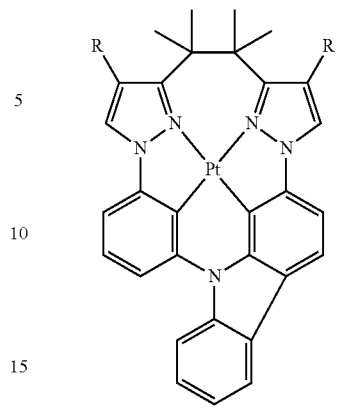

wherein in Compound PtM121: R=H,
in Compound PtM122: R=Me,
in Compound PtM123: R=Et,
in Compound PtM124: R=$^i$Pr,
in Compound PtM125: R=neopentyl,
in Compound PtM126: R=$^i$Bu,
in Compound PtM127: R=$^t$Bu,
in Compound PtM128: R=Ph,
in Compound PtM129: R=4-biphenyl,
in Compound PtM130: R=2,6-($^i$Pr)$_2$Ph,
in Compound PtM131: R=2,6-($^i$Pr)$_2$-4-biphenyl,
in Compound PtM132: R=2,4-($^i$Pr)$_2$-3-dibenzofuran,
Compound PtM133 through PtM141, each represented by the formula wherein in Compound PtM142: R=H,
in Compound PtM143: R=Me,
in Compound PtM144: R=Et,
in Compound PtM145: R=$^i$Pr,
in Compound PtM146: R=neopentyl,
in Compound PtM147: R=$^i$Bu,
in Compound PtM148: R=$^t$Bu,
in Compound PtM149: R=Ph,
in Compound PtM150: R=4-biphenyl,
in Compound PtM151: R=2,6-($^i$Pr)$_2$Ph,
in Compound PtM152: R=2,6-($^i$Pr)$_2$-4-biphenyl,
in Compound PtM153: R=2,4-($^i$Pr)$_2$-3-dibenzofuran,
Compound PtM154 through PtM162, each represented by the formula

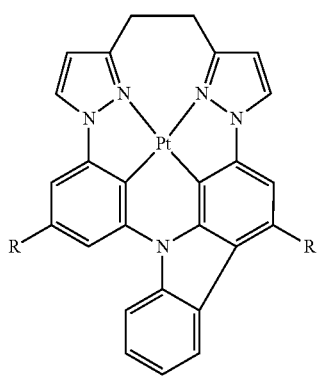

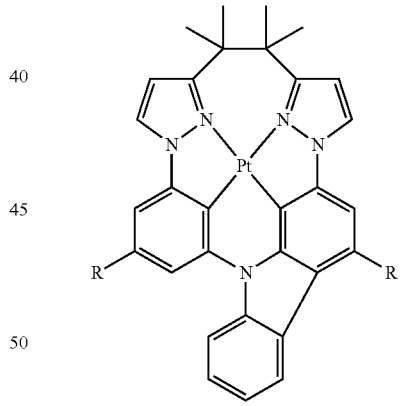

wherein in Compound PtM133: R=Me,
in Compound PtM134: R=Et,
in Compound PtM135: R=$^i$Pr,
in Compound PtM136: R=neopentyl,
in Compound PtM137: R=$^i$Bu,
in Compound PtM138: R=$^t$Bu,
in Compound PtM139: R=Ph,
in Compound PtM140: R=2,6-(Me)$_2$Ph,
in Compound PtM141: R=2,6-($^i$Pr)$_2$Ph,
Compound PtM142 through PtM153, each represented by the formula wherein in Compound PtM154: R=Me,
in Compound PtM155: R=Et,
in Compound PtM156: R=$^i$Pr,
in Compound PtM157: R=neopentyl,
in Compound PtM158: R=$^i$Bu,
in Compound PtM159: R=$^t$Bu,
in Compound PtM160: R=Ph,
in Compound PtM161: R=2,6-(Me)$_2$Ph,
in Compound PtM162: R=2,6-($^i$Pr)$_2$Ph,
Compound PtM163 through PtM174, each represented by the formula

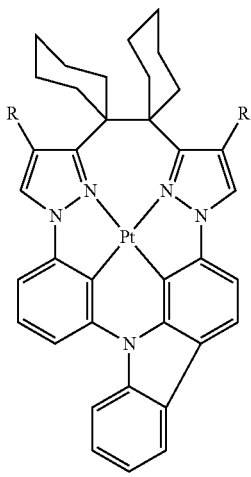

wherein in Compound PtM163: R=H,
in Compound PtM164: R=Me,
in Compound PtM165: R=Et,
in Compound PtM166: R=$^i$Pr,
in Compound PtM167: R=neopentyl,
in Compound PtM168: R=$^i$Bu,
in Compound PtM169: R=$^t$Bu,
in Compound PtM170: R=Ph,
in Compound PtM171: R=4-biphenyl,
in Compound PtM172: R=2,6-($^i$Pr)$_2$Ph,
in Compound PtM173: R=2,6-($^i$Pr)$_2$-4-biphenyl,
in Compound PtM174: R=2,4-($^i$Pr)$_2$-3-dibenzofuran,
Compound PtM175 through PtM183, each represented by the formula

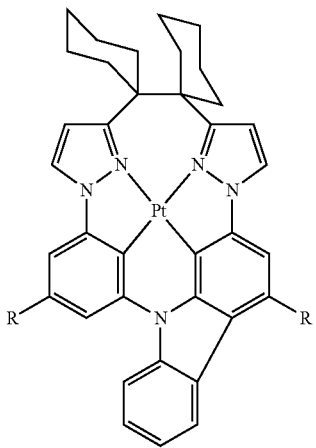

wherein in Compound PtM175: R=Me,
in Compound PtM176: R=Et,
in Compound PtM177: R=$^i$Pr,
in Compound PtM178: R=neopentyl,
in Compound PtM179: R=$^i$Bu,
in Compound PtM180: R=$^t$Bu,
in Compound PtM181: R=Ph,
in Compound PtM182: R=2,6-(Me)$_2$Ph,
in Compound PtM183: R=2,6-($^i$Pr)$_2$Ph,
Compound PtM184 through PtM195, each represented by the formula

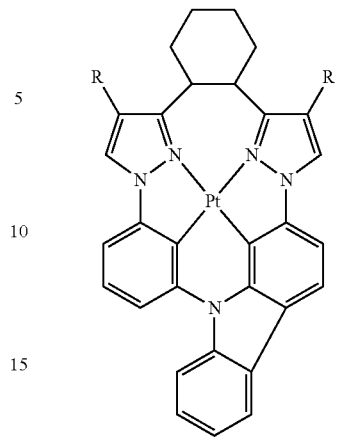

wherein in Compound PtM184: R=H,
in Compound PtM185: R=Me,
in Compound PtM186: R=Et,
in Compound PtM187: R=$^i$Pr,
in Compound PtM188: R=neopentyl,
in Compound PtM189: R=$^i$Bu,
in Compound PtM190: R=$^t$Bu,
in Compound PtM191: R=Ph,
in Compound PtM192: R=4-biphenyl,
in Compound PtM193: R=2,6-($^i$Pr)$_2$Ph,
in Compound PtM194: R=2,6-($^i$Pr)$_2$-4-biphenyl,
in Compound PtM195: R=2,4-($^i$Pr)$_2$-3-dibenzofuran,
Compound PtM196 through PtM204, each represented by the formula

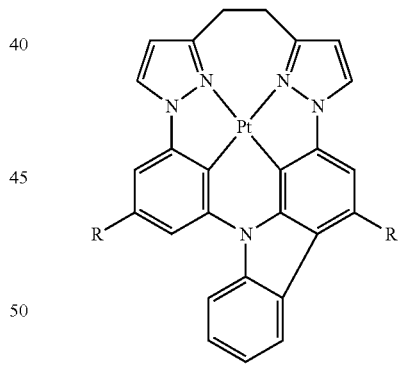

wherein in Compound PtM196: R=Me,
in Compound PtM197: R=Et,
in Compound PtM198: R=$^i$Pr,
in Compound PtM199: R=neopentyl,
in Compound PtM200: R=$^i$Bu,
in Compound PtM201: R=$^t$Bu,
in Compound PtM202: R=Ph,
in Compound PtM203: R=2,6-(Me)$_2$Ph,
in Compound PtM204: R=2,6-($^i$Pr)$_2$Ph,
Compound PtM205 through PtM216, each represented by the formula

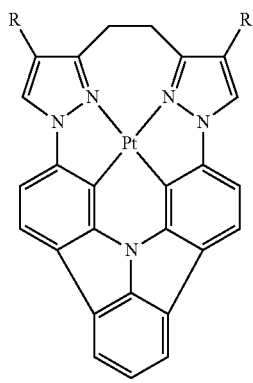

wherein in Compound PtM205: R=H,
in Compound PtM206: R=Me,
in Compound PtM207: R=Et,
in Compound PtM208: R=$^i$Pr,
in Compound PtM209: R=neopentyl,
in Compound PtM210: R=$^i$Bu,
in Compound PtM211: R=$^t$Bu,
in Compound PtM212: R=Ph,
in Compound PtM213: R=4-biphenyl,
in Compound PtM214: R=2,6-($^i$Pr)$_2$Ph,
in Compound PtM215: R=2,6-($^i$Pr)$_2$-4-biphenyl,
in Compound PtM216: R=2,4-($^i$Pr)$_2$-3-dibenzofuran,
Compound PtM217 through PtM225, each represented by the formula

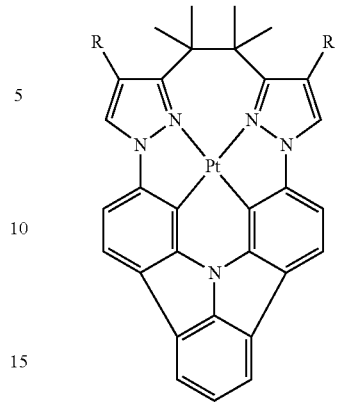

wherein in Compound PtM226: R=H,
in Compound PtM227: R=Me,
in Compound PtM228: R=Et,
in Compound PtM229: R=$^i$Pr,
in Compound PtM230: R=neopentyl,
in Compound PtM231: R=$^i$Bu,
in Compound PtM232: R=$^t$Bu,
in Compound PtM233: R=Ph,
in Compound PtM234: R=4-biphenyl,
in Compound PtM235: R=2,6-($^i$Pr)$_2$Ph,
in Compound PtM236: R=2,6-($^i$Pr)$_2$-4-biphenyl,
in Compound PtM237: R=2,4-($^i$Pr)$_2$-3-dibenzofuran,
Compound PtM238 through PtM246, each represented by the formula

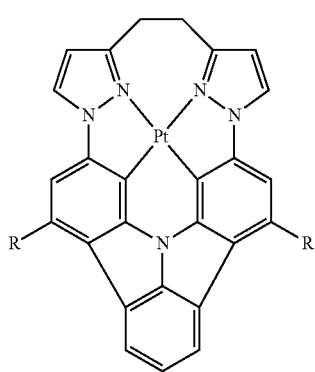

wherein in Compound PtM217: R=Me,
in Compound PtM218: R=Et,
in Compound PtM219: R=$^i$Pr,
in Compound PtM220: R=neopentyl,
in Compound PtM221: R=$^i$Bu,
in Compound PtM222: R=$^t$Bu,
in Compound PtM223: R=Ph,
in Compound PtM224: R=2,6-(Me)$_2$Ph,
in Compound PtM225: R=2,6-($^i$Pr)$_2$Ph,
Compound PtM226 through PtM237, each represented by the formula

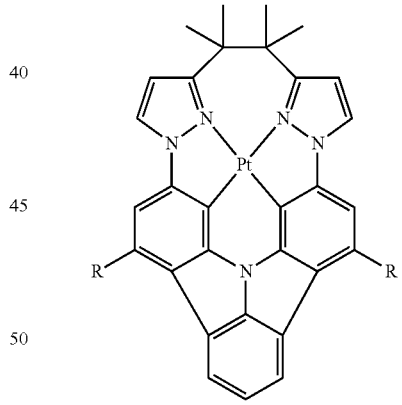

wherein in Compound PtM238: R=Me,
in Compound PtM239: R=Et,
in Compound PtM240: R=$^i$Pr,
in Compound PtM241: R=neopentyl,
in Compound PtM242: R=$^i$Bu,
in Compound PtM243: R=$^t$Bu,
in Compound PtM244: R=Ph,
in Compound PtM245: R=2,6-(Me)$_2$Ph,
in Compound PtM246: R=2,6-($^i$Pr)$_2$Ph,
Compound PtM247 through PtM258, each represented by the formula

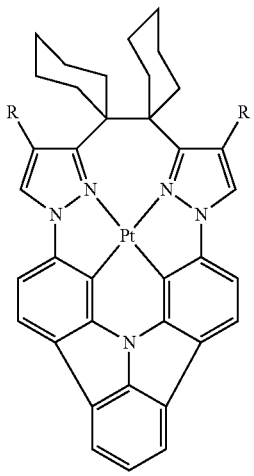

wherein in Compound PtM247: R=H,
in Compound PtM248: R=Me,
in Compound PtM249: R=Et,
in Compound PtM250: R=$^i$Pr,
in Compound PtM251: R=neopentyl,
in Compound PtM252: R=$^i$Bu,
in Compound PtM253: R=$^t$Bu,
in Compound PtM254: R=Ph,
in Compound PtM255: R=4-biphenyl,
in Compound PtM256: R=2,6-($^i$Pr)$_2$Ph,
in Compound PtM257: R=2,6-($^i$Pr)$_2$-4-biphenyl,
in Compound PtM258: R=2,4-($^i$Pr)$_2$-3-dibenzofuran,
Compound PtM259 through PtM267, each represented by the formula

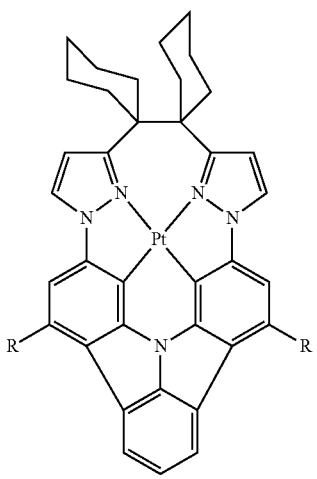

wherein in Compound PtM259: R=Me,
in Compound PtM260: R=Et,
in Compound PtM261: R=$^i$Pr,
in Compound PtM262: R=neopentyl,
in Compound PtM263: R=$^i$Bu,
in Compound PtM264: R=$^t$Bu,
in Compound PtM265: R=Ph,
in Compound PtM266: R=2,6-(Me)$_2$Ph,
in Compound PtM267: R=2,6-($^i$Pr)$_2$Ph,
Compound PtM268 through PtM279, each represented by the formula

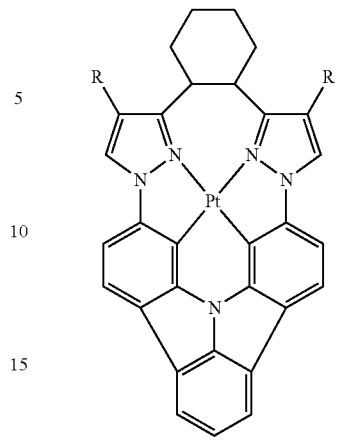

wherein in Compound PtM268: R=H,
in Compound PtM269: R=Me,
in Compound PtM270: R=Et,
in Compound PtM271: R=$^i$Pr,
in Compound PtM272: R=neopentyl,
in Compound PtM273: R=$^i$Bu,
in Compound PtM274: R=$^t$Bu,
in Compound PtM275: R=Ph,
in Compound PtM276: R=4-biphenyl,
in Compound PtM277: R=2,6-($^i$Pr)$_2$Ph,
in Compound PtM278: R=2,6-($^i$Pr)$_2$-4-biphenyl,
in Compound PtM279: R=2,4-($^i$Pr)$_2$-3-dibenzofuran,
Compound PtM280 through PtM288, each represented by the formula

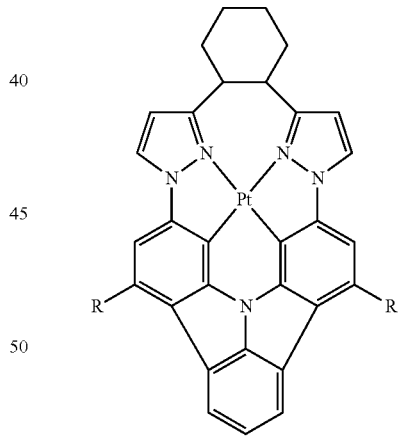

wherein in Compound PtM280: R=Me,
in Compound PtM281: R=Et,
in Compound PtM282: R=$^i$Pr,
in Compound PtM283: R=neopentyl,
in Compound PtM284: R=$^i$Bu,
in Compound PtM285: R=$^t$Bu,
in Compound PtM286: R=Ph,
in Compound PtM287: R=2,6-(Me)$_2$Ph,
in Compound PtM288: R=2,6-($^i$Pr)$_2$Ph,
Compound PtM289 through PtM312, each represented by the formula

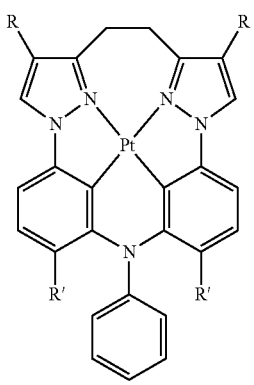

wherein in Compound PtM289: R=Me, R'=Me,
in Compound PtM290: R=Me, R'=$^i$Pr,
in Compound PtM291: R=Me, R'=Ph,
in Compound PtM292: R=Me, R'=2,6-($^i$Pr)$_2$Ph,
in Compound PtM293: R=$^i$Pr, R'=Me,
in Compound PtM294: R=$^i$Pr, R'=$^i$Pr,
in Compound PtM295: R=$^i$Pr, R'=Ph,
in Compound PtM296: R=$^i$Pr, R'=2,6-($^i$Pr)$_2$Ph,
in Compound PtM297: R=Ph, R'=Me,
in Compound PtM298: R=Ph, R'=$^i$Pr,
in Compound PtM299: R=Ph, R'=Ph,
in Compound PtM300: R=Ph, R'=2,6-($^i$Pr)$_2$Ph,
in Compound PtM301: R=2,6-($^i$Pr)$_2$Ph, R'=Me,
in Compound PtM302: R=2,6-($^i$Pr)$_2$Ph, R'=$^i$Pr,
in Compound PtM303: R=2,6-($^i$Pr)$_2$Ph, R'=Ph,
in Compound PtM304: R=2,6-($^i$Pr)$_2$Ph, R'=2,6-($^i$Pr)$_2$Ph,
in Compound PtM305: R=2,6-($^i$Pr)$_2$-4-biphenyl, R'=Me,
in Compound PtM306: R=2,6-($^i$Pr)$_2$-4-biphenyl, R'=$^i$Pr,
in Compound PtM307: R=2,6-($^i$Pr)$_2$-4-biphenyl, R'=Ph,
in Compound PtM308: R=2,6-($^i$Pr)$_2$-4-biphenyl, R'=2,6-($^i$Pr)$_2$Ph,
in Compound PtM309: R=2,4-($^i$Pr)$_2$-3-dibenzofuran, R'=Me,
in Compound PtM310: R=2,4-($^i$Pr)$_2$-3-dibenzofuran, R'=$^i$Pr,
in Compound PtM311: R=2,4-($^i$Pr)$_2$-3-dibenzofuran, R'=Ph,
in Compound PtM312: R=2,4-($^i$Pr)$_2$-3-dibenzofuran, R'=2,6-($^i$Pr)$_2$Ph, Compound PtM313 through PtM336, each represented by the formula

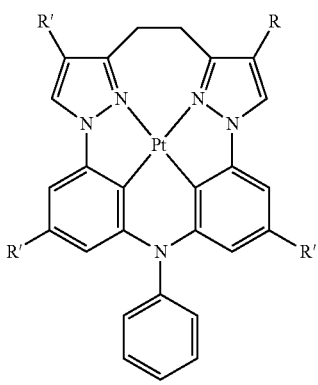

wherein in Compound PtM313: R=Me, R'=Me,
in Compound PtM314: R=Me, R'=$^i$Pr,
in Compound PtM315: R=Me, R'=Ph,
in Compound PtM316: R=Me, R'=2,6-($^i$Pr)$_2$Ph,
in Compound PtM317: R=$^i$Pr, R'=Me,
in Compound PtM318: R=$^i$Pr, R'=$^i$Pr,
in Compound PtM319: R=$^i$Pr, R'=Ph,
in Compound PtM320: R=$^i$Pr, R'=2,6-($^i$Pr)$_2$Ph,
in Compound PtM321: R=Ph, R'=Me,
in Compound PtM322: R=Ph, R'=$^i$Pr,
in Compound PtM323: R=Ph, R'=Ph,
in Compound PtM324: R=Ph, R'=2,6-($^i$Pr)$_2$Ph,
in Compound PtM325: R=2,6-($^i$Pr)$_2$Ph, R'=Me,
in Compound PtM326: R=2,6-($^i$Pr)$_2$Ph, R'=$^i$Pr,
in Compound PtM327: R=2,6-($^i$Pr)$_2$Ph, R'=Ph,
in Compound PtM328: R=2,6-($^i$Pr)$_2$Ph, R'=2,6-($^i$Pr)$_2$Ph,
in Compound PtM329: R=2,6-($^i$Pr)$_2$-4-biphenyl, R'=Me,
in Compound PtM330: R=2,6-($^i$Pr)$_2$-4-biphenyl, R'=$^i$Pr,
in Compound PtM331: R=2,6-($^i$Pr)$_2$-4-biphenyl, R'=Ph,
in Compound PtM332: R=2,6-($^i$Pr)$_2$-4-biphenyl, R'=2,6-($^i$Pr)$_2$Ph,
in Compound PtM333: R=2,4-($^i$Pr)$_2$-3-dibenzofuran, R'=Me,
in Compound PtM334: R=2,4-($^i$Pr)$_2$-3-dibenzofuran, R'=$^i$Pr,
in Compound PtM335: R=2,4-($^i$Pr)$_2$-3-dibenzofuran, R'=Ph,
in Compound PtM336: R=2,4-($^i$Pr)$_2$-3-dibenzofuran, R'=2,6-($^i$Pr)$_2$Ph, Compound PtM337 through PtM360, each represented by the formula

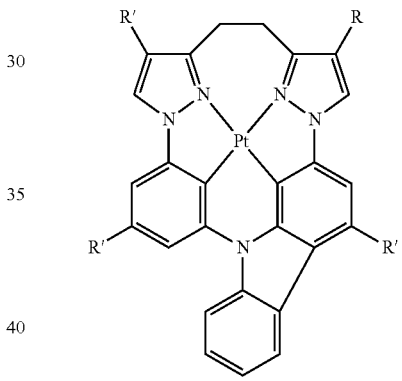

wherein in Compound PtM337: R=Me, R'=Me,
in Compound PtM338: R=Me, R'=$^i$Pr,
in Compound PtM339: R=Me, R'=Ph,
in Compound PtM340: R=Me, R'=2,6-($^i$Pr)$_2$Ph,
in Compound PtM341: R=$^i$Pr, R'=Me,
in Compound PtM342: R=$^i$Pr, R'=$^i$Pr,
in Compound PtM343: R=$^i$Pr, R'=Ph,
in Compound PtM344: R=$^i$Pr, R'=2,6-($^i$Pr)$_2$Ph,
in Compound PtM345: R=Ph, R'=Me,
in Compound PtM346: R=Ph, R'=$^i$Pr,
in Compound PtM347: R=Ph, R'=Ph,
in Compound PtM348: R=Ph, R'=2,6-($^i$Pr)$_2$Ph,
in Compound PtM349: R=2,6-($^i$Pr)$_2$Ph, R'=Me,
in Compound PtM350: R=2,6-($^i$Pr)$_2$Ph, R'=$^i$Pr,
in Compound PtM351: R=2,6-($^i$Pr)$_2$Ph, R'=Ph,
in Compound PtM352: R=2,6-($^i$Pr)$_2$Ph, R'=2,6-($^i$Pr)$_2$Ph,
in Compound PtM353: R=2,6-($^i$Pr)$_2$-4-biphenyl, R'=Me,
in Compound PtM354: R=2,6-($^i$Pr)$_2$-4-biphenyl, R'=$^i$Pr,
in Compound PtM355: R=2,6-($^i$Pr)$_2$-4-biphenyl, R'=Ph,
in Compound PtM356: R=2,6-($^i$Pr)$_2$-4-biphenyl, R'=2,6-($^i$Pr)$_2$Ph,
in Compound PtM357: R=2,4-($^i$Pr)$_2$-3-dibenzofuran, R'=Me,
in Compound PtM358: R=2,4-($^i$Pr)$_2$-3-dibenzofuran, R'=$^i$Pr, in Compound PtM359: R=2,4-($^i$Pr)$_2$-3-dibenzofuran, R'=Ph, in Compound PtM360: R=2,4-($^i$Pr)$_2$-3-dibenzofuran, R'=2,6-($^i$Pr)$_2$Ph, Compound PtM361 through PtM384, each represented by the formula

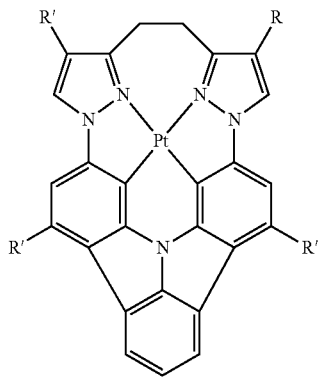

wherein in Compound PtM361: R=Me, R'=Me,
in Compound PtM362: R=Me, R'=$^i$Pr,
in Compound PtM363: R=Me, R'=Ph,
in Compound PtM364: R=Me, R'=2,6-($^i$Pr)$_2$Ph,
in Compound PtM365: R=$^i$Pr, R'=Me,
in Compound PtM366: R=$^i$Pr, R'=$^i$Pr,
in Compound PtM367: R=$^i$Pr, R'=Ph,
in Compound PtM368: R=$^i$Pr, R'=2,6-($^i$Pr)$_2$Ph,
in Compound PtM369: R=Ph, R'=Me,
in Compound PtM370: R=Ph, R'=$^i$Pr,
in Compound PtM371: R=Ph, R'=Ph,
in Compound PtM372: R=Ph, R'=2,6-($^i$Pr)$_2$Ph,
in Compound PtM373: R=2,6-($^i$Pr)$_2$Ph, R'=Me,
in Compound PtM374: R=2,6-($^i$Pr)$_2$Ph, R'=$^i$Pr,
in Compound PtM375: R=2,6-($^i$Pr)$_2$Ph, R'=Ph,
in Compound PtM376: R=2,6-($^i$Pr)$_2$Ph, R'=2,6-($^i$Pr)$_2$Ph,
in Compound PtM377: R=2,6-($^i$Pr)$_2$-4-biphenyl, R'=Me,
in Compound PtM378: R=2,6-($^i$Pr)$_2$-4-biphenyl, R'=$^i$Pr,
in Compound PtM379: R=2,6-($^i$Pr)$_2$-4-biphenyl, R'=Ph,
in Compound PtM380: R=2,6-($^i$Pr)$_2$-4-biphenyl, R'=2,6-($^i$Pr)$_2$Ph,
in Compound PtM381: R=2,4-($^i$Pr)$_2$-3-dibenzofuran, R'=Me,
in Compound PtM382: R=2,4-($^i$Pr)$_2$-3-dibenzofuran, R'=$^i$Pr,
in Compound PtM383: R=2,4-($^i$Pr)$_2$-3-dibenzofuran, R'=Ph,
in Compound PtM384: R=2,4-($^i$Pr)$_2$-3-dibenzofuran, R'=2,6-($^i$Pr)$_2$Ph, Compound PtM385 through PtM408, each represented by the formula

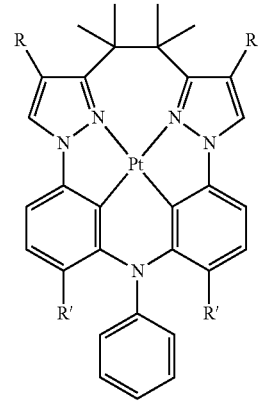

wherein in Compound PtM385: R=Me, R'=Me,
in Compound PtM386: R=Me, R'=$^i$Pr,
in Compound PtM387: R=Me, R'=Ph,
in Compound PtM388: R=Me, R'=2,6-($^i$Pr)$_2$Ph,
in Compound PtM389: R=$^i$Pr, R'=Me,
in Compound PtM390: R=$^i$Pr, R'=$^i$Pr,
in Compound PtM391: R=$^i$Pr, R'=Ph,
in Compound PtM392: R=$^i$Pr, R'=2,6-($^i$Pr)$_2$Ph,
in Compound PtM393: R=Ph, R'=Me,
in Compound PtM394: R=Ph, R'=$^i$Pr,
in Compound PtM395: R=Ph, R'=Ph,
in Compound PtM396: R=Ph, R'=2,6-($^i$Pr)$_2$Ph,
in Compound PtM397: R=2,6-($^i$Pr)$_2$Ph, R'=Me,
in Compound PtM398: R=2,6-($^i$Pr)$_2$Ph, R'=$^i$Pr,
in Compound PtM399: R=2,6-($^i$Pr)$_2$Ph, R'=Ph,
in Compound PtM400: R=2,6-($^i$Pr)$_2$Ph, R'=2,6-($^i$Pr)$_2$Ph,
in Compound PtM401: R=2,6-($^i$Pr)$_2$-4-biphenyl, R'=Me,
in Compound PtM402: R=2,6-($^i$Pr)$_2$-4-biphenyl, R'=$^i$Pr,
in Compound PtM403: R=2,6-($^i$Pr)$_2$-4-biphenyl, R'=Ph,
in Compound PtM404: R=2,6-($^i$Pr)$_2$-4-biphenyl, R'=2,6-($^i$Pr)$_2$Ph,
in Compound PtM405: R=2,4-($^i$Pr)$_2$-3-dibenzofuran, R'=Me,
in Compound PtM406: R=2,4-($^i$Pr)$_2$-3-dibenzofuran, R'=$^i$Pr,
in Compound PtM407: R=2,4-($^i$Pr)$_2$-3-dibenzofuran, R'=Ph,
in Compound PtM408: R=2,4-($^i$Pr)$_2$-3-dibenzofuran, R'=2,6-($^i$Pr)$_2$Ph, Compound PtM409 through PtM432, each represented by the formula

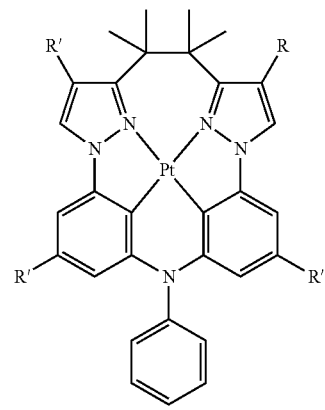

wherein in Compound PtM409: R=Me, R'=Me,
in Compound PtM410: R=Me, R'=$^i$Pr,
in Compound PtM411: R=Me, R'=Ph,
in Compound PtM412: R=Me, R'=2,6-($^i$Pr)$_2$Ph,
in Compound PtM413: R=$^i$Pr, R'=Me,
in Compound PtM414: R=$^i$Pr, R'=$^i$Pr,
in Compound PtM415: R=$^i$Pr, R'=Ph,
in Compound PtM416: R=$^i$Pr, R'=2,6-($^i$Pr)$_2$Ph,
in Compound PtM417: R=Ph, R'=Me,
in Compound PtM418: R=Ph, R'=$^i$Pr,
in Compound PtM419: R=Ph, R'=Ph,
in Compound PtM420: R=Ph, R'=2,6-($^i$Pr)$_2$Ph,
in Compound PtM421: R=2,6-($^i$Pr)$_2$Ph, R'=Me,
in Compound PtM422: R=2,6-($^i$Pr)$_2$Ph, R'=$^i$Pr,
in Compound PtM423: R=2,6-($^i$Pr)$_2$Ph, R'=Ph,
in Compound PtM424: R=2,6-($^i$Pr)$_2$Ph, R'=2,6-($^i$Pr)$_2$Ph,
in Compound PtM425: R=2,6-($^i$Pr)$_2$-4-biphenyl, R'=Me,
in Compound PtM426: R=2,6-($^i$Pr)$_2$-4-biphenyl, R'=$^i$Pr,
in Compound PtM427: R=2,6-($^i$Pr)$_2$-4-biphenyl, R'=Ph,
in Compound PtM428: R=2,6-($^i$Pr)$_2$-4-biphenyl, R'=2,6-($^i$Pr)$_2$Ph,
in Compound PtM429: R=2,4-($^i$Pr)$_2$-3-dibenzofuran, R'=Me,
in Compound PtM430: R=2,4-($^i$Pr)$_2$-3-dibenzofuran, R'=$^i$Pr,
in Compound PtM431: R=2,4-($^i$Pr)$_2$-3-dibenzofuran, R'=Ph,
in Compound PtM432: R=2,4-($^i$Pr)$_2$-3-dibenzofuran, R'=2,6-($^i$Pr)$_2$Ph,
Compound PtM433 through PtM456, each represented by the formula

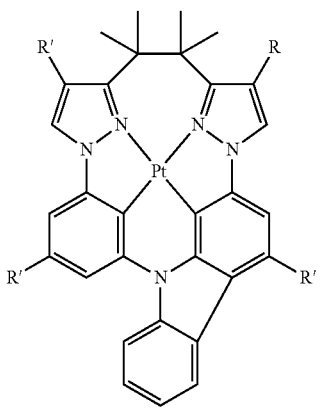

wherein in Compound PtM433: R=Me, R'=Me,
in Compound PtM434: R=Me, R'=$^i$Pr,
in Compound PtM435: R=Me, R'=Ph,
in Compound PtM436: R=Me, R'=2,6-($^i$Pr)$_2$Ph,
in Compound PtM437: R=$^i$Pr, R'=Me,
in Compound PtM438: R=$^i$Pr, R'=$^i$Pr,
in Compound PtM439: R=$^i$Pr, R'=Ph,
in Compound PtM440: R=$^i$Pr, R'=2,6-($^i$Pr)$_2$Ph,
in Compound PtM441: R=Ph, R'=Me,
in Compound PtM442: R=Ph, R'=$^i$Pr,
in Compound PtM443: R=Ph, R'=Ph,
in Compound PtM444: R=Ph, R'=2,6-($^i$Pr)$_2$Ph,
in Compound PtM445: R=2,6-($^i$Pr)$_2$Ph, R'=Me,
in Compound PtM446: R=2,6-($^i$Pr)$_2$Ph, R'=$^i$Pr,
in Compound PtM447: R=2,6-($^i$Pr)$_2$Ph, R'=Ph,
in Compound PtM448: R=2,6-($^i$Pr)$_2$Ph, R'=2,6-($^i$Pr)$_2$Ph,
in Compound PtM449: R=2,6-($^i$Pr)$_2$-4-biphenyl, R'=Me,
in Compound PtM450: R=2,6-($^i$Pr)$_2$-4-biphenyl, R'=$^i$Pr,
in Compound PtM451: R=2,6-($^i$Pr)$_2$-4-biphenyl, R'=Ph,
in Compound PtM452: R=2,6-($^i$Pr)$_2$-4-biphenyl, R'=2,6-($^i$Pr)$_2$Ph,
in Compound PtM453: R=2,4-($^i$Pr)$_2$-3-dibenzofuran, R'=Me,
in Compound PtM454: R=2,4-($^i$Pr)$_2$-3-dibenzofuran, R'=$^i$Pr,
in Compound PtM455: R=2,4-($^i$Pr)$_2$-3-dibenzofuran, R'=Ph,
in Compound PtM456: R=2,4-($^i$Pr)$_2$-3-dibenzofuran, R'=2,6-($^i$Pr)$_2$Ph, and
Compound PtM457 through PtM480, each represented by the formula

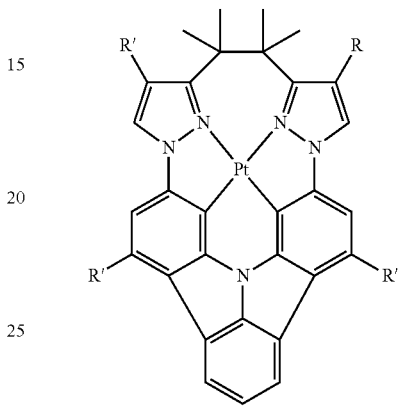

wherein in Compound PtM457: R=Me, R'=Me,
in Compound PtM458: R=Me, R'=$^i$Pr,
in Compound PtM459: R=Me, R'=Ph,
in Compound PtM460: R=Me, R'=2,6-($^i$Pr)$_2$Ph,
in Compound PtM461: R=$^i$Pr, R'=Me,
in Compound PtM462: R=$^i$Pr, R'=$^i$Pr,
in Compound PtM463: R=$^i$Pr, R'=Ph,
in Compound PtM464: R=$^i$Pr, R'=2,6-($^i$Pr)$_2$Ph,
in Compound PtM465: R=Ph, R'=Me,
in Compound PtM466: R=Ph, R'=$^i$Pr,
in Compound PtM467: R=Ph, R'=Ph,
in Compound PtM468: R=Ph, R'=2,6-($^i$Pr)$_2$Ph,
in Compound PtM469: R=2,6-($^i$Pr)$_2$Ph, R'=Me,
in Compound PtM470: R=2,6-($^i$Pr)$_2$Ph, R'=$^i$Pr,
in Compound PtM471: R=2,6-($^i$Pr)$_2$Ph, R'=Ph,
in Compound PtM472: R=2,6-($^i$Pr)$_2$Ph, R'=2,6-($^i$Pr)$_2$Ph,
in Compound PtM473: R=2,6-($^i$Pr)$_2$-4-biphenyl, R'=Me,
in Compound PtM474: R=2,6-($^i$Pr)$_2$-4-biphenyl, R'=$^i$Pr,
in Compound PtM475: R=2,6-($^i$Pr)$_2$-4-biphenyl, R'=Ph,
in Compound PtM476: R=2,6-($^i$Pr)$_2$-4-biphenyl, R'=2,6-($^i$Pr)$_2$Ph,
in Compound PtM477: R=2,4-($^i$Pr)$_2$-3-dibenzofuran, R'=Me,
in Compound PtM478: R=2,4-($^i$Pr)$_2$-3-dibenzofuran, R'=$^i$Pr,
in Compound PtM479: R=2,4-($^i$Pr)$_2$-3-dibenzofuran, R'=Ph,
in Compound PtM480: R=2,4-($^i$Pr)$_2$-3-dibenzofuran, R'=2,6-($^i$Pr)$_2$Ph.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect of the present disclosure, a device that includes one or more organic light emitting devices is also provided. At least one of the one or more organic light emitting devices can include an anode, a cathode, and an organic layer disposed between the anode and the cathode. The organic layer can include a compound selected from the group consisting of Formula $M(L_A)_x(L_B)_y$, and Formula III, and the variations of each as described herein.

The device can be one or more of a consumer product, an electronic component module, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, and $C_nH_{2n}$—$Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

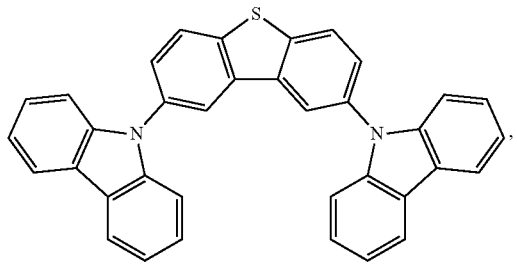

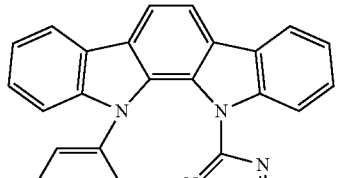

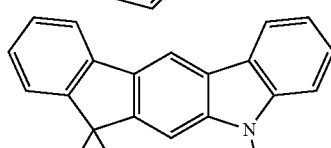

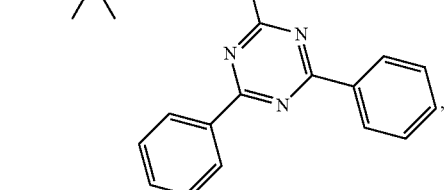

-continued

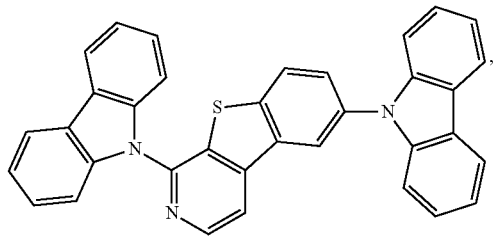

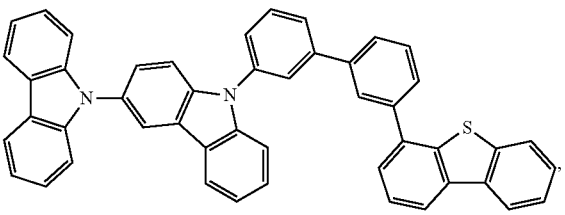

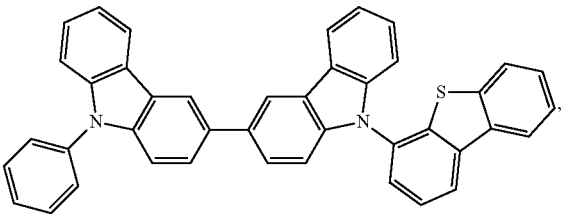

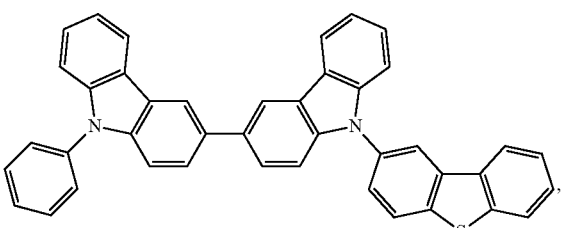

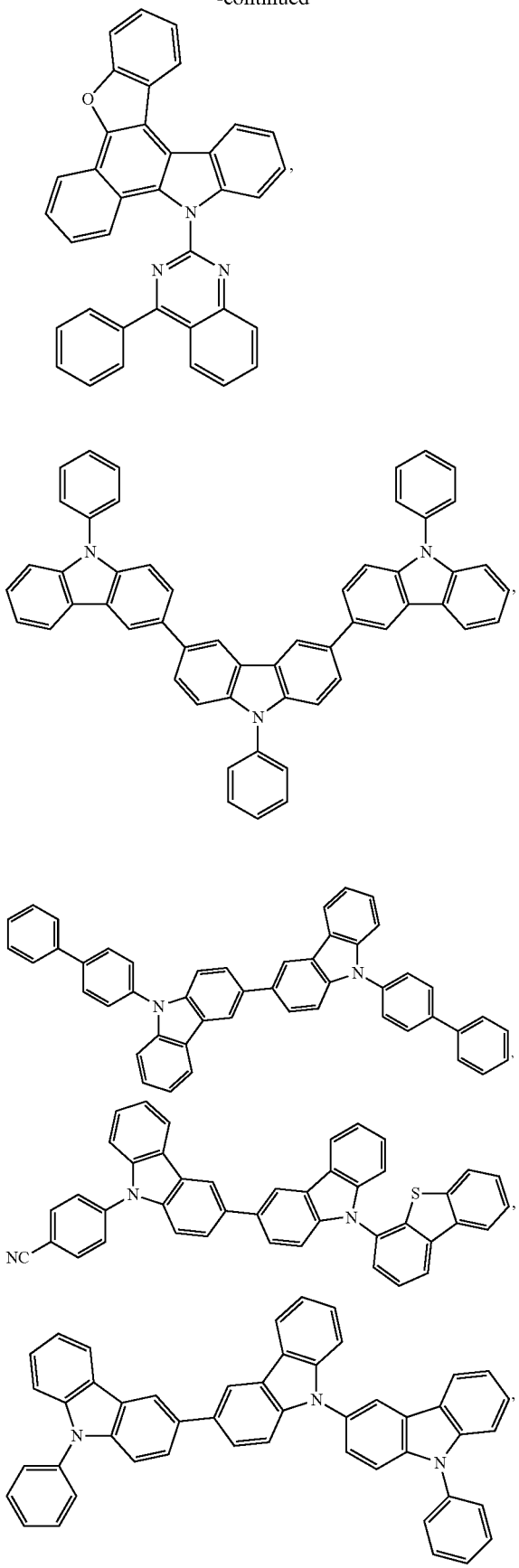

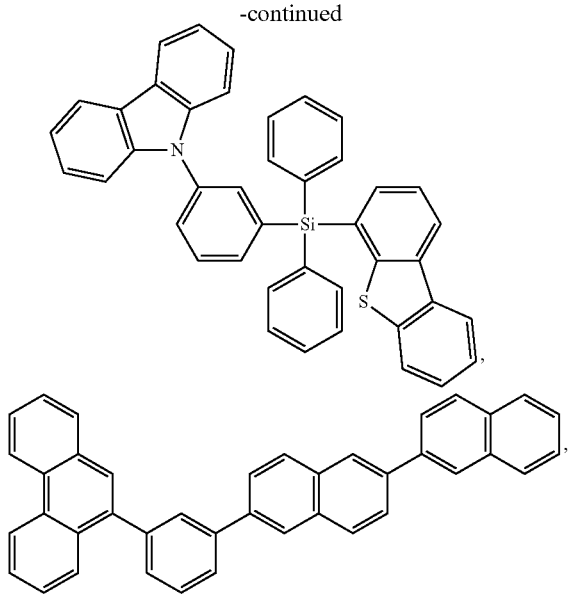

and combinations thereof.

In yet another aspect of the present disclosure, a formulation comprises a compound selected from the group consisting of Formula $M(L_A)_x(L_B)_y$ and Formula III, and the variations of each as described herein. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

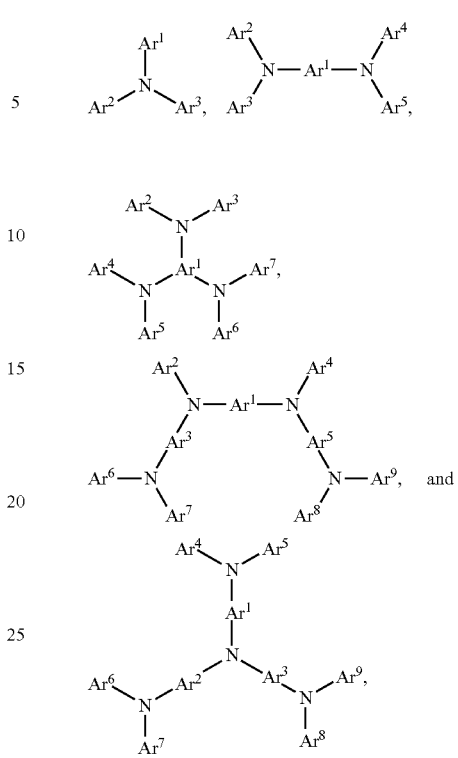

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

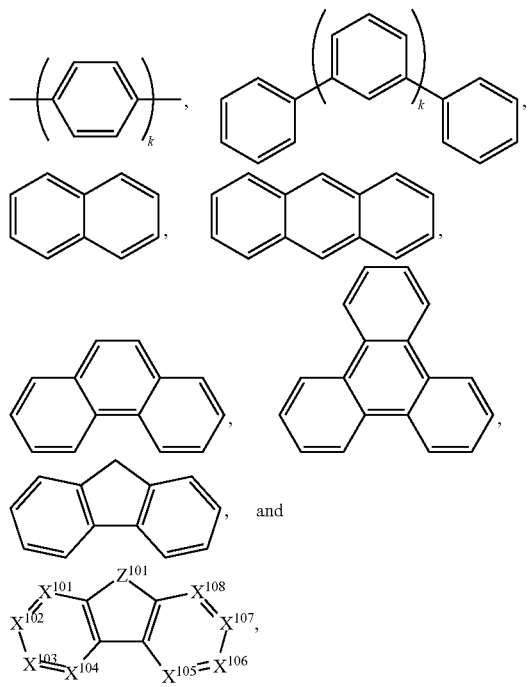

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

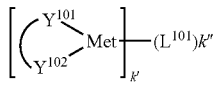

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

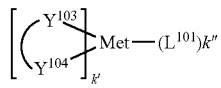

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

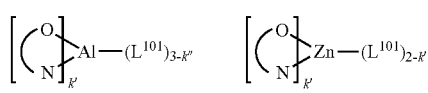

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

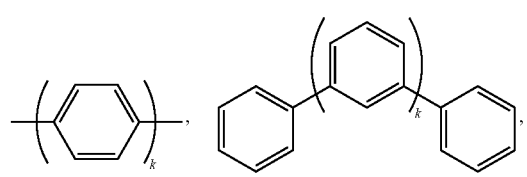

-continued

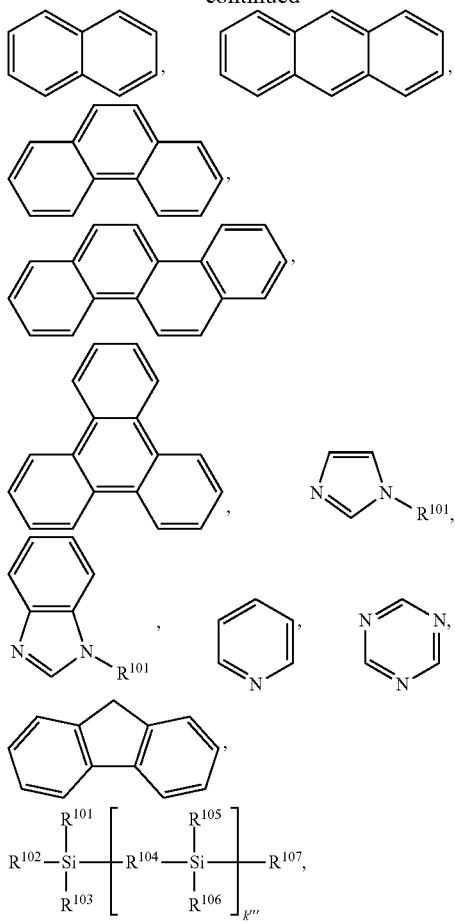

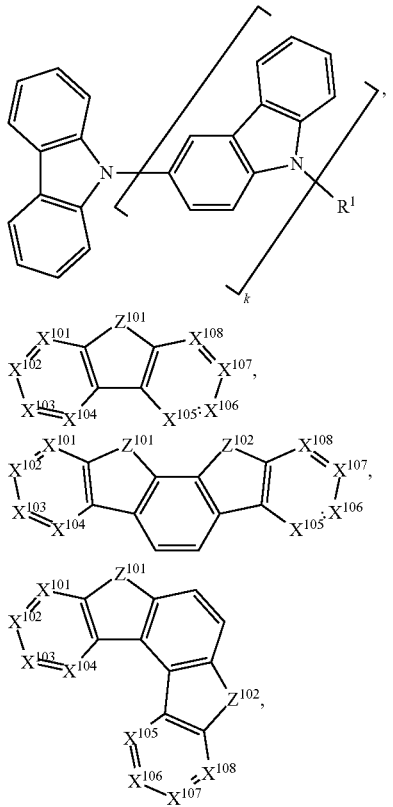

-continued

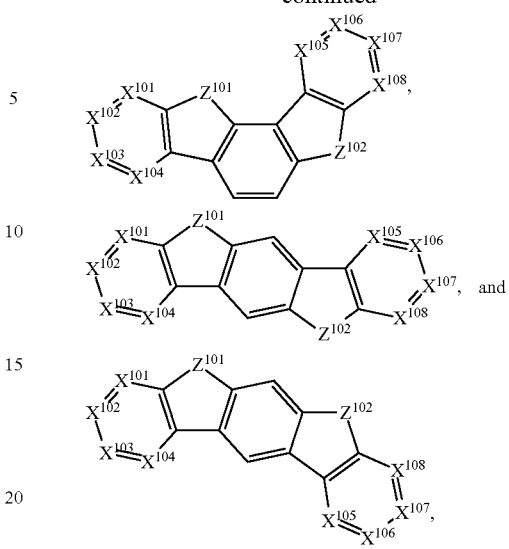

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

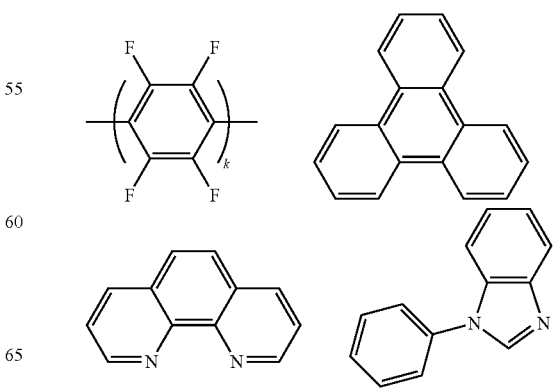

-continued

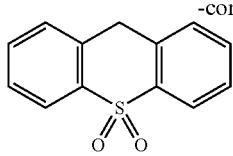 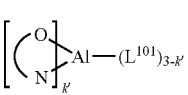

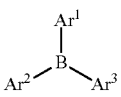

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

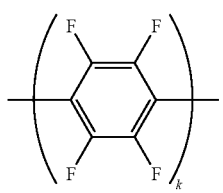 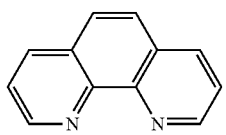

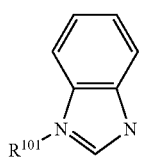 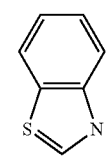 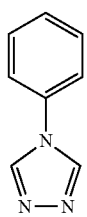 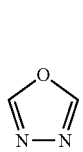

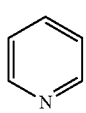 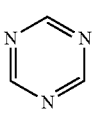 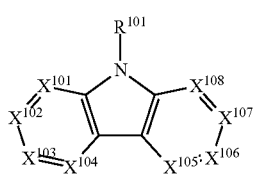

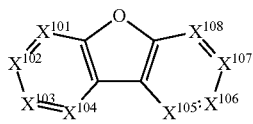

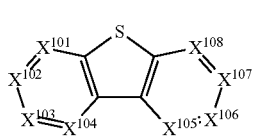 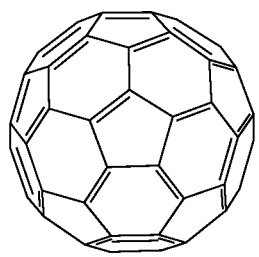

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

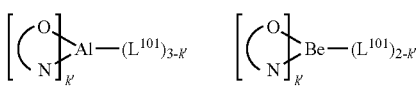

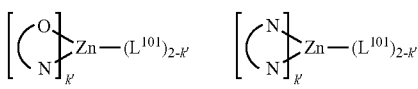

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A
| MATERIAL | EXAMPLES OF MATERIAL | PUBLICATIONS |
|---|---|---|
| Hole injection materials | | |
| Phthalocyanine and porphyrin compounds | 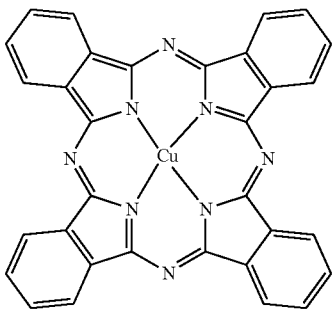 | Appl. Phys. Lett. 69, 2160 (1996) |
| Starburst triarylamines | 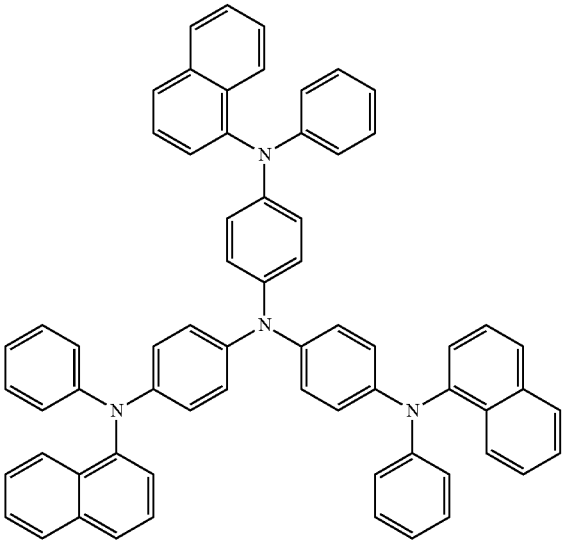 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$, Fluorohydrocarbon polymer | $-\!\!+\!\!CH_xF_y\!\!+_n\!\!-$ | Appl. Phys. Lett. 78, 673 (2001) |
| Conducting polymers (e.g., PEDOT:PSS, polyaniline, polythiophene) | 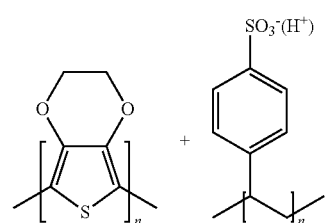 | Synth. Met. 87, 171 (1997) WO2007002683 |
| Phosphonic acid and silane SAMs | 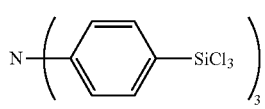 | US20030162053 |

TABLE A-continued
| MATERIAL | EXAMPLES OF MATERIAL | PUBLICATIONS |
|---|---|---|
| Triarylamine or polythiophene polymers with conductivity dopants | 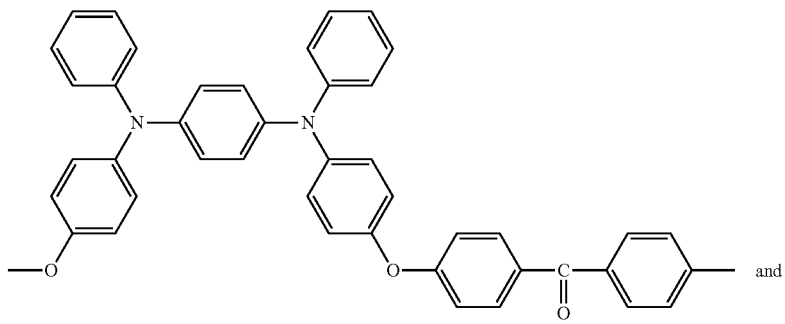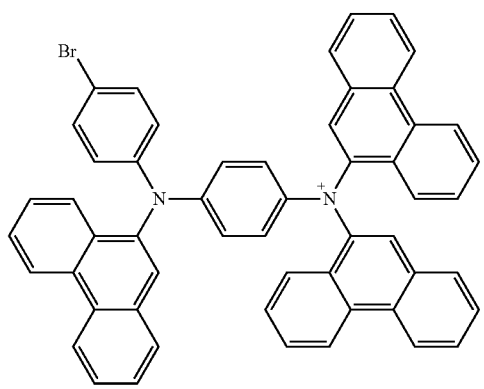 [SMILES: Brc1ccc(N(c2ccc(N(c3cc4ccccc4c4ccccc34)c3cc4ccccc4c4ccccc34)cc2)c2cc3ccccc3c3ccccc23)cc1]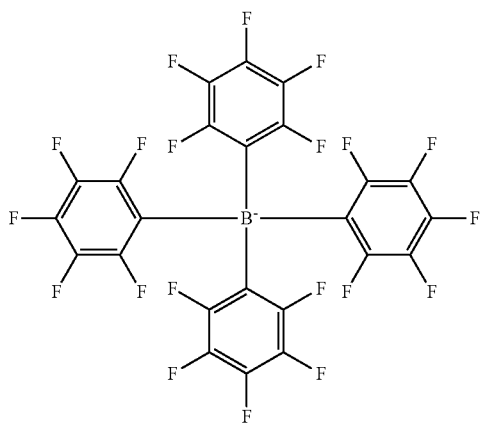 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 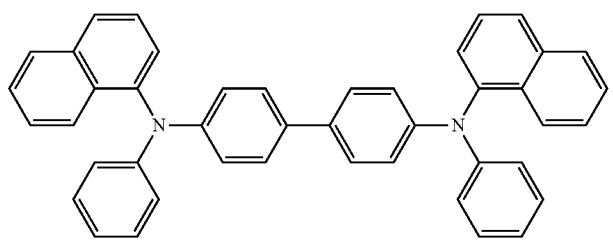 | US20050123751<br>SID Symposium Digest, 37, 923 (2006)<br>WO2009018009 |

TABLE A-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO2011075644 EP2350216 |

TABLE A-continued
| MATERIAL | EXAMPLES OF MATERIAL | PUBLICATIONS |
|---|---|---|
| Hole transporting materials | | |
| Triarylamines (e.g., TPD, α-NPD) | 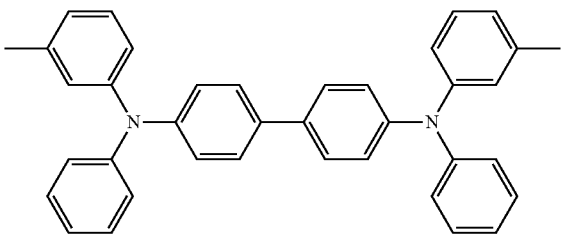 | Appl. Phys. Lett. 51, 913 (1987) |
| | 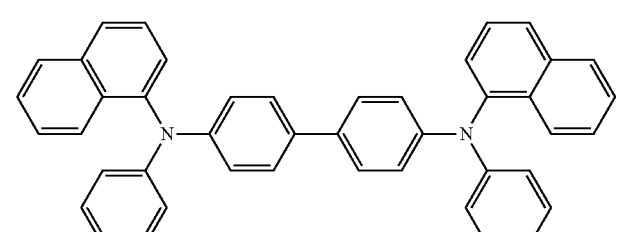 | US5061569 |
| | 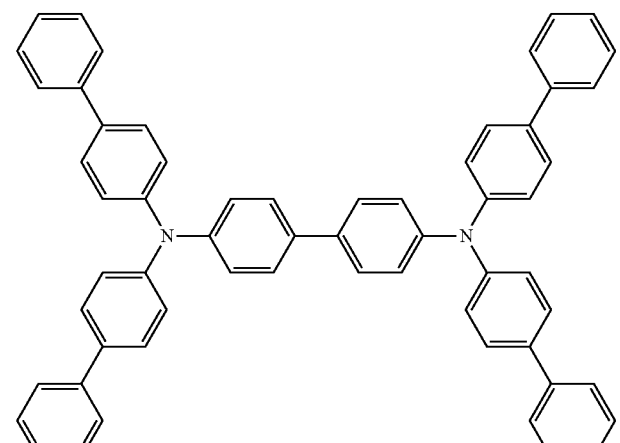 | EP650955 |
| | 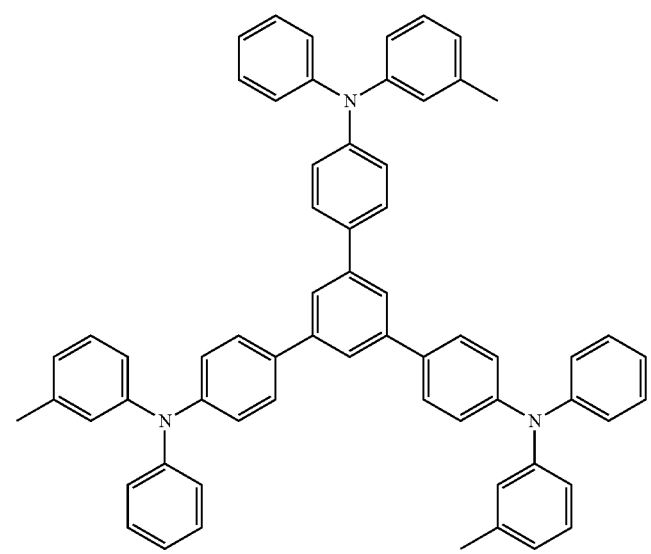 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |

TABLE A-continued
| MATERIAL | EXAMPLES OF MATERIAL | PUBLICATIONS |
| --- | --- | --- |
| Triarylamine with (di)benzothiophene/ (di)benzofuran | 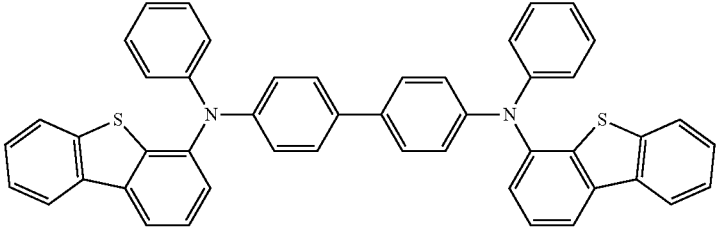 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 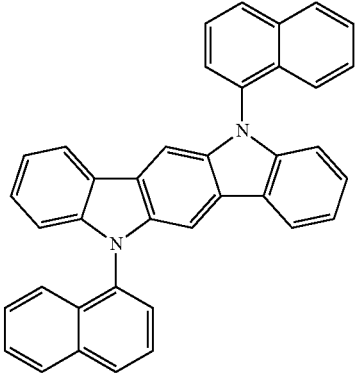 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 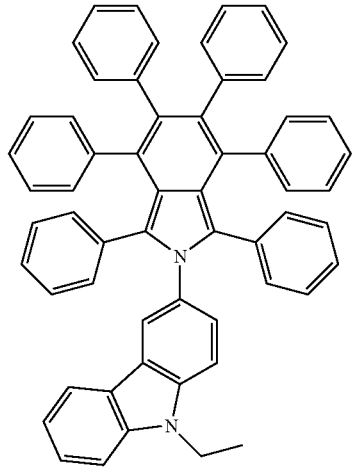 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 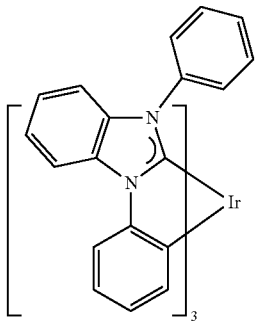 | US20080018221 |

TABLE A-continued
| MATERIAL | EXAMPLES OF MATERIAL | PUBLICATIONS |
|---|---|---|
| Phosphorescent OLED host materials | | |
| Red hosts Arylcarbazoles | 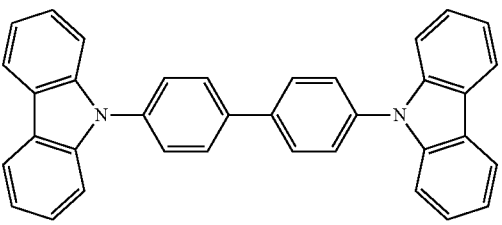 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 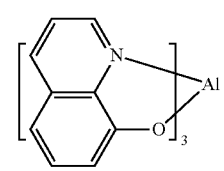 | Nature 395, 151 (1998) |
| | 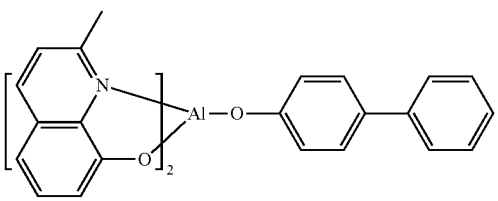 | US20060202194 |
| | 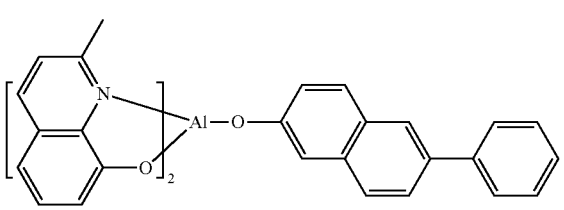 | WO2005014551 |
| | 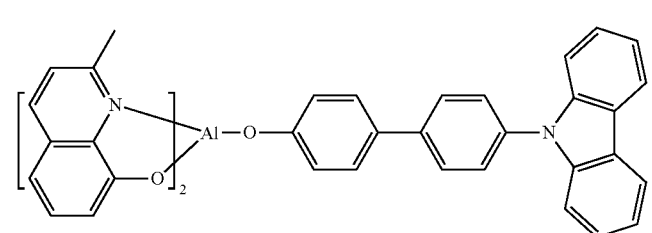 | WO2006072002 |
| Metal phenoxybenzothiazole compounds | 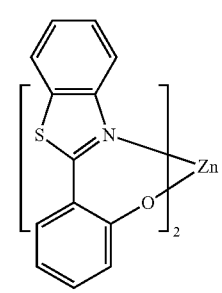 | Appl. Phys. Lett. 90, 123509 (2007) |
| Conjugated oligomers and polymers (e.g., polyfluorene) | 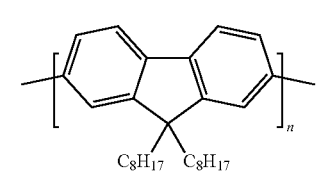 | Org. Electron. 1, 15 (2000) |

TABLE A-continued
| MATERIAL | EXAMPLES OF MATERIAL | PUBLICATIONS |
|---|---|---|
| Aromatic fused rings | 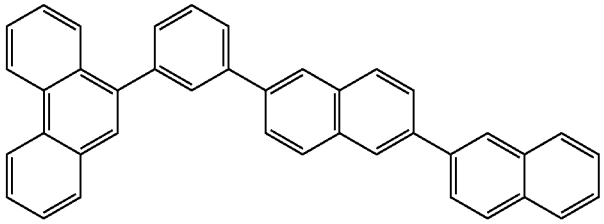 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 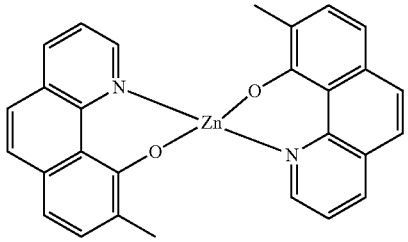 | WO2010056066 |
| Chrysene based compounds | 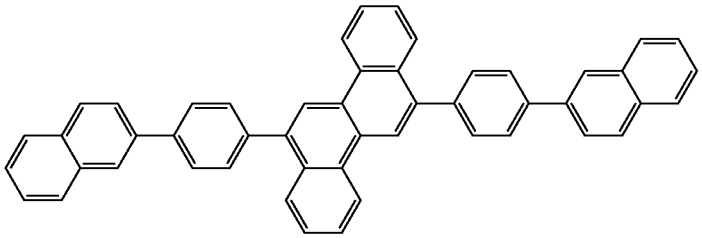 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts Arylcarbazoles | 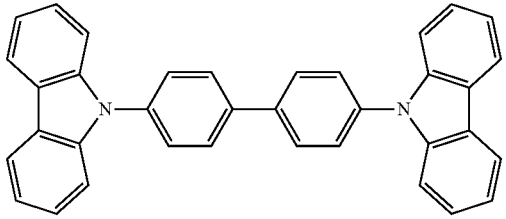 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 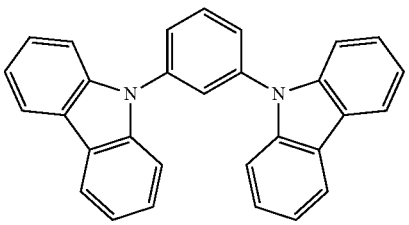 [SMILES: c1cc(-n2c3ccccc3c3ccccc32)cc(-n2c3ccccc3c3ccccc32)c1] | US20030175553 |
| | 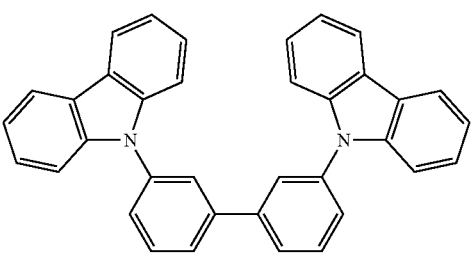 [SMILES: c1cc(-c2cccc(-n3c4ccccc4c4ccccc43)c2)cc(-n2c3ccccc3c3ccccc32)c1] | WO2001039234 |

TABLE A-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

TABLE A-continued

| MATERIAL | EXAMPLES OF MATERIAL | PUBLICATIONS |
|---|---|---|
| | | WO2010107244 |
| Aza-carbazole/ DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE A-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
|---|---|---|
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |
| Blue hosts Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

| MATERIAL | EXAMPLES OF MATERIAL | PUBLICATIONS |
|---|---|---|
| | 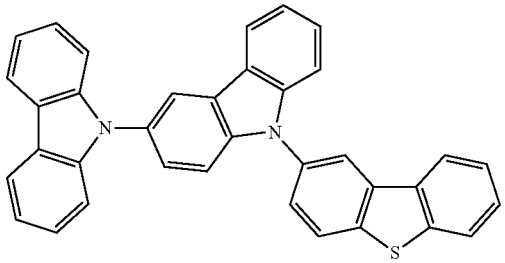 [SMILES: c1ccc2c(c1)sc1ccc(-n3c4ccccc4c4cc(-n5c6ccccc6c6ccccc65)ccc43)cc12] | WO2009086028 |
| | 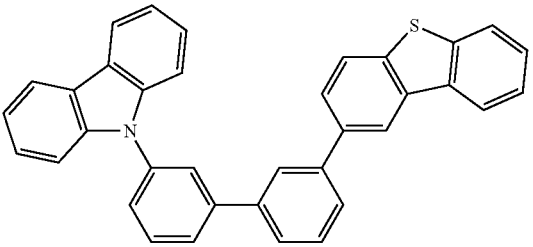 [SMILES: c1cc(-c2cccc(-n3c4ccccc4c4ccccc43)c2)cc(-c2ccc3sc4ccccc4c3c2)c1] | US20090030202, US20090017330 |
| | 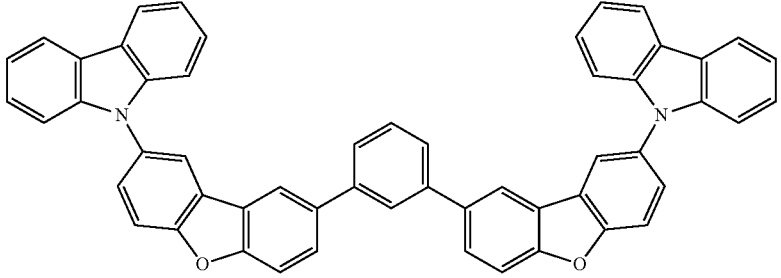 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 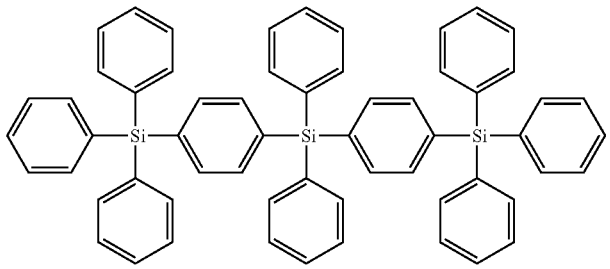 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 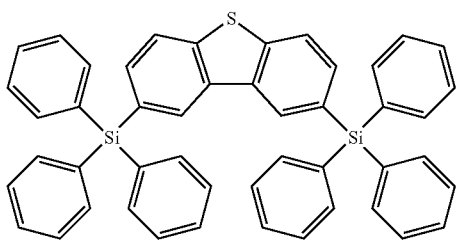 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE A-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | US7154114 |

Phosphorescent dopants

| | | |
| --- | --- | --- |
| Red dopants<br>Heavy metal porphyrins (e.g., PtOEP) | | Nature 395, 151 (1998) |

TABLE A-continued

| MATERIAL | EXAMPLES OF MATERIAL | PUBLICATIONS |
|---|---|---|
| Iridium(III) organometallic complexes | | Appl. Phys. Lett. 78, 1622 (2001) |
| | | US20030072964 |
| | | US20030072964 |
| | | US20060202194 |
| | | US20060202194 |

TABLE A-continued
| MATERIAL | EXAMPLES OF MATERIAL | PUBLICATIONS |
|---|---|---|
| | 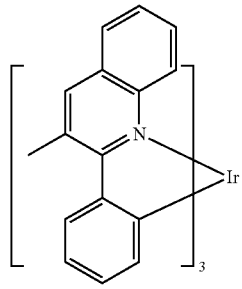 | US20070087321 |
| | 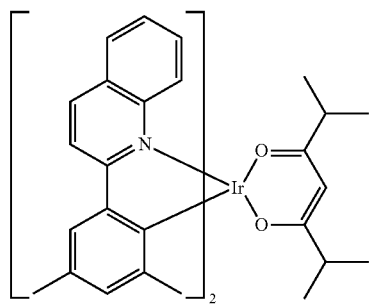 | US20080261076<br>US20100090591 |
| | 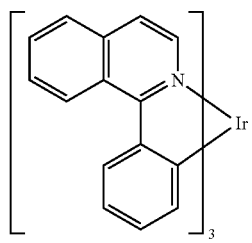 | US20070087321 |
| | 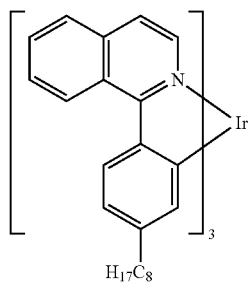 | Adv. Mater. 19, 739 (2007) |
| | 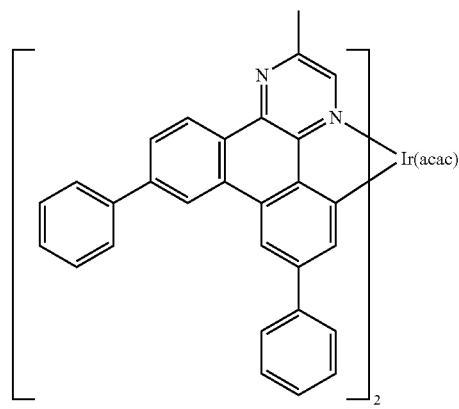 | WO2009100991 |

| MATERIAL | EXAMPLES OF MATERIAL | PUBLICATIONS |
|---|---|---|
| | 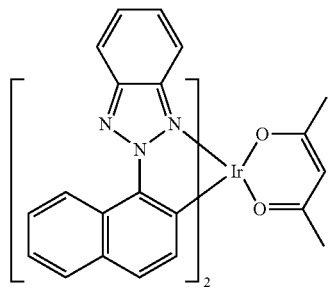 | WO2008101842 |
| | 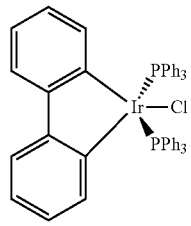 | US7232618 |
| Platinum(II) organometallic complexes | 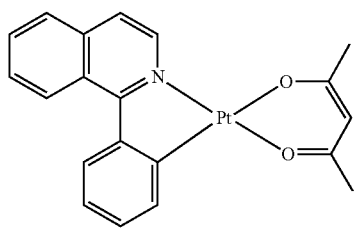 | WO2003040257 |
| | 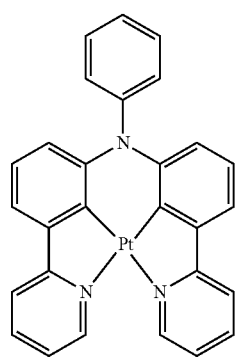 | US20070103060 |
| Osmium(III) complexes | 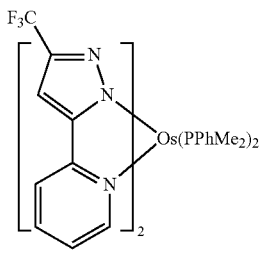 | Chem. Mater. 17, 3532 (2005) |

TABLE A-continued

| MATERIAL | EXAMPLES OF MATERIAL | PUBLICATIONS |
| --- | --- | --- |
| Ruthenium(II) complexes | | Adv. Mater. 17, 1059 (2005) |
| Rhenium (I), (II), and (III) complexes | | US20050244673 |
| Green dopants | | |
| Iridium(III) organometallic complexes | and its derivatives | Inorg. Chem. 40, 1704 (2001) |
| | | US20020034656 |

TABLE A-continued
| MATERIAL | EXAMPLES OF MATERIAL | PUBLICATIONS |
|---|---|---|
| | 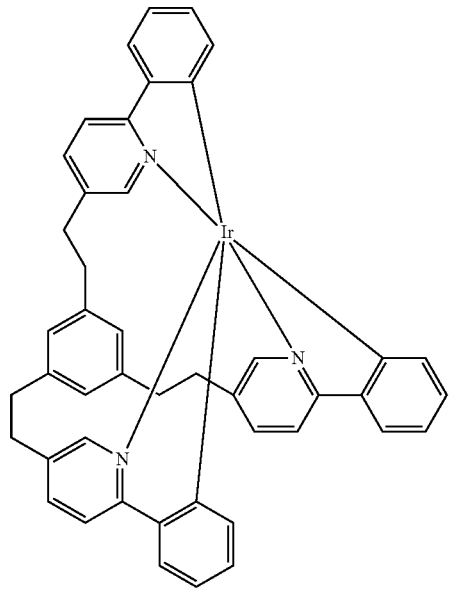 | US7332232 |
| | 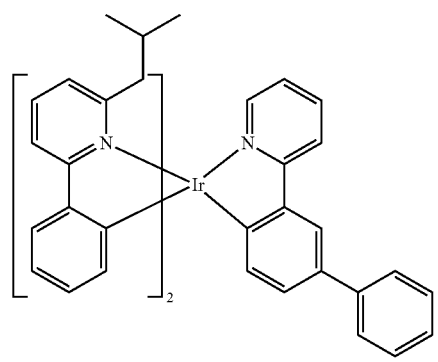 | US20090108737 |
| | 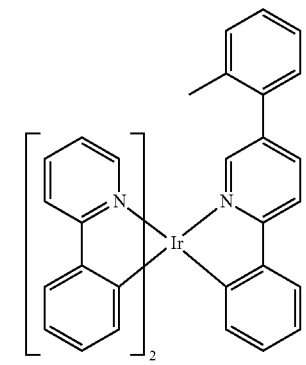 | WO2010028151 |

TABLE A-continued
| MATERIAL | EXAMPLES OF MATERIAL | PUBLICATIONS |
|---|---|---|
| | 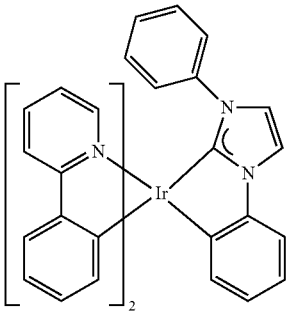 | EP1841834B |
| | 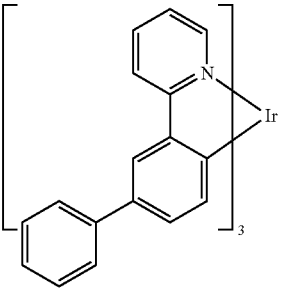 | US20060127696 |
| | 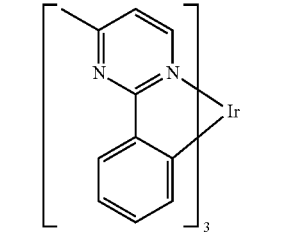 | US20090039776 |
| | 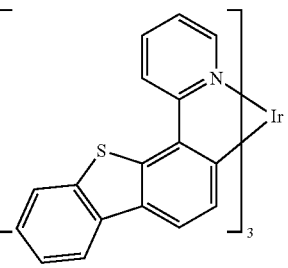 | US6921915 |
| | 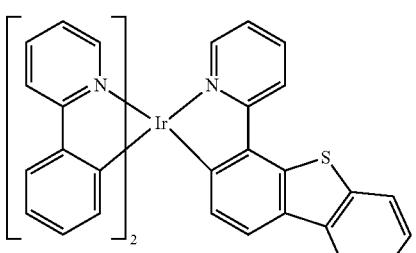 | US20100244004 |

TABLE A-continued
| MATERIAL | EXAMPLES OF MATERIAL | PUBLICATIONS |
|---|---|---|
| | 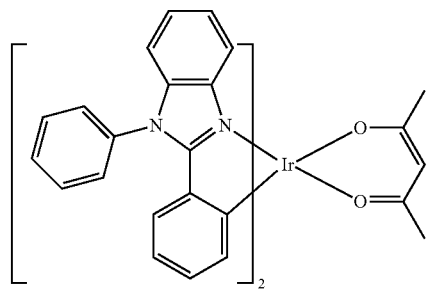 | US6687266 |
| | 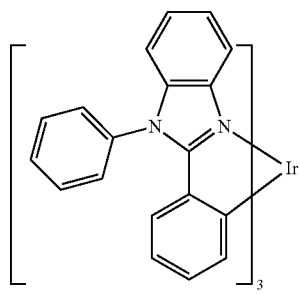 | Chem. Mater. 16, 2480 (2004) |
| | 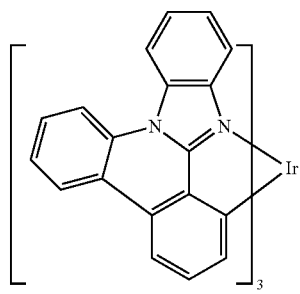 | US20070190359 |
| | 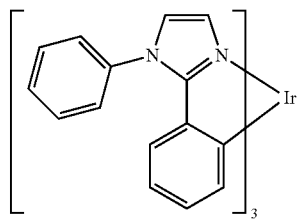 | US 20060008670<br>JP2007123392 |
| | 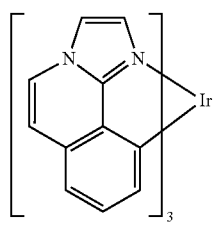 | WO2010086089,<br>WO2011044988 |
| | 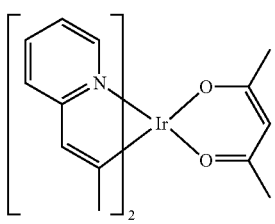 | Adv. Mater. 16, 2003 (2004) |

TABLE A-continued
| MATERIAL | EXAMPLES OF MATERIAL | PUBLICATIONS |
|---|---|---|
| | 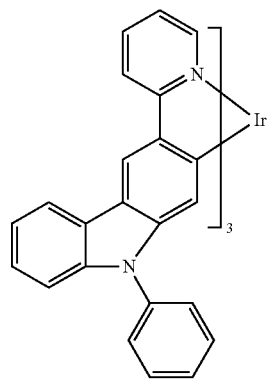 | Angew. Chem. Int. Ed. 2006, 45, 7800 |
| | 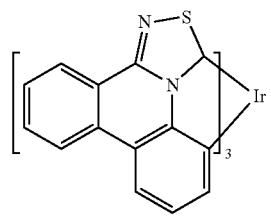 | WO2009050290 |
| | 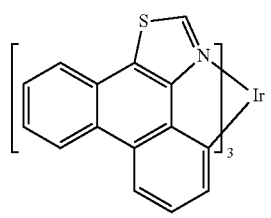 | US20090165846 |
| | 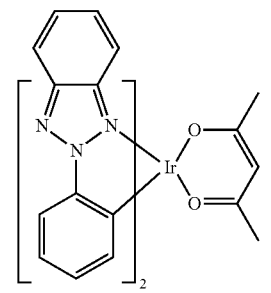 | US20080015355 |
| | 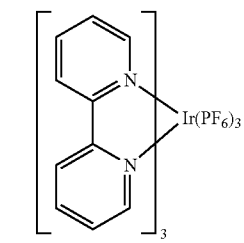 | US20010015432 |
| | 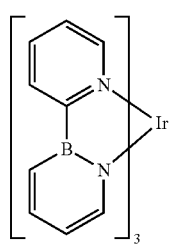 | US20100295032 |

TABLE A-continued

| MATERIAL | EXAMPLES OF MATERIAL | PUBLICATIONS |
| --- | --- | --- |
| Monomer for polymeric metal organometallic compounds | | US 7250226, US7396598 |
| Pt(II) organometallic complexes, including polydentate ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE A-continued

| MATERIAL | EXAMPLES OF MATERIAL | PUBLICATIONS |
|---|---|---|
| | | US20060263635 |
| | | US20060182992<br>US20070103060 |
| | | WO2009000673 |
| | | US20070111026 |

TABLE A-continued
| MATERIAL | EXAMPLES OF MATERIAL | PUBLICATIONS |
|---|---|---|
| | 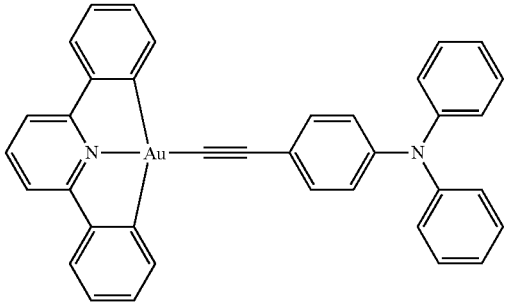 | Chem. Commun. 2906 (2005) |
| Rhenium(III) complexes | 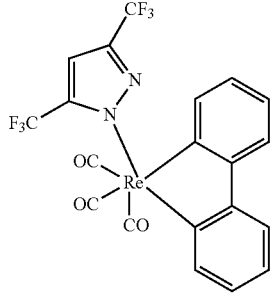 | Inorg. Chem. 42, 1248 (2003) |
| Osmium(II) complexes | 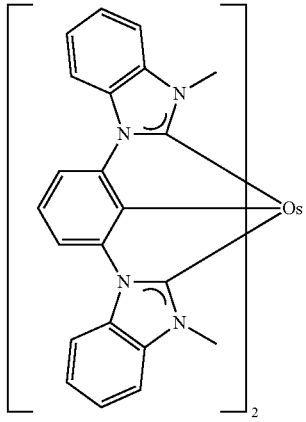 | US7279704 |
| Deuterated organometallic complexes | 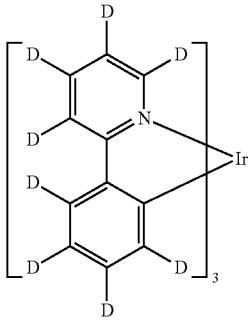 | US20030138657 |

| MATERIAL | EXAMPLES OF MATERIAL | PUBLICATIONS |
|---|---|---|
| Organometallic complexes with two or more metal centers | 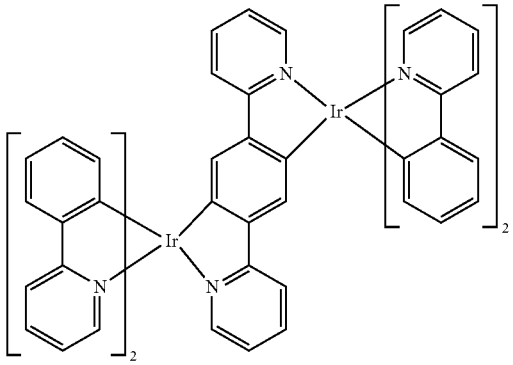 | US20030152802 |
| | 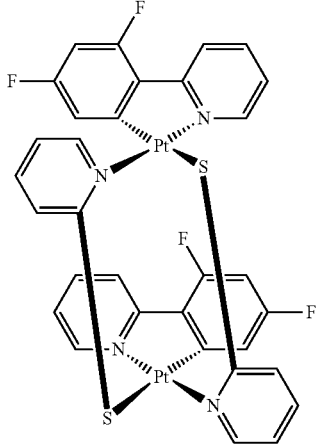 | US7090928 |
| Blue dopants Iridium(III) organometallic complexes | 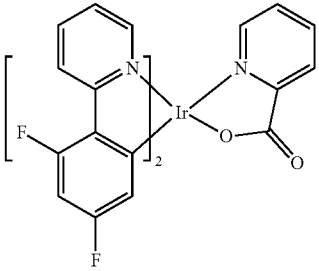 | WO2002002714 |
| | 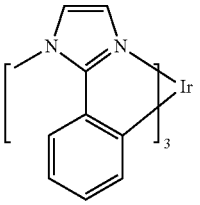 | WO2006009024 |
| | 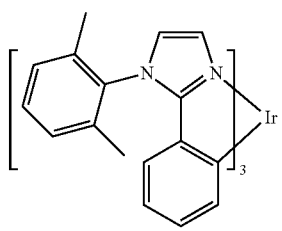 | US20060251923<br>US20110057559<br>US20110204333 |

TABLE A-continued

| MATERIAL | EXAMPLES OF MATERIAL | PUBLICATIONS |
|---|---|---|
| | | US7393599, WO2006056418, US20050260441, WO2005019373 |
| | | US7534505 |
| | | WO2011051404 |
| | | US7445855 |
| | | US20070190359, US20080297033 US20100148663 |

TABLE A-continued

| MATERIAL | EXAMPLES OF MATERIAL | PUBLICATIONS |
|---|---|---|
| | | US7338722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE A-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | US7279704 |

TABLE A-continued

| MATERIAL | EXAMPLES OF MATERIAL | PUBLICATIONS |
|---|---|---|
| | 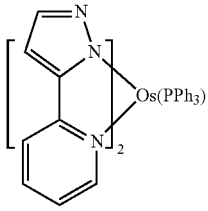 | Organometallics 23, 3745 (2004) |
| Gold complexes | 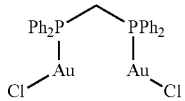 | Appl. Phys. Lett. 74, 1361 (1999) |
| Platinum(II) complexes | 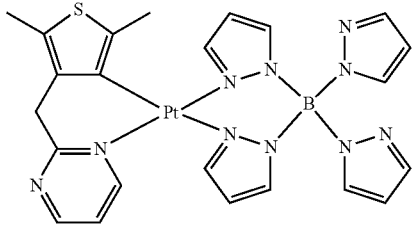 | WO2006098120, WO2006103874 |
| Pt tetradentate complexes with at least one metal-carbene bond | 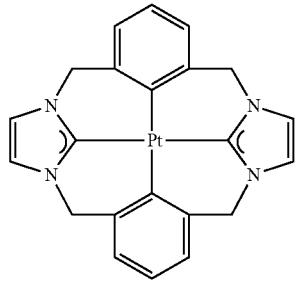 | US7655323 |

Exciton/hole blocking layer materials

| | | |
|---|---|---|
| Bathocuproine compounds (e.g., BCP, BPhen) | 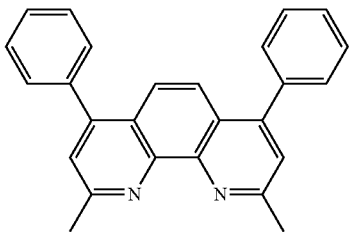 [SMILES: Cc1cc(-c2ccccc2)c2ccc3c(-c4ccccc4)cc(C)nc3c2n1] | Appl. Phys. Lett. 75, 4 (1999) |
| | 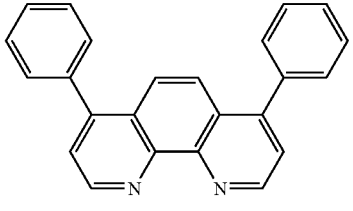 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 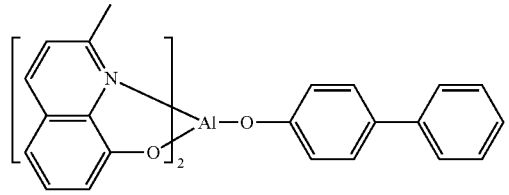 | Appl. Phys. Lett. 81, 162 (2002) |

TABLE A-continued

| MATERIAL | EXAMPLES OF MATERIAL | PUBLICATIONS |
|---|---|---|
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE A-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

Electron transporting materials

| | | |
|---|---|---|
| Anthracene-benzoimidazole compounds | | WO2003060956 |
| | | US20090179554 |

TABLE A-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) US7230107 |
| Metal hydroxybenzoquinolates | | Chem. Lett. 5, 905 (1993) |
| Bathocuproine compounds such as BCP, BPhen, etc | | Appl. Phys. Lett. 91, 263503 (2007) |
| | | Appl. Phys. Lett. 79, 449 (2001) |

TABLE A-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 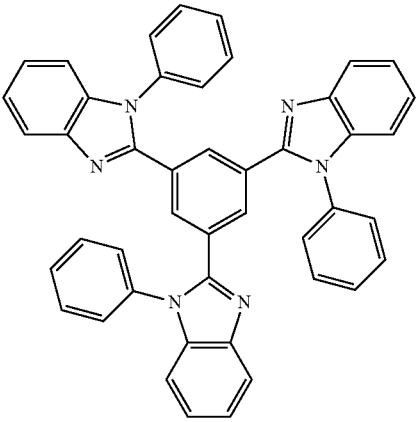 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 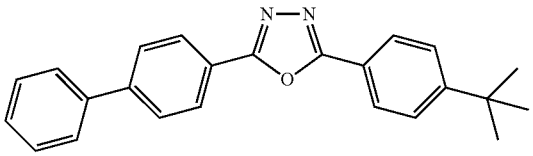 [SMILES: CC(C)(C)c1ccc(-c2nnc(-c3ccc(-c4ccccc4)cc3)o2)cc1] | Appl. Phys. Lett. 55, 1489 (1989) |
| | 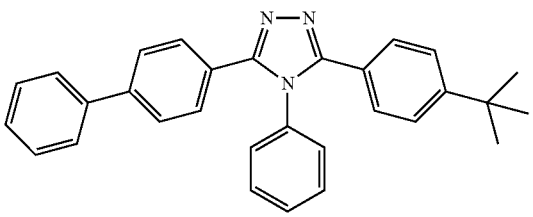 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 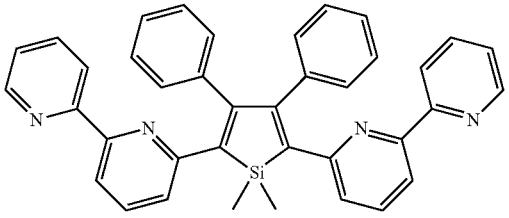 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 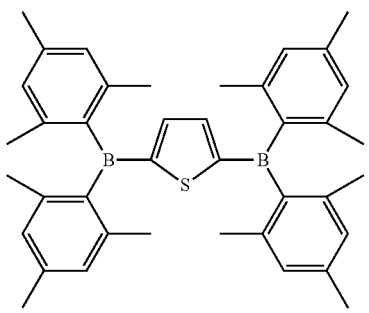 | J. Am. Chem. Soc. 120, 9714 (1998) |
| Fluorinated aromatic compounds | 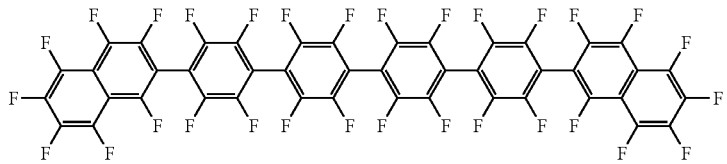 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE A-continued

| MATERIAL | EXAMPLES OF MATERIAL | PUBLICATIONS |
|---|---|---|
| Fullerene (e.g., $C_{60}$) | | US20090101870 |
| Triazine complexes | | US20040036077 |
| Zn ($N^{\wedge}N$) complexes | | US6528187 |

EXPERIMENTAL

Calculations—Tetradentate Platinum Pyrazole Emitters

Computational Methods.

All calculations presented used the Gaussian 09 package. Specifically, the B3LYP functional was employed in conjunction with the CEP-31g effective core potentials and valence base set. The bonds targeted for bond strength evaluation were manually broken and the geometry re-optimized to confirm the bond does not reform. Thermodynamics of bond breaking were calculated as:

Bond Strength=[$^3$product(bond broken)−$^3$reactant (bonded)]*627.51 where the product is in the triplet state ($^3$) and the reactant is taken to be the excited state triplet ($^3$). Thermochemistry is determined at 1 atm and 298.15 K.

Results.

Bond strength calculations were performed on three comparative examples and two compounds described herein. The bonds are defined as shown below and bond strength values are shown in Table 1.

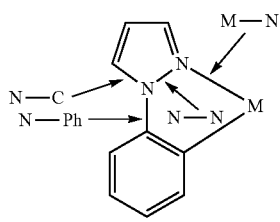

Comparative Examples 1 and Comparative Examples 2 and 3 show the effect on the N—N bond with bottom oxygen tether and top ethyl and phenyl tethers, respectively. Comparative Example 1 has the weakest N—N bond strength with a value of only 1.02 kcal/mol. Using a top tether, such as ethyl or phenyl, strengthens this bond significantly, but the bond strength is even more greatly improved with both a side tether and top tether structure. Compounds Pt55 and Pt445, with such structural tethers, are shown to have further significant increase in N—N bond strength with values of 16.78 and 17.57 kcal/mol, respectively. Therefore it is demonstrated that it is the combination of top and side tethering that leads to biggest increase in N—N bond strength.

Comparative Example 1

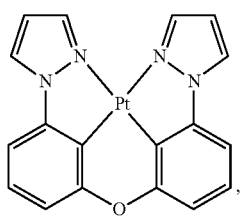

Comparative Example 2

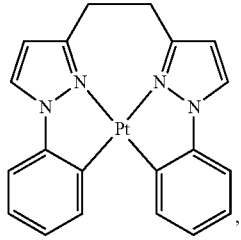

Comparative Example 3

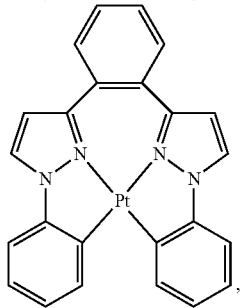

Compound Pt55

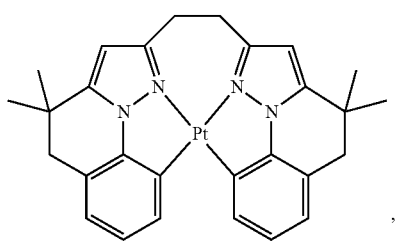

Compound Pt445

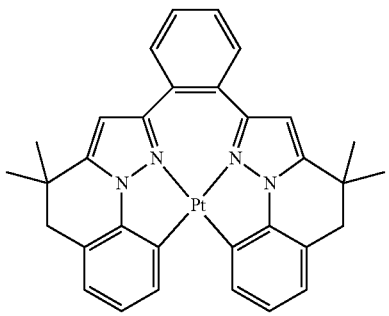

TABLE 1

Triplet energies and bond strengths for the platinum complexes studied. Energies reported in kcal/mol.

| Compound | T1 (nm) | N—Ph | N—C | N—N | M—N |
|---|---|---|---|---|---|
| Comparative Example 1 | 450 | 31.78 | 26.99 | 1.02 | 13.58 |
| Comparative Example 2 | 456 | 31.38 | 27.26 | 7.93 | n/a |
| Comparative Example 3 | 473 | n/a | n/a | 6.0 | n/a |
| Compound Pt55 | 459 | n/a | n/a | 16.78 | n/a |
| Compound Pt445 | 479 | n/a | n/a | 17.57 | n/a |

Synthesis Examples

Synthesis of Compounds Ir1, Ir872, Ir874, and Ir888

The following is a general schematic for the synthesis of Compound Ir1, Compound Ir872, Compound Ir874, and Compound Ir888.

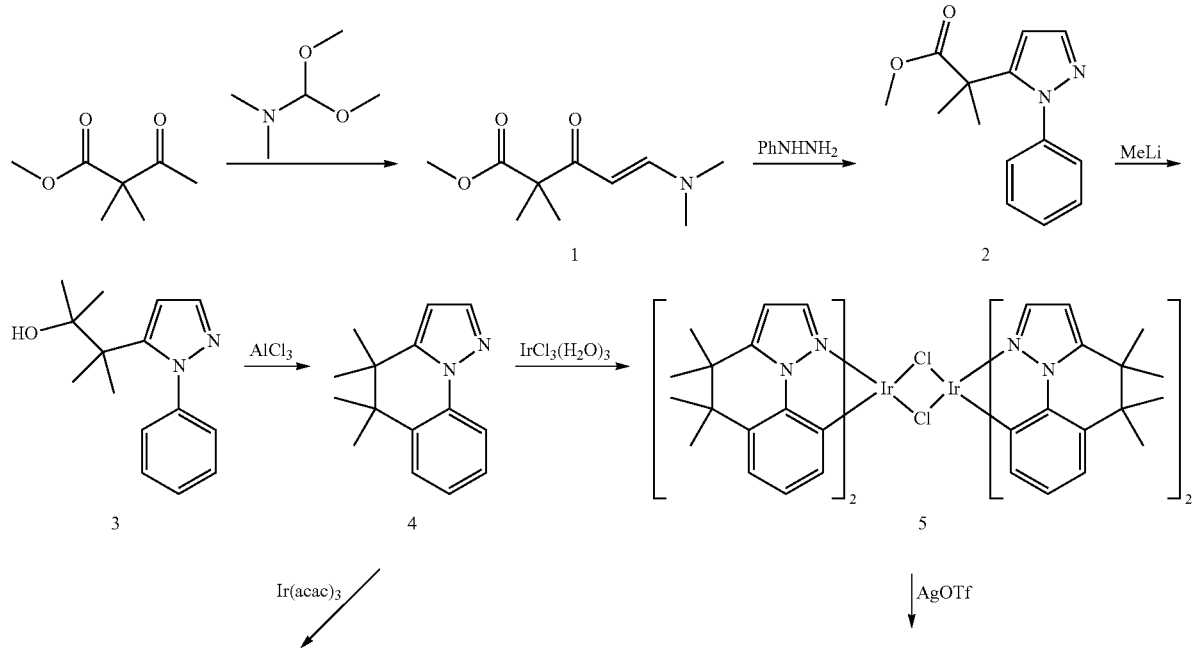

237 238

-continued

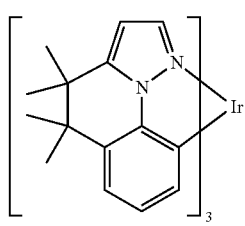

Compound Ir1

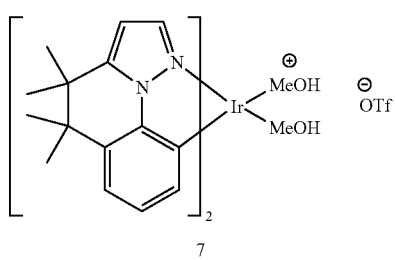

7

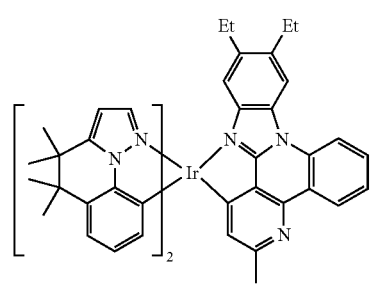

Compound Ir872

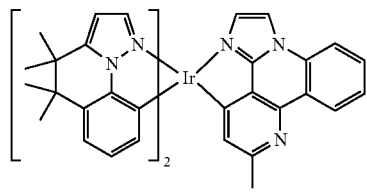

Compound Ir874

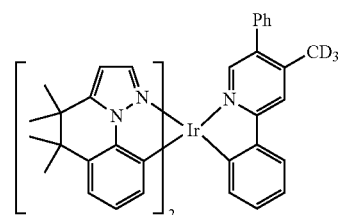

Compound Ir888

Synthesis of (E)-methyl 5-(dimethylamino)-2,2-dimethyl-3-oxopent-4-enoate (1)

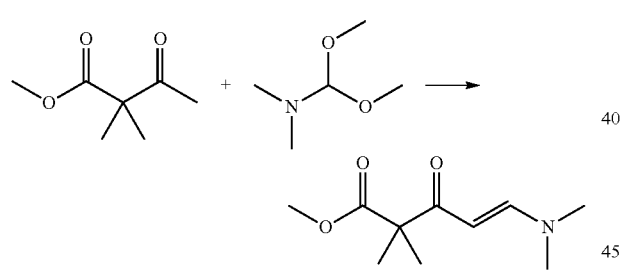

A mixture of methyl 2,2-dimethyl-3-oxobutanoate (5.01 ml, 34.7 mmol) and 1,1-dimethoxy-N,N-dimethylmethanamine (12 ml, 90 mmol) was stirred at 100° C. for three days. 50 mL of toluene was added and the solvents were removed under nitrogen, yielding (E)-methyl 5-(dimethylamino)-2,2-dimethyl-3-oxopent-4-enoate (1) as an orange oil that solidifies slowly, 7.54 g.

Synthesis of methyl 2-methyl-2-(1-phenyl-1H-pyrazol-5-yl)propanoate (2)

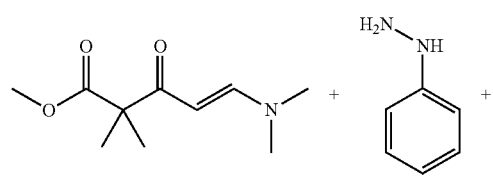

-continued

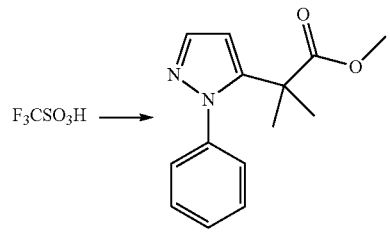

A solution of (E)-methyl 5-(dimethylamino)-2,2-dimethyl-3-oxopent-4-enoate (1) (7.354 g, 36.9 mmol) and phenylhydrazine (4.00 ml, 40.6 mmol) in THF (250 ml) was cooled in an ice bath. Trifluoromethanesulfonic acid (3.58 ml, 40.6 mmol) acid was added and the resulting mixture was stirred cold for 30 minutes, then warmed to room temperature (~22° C.) and stirred overnight. Water, brine, and saturated $Na_2CO_3$ were added to the mixture and the resulting mixture was extracted with EtOAc several times. The combined organics were separated then washed with brine, dried, and vacuumed down to an orange oil that solidifies, 15.8 g. Column chromatography of this mixture yielded methyl 2-methyl-2-(1-phenyl-1H-pyrazol-5-yl)propanoate (2) as a pale yellow, crystalline solid, 7.68 g (85%).

Synthesis of 2,3-dimethyl-3-(1-phenyl-1H-pyrazol-5-yl)butan-2-ol (3)

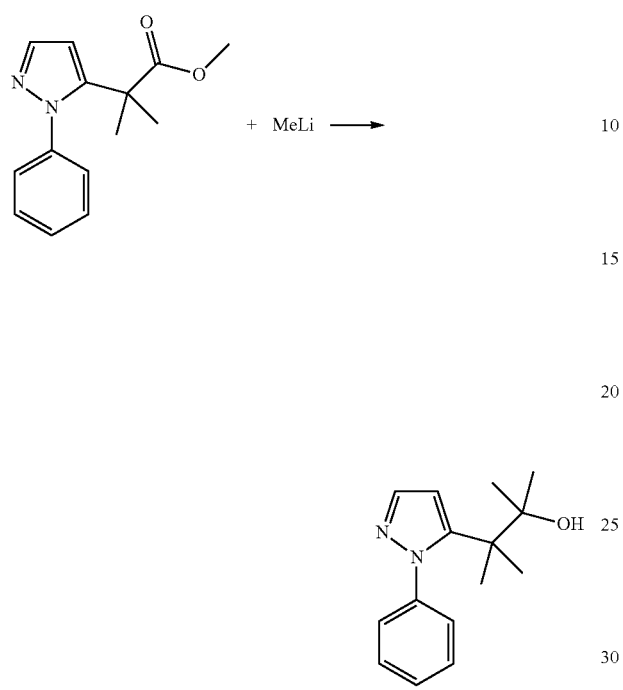

A solution of methyl 2-methyl-2-(1-phenyl-1H-pyrazol-5-yl)propanoate (2) (5.57 g, 22.80 mmol) in THF (150 ml) was cooled in an isopropyl alcohol (iPrOH)/CO₂ bath and a methyllithium solution in ether (1.6M, 57.0 ml, 91 mmol) was added via syringe. The reaction mixture was stirred cold for 6 hours cold then warmed to room temperature (~22° C.), at which point the reaction mixture was quenched with water. Extraction with ethyl acetate (EtOAc) and column chromatography yielded 2.82 g (51%) of 2,3-dimethyl-3-(1-phenyl-1H-pyrazol-5-yl)butan-2-ol (3) as a colorless solid.

Synthesis of 4,4,5,5-tetramethyl-4,5-dihydropyrazolo[1,5-a]quinoline (4)

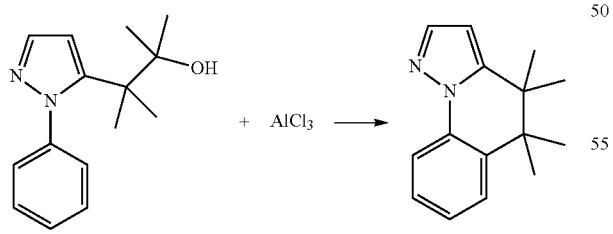

To a solution of 2,3-dimethyl-3-(1-phenyl-1H-pyrazol-5-yl)butan-2-ol (3) (2.82 g, 11.54 mmol) in CHCl₃ (100 ml) was added solid aluminum trichloride (4.62 g, 34.6 mmol) and the mixture was stirred at room temperature for 30 minutes. Quenching followed by filtering through a silica plug with 100% DCM yielded product as a pale yellow oil, 2.8 g (94%).

Synthesis of Dimer (5)

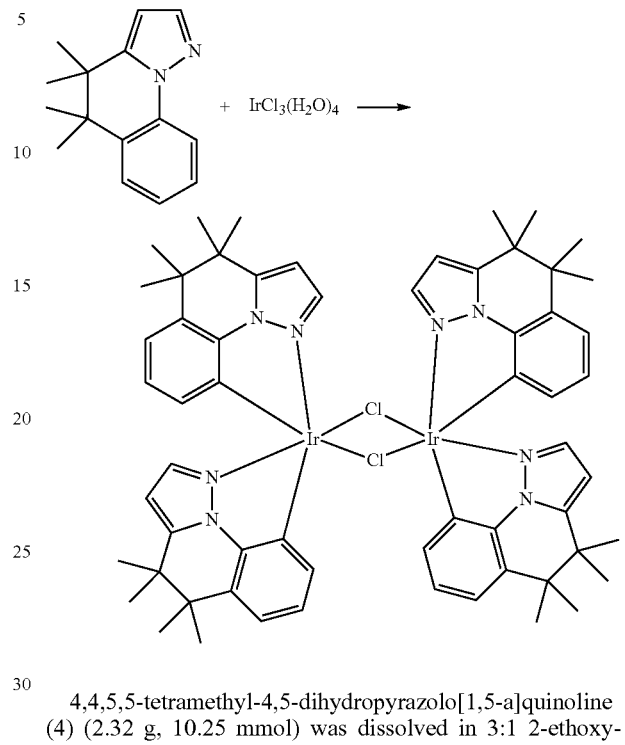

4,4,5,5-tetramethyl-4,5-dihydropyrazolo[1,5-a]quinoline (4) (2.32 g, 10.25 mmol) was dissolved in 3:1 2-ethoxyethanol/water (40 ml), sparged for 15 minutes with nitrogen, then iridium(III) chloride hydrate (1.649 g, 4.45 mmol) was added. Nitrogen sparge was continued for 5 minutes more, then the mixture was stirred at reflux overnight (~12 hours). The mixture was cooled to room temperature (~22° C.), diluted with methyl alcohol (MeOH), and filtered, then the solids were washed with MeOH to yield the dimer 5 as a pale yellow powder, 2.95 g (98%).

Synthesis of Complex Ir1 (6)

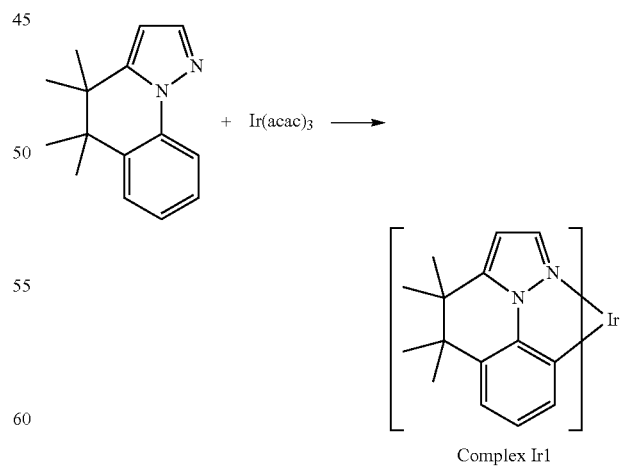

Complex Ir1

4,4,5,5-tetramethyl-4,5-dihydropyrazolo[1,5-a]quinoline (4) (0.63 g, 2.78 mmol) and Ir(acac)₃ (0.27 g, 0.552 mmol) were combined in a schlenk tube with 15 drops of tridecane. The flask was degassed with long vacuum/backfill cycles, then maintained at reflux for three days. The reaction mixture was coated on a silica gel and purified by column chromatography followed by trituration in hot acetonitrile (MeCN) go give 0.055 g of Compound Ir1 (6).

Synthesis of Triflate (7)

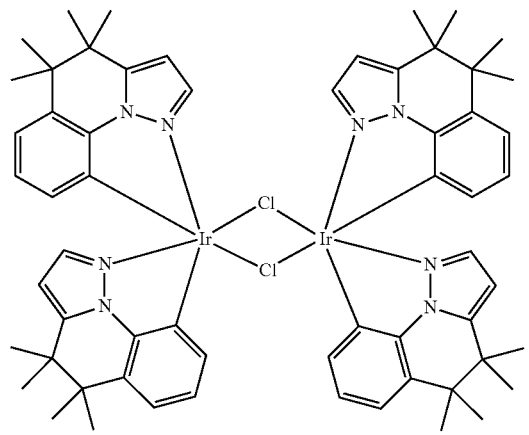

AgOTf →

Silver triflate (0.795 g, 3.10 mmol) in MeOH (7.14 ml) was added to a solution of dimer (5) (2.00 g, 1.47 mmol) in DCM (50 ml), and the teal mixture was stirred overnight (~12 hours) at room temperature (~22° C.), covered in foil. The mixture was then filtered through silica gel, which was then washed with DCM until the filtrates were colorless. The filtrates were vacuumed down to yield triflate (7) as a greenish, foamy solid, 2.48 g (98%).

Synthesis of Compound Ir872

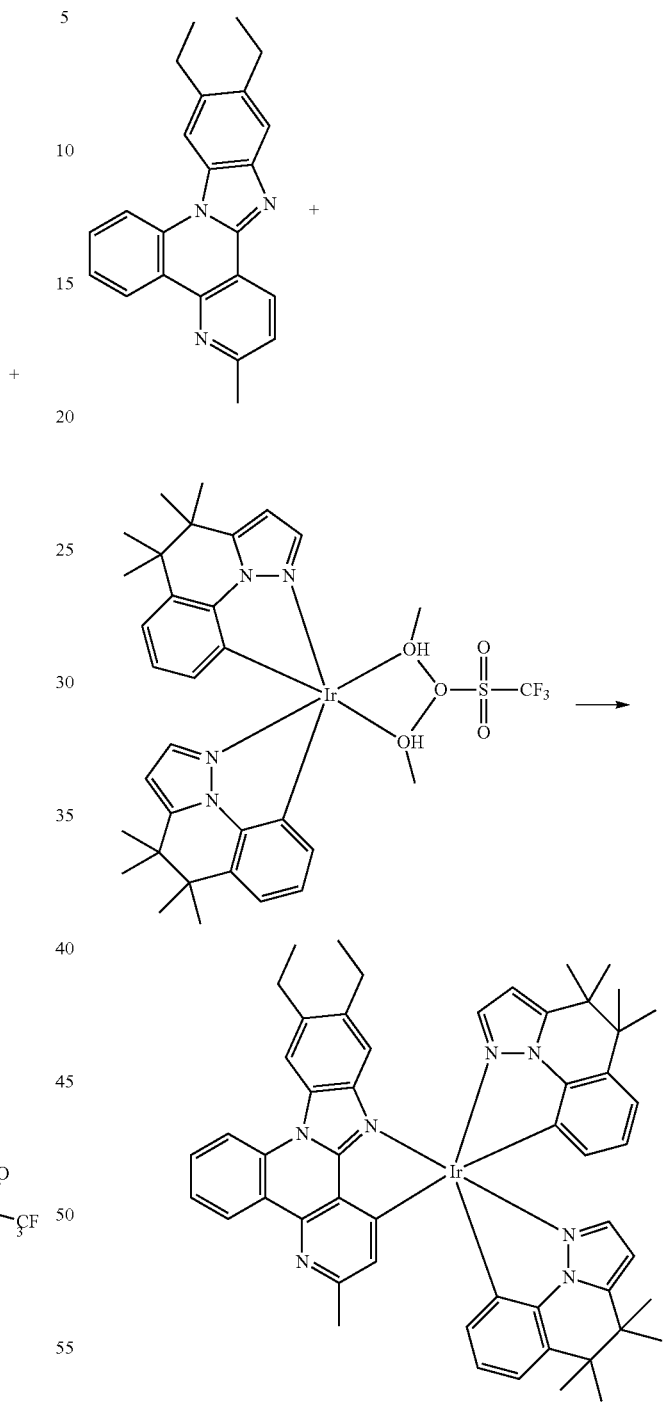

11,12-diethyl-3-methylbenzo[h]benzo[4,5]imidazo[2,1-f][1,6]naphthyridine (0.222 g, 0.654 mmol) and triflate (7) (0.280 g, 0.327 mmol) were combined in 2-ethoxyethanol (2 ml). The mixture was degassed, then refluxed under nitrogen overnight (~12 hours). The resulting mixture was diluted with MeOH and filtered. The crude filtrate was purified by column chromatography to yield 0.031 g of clean Compound Ir872.

Synthesis of Compound Ir874

Synthesis of Compound 888

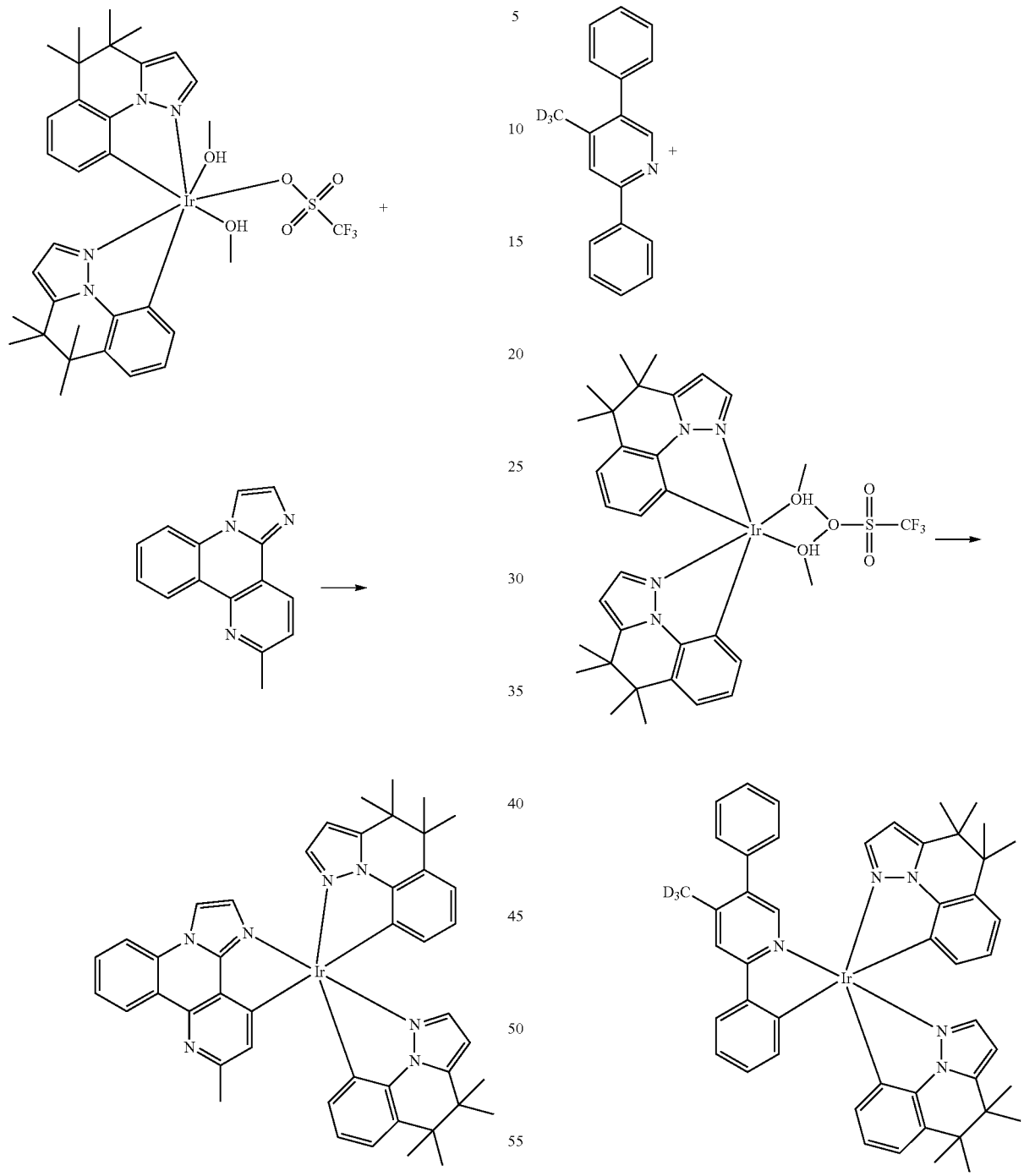

10-methylbenzo[h]imidazo[2,1-f][1,6]naphthyridine (0.373 g, 1.600 mmol) and triflate (7) (0.685 g, 0.800 mmol) were combined in 2-ethoxyethanol (3 ml). The mixture was degassed, then refluxed under nitrogen for 3.5 hours. The mixture was diluted with methanol (MeOH) and filtered. The crude filtrate was purified by column chromatography to afford a yellow solid that was triturated in hot heptanes to yield 0.53 g of Compound Ir874 as a nearly colorless solid (75%).

4-(methyl-d3)-2,5-diphenylpyridine (0.527 g, 2.124 mmol) and triflate 7 (0.606 g, 0.708 mmol) were combined in ethanol (10 ml). The mixture was degassed and refluxed for 2.5 hours. The solvent was then removed under vacuum. The residue was dissolved in dichloromethane (DCM) and passed through a silica column, then the DCM was washed until the color was removed. The filtrates were coated on a plug of silica gel and purified using column chromatography to yield Compound Ir888 as a yellow solid, 0.219 g.

Synthesis of Comparative Examples 13 & 14

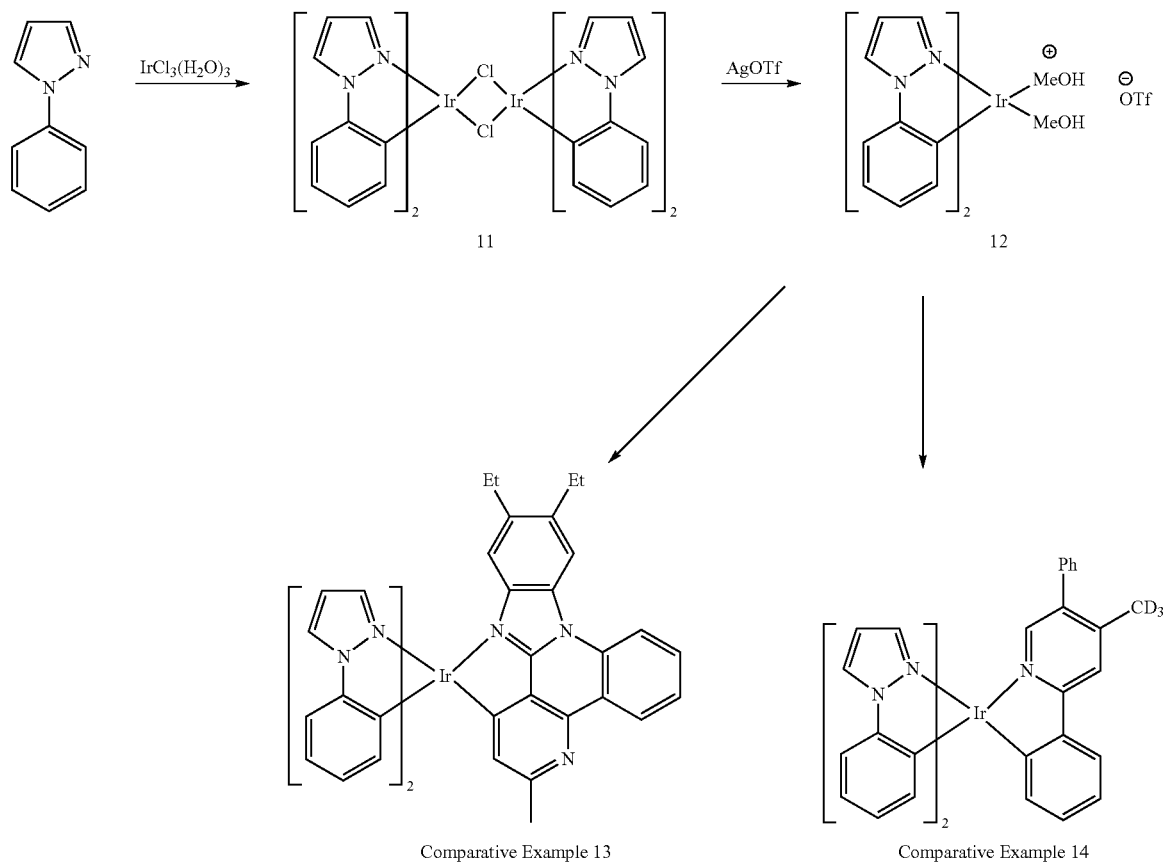

Comparative Example 13

Comparative Example 14

Synthesis of Dimer (11)

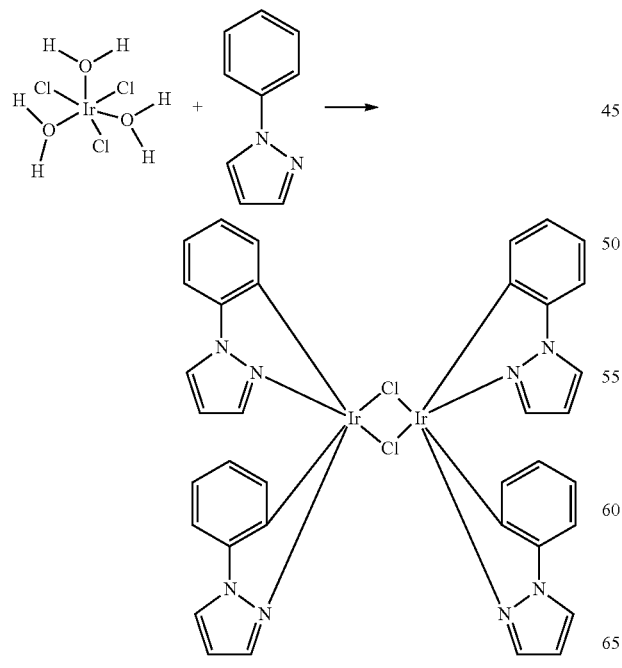

Iridium chloride hydrate (6.00 g, 17.02 mmol) and 1-phenyl-1H-pyrazole (5.89 g, 40.9 mmol) were combined in 2-ethoxyethanol (120 ml) and water (40 ml). The reaction mixture was heated to reflux overnight (~12 hours) under nitrogen. The resulting solid was filtered off and washed with methanol and dried to yield 8.3 g of dimer 11.

Synthesis of Triflate (12)

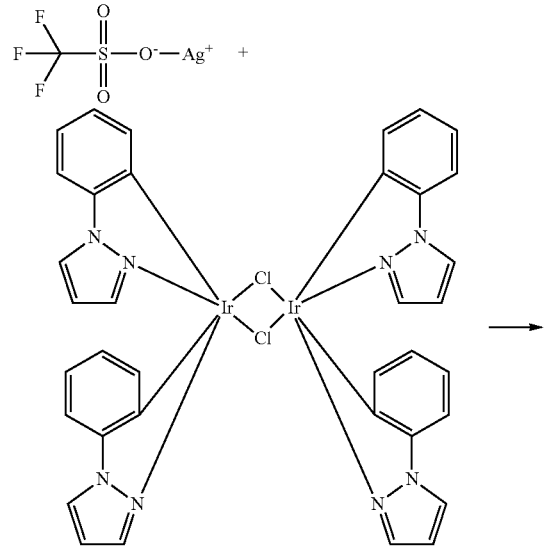

-continued

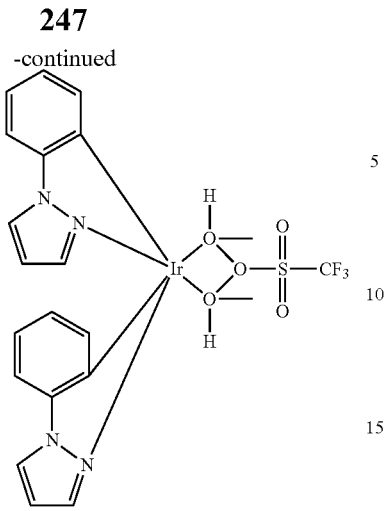

Dimer 11 (8.3 g, 8.07 mmol) was dissolved in 100 mL of DCM and a solution of silver triflate (AgOTf) (4.36 g, 16.96 mmol) in 20 mL of methanol was added. The reaction mixture was stirred at room temperature (~22° C.) under nitrogen for 1 hour. The mixture was filtered through a plug of silica gel and the cake was washed with DCM. The filtrates were evaporated to yield 10.85 g of triflate 12 (97%).

Synthesis of Comparative Example 13

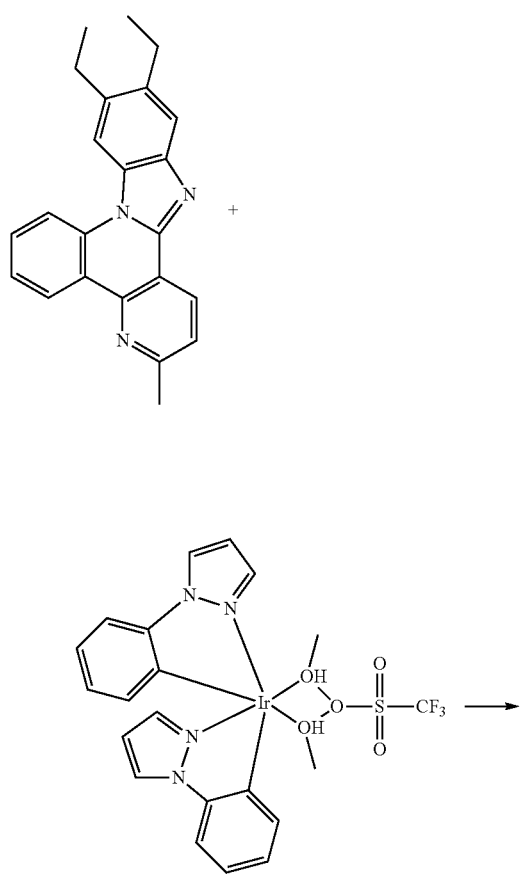

-continued

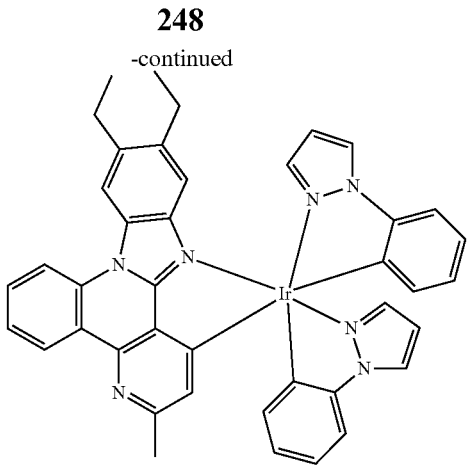

11,12-diethyl-3-methylbenzo[h]benzo[4,5]imidazo[2,1-f][1,6]naphthyridine (0.151 g, 0.445 mmol) and triflate 12 (0.154 g, 0.223 mmol) were combined in 2-ethoxyethanol (2 ml). The mixture was degassed and refluxed overnight (~12 hours). The mixture was cooled to room temperature (~22° C.), diluted with MeOH, and an orange precipitate was filtered and washed with MeOH yielding 0.086 g of Comparative Example 13, 47%.

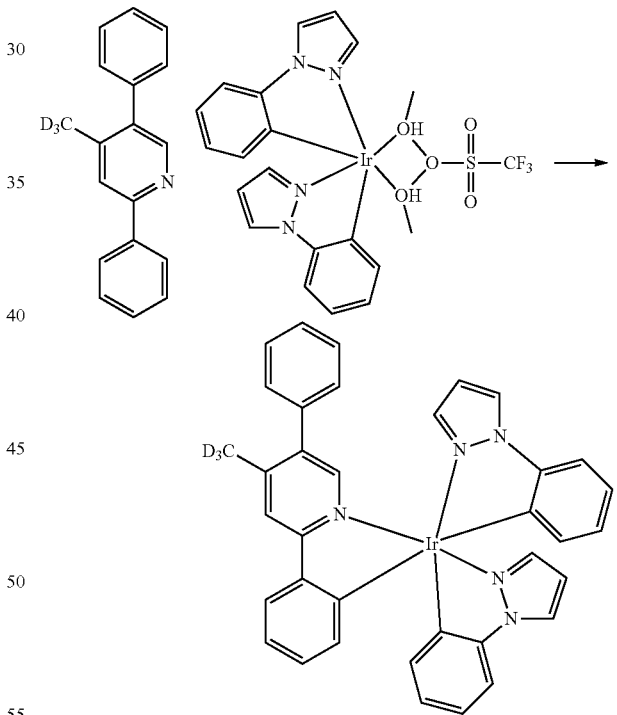

Synthesis of Comparative Example 14

A mixture of 4-(methyl-d3)-2,5-diphenylpyridine (1.077 g, 4.34 mmol) and triflate 11 (1 g, 1.446 mmol) in ethanol (10 ml) was degassed and refluxed overnight (~12 hours). The solvent was removed under vacuum and the residue was dissolved in DCM and filtered through a silica plug. The yellow filtrates were purified by column chromatography to isolate Comparative Example 14, which was triturated twice in hot toluene and once in hot acetonitrile (MeCN) to yield 0.434 g of Comparative Example 14.

Synthesis of Compound Pt1

The following is a general scheme for synthesizing Compound Pt1, and is followed by more detailed explanation of the scheme.

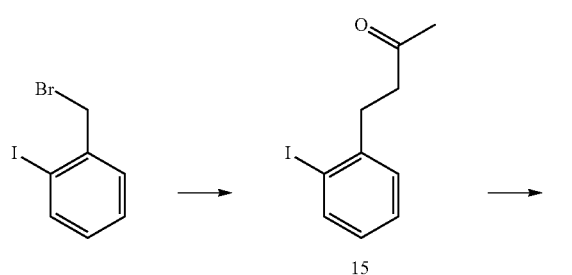
15

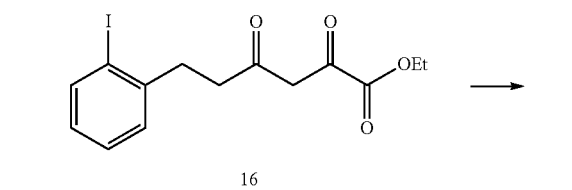
16

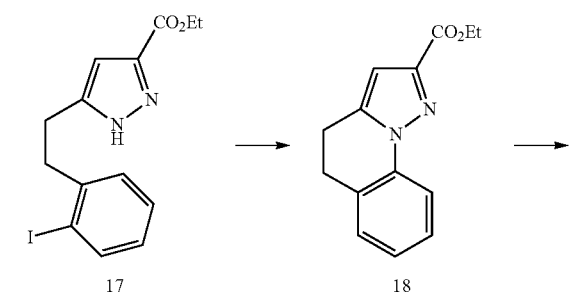
17    18

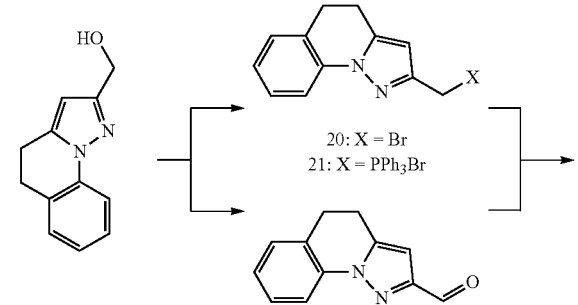
19    20: X = Br
       21: X = PPh₃Br
       22

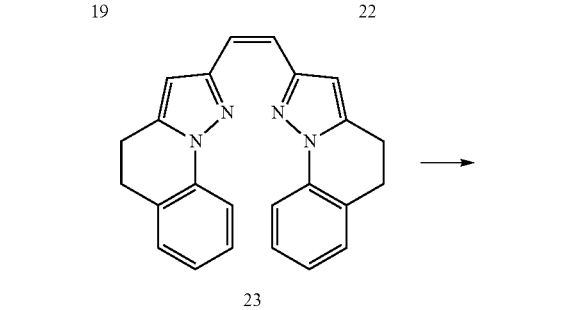
23

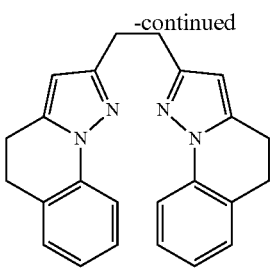
24

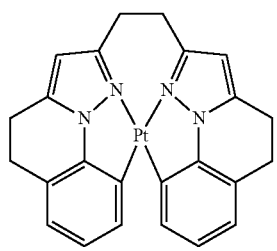

Compound Pt1

Synthesis of 4-(2-Iodophenyl)butan-2-one (15)

A mixture of 2-iodobenzyl bromide (9 g, 30.3 mmol, 1 equiv), potassium carbonate (4.18 g, 30.3 mmol, 1 equiv), and acetyl-acetone (3.4 mL, 33.4 mmol, 1.1 equiv) in absolute ethanol (90 mL) was refluxed overnight (~12 hours). The mixture was cooled to room temperature (~22° C.) and combined with another 1 g reaction mixture. The mixture was diluted with water (200 mL) and methyl tert-butyl ether (MTBE) (200 mL), and the layers were separated. The aqueous layer was extracted with MTBE (200 mL). The combined organic layers were washed with saturated brine, then concentrated under reduced pressure. The residue was purified by column chromatography to yield 4-(2-Iodophenyl)butan-2-one (15) as a colorless oil (5.7 g, 62% yield).

Synthesis of Ethyl 6-(2-iodophenyl)-2,4-dioxohexanoate (16)

21% Sodium ethoxide in ethanol (6 mL, 16.2 mmol, 1.08 equiv) was slowly added to a mixture of 4-(2-Iodophenyl)butan-2-one 15 (4.1 g, 15 mmol, 1 equiv) and diethyl oxalate (2.1 mL, 16.2 mmol, 1.08 equiv) in absolute ethanol (41 mL) maintaining the internal temperature below −2° C. After the addition was complete, the reaction mixture was warmed to room temperature (~22° C.). The mixture was stirred for 3 days. Water (200 mL) was added and the pH was adjusted to 5~6 with 10% HCl. The aqueous solution was extracted with ethyl acetate (3×200 mL). The combined organic layers were washed with saturated brine (2×100 mL) and concentrated under reduced pressure. The residue was purified by column chromatography to give ethyl 6-(2-iodophenyl)-2,4-dioxohexanoate (16) as a yellow oil (3.3 g, 59% yield, 82% purity).

Synthesis of Ethyl 5-(2-iodophenethyl)-1H-pyrazole-3-carboxylate (17)

A mixture of ethyl 6-(2-iodophenyl)-2,4-dioxohexanoate 16 (3.3 g, 8.8 mmol, 1 equiv) and hydrazine monohydrate (0.47 mL, 9.7 mmol, 1.1 equiv) in acetic acid (10 mL) was stirred at 110° C. for 2 hours. The mixture was cooled to room temperature (~22° C.) and poured into ice water (10 mL). The slurry was carefully neutralized with sodium bicarbonate and filtered. The solid was washed with water and dried under vacuum at 40° C., overnight (~12 hours) to give Ethyl 5-(2-iodophenethyl)-1H-pyrazole-3-carboxylate (17) as a tan solid (3.26 g, 99% yield).

Synthesis of Ethyl 4,5-dihydropyrazolo[1,5-a]quinoline-2-carboxylate (18)

A mixture of 17 (3.12 g, 8.43 mmol, 1 equiv), copper(I) iodide (80 mg, 0.42 mmol, 0.05 equiv), potassium carbonate (2.33 g, 16.9 mmol, 2 equiv), and N,N'-dimethyl-ethylenediamine (0.16 mL, 1.89 mmol, 0.22 equiv) in toluene (150 mL) was refluxed for 1 day. The mixture was cooled and quenched with ice water (100 mL). The layers were separated and the aqueous layer was extracted with THF (2×200 mL). The combined organic layers were filtered through a pad of celite and concentrated under reduced pressure. The residue was purified by column chromatography to give ethyl 4,5-dihydropyrazolo[1,5-a]quinoline-2-carboxylate 18 as a yellow oil (1.8 g, 90% yield).

Synthesis of (4,5-Dihydropyrazolo[1,5-a]quinolin-2-yl)methanol (19)

Red-Al® (sodium bis(2-methoxyethoxy)aluminum dihydride, sold by Sigma-Aldrich) (55 mL, 196 mmol, 4 equiv) was slowly added to a solution of ethyl 4,5-dihydropyrazolo[1,5-a]quinoline-2-carboxylate 18 (11.9 g, 49.1 mmol, 1 equiv) in THF (240 mL), maintaining the internal temperature below −5° C. The slurry was stirred overnight (~12 hours). The mixture was carefully acidified with 3N HCl to pH 1-2. The mixture was diluted with water (200 mL) and ethyl acetate (200 mL) and the layers were separated. The aqueous layer was extracted with ethyl acetate (2×400 mL). The combined organic layers were washed with saturated brine (200 mL) and concentrated under reduced pressure. The residue was dried under vacuum at 40° C. for 2 hours to give (4,5-Dihydropyrazolo[1,5-a]quinolin-2-yl)methanol (19) as a yellow solid (9.02 g, 92% yield).

Synthesis of 2-(Bromomethyl)-4,5-dihydropyrazolo[1,5-a]quinolone (20)

Phosphorus tribromide (3 mL, 31.8 mmol, 1.2 equiv) was slowly added to a solution of (4,5-Dihydropyrazolo[1,5-a]quinolin-2-yl)methanol (19) (5.3 g, 26.5 mmol, 1 equiv) in dichloromethane (50 mL), maintaining the internal temperature below −5° C. The solution was stirred at room temperature (~22° C.) overnight (~12 hours). Water (100 mL) was added and the mixture was carefully neutralized with sodium bicarbonate. The layers were separated and the aqueous layer was extracted with dichloromethane (200 mL). The combined organic layers were washed with saturated brine (100 mL) and concentrated under reduced pressure. The solid was dried under vacuum at 40° C. overnight to give 2-(Bromomethyl)-4,5-dihydropyrazolo[1,5-a]quinolone (20) as a yellow solid (6.2 g, 90% yield).

Synthesis of ((4,5-Dihydropyrazolo[1,5-a]quinolin-2-yl)methyl)triphenylphosphonium bromide (21)

A mixture of 2-(bromomethyl)-4,5-dihydropyrazolo[1,5-a]quinolone 20 (6.2 g, 23 mmol, 1 equiv) and triphenylphosphine (6.6 g, 25.3 mmol, 1.1 equiv) in toluene was refluxed for 4 hours. The slurry was cooled and filtered. The solid was dried under vacuum at 40° C. for 3 hours to give ((4,5-Dihydropyrazolo[1,5-a]quinolin-2-yl)methyl)triphenylphosphonium bromide (21) as a white solid (9.31 g, 77% yield).

Synthesis of 4,5-Dihydropyrazolo[1,5-a]quinoline-2-carbaldehyde (22)

A slurry of (4,5-Dihydropyrazolo[1,5-a]quinolin-2-yl)methanol (19) (4.9 g, 24.5 mmol, 1 equiv) and activated manganese oxide (27 g, 318 mmol, 13 equiv) in 1,2-dichloroethane (150 mL) was stirred at 75° C. for 3 hours. The reaction mixture was cooled to room temperature (~22° C.) and filtered through a pad of silica gel. The filtrate was concentrated under reduced pressure to give 4,5-dihydropyrazolo[1,5-a]quinoline-2-carbaldehyde (22) as a yellow oil (3.3 g).

Synthesis of 1,2-bis(4,5-Dihydropyrazolo[1,5-a]quinolin-2-yl)ethane (23)

2.5M n-Butyllithium in hexanes (6.7 mL, 16.8 mmol, 1.03 equiv) was added slowly to a solution of ((4,5-Dihydropyrazolo[1,5-a]quinolin-2-yl)methyl)triphenylphosphonium bromide (21) (9.1 g, 17.3 mmol, 1.06 equiv) in THF (180 mL) while maintaining the reaction temperature below −70° C. After 20 minutes, a solution of 4,5-Dihydropyrazolo[1,5-a]quinoline-2-carbaldehyde (22) (3.23 g, 16.3 mmol, 1 equiv) in THF (10 mL) was slowly added to the mixture while maintaining the reaction temperature below −70° C. The reaction mixture was then stirred at room temperature (~22° C.) overnight (~12 hours). Water (200 mL) and ethyl acetate (100 mL) were added and the layers were separated. The aqueous layer was extracted with ethyl acetate (2×200 mL). The combined organic layers were washed with saturated brine (100 mL) and concentrated under reduced pressure. The resulting solid was triturated with methanol and filtered to give a first crop as an off-white solid (2.8 g). The filtrate was then concentrated under reduced pressure and the residue was purified by column chromatography to give a total of 4.4 g of 1,2-bis(4,5-Dihydropyrazolo[1,5-a]quinolin-2-yl)ethane (23) as an off-white solid (74%).

Synthesis of 1,2-bis(4,5-Dihydropyrazolo[1,5-a]quinolin-2-yl)ethane (24)

A mixture of 1,2-bis(4,5-Dihydropyrazolo[1,5-a]quinolin-2-yl)ethane (23) (4.3 g, 11.8 mmol, 1 equiv) and 10% palladium on carbon (0.86 g) in THF (600 mL) and ethanol (400 mL) was hydrogenated at 50 psi overnight (~12 hours). The solution was filtered through a pad of silica gel and the filtrate was concentrated under reduced pressure. The resulting solid was triturated with 2-propanol (~30 mL) and dried under vacuum at 40° C. overnight (~12 hours) to give 1,2-bis(4,5-Dihydropyrazolo[1,5-a]quinolin-2-yl)ethane (24) as a white solid (3.5 g, 81% yield).

Synthesis of Compound Pt1

A solution of 1,2-bis(4,5-Dihydropyrazolo[1,5-a]quinolin-2-yl)ethane (24) (2.77 g, 7.57 mmol, 1 equiv) in tridecane (310 mL) was sparged with argon for 40 minutes. Pt(acac)$_2$ (2.98 g, 7.57 mmol, 1 equiv) was then added and the reaction mixture was heated at 220-230° C. (external temperature) for 48 hours. After cooling to room temperature (~22° C.), the reaction mixture was passed through a pad of silica gel (30 g) and washed with dichloromethane (80 ml). After removing the solvent under reduced pressure, the residue was purified a total of three times by column chromatography to give Compound Pt1 (210 mg) as a yellow solid.

Synthesis of Compound Pt31

The following is a general scheme for synthesizing Compound Pt31, and is followed by more detailed explanation of the scheme.

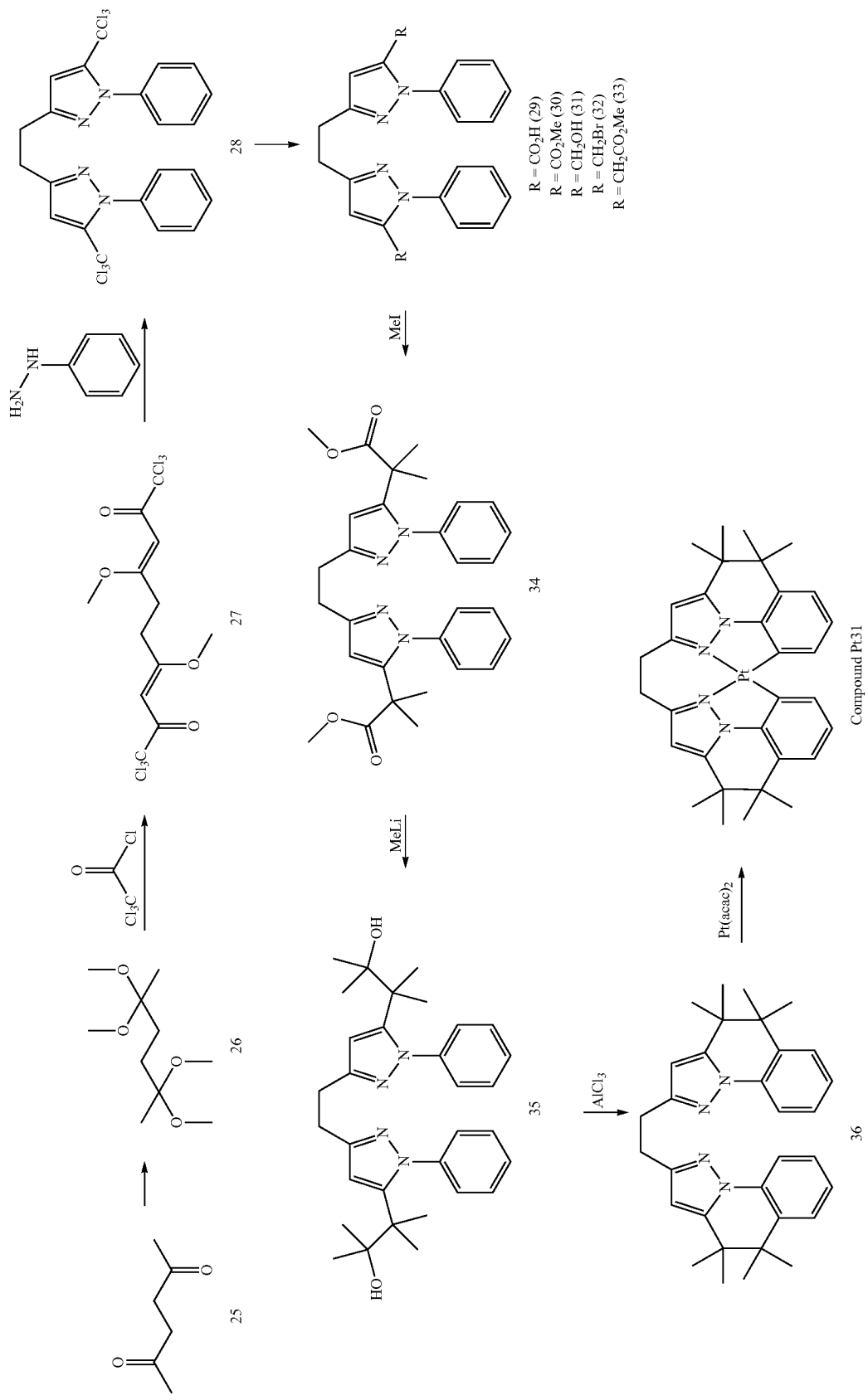

Synthesis of 2,2,5,5-tetramethoxyhexane (26)

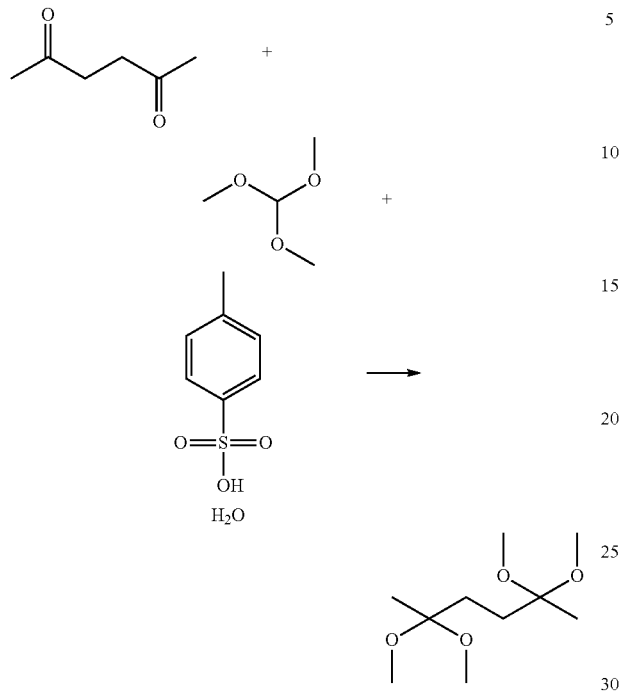

A mixture of hexane-2,5-dione (25) (28 ml, 239 mmol), trimethoxymethane (131 ml, 1193 mmol), and tosylic acid hydrate (1.135 g, 5.97 mmol) in MeOH (250 ml) was refluxed overnight (~12 hours). 2 mL of triethyl amine (Et$_3$N) was added and the solvent was removed under vacuum. The residue was diluted with diethyl ether (Et$_2$O), then washed with 5% NaOH in 50% brine followed by water, then dried and filtered. The filtrate was vacuumed down and distilled under vacuum at 90-100° C./78° C. (bath/vapor temp), yielding 44.19 g of 2,2,5,5-tetramethoxyhexane (26) as a colorless oil (90%).

Synthesis of (3Z,7Z)-1,1,1,10,10,10-hexachloro-4,7-dimethoxydeca-3,7-diene-2,9-dione (27)

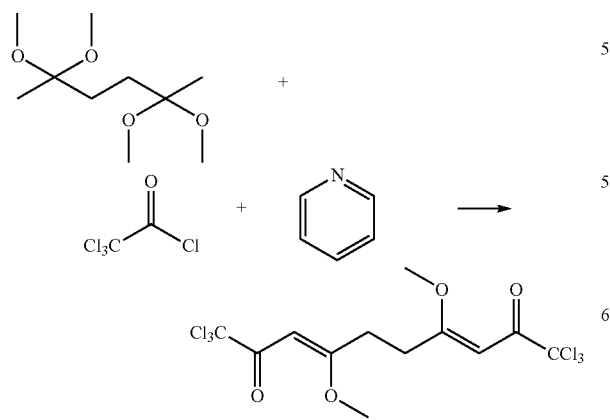

A solution of 2,2,5,5-tetramethoxyhexane (26) (34.7 g, 168 mmol) and pyridine (54.3 ml, 673 mmol) in DCM (400 ml) was stirred at −10° C. and a solution of 2,2,2-trichloroacetyl chloride (75 ml, 673 mmol) in DCM (200 ml) was added dropwise. The reaction mixture was stirred at room temperature (~22° C.) for two days and washed twice with 500 mL 0.1 M HCl, then three times with 250 mL water, before being dried and coated on silica gel. Purification by silica gel chromatography yielded (3Z,7Z)-1,1,1,10,10,10-hexachloro-4,7-dimethoxydeca-3,7-diene-2,9-dione (27) as a yellow oil that solidified upon standing, 53.59 g (74%).

Synthesis of 1,2-bis(1-phenyl-5-(trichloromethyl)-1H-pyrazol-3-yl)ethane (28)

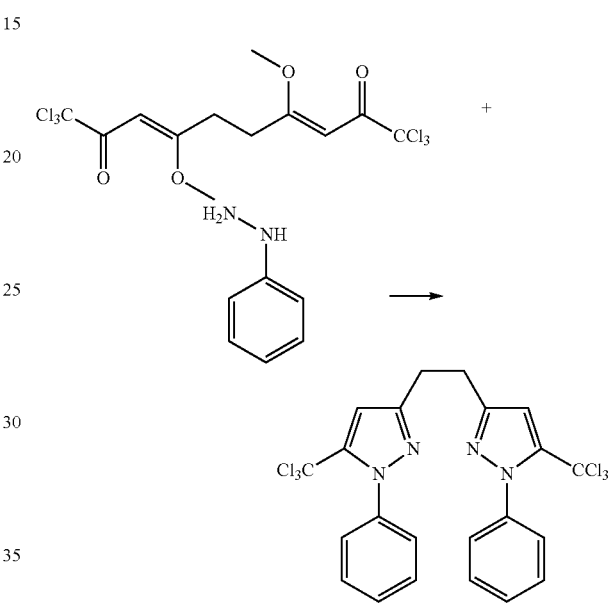

A solution of yielded (3Z,7Z)-1,1,1,10,10,10-hexachloro-4,7-dimethoxydeca-3,7-diene-2,9-dione (27) (21.219 g, 49.0 mmol) in THF (500 ml) was cooled in an ice bath, then phenylhydrazine (10.14 ml, 103 mmol) was added over 15 minutes. The solution was stirred in an ice bath for 9 hours, then overnight (~12 hours) at room temperature (~22° C.). The orange mixture was then stirred at 55° C. for 4 hours, and the solvent was removed under vacuum. The residue was triturated in DCM to yield some clean product as a solid. The filtrate was further chromatographed on silica gel to yield a total of 20.8 g of 1,2-bis(1-phenyl-5-(trichloromethyl)-1H-pyrazol-3-yl)ethane (28) as a beige/yellow solid, 77%.

Synthesis 3,3'-(ethane-1,2-diyl)bis(1-phenyl-1H-pyrazole-5-carboxylic acid) (29)

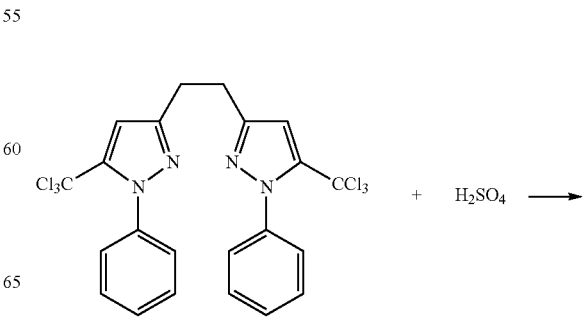

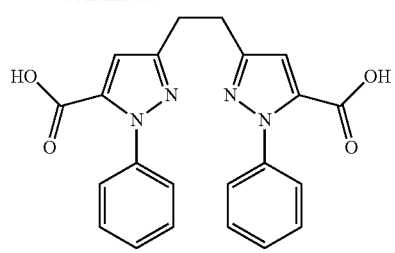

A mixture of 75% sulfuric acid (3:1 dilution of conc. acid and water) (36.5 ml, 493 mmol) and 1,2-bis(1-phenyl-5-(trichloromethyl)-1H-pyrazol-3-yl)ethane (28) (18.045 g, 32.9 mmol) was heated at 100° C., while passing outgassed HCl through a KOH/water trap. After 4 hours the reaction mixture was cooled to room temperature (22° C.) and diluted with 400 mL of ice water. The beige precipitate was filtered, washed twice with water, and dried under vacuum to yield 13.2 g of 3,3'-(ethane-1,2-diyl)bis(1-phenyl-1H-pyrazole-5-carboxylic acid) (29) (quant.).

Synthesis of dimethyl 3,3'-(ethane-1,2-diyl)bis(1-phenyl-1H-pyrazole-5-carboxylate) (30)

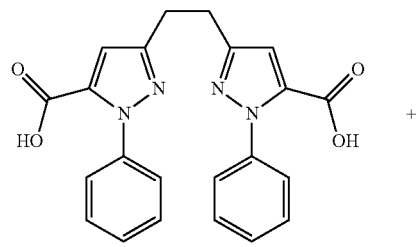

A mixture of 3,3'-(ethane-1,2-diyl)bis(1-phenyl-1H-pyrazole-5-carboxylic acid) (29) (13.25 g, 32.9 mmol), potassium carbonate (18.20 g, 132 mmol), and iodomethane (6.15 ml, 99 mmol) was stirred at room temperature (~22° C.) overnight (~12 hours). The solvent was removed by kugelrohr and the residue was sonicated in 100 mL water, then filtered, and the solids washed with water then ether. The solids were dried to yield dimethyl 3,3'-(ethane-1,2-diyl)bis(1-phenyl-1H-pyrazole-5-carboxylate) (30) as a beige solid, 13.43 g (95%).

Synthesis of (ethane-1,2-diylbis(1-phenyl-1H-pyrazole-3,5-diyl))dimethanol (31)

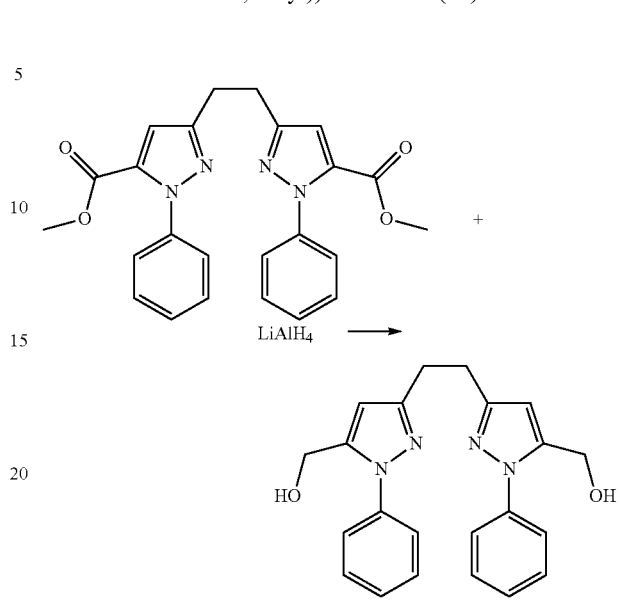

Dimethyl 3,3'-(ethane-1,2-diyl)bis(1-phenyl-1H-pyrazole-5-carboxylate) (30) (13.23 g, 30.7 mmol) was suspended in THF (300 ml), cooled in an ice bath, and lithium aluminum hydride (LAH) solution in THF was added (2M, 70 ml, 140 mmol) and the homogeneous solution was warmed to room temperature (~22° C.). After 2 hours, the reaction solution was cooled in an ice bath and quenched with 8 mL of water, followed by saturated Na$_2$CO$_3$. The solvent was removed under vacuum and the residue was extracted six times with 100 mL warm DMF. DMF was removed from the filtrates by kugelrohr and the beige solid was triturated with 100 mL Et$_2$O, washed with ether and dried to give 11.00 g of (ethane-1,2-diylbis(1-phenyl-1H-pyrazole-3,5-diyl))dimethanol (31) as a solid, (96%).

Synthesis of 1,2-bis(5-(bromomethyl)-1-phenyl-1H-pyrazol-3-yl)ethane (32)

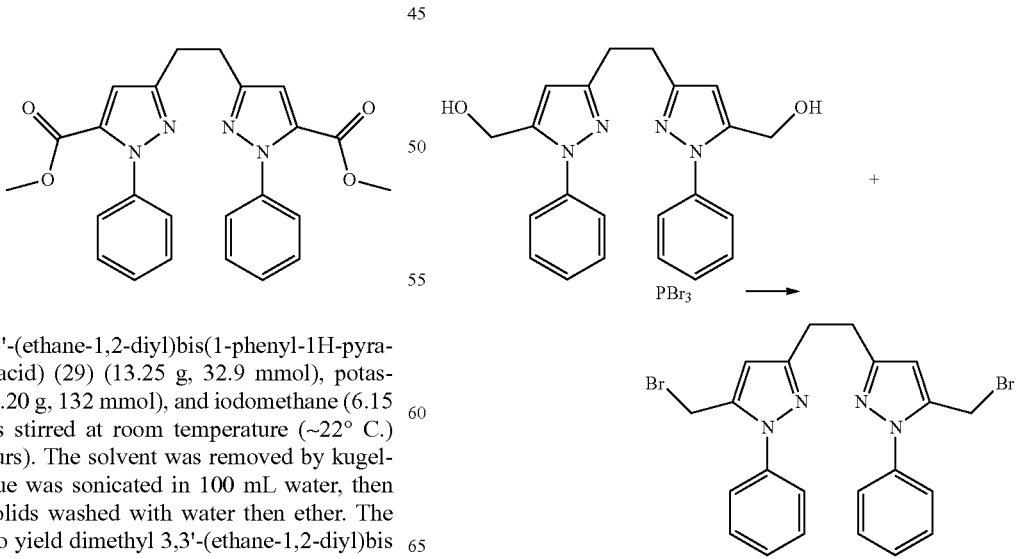

Tribromophosphane (7.78 ml, 83 mmol) was added to a suspension of (ethane-1,2-diylbis(1-phenyl-1H-pyrazole-3,5-diyl))dimethanol (31) (10.33 g, 27.6 mmol) in CHCl₃ (276 ml) in an ice bath. The reaction mixture was stirred at 50° C. for 2 days, cooled in an ice bath, and quenched with water and then basified to pH 9 using aqueous NaOH. The aqueous phase was extracted with DCM, the organics were dried, and the solvent was removed under vacuum. Purification by column chromatography yielded 1,2-bis(5-(bromomethyl)-1-phenyl-1H-pyrazol-3-yl)ethane (32) as a white solid, 11.34 g (82%).

Synthesis of dimethyl 2,2'-(ethane-1,2-diylbis(1-phenyl-1H-pyrazole-3,5-diyl))diacetate (33)

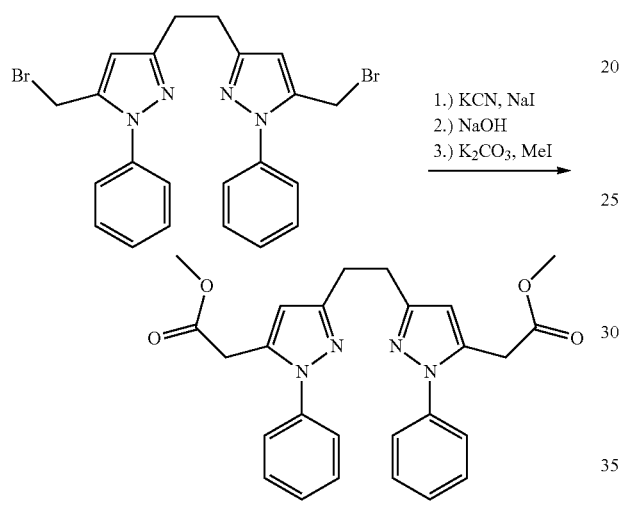

Step 1:
1,2-bis(5-(bromomethyl)-1-phenyl-1H-pyrazol-3-yl)ethane (32) (11.47 g, 22.93 mmol), ground cyanopotassium (4.48 g, 68.8 mmol), and sodium iodide (0.344 g, 2.293 mmol) were stirred in anhydrous DMF (50 ml) for 3 days, then the solvent was removed via kugelrohr. The residue was partitioned between mildly-basic water and EtOAc until all the solids dissolved. After washing the organics with water, 5% LiCl, and sat. NaCl, the solvent was evaporated to yield 9.08 g of an orangish oil that was taken to the next step without further purification.

Step 2:
The crude dinitrile was dissolved in MeOH (125 ml) and heated to reflux, before sodium hydroxide (9.25 g, 231 mmol) dissolved in ~25 mL water was added. The reaction solution was refluxed overnight (~12 hours), the MeOH was removed under vacuum. 500 mL of water was added to the reaction mixture, which was then washed twice with DCM. Next the water layer was acidified with concentrated HCl. The beige solid was filtered, washed with water and dried under vacuum to yield 8.53 g of crude diacid.

Step 3:
The crude diacid was dissolved in DMF (75 ml). Potassium carbonate (10.95 g, 79 mmol) and iodomethane (3.70 ml, 59.4 mmol) were added and the mixture was stirred at room temperature (~22° C.) overnight (~12 hours). The DMF was removed by kugelrohr and the residue was partitioned between water and EtOAc. The organics were dried, and purified by chromatography to yield dimethyl 2,2'-(ethane-1,2-diylbis(1-phenyl-1H-pyrazole-3,5-diyl))diacetate (33) as a pale yellow oil, 3.03 g (30% over three steps).

Synthesis of dimethyl 2,2'-(ethane-1,2-diylbis(1-phenyl-1H-pyrazole-3,5-diyl))bis(2-methylpropanoate) (34)

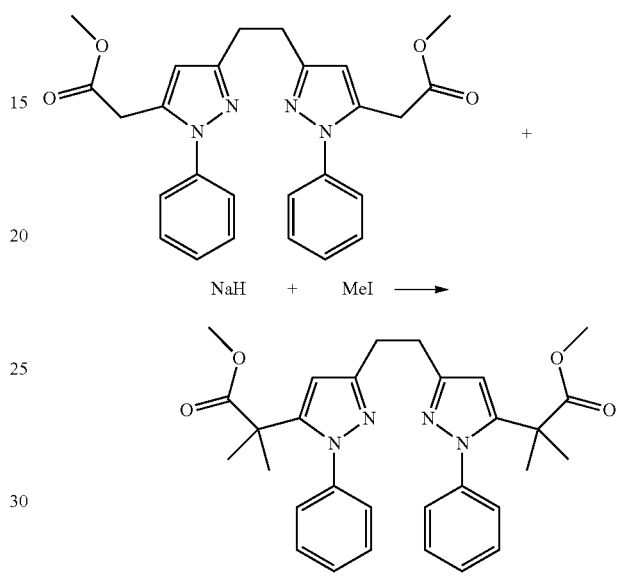

Dimethyl 2,2'-(ethane-1,2-diylbis(1-phenyl-1H-pyrazole-3,5-diyl))diacetate (33) (3.00 g, 6.54 mmol) was dissolved in dry DMF (50 ml), then iodomethane (3.26 ml, 52.3 mmol) was added. The reaction solution was cooled in an ice bath, then a sodium hydride suspension in mineral oil (60%, 2.094 g, 52.3 mmol) was added, and the resulting mixture was stirred overnight under nitrogen at room temperature (~22° C.). The DMF was removed by kugelrohr and the residue was partitioned between water and EtOAc. The organics were dried and vacuumed down to yield dimethyl 2,2'-(ethane-1,2-diylbis(1-phenyl-1H-pyrazole-3,5-diyl))bis(2-methylpropanoate) (34) as a pale yellow solid, 3.49 g (quant.).

Synthesis of 3,3'-(ethane-1,2-diylbis(1-phenyl-1H-pyrazole-3,5-diyl))bis(2,3-dimethylbutan-2-ol) (35)

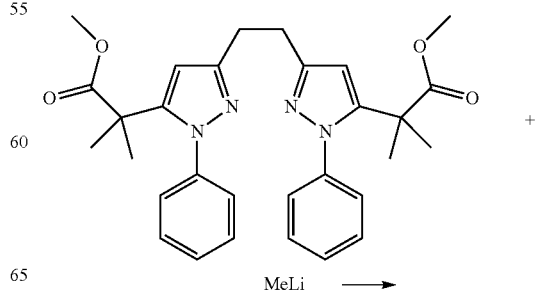

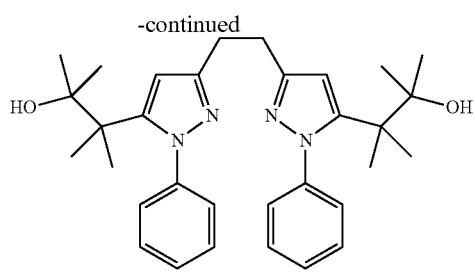

Dimethyl 2,2'-(ethane-1,2-diylbis(1-phenyl-1H-pyrazole-3,5-diyl))bis(2-methylpropanoate) (34) (3.4 g, 6.61 mmol) was dissolved in THF (100 ml), then cooled in an isopropyl alcohol ($^i$PrOH)/CO$_2$ bath. Methyllithium solution in ether (1.6 M, 25 ml, 40.0 mmol) was added and the resulting mixture was stirred cold for 3 hours, then quenched with water/brine, and warmed to room temperature (~22° C.). The mixture was extracted twice with ethyl acetate (EtOAc), then the organics were washed with brine, dried, and chromatographed to yield 3,3'-(ethane-1,2-diylbis(1-phenyl-1H-pyrazole-3,5-diyl))bis(2,3-dimethylbutan-2-ol) (35) as a white solid, 0.78 g (23%).

Synthesis of 1,2-bis(4,4,5,5-tetramethyl-4,5-dihydropyrazolo[1,5-a]quinolin-2-yl)ethane (36)

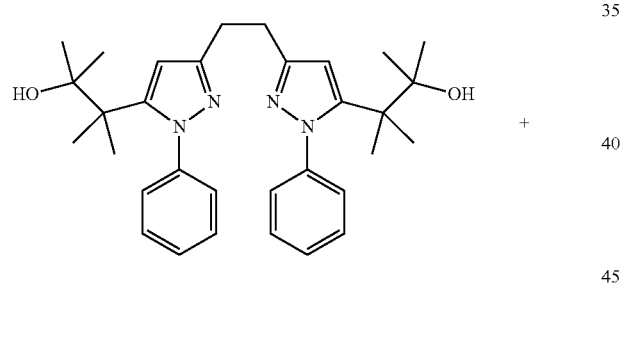

3,3'-(ethane-1,2-diylbis(1-phenyl-1H-pyrazole-3,5-diyl))bis(2,3-dimethylbutan-2-ol) (35) (0.85 g, 1.651 mmol) was dissolved in CHCl$_3$ (50 ml) at room temperature (~22° C.) and aluminum trichloride (1.321 g, 9.91 mmol) was added quickly. The resulting mixture was stirred for one hour, until it turned purple, then quenched with saturated Na$_2$CO$_3$. The mixture was extracted three times with DCM, then the organics were dried and coated on silica gel. The product was purified by column chromatography to yield 1,2-bis(4,4,5,5-tetramethyl-4,5-dihydropyrazolo[1,5-a]quinolin-2-yl)ethane (36) as a colorless solid, 0.50 g (63%).

Synthesis of Compound Pt31

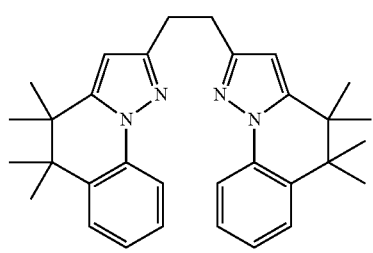

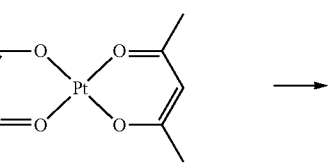

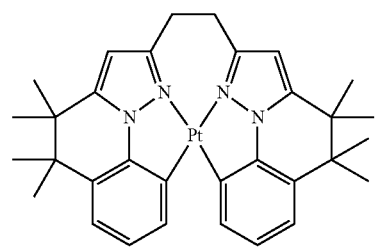

Compound Pt31

1,2-bis(4,4,5,5-tetramethyl-4,5-dihydropyrazolo[1,5-a]quinolin-2-yl)ethane (36) (0.50 g, 1.045 mmol) and Pt(acac)$_2$ (0.411 g, 1.045 mmol) were combined in tridecane (5 ml), then degassed and heated at reflux for 3 days. The mixture was coated on a plug of silica gel, chromatographed, and the resulting solid was triturated in MeOH/DCM to yield Compound Pt31 as a light yellow solid, 0.434 g (65%).

Synthesis of Compound PtM1

The following is a general scheme for synthesizing Compound PtM1, and is followed by more detailed explanation of the scheme.

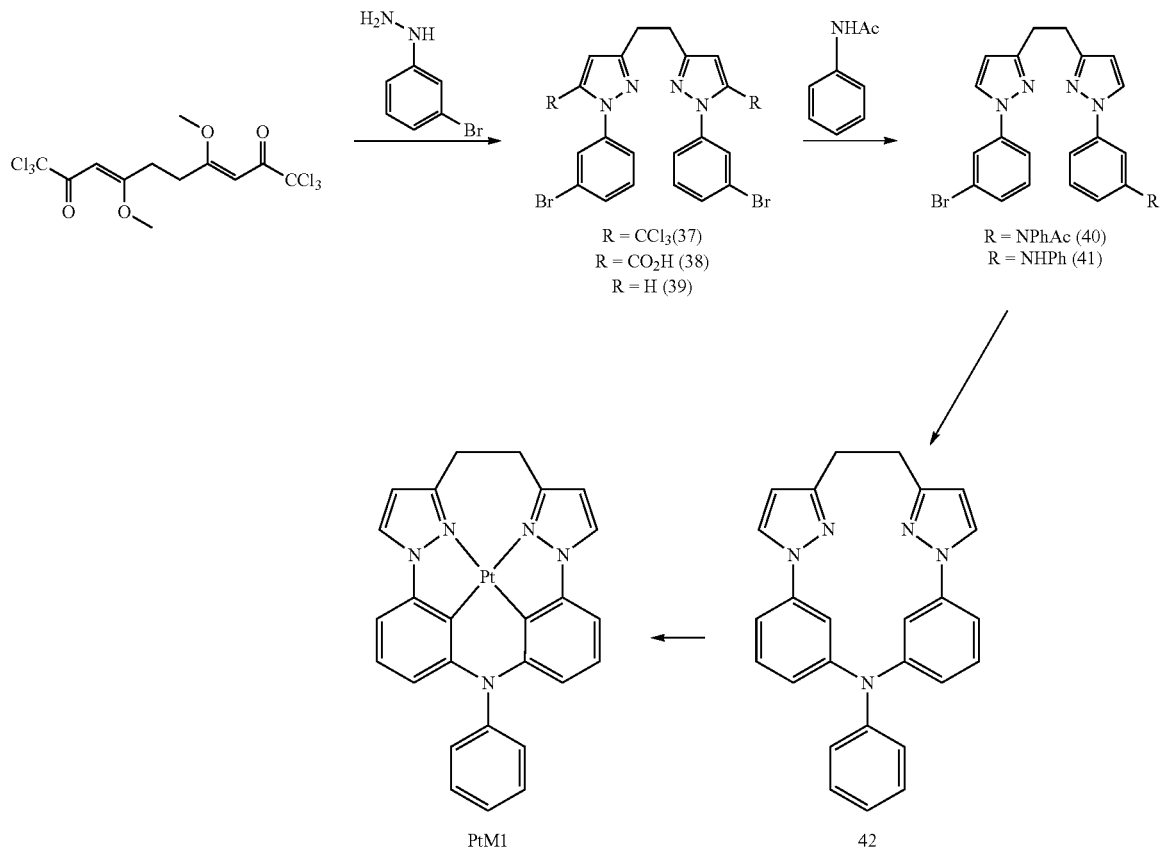

Synthesis of 1,2-bis(1-(3-bromophenyl)-5-(trichloromethyl)-1H-pyrazol-3-yl)ethane (37)

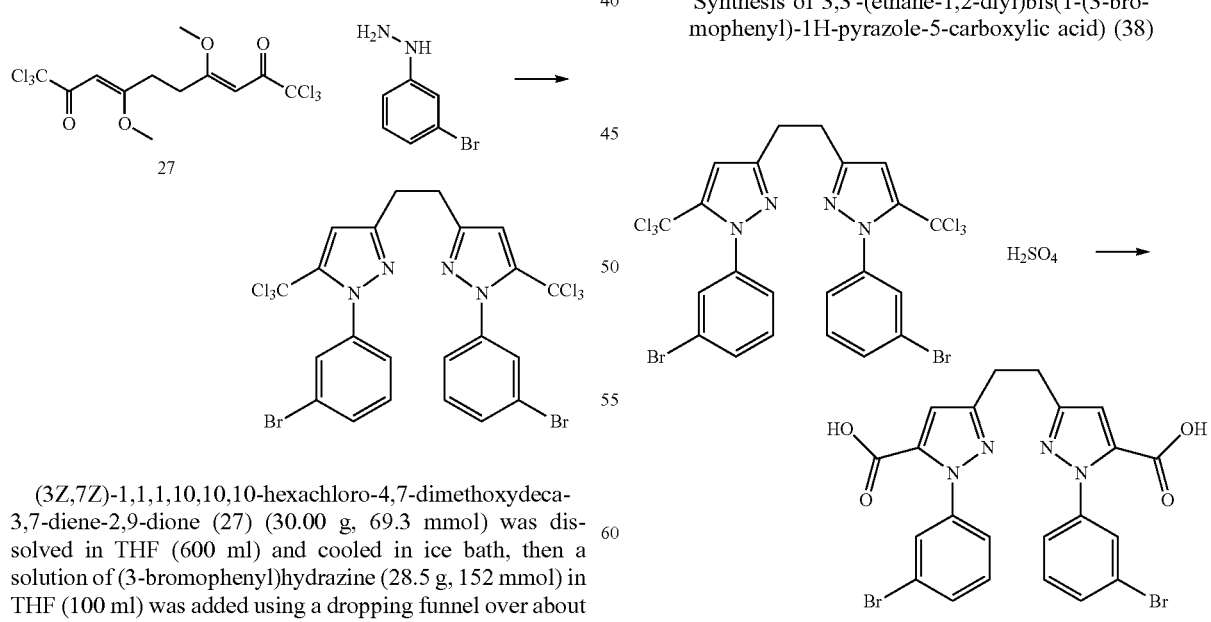

(3Z,7Z)-1,1,1,10,10,10-hexachloro-4,7-dimethoxydeca-3,7-diene-2,9-dione (27) (30.00 g, 69.3 mmol) was dissolved in THF (600 ml) and cooled in ice bath, then a solution of (3-bromophenyl)hydrazine (28.5 g, 152 mmol) in THF (100 ml) was added using a dropping funnel over about 1 hour. The reaction mixture was stirred in an ice bath for 9 hours, then maintained at room temperature (~22° C.) overnight, before being heated to 60° C. for 48 hours to produce a heterogeneous mixture. Removal of solvent and trituration in DCM yielded product 1,2-bis(1-(3-bromophenyl)-5-(trichloromethyl)-1H-pyrazol-3-yl)ethane (37) as a light colored solid, 40.93 g (84%)

Synthesis of 3,3'-(ethane-1,2-diyl)bis(1-(3-bromophenyl)-1H-pyrazole-5-carboxylic acid) (38)

1,2-bis(1-(3-bromophenyl)-5-(trichloromethyl)-1H-pyrazol-3-yl)ethane (37) (40.70 g, 57.6 mmol) was suspended in ~75% sulfuric acid (3:1 dilution of conc. $H_2SO_4$:$H_2O$) (80 ml, 1080 mmol) in a 1 L flask and heated at ~110° C. with stirring, while outgasses passed through a KOH trap. Foaming ensued but subsequently dissipated after approximately 30 minutes. The reaction mixture was stirred two hours more, then cooled to room temperature (~22° C.) and diluted with ice water to ~900 mL and stirred for 15 minutes. The deposited beige powder was filtered, washed with water, and dried to yield 31.10 g of 3,3'-(ethane-1,2-diyl)bis(1-(3-bromophenyl)-1H-pyrazole-5-carboxylic acid) (38) as a pale solid, 96%.

Synthesis of 1,2-bis(1-(3-bromophenyl)-1H-pyrazol-3-yl)ethane (39)

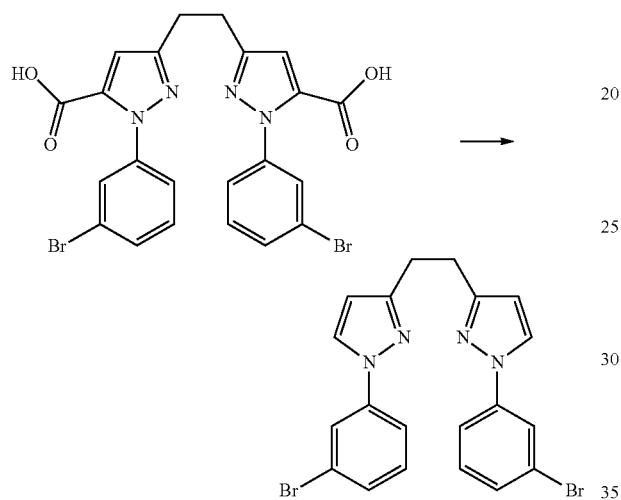

3,3'-(ethane-1,2-diyl)bis(1-(3-bromophenyl)-1H-pyrazole-5-carboxylic acid) (38) (10.08 g, 17.99 mmol) was placed in a flask with a stir bar in a sand bath, then vacuum/backfilled three times with nitrogen. The flask was heated without stirring under nitrogen until the solids began to melt (~225° C. bath temp) and CO₂ gas was evolved. Once the solids were fully melted and degassing had stopped, gentle stirring was started and continued for another 5 minutes. The brown liquid was cooled to room temperature (~22° C.), forming a glass that was purified by column chromatography to yield 1,2-bis(1-(3-bromophenyl)-1H-pyrazol-3-yl)ethane (39) as a pale orange solid, 7.03 g (83%).

Synthesis of N-(3-(3-(2-(1-(3-bromophenyl)-1H-pyrazol-3-yl)ethyl)-1H-pyrazol-1-yl)phenyl)-N-phenylacetamide (40)

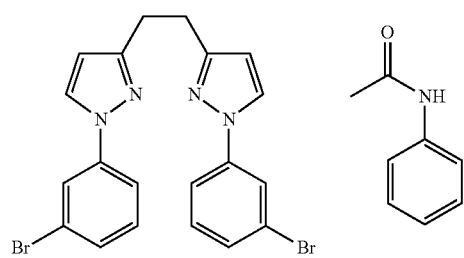

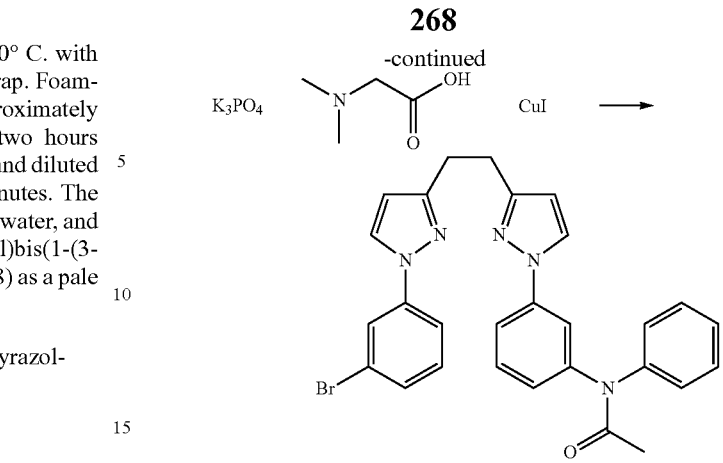

1,2-bis(1-(3-bromophenyl)-1H-pyrazol-3-yl)ethane (39) (6.99 g, 14.80 mmol), N-phenylacetamide (1.00 g, 7.40 mmol), potassium phosphate (3.93 g, 18.50 mmol), N,N-dimethylglycine (0.153 g, 1.480 mmol), and copper(I) iodide (0.282 g, 1.480 mmol) were combined in a schlenk flask that was evacuated/backfilled with nitrogen. DMF was added (15 ml) to the flask via syringe and refluxed overnight (~12 hours). The mixture was poured into water/brine and extracted three times with EtOAc. The organics were then washed with several charges of 5% LiCl (aq) and brine, then dried, and coated on Celite (silica gel). Column chromatography yielded N-(3-(3-(2-(1-(3-bromophenyl)-1H-pyrazol-3-yl)ethyl)-1H-pyrazol-1-yl)phenyl)-N-phenylacetamide 40 as a pale beige foam, 2.10 g (54%).

Synthesis of 3-(3-(2-(1-(3-bromophenyl)-1H-pyrazol-3-yl)ethyl)-1H-pyrazol-1-yl)-N-phenylaniline (41)

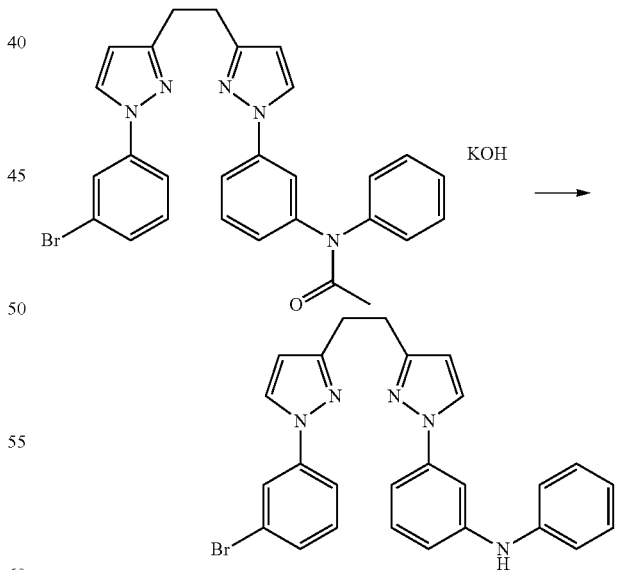

N-(3-(3-(2-(1-(3-bromophenyl)-1H-pyrazol-3-yl)ethyl)-1H-pyrazol-1-yl)phenyl)-N-phenylacetamide (40) (2.05 g, 3.89 mmol) was stirred in a 20 wt % KOH solution in EtOH (80 ml, 3.89 mmol) and refluxed overnight (~12 hours). The mixture was cooled to room temperature (~22° C.), diluted in 500 mL water, and extracted three times with CHCl₃. The organics were washed with water, then brine, before being dried, vacuumed down to yield 3-(3-(2-(1-(3-bromophenyl)-1H-pyrazol-3-yl)ethyl)-1H-pyrazol-1-yl)-N-phenylaniline (41) as a brown/orange, tacky oil, 1.99 g, which was used in the next stage without further purification.

Synthesis of (1²Z,5²Z)-3-phenyl-1¹H,5¹H-3-aza-1,5(1,3)-dipyrazola-2,4(1,3)-dibenzena-cycloheptaphane (42)

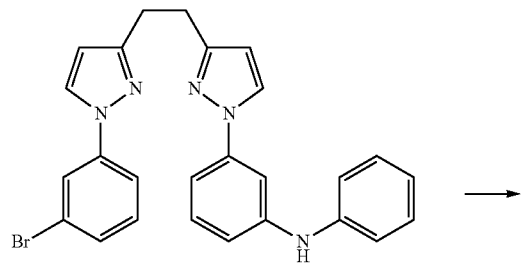

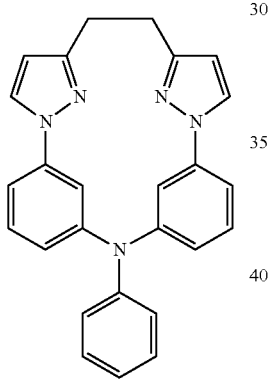

A solution of 3-(3-(2-(1-(3-bromophenyl)-1H-pyrazol-3-yl)ethyl)-1H-pyrazol-1-yl)-N-phenylaniline 41 (683 mg, 1.41 mmol, 1 equiv) in toluene (20 mL) was sparged with nitrogen for 15 minutes. This solution was then added via a syringe pump (1 ml/hr) to a refluxing mixture of tributylphosphonium tetrafluoroborate (46 mg, 0.16 mmol, 0.1 equiv), Pd₂(dba)₃ (73 mg, 0.08 mmol, 0.05 equiv), and sodium t-butoxide (460 mg, 4.8 mmol, 3 equiv) in toluene (400 mL), which had also been initial sparged with nitrogen for 15 minutes. After completing the addition, the resulting mixture was stirred at reflux for thirty minutes, then cooled to room temperature (~22° C.) before 200 mL of water was added. The layers were separated and the organic layer was concentrated under reduced pressure. The residue was purified by column chromatography to yield (1²Z,5²Z)-3-phenyl-1¹H,5¹H-3-aza-1,5(1,3)-dipyrazola-2,4(1,3)-dibenzena-cycloheptaphane (42) as an off-white solid (222 mg, 39% yield).

Synthesis of PtM1

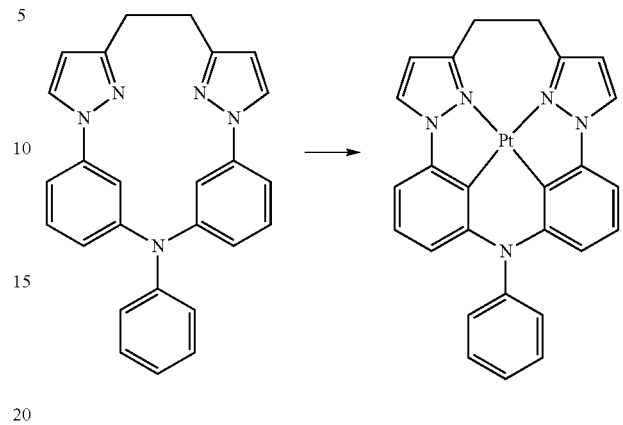

A mixture of (1²Z,5²Z)-3-phenyl-1¹H,5¹H-3-aza-1,5(1,3)-dipyrazola-2,4(1,3)-dibenzena-cycloheptaphane (42) (190 mg, 0.47 mmol, 1 equiv), potassium tetrachloroplatinate (490 mg, 1.18 mmol, 2.5 equiv), and tetrabutylammonium chloride (328 mg, 1.18 mmol, 2.5 equiv) in acetic acid (10 mL) was sparged with nitrogen for 15 minutes. The slurry was stirred at 110° C. for 3 days. The mixture was cooled and the solid was filtered. The solid was washed with deionized water (5 mL) and MTBE (5 ml). The crude product was purified by column chromatography to yield PtM1 as a yellow solid (74 mg, 26% yield).

Synthesis of Comparative Example 15

The following is a general scheme for synthesizing Comparative Example 15, and is followed by more detailed explanation of the scheme.

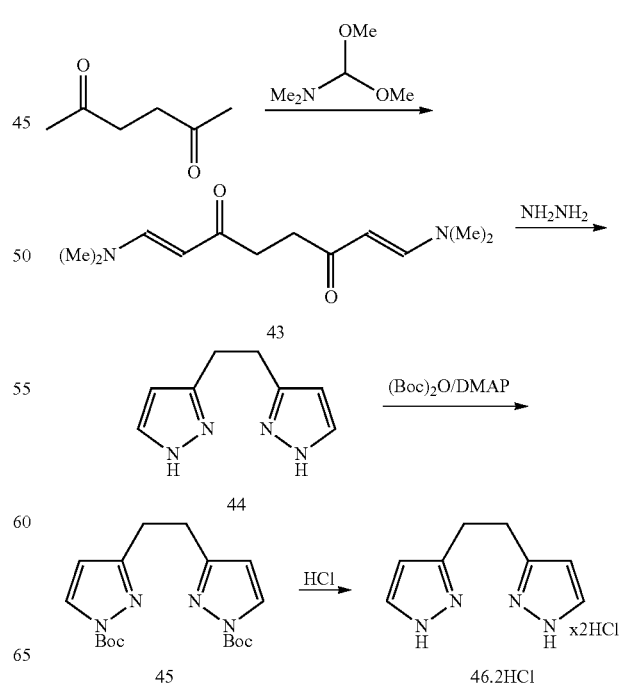

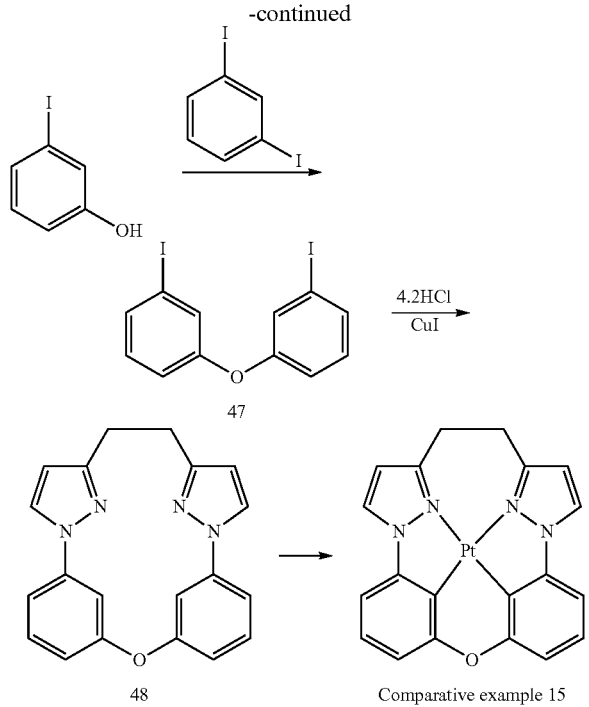

48          Comparative example 15

Synthesis of (1E,7E)-1,8-bis(Dimethylamino)octa-1,7-diene-3,6-dione (43)

A mixture of 2,5-hexanedione (26 g, 226 mmol, 1 equiv) and N,N-dimethylformamide dimethyl acetal (100 mL, 752 mmol, 3.3 equiv) was refluxed overnight (~12 hours). The mixture was then concentrated under reduced pressure. The residue was purified by column chromatography to give partially purified (1E,7E)-1,8-bis(Dimethylamino)octa-1,7-diene-3,6-dione (43) (20 g) as a black oil.

Synthesis of 1,2-Di(1H-pyrazol-3-yl)ethane (44)

A mixture of crude (1E,7E)-1,8-bis(Dimethylamino)octa-1,7-diene-3,6-dione (43) (5 g, 22.4 mmol, 1 equiv) and hydrazine monohydrate (4.8 mL, 98.6 mmol, 4.4 equiv) in ethanol (200 mL) was refluxed overnight (~12 hours). The mixture was concentrated under reduced pressure to give crude 1,2-di(1H-pyrazol-3-yl)ethane (44) (5.4 g) as a black oil, which was used without further purification.

Synthesis of di-tert-butyl 3,3'-(ethane-1,2-diyl)bis(1H-pyrazole-1-carboxylate) (45)

A mixture of 1,2-di(1H-pyrazol-3-yl)ethane (44) (5.4 g, ~33 mmol, 1 equiv), di-tert-butyl dicarbonate (21.8 g, 99.9 mmol, 3 equiv), and 4-dimethylaminopyridine (40 mg, 0.33 mmol, 0.01 equiv) in dichloromethane (100 mL) was stirred at room temperature (~22° C.) overnight (~12 hours). The mixture was concentrated under reduced pressure. The residue was purified by column chromatography to give di-tert-butyl 3,3'-(ethane-1,2-diyl)bis(1H-pyrazole-1-carboxylate) (45) (7 g, 59% yield) as a yellow oil.

Synthesis of 1,2-Di(1H-pyrazol-3-yl)ethane dihydrochloride (46.2HCl)

4M HCl in dioxane (88 mmol, 4.55 equiv) was added to a solution of di-tert-butyl 3,3'-(ethane-1,2-diyl)bis(1H-pyrazole-1-carboxylate) (45) (7 g, 19.3 mmol, 1 equiv) in 1,4-dioxane (35 mL). The slurry was stirred at room temperature (~22° C.) for 2 hours. The solvent was decanted and the residue was washed sequentially with heptanes (25 mL) and MTBE (25 mL). The solid was dried under vacuum at 40° C. for 4 hours to yield 1,2-di(1H-pyrazol-3-yl)ethane dihydrochloride (46.2HCl) (5 g) as a tan solid.

Synthesis of 3,3'-Oxybis(iodobenzene) (47)

A mixture of 3-iodophenol (10 g, 45.4 mmol, 1 equiv), 1,3-diiodobenzene (30 g, 90.8 mmol, 2 equiv), copper(I) iodide (1.7 g, 9.1 mmol, 0.2 equiv), potassium phosphate (19.2 g, 90.8 mmol, 2 equiv), and picolinic acid (2.2 g, 18.2 mmol, 0.4 equiv) in methyl sulfoxide (500 mL) was sparged with nitrogen for 15 minutes. The slurry was stirred at 90° C. for 5 hours. The resulting mixture was cooled and poured into ice water (400 mL) and MTBE (100 mL). The layers were separated and the aqueous layer was extracted twice with MTBE (300 mL). The combined organic layers were filtered through a pad of Celite (silica gel) and concentrated under reduced pressure. The residue was purified by column chromatography to give 3,3'-Oxybis(iodobenzene) (47) as a white solid (9.7 g, 51% yield).

Synthesis of (12Z,52Z)-11H,51H-3-Oxa-1,5(1,3)-dipyrazola-2,4(1,3)-dibenzenacycloheptaphane (48)

A mixture of 47 (4.68 g, 11.1 mmol, 1 equiv), 46.2HCl (3.1 g, ~11.1 mmol, 1 equiv), copper(II) acetate monohydrate (112 mg, 0.56 mmol, 0.05 equiv), and cesium carbonate (21.7 g, 66.6 mmol, 6 equiv) in DMF (4 L) was sparged with nitrogen for 20 minutes. The slurry was stirred at 110° C. for 8 days. Copper (II) acetate monohydrate (112 mg, 0.56 mmol, 0.05 equiv) was added and the mixture was stirred at 130° C. for 3 additional days. The solvent was removed under reduced pressure and the residue was diluted with water (300 mL) and ethyl acetate (300 mL). The layers were separated and the aqueous layer was extracted twice with ethyl acetate (300 mL). The combined organic layers were washed with saturated brine (200 mL) and concentrated under reduced pressure. The residue was purified by column chromatography to yield (12Z,52Z)-11H,51H-3-Oxa-1,5(1,3)-dipyrazola-2,4(1,3)-dibenzenacycloheptaphane (48) as an off-white solid (128 mg, 4% yield).

Synthesis of Comparative Example 15

A mixture of (12Z,52Z)-11H,51H-3-Oxa-1,5(1,3)-dipyrazola-2,4(1,3)-dibenzenacycloheptaphane (48) (125 mg, 0.38 mmol, 1 equiv), potassium tetrachloroplatinate (261 mg, 0.63 mmol, 1.6 equiv) in acetic acid was sparged with nitrogen for 20 minutes. The slurry was stirred at 110° C. for 2 days. The mixture was cooled and the solid was filtered. The solid was washed with water and MTBE. The solid and the filter paper were stirred in DMSO (6.5 mL) and filtered through syringe filter to give a solution of crude 7. The DMSO solution was purified by a preparative HPLC to give Comparative Example 15 as a yellow solid (16 mg, 8% yield).

Compound Data

Density functional theory calculations were performed on PtM1 and Comparative Example 15 in order to compare relative energy levels.

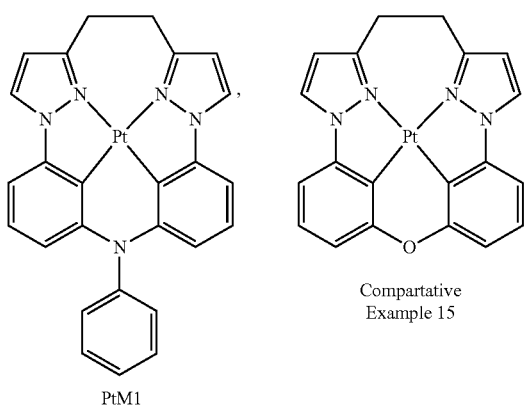

Comparative Example 15

PtM1

Calculations were performed with the Gaussian 09 package using the B3LYP functional and CEP-31g basis set with THF solvent polarization. Calculated (calc) and experimental (exp) values for HOMO, LUMO and T1 values are shown in Table 2. The experimental triplet values were measured as the highest energy peak wavelength in 2-methyl THF solvent at 77K. Solution cyclic voltammetry (CV) and differential pulsed voltammetry (DPV) were performed using a CH Instruments model 6201B potentiostat using anhydrous dimethylformamide solvent and tetrabutylammonium hexafluorophosphate as the supporting electrolyte. A glassy carbon, platinum and silver wire were used as the working, counter and reference electrodes, respectively. Electrochemical potentials were referenced to an internal ferrocene-ferrocenium redox couple (Fc/Fc$^+$) by measuring the peak potential differences from differential pulsed voltammetry. HOMO and LUMO energies were determined by referencing the cationic and anionic redox potentials to ferrocene (4.8 eV vs. vacuum).

TABLE 2

| | HOMO calc (eV) | LUMO calc (eV) | T1 calc (nm) | HOMO exp (eV) | LUMO exp (eV) | T1 exp (nm) |
|---|---|---|---|---|---|---|
| PtM1 | −4.92 | −1.59 | 517 | −4.99 | −1.94 | 487 |
| Comparative Example 15 | −5.40 | −1.69 | 465 | −5.32 | −2.02 | 445 |

Table 2 shows that the HOMO energy of PtM1 with an aryl amine bottom tether is both predicted by calculation and measured experimentally to have a lower oxidation potential than Comparative Example 15. In solution electrochemistry, PtM1 has a lower oxidation potential by 0.33 V than Comparative Example 15. In addition, the fact Compound PtM1 exhibits reversible oxidation in cyclic voltammetry compared to irreversible oxidation for Comparative Example 15, may indicate Compound PtM1 exhibits better oxidation stability. These are desirable features in a device due to the effect of hole trapping, both of which may lead to improved efficiency and stability, and also reduces the need for charge blocking layers. For these reasons, macrocyclic compounds containing a readily oxidized arylamine that bridges the phenyl rings may be preferable over oxygen bridged analogues.

Device and PL Data

The structures for Compound Ir872 and Comparative Example 13 are shown below:

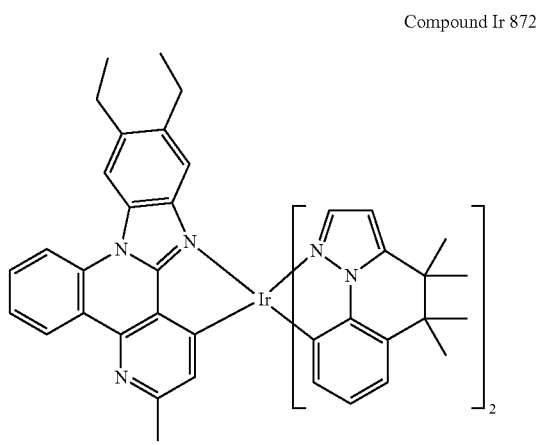

Compound Ir 872

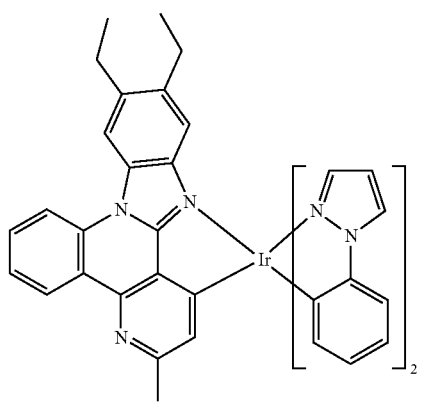

Comparative Example 13

Figure 4:
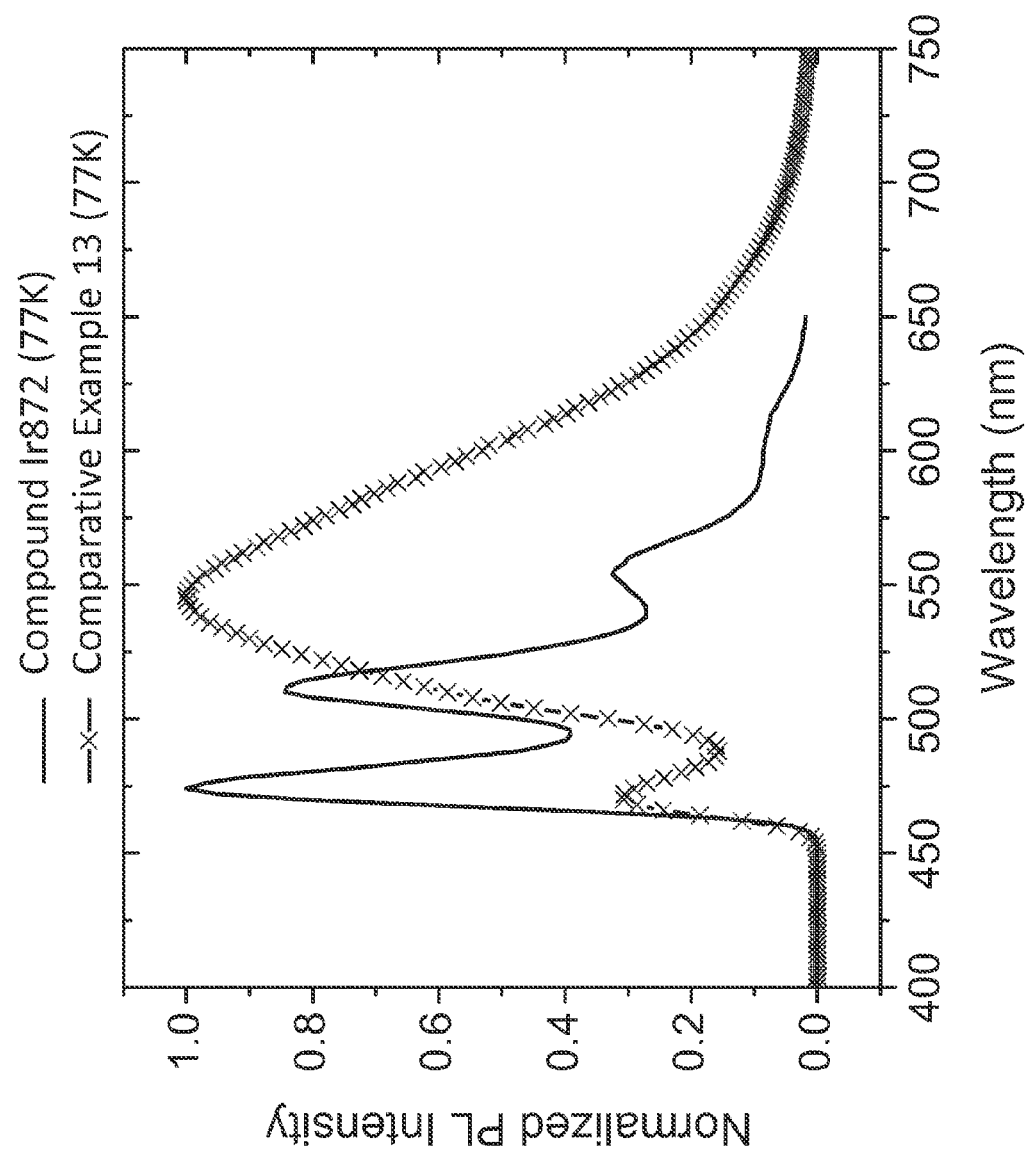
FIG. 4 is a chart showing normalized PL intensity versus wavelength for Compound Ir872 and Comparative Example 13 taken at 77K.
Figure 5:
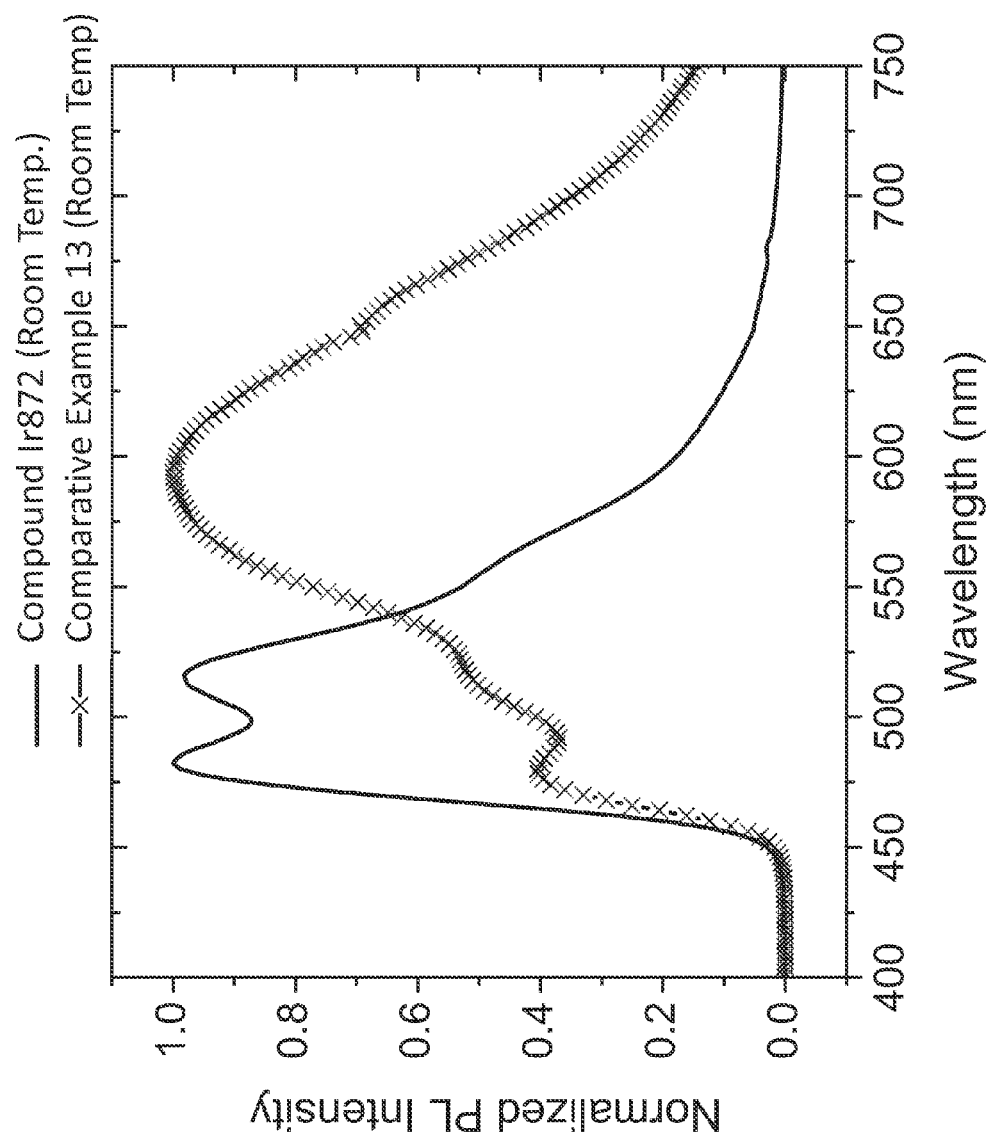
FIG. 5 is a chart showing normalized PL intensity versus wavelength for Compound Ir872 and Comparative Example 13 taken at room temperature (~22° C.).

The emission spectra of Compound Ir872 and Comparative Compound 13 in 2-methyl THF solvent at 77K and room temperature are shown in FIGS. 4 and 5, respectively. It is found that the compounds described herein are markedly blue shifted from the comparative example with vibronic peak emission starting around 470 nm. The comparative example shows a high energy peak in the same region and a broad Gaussian peak that is redshifted. Though not wishing to be bound by theory, the difference between the two compounds is thought to be caused by the rigidity of the strapped phenylpyrazole ligand. Though not wishing to be bound by theory, it is also believed, in the case of the non-strapped comparative example, that a vibration or distortion associated with a very weak Ir—N bond leads to a broad intraligand charge transfer transition (ILCT). When this metal ligand bond is strengthened by adding a strap, the emission comes from a characteristic MLCT transition on the aza-phenanthridine benzimidazole ligand (APBI), similar to what is observed for tris compounds with this ligand.

Additional heteroleptic examples, Complex Ir890, Complex Ir891, Comparative Example 14 and Comparative Example 16, with green emitting phenylpyridine ligands are also compared.

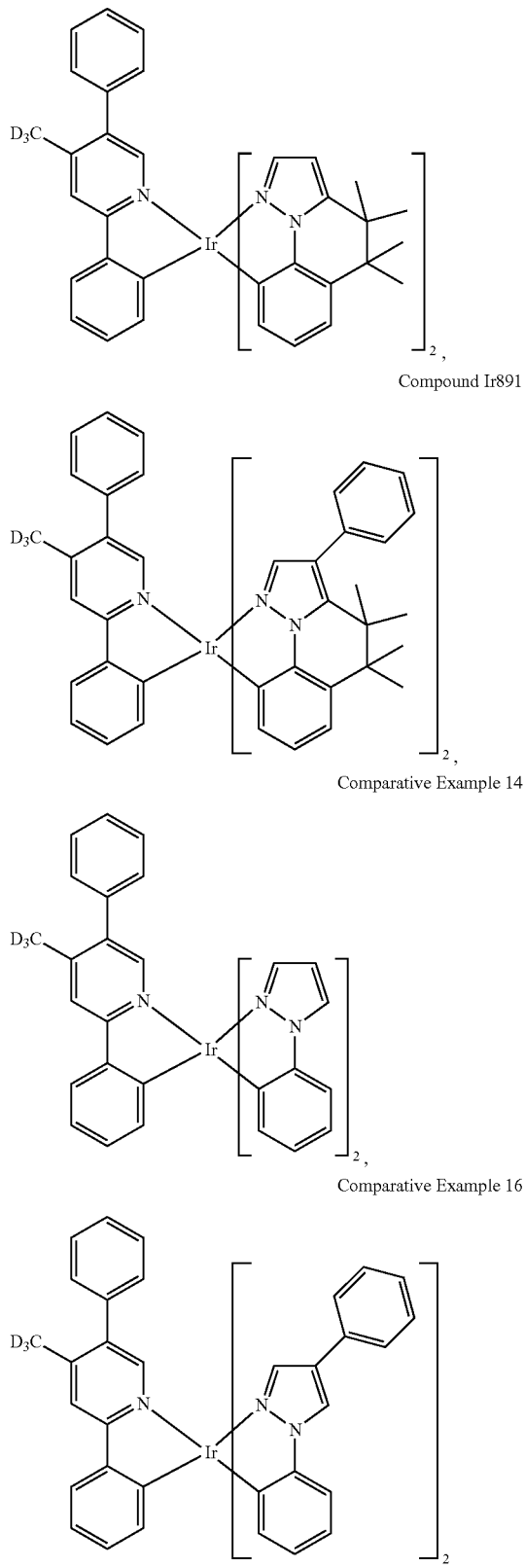

Compound Ir890

Compound Ir891

Comparative Example 14

Comparative Example 16

Figure 6:
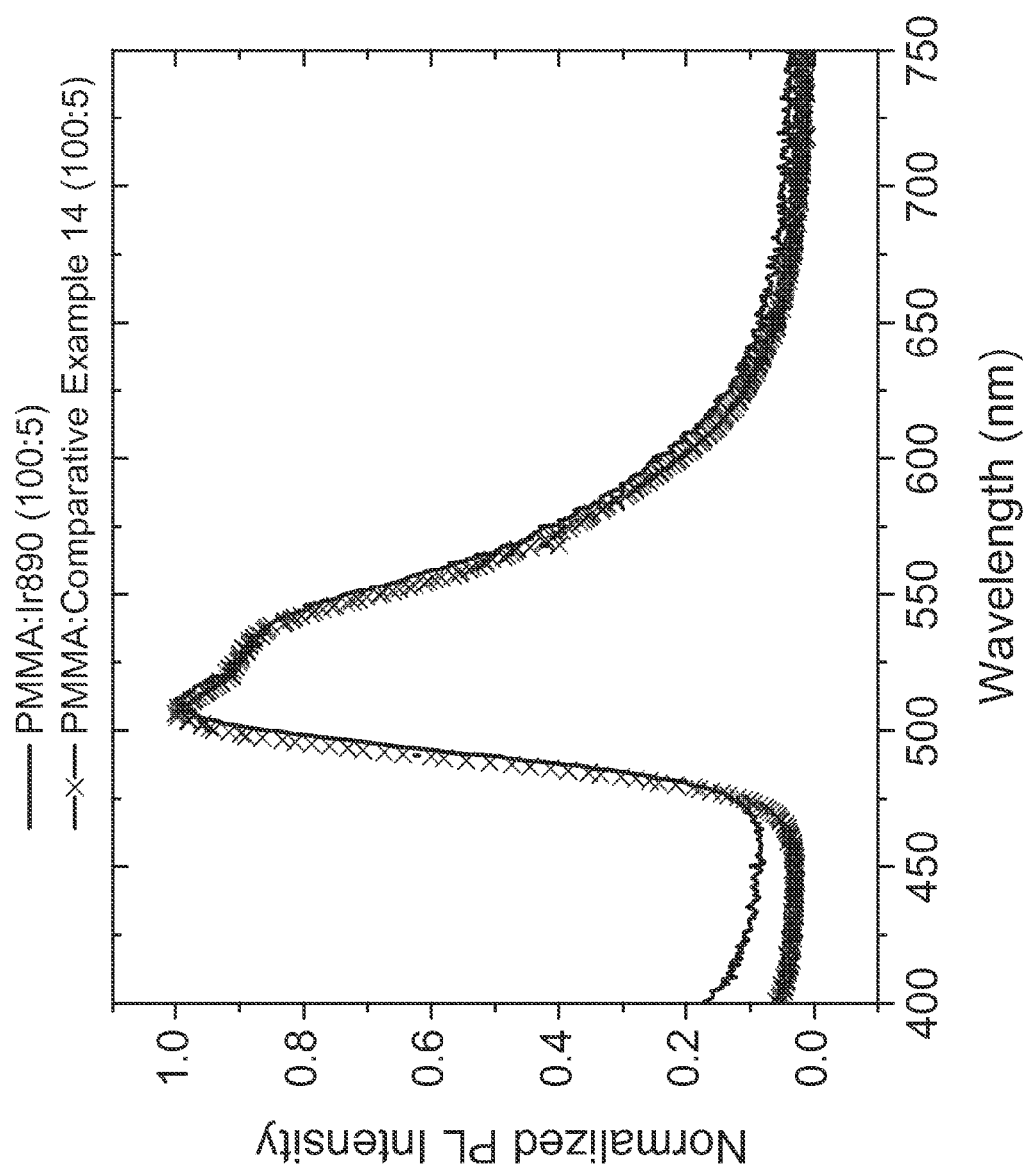
FIG. 6 is a chart showing normalized PL intensity versus wavelength for Compound Ir890 and Comparative Example 14 taken in PMMA.

(PMMA) drop cast matrix at 5 wt % is shown in FIG. 6. Contrary to what was observed for Compound Ir872 and Comparative Example 13, the emission is very similar. Both Compound Ir890 and Comparative Example 14 were measured to have a photoluminescent quantum yield (PLQY) of 99% in PMMA matrix.

Device Examples

OLEDs were fabricated with both Compound Ir890, Compound Ir891, Comparative Example 14, and Comparative Example 16

Device 1=LG101 (100 Å)/HTL1 (450 Å)/Host 1: Comparative Example 16 (400 Å, 10%)/BL1 (50 Å)/AlQ3 (350 Å)/LiF/Al Device 2=LG101 (100 Å)/HTL1 (450 Å)/Host 1: Comparative Example 14 (300 Å, 10%)/BL1 (50 Å)/AlQ3 (450 Å)/LiF/Al Device 3=LG101 (100 Å)/HTL1 (450 Å)/Host 1: Compound Ir890 (400 Å, 10%)/BL1 (50 Å)/AlQ3 (350 Å)/LiF/Al Device 4=LG101 (100 Å)/HTL1 (450 Å)/Host 1: Compound Ir891 (400 Å, 10%)/BL1 (50 Å)/AlQ3 (350 Å)/LiF/Al

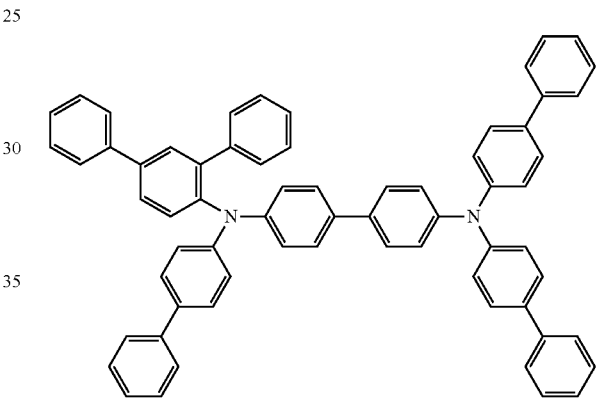

HTL1

Host 1

BL1

The emission spectra of Compound Ir890 and Comparative Example 14 doped in a polymethylmethacrylate As shown in Table 3, below, devices prepared using emissive compounds with a side strap to the ancillary phenylpyrazole ligand exhibit improved device lifetime between 5 to 27 times over Comparative Example 15. These results suggest that the side-strapping group can improve device stability. There are no obvious negative effects on other device performance properties, with Compound Ir890 and Compound Ir891 showing higher LE and EQE than either comparative example.

TABLE 3

| | 1931 CIE | | At 10 mA/cm2 | | | | $LT_{80\%}$ @ 40 mA/cm² |
|---|---|---|---|---|---|---|---|
| | x | y | Voltage | LE [norm] | EQE [norm] | PE [norm] | [norm] |
| Device 1 | 0.294 | 0.629 | 1.0 | 1.0 | 1.0 | 1.0 | 1.0 |
| Device 2 | 0.293 | 0.628 | 0.9 | 0.8 | 0.8 | 0.9 | 1.7 |
| Device 3 | 0.317 | 0.63 | 1.0 | 1.3 | 1.2 | 1.2 | 5.4 |
| Device 4 | 0.312 | 0.629 | 1.1 | 1.1 | 1.0 | 1.0 | 27.4 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a structure according to formula $M(L_A)_x(L_B)_y$:

wherein ligand $L_A$ is

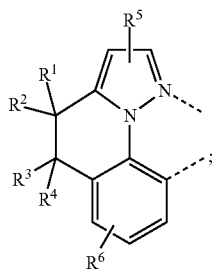

wherein ligand $L_B$ is a mono anionic bidentate ligand;
wherein each $L_A$ and $L_B$ can be the same or different;
wherein M is a metal having an atomic number greater than 40;
wherein x is 1, 2, or 3;
wherein y is 0, 1, or 2;
wherein x+y is the oxidation state of the metal M;
wherein $R^5$ represents mono, or di substitution, or no substitution;
wherein $R^6$ represents mono, di, or tri substitution, or no substitution;
wherein each $R^1$, $R^2$, $R^3$, $R^4$, $R^5$, and $R^6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein each one of $R^1$, $R^2$, $R^3$, $R^4$, $R^5$ and $R^6$ group is optionally joined with any one of adjacent substituents to form a fused or unfused ring; and
wherein $L_A$ and $L_B$ are optionally joined to form a ligand that is at least tetradentate.

2. The compound of claim 1, wherein M is selected from the group consisting of Ir, Rh, Re, Ru, Os, Pt, Au, and Cu.

3. The compound of claim 1, wherein M is Pt.

4. The compound of claim 1, wherein at least one of $R^1$, $R^2$, $R^3$, and $R^4$ is not hydrogen or deuterium.

5. The compound of claim 1, wherein $R^1$, $R^2$, $R^3$, and $R^4$ are each independently selected from the group consisting of hydrogen, deuterium, alkyl, cycloalkyl, and combinations thereof.

6. The compound of claim 1, wherein the compound has the formula:

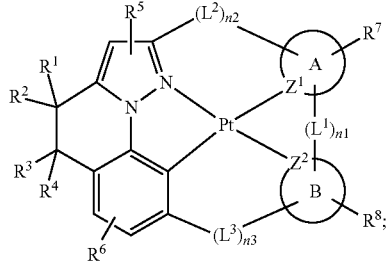

wherein ring A and ring B are each independently a 5- or 6-membered carbocyclic or heterocyclic ring;
wherein $L^1$, $L^2$ and $L^3$ are independently selected from the group consisting of a direct bond, alkyl, cycloalkyl, BR, NR, PR, O, S, Se, C=O, S=O, $SO_2$, SiRR', and GeRR';
wherein $Z^1$ and $Z^2$ are each independently a nitrogen atom or a carbon atom;
wherein $R^7$ and $R^8$ each represent mono, di, tri, or tetra substitution, or no substitution;
wherein R, R', $R^7$ and $R^8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof wherein two adjacent substituents R, R', $R^7$ and $R^8$ are optionally joined to form a fused or unfused ring;
wherein n1 is 0 or 1;
wherein n2 is 0 or 1;
wherein n3 is 0 or 1; and
wherein n1+n2+n3 is at least 2.

7. The compound of claim 6, wherein n2 is 1 and n3 is 0.
8. The compound of claim 6, wherein n2 is 0 and n3 is 1.
9. The compound of claim 6, wherein n2 is 1 and n3 is 1.
10. The compound of claim 6, wherein the compound has the formula:

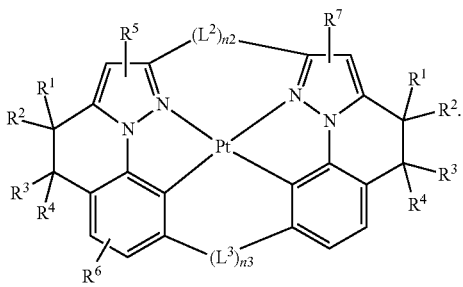

11. The compound of claim 6, wherein rings A and B are selected from the group consisting of benzene, pyridine, pyrazole, benzopyrazole, naphthalene, isoquinoline, aza-isoquinoline, carbazole, and dibenzofuran, each of which may be, optionally, further substituted.

12. The compound of claim 1, wherein the compound is selected from the group consisting of:
Compound Pt1 through Pt12, each represented by the formula

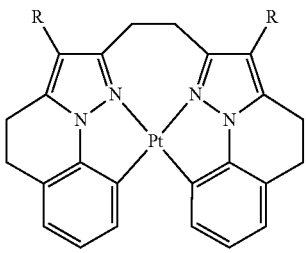

wherein in Compound Pt1: R=H,
in Compound Pt2: R=Me,
in Compound Pt3: R=Et,
in Compound Pt4: R=$^i$Pr,
in Compound Pt5: R=neopentyl,
in Compound Pt6: R=$^i$Bu,
in Compound Pt7: R=$^t$Bu,
in Compound Pt8: R=Ph,
in Compound Pt9: R=4-biphenyl,
in Compound Pt10: R=2,6-($^i$Pr)$_2$Ph,
in Compound Pt11: R=2,6-($^i$Pr)$_2$-4-biphenyl,
in Compound Pt12: R=2,4-($^i$Pr)$_2$-3-dibenzofuran,
Compound Pt13 through Pt21, each represented by the formula

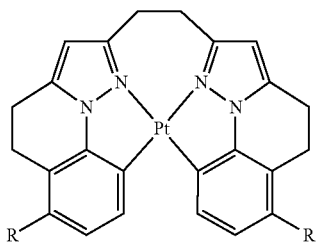

wherein in Compound Pt13: R=Me,
in Compound Pt14: R=Et,
in Compound Pt15: R=$^i$Pr,
in Compound Pt16: R=neopentyl,
in Compound Pt17: R=$^i$Bu,
in Compound Pt18: R=$^t$Bu,
in Compound Pt19: R=Ph,
in Compound Pt20: R=2,6-(Me)$_2$Ph,
in Compound Pt21: R=2,6-($^i$Pr)$_2$Ph,
Compound Pt22 through Pt30, each represented by the formula

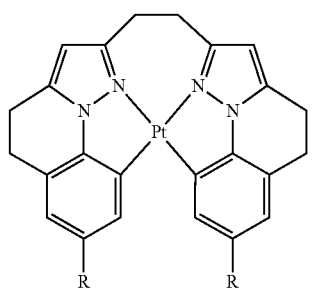

wherein in Compound Pt22: R=Me,
in Compound Pt23: R=Et,
in Compound Pt24: R=$^i$Pr,
in Compound Pt25: R=neopentyl,
in Compound Pt26: R=$^i$Bu,
in Compound Pt27: R=$^t$Bu,
in Compound Pt28: R=Ph,
in Compound Pt29: R=2,6-(Me)$_2$Ph,
in Compound Pt30: R=2,6-($^i$Pr)$_2$Ph,
Compound Pt31 through Pt42, each represented by the formula

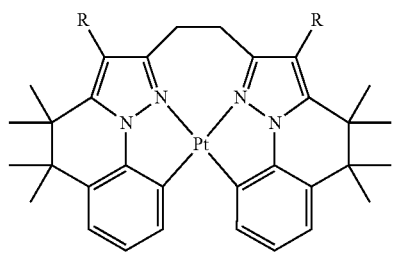

wherein in Compound Pt31: R=H,
in Compound Pt32: R=Me,
in Compound Pt33: R=Et,
in Compound Pt34: R=$^i$Pr,
in Compound Pt35: R=neopentyl,
in Compound Pt36: R=$^i$Bu,
in Compound Pt37: R=$^t$Bu,
in Compound Pt38: R=Ph,
in Compound Pt39: R=4-biphenyl,
in Compound Pt40: R=2,6-($^i$Pr)$_2$Ph,
in Compound Pt41: R=2,6-($^i$Pr)$_2$-4-biphenyl,
in Compound Pt42: R=2,4-($^i$Pr)$_2$-3-dibenzofuran,
Compound Pt43 through Pt45, each represented by the formula

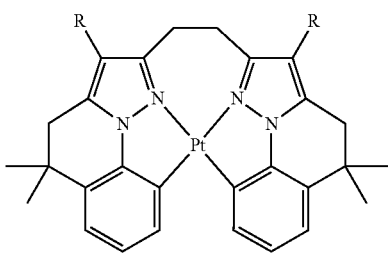

wherein in Compound Pt43: R=H,
in Compound Pt44: R=Me,
in Compound Pt45: R=Et,
in Compound Pt46: R=$^i$Pr,
in Compound Pt47: R=neopentyl,
in Compound Pt48: R=$^i$Bu,
in Compound Pt49: R=$^t$Bu,
in Compound Pt50: R=Ph,
in Compound Pt51: R=4-biphenyl,
in Compound Pt52: R=2,6-($^i$Pr)$_2$Ph,
in Compound Pt53: R=2,6-($^i$Pr)$_2$-4-biphenyl,
in Compound Pt54: R=2,4-($^i$Pr)$_2$-3-dibenzofuran,
Compound Pt55 through Pt66, each represented by the formula

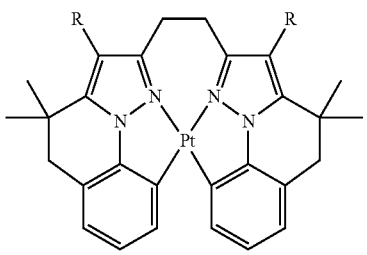

wherein in Compound Pt55: R=H,
in Compound Pt56: R=Me,
in Compound Pt57: R=Et,
in Compound Pt58: R=$^i$Pr,
in Compound Pt59: R=neopentyl,
in Compound Pt60: R=$^i$Bu,
in Compound Pt61: R=$^t$Bu,
in Compound Pt62: R=Ph,
in Compound Pt63: R=4-biphenyl,
in Compound Pt64: R=2,6-($^i$Pr)$_2$Ph,
in Compound Pt65: R=2,6-($^i$Pr)$_2$-4-biphenyl,
in Compound Pt66: R=2,4-($^i$Pr)$_2$-3-dibenzofuran,
Compound Pt67 through Pt75, each represented by the formula

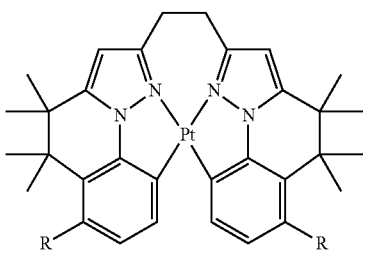

wherein in Compound Pt67: R=Me,
in Compound Pt68: R=Et,
in Compound Pt69: R=$^i$Pr,
in Compound Pt70: R=neopentyl,
in Compound Pt71: R=$^i$Bu,
in Compound Pt72: R=$^t$Bu,
in Compound Pt73: R=Ph,
in Compound Pt74: R=2,6-(Me)$_2$Ph,
in Compound Pt75: R=2,6-($^i$Pr)$_2$Ph,
Compound Pt76 through Pt84, each represented by the formula

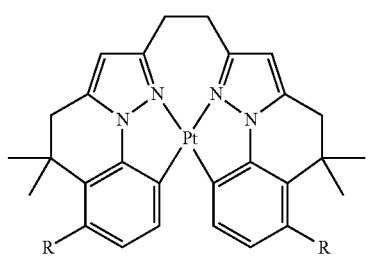

wherein in Compound Pt76: R=Me,
in Compound Pt77: R=Et,
in Compound Pt78: R=$^i$Pr,
in Compound Pt79: R=neopentyl,
in Compound Pt80: R=$^i$Bu,
in Compound Pt81: R=$^t$Bu,
in Compound Pt82: R=Ph,
in Compound Pt83: R=2,6-(Me)$_2$Ph,
in Compound Pt84: R=2,6-($^i$Pr)$_2$Ph,
Compound Pt85 through Pt93, each represented by the formula

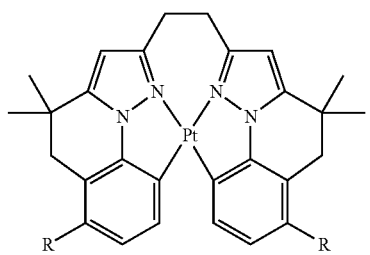

wherein in Compound Pt85: R=Me,
in Compound Pt86: R=Et,
in Compound Pt87: R=$^i$Pr,
in Compound Pt88: R=neopentyl,
in Compound Pt89: R=$^i$Bu,
in Compound Pt90: R=$^t$Bu,
in Compound Pt91: R=Ph,
in Compound Pt92: R=2,6-(Me)$_2$Ph,
in Compound Pt93: R=2,6-($^i$Pr)$_2$Ph,
Compound Pt94 through Pt102, each represented by the formula

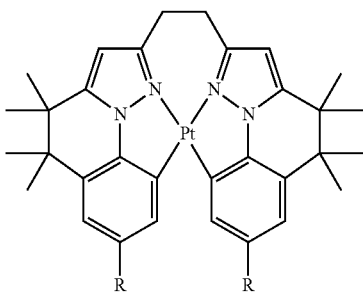

wherein in Compound Pt94: R=Me,
in Compound Pt95: R=Et,
in Compound Pt96: R=$^i$Pr,
in Compound Pt97: R=neopentyl,
in Compound Pt98: R=$^i$Bu,
in Compound Pt99: R=$^t$Bu,
in Compound Pt100: R=Ph,
in Compound Pt101: R=2,6-(Me)$_2$Ph,
in Compound Pt102: R=2,6-($^i$Pr)$_2$Ph,
Compound Pt103 through Pt111, each represented by the formula

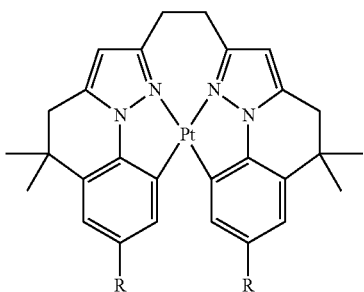

wherein in Compound Pt103: R=Me,
in Compound Pt104: R=Et,
in Compound Pt105: R=$^i$Pr,
in Compound Pt106: R=neopentyl,
in Compound Pt107: R=$^i$Bu,
in Compound Pt108: R=$^t$Bu,
in Compound Pt109: R=Ph,
in Compound Pt110: R=2,6-(Me)$_2$Ph,
in Compound Pt111: R=2,6-($^i$Pr)$_2$Ph,
Compound Pt112 through Pt120, each represented by the formula

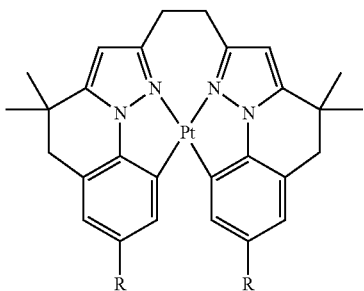

wherein in Compound Pt112: R=Me,
in Compound Pt113: R=Et,
in Compound Pt114: R=$^i$Pr, in Compound Pt115: R=neopentyl,
in Compound Pt116: R=$^i$Bu,
in Compound Pt117: R=$^t$Bu,
in Compound Pt118: R=Ph,
in Compound Pt119: R=2,6-(Me)$_2$Ph,
in Compound Pt120: R=2,6-($^i$Pr)$_2$Ph,
Compound Pt121 through Pt132, each represented by the formula

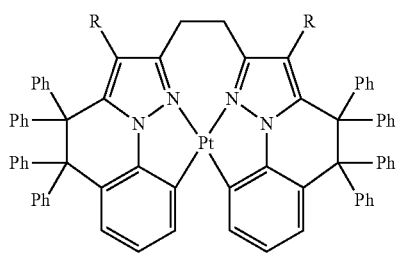

wherein in Compound Pt121: R=H,
in Compound Pt122: R=Me,
in Compound Pt123: R=Et,
in Compound Pt124: R=$^i$Pr,
in Compound Pt125: R=neopentyl,
in Compound Pt126: R=$^i$Bu,
in Compound Pt127: R=$^t$Bu,
in Compound Pt128: R=Ph,
in Compound Pt129: R=4-biphenyl,
in Compound Pt130: R=2,6-($^i$Pr)$_2$Ph,
in Compound Pt131: R=2,6-($^i$Pr)$_2$-4-biphenyl,
in Compound Pt132: R=2,4-($^i$Pr)$_2$-3-dibenzofuran,
Compound Pt133 through Pt144, each represented by the formula

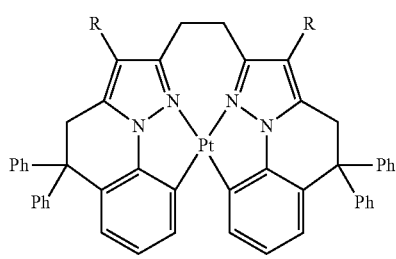

wherein in Compound Pt133: R=H,
in Compound Pt134: R=Me,
in Compound Pt135: R=Et,
in Compound Pt136: R=$^i$Pr,
in Compound Pt137: R=neopentyl,
in Compound Pt138: R=$^i$Bu,
in Compound Pt139: R=$^t$Bu,
in Compound Pt140: R=Ph,
in Compound Pt141: R=4-biphenyl,
in Compound Pt142: R=2,6-($^i$Pr)$_2$Ph,
in Compound Pt143: R=2,6-($^i$Pr)$_2$-4-biphenyl,
in Compound Pt144: R=2,4-($^i$Pr)$_2$-3-dibenzofuran,
Compound Pt145 through Pt156, each represented by the formula

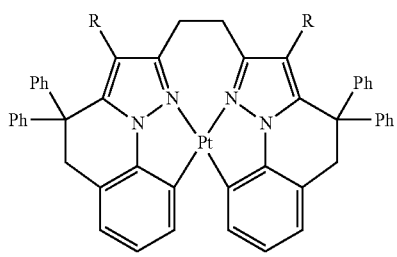

wherein in Compound Pt145: R=H,
in Compound Pt146: R=Me,
in Compound Pt147: R=Et,
in Compound Pt148: R=$^i$Pr,
in Compound Pt149: R=neopentyl,
in Compound Pt150: R=$^i$Bu,
in Compound Pt151: R=$^t$Bu,
in Compound Pt152: R=Ph,
in Compound Pt153: R=4-biphenyl,
in Compound Pt154: R=2,6-($^i$Pr)$_2$Ph,
in Compound Pt155: R=2,6-($^i$Pr)$_2$-4-biphenyl,
in Compound Pt156: R=2,4-($^i$Pr)$_2$-3-dibenzofuran,
Compound Pt157 through Pt165, each represented by the formula

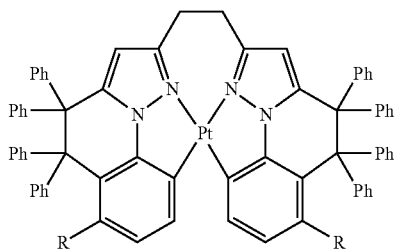

wherein in Compound Pt157: R=Me,
in Compound Pt158: R=Et,
in Compound Pt159: R=$^i$Pr,
in Compound Pt160: R=neopentyl,
in Compound Pt161: R=$^i$Bu,
in Compound Pt162: R=$^t$Bu,
in Compound Pt163: R=Ph,
in Compound Pt164: R=2,6-(Me)$_2$Ph,
in Compound Pt165: R=2,6-($^i$Pr)$_2$Ph,
Compound Pt166 through Pt174, each represented by the formula

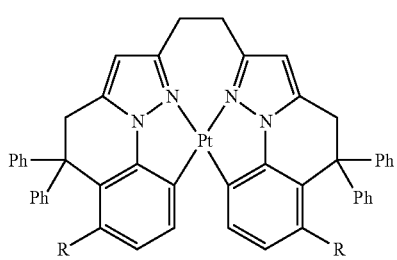

wherein in Compound Pt166: R=Me,
in Compound Pt167: R=Et,
in Compound Pt168: R=$^i$Pr,
in Compound Pt169: R=neopentyl,
in Compound Pt170: R=$^i$Bu, in Compound Pt171: R=$^t$Bu,
in Compound Pt172: R=Ph,
in Compound Pt173: R=2,6-(Me)$_2$Ph,
in Compound Pt174: R=2,6-($^i$Pr)$_2$Ph,
Compound Pt175 through Pt183, each represented by the formula

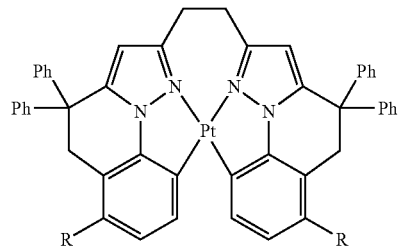

wherein in Compound Pt175: R=Me
in Compound Pt176: R=Et
in Compound Pt177: R=$^i$Pr
in Compound Pt178: R=neopentyl
in Compound Pt179: R=$^i$Bu
in Compound Pt180: R=$^t$Bu
in Compound Pt181: R=Ph
in Compound Pt182: R=2,6-(Me)$_2$Ph
in Compound Pt183: R=2,6-($^i$Pr)$_2$Ph,
Compound Pt184 through Pt192, each represented by the formula

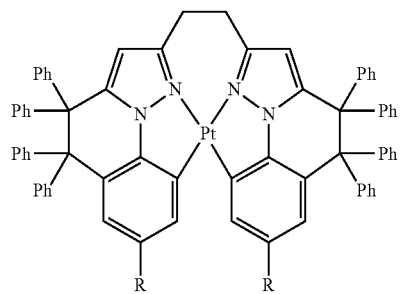

wherein in Compound Pt184: R=Me,
in Compound Pt185: R=Et,
in Compound Pt186: R=$^i$Pr,
in Compound Pt187: R=neopentyl,
in Compound Pt188: R=$^i$Bu,
in Compound Pt189: R=$^t$Bu,
in Compound Pt190: R=Ph,
in Compound Pt191: R=2,6-(Me)$_2$Ph,
in Compound Pt192: R=2,6-($^i$Pr)$_2$Ph,
Compound Pt193 through Pt201, each represented by the formula

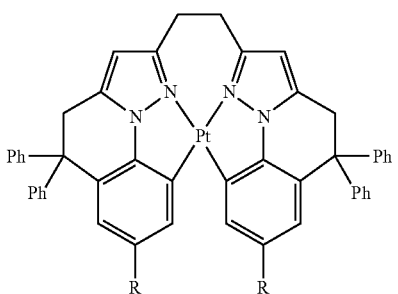

wherein in Compound Pt193: R=Me,
in Compound Pt194: R=Et,
in Compound Pt195: R=$^i$Pr,
in Compound Pt196: R=neopentyl,
in Compound Pt197: R=$^i$Bu,
in Compound Pt198: R=$^t$Bu,
in Compound Pt199: R=Ph,
in Compound Pt200: R=2,6-(Me)$_2$Ph,
in Compound Pt201: R=2,6-($^i$Pr)$_2$Ph,
Compound Pt202 through Pt210, each represented by the formula

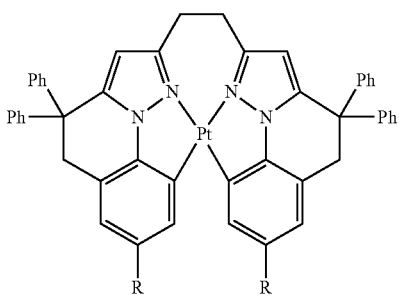

wherein in Compound Pt202: R=Me,
in Compound Pt203: R=Et,
in Compound Pt204: R=$^i$Pr,
in Compound Pt205: R=neopentyl,
in Compound Pt206: R=$^i$Bu,
in Compound Pt207: R=$^t$Bu,
in Compound Pt208: R=Ph,
in Compound Pt209: R=2,6-(Me)$_2$Ph,
in Compound Pt210: R=2,6-($^i$Pr)$_2$Ph,
Compound Pt211 through Pt222, each represented by the formula

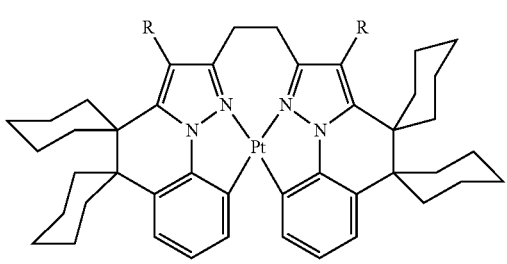

wherein in Compound Pt211: R=H,
in Compound Pt212: R=Me,
in Compound Pt213: R=Et,
in Compound Pt214: R=$^i$Pr, in Compound Pt215: R=neopentyl,
in Compound Pt216: R=$^i$Bu,
in Compound Pt217: R=$^t$Bu,
in Compound Pt218: R=Ph,
in Compound Pt219: R=4-biphenyl,
in Compound Pt220: R=2,6-($^i$Pr)$_2$Ph,
in Compound Pt221: R=2,6-($^i$Pr)$_2$-4-biphenyl,
in Compound Pt222: R=2,4-($^i$Pr)$_2$-3-dibenzofuran,
Compound Pt223 through Pt234, each represented by the formula

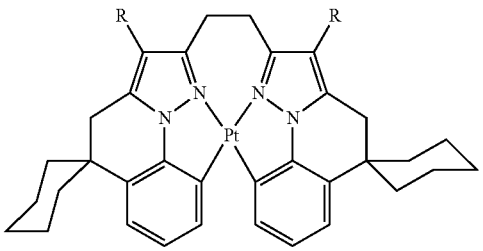

wherein in Compound Pt223: R=H
in Compound Pt224: R=Me
in Compound Pt225: R=Et
in Compound Pt226: R=$^i$Pr
in Compound Pt227: R=neopentyl
in Compound Pt228: R=$^i$Bu
in Compound Pt229: R=$^t$Bu
in Compound Pt230: R=Ph
in Compound Pt231: R=4-biphenyl
in Compound Pt232: R=2,6-($^i$Pr)$_2$Ph
in Compound Pt233: R=2,6-($^i$Pr)$_2$-4-biphenyl
in Compound Pt234: R=2,4-($^i$Pr)$_2$-3-dibenzofuran,
Compound Pt235 through Pt246, each represented by the formula

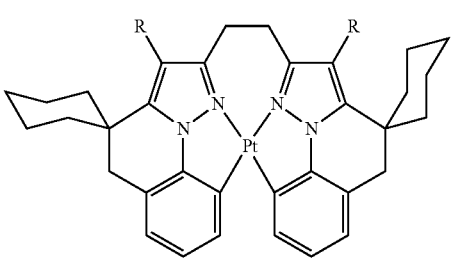

wherein in Compound Pt235: R=H
in Compound Pt236: R=Me
in Compound Pt237: R=Et
in Compound Pt238: R=$^i$Pr
in Compound Pt239: R=neopentyl
in Compound Pt240: R=$^i$Bu
in Compound Pt241: R=$^t$Bu
in Compound Pt242: R=Ph
in Compound Pt243: R=4-biphenyl
in Compound Pt244: R=2,6-($^i$Pr)$_2$Ph
in Compound Pt245: R=2,6-($^i$Pr)$_2$-4-biphenyl
in Compound Pt246: R=2,4-($^i$Pr)$_2$-3-dibenzofuran,
Compound Pt247 through Pt255, each represented by the formula

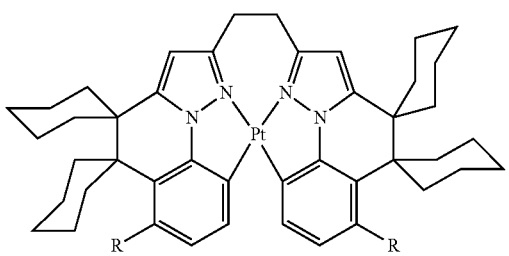

wherein in Compound Pt247: R=Me,
in Compound Pt248: R=Et,
in Compound Pt249: R=$^i$Pr,
in Compound Pt250: R=neopentyl,
in Compound Pt251: R=$^i$Bu,
in Compound Pt252: R=$^t$Bu,
in Compound Pt253: R=Ph,
in Compound Pt254: R=2,6-(Me)$_2$Ph,
in Compound Pt255: R=2,6-($^i$Pr)$_2$Ph,
Compound Pt256 through Pt264, each represented by the formula

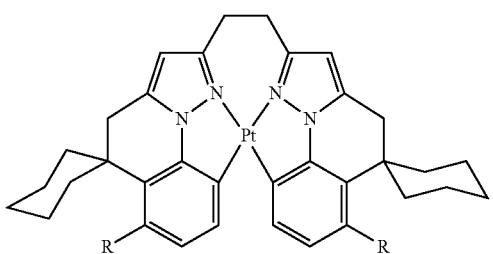

wherein in Compound Pt256: R=Me,
in Compound Pt257: R=Et,
in Compound Pt258: R=$^i$Pr,
in Compound Pt259: R=neopentyl,
in Compound Pt260: R=$^i$Bu,
in Compound Pt261: R=$^t$Bu,
in Compound Pt262: R=Ph,
in Compound Pt263: R=2,6-(Me)$_2$Ph,
in Compound Pt264: R=2,6-($^i$Pr)$_2$Ph,
Compound Pt265 through Pt273, each represented by the formula

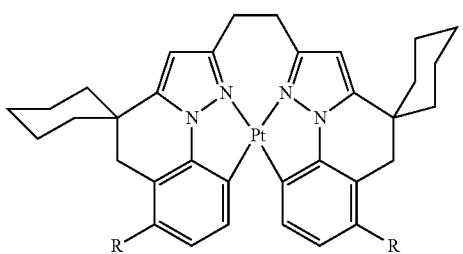

wherein in Compound Pt265: R=Me,
in Compound Pt266: R=Et,
in Compound Pt267: R=$^i$Pr,
in Compound Pt268: R=neopentyl,
in Compound Pt269: R=$^i$Bu,
in Compound Pt270: R=$^t$Bu,
in Compound Pt271: R=Ph, in Compound Pt272: R=2,6-(Me)$_2$Ph,
in Compound Pt273: R=2,6-($^i$Pr)$_2$Ph,
Compound Pt274 through Pt282, each represented by the formula

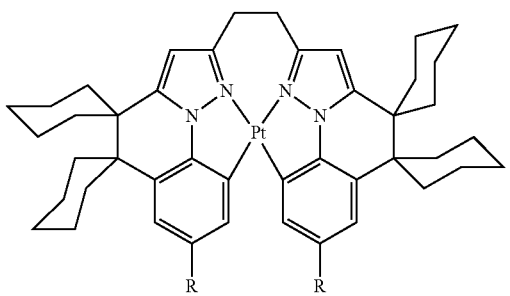

wherein in Compound Pt274: R=Me,
in Compound Pt275: R=Et,
in Compound Pt276: R=$^i$Pr,
in Compound Pt277: R=neopentyl,
in Compound Pt278: R=$^i$Bu,
in Compound Pt279: R=$^t$Bu,
in Compound Pt280: R=Ph,
in Compound Pt281: R=2,6-(Me)$_2$Ph,
in Compound Pt282: R=2,6-($^i$Pr)$_2$Ph,
Compound Pt283 through Pt291, each represented by the formula

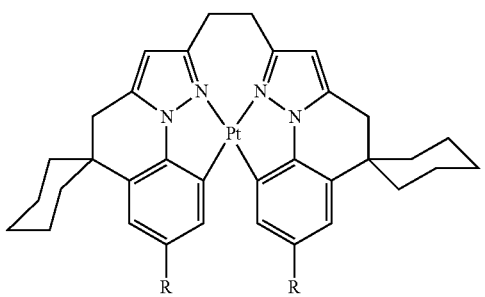

wherein in Compound Pt283: R=Me,
in Compound Pt284: R=Et,
in Compound Pt285: R=$^i$Pr,
in Compound Pt286: R=neopentyl,
in Compound Pt287: R=$^i$Bu,
in Compound Pt288: R=$^t$Bu,
in Compound Pt289: R=Ph,
in Compound Pt290: R=2,6-(Me)$_2$Ph,
in Compound Pt291: R=2,6-($^i$Pr)$_2$Ph,
Compound Pt292 through Pt300, each represented by the formula

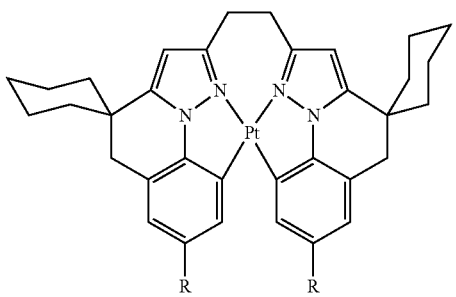

wherein in Compound Pt292: R=Me,
in Compound Pt293: R=Et,
in Compound Pt294: R=$^i$Pr,
in Compound Pt295: R=neopentyl,
in Compound Pt296: R=$^i$Bu,
in Compound Pt297: R=$^t$Bu,
in Compound Pt298: R=Ph,
in Compound Pt299: R=2,6-(Me)$_2$Ph,
in Compound Pt300: R=2,6-($^i$Pr)$_2$Ph,
Compound Pt301 through Pt312, each represented by the formula

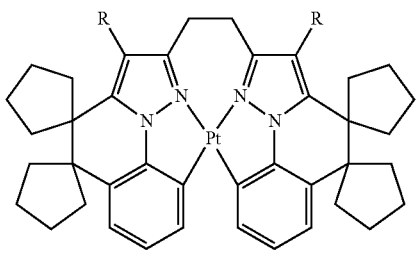

wherein in Compound Pt301: R=H,
in Compound Pt302: R=Me,
in Compound Pt303: R=Et,
in Compound Pt304: R=$^i$Pr,
in Compound Pt305: R=neopentyl,
in Compound Pt306: R=$^i$Bu,
in Compound Pt307: R=$^t$Bu,
in Compound Pt308: R=Ph,
in Compound Pt309: R=4-biphenyl,
in Compound Pt310: R=2,6-($^i$Pr)$_2$Ph,
in Compound Pt311: R=2,6-($^i$Pr)$_2$-4-biphenyl,
in Compound Pt312: R=2,4-($^i$Pr)$_2$-3-dibenzofuran,
Compound Pt313 through Pt324, each represented by the formula

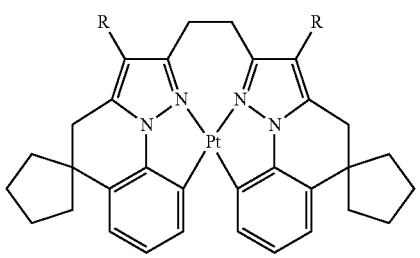

wherein in Compound Pt313: R=H,
in Compound Pt314: R=Me,
in Compound Pt315: R=Et,
in Compound Pt316: R=$^i$Pr,
in Compound Pt317: R=neopentyl,
in Compound Pt318: R=$^i$Bu,
in Compound Pt319: R=$^t$Bu,
in Compound Pt320: R=Ph,
in Compound Pt321: R=4-biphenyl,
in Compound Pt322: R=2,6-($^i$Pr)$_2$Ph,
in Compound Pt323: R=2,6-($^i$Pr)$_2$-4-biphenyl,
in Compound Pt324: R=2,4-($^i$Pr)$_2$-3-dibenzofuran,
Compound Pt325 through Pt336, each represented by the formula

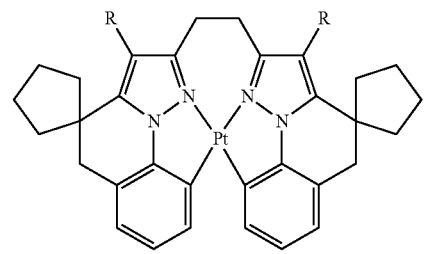

wherein in Compound Pt325: R=H,
in Compound Pt326: R=Me,
in Compound Pt327: R=Et,
in Compound Pt328: R=$^i$Pr,
in Compound Pt329: R=neopentyl,
in Compound Pt330: R=$^i$Bu,
in Compound Pt331: R=$^t$Bu,
in Compound Pt332: R=Ph,
in Compound Pt333: R=4-biphenyl,
in Compound Pt334: R=2,6-($^i$Pr)$_2$Ph,
in Compound Pt335: R=2,6-($^i$Pr)$_2$-4-biphenyl,
in Compound Pt336: R=2,4-($^i$Pr)$_2$-3-dibenzofuran,
Compound Pt337 through Pt345, each represented by the formula

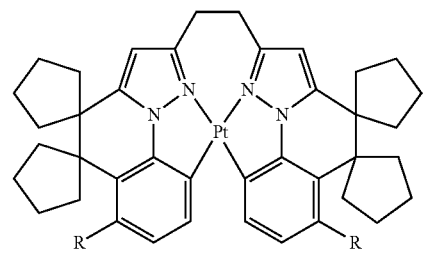

wherein in Compound Pt337: R=Me,
in Compound Pt338: R=Et,
in Compound Pt339: R=$^i$Pr,
in Compound Pt340: R=neopentyl,
in Compound Pt341: R=$^i$Bu,
in Compound Pt342: R=$^t$Bu,
in Compound Pt343: R=Ph,
in Compound Pt344: R=2,6-(Me)$_2$Ph,
in Compound Pt345: R=2,6-($^i$Pr)$_2$Ph,
Compound Pt346 through Pt354, each represented by the formula

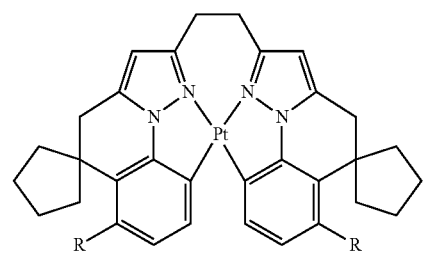

wherein in Compound Pt346: R=Me,
in Compound Pt347: R=Et,
in Compound Pt348: R=$^i$Pr,
in Compound Pt349: R=neopentyl,
in Compound Pt350: R=$^i$Bu, in Compound Pt351: R=$^t$Bu,
in Compound Pt352: R=Ph,
in Compound Pt353: R=2,6-(Me)$_2$Ph,
in Compound Pt354: R=2,6-($^i$Pr)$_2$Ph, Compound Pt355 through Pt363, each represented by the formula

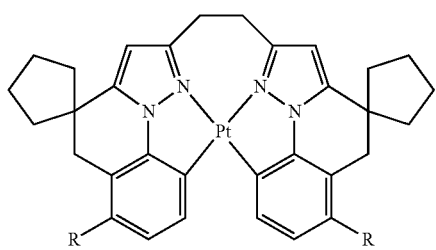

wherein in Compound Pt355: R=Me,
in Compound Pt356: R=Et,
in Compound Pt357: R=$^i$Pr,
in Compound Pt358: R=neopentyl,
in Compound Pt359: R=$^i$Bu,
in Compound Pt360: R=$^t$Bu,
in Compound Pt361: R=Ph,
in Compound Pt362: R=2,6-(Me)$_2$Ph,
in Compound Pt363: R=2,6-($^i$Pr)$_2$Ph, Compound Pt364 through Pt372, each represented by the formula

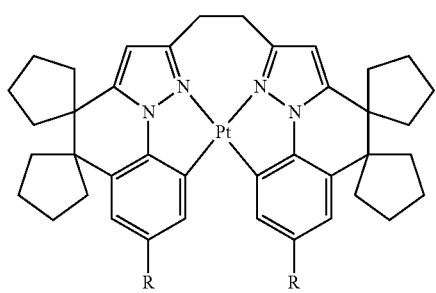

wherein in Compound Pt364: R=Me,
in Compound Pt365: R=Et,
in Compound Pt366: R=$^i$Pr,
in Compound Pt367: R=neopentyl,
in Compound Pt368: R=$^i$Bu,
in Compound Pt369: R=$^t$Bu,
in Compound Pt370: R=Ph,
in Compound Pt371: R=2,6-(Me)$_2$Ph,
in Compound Pt372: R=2,6-($^i$Pr)$_2$Ph, Compound Pt373 through Pt381, each represented by the formula

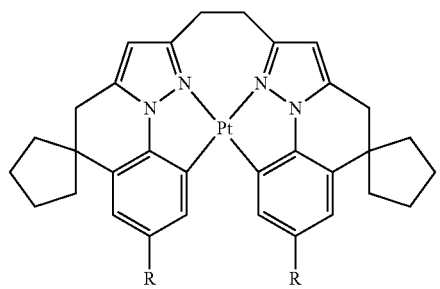

wherein in Compound Pt373: R=Me,
in Compound Pt374: R=Et,
in Compound Pt375: R=$^i$Pr,
in Compound Pt376: R=neopentyl,
in Compound Pt377: R=$^i$Bu,
in Compound Pt378: R=$^t$Bu,
in Compound Pt379: R=Ph,
in Compound Pt380: R=2,6-(Me)$_2$Ph,
in Compound Pt381: R=2,6-($^i$Pr)$_2$Ph, Compound Pt382 through Pt390 represented by the formula

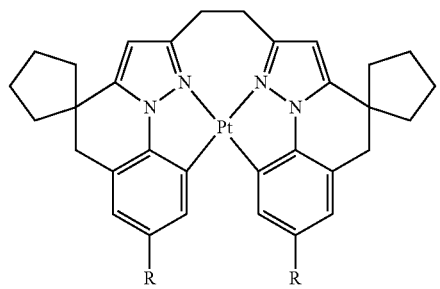

wherein in Compound Pt382: R=Me,
in Compound Pt383: R=Et,
in Compound Pt384: R=$^i$Pr,
in Compound Pt385: R=neopentyl,
in Compound Pt386: R=$^i$Bu,
in Compound Pt387: R=$^t$Bu,
in Compound Pt388: R=Ph,
in Compound Pt389: R=2,6-(Me)$_2$Ph,
in Compound Pt390: R=2,6-($^i$Pr)$_2$Ph, Compound Pt391 through Pt402 each represented by the formula

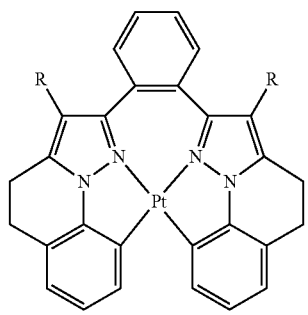

wherein in Compound Pt391: R=H,
in Compound Pt392: R=Me,
in Compound Pt393: R=Et, in Compound Pt394: R=$^i$Pr,
in Compound Pt395: R=neopentyl,
in Compound Pt396: R=$^i$Bu,
in Compound Pt397: R=$^t$Bu,
in Compound Pt398: R=Ph,
in Compound Pt399: R=4-biphenyl,
in Compound Pt400: R=2,6-($^i$Pr)$_2$Ph,
in Compound Pt401: R=2,6-($^i$Pr)$_2$-4-biphenyl,
in Compound Pt402: R=2,4-($^i$Pr)$_2$-3-dibenzofuran,
Compound Pt403 through Pt411, each represented by the formula

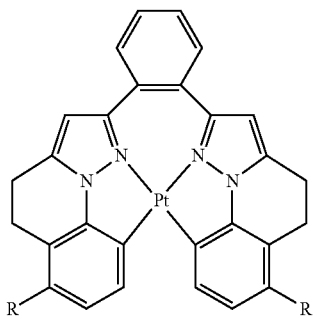

wherein in Compound Pt403: R=Me,
in Compound Pt404: R=Et,
in Compound Pt405: R=$^i$Pr,
in Compound Pt406: R=neopentyl,
in Compound Pt407: R=$^i$Bu,
in Compound Pt408: R=$^t$Bu,
in Compound Pt409: R=Ph
in Compound Pt410: R=2,6-(Me)$_2$Ph,
in Compound Pt411: R=2,6-($^i$Pr)$_2$Ph,
Compound Pt412 through Pt420, each represented by the formula

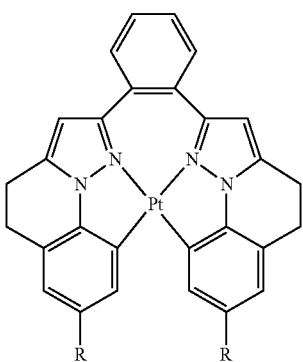

wherein in Compound Pt412: R=Me,
in Compound Pt413: R=Et,
in Compound Pt414: R=$^i$Pr,
in Compound Pt415: R=neopentyl,
in Compound Pt416: R=$^i$Bu,
in Compound Pt417: R=$^t$Bu,
in Compound Pt418: R=Ph,
in Compound Pt419: R=2,6-(Me)$_2$Ph,
in Compound Pt420: R=2,6-($^i$Pr)$_2$Ph,
Compound Pt421 through Pt432, each represented by the formula

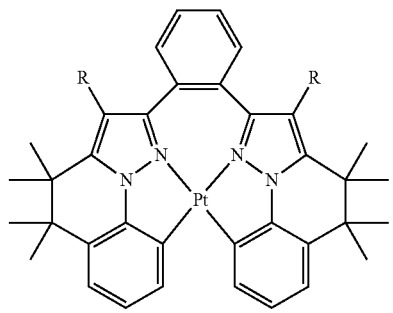

wherein in Compound Pt421: R=H,
in Compound Pt422: R=Me,
in Compound Pt423: R=Et,
in Compound Pt424: R=$^i$Pr,
in Compound Pt425: R=neopentyl,
in Compound Pt426: R=$^i$Bu,
in Compound Pt427: R=$^t$Bu,
in Compound Pt428: R=Ph,
in Compound Pt429: R=4-biphenyl,
in Compound Pt430: R=2,6-($^i$Pr)$_2$Ph,
in Compound Pt431: R=2,6-($^i$Pr)$_2$-4-biphenyl,
in Compound Pt432: R=2,4-($^i$Pr)$_2$-3-dibenzofuran,
Compound Pt433 through Pt444, each represented by the formula

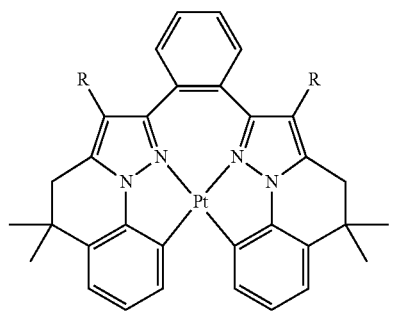

wherein in Compound Pt433: R=H,
in Compound Pt434: R=Me,
in Compound Pt435: R=Et,
in Compound Pt436: R=$^i$Pr,
in Compound Pt437: R=neopentyl,
in Compound Pt438: R=$^i$Bu,
in Compound Pt439: R=$^t$Bu,
in Compound Pt440: R=Ph,
in Compound Pt441: R=4-biphenyl,
in Compound Pt442: R=2,6-($^i$Pr)$_2$Ph,
in Compound Pt443: R=2,6-($^i$Pr)$_2$-4-biphenyl,
in Compound Pt444: R=2,4-($^i$Pr)$_2$-3-dibenzofuran,
Compound Pt445 through Pt456, each represented by the formula

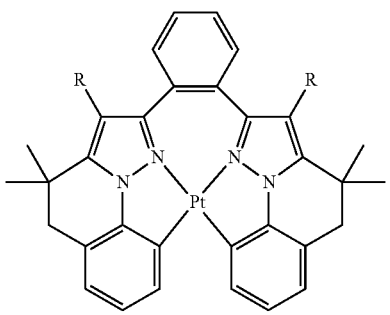

wherein in Compound Pt445: R=H,
in Compound Pt446: R=Me,
in Compound Pt447: R=Et,
in Compound Pt448: R=$^i$Pr,
in Compound Pt449: R=neopentyl,
in Compound Pt450: R=$^i$Bu,
in Compound Pt451: R=$^t$Bu,
in Compound Pt452: R=Ph,
in Compound Pt453: R=4-biphenyl,
in Compound Pt454: R=2,6-($^i$Pr)$_2$Ph,
in Compound Pt455: R=2,6-($^i$Pr)$_2$-4-biphenyl,
in Compound Pt456: R=2,4-($^i$Pr)$_2$-3-dibenzofuran, Compound Pt457 through Pt465, each represented by the formula

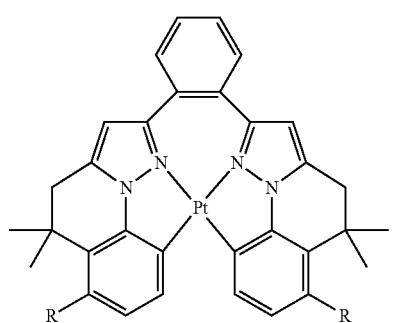

wherein in Compound Pt466: R=Me,
in Compound Pt467: R=Et,
in Compound Pt468: R=$^i$Pr,
in Compound Pt469: R=neopentyl,
in Compound Pt470: R=$^i$Bu,
in Compound Pt471: R=$^t$Bu,
in Compound Pt472: R=Ph,
in Compound Pt473: R=2,6-(Me)$_2$Ph,
in Compound Pt474: R=2,6-($^i$Pr)$_2$Ph, Compound Pt475 through Pt483, each represented by the formula

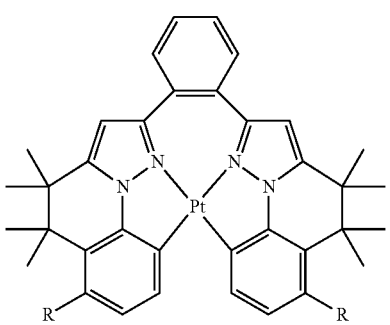

wherein in Compound Pt457: R=Me,
in Compound Pt458: R=Et,
in Compound Pt459: R=$^i$Pr,
in Compound Pt460: R=neopentyl,
in Compound Pt461: R=$^i$Bu,
in Compound Pt462: R=$^t$Bu,
in Compound Pt463: R=Ph,
in Compound Pt464: R=2,6-(Me)$_2$Ph,
in Compound Pt465: R=2,6-($^i$Pr)$_2$Ph, Compound Pt466 through Pt474, each represented by the formula

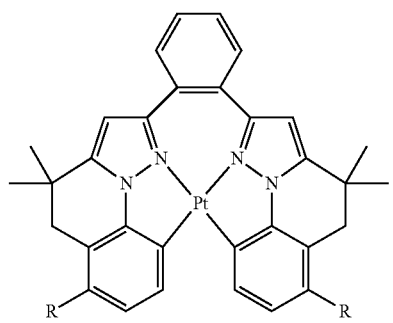

wherein in Compound Pt475: R=Me,
in Compound Pt476: R=Et,
in Compound Pt477: R=$^i$Pr,
in Compound Pt478: R=neopentyl,
in Compound Pt479: R=$^i$Bu,
in Compound Pt480: R=$^t$Bu,
in Compound Pt481: R=Ph,
in Compound Pt482: R=2,6-(Me)$_2$Ph,
in Compound Pt483: R=2,6-($^i$Pr)$_2$Ph, Compound Pt484 through Pt492, each represented by the formula

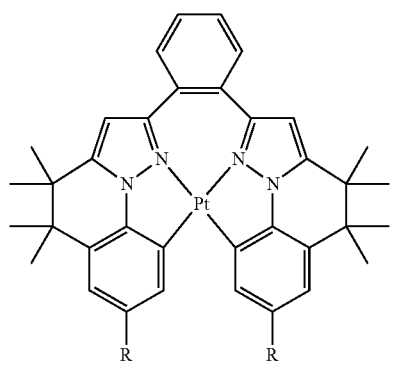

wherein in Compound Pt484: R=Me,
in Compound Pt485: R=Et,
in Compound Pt486: R=$^i$Pr,
in Compound Pt487: R=neopentyl,
in Compound Pt488: R=$^i$Bu,
in Compound Pt489: R=$^t$Bu,
in Compound Pt490: R=Ph,
in Compound Pt491: R=2,6-(Me)$_2$Ph,
in Compound Pt492: R=2,6-($^i$Pr)$_2$Ph, Compound Pt493 through Pt501, each represented by the formula

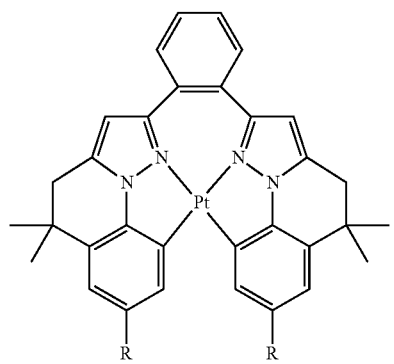

wherein in Compound Pt493: R=Me,
in Compound Pt494: R=Et,
in Compound Pt495: R=$^i$Pr,
in Compound Pt496: R=neopentyl,
in Compound Pt497: R=$^i$Bu,
in Compound Pt498: R=$^t$Bu,
in Compound Pt499: R=Ph,
in Compound Pt500: R=2,6-(Me)$_2$Ph,
in Compound Pt501: R=2,6-($^i$Pr)$_2$Ph, Compound Pt502 through Pt510, each represented by the formula

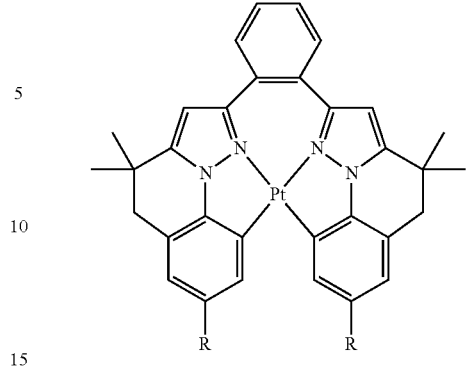

wherein in Compound Pt502: R=Me,
in Compound Pt503: R=Et,
in Compound Pt504: R=$^i$Pr,
in Compound Pt505: R=neopentyl,
in Compound Pt506: R=$^i$Bu,
in Compound Pt507: R=$^t$Bu,
in Compound Pt508: R=Ph,
in Compound Pt509: R=2,6-(Me)$_2$Ph,
in Compound Pt510: R=2,6-($^i$Pr)$_2$Ph, Compound Pt511 through Pt522, each represented by the formula

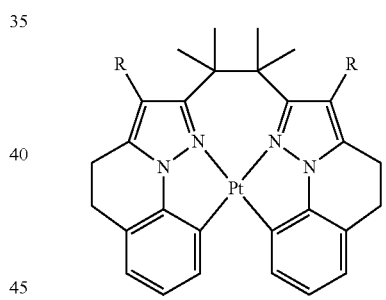

wherein in Compound Pt511: R=H,
in Compound Pt512: R=Me,
in Compound Pt513: R=Et,
in Compound Pt514: R=$^i$Pr,
in Compound Pt515: R=neopentyl,
in Compound Pt516: R=$^i$Bu,
in Compound Pt517: R=$^t$Bu,
in Compound Pt518: R=Ph,
in Compound Pt519: R=4-biphenyl,
in Compound Pt520: R=2,6-($^i$Pr)$_2$Ph,
in Compound Pt521: R=2,6-($^i$Pr)$_2$-4-biphenyl,
in Compound Pt522: R=2,4-($^i$Pr)$_2$-3-dibenzofuran, Compound Pt523 through Pt531, each represented by the formula

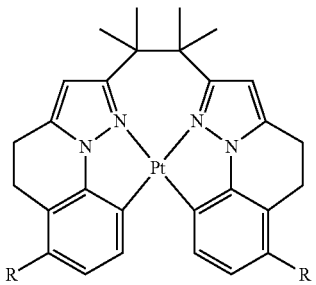

wherein in Compound Pt523: R=Me,
in Compound Pt524: R=Et,
in Compound Pt525: R=$^i$Pr,
in Compound Pt526: R=neopentyl,
in Compound Pt527: R=$^i$Bu,
in Compound Pt528: R=$^t$Bu,
in Compound Pt529: R=Ph,
in Compound Pt530: R=2,6-(Me)$_2$Ph,
in Compound Pt531: R=2,6-($^i$Pr)$_2$Ph,
Compound Pt532 through Pt540, each represented by the formula

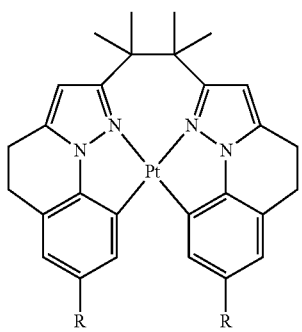

wherein in Compound Pt532: R=Me,
in Compound Pt533: R=Et,
in Compound Pt534: R=$^i$Pr,
in Compound Pt535: R=neopentyl,
in Compound Pt536: R=$^i$Bu,
in Compound Pt537: R=$^t$Bu,
in Compound Pt538: R=Ph,
in Compound Pt539: R=2,6-(Me)$_2$Ph,
in Compound Pt540: R=2,6-($^i$Pr)$_2$Ph,
Compound Pt541 through Pt552, each represented by the formula

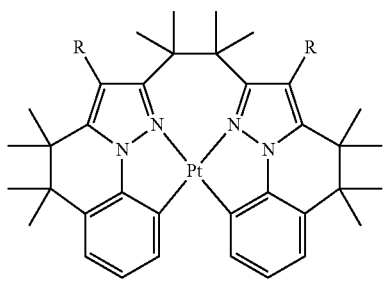

wherein in Compound Pt541: R=H,
in Compound Pt542: R=Me,
in Compound Pt543: R=Et,
in Compound Pt544: R=$^i$Pr,
in Compound Pt545: R=neopentyl,
in Compound Pt546: R=$^i$Bu,
in Compound Pt547: R=$^t$Bu,
in Compound Pt548: R=Ph,
in Compound Pt549: R=4-biphenyl,
in Compound Pt550: R=2,6-($^i$Pr)$_2$Ph,
in Compound Pt551: R=2,6-($^i$Pr)$_2$-4-biphenyl,
in Compound Pt552: R=2,4-($^i$Pr)$_2$-3-dibenzofuran,
Compound Pt553 through Pt564, each represented by the formula

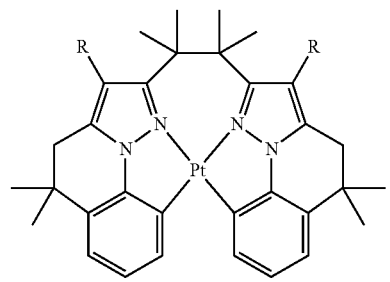

wherein in Compound Pt553: R=H,
in Compound Pt554: R=Me,
in Compound Pt555: R=Et,
in Compound Pt556: R=$^i$Pr,
in Compound Pt557: R=neopentyl,
in Compound Pt558: R=$^i$Bu,
in Compound Pt559: R=$^t$Bu,
in Compound Pt560: R=Ph,
in Compound Pt561: R=4-biphenyl,
in Compound Pt562: R=2,6-($^i$Pr)$_2$Ph,
in Compound Pt563: R=2,6-($^i$Pr)$_2$-4-biphenyl,
in Compound Pt564: R=2,4-($^i$Pr)$_2$-3-dibenzofuran,
Compound Pt565 through Pt576, each represented by the formula

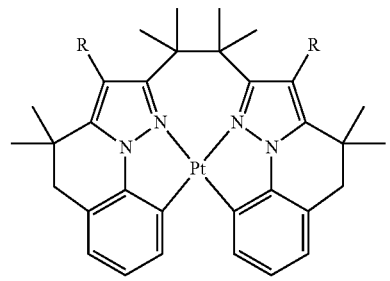

wherein in Compound Pt565: R=H,
in Compound Pt566: R=Me,
in Compound Pt567: R=Et,
in Compound Pt568: R=$^i$Pr,
in Compound Pt569: R=neopentyl,
in Compound Pt570: R=$^i$Bu,
in Compound Pt571: R=$^t$Bu,
in Compound Pt572: R=Ph,
in Compound Pt573: R=4-biphenyl,
in Compound Pt574: R=2,6-($^i$Pr)$_2$Ph,
in Compound Pt575: R=2,6-($^i$Pr)$_2$-4-biphenyl,
in Compound Pt576: R=2,4-($^i$Pr)$_2$-3-dibenzofuran, Compound Pt577 through Pt585, each represented by the formula

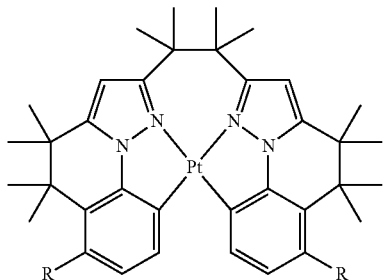

wherein in Compound Pt577: R=Me,
in Compound Pt578: R=Et,
in Compound Pt579: R=$^i$Pr,
in Compound Pt580: R=neopentyl,
in Compound Pt581: R=$^i$Bu,
in Compound Pt582: R=$^t$Bu,
in Compound Pt583: R=Ph,
in Compound Pt584: R=2,6-(Me)$_2$Ph,
in Compound Pt585: R=2,6-($^i$Pr)$_2$Ph, Compound Pt586 through Pt594, each represented by the formula

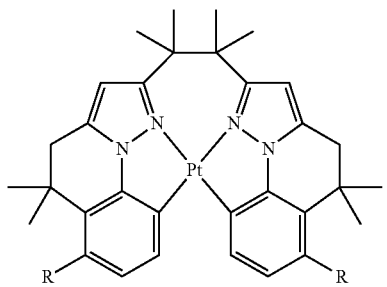

wherein in Compound Pt586: R=Me,
in Compound Pt587: R=Et,
in Compound Pt588: R=$^i$Pr,
in Compound Pt589: R=neopentyl,
in Compound Pt590: R=$^i$Bu,
in Compound Pt591: R=$^t$Bu,
in Compound Pt592: R=Ph,
in Compound Pt593: R=2,6-(Me)$_2$Ph,
in Compound Pt594: R=2,6-($^i$Pr)$_2$Ph, Compound Pt595 through Pt603, each represented by the formula

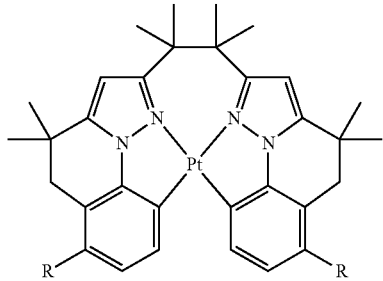

wherein in Compound Pt595: R=Me,
in Compound Pt596: R=Et,
in Compound Pt597: R=$^i$Pr,
in Compound Pt598: R=neopentyl,
in Compound Pt599: R=$^i$Bu,
in Compound Pt600: R=$^t$Bu,
in Compound Pt601: R=Ph,
in Compound Pt602: R=2,6-(Me)$_2$Ph,
in Compound Pt603: R=2,6-($^i$Pr)$_2$Ph, Compound Pt604 through Pt612, each represented by the formula

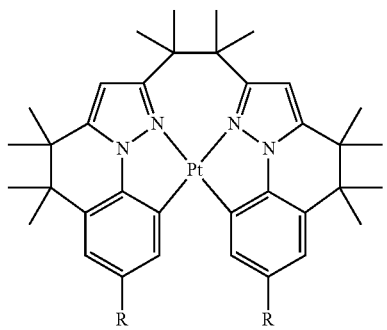

wherein in Compound Pt604: R=Me,
in Compound Pt605: R=Et,
in Compound Pt606: R=$^i$Pr,
in Compound Pt607: R=neopentyl,
in Compound Pt608: R=$^i$Bu,
in Compound Pt609: R=$^t$Bu,
in Compound Pt610: R=Ph,
in Compound Pt611: R=2,6-(Me)$_2$Ph,
in Compound Pt612: R=2,6-($^i$Pr)$_2$Ph, Compound Pt613 through Pt621, each represented by the formula

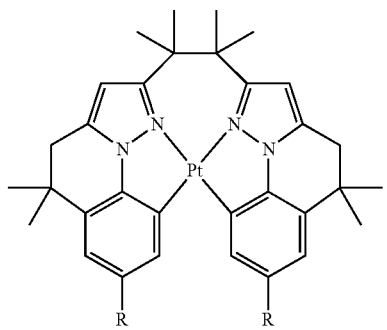

wherein in Compound Pt613: R=Me,
in Compound Pt614: R=Et,
in Compound Pt615: R=$^i$Pr,
in Compound Pt616: R=neopentyl,
in Compound Pt617: R=$^i$Bu,
in Compound Pt618: R=$^t$Bu,
in Compound Pt619: R=Ph,
in Compound Pt620: R=2,6-(Me)$_2$Ph,
in Compound Pt621: R=2,6-($^i$Pr)$_2$Ph, Compound Pt622 through Pt630, each represented by the formula

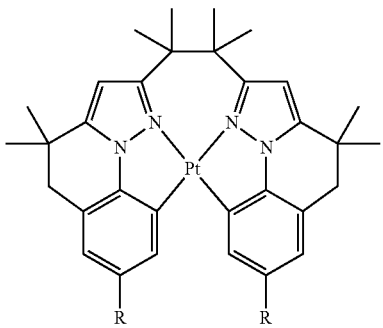

wherein in Compound Pt622: R=Me,
in Compound Pt623: R=Et,
in Compound Pt624: R=$^i$Pr,
in Compound Pt625: R=neopentyl,
in Compound Pt626: R=$^i$Bu,
in Compound Pt627: R=$^t$Bu,
in Compound Pt628: R=Ph,
in Compound Pt629: R=2,6-(Me)$_2$Ph,
in Compound Pt630: R=2,6-($^i$Pr)$_2$Ph, Compound Pt631 through Pt645, each represented by the formula

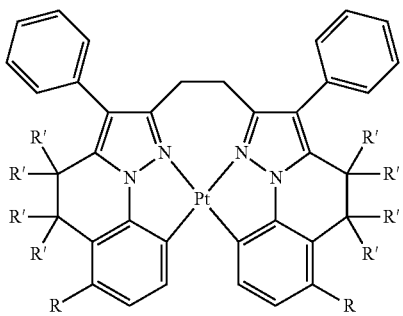

wherein in Compound Pt631: R'=H, R=Me,
in Compound Pt632: R'=H, R=Et,
in Compound Pt633: R'=H, R=$^i$Pr,
in Compound Pt634: R'=H, R=Ph,
in Compound Pt635: R'=H, R=2,6-($^i$Pr)$_2$Ph,
in Compound Pt636: R'=Me, R=Me,
in Compound Pt637: R'=Me, R=Et,
in Compound Pt638: R'=Me, R=$^i$Pr,
in Compound Pt639: R'=Me, R=Ph,
in Compound Pt640: R'=Me, R=2,6-($^i$Pr)$_2$Ph,
in Compound Pt641: R'=Ph, R=Me,
in Compound Pt642: R'=Ph, R=Et,
in Compound Pt643: R'=Ph, R=$^i$Pr,
in Compound Pt644: R'=Ph, R=Ph,
in Compound Pt645: R'=Ph, R=2,6-($^i$Pr)$_2$Ph, Compound Pt646 through Pt660, each represented by the formula

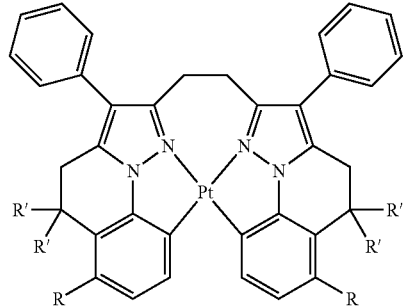

wherein in Compound Pt646: R'=H, R=Me,
in Compound Pt647: R'=H, R=Et,
in Compound Pt648: R'=H, R=$^i$Pr,
in Compound Pt649: R'=H, R=Ph,
in Compound Pt650: R'=H, R=2,6-($^i$Pr)$_2$Ph,
in Compound Pt651: R'=Me, R=Me,
in Compound Pt652: R'=Me, R=Et,
in Compound Pt653: R'=Me, R=$^i$Pr,
in Compound Pt654: R'=Me, R=Ph,
in Compound Pt655: R'=Me, R=2,6-($^i$Pr)$_2$Ph,
in Compound Pt656: R'=Ph, R=Me,
in Compound Pt657: R'=Ph, R=Et,
in Compound Pt658: R'=Ph, R=$^i$Pr,
in Compound Pt659: R'=Ph, R=Ph,
in Compound Pt660: R'=Ph, R=2,6-($^i$Pr)$_2$Ph, Compound Pt661 through Pt675, each represented by the formula

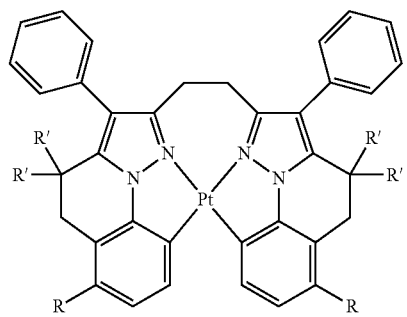

wherein in Compound Pt661: R'=H, R=Me,
in Compound Pt662: R'=H, R=Et,
in Compound Pt663: R'=H, R=$^i$Pr,
in Compound Pt664: R'=H, R=Ph,
in Compound Pt665: R'=H, R=2,6-($^i$Pr)$_2$Ph,
in Compound Pt666: R'=Me, R=Me,
in Compound Pt667: R'=Me, R=Et,
in Compound Pt668: R'=Me, R=$^i$Pr,
in Compound Pt669: R'=Me, R=Ph,
in Compound Pt670: R'=Me, R=2,6-($^i$Pr)$_2$Ph,
in Compound Pt671: R'=Ph, R=Me,
in Compound Pt672: R'=Ph, R=Et,
in Compound Pt673: R'=Ph, R=$^i$Pr,
in Compound Pt674: R'=Ph, R=Ph,
in Compound Pt675: R'=Ph, R=2,6-($^i$Pr)$_2$Ph, Compound Pt676 through Pt690, each represented by the formula

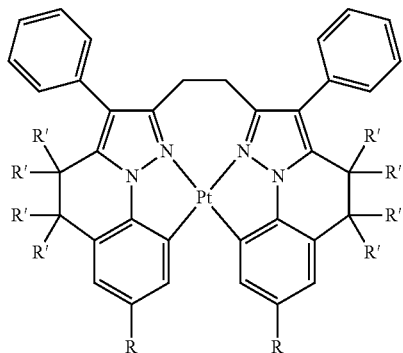

wherein in Compound Pt676: R'=H, R=Me,
in Compound Pt677: R'=H, R=Et,
in Compound Pt678: R'=H, R=$^i$Pr,
in Compound Pt679: R'=H, R=Ph,
in Compound Pt680: R'=H, R=2,6-($^i$Pr)$_2$Ph,
in Compound Pt681: R'=Me, R=Me,
in Compound Pt682: R'=Me, R=Et,
in Compound Pt683: R'=Me, R=$^i$Pr,
in Compound Pt684: R'=Me, R=Ph,
in Compound Pt685: R'=Me, R=2,6-($^i$Pr)$_2$Ph,
in Compound Pt686: R'=Ph, R=Me,
in Compound Pt687: R'=Ph, R=Et,
in Compound Pt688: R'=Ph, R=$^i$Pr,
in Compound Pt689: R'=Ph, R=Ph,
in Compound Pt690: R'=Ph, R=2,6-($^i$Pr)$_2$Ph,
Compound Pt691 through Pt705, each represented by the formula

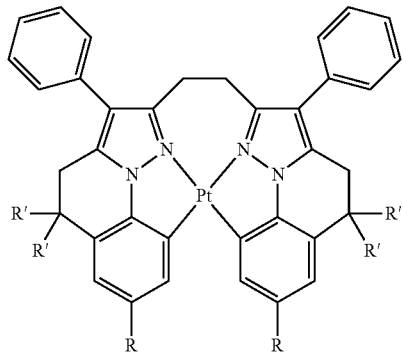

wherein in Compound Pt691: R'=H, R=Me,
in Compound Pt692: R'=H, R=Et,
in Compound Pt693: R'=H, R=$^i$Pr,
in Compound Pt694: R'=H, R=Ph,
in Compound Pt695: R'=H, R=2,6-($^i$Pr)$_2$Ph,
in Compound Pt696: R'=Me, R=Me,
in Compound Pt697: R'=Me, R=Et,
in Compound Pt698: R'=Me, R=$^i$Pr,
in Compound Pt699: R'=Me, R=Ph,
in Compound Pt700: R'=Me, R=2,6-($^i$Pr)$_2$Ph,
in Compound Pt701: R'=Ph, R=Me,
in Compound Pt702: R'=Ph, R=Et,
in Compound Pt703: R'=Ph, R=$^i$Pr,
in Compound Pt704: R'=Ph, R=Ph,
in Compound Pt705: R'=Ph, R=2,6-($^i$Pr)$_2$Ph,
Compound Pt706 through Pt720, each represented by the formula

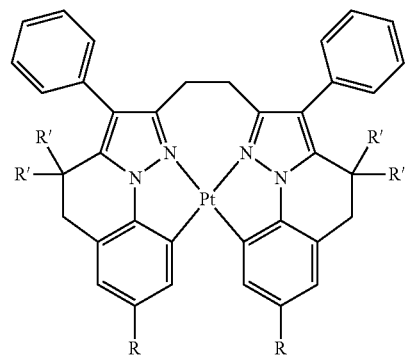

wherein in Compound Pt706: R'=H, R=Me,
in Compound Pt707: R'=H, R=Et,
in Compound Pt708: R'=H, R=$^i$Pr,
in Compound Pt709: R'=H, R=Ph,
in Compound Pt710: R'=H, R=2,6-($^i$Pr)$_2$Ph,
in Compound Pt711: R'=Me, R=Me,
in Compound Pt712: R'=Me, R=Et,
in Compound Pt713: R'=Me, R=$^i$Pr,
in Compound Pt714: R'=Me, R=Ph,
in Compound Pt715: R'=Me, R=2,6-($^i$Pr)$_2$Ph,
in Compound Pt716: R'=Ph, R=Me,
in Compound Pt717: R'=Ph, R=Et,
in Compound Pt718: R'=Ph, R=$^i$Pr,
in Compound Pt719: R'=Ph, R=Ph,
in Compound Pt720: R'=Ph, R=2,6-($^i$Pr)$_2$Ph,
Compound Pt721 through Pt735, each represented by the formula

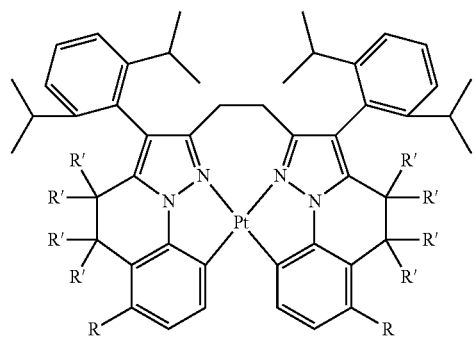

wherein in Compound Pt721: R'=H, R=Me,
in Compound Pt722: R'=H, R=Et,
in Compound Pt723: R'=H, R=$^i$Pr,
in Compound Pt724: R'=H, R=Ph,
in Compound Pt725: R'=H, R=2,6-($^i$Pr)$_2$Ph,
in Compound Pt726: R'=Me, R=Me,
in Compound Pt727: R'=Me, R=Et,
in Compound Pt728: R'=Me, R=$^i$Pr,
in Compound Pt729: R'=Me, R=Ph,
in Compound Pt730: R'=Me, R=2,6-($^i$Pr)$_2$Ph,
in Compound Pt731: R'=Ph, R=Me,
in Compound Pt732: R'=Ph, R=Et,
in Compound Pt733: R'=Ph, R=$^i$Pr,
in Compound Pt734: R'=Ph, R=Ph,
in Compound Pt735: R'=Ph, R=2,6-($^i$Pr)$_2$Ph,
Compound Pt736 through Pt750, each represented by the formula

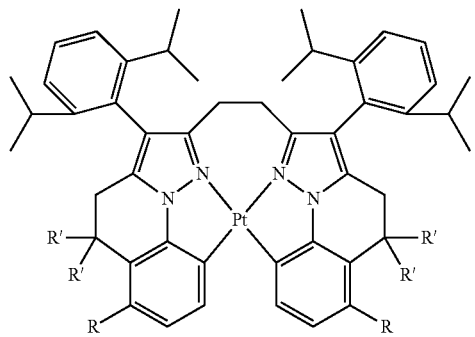

wherein in Compound Pt736: R'=H, R=Me,
in Compound Pt737: R'=H, R=Et,
in Compound Pt738: R'=H, R=$^i$Pr,
in Compound Pt739: R'=H, R=Ph,
in Compound Pt740: R'=H, R=2,6-($^i$Pr)$_2$Ph,
in Compound Pt741: R'=Me, R=Me,
in Compound Pt742: R'=Me, R=Et,
in Compound Pt743: R'=Me, R=$^i$Pr,
in Compound Pt744: R'=Me, R=Ph,
in Compound Pt745: R'=Me, R=2,6-($^i$Pr)$_2$Ph,
in Compound Pt746: R'=Ph, R=Me,
in Compound Pt747: R'=Ph, R=Et,
in Compound Pt748: R'=Ph, R=$^i$Pr,
in Compound Pt749: R'=Ph, R=Ph,
in Compound Pt750: R'=Ph, R=2,6-($^i$Pr)$_2$Ph, Compound Pt751 through Pt765, each represented by the formula

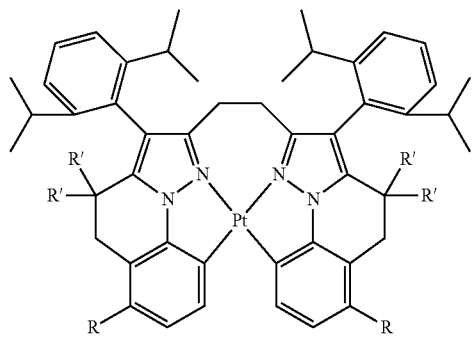

wherein in Compound Pt751: R'=H, R=Me,
in Compound Pt752: R'=H, R=Et,
in Compound Pt753: R'=H, R=$^i$Pr,
in Compound Pt754: R'=H, R=Ph,
in Compound Pt755: R'=H, R=2,6-($^i$Pr)$_2$Ph,
in Compound Pt756: R'=Me, R=Me,
in Compound Pt757: R'=Me, R=Et,
in Compound Pt758: R'=Me, R=$^i$Pr,
in Compound Pt759: R'=Me, R=Ph,
in Compound Pt760: R'=Me, R=2,6-($^i$Pr)$_2$Ph,
in Compound Pt761: R'=Ph, R=Me,
in Compound Pt762: R'=Ph, R=Et,
in Compound Pt763: R'=Ph, R=$^i$Pr,
in Compound Pt764: R'=Ph, R=Ph,
in Compound Pt765: R'=Ph, R=2,6-($^i$Pr)$_2$Ph, Compound Pt766 through Pt780, each represented by the formula

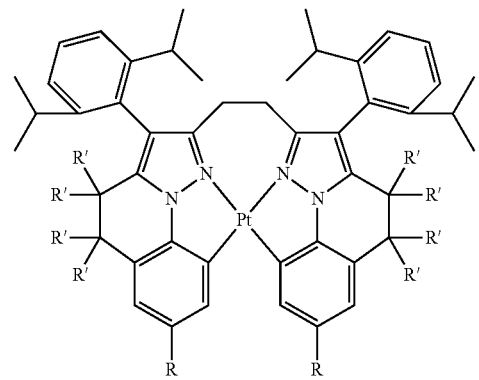

wherein in Compound Pt766: R'=H, R=Me,
in Compound Pt767: R'=H, R=Et,
in Compound Pt768: R'=H, R=$^i$Pr,
in Compound Pt769: R'=H, R=Ph,
in Compound Pt770: R'=H, R=2,6-($^i$Pr)$_2$Ph,
in Compound Pt771: R'=Me, R=Me,
in Compound Pt772: R'=Me, R=Et,
in Compound Pt773: R'=Me, R=$^i$Pr,
in Compound Pt774: R'=Me, R=Ph,
in Compound Pt775: R'=Me, R=2,6-($^i$Pr)$_2$Ph,
in Compound Pt776: R'=Ph, R=Me,
in Compound Pt777: R'=Ph, R=Et,
in Compound Pt778: R'=Ph, R=$^i$Pr,
in Compound Pt779: R'=Ph, R=Ph,
in Compound Pt780: R'=Ph, R=2,6-($^i$Pr)$_2$Ph, Compound Pt781 through Pt795, each represented by the formula

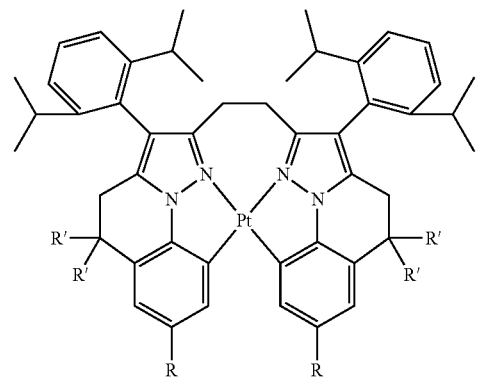

wherein in Compound Pt781: R'=H, R=Me,
in Compound Pt782: R'=H, R=Et,
in Compound Pt783: R'=H, R=$^i$Pr,
in Compound Pt784: R'=H, R=Ph,
in Compound Pt785: R'=H, R=2,6-($^i$Pr)$_2$Ph,
in Compound Pt786: R'=Me, R=Me,
in Compound Pt787: R'=Me, R=Et,
in Compound Pt788: R'=Me, R=$^i$Pr,
in Compound Pt789: R'=Me, R=Ph,
in Compound Pt790: R'=Me, R=2,6-($^i$Pr)$_2$Ph,
in Compound Pt791: R'=Ph, R=Me,
in Compound Pt792: R'=Ph, R=Et,
in Compound Pt793: R'=Ph, R=$^i$Pr,
in Compound Pt794: R'=Ph, R=Ph,
in Compound Pt795: R'=Ph, R=2,6-($^i$Pr)$_2$Ph, Compound Pt796 through Pt810, each represented by the formula

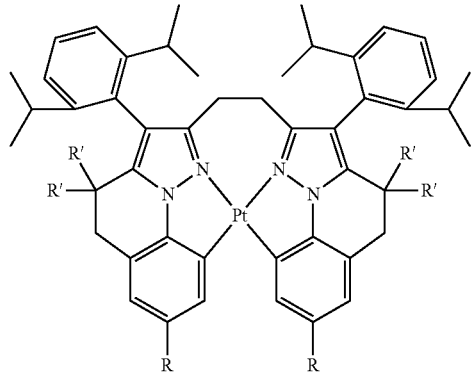

wherein in Compound Pt796: R'=H, R=Me,
in Compound Pt797: R'=H, R'=Et,
in Compound Pt798: R'=H, R=$^i$Pr,
in Compound Pt799: R'=H, R=Ph,
in Compound Pt800: R'=H, R=2,6-($^i$Pr)$_2$Ph,
in Compound Pt801: R'=Me, R=Me,
in Compound Pt802: R'=Me, R=Et,
in Compound Pt803: R'=Me, R=$^i$Pr,
in Compound Pt804: R'=Me, R=Ph,
in Compound Pt805: R'=Me, R=2,6-($^i$Pr)$_2$Ph,
in Compound Pt806: R'=Ph, R=Me,
in Compound Pt807: R'=Ph, R=Et,
in Compound Pt808: R'=Ph, R=$^i$Pr,
in Compound Pt809: R'=Ph, R=Ph,
in Compound Pt810: R'=Ph, R=2,6-($^i$Pr)$_2$Ph, Compound Pt811 through Pt825, each represented by the formula

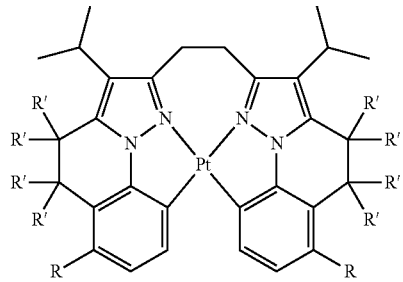

wherein in Compound Pt811: R'=H, R=Me,
in Compound Pt812: R'=H, R=Et,
in Compound Pt813: R'=H, R=$^i$Pr,
in Compound Pt814: R'=H, R=Ph,
in Compound Pt815: R'=H, R=2,6-($^i$Pr)$_2$Ph,
in Compound Pt816: R'=Me, R=Me,
in Compound Pt817: R'=Me, R=Et,
in Compound Pt818: R'=Me, R=$^i$Pr,
in Compound Pt819: R'=Me, R=Ph,
in Compound Pt820: R'=Me, R=2,6-($^i$Pr)$_2$Ph,
in Compound Pt821: R'=Ph, R=Me,
in Compound Pt822: R'=Ph, R=Et,
in Compound Pt823: R'=Ph, R=$^i$Pr,
in Compound Pt824: R'=Ph, R=Ph,
in Compound Pt825: R'=Ph, R=2,6-($^i$Pr)$_2$Ph, Compound Pt826 through Pt840, each represented by the formula

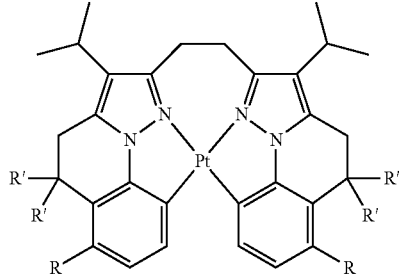

wherein in Compound Pt826: R'=H, R=Me,
in Compound Pt827: R'=H, R=Et,
in Compound Pt828: R'=H, R=$^i$Pr,
in Compound Pt829: R'=H, R=Ph,
in Compound Pt830: R'=H, R=2,6-($^i$Pr)$_2$Ph,
in Compound Pt831: R'=Me, R=Me,
in Compound Pt832: R'=Me, R=Et,
in Compound Pt833: R'=Me, R=$^i$Pr,
in Compound Pt834: R'=Me, R=Ph,
in Compound Pt835: R'=Me, R=2,6-($^i$Pr)$_2$Ph,
in Compound Pt836: R'=Ph, R=Me,
in Compound Pt837: R'=Ph, R=Et,
in Compound Pt838: R'=Ph, R=$^i$Pr,
in Compound Pt839: R'=Ph, R=Ph,
in Compound Pt840: R'=Ph, R=2,6-($^i$Pr)$_2$Ph, Compound Pt841 through Pt855, each represented by the formula

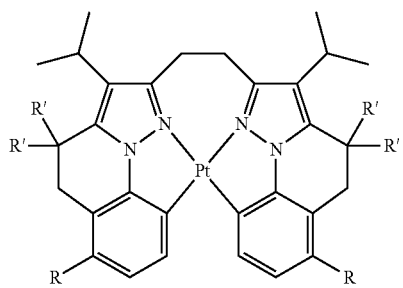

wherein in Compound Pt841: R'=H, R=Me,
in Compound Pt842: R'=H, R=Et,
in Compound Pt843: R'=H, R=$^i$Pr,
in Compound Pt844: R'=H, R=Ph,
in Compound Pt845: R'=H, R=2,6-($^i$Pr)$_2$Ph,
in Compound Pt846: R'=Me, R=Me,
in Compound Pt847: R'=Me, R=Et,
in Compound Pt848: R'=Me, R=$^i$Pr,
in Compound Pt849: R'=Me, R=Ph,
in Compound Pt850: R'=Me, R=2,6-($^i$Pr)$_2$Ph,
in Compound Pt851: R'=Ph, R=Me,
in Compound Pt852: R'=Ph, R=Et,
in Compound Pt853: R'=Ph, R=$^i$Pr,
in Compound Pt854: R'=Ph, R=Ph,
in Compound Pt855: R'=Ph, R=2,6-($^i$Pr)$_2$Ph, Compound Pt856 through Pt870, each represented by the formula

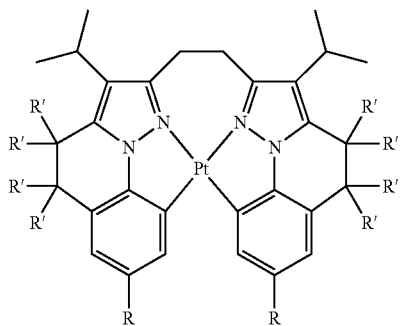

wherein in Compound Pt856: R'=H, R=Me,
in Compound Pt857: R'=H, R=Et,
in Compound Pt858: R'=H, R=$^i$Pr,
in Compound Pt859: R'=H, R=Ph,
in Compound Pt860: R'=H, R=2,6-($^i$Pr)$_2$Ph,
in Compound Pt861: R'=Me, R=Me,
in Compound Pt862: R'=Me, R=Et,
in Compound Pt863: R'=Me, R=$^i$Pr,
in Compound Pt864: R'=Me, R=Ph,
in Compound Pt865: R'=Me, R=2,6-($^i$Pr)$_2$Ph,
in Compound Pt866: R'=Ph, R=Me,
in Compound Pt867: R'=Ph, R=Et,
in Compound Pt868: R'=Ph, R=$^i$Pr,
in Compound Pt869: R'=Ph, R=Ph,
in Compound Pt870: R'=Ph, R=2,6-($^i$Pr)$_2$Ph, Compound Pt871 through Pt885, each represented by the formula

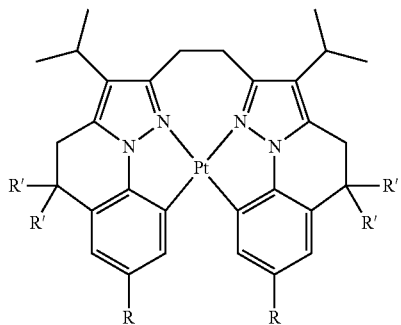

wherein in Compound Pt871: R'=H, R=Me,
in Compound Pt872: R'=H, R=Et,
in Compound Pt873: R'=H, R=$^i$Pr,
in Compound Pt874: R'=H, R=Ph,
in Compound Pt875: R'=H, R=2,6-($^i$Pr)$_2$Ph,
in Compound Pt876: R'=Me, R=Me,
in Compound Pt877: R'=Me, R=Et,
in Compound Pt878: R'=Me, R=$^i$Pr,
in Compound Pt879: R'=Me, R=Ph,
in Compound Pt880: R'=Me, R=2,6-($^i$Pr)$_2$Ph,
in Compound Pt881: R'=Ph, R=Me,
in Compound Pt882: R'=Ph, R=Et,
in Compound Pt883: R'=Ph, R=$^i$Pr,
in Compound Pt884: R'=Ph, R=Ph,
in Compound Pt885: R'=Ph, R=2,6-($^i$Pr)$_2$Ph, Compound Pt886 through Pt900, each represented by the formula

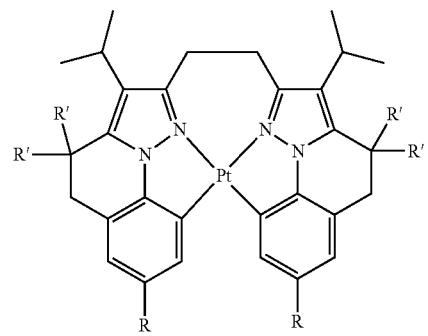

wherein in Compound Pt886: R'=H, R=Me,
in Compound Pt887: R'=H, R=Et,
in Compound Pt888: R'=H, R=$^i$Pr,
in Compound Pt889: R'=H, R=Ph,
in Compound Pt890: R'=H, R=2,6-($^i$Pr)$_2$Ph,
in Compound Pt891: R'=Me, R=Me,
in Compound Pt892: R'=Me, R=Et,
in Compound Pt893: R'=Me, R=$^i$Pr,
in Compound Pt894: R'=Me, R=Ph,
in Compound Pt895: R'=Me, R=2,6-($^i$Pr)$_2$Ph,
in Compound Pt896: R'=Ph, R=Me,
in Compound Pt897: R'=Ph, R=Et,
in Compound Pt898: R'=Ph, R=$^i$Pr,
in Compound Pt899: R'=Ph, R=Ph,
in Compound Pt900: R'=Ph, R=2,6-($^i$Pr)$_2$Ph, Compound Pt901 through Pt912, each represented by the formula

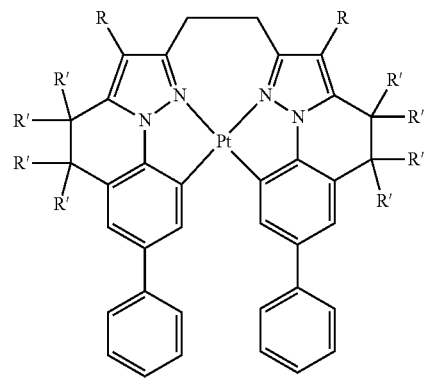

wherein in Compound Pt901: R'=H, R=Me,
in Compound Pt902: R'=H, R=Et,
in Compound Pt903: R'=H, R=2,6-($^i$Pr)$_2$-4-biphenyl,
in Compound Pt904: R'=H, R=2,4-($^i$Pr)$_2$-3-dibenzofuran,
in Compound Pt905: R'=Me, R=Me,
in Compound Pt906: R'=Me, R=Et,
in Compound Pt907: R'=Me, R=2,6-($^i$Pr)$_2$-4-biphenyl,
in Compound Pt908: R'=Me, R=2,4-($^i$Pr)$_2$-3-dibenzofuran,
in Compound Pt909: R'=Ph, R=Me,
in Compound Pt910: R'=Ph, R=Et,
in Compound Pt911: R'=Ph, R=2,6-($^i$Pr)$_2$-4-biphenyl,
in Compound Pt912: R'=Ph, R=2,4-($^i$Pr)$_2$-3-dibenzofuran, Compound Pt913 through Pt924, each represented by the formula

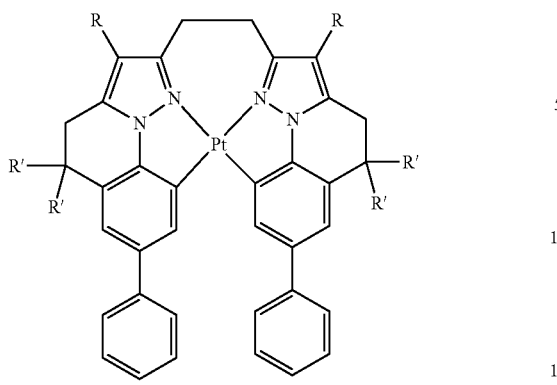

wherein in Compound Pt913: R'=H, R=Me,
in Compound Pt914: R'=H, R=Et,
in Compound Pt915: R'=H, R=2,6-($^i$Pr)$_2$-4-biphenyl,
in Compound Pt916: R'=H, R=2,4-($^i$Pr)$_2$-3-dibenzofuran,
in Compound Pt917: R'=Me, R=Me,
in Compound Pt918: R'=Me, R=Et,
in Compound Pt919: R'=Me, R=2,6-($^i$Pr)$_2$-4-biphenyl,
in Compound Pt920: R'=Me, R=2,4-($^i$Pr)$_2$-3-dibenzofuran,
in Compound Pt921: R'=Ph, R=Me,
in Compound Pt922: R'=Ph, R=Et,
in Compound Pt923: R'=Ph, R=2,6-($^i$Pr)$_2$-4-biphenyl,
in Compound Pt924: R'=Ph, R=2,4-($^i$Pr)$_2$-3-dibenzofuran,
Compound Pt925 through Pt936, each represented by the formula

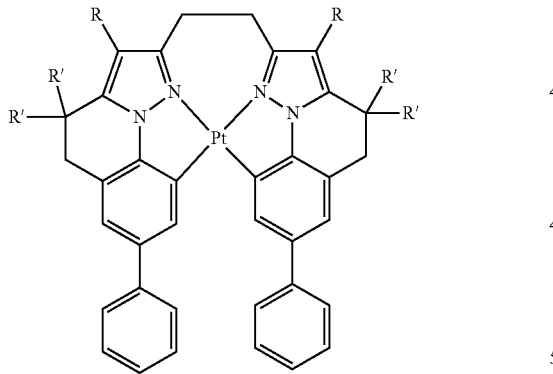

wherein in Compound Pt925: R'=H, R=Me,
in Compound Pt926: R'=H, R=Et,
in Compound Pt927: R'=H, R=2,6-($^i$Pr)$_2$-4-biphenyl,
in Compound Pt928: R'=H, R=2,4-($^i$Pr)$_2$-3-dibenzofuran,
in Compound Pt929: R'=Me, R=Me,
in Compound Pt930: R'=Me, R=Et,
in Compound Pt931: R'=Me, R=2,6-($^i$Pr)$_2$-4-biphenyl,
in Compound Pt932: R'=Me, R=2,4-($^i$Pr)$_2$-3-dibenzofuran,
in Compound Pt933: R'=Ph, R=Me,
in Compound Pt934: R'=Ph, R=Et,
in Compound Pt935: R'=Ph, R=2,6-($^i$Pr)$_2$-4-biphenyl,
in Compound Pt936: R'=Ph, R=2,4-($^i$Pr)$_2$-3-dibenzofuran, Compound Pt937 through Pt948, each represented by the formula

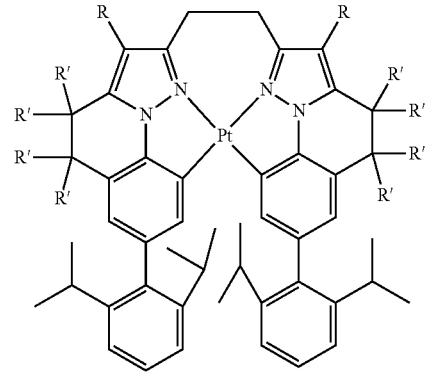

wherein in Compound Pt937: R'=H, R=Me,
in Compound Pt938: R'=H, R=Et,
in Compound Pt939: R'=H, R=2,6-($^i$Pr)$_2$-4-biphenyl,
in Compound Pt940: R'=H, R=2,4-($^i$Pr)$_2$-3-dibenzofuran,
in Compound Pt941: R'=Me, R=Me,
in Compound Pt942: R'=Me, R=Et,
in Compound Pt943: R'=Me, R=2,6-($^i$Pr)$_2$-4-biphenyl,
in Compound Pt944: R'=Me, R=2,4-($^i$Pr)$_2$-3-dibenzofuran,
in Compound Pt945: R'=Ph, R=Me,
in Compound Pt946: R'=Ph, R=Et,
in Compound Pt947: R'=Ph, R=2,6-($^i$Pr)$_2$-4-biphenyl,
in Compound Pt948: R'=Ph, R=2,4-($^i$Pr)$_2$-3-dibenzofuran,
Compound Pt949 through Pt960, each represented by the formula

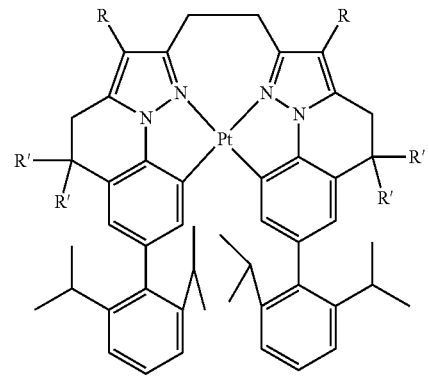

wherein in Compound Pt949: R'=H, R=Me,
in Compound Pt950: R'=H, R=Et,
in Compound Pt951: R'=H, R=2,6-($^i$Pr)$_2$-4-biphenyl,
in Compound Pt952: R'=H, R=2,4-($^i$Pr)$_2$-3-dibenzofuran,
in Compound Pt953: R'=Me, R=Me,
in Compound Pt954: R'=Me, R=Et,
in Compound Pt955: R'=Me, R=2,6-($^i$Pr)$_2$-4-biphenyl,
in Compound Pt956: R'=Me, R=2,4-($^i$Pr)$_2$-3-dibenzofuran,
in Compound Pt957: R'=Ph, R=Me,
in Compound Pt958: R'=Ph, R=Et,
in Compound Pt959: R'=Ph, R=2,6-($^i$Pr)$_2$-4-biphenyl, in Compound Pt960: R'=Ph, R=2,4-($^i$Pr)$_2$-3-dibenzofuran, Compound Pt961 through Pt972, each represented by the formula

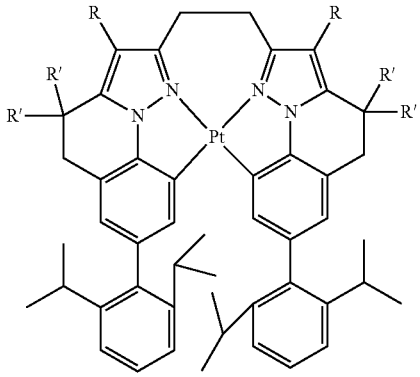

wherein in Compound Pt961: R'=H, R=Me,
in Compound Pt962: R'=H, R=Et,
in Compound Pt963: R'=H, R=2,6-($^i$Pr)$_2$-4-biphenyl,
in Compound Pt964: R'=H, R=2,4-($^i$Pr)$_2$-3-dibenzofuran,
in Compound Pt965: R'=Me, R=Me,
in Compound Pt966: R'=Me, R=Et,
in Compound Pt967: R'=Me, R=2,6-($^i$Pr)$_2$-4-biphenyl,
in Compound Pt968: R'=Me, R=2,4-($^i$Pr)$_2$-3-dibenzofuran,
in Compound Pt969: R'=Ph, R=Me,
in Compound Pt970: R'=Ph, R=Et,
in Compound Pt971: R'=Ph, R=2,6-($^i$Pr)$_2$-4-biphenyl,
in Compound Pt972: R'=Ph, R=2,4-($^i$Pr)$_2$-3-dibenzofuran, Compound Pt973 through Pt984, each represented by the formula

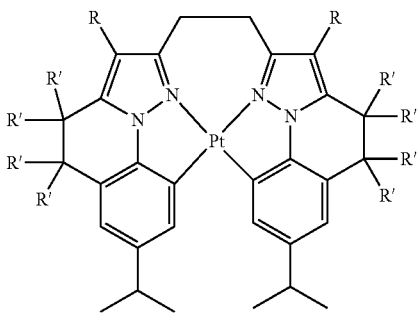

wherein in Compound Pt973: R'=H, R=Me,
in Compound Pt974: R'=H, R=Et,
in Compound Pt975: R'=H, R=2,6-($^i$Pr)$_2$-4-biphenyl,
in Compound Pt976: R'=H, R=2,4-($^i$Pr)$_2$-3-dibenzofuran,
in Compound Pt977: R'=Me, R=Me,
in Compound Pt978: R'=Me, R=Et,
in Compound Pt979: R'=Me, R=2,6-($^i$Pr)$_2$-4-biphenyl,
in Compound Pt980: R'=Me, R=2,4-($^i$Pr)$_2$-3-dibenzofuran,
in Compound Pt981: R'=Ph, R=Me,
in Compound Pt982: R'=Ph, R=Et,
in Compound Pt983: R'=Ph, R=2,6-($^i$Pr)$_2$-4-biphenyl,
in Compound Pt984: R'=Ph, R=2,4-($^i$Pr)$_2$-3-dibenzofuran, Compound Pt985 through Pt996, each represented by the formula

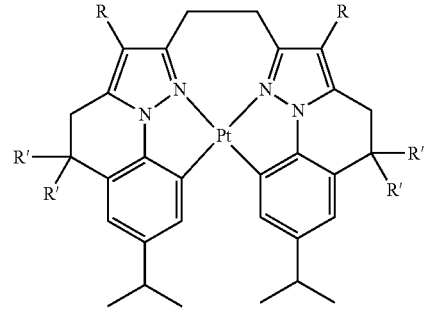

wherein in Compound Pt985: R'=H, R=Me,
in Compound Pt986: R'=H, R=Et,
in Compound Pt987: R'=H, R=2,6-($^i$Pr)$_2$-4-biphenyl,
in Compound Pt988: R'=H, R=2,4-($^i$Pr)$_2$-3-dibenzofuran,
in Compound Pt989: R'=Me, R=Me,
in Compound Pt990: R'=Me, R=Et,
in Compound Pt991: R'=Me, R=2,6-($^i$Pr)$_2$-4-biphenyl,
in Compound Pt992: R'=Me, R=2,4-($^i$Pr)$_2$-3-dibenzofuran,
in Compound Pt993: R'=Ph, R=Me,
in Compound Pt994: R'=Ph, R=Et,
in Compound Pt995: R'=Ph, R=2,6-($^i$Pr)$_2$-4-biphenyl,
in Compound Pt996: R'=Ph, R=2,4-($^i$Pr)$_2$-3-dibenzofuran, Compound Pt997 through Pt1008, each represented by the formula

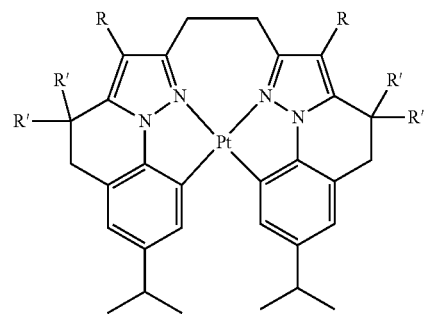

wherein in Compound Pt997: R'=H, R=Me,
in Compound Pt998: R'=H, R=Et,
in Compound Pt999: R'=H, R=2,6-($^i$Pr)$_2$-4-biphenyl,
in Compound Pt1000: R'=H, R=2,4-($^i$Pr)$_2$-3-dibenzofuran,
in Compound Pt1001: R'=Me, R=Me,
in Compound Pt1002: R'=Me, R=Et,
in Compound Pt1003: R'=Me, R=2,6-($^i$Pr)$_2$-4-biphenyl,
in Compound Pt1004: R'=Me, R=2,4-($^i$Pr)$_2$-3-dibenzofuran,
in Compound Pt1005: R'=Ph, R=Me,
in Compound Pt1006: R'=Ph, R=Et,
in Compound Pt1007: R'=Ph, R=2,6-($^i$Pr)$_2$-4-biphenyl,
in Compound Pt1008: R'=Ph, R=2,4-($^i$Pr)$_2$-3-dibenzofuran, Compound Pt1009 through Pt1023, each represented by the formula

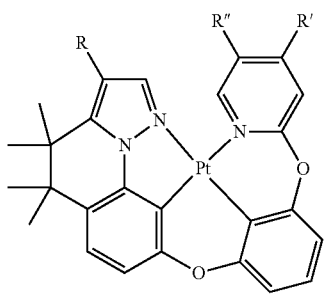

wherein in Compound Pt1009: R'=H, R"=H, R=H,
in Compound Pt1010: R'=H, R"=H, R=Me,
in Compound Pt1011: R'=H, R"=H, R=Ph,
in Compound Pt1012: R'=H, R"=H, R=2,6-($^i$Pr)$_2$Ph,
in Compound Pt1013: R'=H, R"=H, R=2,6-($^i$Pr)$_2$-4-biphenyl,
in Compound Pt1014: R'=H, R"=Me, R=H,
in Compound Pt1015: R'=H, R"=Me, R=Me,
in Compound Pt1016: R'=H, R"=Me, R=Ph,
in Compound Pt1017: R'=H, R"=Me, R=2,6-($^i$Pr)$_2$Ph,
in Compound Pt1018: R'=H, R"=Me, R=2,6-($^i$Pr)$_2$-4-biphenyl,
in Compound Pt1019: R'=Me, R"=H, R=H,
in Compound Pt1020: R'=Me, R"=H, R=Me,
in Compound Pt1021: R'=Me, R"=H, R=Ph,
in Compound Pt1022: R'=Me, R"=H, R=2,6-($^i$Pr)$_2$Ph,
in Compound Pt1023: R'=Me, R"=H, R=2,6-($^i$Pr)$_2$-4-biphenyl, Compound Pt1024 through Pt1038, each represented by the formula

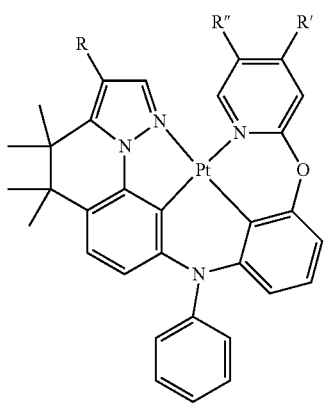

wherein in Compound Pt1024: R'=H, R"=H, R=H,
in Compound Pt1025: R'=H, R"=H, R=Me,
in Compound Pt1026: R'=H, R"=H, R=Ph,
in Compound Pt1027: R'=H, R"=H, R=2,6-($^i$Pr)$_2$Ph,
in Compound Pt1028: R'=H, R"=H, R=2,6-($^i$Pr)$_2$-4-biphenyl,
in Compound Pt1029: R'=H, R"=Me, R=H,
in Compound Pt1030: R'=H, R"=Me, R=Me,
in Compound Pt1031: R'=H, R"=Me, R=Ph,
in Compound Pt1032: R'=H, R"=Me, R=2,6-($^i$Pr)$_2$Ph,
in Compound Pt1033: R'=H, R"=Me, R=2,6-($^i$Pr)$_2$-4-biphenyl,
in Compound Pt1034: R'=Me, R"=H, R=H,
in Compound Pt1035: R'=Me, R"=H, R=Me,
in Compound Pt1036: R'=Me, R"=H, R=Ph,
in Compound Pt1037: R'=Me, R"=H, R=2,6-($^i$Pr)$_2$Ph,
in Compound Pt1038: R'=Me, R"=H, R=2,6-($^i$Pr)$_2$-4-biphenyl, Compound Pt1039 through Pt1053, each represented by the formula

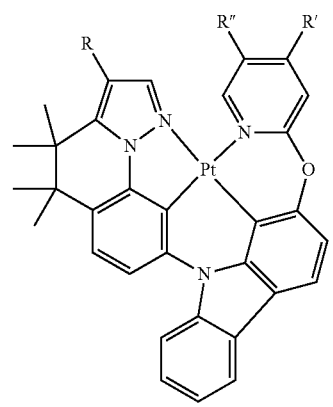

wherein in Compound Pt1039: R'=H, R"=H, R=H,
in Compound Pt1040: R'=H, R"=H, R=Me,
in Compound Pt1041: R'=H, R"=H, R=Ph,
in Compound Pt1042: R'=H, R"=H, R=2,6-($^i$Pr)$_2$Ph,
in Compound Pt1043: R'=H, R"=H, R=2,6-($^i$Pr)$_2$-4-biphenyl,
in Compound Pt1044: R'=H, R"=Me, R=H,
in Compound Pt1045: R'=H, R"=Me, R=Me,
in Compound Pt1046: R'=H, R"=Me, R=Ph,
in Compound Pt1047: R'=H, R"=Me, R=2,6-($^i$Pr)$_2$Ph,
in Compound Pt1048: R'=H, R"=Me, R=2,6-($^i$Pr)$_2$-4-biphenyl,
in Compound Pt1049: R'=Me, R"=H, R=H,
in Compound Pt1050: R'=Me, R"=H, R=Me,
in Compound Pt1051: R'=Me, R"=H, R=Ph,
in Compound Pt1052: R'=Me, R"=H, R=2,6-($^i$Pr)$_2$Ph,
in Compound Pt1053: R'=Me, R"=H, R=2,6-($^i$Pr)$_2$-4-biphenyl, Compound Pt1054 through Pt1068, each represented by the formula

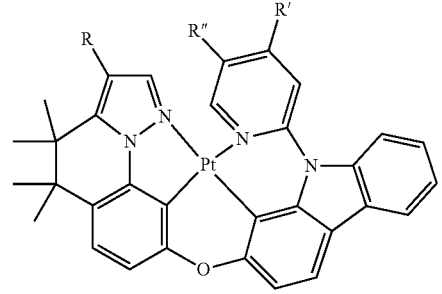

wherein in Compound Pt1054: R'=H, R"=H, R=H,
in Compound Pt1055: R'=H, R"=H, R=Me,
in Compound Pt1056: R'=H, R"=H, R=Ph,
in Compound Pt1057: R'=H, R"=H, R=2,6-($^i$Pr)$_2$Ph,
in Compound Pt1058: R'=H, R"=H, R=2,6-($^i$Pr)$_2$-4-biphenyl, in Compound Pt1059: R'=H, R"=Me, R=H,
in Compound Pt1060: R'=H, R"=Me, R=Me,
in Compound Pt1061: R'=H, R"=Me, R=Ph,
in Compound Pt1062: R'=H, R"=Me, R=2,6-($^i$Pr)$_2$Ph,
in Compound Pt1063: R'=H, R"=Me, R=2,6-($^i$Pr)$_2$-4-biphenyl,
in Compound Pt1064: R'=Me, R"=H, R=H,
in Compound Pt1065: R'=Me, R"=H, R=Me,
in Compound Pt1066: R'=Me, R"=H, R=Ph,
in Compound Pt1067: R'=Me, R"=H, R=2,6-($^i$Pr)$_2$Ph,
in Compound Pt1068: R'=Me, R"=H, R=2,6-($^i$Pr)$_2$-4-biphenyl, Compound Pt1069 through Pt1083, each represented by the formula

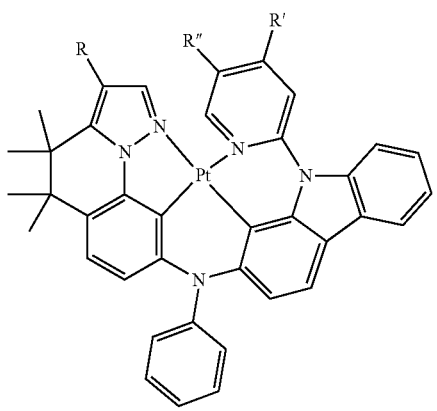

wherein in Compound Pt1069: R'=H, R"=H, R=H,
in Compound Pt1070: R'=H, R"=H, R=Me,
in Compound Pt1071: R'=H, R"=H, R=Ph,
in Compound Pt1072: R'=H, R"=H, R=2,6-($^i$Pr)$_2$Ph,
in Compound Pt1073: R'=H, R"=H, R=2,6-($^i$Pr)$_2$-4-biphenyl,
in Compound Pt1074: R'=H, R"=Me, R=H,
in Compound Pt1075: R'=H, R"=Me, R=Me,
in Compound Pt1076: R'=H, R"=Me, R=Ph,
in Compound Pt1077: R'=H, R"=Me, R=2,6-($^i$Pr)$_2$Ph,
in Compound Pt1078: R'=H, R"=Me, R=2,6-($^i$Pr)$_2$-4-biphenyl,
in Compound Pt1079: R'=Me, R"=H, R=H,
in Compound Pt1080: R'=Me, R"=H, R=Me,
in Compound Pt1081: R'=Me, R"=H, R=Ph,
in Compound Pt1082: R'=Me, R"=H, R=2,6-($^i$Pr)$_2$Ph,
in Compound Pt1083: R'=Me, R"=H, R=2,6-($^i$Pr)$_2$-4-biphenyl, Compound Pt1084 through Pt1097, each represented by the formula

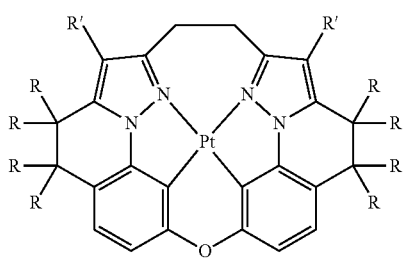

wherein in Compound Pt1084: R=Me, R'=H,
in Compound Pt1085: R=Me, R'=Me,
in Compound Pt1086: R=Me, R'=$^i$Pr,
in Compound Pt1087: R=Me, R'=Ph,
in Compound Pt1088: R=Me, R'=2,6-($^i$Pr)$_2$Ph,
in Compound Pt1089: R=Me, R'=2,6-($^i$Pr)$_2$-4-biphenyl,
in Compound Pt1090: R=Me, R'=2,4-($^i$Pr)$_2$-3-dibenzofuran,
in Compound Pt1091: R=Ph, R'=H,
in Compound Pt1092: R=Ph, R'=Me,
in Compound Pt1093: R=Ph, R'=$^i$Pr,
in Compound Pt1094: R=Ph, R'=Ph,
in Compound Pt1095: R=Ph, R'=2,6-($^i$Pr)$_2$Ph,
in Compound Pt1096: R=Ph, R'=2,6-($^i$Pr)$_2$-4-biphenyl,
in Compound Pt1097: R=Ph, R'=2,4-($^i$Pr)$_2$-3-dibenzofuran, Compound Pt1098 through Pt1111, each represented by the formula

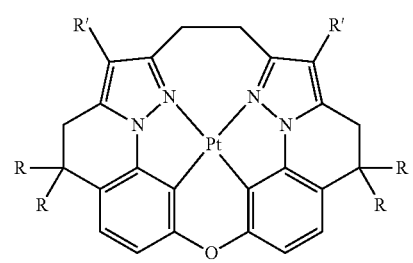

wherein in Compound Pt1098: R=Me, R'=H,
in Compound Pt1099: R=Me, R'=Me,
in Compound Pt1100: R=Me, R'=$^i$Pr,
in Compound Pt1101: R=Me, R'=Ph,
in Compound Pt1102: R=Me, R'=2,6-($^i$Pr)$_2$Ph,
in Compound Pt1103: R=Me, R'=2,6-($^i$Pr)$_2$-4-biphenyl,
in Compound Pt1104: R=Me, R'=2,4-($^i$Pr)$_2$-3-dibenzofuran,
in Compound Pt1105: R=Ph, R'=H,
in Compound Pt1106: R=Ph, R'=Me,
in Compound Pt1107: R=Ph, R'=$^i$Pr,
in Compound Pt1108: R=Ph, R'=Ph,
in Compound Pt1109: R=Ph, R'=2,6-($^i$Pr)$_2$Ph,
in Compound Pt1110: R=Ph, R'=2,6-($^i$Pr)$_2$-4-biphenyl,
in Compound Pt1111: R=Ph, R'=2,4-($^i$Pr)$_2$-3-dibenzofuran, Compound Pt1112 through Pt1125, each represented by the formula

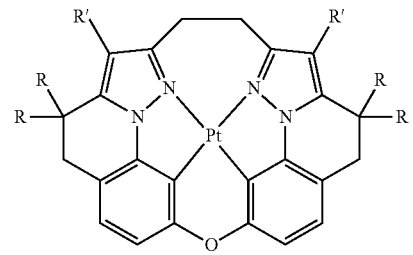

wherein in Compound Pt1112: R=Me, R'=H,
in Compound Pt1113: R=Me, R'=Me,
in Compound Pt1114: R=Me, R'=$^i$Pr,
in Compound Pt1115: R=Me, R'=Ph,
in Compound Pt1116: R=Me, R'=2,6-($^i$Pr)$_2$Ph, in Compound Pt1117: R=Me, R'=2,6-($^i$Pr)$_2$-4-biphenyl,
in Compound Pt1118: R=Me, R'=2,4-($^i$Pr)$_2$-3-dibenzofuran,
in Compound Pt1119: R=Ph, R'=H,
in Compound Pt1120: R=Ph, R'=Me,
in Compound Pt1121: R=Ph, R'=$^i$Pr,
in Compound Pt1122: R=Ph, R'=Ph,
in Compound Pt1123: R=Ph, R'=2,6-($^i$Pr)$_2$Ph,
in Compound Pt1124: R=Ph, R'=2,6-($^i$Pr)$_2$-4-biphenyl,
in Compound Pt1125: R=Ph, R'=2,4-($^i$Pr)$_2$-3-dibenzofuran, Compound Pt1126 through Pt1139, each represented by the formula

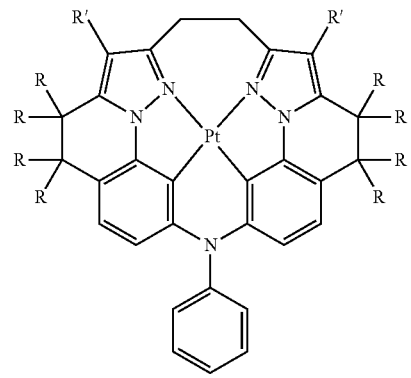

wherein in Compound Pt1126: R=Me, R'=H,
in Compound Pt1127: R=Me, R'=Me,
in Compound Pt1128: R=Me, R'=$^i$Pr,
in Compound Pt1129: R=Me, R'=Ph,
in Compound Pt1130: R=Me, R'=2,6-($^i$Pr)$_2$Ph,
in Compound Pt1131: R=Me, R'=2,6-($^i$Pr)$_2$-4-biphenyl,
in Compound Pt1132: R=Me, R'=2,4-($^i$Pr)$_2$-3-dibenzofuran,
in Compound Pt1133: R=Ph, R'=H,
in Compound Pt1134: R=Ph, R'=Me,
in Compound Pt1135: R=Ph, R'=$^i$Pr,
in Compound Pt1136: R=Ph, R'=Ph,
in Compound Pt1137: R=Ph, R'=2,6-($^i$Pr)$_2$Ph,
in Compound Pt1138: R=Ph, R'=2,6-($^i$Pr)$_2$-4-biphenyl,
in Compound Pt1139: R=Ph, R'=2,4-($^i$Pr)$_2$-3-dibenzofuran, Compound Pt1140 through Pt1153, each represented by the formula

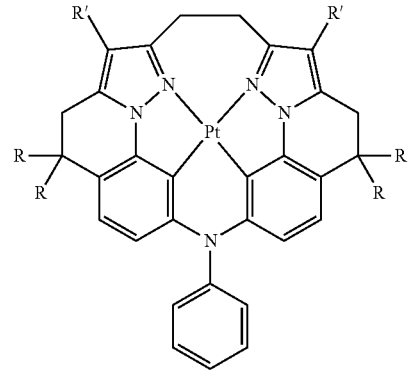

wherein in Compound Pt1140: R=Me, R'=H,
in Compound Pt1141: R=Me, R'=Me,
in Compound Pt1142: R=Me, R'=$^i$Pr,
in Compound Pt1143: R=Me, R'=Ph,
in Compound Pt1144: R=Me, R'=2,6-($^i$Pr)$_2$Ph,
in Compound Pt1145: R=Me, R'=2,6-($^i$Pr)$_2$-4-biphenyl,
in Compound Pt1146: R=Me, R'=2,4-($^i$Pr)$_2$-3-dibenzofuran,
in Compound Pt1147: R=Ph, R'=H,
in Compound Pt1148: R=Ph, R'=Me,
in Compound Pt1149: R=Ph, R'=$^i$Pr,
in Compound Pt1150: R=Ph, R'=Ph,
in Compound Pt1151: R=Ph, R'=2,6-($^i$Pr)$_2$Ph,
in Compound Pt1152: R=Ph, R'=2,6-($^i$Pr)$_2$-4-biphenyl,
in Compound Pt1153: R=Ph, R'=2,4-($^i$Pr)$_2$-3-dibenzofuran, Compound Pt1154 through Pt1167, each represented by the formula

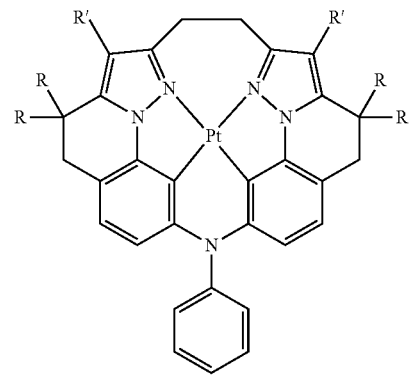

wherein in Compound Pt1154: R=Me, R'=H,
in Compound Pt1155: R=Me, R'=Me,
in Compound Pt1156: R=Me, R'=$^i$Pr,
in Compound Pt1157: R=Me, R'=Ph,
in Compound Pt1158: R=Me, R'=2,6-($^i$Pr)$_2$Ph,
in Compound Pt1159: R=Me, R'=2,6-($^i$Pr)$_2$-4-biphenyl,
in Compound Pt1160: R=Me, R'=2,4-($^i$Pr)$_2$-3-dibenzofuran,
in Compound Pt1161: R=Ph, R'=H,
in Compound Pt1162: R=Ph, R'=Me,
in Compound Pt1163: R=Ph, R'=$^i$Pr,
in Compound Pt1164: R=Ph, R'=Ph,
in Compound Pt1165: R=Ph, R'=2,6-($^i$Pr)$_2$Ph,
in Compound Pt1166: R=Ph, R'=2,6-($^i$Pr)$_2$-4-biphenyl,
in Compound Pt1167: R=Ph, R'=2,4-($^i$Pr)$_2$-3-dibenzofuran, Compound Pt1168 through Pt1181, each represented by the formula

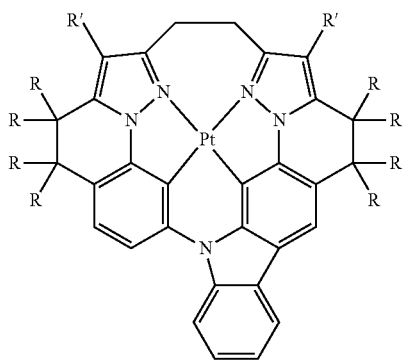

wherein in Compound Pt1168: R=Me, R'=H,
in Compound Pt1169: R=Me, R'=Me,
in Compound Pt1170: R=Me, R'=$^{i}$Pr,
in Compound Pt1171: R=Me, R'=Ph,
in Compound Pt1172: R=Me, R'=2,6-($^{i}$Pr)$_2$Ph,
in Compound Pt1173: R=Me, R'=2,6-($^{i}$Pr)$_2$-4-biphenyl,
in Compound Pt1174: R=Me, R'=2,4-($^{i}$Pr)$_2$-3-dibenzofuran,
in Compound Pt1175: R=Ph, R'=H,
in Compound Pt1176: R=Ph, R'=Me,
in Compound Pt1177: R=Ph, R'=$^{i}$Pr,
in Compound Pt1178: R=Ph, R'=Ph,
in Compound Pt1179: R=Ph, R'=2,6-($^{i}$Pr)$_2$Ph,
in Compound Pt1180: R=Ph, R'=2,6-($^{i}$Pr)$_2$-4-biphenyl,
in Compound Pt1181: R=Ph, R'=2,4-($^{i}$Pr)$_2$-3-dibenzofuran, Compound Pt1182 through Pt1195, each represented by the formula

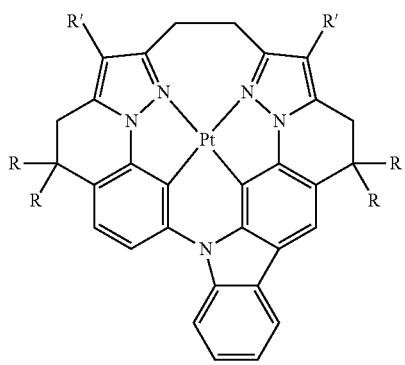

wherein in Compound Pt1182: R=Me, R'=H,
in Compound Pt1183: R=Me, R'=Me,
in Compound Pt1184: R=Me, R'=$^{i}$Pr,
in Compound Pt1185: R=Me, R'=Ph,
in Compound Pt1186: R=Me, R'=2,6-($^{i}$Pr)$_2$Ph,
in Compound Pt1187: R=Me, R'=2,6-($^{i}$Pr)$_2$-4-biphenyl,
in Compound Pt1188: R=Me, R'=2,4-($^{i}$Pr)$_2$-3-dibenzofuran,
in Compound Pt1189: R=Ph, R'=H,
in Compound Pt1190: R=Ph, R'=Me,
in Compound Pt1191: R=Ph, R'=$^{i}$Pr,
in Compound Pt1192: R=Ph, R'=Ph,
in Compound Pt1193: R=Ph, R'=2,6-($^{i}$Pr)$_2$Ph,
in Compound Pt1194: R=Ph, R'=2,6-($^{i}$Pr)$_2$-4-biphenyl,
in Compound Pt1195: R=Ph, R'=2,4-($^{i}$Pr)$_2$-3-dibenzofuran, Compound Pt1196 through Pt1209, each represented by the formula

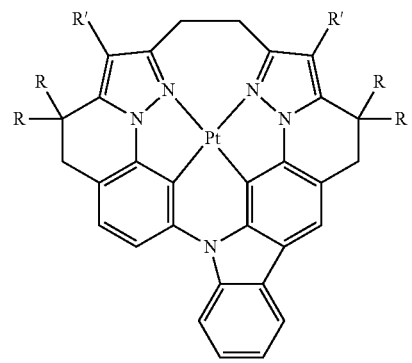

wherein in Compound Pt1196: R=Me, R'=H,
in Compound Pt1197: R=Me, R'=Me,
in Compound Pt1198: R=Me, R'=$^{i}$Pr,
in Compound Pt1199: R=Me, R'=Ph,
in Compound Pt1200: R=Me, R'=2,6-($^{i}$Pr)$_2$Ph,
in Compound Pt1201: R=Me, R'=2,6-($^{i}$Pr)$_2$-4-biphenyl,
in Compound Pt1202: R=Me, R'=2,4-($^{i}$Pr)$_2$-3-dibenzofuran,
in Compound Pt1203: R=Ph, R'=H,
in Compound Pt1204: R=Ph, R'=Me,
in Compound Pt1205: R=Ph, R'=$^{i}$Pr,
in Compound Pt1206: R=Ph, R'=Ph,
in Compound Pt1207: R=Ph, R'=2,6-($^{i}$Pr)$_2$Ph,
in Compound Pt1208: R=Ph, R'=2,6-($^{i}$Pr)$_2$-4-biphenyl,
in Compound Pt1209: R=Ph, R'=2,4-($^{i}$Pr)$_2$-3-dibenzofuran, Compound Pt1210 through Pt1223, each represented by the formula

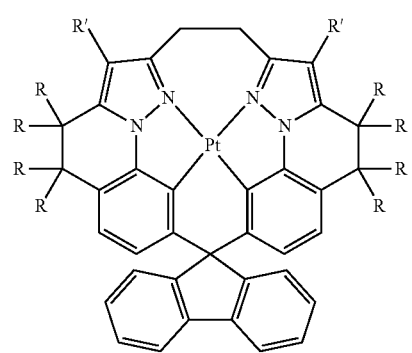

wherein in Compound Pt1210: R=Me, R'=H,
in Compound Pt1211: R=Me, R'=Me,
in Compound Pt1212: R=Me, R'=$^{i}$Pr,
in Compound Pt1213: R=Me, R'=Ph,
in Compound Pt1214: R=Me, R'=2,6-($^{i}$Pr)$_2$Ph,
in Compound Pt1215: R=Me, R'=2,6-($^{i}$Pr)$_2$-4-biphenyl,
in Compound Pt1216: R=Me, R'=2,4-($^{i}$Pr)$_2$-3-dibenzofuran,
in Compound Pt1217: R=Ph, R'=H,
in Compound Pt1218: R=Ph, R'=Me,
in Compound Pt1219: R=Ph, R'=$^{i}$Pr,
in Compound Pt1220: R=Ph, R'=Ph, in Compound Pt1221: R=Ph, R'=2,6-($^{i}$Pr)$_2$Ph,
in Compound Pt1222: R=Ph, R'=2,6-($^{i}$Pr)$_2$-4-biphenyl,
in Compound Pt1223: R=Ph, R'=2,4-($^{i}$Pr)$_2$-3-dibenzofuran, Compound Pt1224 through Pt1237, each represented by the formula

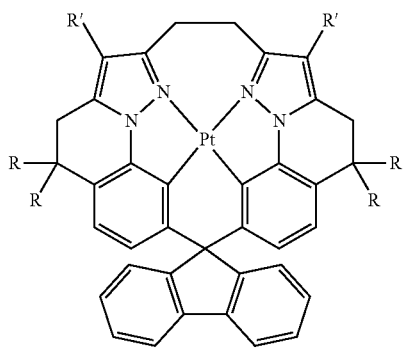

wherein in Compound Pt1224: R=Me, R'=H,
in Compound Pt1225: R=Me, R'=Me,
in Compound Pt1226: R=Me, R'=$^{i}$Pr,
in Compound Pt1227: R=Me, R'=Ph,
in Compound Pt1228: R=Me, R'=2,6-($^{i}$Pr)$_2$Ph,
in Compound Pt1229: R=Me, R'=2,6-($^{i}$Pr)$_2$-4-biphenyl,
in Compound Pt1230: R=Me, R'=2,4-($^{i}$Pr)$_2$-3-dibenzofuran,
in Compound Pt1231: R=Ph, R'=H,
in Compound Pt1232: R=Ph, R'=Me,
in Compound Pt1233: R=Ph, R'=$^{i}$Pr,
in Compound Pt1234: R=Ph, R'=Ph,
in Compound Pt1235: R=Ph, R'=2,6-($^{i}$Pr)$_2$Ph,
in Compound Pt1236: R=Ph, R'=2,6-($^{i}$Pr)$_2$-4-biphenyl,
in Compound Pt1237: R=Ph, R'=2,4-($^{i}$Pr)$_2$-3-dibenzofuran, Compound Pt1238 through Pt1251, each represented by the formula

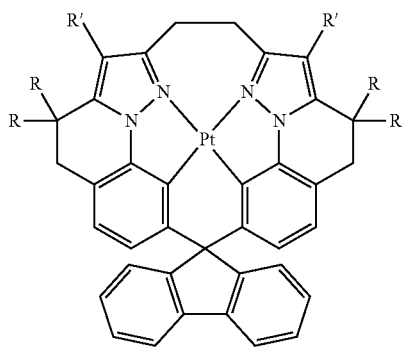

wherein in Compound Pt1238: R=Me, R'=H,
in Compound Pt1239: R=Me, R'=Me,
in Compound Pt1240: R=Me, R'=$^{i}$Pr,
in Compound Pt1241: R=Me, R'=Ph,
in Compound Pt1242: R=Me, R'=2,6-($^{i}$Pr)$_2$Ph,
in Compound Pt1243: R=Me, R'=2,6-($^{i}$Pr)$_2$-4-biphenyl,
in Compound Pt1244: R=Me, R'=2,4-($^{i}$Pr)$_2$-3-dibenzofuran,
in Compound Pt1245: R=Ph, R'=H,
in Compound Pt1246: R=Ph, R'=Me,
in Compound Pt1247: R=Ph, R'=$^{i}$Pr,
in Compound Pt1248: R=Ph, R'=Ph,
in Compound Pt1249: R=Ph, R'=2,6-($^{i}$Pr)$_2$Ph,
in Compound Pt1250: R=Ph, R'=2,6-($^{i}$Pr)$_2$-4-biphenyl,
in Compound Pt1251: R=Ph, R'=2,4-($^{i}$Pr)$_2$-3-dibenzofuran, Compound Pt1252 through Pt1265, each represented by the formula

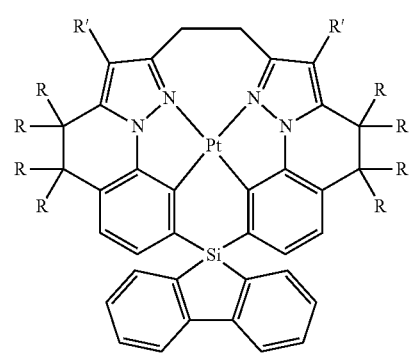

wherein in Compound Pt1252: R=Me, R'=H,
in Compound Pt1253: R=Me, R'=Me,
in Compound Pt1254: R=Me, R'=$^{i}$Pr,
in Compound Pt1255: R=Me, R'=Ph,
in Compound Pt1256: R=Me, R'=2,6-($^{i}$Pr)$_2$Ph,
in Compound Pt1257: R=Me, R'=2,6-($^{i}$Pr)$_2$-4-biphenyl,
in Compound Pt1258: R=Me, R'=2,4-($^{i}$Pr)$_2$-3-dibenzofuran,
in Compound Pt1259: R=Ph, R'=H,
in Compound Pt1260: R=Ph, R'=Me,
in Compound Pt1261: R=Ph, R'=$^{i}$Pr,
in Compound Pt1262: R=Ph, R'=Ph,
in Compound Pt1263: R=Ph, R'=2,6-($^{i}$Pr)$_2$Ph,
in Compound Pt1264: R=Ph, R'=2,6-($^{i}$Pr)$_2$-4-biphenyl,
in Compound Pt1265: R=Ph, R'=2,4-($^{i}$Pr)$_2$-3-dibenzofuran, Compound Pt1266 through Pt1279, each represented by the formula

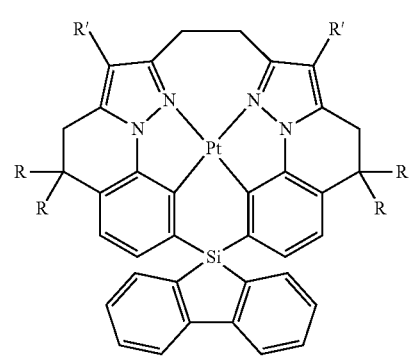

wherein in Compound Pt1266: R=Me, R'=H,
in Compound Pt1267: R=Me, R'=Me,
in Compound Pt1268: R=Me, R'=$^{i}$Pr,
in Compound Pt1269: R=Me, R'=Ph,
in Compound Pt1270: R=Me, R'=2,6-($^{i}$Pr)$_2$Ph, in Compound Pt1271: R=Me, R'=2,6-($^i$Pr)$_2$-4-biphenyl, in Compound Pt1272: R=Me, R'=2,4-($^i$Pr)$_2$-3-dibenzofuran, in Compound Pt1273: R=Ph, R'=H, in Compound Pt1274: R=Ph, R'=Me, in Compound Pt1275: R=Ph, R'=$^i$Pr, in Compound Pt1276: R=Ph, R'=Ph, in Compound Pt1277: R=Ph, R'=2,6-($^i$Pr)$_2$Ph, in Compound Pt1278: R=Ph, R'=2,6-($^i$Pr)$_2$-4-biphenyl, in Compound Pt1279: R=Ph, R'=2,4-($^i$Pr)$_2$-3-dibenzofuran, Compound Pt1280 through Pt1293, each represented by the formula

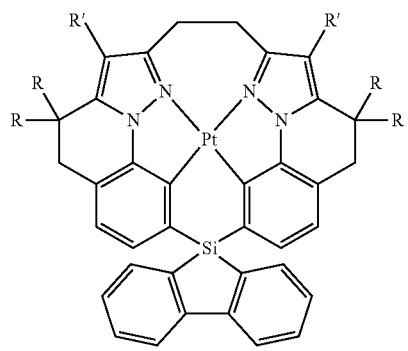

wherein in Compound Pt1280: R=Me, R'=H, in Compound Pt1281: R=Me, R'=Me, in Compound Pt1282: R=Me, R'=$^i$Pr, in Compound Pt1283: R=Me, R'=Ph, in Compound Pt1284: R=Me, R'=2,6-($^i$Pr)$_2$Ph, in Compound Pt1285: R=Me, R'=2,6-($^i$Pr)$_2$-4-biphenyl, in Compound Pt1286: R=Me, R'=2,4-($^i$Pr)$_2$-3-dibenzofuran, in Compound Pt1287: R=Ph, R'=H, in Compound Pt1288: R=Ph, R'=Me, in Compound Pt1289: R=Ph, R'=$^i$Pr, in Compound Pt1290: R=Ph, R'=Ph, in Compound Pt1291: R=Ph, R'=2,6-($^i$Pr)$_2$Ph, in Compound Pt1292: R=Ph, R'=2,6-($^i$Pr)$_2$-4-biphenyl, in Compound Pt1293: R=Ph, R'=2,4-($^i$Pr)$_2$-3-dibenzofuran, Compound Pt1294 through Pt1307, each represented by the formula

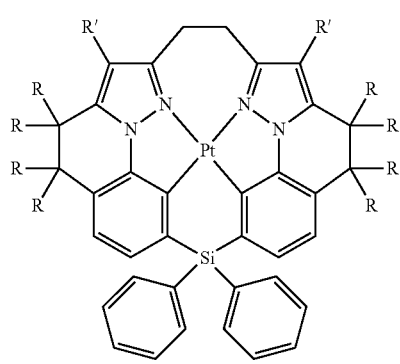

wherein in Compound Pt1294: R=Me, R'=H, in Compound Pt1295: R=Me, R'=Me, in Compound Pt1296: R=Me, R'=$^i$Pr, in Compound Pt1297: R=Me, R'=Ph, in Compound Pt1298: R=Me, R'=2,6-($^i$Pr)$_2$Ph, in Compound Pt1299: R=Me, R'=2,6-($^i$Pr)$_2$-4-biphenyl, in Compound Pt1300: R=Me, R'=2,4-($^i$Pr)$_2$-3-dibenzofuran, in Compound Pt1301: R=Ph, R'=H, in Compound Pt1302: R=Ph, R'=Me, in Compound Pt1303: R=Ph, R'=$^i$Pr, in Compound Pt1304: R=Ph, R'=Ph, in Compound Pt1305: R=Ph, R'=2,6-($^i$Pr)$_2$Ph, in Compound Pt1306: R=Ph, R'=2,6-($^i$Pr)$_2$-4-biphenyl, in Compound Pt1307: R=Ph, R'=2,4-($^i$Pr)$_2$-3-dibenzofuran, Compound Pt1308 through Pt1321, each represented by the formula

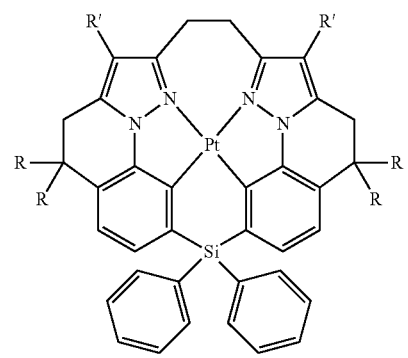

wherein in Compound Pt1308: R=Me, R'=H, in Compound Pt1309: R=Me, R'=Me, in Compound Pt1310: R=Me, R'=$^i$Pr, in Compound Pt1311: R=Me, R'=Ph, in Compound Pt1312: R=Me, R'=2,6-($^i$Pr)$_2$Ph, in Compound Pt1313: R=Me, R'=2,6-($^i$Pr)$_2$-4-biphenyl, in Compound Pt1314: R=Me, R'=2,4-($^i$Pr)$_2$-3-dibenzofuran, in Compound Pt1315: R=Ph, R'=H, in Compound Pt1316: R=Ph, R'=Me, in Compound Pt1317: R=Ph, R'=$^i$Pr, in Compound Pt1318: R=Ph, R'=Ph, in Compound Pt1319: R=Ph, R'=2,6-($^i$Pr)$_2$Ph, in Compound Pt1320: R=Ph, R'=2,6-($^i$Pr)$_2$-4-biphenyl, in Compound Pt1321: R=Ph, R'=2,4-($^i$Pr)$_2$-3-dibenzofuran, Compound Pt1322 through Pt1335, each represented by the formula

331

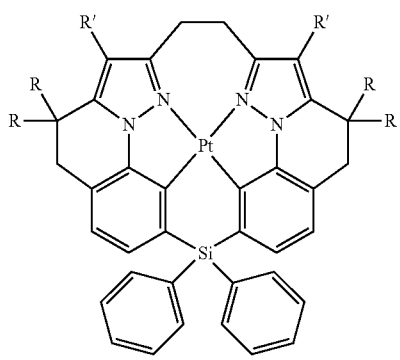

wherein in Compound Pt1322: R=Me, R'=H,
in Compound Pt1323: R=Me, R'=Me,
in Compound Pt1324: R=Me, R'=$^i$Pr,
in Compound Pt1325: R=Me, R'=Ph,
in Compound Pt1326: R=Me, R'=2,6-($^i$Pr)$_2$Ph,
in Compound Pt1327: R=Me, R'=2,6-($^i$Pr)$_2$-4-biphenyl,
in Compound Pt1328: R=Me, R'=2,4-($^i$Pr)$_2$-3-dibenzofuran,
in Compound Pt1329: R=Ph, R'=H,
in Compound Pt1330: R=Ph, R'=Me,
in Compound Pt1331: R=Ph, R'=$^i$Pr,
in Compound Pt3332: R=Ph, R'=Ph,
in Compound Pt1333: R=Ph, R'=2,6-($^i$Pr)$_2$Ph,
in Compound Pt1334: R=Ph, R'=2,6-($^i$Pr)$_2$-4-biphenyl,
in Compound Pt1335: R=Ph, R'=2,4-($^i$Pr)$_2$-3-dibenzofuran, Compound Pt1336 through Pt1349, each represented by the formula

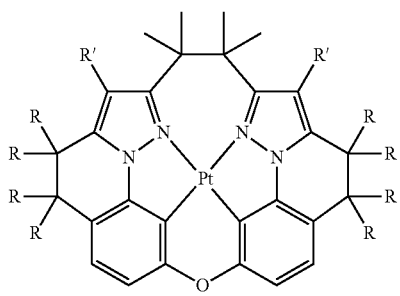

wherein in Compound Pt1336: R=Me, R'=H,
in Compound Pt1337: R=Me, R'=Me,
in Compound Pt1338: R=Me, R'=$^i$Pr,
in Compound Pt1339: R=Me, R'=Ph,
in Compound Pt1340: R=Me, R'=2,6-($^i$Pr)$_2$Ph,
in Compound Pt1341: R=Me, R'=2,6-($^i$Pr)$_2$-4-biphenyl,
in Compound Pt1342: R=Me, R'=2,4-($^i$Pr)$_2$-3-dibenzofuran,
in Compound Pt1343: R=Ph, R'=H,
in Compound Pt1344: R=Ph, R'=Me,
in Compound Pt1345: R=Ph, R'=$^i$Pr,
in Compound Pt1346: R=Ph, R'=Ph,
in Compound Pt1347: R=Ph, R'=2,6-($^i$Pr)$_2$Ph,
in Compound Pt1348: R=Ph, R'=2,6-($^i$Pr)$_2$-4-biphenyl,
in Compound Pt1349: R=Ph, R'=2,4-($^i$Pr)$_2$-3-dibenzofuran,

332

Compound Pt1350 through Pt1363, each represented by the formula

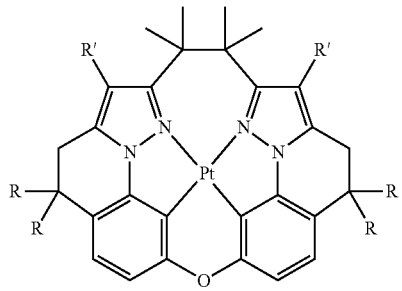

wherein in Compound Pt1350: R=Me, R'=H,
in Compound Pt1351: R=Me, R'=Me,
in Compound Pt1352: R=Me, R'=$^i$Pr,
in Compound Pt1353: R=Me, R'=Ph,
in Compound Pt1354: R=Me, R'=2,6-($^i$Pr)$_2$Ph,
in Compound Pt1355: R=Me, R'=2,6-($^i$Pr)$_2$-4-biphenyl,
in Compound Pt1356: R=Me, R'=2,4-($^i$Pr)$_2$-3-dibenzofuran,
in Compound Pt1357: R=Ph, R'=H,
in Compound Pt1358: R=Ph, R'=Me,
in Compound Pt1359: R=Ph, R'=$^i$Pr,
in Compound Pt1360: R=Ph, R'=Ph,
in Compound Pt1361: R=Ph, R'=2,6-($^i$Pr)$_2$Ph,
in Compound Pt1362: R=Ph, R'=2,6-($^i$Pr)$_2$-4-biphenyl,
in Compound Pt1363: R=Ph, R'=2,4-($^i$Pr)$_2$-3-dibenzofuran, Compound Pt1364 through Pt1377, each represented by the formula

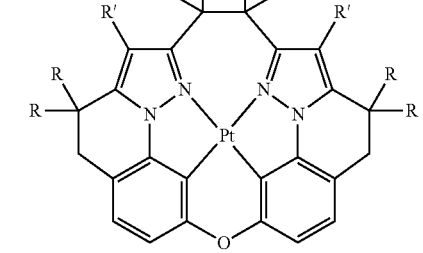

wherein in Compound Pt1364: R=Me, R'=H,
in Compound Pt1365: R=Me, R'=Me,
in Compound Pt1366: R=Me, R'=$^i$Pr,
in Compound Pt1367: R=Me, R'=Ph,
in Compound Pt1368: R=Me, R'=2,6-($^i$Pr)$_2$Ph,
in Compound Pt1369: R=Me, R'=2,6-($^i$Pr)$_2$-4-biphenyl,
in Compound Pt1370: R=Me, R'=2,4-($^i$Pr)$_2$-3-dibenzofuran,
in Compound Pt1371: R=Ph, R'=H,
in Compound Pt1372: R=Ph, R'=Me,
in Compound Pt1373: R=Ph, R'=$^i$Pr,
in Compound Pt1374: R=Ph, R'=Ph,
in Compound Pt1375: R=Ph, R'=2,6-($^i$Pr)$_2$Ph,
in Compound Pt1376: R=Ph, R'=2,6-($^i$Pr)$_2$-4-biphenyl,
in Compound Pt1377: R=Ph, R'=2,4-($^i$Pr)$_2$-3-dibenzofuran, Compound Pt1378 through Pt1391, each represented by the formula

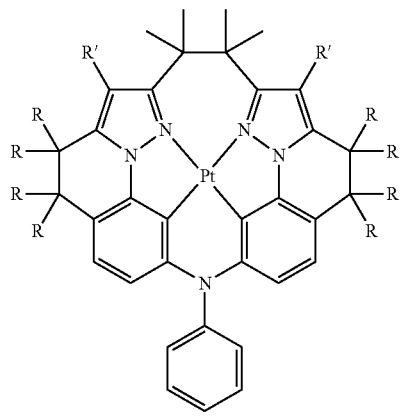

wherein in Compound Pt1378: R=Me, R'=H,
in Compound Pt1379: R=Me, R'=Me,
in Compound Pt1380: R=Me, R'=$^i$Pr,
in Compound Pt1381: R=Me, R'=Ph,
in Compound Pt1382: R=Me, R'=2,6-($^i$Pr)$_2$Ph,
in Compound Pt1383: R=Me, R'=2,6-($^i$Pr)$_2$-4-biphenyl,
in Compound Pt1384: R=Me, R'=2,4-($^i$Pr)$_2$-3-dibenzofuran,
in Compound Pt1385: R=Ph, R'=H,
in Compound Pt1386: R=Ph, R'=Me,
in Compound Pt1387: R=Ph, R'=$^i$Pr,
in Compound Pt1388: R=Ph, R'=Ph,
in Compound Pt1389: R=Ph, R'=2,6-($^i$Pr)$_2$Ph,
in Compound Pt1390: R=Ph, R'=2,6-($^i$Pr)$_2$-4-biphenyl,
in Compound Pt1391: R=Ph, R'=2,4-($^i$Pr)$_2$-3-dibenzofuran, Compound Pt1392 through Pt1405, each represented by the formula

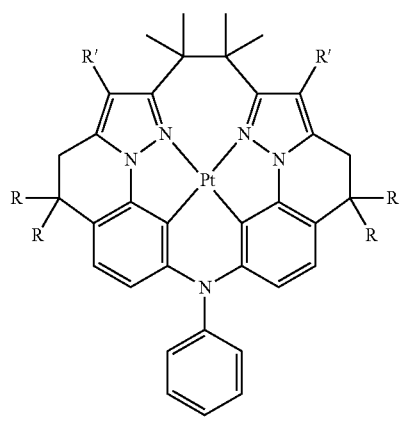

wherein in Compound Pt1392: R=Me, R'=H
in Compound Pt1393: R=Me, R'=Me
in Compound Pt1394: R=Me, R'=$^i$Pr
in Compound Pt1395: R=Me, R'=Ph
in Compound Pt1396: R=Me, R'=2,6-($^i$Pr)$_2$Ph
in Compound Pt1397: R=Me, R'=2,6-($^i$Pr)$_2$-4-biphenyl
in Compound Pt1398: R=Me, R'=2,4-($^i$Pr)$_2$-3-dibenzofuran in Compound Pt1399: R=Ph, R'=H
in Compound Pt1400: R=Ph, R'=Me
in Compound Pt1401: R=Ph, R'=$^i$Pr
in Compound Pt1402: R=Ph, R'=Ph
in Compound Pt1403: R=Ph, R'=2,6-($^i$Pr)$_2$Ph
in Compound Pt1404: R=Ph, R'=2,6-($^i$Pr)$_2$-4-biphenyl
in Compound Pt1405: R=Ph, R'=2,4-($^i$Pr)$_2$-3-dibenzofuran Compound Pt1406 through Pt1419, each represented by the formula

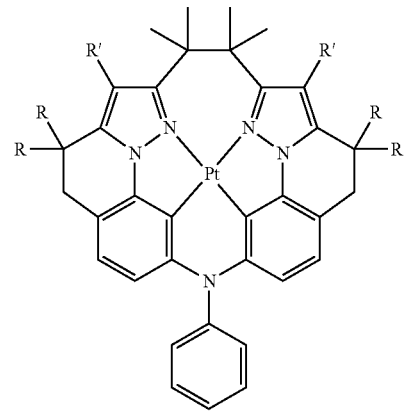

wherein in Compound Pt1406: R=Me, R'=H,
in Compound Pt1407: R=Me, R'=Me,
in Compound Pt1408: R=Me, R'=$^i$Pr,
in Compound Pt1409: R=Me, R'=Ph,
in Compound Pt1410: R=Me, R'=2,6-($^i$Pr)$_2$Ph,
in Compound Pt1411: R=Me, R'=2,6-($^i$Pr)$_2$-4-biphenyl,
in Compound Pt1412: R=Me, R'=2,4-($^i$Pr)$_2$-3-dibenzofuran,
in Compound Pt1413: R=Ph, R'=H,
in Compound Pt1414: R=Ph, R'=Me,
in Compound Pt1415: R=Ph, R'=$^i$Pr,
in Compound Pt1416: R=Ph, R'=Ph,
in Compound Pt1417: R=Ph, R'=2,6-($^i$Pr)$_2$Ph,
in Compound Pt1418: R=Ph, R'=2,6-($^i$Pr)$_2$-4-biphenyl,
in Compound Pt1419: R=Ph, R'=2,4-($^i$Pr)$_2$-3-dibenzofuran, Compound Pt1420 through Pt1433, each represented by the formula

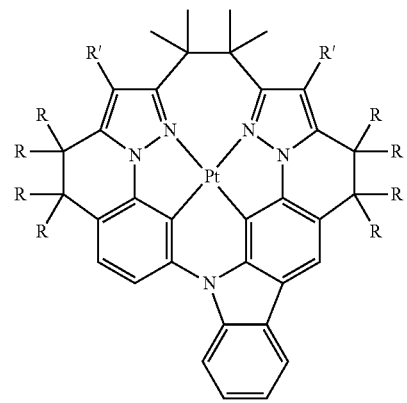

wherein in Compound Pt1420: R=Me, R'=H,
in Compound Pt1421: R=Me, R'=Me,
in Compound Pt1422: R=Me, R'=$^{i}$Pr,
in Compound Pt1423: R=Me, R'=Ph,
in Compound Pt1424: R=Me, R'=2,6-($^{i}$Pr)$_2$Ph,
in Compound Pt1425: R=Me, R'=2,6-($^{i}$Pr)$_2$-4-biphenyl,
in Compound Pt1426: R=Me, R'=2,4-($^{i}$Pr)$_2$-3-dibenzofuran,
in Compound Pt1427: R=Ph, R'=H,
in Compound Pt1428: R=Ph, R'=Me,
in Compound Pt1429: R=Ph, R'=$^{i}$Pr,
in Compound Pt1430: R=Ph, R'=Ph,
in Compound Pt1431: R=Ph, R'=2,6-($^{i}$Pr)$_2$Ph,
in Compound Pt1432: R=Ph, R'=2,6-($^{i}$Pr)$_2$-4-biphenyl,
in Compound Pt1433: R=Ph, R'=2,4-($^{i}$Pr)$_2$-3-dibenzofuran, Compound Pt1434 through Pt1447, each represented by the formula

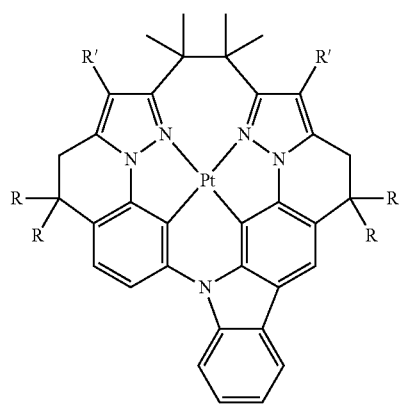

wherein in Compound Pt1434: R=Me, R'=H,
in Compound Pt1435: R=Me, R'=Me,
in Compound Pt1436: R=Me, R'=$^{i}$Pr,
in Compound Pt1437: R=Me, R'=Ph,
in Compound Pt1438: R=Me, R'=2,6-($^{i}$Pr)$_2$Ph,
in Compound Pt1439: R=Me, R'=2,6-($^{i}$Pr)$_2$-4-biphenyl,
in Compound Pt1440: R=Me, R'=2,4-($^{i}$Pr)$_2$-3-dibenzofuran,
in Compound Pt1441: R=Ph, R'=H,
in Compound Pt1442: R=Ph, R'=Me,
in Compound Pt1443: R=Ph, R'=$^{i}$Pr,
in Compound Pt1444: R=Ph, R'=Ph,
in Compound Pt1445: R=Ph, R'=2,6-($^{i}$Pr)$_2$Ph,
in Compound Pt1446: R=Ph, R'=2,6-($^{i}$Pr)$_2$-4-biphenyl,
in Compound Pt1447: R=Ph, R'=2,4-($^{i}$Pr)$_2$-3-dibenzofuran, Compound Pt1448 through Pt1461, each represented by the formula

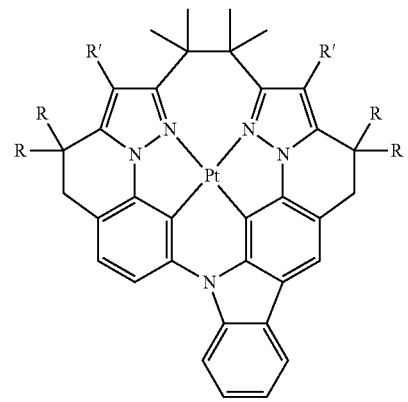

wherein in Compound Pt1448: R=Me, R'=H,
in Compound Pt1449: R=Me, R'=Me,
in Compound Pt1450: R=Me, R'=$^{i}$Pr,
in Compound Pt1451: R=Me, R'=Ph,
in Compound Pt1452: R=Me, R'=2,6-($^{i}$Pr)$_2$Ph,
in Compound Pt1453: R=Me, R'=2,6-($^{i}$Pr)$_2$-4-biphenyl,
in Compound Pt1454: R=Me, R'=2,4-($^{i}$Pr)$_2$-3-dibenzofuran,
in Compound Pt1455: R=Ph, R'=H,
in Compound Pt1456: R=Ph, R'=Me,
in Compound Pt1457: R=Ph, R'=$^{i}$Pr,
in Compound Pt1458: R=Ph, R'=Ph,
in Compound Pt1459: R=Ph, R'=2,6-($^{i}$Pr)$_2$Ph,
in Compound Pt1460: R=Ph, R'=2,6-($^{i}$Pr)$_2$-4-biphenyl,
in Compound Pt1461: R=Ph, R'=2,4-($^{i}$Pr)$_2$-3-dibenzofuran, Compound Pt1462 through Pt1475, each represented by the formula

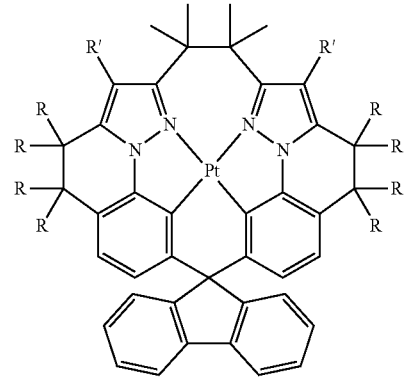

wherein in Compound Pt1462: R=Me, R'=H,
in Compound Pt1463: R=Me, R'=Me,
in Compound Pt1464: R=Me, R'=$^{i}$Pr,
in Compound Pt1465: R=Me, R'=Ph,
in Compound Pt1466: R=Me, R'=2,6-($^{i}$Pr)$_2$Ph,
in Compound Pt1467: R=Me, R'=2,6-($^{i}$Pr)$_2$-4-biphenyl,
in Compound Pt1468: R=Me, R'=2,4-($^{i}$Pr)$_2$-3-dibenzofuran,
in Compound Pt1469: R=Ph, R'=H,
in Compound Pt1470: R=Ph, R'=Me,
in Compound Pt1471: R=Ph, R'=$^{i}$Pr,
in Compound Pt1472: R=Ph, R'=Ph, in Compound Pt1473: R=Ph, R'=2,6-($^i$Pr)$_2$Ph,
in Compound Pt1474: R=Ph, R'=2,6-($^i$Pr)$_2$-4-biphenyl,
in Compound Pt1475: R=Ph, R'=2,4-($^i$Pr)$_2$-3-dibenzofuran, Compound Pt1476 through Pt1489, each represented by the formula

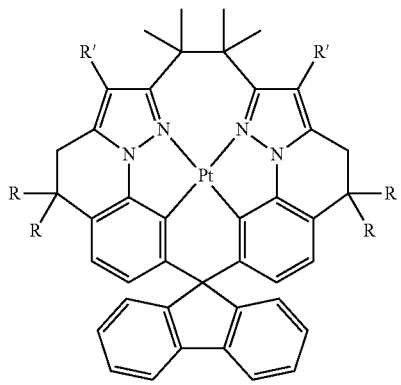

wherein in Compound Pt1476: R=Me, R'=H,
in Compound Pt1477: R=Me, R'=Me,
in Compound Pt1478: R=Me, R'=$^i$Pr,
in Compound Pt1479: R=Me, R'=Ph,
in Compound Pt1480: R=Me, R'=2,6-($^i$Pr)$_2$Ph,
in Compound Pt1481: R=Me, R'=2,6-($^i$Pr)$_2$-4-biphenyl,
in Compound Pt1482: R=Me, R'=2,4-($^i$Pr)$_2$-3-dibenzofuran,
in Compound Pt1483: R=Ph, R'=H,
in Compound Pt1484: R=Ph, R'=Me,
in Compound Pt1485: R=Ph, R'=$^i$Pr,
in Compound Pt1486: R=Ph, R'=Ph,
in Compound Pt1487: R=Ph, R'=2,6-($^i$Pr)$_2$Ph,
in Compound Pt1488: R=Ph, R'=2,6-($^i$Pr)$_2$-4-biphenyl,
in Compound Pt1489: R=Ph, R'=2,4-($^i$Pr)$_2$-3-dibenzofuran, Compound Pt1490 through Pt1503, each represented by the formula

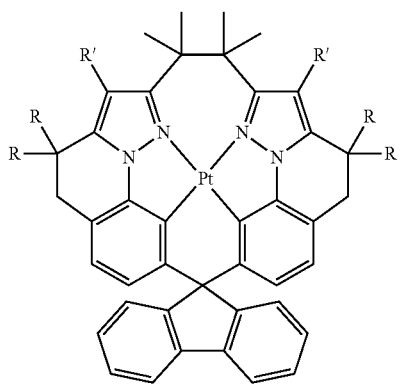

wherein in Compound Pt1490: R=Me, R'=H,
in Compound Pt1491: R=Me, R'=Me,
in Compound Pt1492: R=Me, R'=$^i$Pr,
in Compound Pt1493: R=Me, R'=Ph,
in Compound Pt1494: R=Me, R'=2,6-($^i$Pr)$_2$Ph,
in Compound Pt1495: R=Me, R'=2,6-($^i$Pr)$_2$-4-biphenyl,
in Compound Pt1496: R=Me, R'=2,4-($^i$Pr)$_2$-3-dibenzofuran,
in Compound Pt1497: R=Ph, R'=H,
in Compound Pt1498: R=Ph, R'=Me,
in Compound Pt1499: R=Ph, R'=$^i$Pr,
in Compound Pt1500: R=Ph, R'=Ph,
in Compound Pt1501: R=Ph, R'=2,6-($^i$Pr)$_2$Ph,
in Compound Pt1502: R=Ph, R'=2,6-($^i$Pr)$_2$-4-biphenyl,
in Compound Pt1503: R=Ph, R'=2,4-($^i$Pr)$_2$-3-dibenzofuran, Compound Pt1504 through Pt1517, each represented by the formula

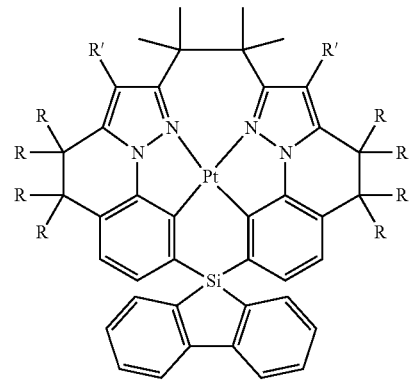

wherein in Compound Pt1504: R=Me, R'=H,
in Compound Pt1505: R=Me, R'=Me,
in Compound Pt1506: R=Me, R'=$^i$Pr,
in Compound Pt1507: R=Me, R'=Ph,
in Compound Pt1508: R=Me, R'=2,6-($^i$Pr)$_2$Ph,
in Compound Pt1509: R=Me, R'=2,6-($^i$Pr)$_2$-4-biphenyl,
in Compound Pt1510: R=Me, R'=2,4-($^i$Pr)$_2$-3-dibenzofuran,
in Compound Pt1511: R=Ph, R'=H,
in Compound Pt1512: R=Ph, R'=Me,
in Compound Pt1513: R=Ph, R'=$^i$Pr,
in Compound Pt1514: R=Ph, R'=Ph,
in Compound Pt1515: R=Ph, R'=2,6-($^i$Pr)$_2$Ph,
in Compound Pt1516: R=Ph, R'=2,6-($^i$Pr)$_2$-4-biphenyl,
in Compound Pt1517: R=Ph, R'=2,4-($^i$Pr)$_2$-3-dibenzofuran, Compound Pt1518 through Pt1531, each represented by the formula

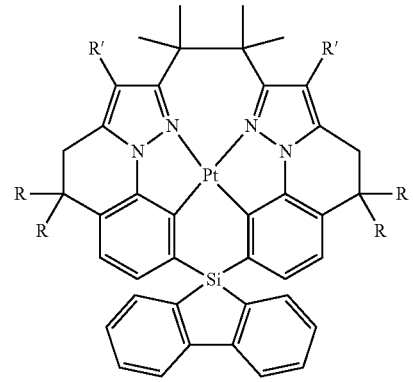

wherein in Compound Pt1518: R=Me, R'=H,
in Compound Pt1519: R=Me, R'=Me,
in Compound Pt1520: R=Me, R'=$^i$Pr,
in Compound Pt1521: R=Me, R'=Ph,
in Compound Pt1522: R=Me, R'=2,6-($^i$Pr)$_2$Ph,
in Compound Pt1523: R=Me, R'=2,6-($^i$Pr)$_2$-4-biphenyl,
in Compound Pt1524: R=Me, R'=2,4-($^i$Pr)$_2$-3-dibenzofuran,
in Compound Pt1525: R=Ph, R'=H,
in Compound Pt1526: R=Ph, R'=Me,
in Compound Pt1527: R=Ph, R'=$^i$Pr,
in Compound Pt1528: R=Ph, R'=Ph,
in Compound Pt1529: R=Ph, R'=2,6-($^i$Pr)$_2$Ph,
in Compound Pt1530: R=Ph, R'=2,6-($^i$Pr)$_2$-4-biphenyl,
in Compound Pt1531: R=Ph, R'=2,4-($^i$Pr)$_2$-3-dibenzofuran, Compound Pt1532 through Pt1545, each represented by the formula

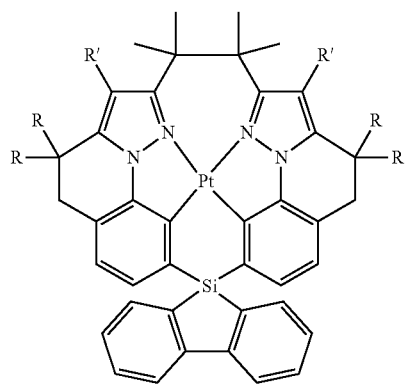

wherein in Compound Pt1532: R=Me, R'=H,
in Compound Pt1533: R=Me, R'=Me,
in Compound Pt1534: R=Me, R'=$^i$Pr,
in Compound Pt1535: R=Me, R'=Ph,
in Compound Pt1536: R=Me, R'=2,6-($^i$Pr)$_2$Ph,
in Compound Pt1537: R=Me, R'=2,6-($^i$Pr)$_2$-4-biphenyl,
in Compound Pt1538: R=Me, R'=2,4-($^i$Pr)$_2$-3-dibenzofuran,
in Compound Pt1539: R=Ph, R'=H,
in Compound Pt1540: R=Ph, R'=Me,
in Compound Pt1541: R=Ph, R'=$^i$Pr,
in Compound Pt1542: R=Ph, R'=Ph,
in Compound Pt1543: R=Ph, R'=2,6-($^i$Pr)$_2$Ph,
in Compound Pt1544: R=Ph, R'=2,6-($^i$Pr)$_2$-4-biphenyl,
in Compound Pt1545: R=Ph, R'=2,4-($^i$Pr)$_2$-3-dibenzofuran, Compound Pt1546 through Pt1559, each represented by the formula

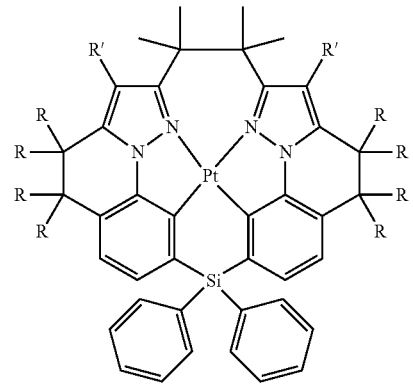

wherein in Compound Pt1546: R=Me, R'=H,
in Compound Pt1547: R=Me, R'=Me,
in Compound Pt1548: R=Me, R'=$^i$Pr,
in Compound Pt1549: R=Me, R'=Ph,
in Compound Pt1550: R=Me, R'=2,6-($^i$Pr)$_2$Ph,
in Compound Pt1551: R=Me, R'=2,6-($^i$Pr)$_2$-4-biphenyl,
in Compound Pt1552: R=Me, R'=2,4-($^i$Pr)$_2$-3-dibenzofuran,
in Compound Pt1553: R=Ph, R'=H,
in Compound Pt1554: R=Ph, R'=Me,
in Compound Pt1555: R=Ph, R'=$^i$Pr,
in Compound Pt1556: R=Ph, R'=Ph,
in Compound Pt1557: R=Ph, R'=2,6-($^i$Pr)$_2$Ph,
in Compound Pt1558: R=Ph, R'=2,6-($^i$Pr)$_2$-4-biphenyl,
in Compound Pt1559: R=Ph, R'=2,4-($^i$Pr)$_2$-3-dibenzofuran, Compound Pt1560 through Pt1573, each represented by the formula

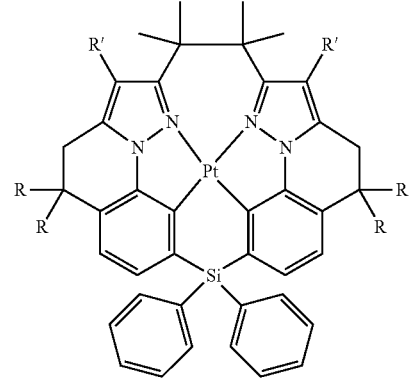

wherein in Compound Pt1560: R=Me, R'=H,
in Compound Pt1561: R=Me, R'=Me,
in Compound Pt1562: R=Me, R'=$^i$Pr,
in Compound Pt1563: R=Me, R'=Ph,
in Compound Pt1564: R=Me, R'=2,6-($^i$Pr)$_2$Ph,
in Compound Pt1565: R=Me, R'=2,6-($^i$Pr)$_2$-4-biphenyl,
in Compound Pt1566: R=Me, R'=2,4-($^i$Pr)$_2$-3-dibenzofuran,
in Compound Pt1567: R=Ph, R'=H,
in Compound Pt1568: R=Ph, R'=Me,
in Compound Pt1569: R=Ph, R'=$^i$Pr,
in Compound Pt1570: R=Ph, R'=Ph, in Compound Pt1571: R=Ph, R'=2,6-($^{i}$Pr)$_2$Ph,
in Compound Pt1572: R=Ph, R'=2,6-($^{i}$Pr)$_2$-4-biphenyl,
in Compound Pt1573: R=Ph, R'=2,4-($^{i}$Pr)$_2$-3-dibenzofuran, Compound Pt1574 through Pt1587, each represented by the formula

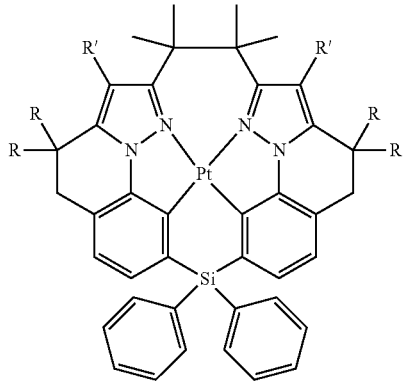

wherein in Compound Pt1574: R=Me, R'=H,
in Compound Pt1575: R=Me, R'=Me,
in Compound Pt1576: R=Me, R'=$^{i}$Pr,
in Compound Pt1577: R=Me, R'=Ph,
in Compound Pt1578: R=Me, R'=2,6-($^{i}$Pr)$_2$Ph,
in Compound Pt1579: R=Me, R'=2,6-($^{i}$Pr)$_2$-4-biphenyl,
in Compound Pt1580: R=Me, R'=2,4-($^{i}$Pr)$_2$-3-dibenzofuran,
in Compound Pt1581: R=Ph, R'=H,
in Compound Pt1582: R=Ph, R'=Me,
in Compound Pt1583: R=Ph, R'=$^{i}$Pr,
in Compound Pt1584: R=Ph, R'=Ph,
in Compound Pt1585: R=Ph, R'=2,6-($^{i}$Pr)$_2$Ph,
in Compound Pt1586: R=Ph, R'=2,6-($^{i}$Pr)$_2$-4-biphenyl,
in Compound Pt1587: R=Ph, R'=2,4-($^{i}$Pr)$_2$-3-dibenzofuran, Compound Pt1588 through Pt1601, each represented by the formula

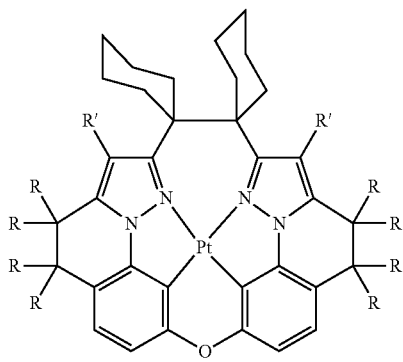

wherein in Compound Pt1588: R=Me, R'=H,
in Compound Pt1589: R=Me, R'=Me,
in Compound Pt1590: R=Me, R'=$^{i}$Pr,
in Compound Pt1591: R=Me, R'=Ph,
in Compound Pt1592: R=Me, R'=2,6-($^{i}$Pr)$_2$Ph,
in Compound Pt1593: R=Me, R'=2,6-($^{i}$Pr)$_2$-4-biphenyl,
in Compound Pt1594: R=Me, R'=2,4-($^{i}$Pr)$_2$-3-dibenzofuran,
in Compound Pt1595: R=Ph, R'=H,
in Compound Pt1596: R=Ph, R'=Me,
in Compound Pt1597: R=Ph, R'=$^{i}$Pr,
in Compound Pt1598: R=Ph, R'=Ph,
in Compound Pt1599: R=Ph, R'=2,6-($^{i}$Pr)$_2$Ph,
in Compound Pt1600: R=Ph, R'=2,6-($^{i}$Pr)$_2$-4-biphenyl,
in Compound Pt1601: R=Ph, R'=2,4-($^{i}$Pr)$_2$-3-dibenzofuran, Compound Pt1602 through Pt1615, each represented by the formula

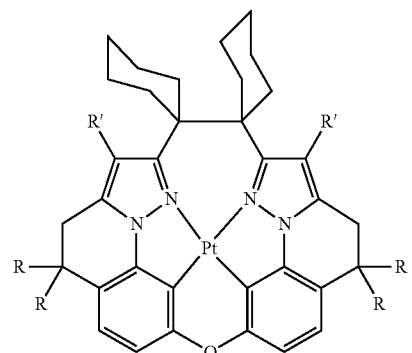

wherein in Compound Pt1602: R=Me, R'=H,
in Compound Pt1603: R=Me, R'=Me,
in Compound Pt1604: R=Me, R'=$^{i}$Pr,
in Compound Pt1605: R=Me, R'=Ph,
in Compound Pt1606: R=Me, R'=2,6-($^{i}$Pr)$_2$Ph,
in Compound Pt1607: R=Me, R'=2,6-($^{i}$Pr)$_2$-4-biphenyl,
in Compound Pt1608: R=Me, R'=2,4-($^{i}$Pr)$_2$-3-dibenzofuran,
in Compound Pt1609: R=Ph, R'=H,
in Compound Pt1610: R=Ph, R'=Me,
in Compound Pt1611: R=Ph, R'=$^{i}$Pr,
in Compound Pt1612: R=Ph, R'=Ph,
in Compound Pt1613: R=Ph, R'=2,6-($^{i}$Pr)$_2$Ph,
in Compound Pt1614: R=Ph, R'=2,6-($^{i}$Pr)$_2$-4-biphenyl,
in Compound Pt1615: R=Ph, R'=2,4-($^{i}$Pr)$_2$-3-dibenzofuran, Compound Pt1616 through Pt1629, each represented by the formula

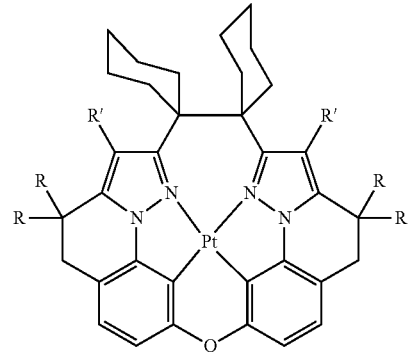

wherein in Compound Pt1616: R=Me, R'=H,
in Compound Pt1617: R=Me, R'=Me,
in Compound Pt1618: R=Me, R'=$^i$Pr,
in Compound Pt1619: R=Me, R'=Ph,
in Compound Pt1620: R=Me, R'=2,6-($^i$Pr)$_2$Ph,
in Compound Pt1621: R=Me, R'=2,6-($^i$Pr)$_2$-4-biphenyl,
in Compound Pt1622: R=Me, R'=2,4-($^i$Pr)$_2$-3-dibenzofuran,
in Compound Pt1623: R=Ph, R'=H,
in Compound Pt1624: R=Ph, R'=Me,
in Compound Pt1625: R=Ph, R'=$^i$Pr,
in Compound Pt1626: R=Ph, R'=Ph,
in Compound Pt1627: R=Ph, R'=2,6-($^i$Pr)$_2$Ph,
in Compound Pt1628: R=Ph, R'=2,6-($^i$Pr)$_2$-4-biphenyl,
in Compound Pt1629: R=Ph, R'=2,4-($^i$Pr)$_2$-3-dibenzofuran, Compound Pt1630 through Pt1643, each represented by the formula

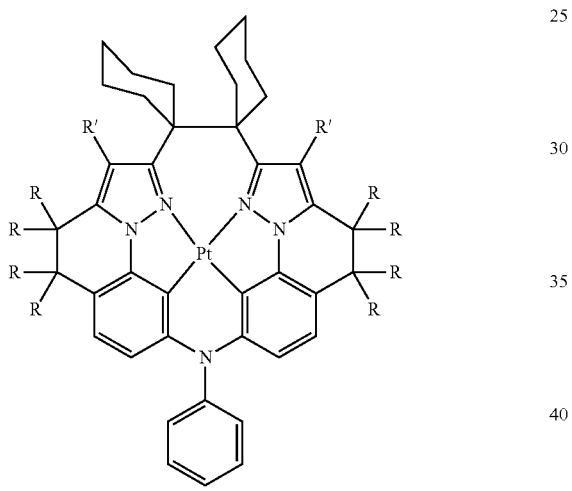

wherein in Compound Pt1630: R=Me, R'=H,
in Compound Pt1631: R=Me, R'=Me,
in Compound Pt1632: R=Me, R'=$^i$Pr,
in Compound Pt1633: R=Me, R'=Ph,
in Compound Pt1634: R=Me, R'=2,6-($^i$Pr)$_2$Ph,
in Compound Pt1635: R=Me, R'=2,6-($^i$Pr)$_2$-4-biphenyl,
in Compound Pt1636: R=Me, R'=2,4-($^i$Pr)$_2$-3-dibenzofuran,
in Compound Pt1637: R=Ph, R'=H,
in Compound Pt1638: R=Ph, R'=Me,
in Compound Pt1639: R=Ph, R'=$^i$Pr,
in Compound Pt1640: R=Ph, R'=Ph,
in Compound Pt1641: R=Ph, R'=2,6-($^i$Pr)$_2$Ph,
in Compound Pt1642: R=Ph, R'=2,6-($^i$Pr)$_2$-4-biphenyl,
in Compound Pt1643: R=Ph, R'=2,4-($^i$Pr)$_2$-3-dibenzofuran, Compound Pt1644 through Pt1657, each represented by the formula

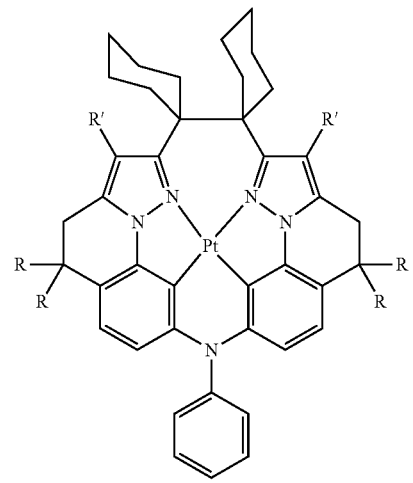

wherein in Compound Pt1644: R=Me, R'=H,
in Compound Pt1645: R=Me, R'=Me,
in Compound Pt1646: R=Me, R'=$^i$Pr,
in Compound Pt1647: R=Me, R'=Ph,
in Compound Pt1648: R=Me, R'=2,6-($^i$Pr)$_2$Ph,
in Compound Pt1649: R=Me, R'=2,6-($^i$Pr)$_2$-4-biphenyl,
in Compound Pt1650: R=Me, R'=2,4-($^i$Pr)$_2$-3-dibenzofuran,
in Compound Pt1651: R=Ph, R'=H,
in Compound Pt1652: R=Ph, R'=Me,
in Compound Pt1653: R=Ph, R'=$^i$Pr,
in Compound Pt1654: R=Ph, R'=Ph,
in Compound Pt1655: R=Ph, R'=2,6-($^i$Pr)$_2$Ph,
in Compound Pt1656: R=Ph, R'=2,6-($^i$Pr)$_2$-4-biphenyl,
in Compound Pt1657: R=Ph, R'=2,4-($^i$Pr)$_2$-3-dibenzofuran, Compound Pt1658 through Pt1671, each represented by the formula

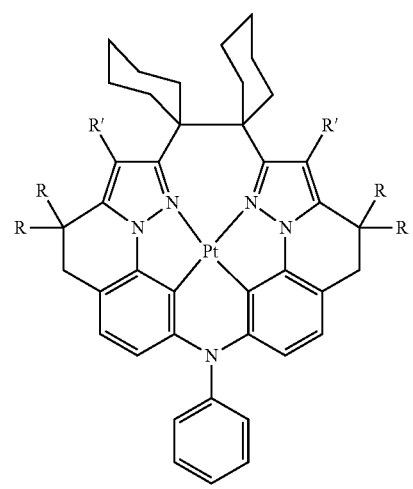

wherein in Compound Pt1658: R=Me, R'=H,
in Compound Pt1659: R=Me, R'=Me,
in Compound Pt1660: R=Me, R'=$^i$Pr,
in Compound Pt1661: R=Me, R'=Ph,
in Compound Pt1662: R=Me, R'=2,6-($^i$Pr)$_2$Ph,
in Compound Pt1663: R=Me, R'=2,6-($^i$Pr)$_2$-4-biphenyl, in Compound Pt1664: R=Me, R'=2,4-($^i$Pr)$_2$-3-dibenzofuran, in Compound Pt1665: R=Ph, R'=H, in Compound Pt1666: R=Ph, R'=Me, in Compound Pt1667: R=Ph, R'=$^i$Pr, in Compound Pt1668: R=Ph, R'=Ph, in Compound Pt1669: R=Ph, R'=2,6-($^i$Pr)$_2$Ph, in Compound Pt1670: R=Ph, R'=2,6-($^i$Pr)$_2$-4-biphenyl, in Compound Pt1671: R=Ph, R'=2,4-($^i$Pr)$_2$-3-dibenzofuran, Compound Pt1672 through Pt1685, each represented by the formula

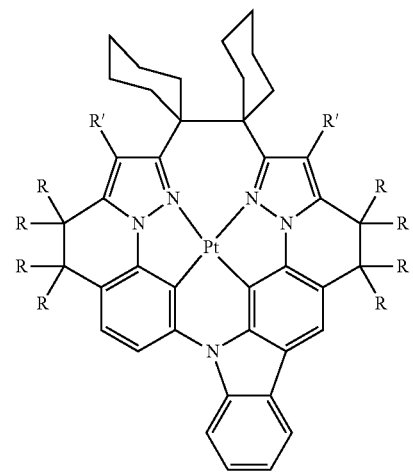

wherein in Compound Pt1672: R=Me, R'=H, in Compound Pt1673: R=Me, R'=Me, in Compound Pt1674: R=Me, R'=$^i$Pr, in Compound Pt1675: R=Me, R'=Ph, in Compound Pt1676: R=Me, R'=2,6-($^i$Pr)$_2$Ph, in Compound Pt1677: R=Me, R'=2,6-($^i$Pr)$_2$-4-biphenyl, in Compound Pt1678: R=Me, R'=2,4-($^i$Pr)$_2$-3-dibenzofuran, in Compound Pt1679: R=Ph, R'=H, in Compound Pt1680: R=Ph, R'=Me, in Compound Pt1681: R=Ph, R'=$^i$Pr, in Compound Pt1682: R=Ph, R'=Ph, in Compound Pt1683: R=Ph, R'=2,6-($^i$Pr)$_2$Ph, in Compound Pt1684: R=Ph, R'=2,6-($^i$Pr)$_2$-4-biphenyl, in Compound Pt1685: R=Ph, R'=2,4-($^i$Pr)$_2$-3-dibenzofuran, Compound Pt1686 through Pt1699, each represented by the formula

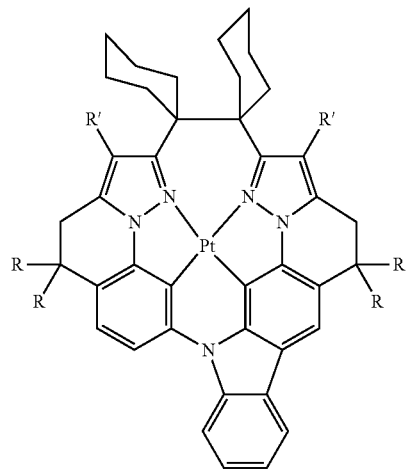

wherein in Compound Pt1686: R=Me, R'=H, in Compound Pt1687: R=Me, R'=Me, in Compound Pt1688: R=Me, R'=$^i$Pr, in Compound Pt1689: R=Me, R'=Ph, in Compound Pt1690: R=Me, R'=2,6-($^i$Pr)$_2$Ph, in Compound Pt1691: R=Me, R'=2,6-($^i$Pr)$_2$-4-biphenyl, in Compound Pt1692: R=Me, R'=2,4-($^i$Pr)$_2$-3-dibenzofuran, in Compound Pt1693: R=Ph, R'=H, in Compound Pt1694: R=Ph, R'=Me, in Compound Pt1695: R=Ph, R'=$^i$Pr, in Compound Pt1696: R=Ph, R'=Ph, in Compound Pt1697: R=Ph, R'=2,6-($^i$Pr)$_2$Ph, in Compound Pt1698: R=Ph, R'=2,6-($^i$Pr)$_2$-4-biphenyl, in Compound Pt1699: R=Ph, R'=2,4-($^i$Pr)$_2$-3-dibenzofuran, Compound Pt1700 through Pt1713, each represented by the formula

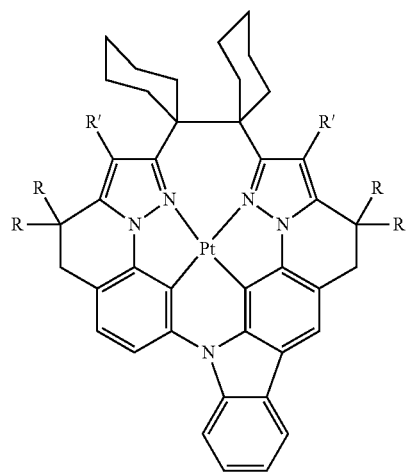

wherein in Compound Pt1700: R=Me, R'=H, in Compound Pt1701: R=Me, R'=Me, in Compound Pt1702: R=Me, R'=$^i$Pr, in Compound Pt1703: R=Me, R'=Ph, in Compound Pt1704: R=Me, R'=2,6-($^i$Pr)$_2$Ph, in Compound Pt1705: R=Me, R'=2,6-($^i$Pr)$_2$-4-biphenyl, in Compound Pt1706: R=Me, R'=2,4-($^{i}$Pr)$_2$-3-dibenzofuran,
in Compound Pt1707: R=Ph, R'=H,
in Compound Pt1708: R=Ph, R'=Me,
in Compound Pt1709: R=Ph, R'=$^{i}$Pr,
in Compound Pt1710: R=Ph, R'=Ph,
in Compound Pt1711: R=Ph, R'=2,6-($^{i}$Pr)$_2$Ph,
in Compound Pt1712: R=Ph, R'=2,6-($^{i}$Pr)$_2$-4-biphenyl,
in Compound Pt1713: R=Ph, R'=2,4-($^{i}$Pr)$_2$-3-dibenzofuran, Compound Pt1714 through Pt1727, each represented by the formula

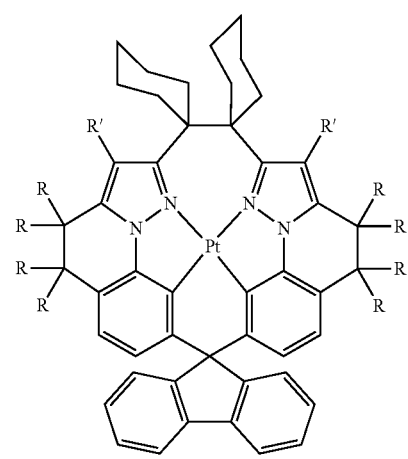

wherein in Compound Pt1714: R=Me, R'=H,
in Compound Pt1715: R=Me, R'=Me,
in Compound Pt1716: R=Me, R'=$^{i}$Pr,
in Compound Pt1717: R=Me, R'=Ph,
in Compound Pt1718: R=Me, R'=2,6-($^{i}$Pr)$_2$Ph,
in Compound Pt1719: R=Me, R'=2,6-($^{i}$Pr)$_2$-4-biphenyl,
in Compound Pt1720: R=Me, R'=2,4-($^{i}$Pr)$_2$-3-dibenzofuran,
in Compound Pt1721: R=Ph, R'=H,
in Compound Pt1722: R=Ph, R'=Me,
in Compound Pt1723: R=Ph, R'=$^{i}$Pr,
in Compound Pt1724: R=Ph, R'=Ph,
in Compound Pt1725: R=Ph, R'=2,6-($^{i}$Pr)$_2$Ph,
in Compound Pt1726: R=Ph, R'=2,6-($^{i}$Pr)$_2$-4-biphenyl,
in Compound Pt1727: R=Ph, R'=2,4-($^{i}$Pr)$_2$-3-dibenzofuran, Compound Pt1728 through Pt1741, each represented by the formula

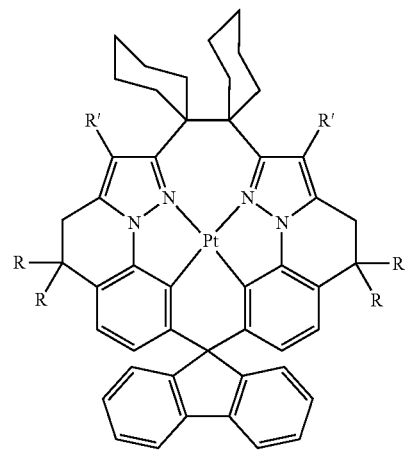

wherein in Compound Pt1728: R=Me, R'=H,
in Compound Pt1729: R=Me, R'=Me,
in Compound Pt1730: R=Me, R'=$^{i}$Pr,
in Compound Pt1731: R=Me, R'=Ph,
in Compound Pt1732: R=Me, R'=2,6-($^{i}$Pr)$_2$Ph,
in Compound Pt1733: R=Me, R'=2,6-($^{i}$Pr)$_2$-4-biphenyl,
in Compound Pt1734: R=Me, R'=2,4-($^{i}$Pr)$_2$-3-dibenzofuran,
in Compound Pt1735: R=Ph, R'=H,
in Compound Pt1736: R=Ph, R'=Me,
in Compound Pt1737: R=Ph, R'=$^{i}$Pr,
in Compound Pt1738: R=Ph, R'=Ph,
in Compound Pt1739: R=Ph, R'=2,6-($^{i}$Pr)$_2$Ph,
in Compound Pt1740: R=Ph, R'=2,6-($^{i}$Pr)$_2$-4-biphenyl,
in Compound Pt1741: R=Ph, R'=2,4-($^{i}$Pr)$_2$-3-dibenzofuran, Compound Pt1742 through Pt1755, each represented by the formula

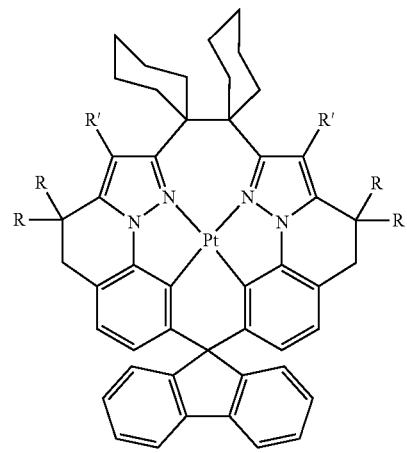

wherein in Compound Pt1742: R=Me, R'=H,
in Compound Pt1743: R=Me, R'=Me,
in Compound Pt1744: R=Me, R'=$^{i}$Pr,
in Compound Pt1745: R=Me, R'=Ph,
in Compound Pt1746: R=Me, R'=2,6-($^{i}$Pr)$_2$Ph,
in Compound Pt1747: R=Me, R'=2,6-($^{i}$Pr)$_2$-4-biphenyl,
in Compound Pt1748: R=Me, R'=2,4-($^{i}$Pr)$_2$-3-dibenzofuran, in Compound Pt1749: R=Ph, R'=H,
in Compound Pt1750: R=Ph, R'=Me,
in Compound Pt1751: R=Ph, R'=$^i$Pr,
in Compound Pt1752: R=Ph, R'=Ph,
in Compound Pt1753: R=Ph, R'=2,6-($^i$Pr)$_2$Ph,
in Compound Pt1754: R=Ph, R'=2,6-($^i$Pr)$_2$-4-biphenyl,
in Compound Pt1755: R=Ph, R'=2,4-($^i$Pr)$_2$-3-dibenzofuran, Compound Pt1756 through Pt1769, each represented by the formula

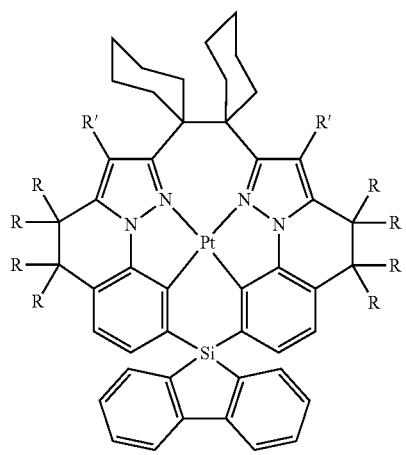

wherein in Compound Pt1756: R=Me, R'=H,
in Compound Pt1757: R=Me, R'=Me,
in Compound Pt1758: R=Me, R'=$^i$Pr,
in Compound Pt1759: R=Me, R'=Ph,
in Compound Pt1760: R=Me, R'=2,6-($^i$Pr)$_2$Ph,
in Compound Pt1761: R=Me, R'=2,6-($^i$Pr)$_2$-4-biphenyl,
in Compound Pt1762: R=Me, R'=2,4-($^i$Pr)$_2$-3-dibenzofuran,
in Compound Pt1763: R=Ph, R'=H,
in Compound Pt1764: R=Ph, R'=Me,
in Compound Pt1765: R=Ph, R'=$^i$Pr,
in Compound Pt1766: R=Ph, R'=Ph,
in Compound Pt1767: R=Ph, R'=2,6-($^i$Pr)$_2$Ph,
in Compound Pt1768: R=Ph, R'=2,6-($^i$Pr)$_2$-4-biphenyl,
in Compound Pt1769: R=Ph, R'=2,4-($^i$Pr)$_2$-3-dibenzofuran, Compound Pt1770 through Pt1783, each represented by the formula

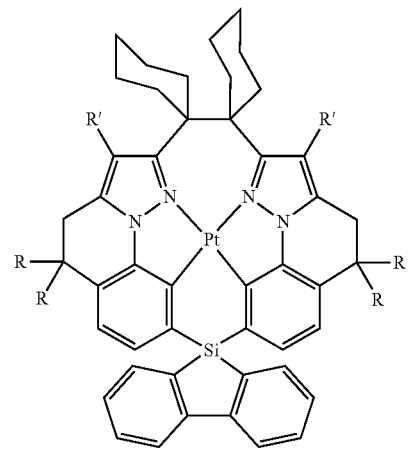

wherein in Compound Pt1770: R=Me, R'=H,
in Compound Pt1771: R=Me, R'=Me,
in Compound Pt1772: R=Me, R'=$^i$Pr,
in Compound Pt1773: R=Me, R'=Ph,
in Compound Pt1774: R=Me, R'=2,6-($^i$Pr)$_2$Ph,
in Compound Pt1775: R=Me, R'=2,6-($^i$Pr)$_2$-4-biphenyl,
in Compound Pt1776: R=Me, R'=2,4-($^i$Pr)$_2$-3-dibenzofuran,
in Compound Pt1777: R=Ph, R'=H,
in Compound Pt1778: R=Ph, R'=Me,
in Compound Pt1779: R=Ph, R'=$^i$Pr,
in Compound Pt1780: R=Ph, R'=Ph,
in Compound Pt1781: R=Ph, R'=2,6-($^i$Pr)$_2$Ph,
in Compound Pt1782: R=Ph, R'=2,6-($^i$Pr)$_2$-4-biphenyl,
in Compound Pt1783: R=Ph, R'=2,4-($^i$Pr)$_2$-3-dibenzofuran, Compound Pt1784 through Pt1797, each represented by the formula

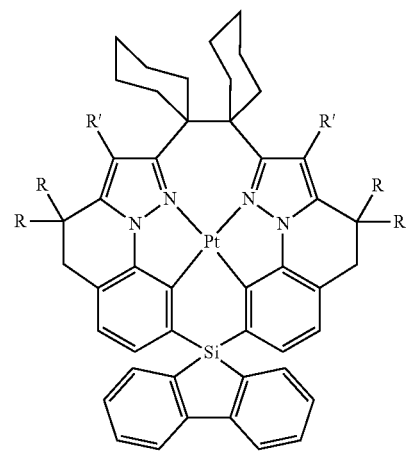

wherein in Compound Pt1784: R=Me, R'=H,
in Compound Pt1785: R=Me, R'=Me,
in Compound Pt1786: R=Me, R'=$^i$Pr,
in Compound Pt1787: R=Me, R'=Ph,
in Compound Pt1788: R=Me, R'=2,6-($^i$Pr)$_2$Ph,
in Compound Pt1789: R=Me, R'=2,6-($^i$Pr)$_2$-4-biphenyl,
in Compound Pt1790: R=Me, R'=2,4-($^i$Pr)$_2$-3-dibenzofuran, in Compound Pt1791: R=Ph, R'=H,
in Compound Pt1792: R=Ph, R'=Me,
in Compound Pt1793: R=Ph, R'=$^i$Pr,
in Compound Pt1794: R=Ph, R'=Ph,
in Compound Pt1795: R=Ph, R'=2,6-($^i$Pr)$_2$Ph,
in Compound Pt1796: R=Ph, R'=2,6-($^i$Pr)$_2$-4-biphenyl,
in Compound Pt1797: R=Ph, R'=2,4-($^i$Pr)$_2$-3-dibenzofuran, Compound Pt1798 through Pt1811, each represented by the formula

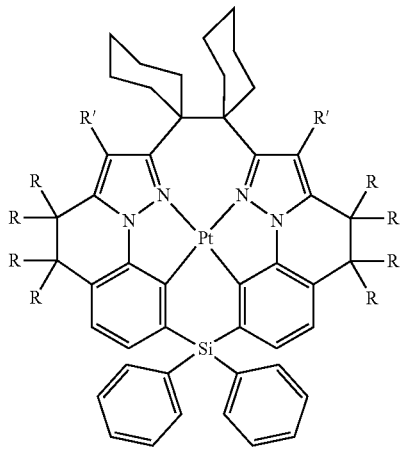

wherein in Compound Pt1798: R=Me, R'=H,
in Compound Pt1799: R=Me, R'=Me,
in Compound Pt1800: R=Me, R'=$^i$Pr,
in Compound Pt1801: R=Me, R'=Ph,
in Compound Pt1802: R=Me, R'=2,6-($^i$Pr)$_2$Ph,
in Compound Pt1803: R=Me, R'=2,6-($^i$Pr)$_2$-4-biphenyl,
in Compound Pt1804: R=Me, R'=2,4-($^i$Pr)$_2$-3-dibenzofuran,
in Compound Pt1805: R=Ph, R'=H,
in Compound Pt1806: R=Ph, R'=Me,
in Compound Pt1807: R=Ph, R'=$^i$Pr,
in Compound Pt1808: R=Ph, R'=Ph,
in Compound Pt1809: R=Ph, R'=2,6-($^i$Pr)$_2$Ph,
in Compound Pt1810: R=Ph, R'=2,6-($^i$Pr)$_2$-4-biphenyl,
in Compound Pt1811: R=Ph, R'=2,4-($^i$Pr)$_2$-3-dibenzofuran, Compound Pt1812 through Pt1825, each represented by the formula

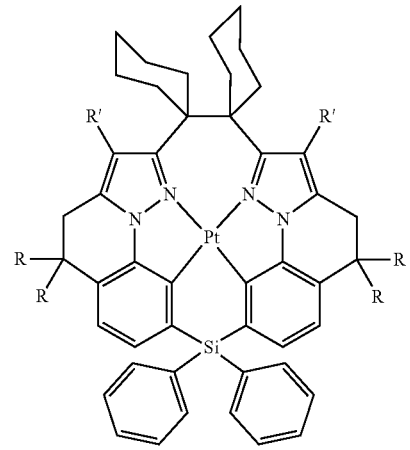

wherein in Compound Pt1812: R=Me, R'=H,
in Compound Pt1813: R=Me, R'=Me,
in Compound Pt1814: R=Me, R'=$^i$Pr,
in Compound Pt1815: R=Me, R'=Ph,
in Compound Pt1816: R=Me, R'=2,6-($^i$Pr)$_2$Ph,
in Compound Pt1817: R=Me, R'=2,6-($^i$Pr)$_2$-4-biphenyl,
in Compound Pt1818: R=Me, R'=2,4-($^i$Pr)$_2$-3-dibenzofuran,
in Compound Pt1819: R=Ph, R'=H,
in Compound Pt1820: R=Ph, R'=Me,
in Compound Pt1821: R=Ph, R'=$^i$Pr,
in Compound Pt1822: R=Ph, R'=Ph,
in Compound Pt1823: R=Ph, R'=2,6-($^i$Pr)$_2$Ph,
in Compound Pt1824: R=Ph, R'=2,6-($^i$Pr)$_2$-4-biphenyl,
in Compound Pt1825: R=Ph, R'=2,4-($^i$Pr)$_2$-3-dibenzofuran, Compound Pt1826 through Pt1839, each represented by the formula

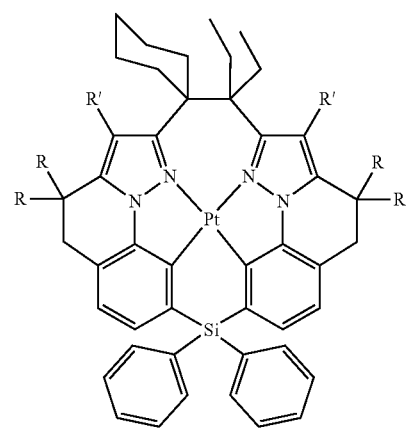

wherein in Compound Pt1826: R=Me, R'=H,
in Compound Pt1827: R=Me, R'=Me,
in Compound Pt1828: R=Me, R'=$^i$Pr,
in Compound Pt1829: R=Me, R'=Ph,
in Compound Pt1830: R=Me, R'=2,6-($^i$Pr)$_2$Ph,
in Compound Pt1831: R=Me, R'=2,6-($^i$Pr)$_2$-4-biphenyl,
in Compound Pt1832: R=Me, R'=2,4-($^i$Pr)$_2$-3-dibenzofuran, in Compound Pt1833: R=Ph, R'=H,
in Compound Pt1834: R=Ph, R'=Me,
in Compound Pt1835: R=Ph, R'=$^i$Pr,
in Compound Pt1836: R=Ph, R'=Ph,
in Compound Pt1837: R=Ph, R'=2,6-($^i$Pr)$_2$Ph,
in Compound Pt1838: R=Ph, R'=2,6-($^i$Pr)$_2$-4-biphenyl,
in Compound Pt1839: R=Ph, R'=2,4-($^i$Pr)$_2$-3-dibenzofuran, Compound Pt1840 through Pt1853, each represented by the formula

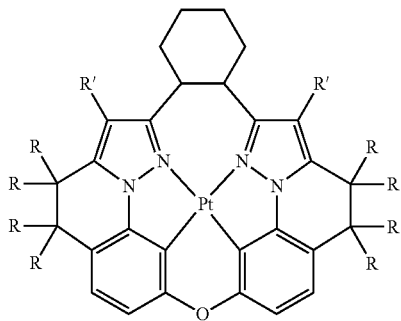

wherein in Compound Pt1840: R=Me, R'=H,
in Compound Pt1841: R=Me, R'=Me,
in Compound Pt1842: R=Me, R'=$^i$Pr,
in Compound Pt1843: R=Me, R'=Ph,
in Compound Pt1844: R=Me, R'=2,6-($^i$Pr)$_2$Ph,
in Compound Pt1845: R=Me, R'=2,6-($^i$Pr)$_2$-4-biphenyl,
in Compound Pt1846: R=Me, R'=2,4-($^i$Pr)$_2$-3-dibenzofuran,
in Compound Pt1847: R=Ph, R'=H,
in Compound Pt1848: R=Ph, R'=Me,
in Compound Pt1849: R=Ph, R'=$^i$Pr,
in Compound Pt1850: R=Ph, R'=Ph,
in Compound Pt1851: R=Ph, R'=2,6-($^i$Pr)$_2$Ph,
in Compound Pt1852: R=Ph, R'=2,6-($^i$Pr)$_2$-4-biphenyl,
in Compound Pt1853: R=Ph, R'=2,4-($^i$Pr)$_2$-3-dibenzofuran, Compound Pt1854 through Pt1867, each represented by the formula

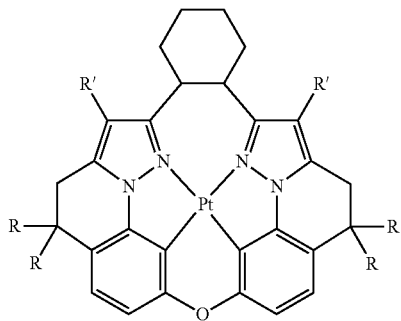

wherein in Compound Pt1854: R=Me, R'=H,
in Compound Pt1855: R=Me, R'=Me,
in Compound Pt1856: R=Me, R'=$^i$Pr,
in Compound Pt1857: R=Me, R'=Ph,
in Compound Pt1858: R=Me, R'=2,6-($^i$Pr)$_2$Ph,
in Compound Pt1859: R=Me, R'=2,6-($^i$Pr)$_2$-4-biphenyl,
in Compound Pt1860: R=Me, R'=2,4-($^i$Pr)$_2$-3-dibenzofuran,
in Compound Pt1861: R=Ph, R'=H,
in Compound Pt1862: R=Ph, R'=Me,
in Compound Pt1863: R=Ph, R'=$^i$Pr,
in Compound Pt1864: R=Ph, R'=Ph,
in Compound Pt1865: R=Ph, R'=2,6-($^i$Pr)$_2$Ph,
in Compound Pt1866: R=Ph, R'=2,6-($^i$Pr)$_2$-4-biphenyl,
in Compound Pt1867: R=Ph, R'=2,4-($^i$Pr)$_2$-3-dibenzofuran, Compound Pt1868 through Pt1881, each represented by the formula

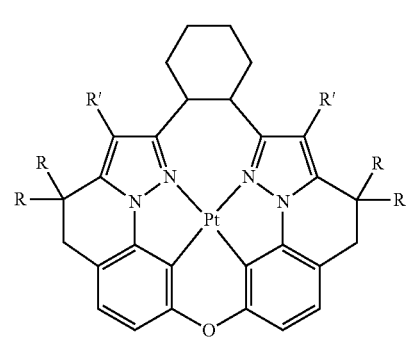

wherein in Compound Pt1868: R=Me, R'=H,
in Compound Pt1869: R=Me, R'=Me,
in Compound Pt1870: R=Me, R'=$^i$Pr,
in Compound Pt1871: R=Me, R'=Ph,
in Compound Pt1872: R=Me, R'=2,6-($^i$Pr)$_2$Ph,
in Compound Pt1873: R=Me, R'=2,6-($^i$Pr)$_2$-4-biphenyl,
in Compound Pt1874: R=Me, R'=2,4-($^i$Pr)$_2$-3-dibenzofuran,
in Compound Pt1875: R=Ph, R'=H,
in Compound Pt1876: R=Ph, R'=Me,
in Compound Pt1877: R=Ph, R'=$^i$Pr,
in Compound Pt1878: R=Ph, R'=Ph,
in Compound Pt1879: R=Ph, R'=2,6-($^i$Pr)$_2$Ph,
in Compound Pt1880: R=Ph, R'=2,6-($^i$Pr)$_2$-4-biphenyl,
in Compound Pt1881: R=Ph, R'=2,4-($^i$Pr)$_2$-3-dibenzofuran, Compound Pt1882 through Pt1895, each represented by the formula

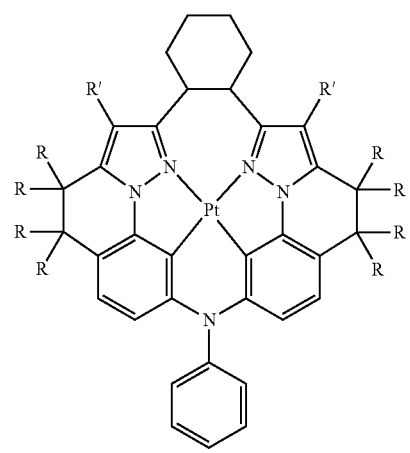

wherein in Compound Pt1882: R=Me, R'=H,
in Compound Pt1883: R=Me, R'=Me,
in Compound Pt1884: R=Me, R'=$^i$Pr,
in Compound Pt1885: R=Me, R'=Ph,
in Compound Pt1886: R=Me, R'=2,6-($^i$Pr)$_2$Ph,
in Compound Pt1887: R=Me, R'=2,6-($^i$Pr)$_2$-4-biphenyl,
in Compound Pt1888: R=Me, R'=2,4-($^i$Pr)$_2$-3-dibenzofuran,
in Compound Pt1889: R=Ph, R'=H,
in Compound Pt1890: R=Ph, R'=Me,
in Compound Pt1891: R=Ph, R'=$^i$Pr,
in Compound Pt1892: R=Ph, R'=Ph,
in Compound Pt1893: R=Ph, R'=2,6-($^i$Pr)$_2$Ph,
in Compound Pt1894: R=Ph, R'=2,6-($^i$Pr)$_2$-4-biphenyl,
in Compound Pt1895: R=Ph, R'=2,4-($^i$Pr)$_2$-3-dibenzofuran, Compound Pt1896 through Pt1909, each represented by the formula

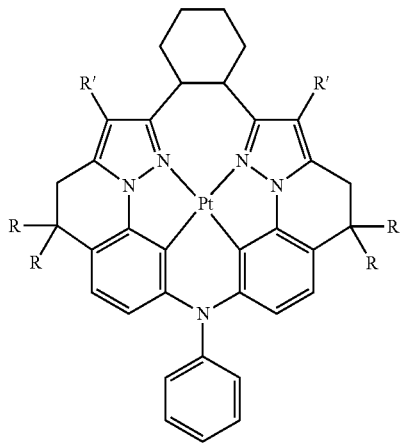

wherein in Compound Pt1896: R=Me, R'=H,
in Compound Pt1897: R=Me, R'=Me,
in Compound Pt1898: R=Me, R'=$^i$Pr,
in Compound Pt1899: R=Me, R'=Ph,
in Compound Pt1900: R=Me, R'=2,6-($^i$Pr)$_2$Ph,
in Compound Pt1901: R=Me, R'=2,6-($^i$Pr)$_2$-4-biphenyl,
in Compound Pt1902: R=Me, R'=2,4-($^i$Pr)$_2$-3-dibenzofuran,
in Compound Pt1903: R=Ph, R'=H,
in Compound Pt1904: R=Ph, R'=Me,
in Compound Pt1905: R=Ph, R'=$^i$Pr,
in Compound Pt1906: R=Ph, R'=Ph,
in Compound Pt1907: R=Ph, R'=2,6-($^i$Pr)$_2$Ph,
in Compound Pt1908: R=Ph, R'=2,6-($^i$Pr)$_2$-4-biphenyl,
in Compound Pt1909: R=Ph, R'=2,4-($^i$Pr)$_2$-3-dibenzofuran, Compound Pt1910 through Pt1923, each represented by the formula

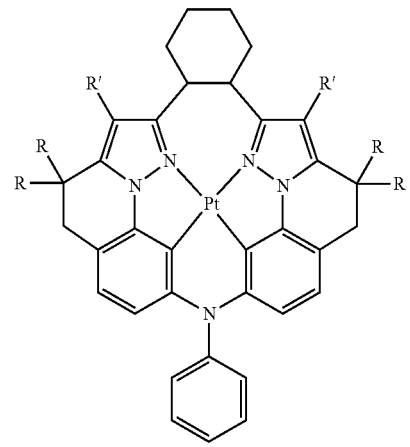

wherein in Compound Pt1910: R=Me, R'=H,
in Compound Pt1911: R=Me, R'=Me,
in Compound Pt1912: R=Me, R'=$^i$Pr,
in Compound Pt1913: R=Me, R'=Ph,
in Compound Pt1914: R=Me, R'=2,6-($^i$Pr)$_2$Ph,
in Compound Pt1915: R=Me, R'=2,6-($^i$Pr)$_2$-4-biphenyl,
in Compound Pt1916: R=Me, R'=2,4-($^i$Pr)$_2$-3-dibenzofuran,
in Compound Pt1917: R=Ph, R'=H,
in Compound Pt1918: R=Ph, R'=Me,
in Compound Pt1919: R=Ph, R'=$^i$Pr,
in Compound Pt1920: R=Ph, R'=Ph,
in Compound Pt1921: R=Ph, R'=2,6-($^i$Pr)$_2$Ph,
in Compound Pt1922: R=Ph, R'=2,6-($^i$Pr)$_2$-4-biphenyl,
in Compound Pt1923: R=Ph, R'=2,4-($^i$Pr)$_2$-3-dibenzofuran, Compound Pt1924 through Pt1937, each represented by the formula

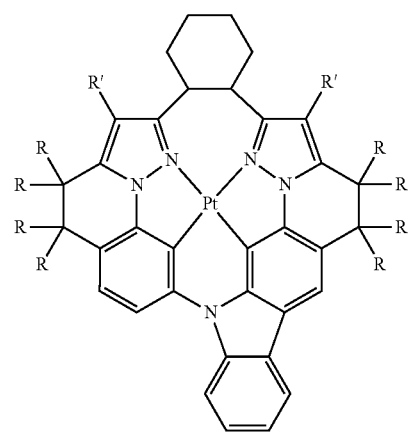

wherein in Compound Pt1924: R=Me, R'=H,
in Compound Pt1925: R=Me, R'=Me,
in Compound Pt1926: R=Me, R'=$^i$Pr,
in Compound Pt1927: R=Me, R'=Ph,
in Compound Pt1928: R=Me, R'=2,6-($^i$Pr)$_2$Ph,
in Compound Pt1929: R=Me, R'=2,6-($^i$Pr)$_2$-4-biphenyl,
in Compound Pt1930: R=Me, R'=2,4-($^i$Pr)$_2$-3-dibenzofuran, in Compound Pt1931: R=Ph, R'=H,
in Compound Pt1932: R=Ph, R'=Me,
in Compound Pt1933: R=Ph, R'=$^i$Pr,
in Compound Pt1934: R=Ph, R'=Ph,
in Compound Pt1935: R=Ph, R'=2,6-($^i$Pr)$_2$Ph,
in Compound Pt1936: R=Ph, R'=2,6-($^i$Pr)$_2$-4-biphenyl,
in Compound Pt1937: R=Ph, R'=2,4-($^i$Pr)$_2$-3-dibenzofuran, Compound Pt1938 through Pt1951, each represented by the formula

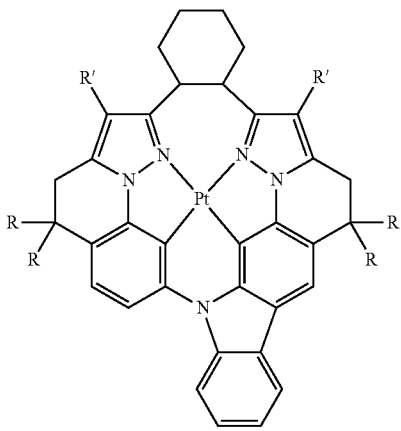

wherein in Compound Pt1938: R=Me, R'=H,
in Compound Pt1939: R=Me, R'=Me,
in Compound Pt1940: R=Me, R'=$^i$Pr,
in Compound Pt1941: R=Me, R'=Ph,
in Compound Pt1942: R=Me, R'=2,6-($^i$Pr)$_2$Ph,
in Compound Pt1943: R=Me, R'=2,6-($^i$Pr)$_2$-4-biphenyl,
in Compound Pt1944: R=Me, R'=2,4-($^i$Pr)$_2$-3-dibenzofuran,
in Compound Pt1945: R=Ph, R'=H,
in Compound Pt1946: R=Ph, R'=Me,
in Compound Pt1947: R=Ph, R'=$^i$Pr,
in Compound Pt1948: R=Ph, R'=Ph,
in Compound Pt1949: R=Ph, R'=2,6-($^i$Pr)$_2$Ph,
in Compound Pt1950: R=Ph, R'=2,6-($^i$Pr)$_2$-4-biphenyl,
in Compound Pt1951: R=Ph, R'=2,4-($^i$Pr)$_2$-3-dibenzofuran, Compound Pt1952 through Pt1965, each represented by the formula

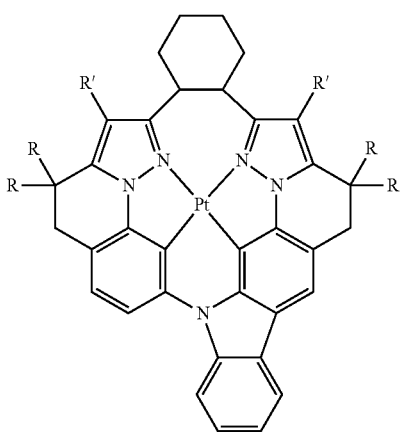

wherein in Compound Pt1952: R=Me, R'=H,
in Compound Pt1953: R=Me, R'=Me,
in Compound Pt1954: R=Me, R'=$^i$Pr,
in Compound Pt1955: R=Me, R'=Ph,
in Compound Pt1956: R=Me, R'=2,6-($^i$Pr)$_2$Ph,
in Compound Pt1957: R=Me, R'=2,6-($^i$Pr)$_2$-4-biphenyl,
in Compound Pt1958: R=Me, R'=2,4-($^i$Pr)$_2$-3-dibenzofuran,
in Compound Pt1959: R=Ph, R'=H,
in Compound Pt1960: R=Ph, R'=Me,
in Compound Pt1961: R=Ph, R'=$^i$Pr,
in Compound Pt1962: R=Ph, R'=Ph,
in Compound Pt1963: R=Ph, R'=2,6-($^i$Pr)$_2$Ph,
in Compound Pt1964: R=Ph, R'=2,6-($^i$Pr)$_2$-4-biphenyl,
in Compound Pt1965: R=Ph, R'=2,4-($^i$Pr)$_2$-3-dibenzofuran, Compound Pt1966 through Pt1979, each represented by the formula

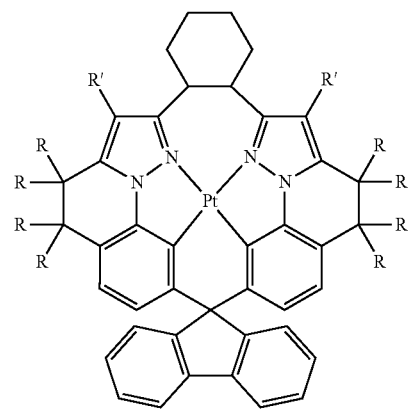

wherein in Compound Pt1966: R=Me, R'=H,
in Compound Pt1967: R=Me, R'=Me,
in Compound Pt1968: R=Me, R'=$^i$Pr,
in Compound Pt1969: R=Me, R'=Ph,
in Compound Pt1970: R=Me, R'=2,6-($^i$Pr)$_2$Ph,
in Compound Pt1971: R=Me, R'=2,6-($^i$Pr)$_2$-4-biphenyl,
in Compound Pt1972: R=Me, R'=2,4-($^i$Pr)$_2$-3-dibenzofuran,
in Compound Pt1973: R=Ph, R'=H,
in Compound Pt1974: R=Ph, R'=Me,
in Compound Pt1975: R=Ph, R'=$^i$Pr,
in Compound Pt1976: R=Ph, R'=Ph,
in Compound Pt1977: R=Ph, R'=2,6-($^i$Pr)$_2$Ph,
in Compound Pt1978: R=Ph, R'=2,6-($^i$Pr)$_2$-4-biphenyl,
in Compound Pt1979: R=Ph, R'=2,4-($^i$Pr)$_2$-3-dibenzofuran, Compound Pt1980 through Pt1993, each represented by the formula

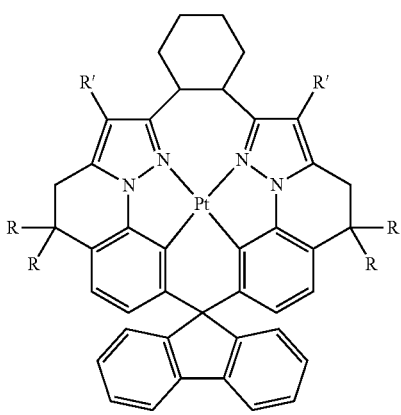

wherein in Compound Pt1980: R=Me, R'=H,
in Compound Pt1981: R=Me, R'=Me,
in Compound Pt1982: R=Me, R'=$^i$Pr,
in Compound Pt1983: R=Me, R'=Ph,
in Compound Pt1984: R=Me, R'=2,6-($^i$Pr)$_2$Ph,
in Compound Pt1985: R=Me, R'=2,6-($^i$Pr)$_2$-4-biphenyl,
in Compound Pt1986: R=Me, R'=2,4-($^i$Pr)$_2$-3-dibenzofuran,
in Compound Pt1987: R=Ph, R'=H,
in Compound Pt1988: R=Ph, R'=Me,
in Compound Pt1989: R=Ph, R'=$^i$Pr,
in Compound Pt1990: R=Ph, R'=Ph,
in Compound Pt1991: R=Ph, R'=2,6-($^i$Pr)$_2$Ph,
in Compound Pt1992: R=Ph, R'=2,6-($^i$Pr)$_2$-4-biphenyl,
in Compound Pt1993: R=Ph, R'=2,4-($^i$Pr)$_2$-3-dibenzofuran, Compound Pt1994 through Pt2007, each represented by the formula

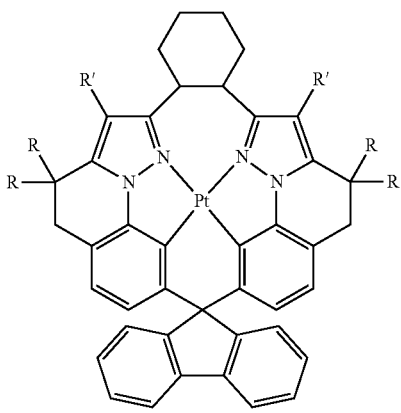

wherein in Compound Pt1994: R=Me, R'=H,
in Compound Pt1995: R=Me, R'=Me,
in Compound Pt1996: R=Me, R'=$^i$Pr,
in Compound Pt1997: R=Me, R'=Ph,
in Compound Pt1998: R=Me, R'=2,6-($^i$Pr)$_2$Ph,
in Compound Pt1999: R=Me, R'=2,6-($^i$Pr)$_2$-4-biphenyl,
in Compound Pt2000: R=Me, R'=2,4-($^i$Pr)$_2$-3-dibenzofuran,
in Compound Pt2001: R=Ph, R'=H,
in Compound Pt2002: R=Ph, R'=Me,
in Compound Pt2003: R=Ph, R'=$^i$Pr,
in Compound Pt2004: R=Ph, R'=Ph,
in Compound Pt2005: R=Ph, R'=2,6-($^i$Pr)$_2$Ph,
in Compound Pt2006: R=Ph, R'=2,6-($^i$Pr)$_2$-4-biphenyl,
in Compound Pt2007: R=Ph, R'=2,4-($^i$Pr)$_2$-3-dibenzofuran, Compound Pt2008 through Pt2021, each represented by the formula

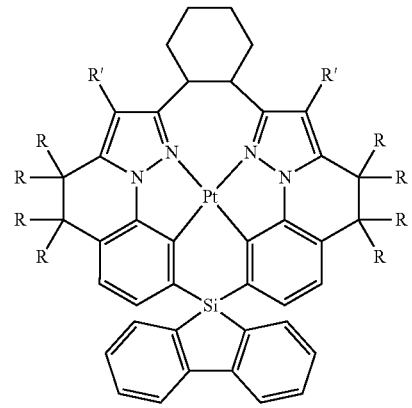

wherein in Compound Pt2008: R=Me, R'=H,
in Compound Pt2009: R=Me, R'=Me,
in Compound Pt2010: R=Me, R'=$^i$Pr,
in Compound Pt2011: R=Me, R'=Ph,
in Compound Pt2012: R=Me, R'=2,6-($^i$Pr)$_2$Ph,
in Compound Pt2013: R=Me, R'=2,6-($^i$Pr)$_2$-4-biphenyl,
in Compound Pt2014: R=Me, R'=2,4-($^i$Pr)$_2$-3-dibenzofuran,
in Compound Pt2015: R=Ph, R'=H,
in Compound Pt2016: R=Ph, R'=Me,
in Compound Pt2017: R=Ph, R'=$^i$Pr,
in Compound Pt2018: R=Ph, R'=Ph,
in Compound Pt2019: R=Ph, R'=2,6-($^i$Pr)$_2$Ph,
in Compound Pt2020: R=Ph, R'=2,6-($^i$Pr)$_2$-4-biphenyl,
in Compound Pt2021: R=Ph, R'=2,4-($^i$Pr)$_2$-3-dibenzofuran, Compound Pt2022 through Pt2035, each represented by the formula

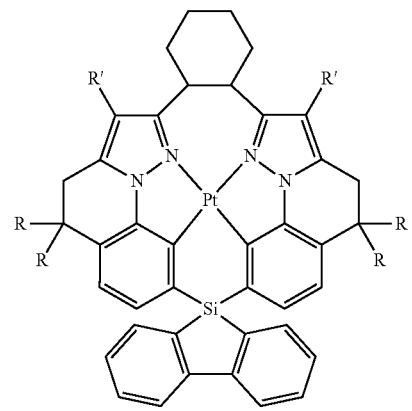

wherein in Compound Pt2022: R=Me, R'=H,
in Compound Pt2023: R=Me, R'=Me,
in Compound Pt2024: R=Me, R'=$^i$Pr, in Compound Pt2025: R=Me, R'=Ph,
in Compound Pt2026: R=Me, R'=2,6-($^i$Pr)$_2$Ph,
in Compound Pt2027: R=Me, R'=2,6-($^i$Pr)$_2$-4-biphenyl,
in Compound Pt2028: R=Me, R'=2,4-($^i$Pr)$_2$-3-dibenzofuran,
in Compound Pt2029: R=Ph, R'=H,
in Compound Pt2030: R=Ph, R'=Me,
in Compound Pt2031: R=Ph, R'=$^i$Pr,
in Compound Pt2032: R=Ph, R'=Ph,
in Compound Pt2033: R=Ph, R'=2,6-($^i$Pr)$_2$Ph,
in Compound Pt2034: R=Ph, R'=2,6-($^i$Pr)$_2$-4-biphenyl,
in Compound Pt2035: R=Ph, R'=2,4-($^i$Pr)$_2$-3-dibenzofuran, Compound Pt2036 through Pt2049, each represented by the formula

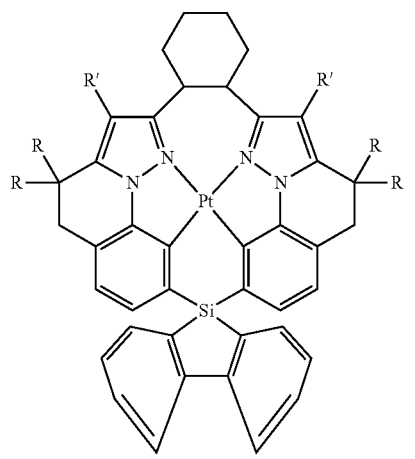

wherein in Compound Pt2036: R=Me, R'=H,
in Compound Pt2037: R=Me, R'=Me,
in Compound Pt2038: R=Me, R'=$^i$Pr,
in Compound Pt2039: R=Me, R'=Ph,
in Compound Pt2040: R=Me, R'=2,6-($^i$Pr)$_2$Ph,
in Compound Pt2041: R=Me, R'=2,6-($^i$Pr)$_2$-4-biphenyl,
in Compound Pt2042: R=Me, R'=2,4-($^i$Pr)$_2$-3-dibenzofuran,
in Compound Pt2043: R=Ph, R'=H,
in Compound Pt2044: R=Ph, R'=Me,
in Compound Pt2045: R=Ph, R'=$^i$Pr,
in Compound Pt2046: R=Ph, R'=Ph,
in Compound Pt2047: R=Ph, R'=2,6-($^i$Pr)$_2$Ph,
in Compound Pt2048: R=Ph, R'=2,6-($^i$Pr)$_2$-4-biphenyl,
in Compound Pt2049: R=Ph, R'=2,4-($^i$Pr)$_2$-3-dibenzofuran, Compound Pt2050 through Pt2063, each represented by the formula

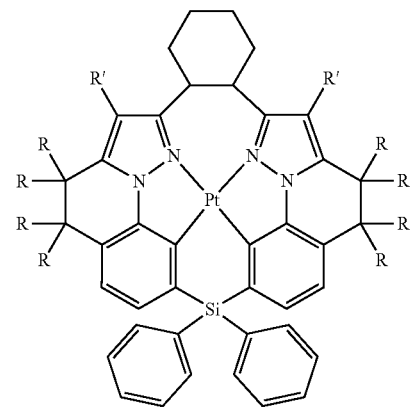

wherein in Compound Pt2050: R=Me, R'=H,
in Compound Pt2051: R=Me, R'=Me,
in Compound Pt2052: R=Me, R'=$^i$Pr,
in Compound Pt2053: R=Me, R'=Ph,
in Compound Pt2054: R=Me, R'=2,6-($^i$Pr)$_2$Ph,
in Compound Pt2055: R=Me, R'=2,6-($^i$Pr)$_2$-4-biphenyl,
in Compound Pt2056: R=Me, R'=2,4-($^i$Pr)$_2$-3-dibenzofuran,
in Compound Pt2057: R=Ph, R'=H,
in Compound Pt2058: R=Ph, R'=Me,
in Compound Pt2059: R=Ph, R'=$^i$Pr,
in Compound Pt2060: R=Ph, R'=Ph,
in Compound Pt2061: R=Ph, R'=2,6-($^i$Pr)$_2$Ph,
in Compound Pt2062: R=Ph, R'=2,6-($^i$Pr)$_2$-4-biphenyl,
in Compound Pt2063: R=Ph, R'=2,4-($^i$Pr)$_2$-3-dibenzofuran, Compound Pt2064 through Pt2077, each represented by the formula

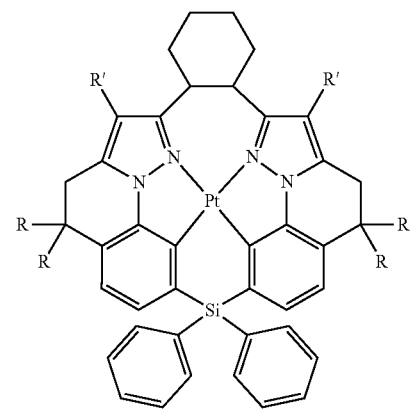

wherein in Compound Pt2064: R=Me, R'=H,
in Compound Pt2065: R=Me, R'=Me,
in Compound Pt2066: R=Me, R'=$^i$Pr,
in Compound Pt2067: R=Me, R'=Ph,
in Compound Pt2068: R=Me, R'=2,6-($^i$Pr)$_2$Ph,
in Compound Pt2069: R=Me, R'=2,6-($^i$Pr)$_2$-4-biphenyl,
in Compound Pt2070: R=Me, R'=2,4-($^i$Pr)$_2$-3-dibenzofuran,
in Compound Pt2071: R=Ph, R'=H,
in Compound Pt2072: R=Ph, R'=Me, in Compound Pt2073: R=Ph, R'=$^i$Pr,
in Compound Pt2074: R=Ph, R'=Ph,
in Compound Pt2075: R=Ph, R'=2,6-($^i$Pr)$_2$Ph,
in Compound Pt2076: R=Ph, R'=2,6-($^i$Pr)$_2$-4-biphenyl,
in Compound Pt2077: R=Ph, R'=2,4-($^i$Pr)$_2$-3-dibenzofuran, Compound Pt2078 through Pt2091, each represented by the formula

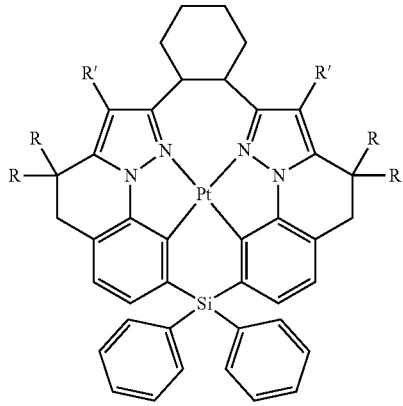

wherein in Compound Pt2078: R=Me, R'=H,
in Compound Pt2079: R=Me, R'=Me,
in Compound Pt2080: R=Me, R'=$^i$Pr,
in Compound Pt2081: R=Me, R'=Ph,
in Compound Pt2082: R=Me, R'=2,6-($^i$Pr)$_2$Ph,
in Compound Pt2083: R=Me, R'=2,6-($^i$Pr)$_2$-4-biphenyl,
in Compound Pt2084: R=Me, R'=2,4-($^i$Pr)$_2$-3-dibenzofuran,
in Compound Pt2085: R=Ph, R'=H,
in Compound Pt2086: R=Ph, R'=Me,
in Compound Pt2087: R=Ph, R'=$^i$Pr,
in Compound Pt2088: R=Ph, R'=Ph,
in Compound Pt2089: R=Ph, R'=2,6-($^i$Pr)$_2$Ph,
in Compound Pt2090: R=Ph, R'=2,6-($^i$Pr)$_2$-4-biphenyl,
in Compound Pt2091: R=Ph, R'=2,4-($^i$Pr)$_2$-3-dibenzofuran, and

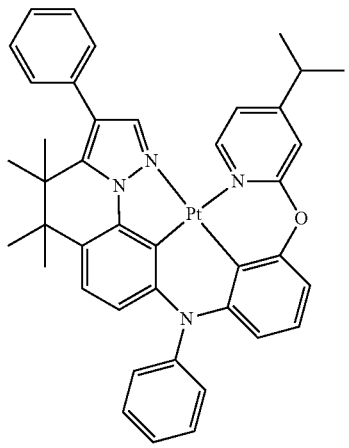

Compound Pt2092.

13. The compound of claim 1, wherein M is Ir.

14. The compound of claim 13, wherein the compound is heteroleptic.

15. The compound of claim 13, wherein the compound is homoleptic.

16. The compound of claim 1, wherein L$_B$ is different from L$_A$ and L$_B$ is selected from the group consisting of:

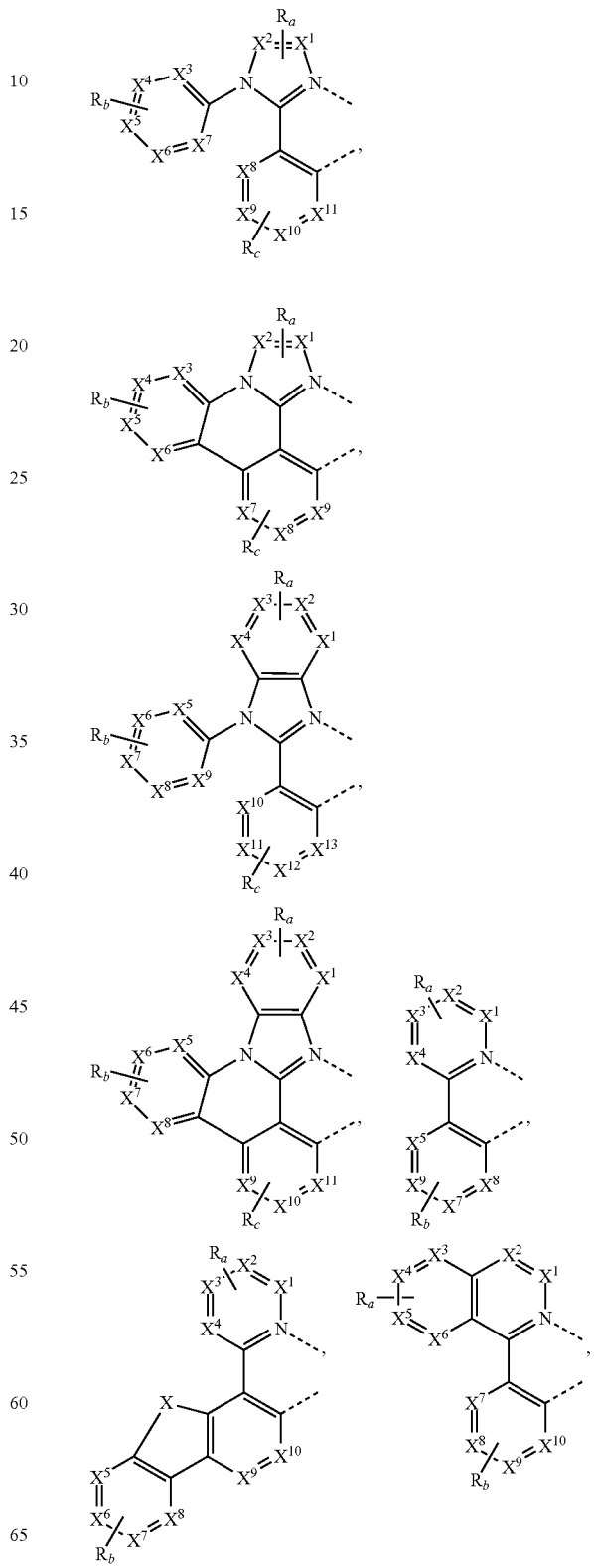

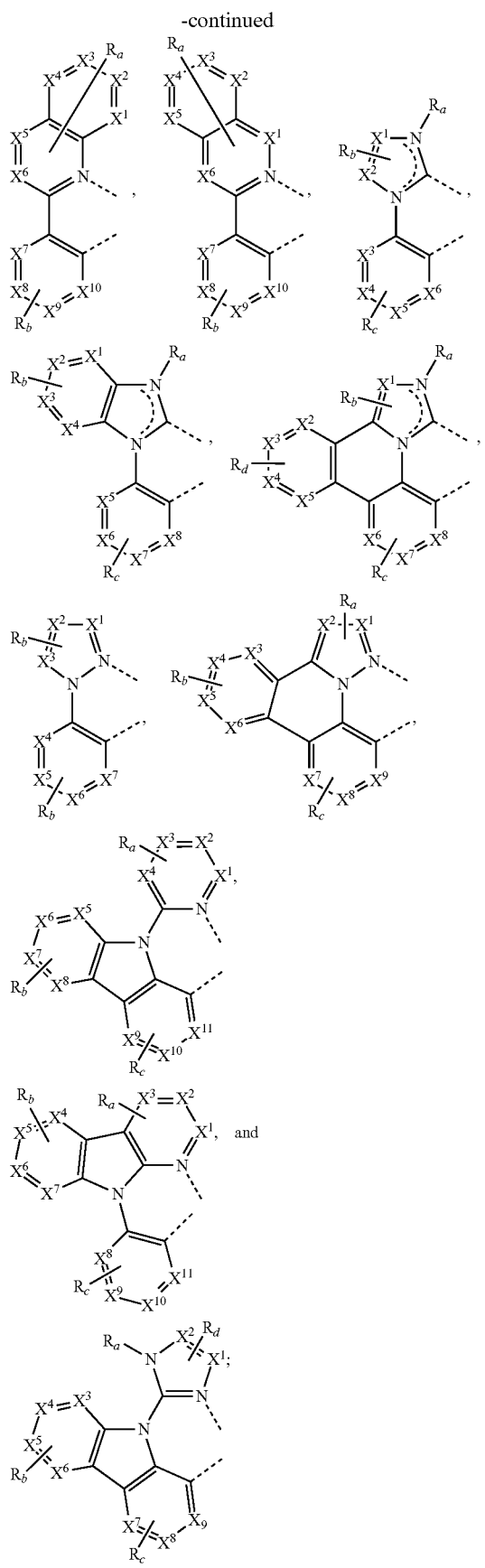

wherein each of $X^1$ to $X^{13}$ is independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally joined to form a fused or unfused ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally joined to form a fused or unfused ring or form a multidentate ligand.

17. The compound of claim 1, wherein the compound is selected from the group consisting of:

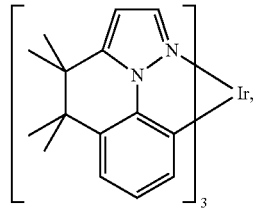

Ir1

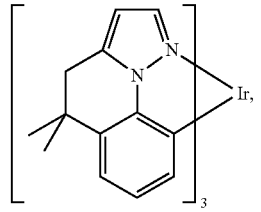

Ir2

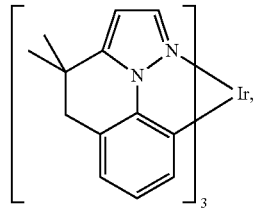

Ir3

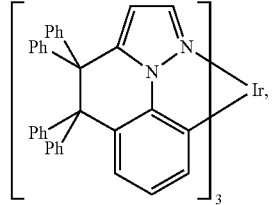

Ir4

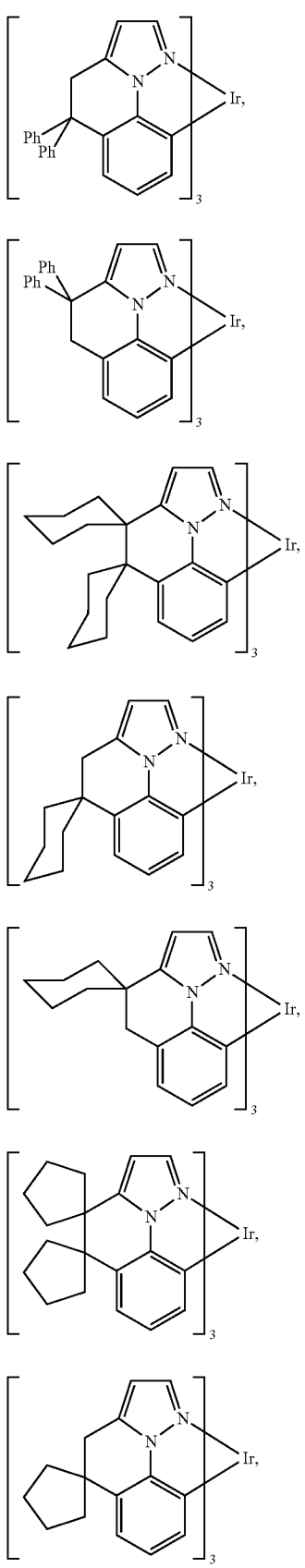

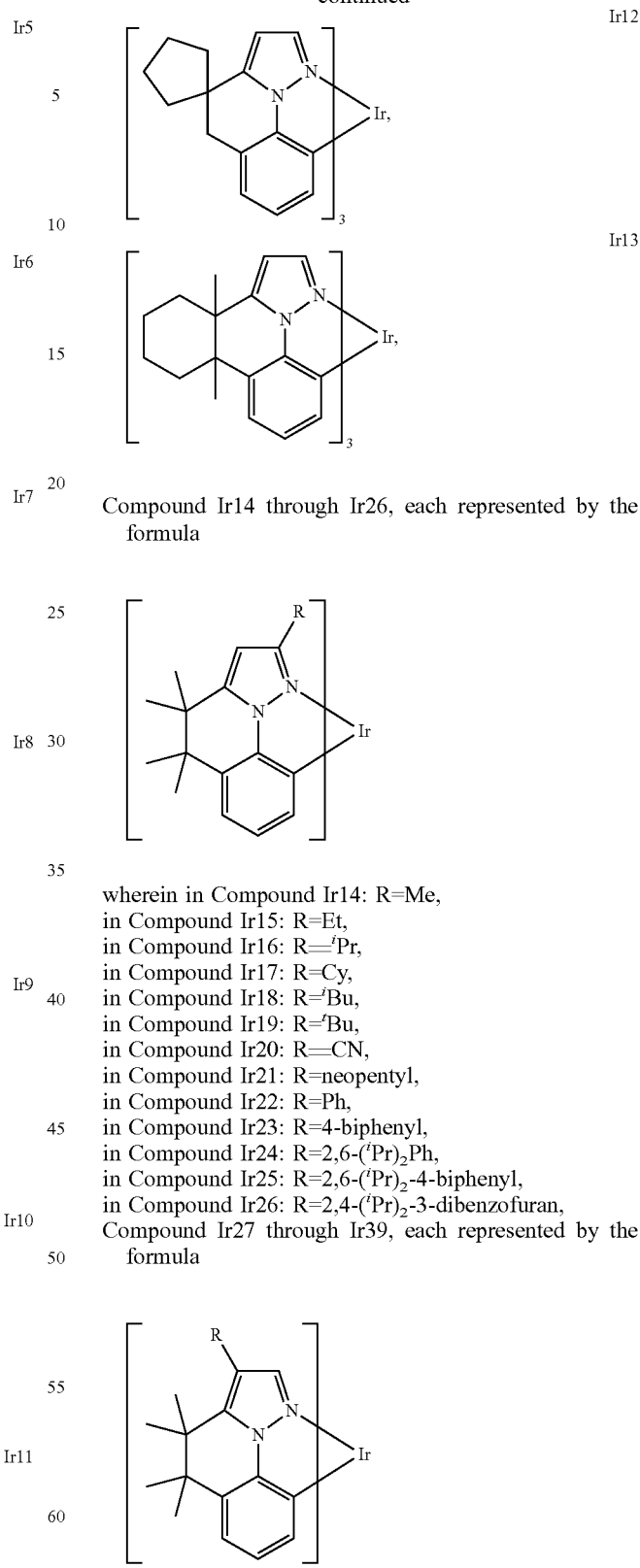

Compound Ir14 through Ir26, each represented by the formula wherein in Compound Ir14: R=Me,
in Compound Ir15: R=Et,
in Compound Ir16: R=$^i$Pr,
in Compound Ir17: R=Cy,
in Compound Ir18: R=$^i$Bu,
in Compound Ir19: R=$^t$Bu,
in Compound Ir20: R=CN,
in Compound Ir21: R=neopentyl,
in Compound Ir22: R=Ph,
in Compound Ir23: R=4-biphenyl,
in Compound Ir24: R=2,6-($^i$Pr)$_2$Ph,
in Compound Ir25: R=2,6-($^i$Pr)$_2$-4-biphenyl,
in Compound Ir26: R=2,4-($^i$Pr)$_2$-3-dibenzofuran,
Compound Ir27 through Ir39, each represented by the formula wherein in Compound Ir27: R=Me,
in Compound Ir28: R=Et,
in Compound Ir29: R=$^i$Pr,
in Compound Ir30: R=Cy, in Compound Ir31: R=$^i$Bu,
in Compound Ir32: R=$^t$Bu,
in Compound Ir33: R=CN,
in Compound Ir34: R=neopentyl,
in Compound Ir35: R=Ph,
in Compound Ir36: R=4-biphenyl,
in Compound Ir37: R=2,6-($^i$Pr)$_2$Ph,
in Compound Ir38: R=2,6-($^i$Pr)$_2$-4-biphenyl,
in Compound Ir39: R=2,4-($^i$Pr)$_2$-3-dibenzofuran,
Compound Ir40 through Ir52, each represented by the formula

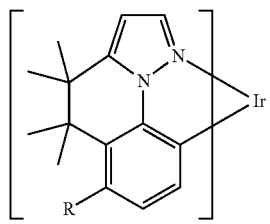

wherein in Compound Ir40: R=Me,
in Compound Ir41: R=Et,
in Compound Ir42: R=$^i$Pr,
in Compound Ir43: R=Cy,
in Compound Ir44: R=$^i$Bu,
in Compound Ir45: R=$^t$Bu,
in Compound Ir46: R=CN,
in Compound Ir47: R=neopentyl,
in Compound Ir48: R=Ph,
in Compound Ir49: R=4-biphenyl,
in Compound Ir50: R=2,6-($^i$Pr)$_2$Ph,
in Compound Ir51: R=2,6-($^i$Pr)$_2$-4-biphenyl,
in Compound Ir52: R=2,4-($^i$Pr)$_2$-3-dibenzofuran,
Compound Ir53 through Ir65, each represented by the formula

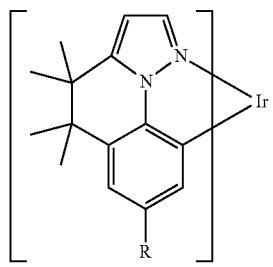

wherein in Compound Ir53: R=Me,
in Compound Ir54: R=Et,
in Compound Ir55: R=$^i$Pr,
in Compound Ir56: R=Cy,
in Compound Ir57: R=$^i$Bu,
in Compound Ir58: R=$^t$Bu,
in Compound Ir59: R=CN,
in Compound Ir60: R=neopentyl,
in Compound Ir61: R=Ph,
in Compound Ir62: R=4-biphenyl,
in Compound Ir63: R=2,6-($^i$Pr)$_2$Ph,
in Compound Ir64: R=2,6-($^i$Pr)$_2$-4-biphenyl,
in Compound Ir65: R=2,4-($^i$Pr)$_2$-3-dibenzofuran,
Compound Ir66 through Ir78, each represented by the formula

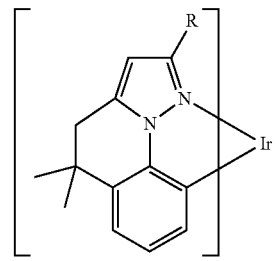

wherein in Compound Ir66: R=Me,
in Compound Ir67: R=Et,
in Compound Ir68: R=$^i$Pr,
in Compound Ir69: R=Cy,
in Compound Ir70: R=$^i$Bu,
in Compound Ir71: R=$^t$Bu,
in Compound Ir72: R=CN,
in Compound Ir73: R=neopentyl,
in Compound Ir74: R=Ph,
in Compound Ir75: R=4-biphenyl,
in Compound Ir76: R=2,6-($^i$Pr)$_2$Ph,
in Compound Ir77: R=2,6-($^i$Pr)$_2$-4-biphenyl,
in Compound Ir78: R=2,4-($^i$Pr)$_2$-3-dibenzofuran,
Compound Ir79 through Ir91, each represented by the formula

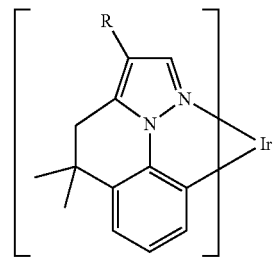

wherein in Compound Ir79: R=Me,
in Compound Ir80: R=Et,
in Compound Ir81: R=$^i$Pr,
in Compound Ir82: R=Cy,
in Compound Ir83: R=$^i$Bu,
in Compound Ir84: R=$^t$Bu,
in Compound Ir85: R=CN,
in Compound Ir86: R=neopentyl,
in Compound Ir87: R=Ph,
in Compound Ir88: R=4-biphenyl,
in Compound Ir89: R=2,6-($^i$Pr)$_2$Ph,
in Compound Ir90: R=2,6-($^i$Pr)$_2$-4-biphenyl,
in Compound Ir91: R=2,4-($^i$Pr)$_2$-3-dibenzofuran,
Compound Ir92 through Ir104, each represented by the formula

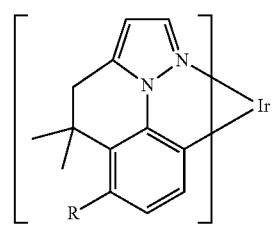

wherein in Compound Ir92: R=Me,
in Compound Ir93: R=Et,
in Compound Ir94: R=$^i$Pr,
in Compound Ir95: R=Cy,
in Compound Ir96: R=$^i$Bu,
in Compound Ir97: R=$^t$Bu,
in Compound Ir98: R=CN,
in Compound Ir99: R=neopentyl,
in Compound Ir100: R=Ph,
in Compound Ir101: R=4-biphenyl,
in Compound Ir102: R=2,6-($^i$Pr)$_2$Ph,
in Compound Ir103: R=2,6-($^i$Pr)$_2$-4-biphenyl,
in Compound Ir104: R=2,4-($^i$Pr)$_2$-3-dibenzofuran,
Compound Ir105 through Ir117, each represented by the formula

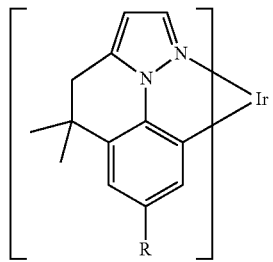

wherein in Compound Ir105: R=Me,
in Compound Ir106: R=Et,
in Compound Ir107: R=$^i$Pr,
in Compound Ir108: R=Cy,
in Compound Ir109: R=$^i$Bu,
in Compound Ir110: R=$^t$Bu,
in Compound Ir111: R=CN,
in Compound Ir112: R=neopentyl,
in Compound Ir113: R=Ph,
in Compound Ir114: R=4-biphenyl,
in Compound Ir115: R=2,6-($^i$Pr)$_2$Ph,
in Compound Ir116: R=2,6-($^i$Pr)$_2$-4-biphenyl,
in Compound Ir117: R=2,4-($^i$Pr)$_2$-3-dibenzofuran,
Compound Ir118 through Ir130, each represented by the formula

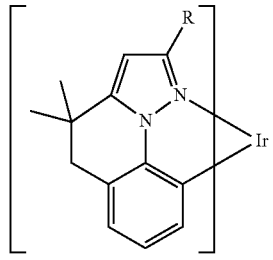

wherein in Compound Ir118: R=Me,
in Compound Ir119: R=Et,
in Compound Ir120: R=$^i$Pr,
in Compound Ir121: R=Cy,
in Compound Ir122: R=$^i$Bu,
in Compound Ir123: R=$^t$Bu,
in Compound Ir124: R=CN,
in Compound Ir125: R=neopentyl,
in Compound Ir126: R=Ph,
in Compound Ir127: R=4-biphenyl,
in Compound Ir128: R=2,6-($^i$Pr)$_2$Ph,
in Compound Ir129: R=2,6-($^i$Pr)$_2$-4-biphenyl,
in Compound Ir130: R=2,4-($^i$Pr)$_2$-3-dibenzofuran,
Compound Ir131 through Ir143, each represented by the formula

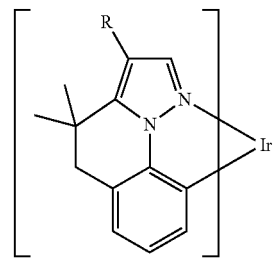

wherein in Compound Ir131: R=Me,
in Compound Ir132: R=Et,
in Compound Ir133: R=$^i$Pr,
in Compound Ir134: R=Cy,
in Compound Ir135: R=$^i$Bu,
in Compound Ir136: R=$^t$Bu,
in Compound Ir137: R=CN,
in Compound Ir138: R=neopentyl,
in Compound Ir139: R=Ph,
in Compound Ir140: R=4-biphenyl,
in Compound Ir141: R=2,6-($^i$Pr)$_2$Ph,
in Compound Ir142: R=2,6-($^i$Pr)$_2$-4-biphenyl,
in Compound Ir143: R=2,4-($^i$Pr)$_2$-3-dibenzofuran,
Compound Ir144 through Ir156, each represented by the formula

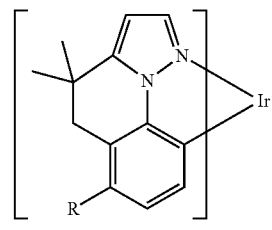

wherein in Compound Ir144: R=Me,
in Compound Ir145: R=Et,
in Compound Ir146: R=$^i$Pr,
in Compound Ir147: R=Cy,
in Compound Ir148: R=$^i$Bu,
in Compound Ir149: R=$^t$Bu,
in Compound Ir150: R=CN,
in Compound Ir151: R=neopentyl,
in Compound Ir152: R=Ph,
in Compound Ir153: R=4-biphenyl,
in Compound Ir154: R=2,6-($^i$Pr)$_2$Ph,
in Compound Ir155: R=2,6-($^i$Pr)$_2$-4-biphenyl,
in Compound Ir156: R=2,4-($^i$Pr)$_2$-3-dibenzofuran,
Compound Ir157 through Ir169, each represented by the formula

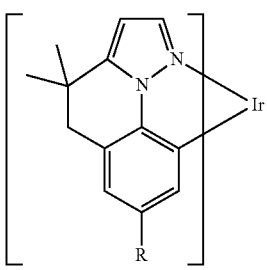

wherein in Compound Ir157: R=Me,
in Compound Ir158: R=Et,
in Compound Ir159: R=$^i$Pr,
in Compound Ir160: R=Cy,
in Compound Ir161: R=$^i$Bu,
in Compound Ir162: R=$^t$Bu,
in Compound Ir163: R≡CN,
in Compound Ir164: R=neopentyl,
in Compound Ir165: R=Ph,
in Compound Ir166: R=4-biphenyl,
in Compound Ir167: R=2,6-($^i$Pr)$_2$Ph,
in Compound Ir168: R=2,6-($^i$Pr)$_2$-4-biphenyl,
in Compound Ir169: R=2,4-($^i$Pr)$_2$-3-dibenzofuran,
Compound Ir170 through Ir182, each represented by the formula

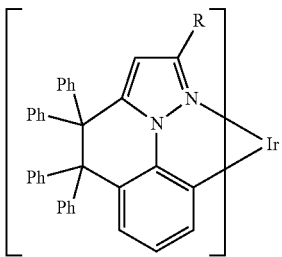

wherein in Compound Ir170: R=Me,
in Compound Ir171: R=Et,
in Compound Ir172: R=$^i$Pr,
in Compound Ir173: R=Cy,
in Compound Ir174: R=$^i$Bu,
in Compound Ir175: R=$^t$Bu,
in Compound Ir176: R≡CN,
in Compound Ir177: R=neopentyl,
in Compound Ir178: R=Ph,
in Compound Ir179: R=4-biphenyl,
in Compound Ir180: R=2,6-($^i$Pr)$_2$Ph,
in Compound Ir181: R=2,6-($^i$Pr)$_2$-4-biphenyl,
in Compound Ir182: R=2,4-($^i$Pr)$_2$-3-dibenzofuran,
Compound Ir183 through Ir195, each represented by the formula

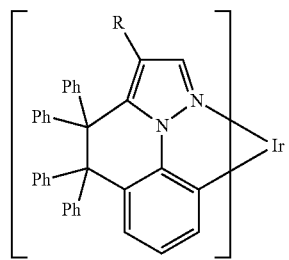

wherein in Compound Ir183: R=Me,
in Compound Ir184: R=Et,
in Compound Ir185: R=$^i$Pr,
in Compound Ir186: R=Cy,
in Compound Ir187: R=$^i$Bu,
in Compound Ir188: R=$^t$Bu,
in Compound Ir189: R≡CN,
in Compound Ir190: R=neopentyl,
in Compound Ir191: R=Ph,
in Compound Ir192: R=4-biphenyl,
in Compound Ir193: R=2,6-($^i$Pr)$_2$Ph,
in Compound Ir194: R=2,6-($^i$Pr)$_2$-4-biphenyl,
in Compound Ir195: R=2,4-($^i$Pr)$_2$-3-dibenzofuran,
Compound Ir196 through Ir208, each represented by the formula

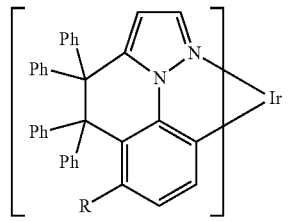

wherein in Compound Ir196: R=Me,
in Compound Ir197: R=Et,
in Compound Ir198: R=$^i$Pr,
in Compound Ir199: R=Cy,
in Compound Ir200: R=$^i$Bu,
in Compound Ir201: R=$^t$Bu,
in Compound Ir202: R≡CN,
in Compound Ir203: R=neopentyl,
in Compound Ir204: R=Ph,
in Compound Ir205: R=4-biphenyl,
in Compound Ir206: R=2,6-($^i$Pr)$_2$Ph,
in Compound Ir207: R=2,6-($^i$Pr)$_2$-4-biphenyl,
in Compound Ir208: R=2,4-($^i$Pr)$_2$-3-dibenzofuran,
Compound Ir209 through Ir221, each represented by the formula

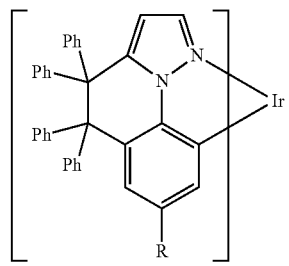

wherein in Compound Ir209: R=Me,
in Compound Ir210: R=Et,
in Compound Ir211: R=$^i$Pr,
in Compound Ir212: R=Cy,
in Compound Ir213: R=$^i$Bu,
in Compound Ir214: R=$^t$Bu,
in Compound Ir215: R=CN,
in Compound Ir216: R=neopentyl,
in Compound Ir217: R=Ph,
in Compound Ir218: R=4-biphenyl,
in Compound Ir219: R=2,6-($^i$Pr)$_2$Ph,
in Compound Ir220: R=2,6-($^i$Pr)$_2$-4-biphenyl,
in Compound Ir221: R=2,4-($^i$Pr)$_2$-3-dibenzofuran,
Compound Ir222 through Ir234, each represented by the formula

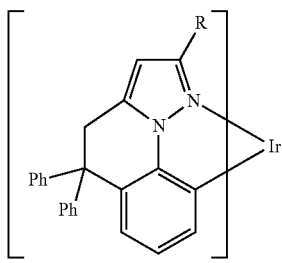

wherein in Compound Ir222: R=Me,
in Compound Ir223: R=Et,
in Compound Ir224: R=$^i$Pr,
in Compound Ir225: R=Cy,
in Compound Ir226: R=$^i$Bu,
in Compound Ir227: R=$^t$Bu,
in Compound Ir228: R=CN,
in Compound Ir229: R=neopentyl,
in Compound Ir230: R=Ph,
in Compound Ir231: R=4-biphenyl,
in Compound Ir232: R=2,6-($^i$Pr)$_2$Ph,
in Compound Ir233: R=2,6-($^i$Pr)$_2$-4-biphenyl,
in Compound Ir234: R=2,4-($^i$Pr)$_2$-3-dibenzofuran,
Compound Ir235 through Ir247, each represented by the formula

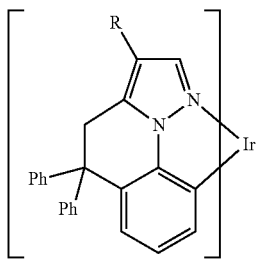

wherein in Compound Ir235: R=Me,
in Compound Ir236: R=Et,
in Compound Ir237: R=$^i$Pr,
in Compound Ir238: R=Cy,
in Compound Ir239: R=$^i$Bu,
in Compound Ir240: R=$^t$Bu,
in Compound Ir241: R=CN,
in Compound Ir242: R=neopentyl,
in Compound Ir243: R=Ph,
in Compound Ir244: R=4-biphenyl,
in Compound Ir245: R=2,6-($^i$Pr)$_2$Ph,
in Compound Ir246: R=2,6-($^i$Pr)$_2$-4-biphenyl,
in Compound Ir247: R=2,4-($^i$Pr)$_2$-3-dibenzofuran,
Compound Ir248 through Ir260, each represented by the formula

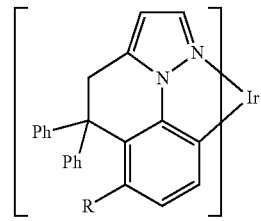

wherein in Compound Ir248: R=Me,
in Compound Ir249: R=Et,
in Compound Ir250: R=$^i$Pr,
in Compound Ir251: R=Cy,
in Compound Ir252: R=$^i$Bu,
in Compound Ir253: R=$^t$Bu,
in Compound Ir254: R=CN,
in Compound Ir255: R=neopentyl,
in Compound Ir256: R=Ph,
in Compound Ir257: R=4-biphenyl,
in Compound Ir258: R=2,6-($^i$Pr)$_2$Ph,
in Compound Ir259: R=2,6-($^i$Pr)$_2$-4-biphenyl,
in Compound Ir260: R=2,4-($^i$Pr)$_2$-3-dibenzofuran,
Compound Ir261 through Ir273, each represented by the formula

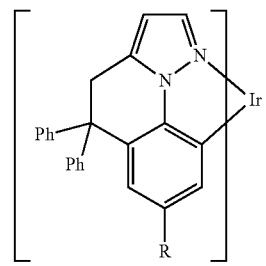

wherein in Compound Ir261: R=Me,
in Compound Ir262: R=Et,
in Compound Ir263: R=$^i$Pr,
in Compound Ir264: R=Cy,
in Compound Ir265: R=$^i$Bu,
in Compound Ir266: R=$^t$Bu,
in Compound Ir267: R=CN,
in Compound Ir268: R=neopentyl,
in Compound Ir269: R=Ph,
in Compound Ir270: R=4-biphenyl,
in Compound Ir271: R=2,6-($^i$Pr)$_2$Ph,
in Compound Ir272: R=2,6-($^i$Pr)$_2$-4-biphenyl,
in Compound Ir273: R=2,4-($^i$Pr)$_2$-3-dibenzofuran,
Compound Ir274 through Ir286, each represented by the formula

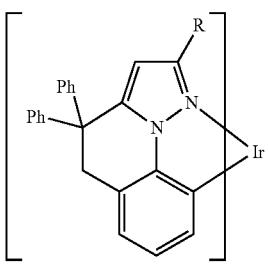

wherein in Compound Ir274: R=Me,
in Compound Ir275: R=Et,
in Compound Ir276: R=$^i$Pr,
in Compound Ir277: R=Cy,
in Compound Ir278: R=$^i$Bu,
in Compound Ir279: R=$^t$Bu,
in Compound Ir280: R=CN,
in Compound Ir281: R=neopentyl,
in Compound Ir282: R=Ph,
in Compound Ir283: R=4-biphenyl,
in Compound Ir284: R=2,6-($^i$Pr)$_2$Ph,
in Compound Ir285: R=2,6-($^i$Pr)$_2$-4-biphenyl,
in Compound Ir286: R=2,4-($^i$Pr)$_2$-3-dibenzofuran,
Compound Ir287 through Ir299, each represented by the formula

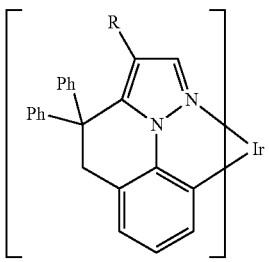

wherein in Compound Ir287: R=Me,
in Compound Ir288: R=Et,
in Compound Ir289: R=$^i$Pr,
in Compound Ir290: R=Cy,
in Compound Ir291: R=$^i$Bu,
in Compound Ir292: R=$^t$Bu,
in Compound Ir293: R=CN,
in Compound Ir294: R=neopentyl,
in Compound Ir295: R=Ph,
in Compound Ir296: R=4-biphenyl,
in Compound Ir297: R=2,6-($^i$Pr)$_2$Ph,
in Compound Ir298: R=2,6-($^i$Pr)$_2$-4-biphenyl,
in Compound Ir299: R=2,4-($^i$Pr)$_2$-3-dibenzofuran,
Compound Ir300 through Ir312, each represented by the formula

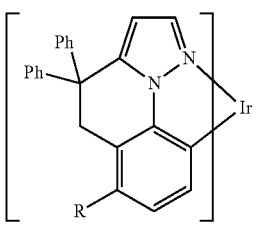

wherein in Compound Ir300: R=Me,
in Compound Ir301: R=Et,
in Compound Ir302: R=$^i$Pr,
in Compound Ir303: R=Cy,
in Compound Ir304: R=$^i$Bu,
in Compound Ir305: R=$^t$Bu,
in Compound Ir306: R=CN,
in Compound Ir307: R=neopentyl,
in Compound Ir308: R=Ph,
in Compound Ir309: R=4-biphenyl,
in Compound Ir310: R=2,6-($^i$Pr)$_2$Ph,
in Compound Ir311: R=2,6-($^i$Pr)$_2$-4-biphenyl,
in Compound Ir312: R=2,4-($^i$Pr)$_2$-3-dibenzofuran,
Compound Ir313 through Ir325, each represented by the formula

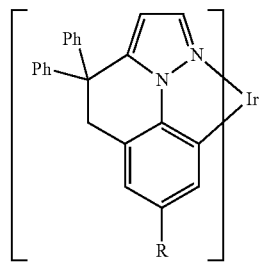

wherein in Compound Ir313: R=Me,
in Compound Ir314: R=Et,
in Compound Ir315: R=$^i$Pr,
in Compound Ir316: R=Cy,
in Compound Ir317: R=$^i$Bu,
in Compound Ir318: R=$^t$Bu,
in Compound Ir319: R=CN,
in Compound Ir320: R=neopentyl,
in Compound Ir321: R=Ph,
in Compound Ir322: R=4-biphenyl,
in Compound Ir323: R=2,6-($^i$Pr)$_2$Ph,
in Compound Ir324: R=2,6-($^i$Pr)$_2$-4-biphenyl,
in Compound Ir325: R=2,4-($^i$Pr)$_2$-3-dibenzofuran,
Compound Ir326 through Ir338, each represented by the formula

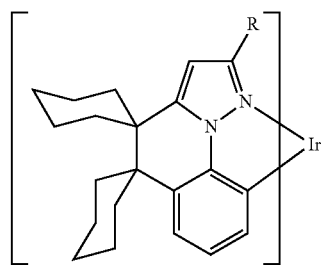

wherein in Compound Ir326: R=Me,
in Compound Ir327: R=Et,
in Compound Ir328: R=$^i$Pr,
in Compound Ir329: R=Cy,
in Compound Ir330: R=$^i$Bu,
in Compound Ir331: R=$^t$Bu,
in Compound Ir332: R=CN,
in Compound Ir333: R=neopentyl,
in Compound Ir334: R=Ph,
in Compound Ir335: R=4-biphenyl, in Compound Ir336: R=2,6-($^i$Pr)$_2$Ph,
in Compound Ir337: R=2,6-($^i$Pr)$_2$-4-biphenyl,
in Compound Ir338: R=2,4-($^i$Pr)$_2$-3-dibenzofuran,
Compound Ir339 through Ir351, each represented by the formula

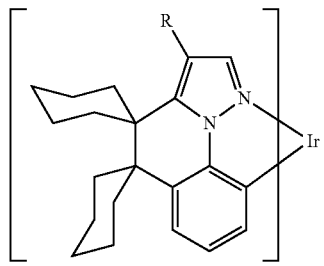

wherein in Compound Ir339: R=Me,
in Compound Ir340: R=Et,
in Compound Ir341: R=$^i$Pr,
in Compound Ir342: R=Cy,
in Compound Ir343: R=$^i$Bu,
in Compound Ir344: R=$^t$Bu,
in Compound Ir345: R=CN,
in Compound Ir346: R=neopentyl,
in Compound Ir347: R=Ph,
in Compound Ir348: R=4-biphenyl,
in Compound Ir349: R=2,6-($^i$Pr)$_2$Ph,
in Compound Ir350: R=2,6-($^i$Pr)$_2$-4-biphenyl,
in Compound Ir351: R=2,4-($^i$Pr)$_2$-3-dibenzofuran,
Compound Ir352 through Ir364, each represented by the formula

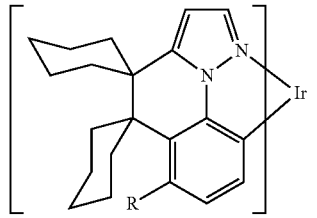

wherein in Compound Ir352: R=Me,
in Compound Ir353: R=Et,
in Compound Ir354: R=$^i$Pr,
in Compound Ir355: R=Cy,
in Compound Ir356: R=$^i$Bu,
in Compound Ir357: R=$^t$Bu,
in Compound Ir358: R=CN,
in Compound Ir359: R=neopentyl,
in Compound Ir360: R=Ph,
in Compound Ir361: R=4-biphenyl,
in Compound Ir362: R=2,6-($^i$Pr)$_2$Ph,
in Compound Ir363: R=2,6-($^i$Pr)$_2$-4-biphenyl,
in Compound Ir364: R=2,4-($^i$Pr)$_2$-3-dibenzofuran,
Compound Ir365 through Ir377, each represented by the formula

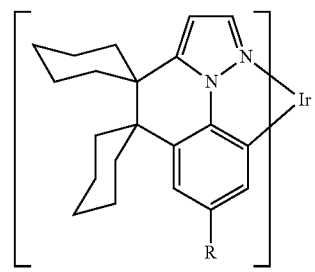

wherein in Compound Ir365: R=Me,
in Compound Ir366: R=Et,
in Compound Ir367: R=$^i$Pr,
in Compound Ir368: R=Cy,
in Compound Ir369: R=$^i$Bu,
in Compound Ir370: R=$^t$Bu,
in Compound Ir371: R=CN,
in Compound Ir372: R=neopentyl,
in Compound Ir373: R=Ph,
in Compound Ir374: R=4-biphenyl,
in Compound Ir375: R=2,6-($^i$Pr)$_2$Ph,
in Compound Ir376: R=2,6-($^i$Pr)$_2$-4-biphenyl,
in Compound Ir377: R=2,4-($^i$Pr)$_2$-3-dibenzofuran,
Compound Ir378 through Ir390, each represented by the formula

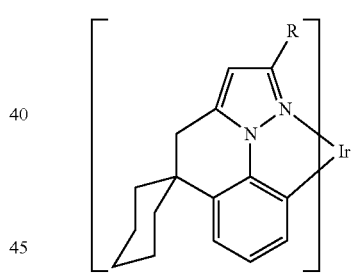

wherein in Compound Ir378: R=Me,
in Compound Ir379: R=Et,
in Compound Ir380: R=$^i$Pr,
in Compound Ir381: R=Cy,
in Compound Ir382: R=$^i$Bu,
in Compound Ir383: R=$^t$Bu,
in Compound Ir384: R=CN,
in Compound Ir385: R=neopentyl,
in Compound Ir386: R=Ph,
in Compound Ir387: R=4-biphenyl,
in Compound Ir388: R=2,6-($^i$Pr)$_2$Ph,
in Compound Ir389: R=2,6-($^i$Pr)$_2$-4-biphenyl,
in Compound Ir390: R=2,4-($^i$Pr)$_2$-3-dibenzofuran,
Compound Ir391 through Ir403, each represented by the formula

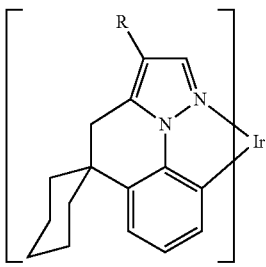

wherein in Compound Ir391: R=Me,
in Compound Ir392: R=Et,
in Compound Ir393: R=$^i$Pr,
in Compound Ir394: R=Cy,
in Compound Ir395: R=$^i$Bu,
in Compound Ir396: R=$^t$Bu,
in Compound Ir397: R=CN,
in Compound Ir398: R=neopentyl,
in Compound Ir399: R=Ph,
in Compound Ir400: R=4-biphenyl,
in Compound Ir401: R=2,6-($^i$Pr)$_2$Ph,
in Compound Ir402: R=2,6-($^i$Pr)$_2$-4-biphenyl,
in Compound Ir403: R=2,4-($^i$Pr)$_2$-3-dibenzofuran,
Compound Ir404 through Ir416, each represented by the formula

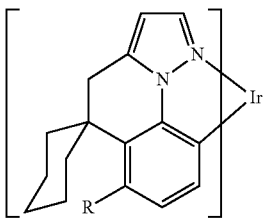

wherein in Compound Ir404: R=Me,
in Compound Ir405: R=Et,
in Compound Ir406: R=$^i$Pr,
in Compound Ir407: R=Cy,
in Compound Ir408: R=$^i$Bu,
in Compound Ir409: R=$^t$Bu,
in Compound Ir410: R=CN,
in Compound Ir411: R=neopentyl,
in Compound Ir412: R=Ph,
in Compound Ir413: R=4-biphenyl,
in Compound Ir414: R=2,6-($^i$Pr)$_2$Ph,
in Compound Ir415: R=2,6-($^i$Pr)$_2$-4-biphenyl,
in Compound Ir416: R=2,4-($^i$Pr)$_2$-3-dibenzofuran,
Compound Ir417 through Ir429, each represented by the formula

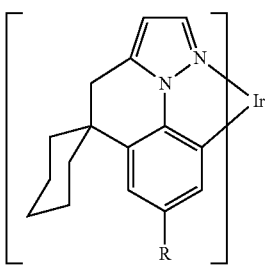

wherein in Compound Ir417: R=Me,
in Compound Ir418: R=Et,
in Compound Ir419: R=$^i$Pr,
in Compound Ir420: R=Cy,
in Compound Ir421: R=$^i$Bu,
in Compound Ir422: R=$^t$Bu,
in Compound Ir423: R=CN,
in Compound Ir424: R=neopentyl,
in Compound Ir425: R=Ph,
in Compound Ir426: R=4-biphenyl,
in Compound Ir427: R=2,6-($^i$Pr)$_2$Ph,
in Compound Ir428: R=2,6-($^i$Pr)$_2$-4-biphenyl,
in Compound Ir429: R=2,4-($^i$Pr)$_2$-3-dibenzofuran,
Compound Ir430 through Ir442, each represented by the formula

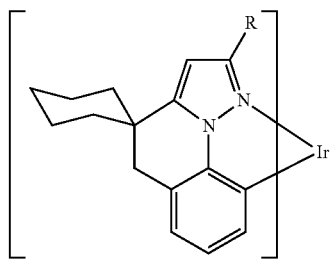

wherein in Compound Ir430: R=Me,
in Compound Ir431: R=Et,
in Compound Ir432: R=$^i$Pr,
in Compound Ir433: R=Cy,
in Compound Ir434: R=$^i$Bu,
in Compound Ir435: R=$^t$Bu,
in Compound Ir436: R=CN,
in Compound Ir437: R=neopentyl,
in Compound Ir438: R=Ph,
in Compound Ir439: R=4-biphenyl,
in Compound Ir440: R=2,6-($^i$Pr)$_2$Ph,
in Compound Ir441: R=2,6-($^i$Pr)$_2$-4-biphenyl,
in Compound Ir442: R=2,4-($^i$Pr)$_2$-3-dibenzofuran,
Compound Ir443 through Ir455, each represented by the formula

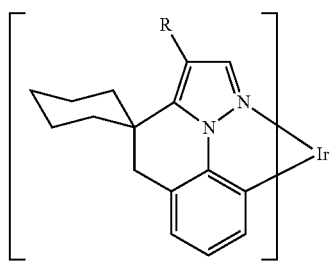

wherein in Compound Ir443: R=Me,
in Compound Ir444: R=Et,
in Compound Ir445: R=$^i$Pr,
in Compound Ir446: R=Cy,
in Compound Ir447: R=$^i$Bu,
in Compound Ir448: R=$^t$Bu,
in Compound Ir449: R=CN,
in Compound Ir450: R=neopentyl,
in Compound Ir451: R=Ph,
in Compound Ir452: R=4-biphenyl,
in Compound Ir453: R=2,6-($^i$Pr)$_2$Ph, in Compound Ir454: R=2,6-($^i$Pr)$_2$-4-biphenyl,
in Compound Ir455: R=2,4-($^i$Pr)$_2$-3-dibenzofuran,
Compound Ir456 through Ir468, each represented by the formula

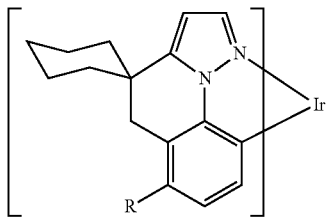

wherein in Compound Ir456: R=Me,
in Compound Ir457: R=Et,
in Compound Ir458: R=$^i$Pr,
in Compound Ir459: R=Cy,
in Compound Ir460: R=$^i$Bu,
in Compound Ir461: R=$^t$Bu,
in Compound Ir462: R=CN,
in Compound Ir463: R=neopentyl,
in Compound Ir464: R=Ph,
in Compound Ir465: R=4-biphenyl,
in Compound Ir466: R=2,6-($^i$Pr)$_2$Ph,
in Compound Ir467: R=2,6-($^i$Pr)$_2$-4-biphenyl,
in Compound Ir468: R=2,4-($^i$Pr)$_2$-3-dibenzofuran,
Compound Ir469 through Ir481, each represented by the formula

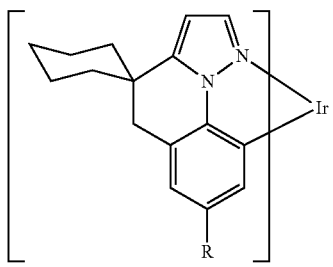

wherein in Compound Ir469: R=Me,
in Compound Ir470: R=Et,
in Compound Ir471: R=$^i$Pr,
in Compound Ir472: R=Cy,
in Compound Ir473: R=$^i$Bu,
in Compound Ir474: R=$^t$Bu,
in Compound Ir475: R=CN,
in Compound Ir476: R=neopentyl,
in Compound Ir477: R=Ph,
in Compound Ir478: R=4-biphenyl,
in Compound Ir479: R=2,6-($^i$Pr)$_2$Ph,
in Compound Ir480: R=2,6-($^i$Pr)$_2$-4-biphenyl,
in Compound Ir481: R=2,4-($^i$Pr)$_2$-3-dibenzofuran,
Compound Ir482 through Ir494, each represented by the formula

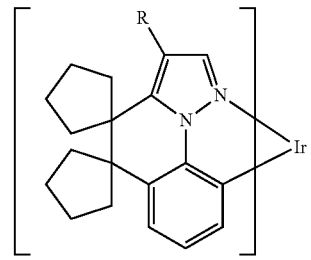

wherein in Compound Ir482: R=Me,
in Compound Ir483: R=Et,
in Compound Ir484: R=$^i$Pr,
in Compound Ir485: R=Cy,
in Compound Ir486: R=$^i$Bu,
in Compound Ir487: R=$^t$Bu,
in Compound Ir488: R=CN,
in Compound Ir489: R=neopentyl,
in Compound Ir490: R=Ph,
in Compound Ir491: R=4-biphenyl,
in Compound Ir492: R=2,6-($^i$Pr)$_2$Ph,
in Compound Ir493: R=2,6-($^i$Pr)$_2$-4-biphenyl,
in Compound Ir494: R=2,4-($^i$Pr)$_2$-3-dibenzofuran,
Compound Ir495 through Ir507, each represented by the formula

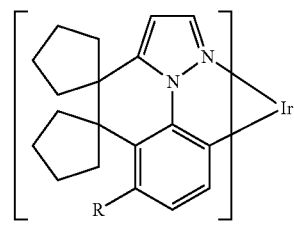

wherein in Compound Ir495: R=Me,
in Compound Ir496: R=Et,
in Compound Ir497: R=$^i$Pr,
in Compound Ir498: R=Cy,
in Compound Ir499: R=$^i$Bu,
in Compound Ir500: R=$^t$Bu,
in Compound Ir501: R=CN,
in Compound Ir502: R=neopentyl,
in Compound Ir503: R=Ph,
in Compound Ir504: R=4-biphenyl,
in Compound Ir505: R=2,6-($^i$Pr)$_2$Ph,
in Compound Ir506: R=2,6-($^i$Pr)$_2$-4-biphenyl,
in Compound Ir507: R=2,4-($^i$Pr)$_2$-3-dibenzofuran,
Compound Ir508 through Ir520, each represented by the formula wherein in Compound Ir508: R=Me,
in Compound Ir509: R=Et,
in Compound Ir510: R=$^i$Pr,
in Compound Ir511: R=Cy,
in Compound Ir512: R=$^i$Bu,
in Compound Ir513: R=$^t$Bu,
in Compound Ir514: R=CN,
in Compound Ir515: R=neopentyl,
in Compound Ir516: R=Ph,
in Compound Ir517: R=4-biphenyl,
in Compound Ir518: R=2,6-($^i$Pr)$_2$Ph,
in Compound Ir519: R=2,6-($^i$Pr)$_2$-4-biphenyl,
in Compound Ir520: R=2,4-($^i$Pr)$_2$-3-dibenzofuran,
Compound Ir521 through Ir533, each represented by the formula

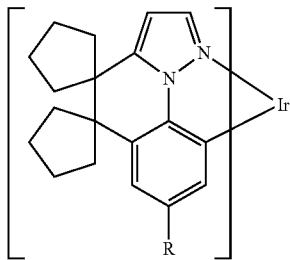

wherein in Compound Ir521: R=Me,
in Compound Ir522: R=Et,
in Compound Ir523: R=$^i$Pr,
in Compound Ir524: R=Cy,
in Compound Ir525: R=$^i$Bu,
in Compound Ir526: R=$^t$Bu,
in Compound Ir527: R=CN,
in Compound Ir528: R=neopentyl,
in Compound Ir529: R=Ph,
in Compound Ir530: R=4-biphenyl,
in Compound Ir531: R=2,6-($^i$Pr)$_2$Ph,
in Compound Ir532: R=2,6-($^i$Pr)$_2$-4-biphenyl,
in Compound Ir533: R=2,4-($^i$Pr)$_2$-3-dibenzofuran,
Compound Ir534 through Ir546, each represented by the formula

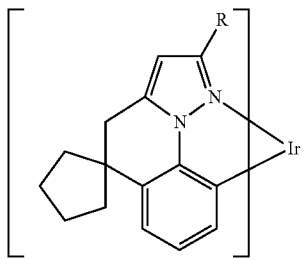

wherein in Compound Ir534: R=Me,
in Compound Ir535: R=Et,
in Compound Ir536: R=$^i$Pr,
in Compound Ir537: R=Cy,
in Compound Ir538: R=$^i$Bu,
in Compound Ir539: R=$^t$Bu,
in Compound Ir540: R=CN,
in Compound Ir541: R=neopentyl,
in Compound Ir542: R=Ph,
in Compound Ir543: R=4-biphenyl,
in Compound Ir544: R=2,6-($^i$Pr)$_2$Ph,
in Compound Ir545: R=2,6-($^i$Pr)$_2$-4-biphenyl,
in Compound Ir546: R=2,4-($^i$Pr)$_2$-3-dibenzofuran,
Compound Ir547 through Ir559, each represented by the formula

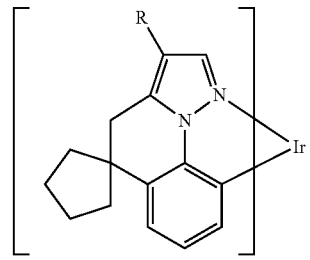

wherein in Compound Ir547: R=Me,
in Compound Ir548: R=Et,
in Compound Ir549: R=$^i$Pr,
in Compound Ir550: R=Cy,
in Compound Ir551: R=$^i$Bu,
in Compound Ir552: R=$^t$Bu,
in Compound Ir553: R=CN,
in Compound Ir554: R=neopentyl,
in Compound Ir555: R=Ph,
in Compound Ir556: R=4-biphenyl,
in Compound Ir557: R=2,6-($^i$Pr)$_2$Ph,
in Compound Ir558: R=2,6-($^i$Pr)$_2$-4-biphenyl,
in Compound Ir559: R=2,4-($^i$Pr)$_2$-3-dibenzofuran,
Compound Ir560 through Ir572, each represented by the formula

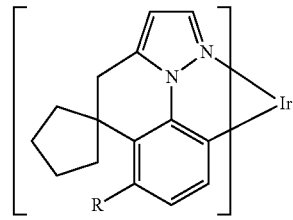

wherein in Compound Ir560: R=Me,
in Compound Ir561: R=Et,
in Compound Ir562: R=$^i$Pr,
in Compound Ir563: R=Cy,
in Compound Ir564: R=$^i$Bu,
in Compound Ir565: R=$^t$Bu,
in Compound Ir566: R=CN,
in Compound Ir567: R=neopentyl,
in Compound Ir568: R=Ph,
in Compound Ir569: R=4-biphenyl,
in Compound Ir570: R=2,6-($^i$Pr)$_2$Ph,
in Compound Ir571: R=2,6-($^i$Pr)$_2$-4-biphenyl,
in Compound Ir572: R=2,4-($^i$Pr)$_2$-3-dibenzofuran,
Compound Ir573 through Ir585, each represented by the formula

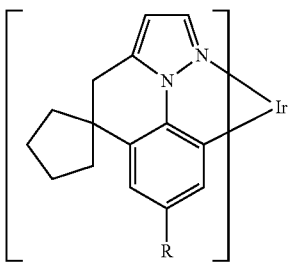

wherein in Compound Ir573: R=Me,
in Compound Ir574: R=Et,
in Compound Ir575: R=$^i$Pr,
in Compound Ir576: R=Cy,
in Compound Ir577: R=$^i$Bu,
in Compound Ir578: R=$^t$Bu,
in Compound Ir579: R=CN,
in Compound Ir580: R=neopentyl,
in Compound Ir581: R=Ph,
in Compound Ir582: R=4-biphenyl,
in Compound Ir583: R=2,6-($^i$Pr)$_2$Ph,
in Compound Ir584: R=2,6-($^i$Pr)$_2$-4-biphenyl,
in Compound Ir585: R=2,4-($^i$Pr)$_2$-3-dibenzofuran,
Compound Ir586 through Ir598, each represented by the formula

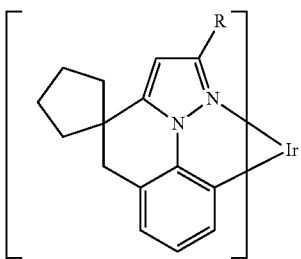

wherein in Compound Ir586: R=Me,
in Compound Ir587: R=Et,
in Compound Ir588: R=$^i$Pr,
in Compound Ir589: R=Cy,
in Compound Ir590: R=$^i$Bu,
in Compound Ir591: R=$^t$Bu,
in Compound Ir592: R=CN,
in Compound Ir593: R=neopentyl,
in Compound Ir594: R=Ph,
in Compound Ir595: R=4-biphenyl,
in Compound Ir596: R=2,6-($^i$Pr)$_2$Ph,
in Compound Ir597: R=2,6-($^i$Pr)$_2$-4-biphenyl,
in Compound Ir598: R=2,4-($^i$Pr)$_2$-3-dibenzofuran,
Compound Ir599 through Ir611, each represented by the formula

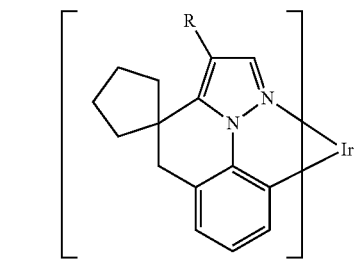

wherein in Compound Ir599: R=Me,
in Compound Ir600: R=Et,
in Compound Ir601: R=$^i$Pr,
in Compound Ir602: R=Cy,
in Compound Ir603: R=$^i$Bu,
in Compound Ir604: R=$^t$Bu,
in Compound Ir605: R=CN,
in Compound Ir606: R=neopentyl,
in Compound Ir607: R=Ph,
in Compound Ir608: R=4-biphenyl,
in Compound Ir609: R=2,6-($^i$Pr)$_2$Ph,
in Compound Ir610: R=2,6-($^i$Pr)$_2$-4-biphenyl,
in Compound Ir611: R=2,4-($^i$Pr)$_2$-3-dibenzofuran,
Compound Ir612 through Ir624, each represented by the formula

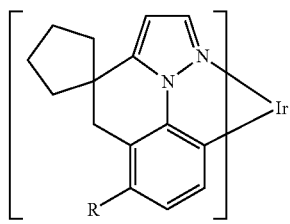

wherein in Compound Ir612: R=Me,
in Compound Ir613: R=Et,
in Compound Ir614: R=$^i$Pr,
in Compound Ir615: R=Cy,
in Compound Ir616: R=Bu,
in Compound Ir617: R=$^t$Bu,
in Compound Ir618: R=CN,
in Compound Ir619: R=neopentyl,
in Compound Ir620: R=Ph,
in Compound Ir621: R=4-biphenyl,
in Compound Ir622: R=2,6-($^i$Pr)$_2$Ph,
in Compound Ir623: R=2,6-($^i$Pr)$_2$-4-biphenyl,
in Compound Ir624: R=2,4-($^i$Pr)$_2$-3-dibenzofuran,
Compound Ir625 through Ir637, each represented by the formula

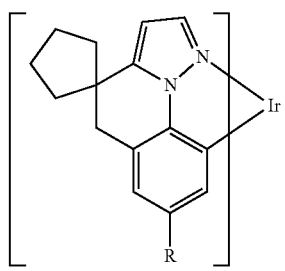

wherein in Compound Ir625: R=Me,
in Compound Ir626: R=Et,
in Compound Ir627: R=$^i$Pr,
in Compound Ir628: R=Cy,
in Compound Ir629: R=$^i$Bu,
in Compound Ir630: R=$^t$Bu,
in Compound Ir631: R=CN,
in Compound Ir632: R=neopentyl,
in Compound Ir633: R=Ph,
in Compound Ir634: R=4-biphenyl,
in Compound Ir635: R=2,6-($^i$Pr)$_2$Ph,
in Compound Ir636: R=2,6-($^i$Pr)$_2$-4-biphenyl,
in Compound Ir637: R=2,4-($^i$Pr)$_2$-3-dibenzofuran,
Compound Ir638 through Ir650, each represented by the formula

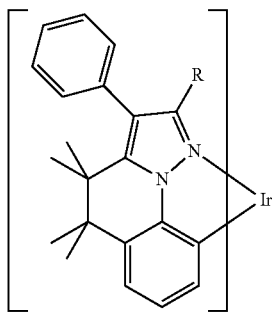

wherein in Compound Ir638: R=Me,
in Compound Ir639: R=Et,
in Compound Ir640: R=$^i$Pr,
in Compound Ir641: R=Cy,
in Compound Ir642: R=$^i$Bu,
in Compound Ir643: R=$^t$Bu,
in Compound Ir644: R=CN,
in Compound Ir645: R=neopentyl,
in Compound Ir646: R=Ph,
in Compound Ir647: R=4-biphenyl,
in Compound Ir648: R=2,6-($^i$Pr)$_2$Ph,
in Compound Ir649: R=2,6-($^i$Pr)$_2$-4-biphenyl,
in Compound Ir650: R=2,4-($^i$Pr)$_2$-3-dibenzofuran,
Compound Ir651 through Ir663, each represented by the formula

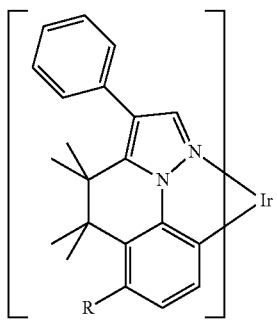

wherein in Compound Ir651: R=Me,
in Compound Ir652: R=Et,
in Compound Ir653: R=$^i$Pr,
in Compound Ir654: R=Cy,
in Compound Ir655: R=$^i$Bu,
in Compound Ir656: R=$^t$Bu,
in Compound Ir657: R=CN,
in Compound Ir658: R=neopentyl,
in Compound Ir659: R=Ph,
in Compound Ir660: R=4-biphenyl,
in Compound Ir661: R=2,6-($^i$Pr)$_2$Ph,
in Compound Ir662: R=2,6-($^i$Pr)$_2$-4-biphenyl,
in Compound Ir663: R=2,4-($^i$Pr)$_2$-3-dibenzofuran,
Compound Ir664 through Ir676, each represented by the formula

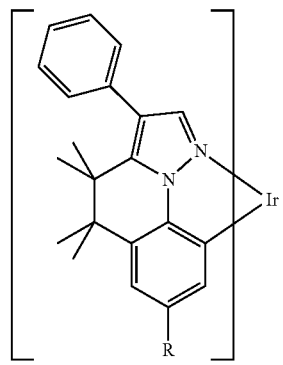

wherein in Compound Ir664: R=Me,
in Compound Ir665: R=Et,
in Compound Ir666: R=$^i$Pr,
in Compound Ir667: R=Cy,
in Compound Ir668: R=$^i$Bu,
in Compound Ir669: R=$^t$Bu,
in Compound Ir670: R=CN,
in Compound Ir671: R=neopentyl,
in Compound Ir672: R=Ph,
in Compound Ir673: R=4-biphenyl,
in Compound Ir674: R=2,6-($^i$Pr)$_2$Ph,
in Compound Ir675: R=2,6-($^i$Pr)$_2$-4-biphenyl,
in Compound Ir676: R=2,4-($^i$Pr)$_2$-3-dibenzofuran,
Compound Ir677 through Ir689, each represented by the formula

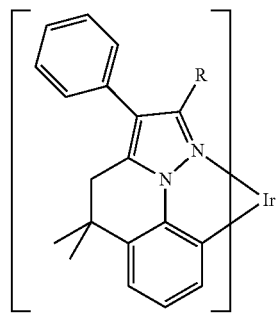

wherein in Compound Ir677: R=Me,
in Compound Ir678: R=Et,
in Compound Ir679: R=$^i$Pr,
in Compound Ir680: R=Cy,
in Compound Ir681: R=$^i$Bu,
in Compound Ir682: R=$^t$Bu,
in Compound Ir683: R=CN,
in Compound Ir684: R=neopentyl,
in Compound Ir685: R=Ph,
in Compound Ir686: R=4-biphenyl,
in Compound Ir687: R=2,6-($^i$Pr)$_2$Ph, in Compound Ir688: R=2,6-($^i$Pr)$_2$-4-biphenyl,
in Compound Ir689: R=2,4-($^i$Pr)$_2$-3-dibenzofuran,
Compound Ir690 through Ir702, each represented by the formula

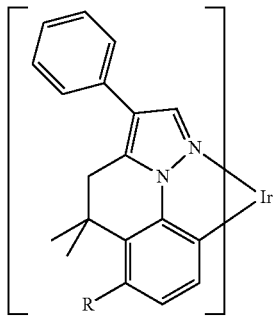

wherein in Compound Ir690: R=Me,
in Compound Ir691: R=Et,
in Compound Ir692: R=$^i$Pr,
in Compound Ir693: R=Cy,
in Compound Ir694: R=$^i$Bu,
in Compound Ir695: R=$^t$Bu,
in Compound Ir696: R=CN,
in Compound Ir697: R=neopentyl,
in Compound Ir698: R=Ph,
in Compound Ir699: R=4-biphenyl,
in Compound Ir700: R=2,6-($^i$Pr)$_2$Ph,
in Compound Ir701: R=2,6-($^i$Pr)$_2$-4-biphenyl,
in Compound Ir702: R=2,4-($^i$Pr)$_2$-3-dibenzofuran,
Compound Ir703 through Ir715, each represented by the formula

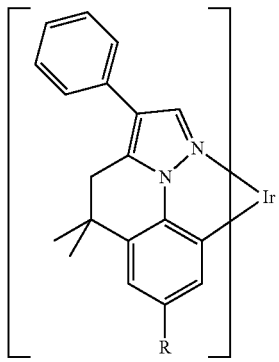

wherein in Compound Ir703: R=Me,
in Compound Ir704: R=Et,
in Compound Ir705: R=$^i$Pr,
in Compound Ir706: R=Cy,
in Compound Ir707: R=$^i$Bu,
in Compound Ir708: R=$^t$Bu,
in Compound Ir709: R=CN,
in Compound Ir710: R=neopentyl,
in Compound Ir711: R=Ph,
in Compound Ir712: R=4-biphenyl,
in Compound Ir713: R=2,6-($^i$Pr)$_2$Ph,
in Compound Ir714: R=2,6-($^i$Pr)$_2$-4-biphenyl,
in Compound Ir715: R=2,4-($^i$Pr)$_2$-3-dibenzofuran,
Compound Ir716 through Ir728, each represented by the formula

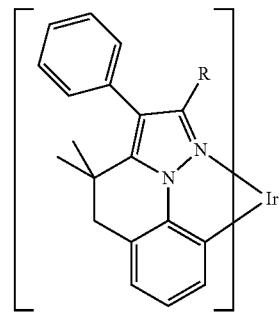

wherein in Compound Ir716: R=Me,
in Compound Ir717: R=Et,
in Compound Ir718: R=$^i$Pr,
in Compound Ir719: R=Cy,
in Compound Ir720: R=$^i$Bu,
in Compound Ir721: R=$^t$Bu,
in Compound Ir722: R=CN,
in Compound Ir723: R=neopentyl,
in Compound Ir724: R=Ph,
in Compound Ir725: R=4-biphenyl,
in Compound Ir726: R=2,6-($^i$Pr)$_2$Ph,
in Compound Ir727: R=2,6-($^i$Pr)$_2$-4-biphenyl,
in Compound Ir728: R=2,4-($^i$Pr)$_2$-3-dibenzofuran,
Compound Ir729 through Ir741, each represented by the formula

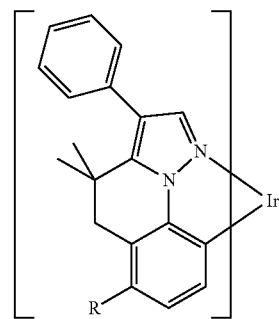

wherein in Compound Ir729: R=Me,
in Compound Ir730: R=Et,
in Compound Ir731: R=$^i$Pr,
in Compound Ir732: R=Cy,
in Compound Ir733: R=$^i$Bu,
in Compound Ir734: R=$^t$Bu,
in Compound Ir735: R=CN,
in Compound Ir736: R=neopentyl,
in Compound Ir737: R=Ph,
in Compound Ir738: R=4-biphenyl,
in Compound Ir739: R=2,6-($^i$Pr)$_2$Ph,
in Compound Ir740: R=2,6-($^i$Pr)$_2$-4-biphenyl,
in Compound Ir741: R=2,4-($^i$Pr)$_2$-3-dibenzofuran,
Compound Ir742 through Ir754, each represented by the formula

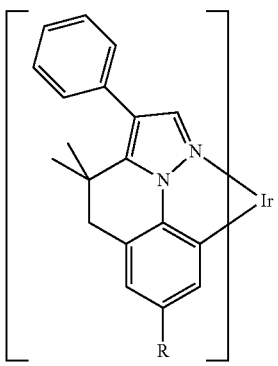

wherein in Compound Ir742: R=Me,
in Compound Ir743: R=Et,
in Compound Ir744: R=$^i$Pr,
in Compound Ir745: R=Cy,
in Compound Ir746: R=$^i$Bu,
in Compound Ir747: R=$^t$Bu,
in Compound Ir748: R=CN,
in Compound Ir749: R=neopentyl,
in Compound Ir750: R=Ph,
in Compound Ir751: R=4-biphenyl,
in Compound Ir752: R=2,6-($^i$Pr)$_2$Ph,
in Compound Ir753: R=2,6-($^i$Pr)$_2$-4-biphenyl,
in Compound Ir754: R=2,4-($^i$Pr)$_2$-3-dibenzofuran,
Compound Ir755 through Ir767, each represented by the formula

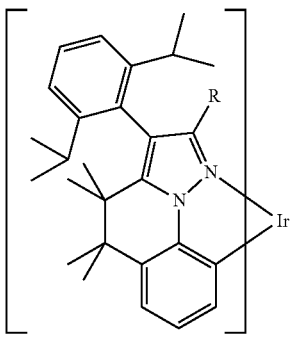

wherein in Compound Ir755: R=Me,
in Compound Ir756: R=Et,
in Compound Ir757: R=$^i$Pr,
in Compound Ir758: R=Cy,
in Compound Ir759: R=$^i$Bu,
in Compound Ir760: R=$^t$Bu,
in Compound Ir761: R=CN,
in Compound Ir762: R=neopentyl,
in Compound Ir763: R=Ph,
in Compound Ir764: R=4-biphenyl,
in Compound Ir765: R=2,6-($^i$Pr)$_2$Ph,
in Compound Ir766: R=2,6-($^i$Pr)$_2$-4-biphenyl,
in Compound Ir767: R=2,4-($^i$Pr)$_2$-3-dibenzofuran,
Compound Ir768 through Ir780, each represented by the formula

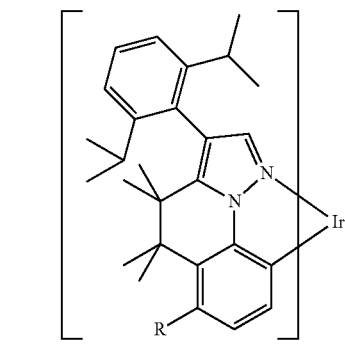

wherein in Compound Ir768: R=Me,
in Compound Ir769: R=Et,
in Compound Ir770: R=$^i$Pr,
in Compound Ir771: R=Cy,
in Compound Ir772: R=Bu,
in Compound Ir773: R=$^t$Bu,
in Compound Ir774: R=CN,
in Compound Ir775: R=neopentyl,
in Compound Ir776: R=Ph,
in Compound Ir777: R=4-biphenyl,
in Compound Ir778: R=2,6-($^i$Pr)$_2$Ph,
in Compound Ir779: R=2,6-($^i$Pr)$_2$-4-biphenyl,
in Compound Ir780: R=2,4-($^i$Pr)$_2$-3-dibenzofuran,
Compound Ir781 through Ir793, each represented by the formula

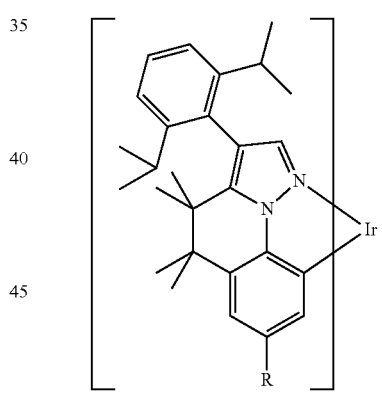

wherein in Compound Ir781: R=Me,
in Compound Ir782: R=Et,
in Compound Ir783: R=$^i$Pr,
in Compound Ir784: R=Cy,
in Compound Ir785: R=$^i$Bu,
in Compound Ir786: R=$^t$Bu,
in Compound Ir787: R=CN,
in Compound Ir788: R=neopentyl,
in Compound Ir789: R=Ph,
in Compound Ir790: R=4-biphenyl,
in Compound Ir791: R=2,6-($^i$Pr)$_2$Ph,
in Compound Ir792: R=2,6-($^i$Pr)$_2$-4-biphenyl,
in Compound Ir793: R=2,4-($^i$Pr)$_2$-3-dibenzofuran,
Compound Ir794 through Ir806, each represented by the formula

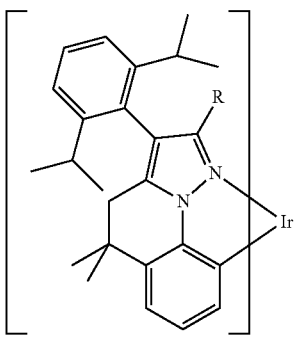

wherein in Compound Ir794: R=Me,
in Compound Ir795: R=Et,
in Compound Ir796: R=$^i$Pr,
in Compound Ir797: R=Cy,
in Compound Ir798: R=$^i$Bu,
in Compound Ir799: R=$^t$Bu,
in Compound Ir800: R=CN,
in Compound Ir801: R=neopentyl,
in Compound Ir802: R=Ph,
in Compound Ir803: R=4-biphenyl,
in Compound Ir804: R=2,6-($^i$Pr)$_2$Ph,
in Compound Ir805: R=2,6-($^i$Pr)$_2$-4-biphenyl,
in Compound Ir806: R=2,4-($^i$Pr)$_2$-3-dibenzofuran,
Compound Ir807 through Ir819, each represented by the formula

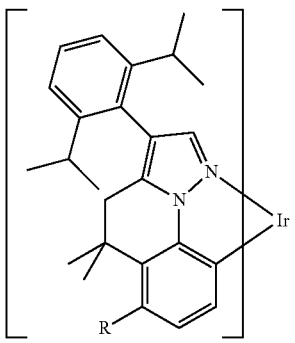

wherein in Compound Ir807: R=Me,
in Compound Ir808: R=Et,
in Compound Ir809: R=$^i$Pr,
in Compound Ir810: R=Cy,
in Compound Ir811: R=$^i$Bu,
in Compound Ir812: R=$^t$Bu,
in Compound Ir813: R=CN,
in Compound Ir814: R=neopentyl,
in Compound Ir815: R=Ph,
in Compound Ir816: R=4-biphenyl,
in Compound Ir817: R=2,6-($^i$Pr)$_2$Ph,
in Compound Ir818: R=2,6-($^i$Pr)$_2$-4-biphenyl,
in Compound Ir819: R=2,4-($^i$Pr)$_2$-3-dibenzofuran,
Compound Ir820 through Ir832, each represented by the formula

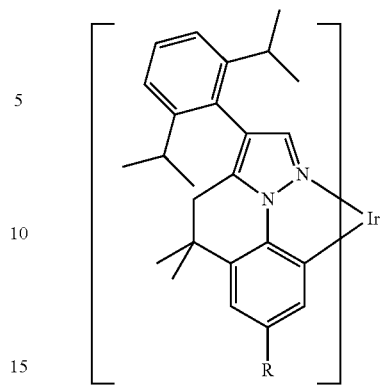

wherein in Compound Ir820: R=Me,
in Compound Ir821: R=Et,
in Compound Ir822: R=$^i$Pr,
in Compound Ir823: R=Cy,
in Compound Ir824: R=$^i$Bu,
in Compound Ir825: R=$^t$Bu,
in Compound Ir826: R=CN,
in Compound Ir827: R=neopentyl,
in Compound Ir828: R=Ph,
in Compound Ir829: R=4-biphenyl,
in Compound Ir830: R=2,6-($^i$Pr)$_2$Ph,
in Compound Ir831: R=2,6-($^i$Pr)$_2$-4-biphenyl,
in Compound Ir832: R=2,4-($^i$Pr)$_2$-3-dibenzofuran,
Compound Ir833 through Ir845, each represented by the formula

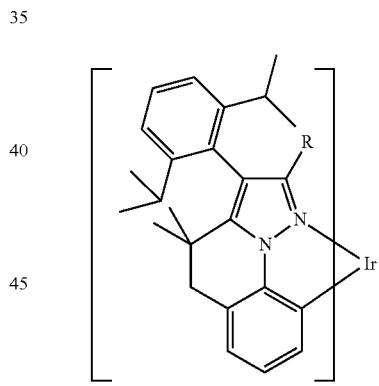

wherein in Compound Ir833: R=Me,
in Compound Ir834: R=Et,
in Compound Ir835: R=$^i$Pr,
in Compound Ir836: R=Cy,
in Compound Ir837: R=$^i$Bu,
in Compound Ir838: R=$^t$Bu,
in Compound Ir839: R=CN,
in Compound Ir840: R=neopentyl,
in Compound Ir841: R=Ph,
in Compound Ir842: R=4-biphenyl,
in Compound Ir843: R=2,6-($^i$Pr)$_2$Ph,
in Compound Ir844: R=2,6-($^i$Pr)$_2$-4-biphenyl,
in Compound Ir845: R=2,4-($^i$Pr)$_2$-3-dibenzofuran,
Compound Ir846 through Ir858, each represented by the formula

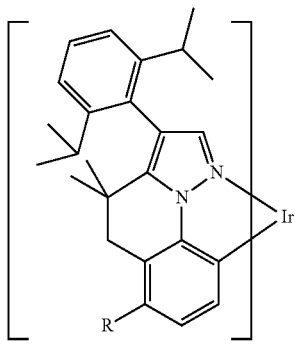

wherein in Compound Ir846: R=Me,
in Compound Ir847: R=Et,
in Compound Ir848: R=$^i$Pr,
in Compound Ir849: R=Cy,
in Compound Ir850: R=$^i$Bu,
in Compound Ir851: R=$^t$Bu,
in Compound Ir852: R=CN,
in Compound Ir853: R=neopentyl,
in Compound Ir854: R=Ph,
in Compound Ir855: R=4-biphenyl,
in Compound Ir856: R=2,6-($^i$Pr)$_2$Ph,
in Compound Ir857: R=2,6-($^i$Pr)$_2$-4-biphenyl,
in Compound Ir858: R=2,4-($^i$Pr)$_2$-3-dibenzofuran,
Compound Ir859 through Ir871, each represented by the formula

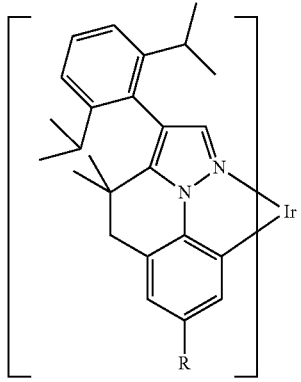

wherein in Compound Ir859: R=Me,
in Compound Ir860: R=Et,
in Compound Ir861: R=$^i$Pr,
in Compound Ir862: R=Cy,
in Compound Ir863: R=$^i$Bu,
in Compound Ir864: R=$^t$Bu,
in Compound Ir865: R=CN,
in Compound Ir866: R=neopentyl,
in Compound Ir867: R=Ph,
in Compound Ir868: R=4-biphenyl,
in Compound Ir869: R=2,6-($^i$Pr)$_2$Ph,
in Compound Ir870: R=2,6-($^i$Pr)$_2$-4-biphenyl,
in Compound Ir871: R=2,4-($^i$Pr)$_2$-3-dibenzofuran,
Compound Ir872 through Ir873, each represented by the formula

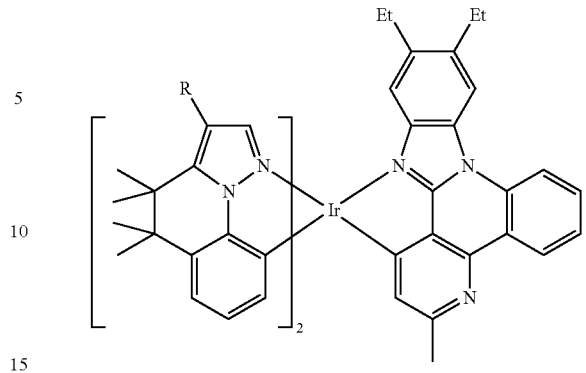

wherein in Compound Ir872: R=H,
in Compound Ir873: R=Ph,
Compound Ir874 through Ir875, each represented by the formula

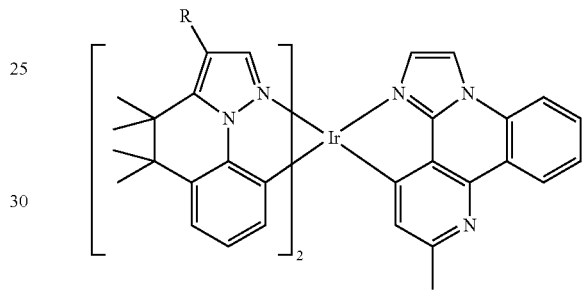

wherein in Compound Ir874: R=H,
in Compound Ir875: R=Ph,
Compound Ir876 through Ir887, each represented by the formula

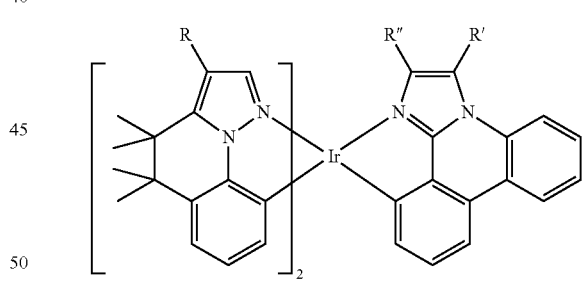

wherein in Compound Ir876: R=H, R'=2,6-($^i$Pr)Ph, R"=H,
in Compound Ir877: R=H, R'=2,6-($^t$Bu)Ph, R"=H,
in Compound Ir878: R=H, R'=Cy, R"=H,
in Compound Ir879: R=Ph, R'=2,6-($^i$Pr)Ph, R"=H,
in Compound Ir880: R=Ph, R'=2,6-($^t$Bu)Ph, R"=H,
in Compound Ir881: R=Ph, R'=Cy, R"=H,
in Compound Ir882: R=H, R'=2,6-($^i$Pr)Ph, R"=Me,
in Compound Ir883: R=H, R'=2,6-($^t$Bu)Ph, R"=Me,
in Compound Ir884: R=H, R'=Cy, R"=Me,
in Compound Ir885: R=Ph, R'=2,6-($^i$Pr)Ph, R"=Me,
in Compound Ir886: R=Ph, R'=2,6-($^t$Bu)Ph, R"=Me,
in Compound Ir887: R=Ph, R'=Cy, R"=Me,
Compound Ir888 through Ir889, each represented by the formula

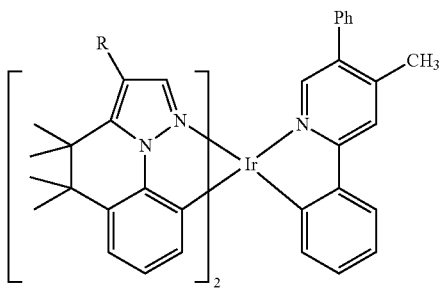

wherein in Compound Ir888: R=H,
in Compound Ir889: R=Ph,
Compound Ir890 through Ir891, each represented by the formula

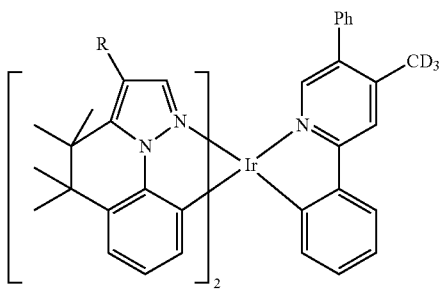

wherein in Compound Ir890: R=H,
in Compound Ir891: R=Ph,
Compound Ir892 through Ir895, each represented by the formula

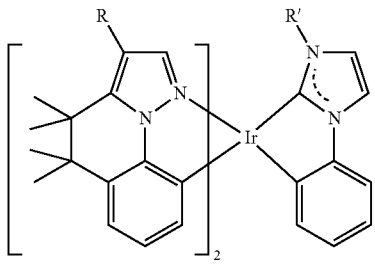

wherein in Compound Ir892: R=H, R'=Me,
in Compound Ir893: R=H, R'=Ph,
in Compound Ir894: R=Ph, R'=Me,
in Compound Ir895: R=Ph, R'=Ph,
Compound Ir896 through Ir899, each represented by the formula

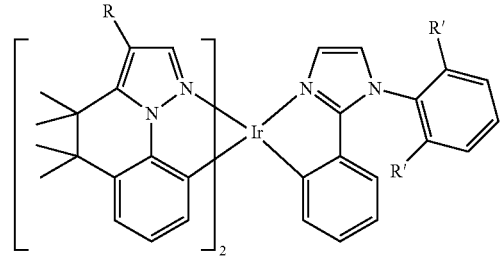

wherein in Compound Ir896: R=H, R'=Me,
in Compound Ir897: R=H, R'=$^i$Pr,
in Compound Ir898: R=Ph, R'=Me,
in Compound Ir899: R=Ph, R'=$^i$Pr,
Compound Ir900 through Ir903, each represented by the formula

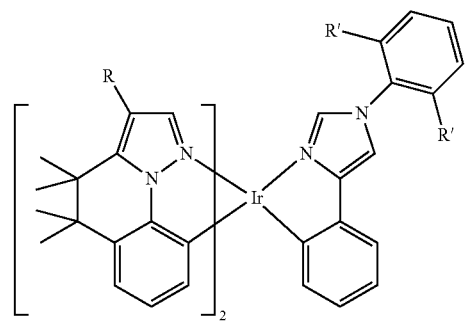

wherein in Compound Ir900: R=H, R'=Me,
in Compound Ir901: R=H, R'=$^i$Pr,
in Compound Ir902: R=Ph, R'=Me,
in Compound Ir903: R=Ph, R'=$^i$Pr, and
Compound Ir904 through Ir907, each represented by the formula

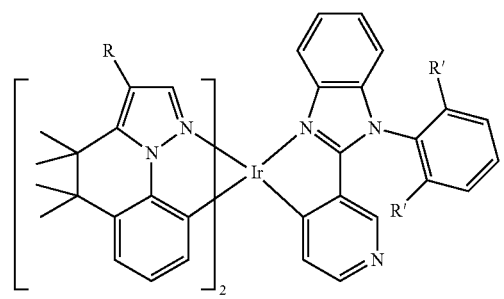

wherein in Compound Ir904: R=H, R'=Me,
in Compound Ir905: R=H, R'=$^i$Pr,
in Compound Ir906: R=Ph, R'=Me,
in Compound Ir907: R=Ph, R'=$^i$Pr.

18. A first device comprising a first organic light emitting device, the first organic light emitting device comprising:
an anode;
a cathode; and
an organic layer, disposed between the anode and the cathode, comprising a compound having the structure of formula

401

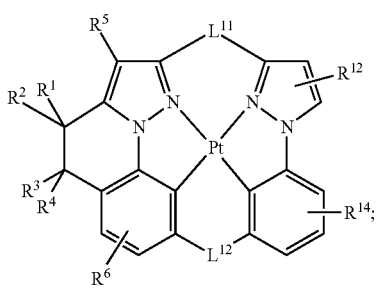

wherein R⁶ represents mono or di substitution, or no substitution;

wherein each $R^1$, $R^2$, $R^3$, $R^4$, $R^5$, $R^6$, $R^{12}$, $R^{14}$, and $R^{15}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any adjacent $R^1$, $R^2$, $R^3$, $R^4$, $R^5$, $R^6$, $L^{11}$, $L_{12}$, $R_{12}$, $R_{14}$, and $R^{15}$ groups are optionally joined to form a fused or unfused ring;

wherein $R^{12}$ represents mono, or di substitution, or no substitution;

wherein $R^{14}$ represents mono, di, tri, or tetra substitution, or no substitution;

wherein $L^{11}$ represents a linking group selected from the group consisting of alkyl, cycloalkyl, aryl, and heteroaryl; and wherein $L^{12}$ represents a linking group selected from the group consisting of $NR^{15}$, and $PR^{15}$.

19. The first device of claim 18, wherein the first device is a consumer product selected from the group consisting of flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, wall, theater or stadium screens, and signs.

20. The first device of claim 18, wherein the organic layer is an emissive layer and the compound is an emissive dopant or a non-emissive dopant.

21. The first device of claim 18, wherein the organic layer further comprises a host, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1$-$Ar_2$, and $C_nH_{2n}$—$Ar_1$, or the host has no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

22. The first device of claim 18, wherein the organic layer further comprises a host; wherein the host comprises at least one chemical group selected from the group consisting of triphenylene, carbazole, dibenzothiophene, dibenzofuran,

402 dibenzoselenophene, azatriphenylene, azacarbazole, aza-dibenzothiophene, aza-dibenzofuran, and aza-dibenzoselenophene.

23. The first device of claim 18, wherein the organic layer further comprises a host, wherein the host is selected from the group consisting of:

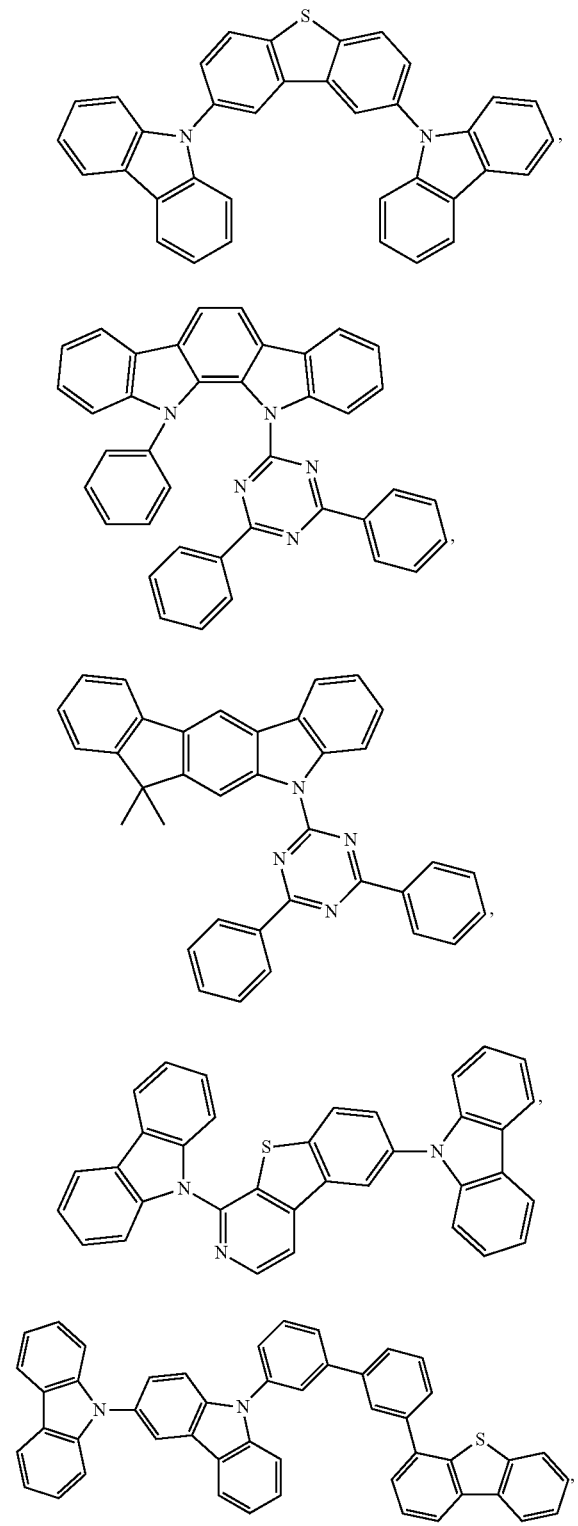

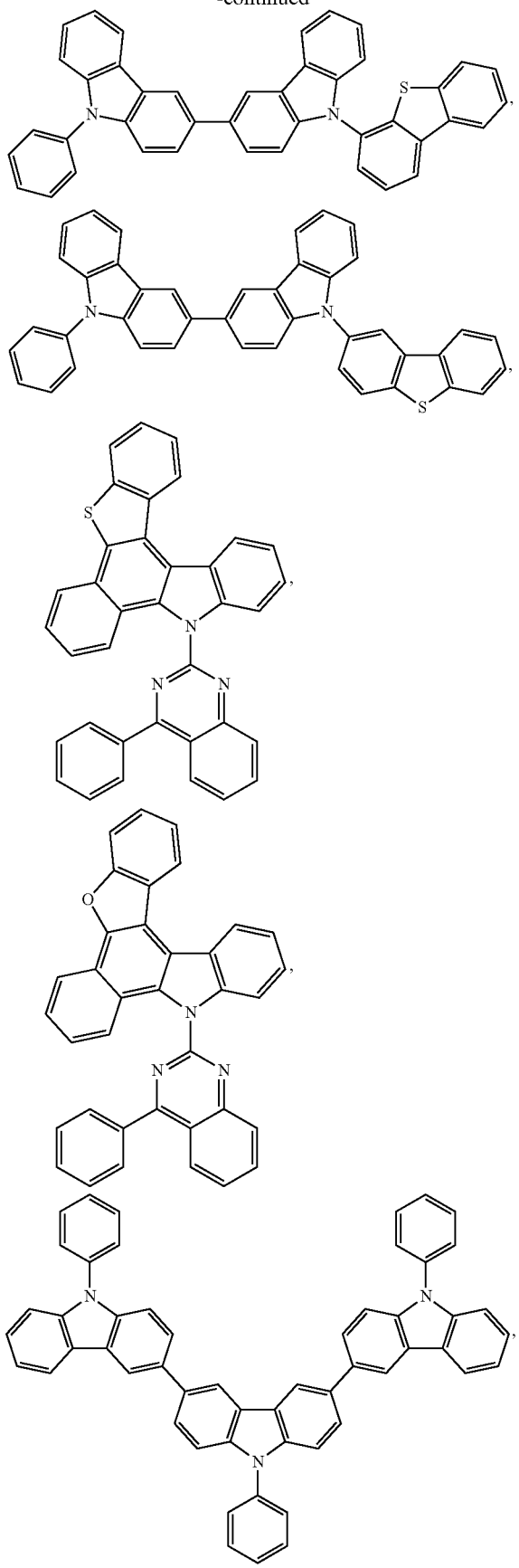

405
-continued

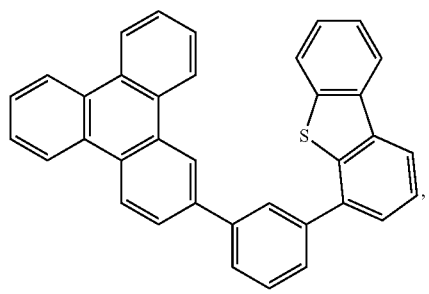

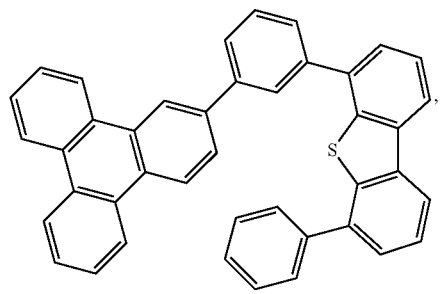

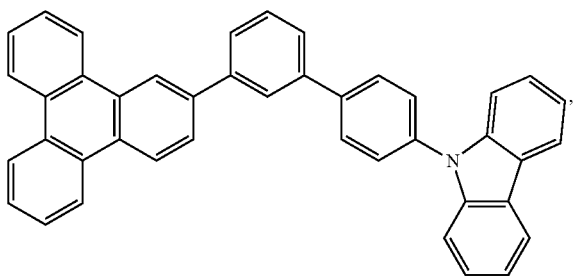

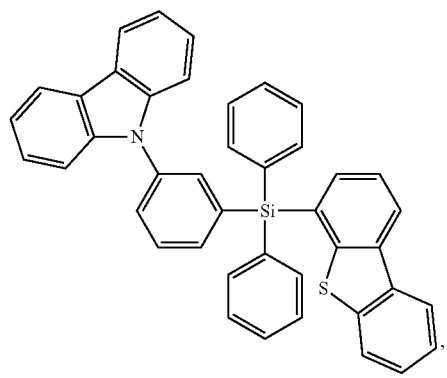

406
-continued

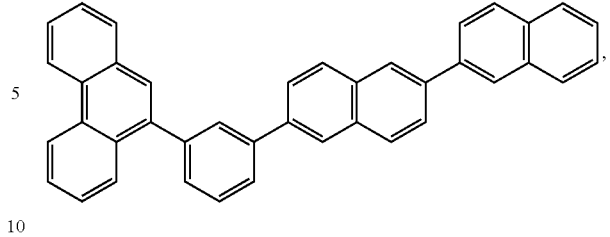

and combinations thereof.

24. The first device of claim 18, wherein the organic layer further comprises a host and the host comprises a metal complex.

25. A formulation comprising a compound having the structure of formula

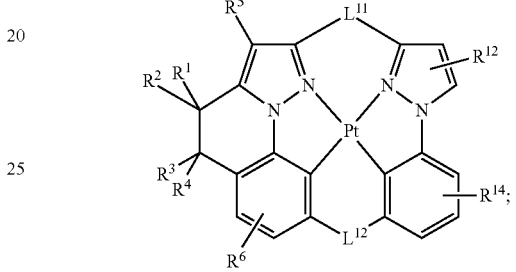

wherein $R^6$ represents mono or di substitution, or no substitution;

wherein each $R^1$, $R^2$, $R^3$, $R^4$, $R^5$, $R^6$, $R^{12}$, $R^{14}$, and $R^{15}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any adjacent $R^1$, $R^2$, $R^3$, $R^4$, $R^5$, $R^6$, $L^{11}$, $L^{12}$, $R^{12}$, $R^{14}$, and $R^{15}$ groups are optionally joined to form a fused or unfused ring;

wherein $R^{12}$ represents mono, or di substitution, or no substitution;

wherein $R^{14}$ represents mono, di, tri, or tetra substitution, or no substitution;

wherein $L^{11}$ represents a linking group selected from the group consisting of alkyl, cycloalkyl, aryl, and heteroaryl; and wherein $L^{12}$ represents a linking group selected from the group consisting of $NR^{15}$, and $PR^{15}$.

* * * * *